US012698328B2

(12) United States Patent
Polyakova et al.

(10) Patent No.: US 12,698,328 B2
(45) Date of Patent: Aug. 4, 2026

(54) ANTIBODIES

(71) Applicant: GammaDelta Therapeutics Limited, London (GB)

(72) Inventors: Oxana Polyakova, London (GB); Oliver Nussbaumer, London (GB); Adrian Hayday, London (GB); Pierre Vantourout, London (GB)

(73) Assignee: GammaDelta Therapeutics Limited, London (GB)

( * ) Notice: Subject to any disclaimer, the term of this patent is extended or adjusted under 35 U.S.C. 154(b) by 919 days.

(21) Appl. No.: 17/801,786

(22) PCT Filed: Feb. 24, 2021

(86) PCT No.: PCT/GB2021/050459
§ 371 (c)(1),
(2) Date: Aug. 23, 2022

(87) PCT Pub. No.: WO2021/171002
PCT Pub. Date: Sep. 2, 2021

(65) Prior Publication Data
US 2023/0090901 A1 Mar. 23, 2023

(30) Foreign Application Priority Data

Feb. 24, 2020 (GB) ..................................... 2002581

(51) Int. Cl.
| | |
|---|---|
| C07K 16/28 | (2006.01) |
| A61K 39/00 | (2006.01) |
| A61P 35/00 | (2006.01) |
| C12N 5/078 | (2010.01) |

(52) U.S. Cl.
CPC .......... C07K 16/2809 (2013.01); A61P 35/00 (2018.01); C12N 5/0634 (2013.01); *A61K 2039/505* (2013.01); *C07K 2317/21* (2013.01); *C07K 2317/34* (2013.01); *C07K 2317/565* (2013.01); *C07K 2317/622* (2013.01); *C07K 2317/74* (2013.01); *C07K 2317/92* (2013.01); *C12N 2501/23* (2013.01)

(58) Field of Classification Search
None
See application file for complete search history.

(56) References Cited

U.S. PATENT DOCUMENTS

| | | | |
|---|---|---|---|
| 9,334,331 | B2 | 5/2016 | Igawa et al. |
| 10,421,807 | B2 | 9/2019 | Gonzales et al. |
| 11,629,193 | B2 | 4/2023 | Tuna et al. |
| 12,312,408 | B2 | 5/2025 | Tuna et al. |
| 2018/0228566 | A9 | 8/2018 | McAfee |
| 2019/0119634 | A1 | 4/2019 | Jakobovits et al. |
| 2022/0403025 | A1 | 12/2022 | Mount et al. |
| 2023/0028110 | A1 | 1/2023 | Tuna et al. |
| 2024/0132599 | A1 | 4/2024 | Tuna et al. |
| 2024/0376215 | A1 | 11/2024 | Tuna et al. |

FOREIGN PATENT DOCUMENTS

| | | |
|---|---|---|
| CN | 101031641 A | 9/2007 |
| CN | 109414480 A | 3/2019 |
| JP | 2018-532383 A | 11/2018 |
| JP | 2019-519210 A | 7/2019 |
| WO | WO 03/080672 A1 | 10/2003 |
| WO | WO 2016/166544 A1 | 10/2016 |
| WO | WO 2016/198480 A1 | 12/2016 |
| WO | WO 2017/037707 A1 | 3/2017 |
| WO | WO 2017/197347 A1 | 11/2017 |
| WO | WO 2019/005637 A2 | 1/2019 |
| WO | WO 2019/147735 A1 | 8/2019 |
| WO | WO 2020/060406 A1 | 3/2020 |
| WO | WO 2020/154548 A2 | 7/2020 |
| WO | WO 2020/159368 A1 | 8/2020 |
| WO | WO 2020/210232 A1 | 10/2020 |
| WO | WO 2021/032951 A1 | 2/2021 |
| WO | WO 2021/032960 A1 | 2/2021 |
| WO | WO 2021/032961 A1 | 2/2021 |
| WO | WO 2021/032963 A1 | 2/2021 |
| WO | WO 2022/175413 A1 | 8/2022 |
| WO | WO 2022/175414 A1 | 8/2022 |

OTHER PUBLICATIONS

International Search Report and Written Opinion for Application No. PCT/GB2020/051959, mailed Mar. 3, 2022.
International Preliminary Report on Patentability for Application No. PCT/GB2020/051959, mailed Oct. 30, 2020.
International Search Report and Written Opinion for Application No. PCT/EP2022/054011, mailed May 30, 2022.
International Preliminary Report on Patentability for Application No. PCT/EP2022/054011, mailed Aug. 31, 2023.
International Search Report and Written Opinion for Application No. PCT/EP2022/054004, mailed May 24, 2022.
International Preliminary Report on Patentability for Application No. PCT/EP2022/054004, mailed Aug. 31, 2023.
Almagro et al., Progress and Challenges in the Design and Clinical Development of Antibodies for Cancer Therapy. Front Immunol. Jan. 4, 2018:8:1751. doi: 10.3389/fimmu.2017.01751. eCollection 2017.
Almeida et al., Delta One T Cells for Immunotherapy of Chronic Lymphocytic Leukemia: Clinical-Grade Expansion/Differentiation and Preclinical Proof of Concept. Clin Cancer Res. Dec. 1, 2016;22(23):5795-5804. doi: 10.1158/1078-0432.CCR-16-0597. Epub Jun. 15, 2016.
Brown et al., Tolerance of single, but not multiple, amino acid replacements in antibody VH CDR 2: a means of minimizing B cell wastage from somatic hypermutation? J Immunol. May 1, 1996;156(9):3285-91.

(Continued)

*Primary Examiner* — Brian Gangle
(74) *Attorney, Agent, or Firm* — Wolf, Greenfield & Sacks, P.C.

(57) ABSTRACT
An isolated antibody or fragment thereof, which specifically binds to a gamma variable 4 (Vγ4) chain of a γδ T cell receptor (TCR) and not to a gamma variable 2 (Vγ2) chain of a γδ TCR is provided herein. Methods of treatment and other uses of said antibodies are also provided along with methods of producing said antibodies.

15 Claims, 12 Drawing Sheets

Specification includes a Sequence Listing.

(56) References Cited

OTHER PUBLICATIONS

Chitadze et al., The Ambiguous Role of γδ T Lymphocytes in Antitumor Immunity. Trends Immunol. Sep. 2017;38(9):668-678. doi: 10.1016/j.it.2017.06.004. Epub Jul. 11, 2017.

Chiu et al., Antibody Structure and Function: The Basis for Engineering Therapeutics. Antibodies (Basel). Dec. 3, 2019;8(4):55. doi: 10.3390/antib8040055.

Cordova et al., Characterization of human γδ T lymphocytes infiltrating primary malignant melanomas. Plos One. 2012;7(11):e49878. doi: 10.1371/journal.pone.0049878. Epub Nov. 26, 2012.

Davey et al., Clonal selection in the human Vδ1 T cell repertoire indicates γδ TCR-dependent adaptive immune surveillance. Nat Commun. Mar. 1, 2017;8:14760. doi: 10.1038/ncomms14760.

De Bruin et al., A bispecific nanobody approach to leverage the potent and widely applicable tumor cytolytic capacity of Vγ9Vδ2-T cells. Oncoimmunology. Oct. 20, 2017;7(1):e1375641. doi: 10.1080/2162402X.2017.1375641. eCollection 2017.

De Weerdt et al., A Bispecific Single-Domain Antibody Boosts Autologous Vγ9Vδ2-T Cell Responses Toward CD1d in Chronic Lymphocytic Leukemia. Clin Cancer Res. Mar. 15, 2021;27(6):1744-1755. doi: 10.1158/1078-0432.CCR-20-4576. Epub Jan. 15, 2021.

Deniger et al., Clinical applications of gamma delta T cells with multivalent immunity. Front Immunol. Dec. 11, 2014;5:636. doi: 10.3389/fimmu.2014.00636. eCollection 2014.

Di Lorenzo et al., Broad Cytotoxic Targeting of Acute Myeloid Leukemia by Polyclonal Delta One T Cells. Cancer Immunol Res. Apr. 2019;7(4):552-558. doi: 10.1158/2326-6066.CIR-18-0647. Epub Mar. 20, 2019.

Dondelinger et al., Understanding the Significance and Implications of Antibody Numbering and Antigen-Binding Surface/Residue Definition. Front Immunol. Oct. 16, 2018;9:2278. doi: 10.3389/fimmu.2018.02278. eCollection 2018.

Dutta et al., Apoptosis Induced via Gamma Delta T Cell Antigen Receptor "Blocking" Antibodies: A Cautionary Tale. Front Immunol. Jun. 30, 2017;8:776. doi: 10.3389/fimmu.2017.00776. eCollection 2017.

Ferrarini et al., Killing of laminin receptor-positive human lung cancers by tumor-infiltrating lymphocytes bearing γδ+ T-cell receptors. J Natl Cancer Inst. Apr. 3, 1996;88(7):436-41. doi: 10.1093/jnci/88.7.436.

Fisher et al., Engineering Approaches in Human Gamma Delta T Cells for Cancer Immunotherapy. Front Immunol. Jun. 26, 2018;9:1409. doi: 10.3389/fimmu.2018.01409. eCollection 2018.

Fisher et al., Neuroblastoma killing properties of Vδ2 and Vδ2-negative γδT cells following expansion by artificial antigen-presenting cells. Clin Cancer Res. Nov. 15, 2014;20(22):5720-32. doi: 10.1158/1078-0432.CCR-13-3464. Epub Jun. 3, 2014.

Garber, γδ T cells bring unconventional cancer-targeting to the clinic—again. Nat Biotechnol. Apr. 2020;38(4):389-391. doi: 10.1038/s41587-020-0487-2.

Groh et al., Broad tumor-associated expression and recognition by tumor-derived gamma delta T cells of MICA and MICB. Proc Natl Acad Sci U S A. Jun. 8, 1999;96(12):6879-84. doi: 10.1073/pnas.96.12.6879.

Jefferis et al., Human immunoglobulin allotypes: possible implications for immunogenicity. Mabs. Jul.-Aug. 2009;1(4):332-8. doi: 10.4161/mabs.1.4.9122.

Kitayama et al., Functional analysis of TCR gamma delta+ T cells in tumour-infiltrating lymphocytes (TIL) of human pancreatic cancer. Clin Exp Immunol. Sep. 1993;93(3):442-7. doi: 10.1111/j.1365-2249.1993.tb08198.x.

Knight et al., Human Vdeltal gamma-delta T cells exert potent specific cytotoxicity against primary multiple myeloma cells. Cytotherapy. Oct. 2012;14(9):1110-8. doi: 10.3109/14653249.2012.700766. Epub Jul. 17, 2012.

Luoma et al., Crystal structure of Vδ1 T cell receptor in complex with CD1d-sulfatide shows MHC-like recognition of a self-lipid by human γδ T cells. Immunity. Dec. 12, 2013;39(6):1032-42. doi: 10.1016/j.immuni.2013.11.001. Epub Nov. 14, 2013.

Maeurer et al., Human intestinal Vdelta1+ lymphocytes recognize tumor cells of epithelial origin. J Exp Med. Apr. 1, 1996;183(4):1681-96. doi: 10.1084/jem.183.4.1681.

Mahvi et al., Overexpression of 27-kDa heat-shock protein in MCF-7 breast cancer cells: effects on lymphocyte-mediated killing by natural killer and gamma delta T cells. Cancer Immunol Immunother. Aug. 1993;37(3):181-6. doi: 10.1007/BF01525433.

Mikulak et al., NKp46-expressing human gut-resident intraepithelial Vδ1 T cell subpopulation exhibits high antitumor activity against colorectal cancer. JCI Insight. Dec. 19, 2019;4(24):e125884. doi: 10.1172/jci.insight.125884.

Oberg et al., Bispecific antibodies enhance tumor-infiltrating T cell cytotoxicity against autologous HER-2-expressing high-grade ovarian tumors. J Leukoc Biol. Jun. 2020;107(6):1081-1095. doi: 10.1002/JLB.5MA1119-265R. Epub Dec. 13, 2019.

Oberg et al., Novel bispecific antibodies increase γδ T-cell cytotoxicity against pancreatic cancer cells. Cancer Res. Mar. 1, 2014;74(5):1349-60. doi: 10.1158/0008-5472.CAN-13-0675. Epub Jan. 21, 2014.

Romagné et al., Structural analysis of γδ TCR using a novel set of TCR γ and δ chain-specific monoclonal antibodies generated against soluble γδ TCR: Evidence for a specific conformation adopted by the Jδ2 region and for a Vδ1 polymorphism. J Immunol Methods. Jan. 16, 1996;189(1):25-36. doi: 10.1016/0022-1759(95)00224-3.

Rudikoff et al., Single amino acid substitution altering antigen-binding specificity. Proc Natl Acad Sci U S A. Mar. 1982;79(6):1979-83. doi: 10.1073/pnas.79.6.1979.

Sebestyen et al., Translating gammadelta (γδ) T cells and their receptors into cancer cell therapies. Nat Rev Drug Discov. Mar. 2020;19(3):169-184. doi: 10.1038/s41573-019-0038-z. Epub Sep. 6, 2019.

Sela-Culang et al., The structural basis of antibody-antigen recognition. Front Immunol. Oct. 8, 2013;4:302. doi: 10.3389/fimmu.2013.00302.

Siegers et al., Cytotoxic and regulatory properties of circulating Vδ1+ γδ T cells: a new player on the cell therapy field? Mol Ther. Aug. 2014;22(8):1416-1422. doi: 10.1038/mt.2014.104. Epub Jun. 4, 2014.

Wu et al., Ex vivo expanded human circulating Vδ1 γδT cells exhibit favorable therapeutic potential for colon cancer. OncoImmunology. Jan. 22, 2015;4(3):e992749. doi: 10.4161/2162402X.2014.992749. eCollection Mar. 2015.

Xu et al., Crystal structure of a γδ T-cell receptor specific for the human MHC class I homolog MICA. Proc Natl Acad Sci U S A. Feb. 8, 2011;108(6):2414-9. doi: 10.1073/pnas.1015433108. Epub Jan. 24, 2011.

Invitation to Pay Additional Fees for Application No. PCT/GB2021/050459, mailed Jun. 7, 2021.

International Search Report and Written Opinion for Application No. PCT/GB2021/050459, mailed Jul. 28, 2021.

International Preliminary Report on Patentability for Application No. PCT/GB2021/050459, mailed Sep. 9, 2022.

Blink et al., γδ T cell subsets play opposing roles in regulating experimental autoimmune encephalomyelitis. Cell Immunol. Jul. 2014;290(1):39-51. doi: 10.1016/j.cellimm.2014.04.013. Epub May 10, 2014. Author Manuscript (29 pages).

Davodeau et al., Surface expression of two distinct functional antigen receptors on human gamma delta T cells. Science. Jun. 18, 1993;260(5115):1800-2. doi: 10.1126/science.8390096.

De Libero et al., Selection by two powerful antigens may account for the presence of the major population of human peripheral gamma/delta T cells. J Exp Med. Jun. 1, 1991;173(6):1311-22. doi: 10.1084/jem.173.6.1311.

Khairallah et al., γδ T cells confer protection against murine cytomegalovirus (MCMV) PLoS Pathog. Mar. 6, 2015;11(3):e1004702. doi: 10.1371/journal.ppat.1004702. eCollection Mar. 2015.

Langerak et al., Immunophenotypic and immunogenotypic characteristics of TCRgammadelta+ T cell acute lymphoblastic leukemia. Leukemia. Feb. 1999;13(2):206-14. doi: 10.1038/sj.leu.2401276.

No Author Listed, Purified anti-mouse TCR V[gamma]4 Antibody Antigen. Biolegend. Version 1. Last revised: Aug. 10, 2020. Retrieved from the Internet: URL: https://www.biolegend.com/en-ie/global-elements/pdg-popup/purified-anti-mouse-ter-vy4-antibody-19846?

(56)          References Cited

OTHER PUBLICATIONS filename=Purified%20anti-mouse%20TCE%20Vgamma4%
20Antibody.pdf&pdfgen=true. [retrieved on Sep. 29, 2022].

Abeler-Dörner et al., Butyrophilins: an emerging family of immune regulators. Trends Immunol. Jan. 2012;33(1):34-41. doi: 10.1016/j.it.2011.09.007. Epub Oct. 24, 2011.

Mayassi et al., Chronic Inflammation Permanently Reshapes Tissue-Resident Immunity in Celiac Disease. Cell. Feb. 21, 2019;176(5):967-981.e19. doi: 10.1016/j.cell.2018.12.039. Epub Feb. 7, 2019.

Yamashiro et al., Stimulation of human butyrophilin 3 molecules results in negative regulation of cellular immunity. J Leukoc Biol. Oct. 2010;88(4):757-67. doi: 10.1189/jlb.0309156. Epub Jul. 7, 2010.

Al Qaraghuli et al., Antibody-protein binding and conformational changes: identifying allosteric signalling pathways to engineer a better effector response. Sci Rep. 2020; 10: 13696. Published online Aug. 13, 2020. doi: 10.1038/s41598-020-70680-0.

An et al., IgG2m4, an engineered antibody isotype with reduced Fc function. MAbs. Nov.-Dec. 2009;1(6):572-9. doi: 10.4161/mabs.1.6.10185.

Aruda et al., Impact of gd T cells on clinical outcome of hematopoietic stem cell transplantation: systematic review and meta-analysis. Blood Adv. 2019; 3 (21): 3436-3448. https://doi.org/10.1182/bloodadvances.2019000682.

Bruhns et al., Specificity and affinity of human Fcgamma receptors and their polymorphic variants for human IgG subclasses. Blood. Apr. 16, 2009;113(16):3716-25. doi: 10.1182/blood-2008-09-179754. Epub Nov. 18, 2008.

Catellani et al., Expansion of Vdelta1 T lymphocytes producing IL-4 in low-grade non-Hodgkin lymphomas expressing UL-16-binding proteins. Blood. Mar. 1, 2007;109(5):2078-85. doi: 10.1182/blood-2006-06-028985. Epub Sep. 14, 2006.

Chen et al., Distribution and functions of γδ T cells infiltrated in the ovarian cancer microenvironment. J Transl Med. May 7, 2019;17(1):144. doi: 10.1186/s12967-019-1897-0.

Chothia et al., Conformations of immunoglobulin hypervariable regions. Nature. Dec. 1989;342(6252):877-83. doi: 10.1038/342877a0.

Crescioli et al., IgG4 Characteristics and Functions in Cancer Immunity. Curr Allergy Asthma Rep. Jan. 2016;16(1):7. doi: 10.1007/s11882-015-0580-7.

Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.

Daley et al., γδ T Cells Support Pancreatic Oncogenesis by Restraining αβ T Cell Activation. Cell. Sep. 8, 2016;166(6):1485-1499.e15. doi: 10.1016/j.cell.2016.07.046. Epub Aug. 25, 2016.

Declaration and Curriculum Vitae of Professor Frits Koning. Signed Mar. 11, 2025. 48 pages.

Deniger et al., Activating and propagating polyclonal gamma delta T cells with broad specificity for malignancies. Clin Cancer Res. Nov. 15, 2014;20(22):5708-19. doi: 10.1158/1078-0432.CCR-13-3451. Epub May 15, 2014.

Dopfer et al., The CD3 conformational change in the γδ T cell receptor is not triggered by antigens but can be enforced to enhance tumor killing. Cell Rep. Jun. 12, 2014;7(5):1704-1715. doi: 10.1016/j.celrep.2014.04.049. Epub May 22, 2014.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

Einsele et al., The BiTE (bispecific T-cell engager) platform: Development and future potential of a targeted immuno-oncology therapy across tumor types. Cancer. Jul. 15, 2020;126(14):3192-3201. doi: 10.1002/cncr.32909. Epub May 13, 2020.

Gaspar et al., CD137/OX40 Bispecific Antibody Induces Potent Antitumor Activity that Is Dependent on Target Coengagement. Cancer Immunol Res. Jun. 2020;8(6):781-793. doi: 10.1158/2326-6066.CIR-19-0798. Epub Apr. 9, 2020.

Gentles et al., The prognostic landscape of genes and infiltrating immune cells across human cancers. Nat Med. Author manuscript; available in PMC May 2, 2016. Published in final edited form as: Nat Med. Aug. 2015; 21(8): 938-945. Published online Jul. 20, 2015. doi: 10.1038/nm.3909.

Godder et al., Long term disease-free survival in acute leukemia patients recovering with increased gammadelta T cells after partially mismatched related donor bone marrow transplantation. Bone Marrow Transplant. Jun. 2007;39(12):751-7. doi: 10.1038/sj.bmt.1705650. Epub Apr. 23, 2007.

Goel et al., Plasticity within the antigen-combining site may manifest as molecular mimicry in the humoral immune response. J Immunol. Dec. 15, 2004;173(12):7358-67. doi: 10.4049/jimmunol.173.12.7358.

Gonzales et al., Minimizing the Immunogenicity of Antibodies for Clinical Application. Tumour Biol. Jan.-Feb. 2005;26(1):31-43. doi: 10.1159/000084184.

He et al., Naturally activated V gamma 4 gamma delta T cells play a protective role in tumor immunity through expression of eomesodermin. J Immunol. Jul. 1, 2010;185(1):126-33. doi: 10.4049/jimmunol.0903767. Epub Jun. 4, 2010.

Herrman et al., Bifunctional PD-1×αCD3×αCD33 fusion protein reverses adaptive immune escape in acute myeloid leukemia. Blood. Dec. 6, 2018;132(23):2484-2494. doi: 10.1182/blood-2018-05-849802. Epub Oct. 1, 2018.

Kabat et al., Sequences of Proteins of Immunological Interest. vol. 1. Fifth Edition. U.S. Department of Health and Human Services. National Institutes of Health. 1991. NIH Publication No. 91-3242.

Khan et al., Adjustable locks and flexible keys: plasticity of epitope-paratope interactions in germline antibodies. J Immunol. Jun. 1, 2014;192(11):5398-405. doi: 10.4049/jimmunol.1302143. Epub Apr. 30, 2014.

Kim et al., Spectrum of EGFR Gene Copy Number Changes and KRAS Gene Mutation Status in Korean Triple Negative Breast Cancer Patients. PLoS One. Oct. 30, 2013;8(10):e79014. doi: 10.1371/journal.pone.0079014. eCollection 2013.

Kontermann, Strategies to Extend Plasma Half-Lives of Recombinant Antibodies. BioDrugs. 2009;23(2):93-109. doi: 10.2165/00063030-200923020-00003.

Kunik et al., Structural Consensus among Antibodies Defines the Antigen Binding Site. PLoS Comput Biol. 2012;8(2):e1002388. doi: 10.1371/journal.pcbi.1002388. Epub Feb. 23, 2012.

Lejeune et al., Bispecific, T-Cell-Recruiting Antibodies in B-Cell Malignancies. Front Immunol. May 7, 2020:11:762. doi: 10.3389/fimmu.2020.00762. eCollection 2020.

Li et al., Membrane-Proximal Epitope Facilitates Efficient T Cell Synapse Formation by Anti-FcRH5/CD3 and Is a Requirement for Myeloma Cell Killing. Cancer Cell. Mar. 13, 2017;31(3):383-395. doi: 10.1016/j.ccell.2017.02.001. Epub Mar. 2, 2017.

Li et al., The Dual Roles of Human yo T Cells: Anti-Tumor or Tumor-Promoting. Front Immunol. Feb. 16, 2021:11:619954. doi: 10.3389/fimmu.2020.619954. eCollection 2020.

Licitra et al., Evaluation of EGFR gene copy number as a predictive biomarker for the efficacy of cetuximab in combination with chemotherapy in the first-line treatment of recurrent and/or metastatic squamous cell carcinoma of the head and neck: Extreme study. Ann Oncol. May 2011;22(5):1078-1087. doi: 10.1093/annonc/mdq588. Epub Nov. 3, 2010.

Liu et al., The Role of Human γδ T Cells in Anti-Tumor Immunity and Their Potential for Cancer Immunotherapy. Cells. May 13, 2020;9(5):1206. doi: 10.3390/cells9051206.

Liu, Pharmacokinetics of monoclonal antibodies and Fc-fusion proteins. Protein Cell. Jan. 2018;9(1):15-32. doi: 10.1007/s13238-017-0408-4. Epub Apr. 19, 2017.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Lucchese et al., How a single amino acid change may alter the immunological information of a peptide. Front Biosci (Elite Ed). Jan. 1, 2012;4(5):1843-52. doi: 10.2741/e506.

(56)     References Cited

OTHER PUBLICATIONS

Lum et al., Targeting T Cells with Bispecific Antibodies for Cancer Therapy. BioDrugs. Author manuscript; available in PMC: Oct. 8, 2013. Published in final edited form as: BioDrugs. Dec. 1, 2011;25(6):365-379. doi: 10.2165/11595950-000000000-00000.

Ma et al., A novel bispecific nanobody with PD-L1/TIGIT dual immune checkpoint blockade. Biochem Biophys Res Commun. Oct. 15, 2020;531(2):144-151. doi: 10.1016/j.bbrc.2020.07.072. Epub Aug. 8, 2020.

Ma et al., IL-17A produced by γδ T cells promotes tumor growth in hepatocellular carcinoma. Cancer Res. Apr. 1, 2014;74(7):1969-82. doi: 10.1158/0008-5472.CAN-13-2534. Epub Feb. 13, 2014.

Mix et al., Immunoglobulins—Basic considerations. J Neurol. Sep. 2006:253 Suppl 5:V9-17. doi: 10.1007/s00415-006-5002-2.

No Author Listed, Certified copy of priority document for Application No. GB1911799.3, filed Aug. 16, 2019. 82 pages.

No Author Listed, Certified copy of priority document for Application No. GB2010760.3, filed Jul. 13, 2020. 96 pages.

No Author Listed, Certified copy of priority document for Application No. GB2012172.9, filed Aug. 5, 2020. 131 pages.

No Author Listed, NCBI Gene ID: 2191; FAP fibroblast activation protein alpha [ *Homo sapiens* (human) ]. Last Updated: Jul. 5, 2025. Accessed at: https://www.ncbi.nlm.nih.gov/gene?Db=gene&Cmd=ShowDetailView&TermToSearch=2191 [last accessed Jul. 18, 2025].

No Author Listed, Sequence Listing for WO2021032960. GammaDelta Therapeutics Limited. 99 pages.

Oberg et al., Monitoring Circulating γδ T Cells in Cancer Patients to Optimize γδ T Cell-Based Immunotherapy. Front Immunol. Dec. 17, 2014;5:643. doi: 10.3389/fimmu.2014.00643. eCollection 2014.

Padlan, Anatomy of the antibody molecule. Mol Immunol. Feb. 1994;31(3):169-217. doi: 10.1016/0161-5890(94)90001-9.

Panka et al., Variable region framework differences result in decreased or increased affinity of variant anti-digoxin antibodies. Proc Natl Acad Sci U S A. May 1988;85(9):3080-4. doi: 10.1073/pnas.85.9. 3080.

Peng et al., Tumor-infiltrating gammadelta T cells suppress T and dendritic cell function via mechanisms controlled by a unique toll-like receptor signaling pathway. Immunity. Aug. 2007;27(2):334-48. doi: 10.1016/j.immuni.2007.05.020. Epub Jul. 26, 2007.

Poccia et al., Anti-severe acute respiratory syndrome coronavirus immune responses: the role played by V gamma 9V delta 2 T cells. J Infect Dis. May 1, 2006;193(9):1244-9. doi: 10.1086/502975. Epub Mar. 27, 2006.

Poosarla et al., Computational de novo design of antibodies binding to a peptide with high affinity. Biotechnol Bioeng. Jun. 2017;114(6):1331-1342. doi: 10.1002/bit.26244. Epub Feb. 2, 2017.

Qin et al., Novel immune checkpoint targets: moving beyond PD-1 and CTLA-4. Mol Cancer. Nov. 6, 2019;18(1):155. doi: 10.1186/s12943-019-1091-2.

Siegers et al., Human Vδ1 γδ T cells expanded from peripheral blood exhibit specific cytotoxicity against B-cell chronic lymphocytic leukemia-derived cells. Cytotherapy. Jul. 2011;13(6):753-64. doi: 10.3109/14653249.2011.553595. Epub Feb. 11, 2011.

Strohl et al., Bispecific T-Cell Redirection versus Chimeric Antigen Receptor (CAR)-T Cells as Approaches to Kill Cancer Cells. Antibodies (Basel). Jul. 3, 2019;8(3):41. doi: 10.3390/antib8030041.

Strohl et al., Therapeutic antibody classes. Chapter 9 in: Therapeutic Antibody Engineering: Current and Future Advances Driving the Strongest Growth Area in the Pharmaceutical Industry. 1st edition. Woodhead Publishing Limited, eds. 2012; 197-223 and 459-595.

Tamura et al., Structural Correlates of an Anticarcinoma Antibody: Identification of Specificity-Determining Residues (SDRs) and Development of a Minimally Immunogenic Antibody Variant by Retention of SDRs Only. J Immunol. Feb. 1, 2000;164(3):1432-41. doi: 10.4049/jimmunol.164.3.1432.

Ternant et al., Pharmacokinetics and concentration-effect relationships of therapeutic monoclonal antibodies and fusion proteins. Expert Opin Biol Ther. Sep. 2005:5 Suppl 1:S37-47. doi: 10.1517/14712598.5.1.s37.

Van Dorp et al., Therapeutic Potential of Gammadelta T-Cells in Controlling CMV After Allogeneic Stem Cell Transplantation. Biology of Blood and Marrow Transplantation. 2011; 17(2): S217.

Vidarsson et al., IgG subclasses and allotypes: from structure to effector functions. Front Immunol. Oct. 20, 2014:5:520. doi: 10.3389/fimmu.2014.00520. eCollection 2014.

Wark et al., Latest technologies for the enhancement of antibody affinityB. Adv Drug Deliv Rev. Aug. 7, 2006;58(5-6):657-70. doi: 10.1016/j.addr.2006.01.025. Epub May 22, 2006.

Wu et al., An innate-like Vδ1+ γδ T cell compartment in the human breast is associated with remission in triple-negative breast cancer. Sci Transl Med. Oct. 9, 2019;11(513):eaax9364. doi: 10.1126/scitranslmed.aax9364.

Wu et al., Humanization of a Murine Monoclonal Antibody by Simultaneous Optimization of Framework and CDR Residues. J Mol Biol. Nov. 19, 1999;294(1):151-62. doi: 10.1006/jmbi.1999. 3141.

Xenaki et al., Antibody or Antibody Fragments: Implications for Molecular Imaging and Targeted Therapy of Solid Tumors. Front Immunol. Oct. 12, 2017:8:1287. doi: 10.3389/fimmu.2017.01287. eCollection 2017.

Xu et al., In vitro characterization of five humanized OKT3 effector function variant antibodies. Cell Immunol. Feb. 25, 2000;200(1):16-26. doi: 10.1006/cimm.2000.1617.

Ye et al., Specific recruitment of γδ regulatory T cells in human breast cancer. Cancer Res. Oct. 15, 2013;73(20):6137-48. doi: 10.1158/0008-5472.CAN-13-0348. Epub Aug. 19, 2013.

Zhang et al., Epidermal growth factor receptor expression and gene copy number analysis in gastric carcinoma samples from Chinese patients. Oncol Lett. Jan. 2016;11(1):173-181. doi: 10.3892/01.2015. 3875. Epub Nov. 5, 2015.

Zhao et al., Protective Role of γδ T Cells in Different Pathogen Infections and Its Potential Clinical Application. J Immunol Res. Jul. 10, 2018:2018:5081634. doi: 10.1155/2018/5081634. eCollection 2018.

| Clone ID | Alias | Heavy CDR1 | SEQ ID NO. | Heavy CDR2 | SEQ ID NO. | Heavy CDR3 | SEQ ID NO. | Light CDR1 | SEQ ID NO. | Light CDR2 | SEQ ID NO. | Light CDR3 | SEQ ID NO. |
|---|---|---|---|---|---|---|---|---|---|---|---|---|---|
| 1138_P01_F06 | G4.1 | GFTFSSYS | 71 | ISSSSSYI | 48 | GRAYFDL | 2 | QDISNY | 94 | DAS | A1 | QQGYSTPVT | 25 |
| 1138_P01_B03 | G4.2 | GYPFTGYY | 72 | VCPETGGS | 49 | FPVRGFYGMDV | 3 | QDISNY | 95 | AAS | A2 | LEGYNVLWT | 26 |
| 1138_P01_A04 | G4.3 | GFTFSSYS | 73 | ISSSSSYI | 50 | EGMLYDY | 4 | QDISNY | 96 | DAS | A3 | QQSYSTPQT | 27 |
| 1247_P01_E02 | G4.4 | GFTFSSYA | 74 | ISGSGGST | 51 | SSVGWNSFDY | 5 | QSVLSSSNNKNY | 97 | WAS | A4 | QQYYSTPLT | 28 |
| 1247_P02_H01 | G4.5 | GYTFTGYG | 75 | ISAYNGNT | 52 | GGTGGDHWFAY | 6 | QSSSY | 98 | AAS | A5 | QQSYSTPPT | 29 |
| 1247_P02_A03 | G4.6 | GFTFSSYA | 76 | ISGRGGST | 53 | ADYGVAYYFDY | 7 | QSISTY | 99 | AAS | A6 | QQSYSTPPT | 30 |
| 1247_P02_A04 | G4.7 | GFTFSHYW | 77 | IKGDGSII | 54 | GSYSSSSFDY | 8 | QSLLHSNRFNY | 100 | LGS | A7 | MQGLQTPYT | 31 |
| 1253_P02_H04 | G4_10 | GFTFSSYA | 78 | ISGSGGST | 55 | DCEAVDFWRNGMDV | 9 | QSLFYSSGNTY | 101 | KVS | A8 | MQGTLWPPT | 32 |
| 1140_P01_G06 | G4.12 | GFTVSSNY | 79 | IYYSGST | 56 | VANGDFLDY | 10 | SSDVGGYNF | 102 | EVT | A9 | SSHASPPPV | 33 |
| 1246_P01_B01 | G4.13 | GFTFSSYS | 80 | ISGTSSYI | 57 | GGLGMVDP | 11 | SGSASNY | 103 | EDN | A10 | QSYDSSYVV | 34 |
| 1246_P01_C01 | G4.14 | GYSFTSYY | 81 | IDPSDSYT | 58 | DTAHGRIDV | 12 | SGSIASNY | 104 | KDX | A11 | QSYDSSTHAV | 35 |
| 1246_P01_D09 | G4.15 | GYTFTRHY | 82 | MPSGGST | 59 | DMSHLXDVWWFUP | 13 | SSDVSGDYYV | 105 | DVS | A12 | SSYGSGSY | 36 |
| 1254_P01_H04 | G4.16 | GYTFTGYY | 83 | MPNSGGT | 60 | DYGSFYGMDV | 14 | SSDGSPNS | 106 | BT | A13 | TSYAGSNTU | 37 |
| 1246_P02_G06 | G4.19 | GYTLTSYY | 84 | MPSGGST | 61 | ERLOLSSLOY | 15 | ALAKQY | 107 | RGS | A14 | QSADSSGTYYV | 38 |
| 1254_P01_G06 | G4.20 | GFTFSSYA | 85 | IPFFGTA | 62 | ERGYSYGDGMDV | 16 | SGSIASNY | 108 | COD | A15 | GSYDSSNWAV | 39 |
| 1247_P01_B10 | G4.21 | GFTFSSYA | 86 | VSGSGDTT | 63 | GNSRSDAFDI | 17 | KLGRXF | 109 | CDS | A16 | QAHDSSTVV | 40 |
| 1247_P03_H05 | G4.22 | GFTFSSYG | 87 | IWYERGNK | 64 | DSTAVTDWFDP | 18 | QDISNY | 110 | AAS | A17 | QQSYNPWT | 41 |
| 1247_P01_B04 | G4.23 | GASVSSNSVA | 88 | TYYGSRKYN | 65 | GEVAALYYFDY | 19 | QGISNS | 111 | AAS | A18 | QQYYSTPRT | 42 |
| 1246_P01_E05 | G4.25 | GGTFSSYA | 89 | IPFFGTA | 66 | DWKSTRSFDY | 20 | QSVLYSSANKNY | 112 | AAS | A19 | QQYYSTPPT | 43 |
| 1246_P02_C01 | G4.26 | GGTFSYYY | 90 | IPFFGTA | 67 | SLRDQYWYGSLGY | 21 | SSDVGGYNY | 113 | EVS | A20 | SSYGSGSY | 44 |
| 1246_P02_C10 | G4.27 | GYSFTSYW | 91 | IYPGSGST | 68 | SRGSGWFPLGY | 22 | SSDVGSSYNL | 114 | EVS | A21 | SSFGSGS | 45 |
| 1246_P02_F12 | G4.28 | GFTFDGYA | 92 | ISAGGGST | 69 | HGAYGLYHDDTPDS | 23 | SLRNPY | 115 | GRN | A22 | NSRDSSGNHKLV | 46 |
|  |  |  | 93 |  | 70 | SYYQTAHRYYYYKPDV | 24 | SLRNYY | 116 | SKN | A23 | NSRDSSGYV | 47 |

FIGURE 1

| Alias | Clone ID | Antigens | | | | | DV1-GV4 specificity over DV1-GV2 (fold improvement after background (L3 subtraction)) | DV1-GV4 specificity over DV1-GV2 (% fold improvement after background subtraction) |
|---|---|---|---|---|---|---|---|---|
| | | BSA | L1 (DV1-GV4) | L2 (DV1-GV2) | L3 (DV1-GV8) | L4 (DV1-GV4) | | |
| G4_1 | 1138_P01_E06 | 78 | 302446 | 108 | 244 | 151594 | 582 | 582167 |
| G4_2 | 1139_P01_B09 | 96 | 280371 | 88 | 271 | 68611 | 914 | 911886 |
| G4_3 | 1139_P01_A04 | 88 | 218198 | 216 | 229 | 167686 | 1402 | 140202 |
| G4_4 | 1247_P01_E03 | 121 | 197677 | 80 | 198 | 113097 | 7617 | 761719 |
| G4_5 | 1247_P01_H01 | 88 | 162569 | 93 | 173 | 53057 | 5802 | 580248 |
| G4_6 | 1247_P02_A08 | 122 | 155288 | 113 | 255 | 123862 | 3190 | 318996 |
| G4_7 | 1247_P02_A04 | 134 | 163326 | 86 | 238 | 53157 | 1570 | 156957 |
| G4_10 | 1253_P02_H04 | 57 | 145186 | 108 | 187 | 34800 | 3224 | 322453 |
| G4_12 | 1246_P01_G08 | 60 | 230812 | 229 | 252 | 195128 | 1435 | 143467 |
| G4_13 | 1248_P01_B01 | 78 | 196524 | 94 | 270 | 180795 | 6531 | 653118 |
| G4_14 | 1246_P01_C01 | 135 | 205474 | 199 | 223 | 146754 | 1544 | 154354 |
| G4_15 | 1248_P01_D06 | 63 | 119133 | 84 | 136 | 38039 | 153 | 15282 |
| G4_16 | 1248_P02_D10 | 69 | 178442 | 84 | 118 | 89621 | 8918 | 891755 |
| G4_18 | 1254_P01_H04 | 67 | 198866 | 66 | 165 | 144733 | 98807 | 9880650 |
| G4_19 | 1253_P01_G06 | 55 | 142432 | 73 | 132 | 34672 | 13836 | 1383567 |
| G4_20 | 1254_P01_G02 | 132 | 184442 | 147 | 239 | 140291 | 2236 | 223778 |
| D1.3 (Assay 1) | Anti-Chick Lysozyme (DL3) | 66 | 91 | 64 | 125 | 83 | NA | NA |
| G4_22 | 1247_P02_B10 | 47 | 189257 | 567 | 88 | 5882 | 678 | 67817 |
| G4_23 | 1253_P03_H05 | 53 | 196478 | 618 | 1079 | 34899 | 978 | 97791 |
| G4_24 | 1247_P01_B04 | 53 | 154317 | 534 | 966 | 15859 | 1181 | 118061 |
| G4_25 | 1248_P02_E03 | 68 | 21678 | 486 | 865 | 8651 | 299 | 29901 |
| G4_26 | 1248_P02_C01 | 51 | 22796 | 688 | 870 | 1894 | 88 | 8839 |
| G4_27 | 1248_P02_C10 | 60 | 138249 | 573 | 1086 | 9330 | 791 | 79052 |
| G4_28 | 1248_P02_E11 | 65 | 227097 | 578 | 984 | 22778 | 1224 | 122402 |
| D1.3 (Assay 2) | Anti-Chick Lysozyme (DL3) | 51 | 690 | 405 | 717 | 49 | NA | NA |

FIGURE 2B

A
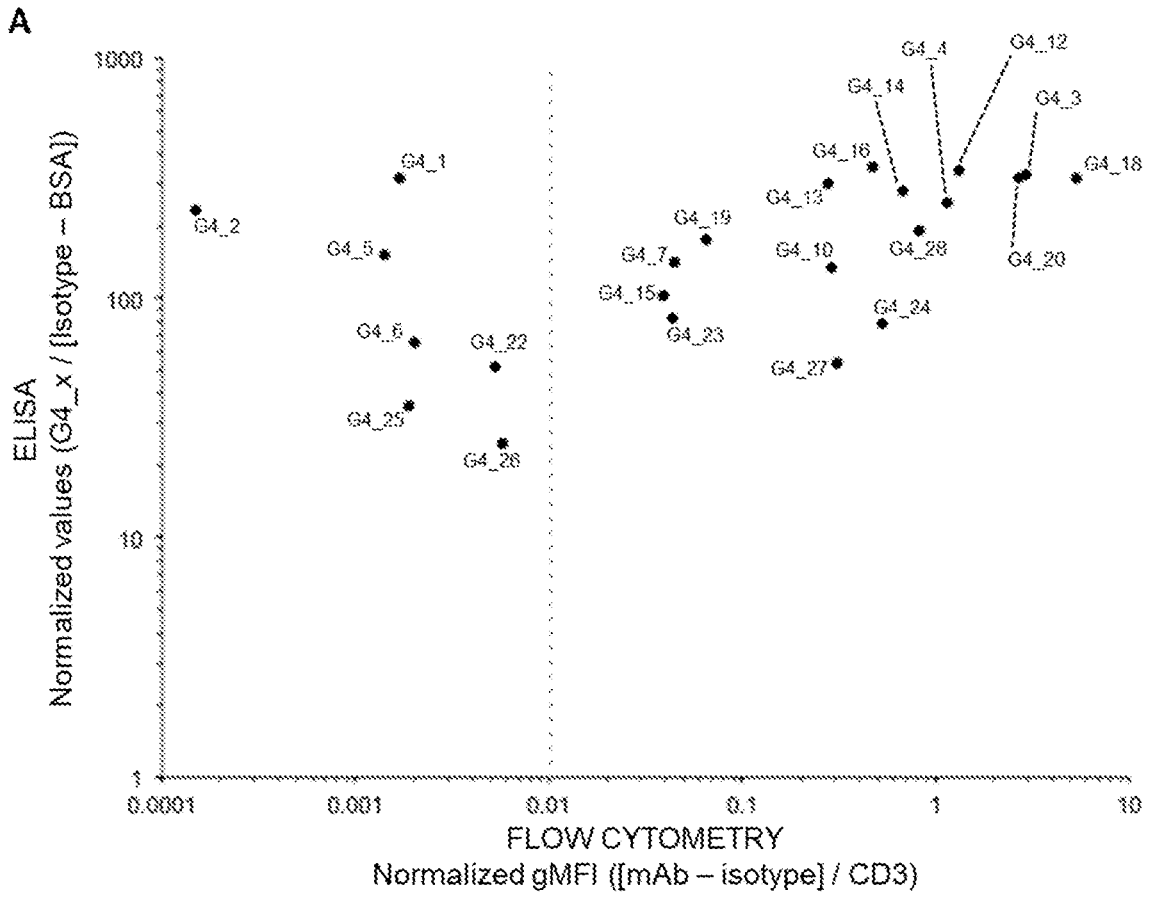
B
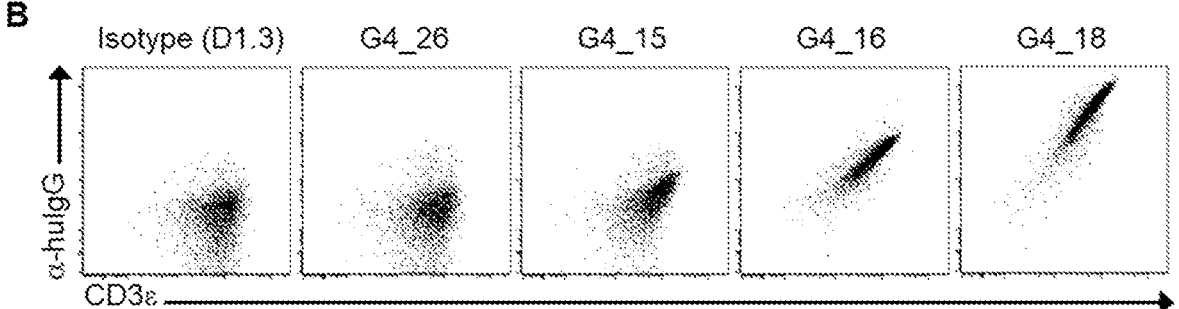
FIGURE 3

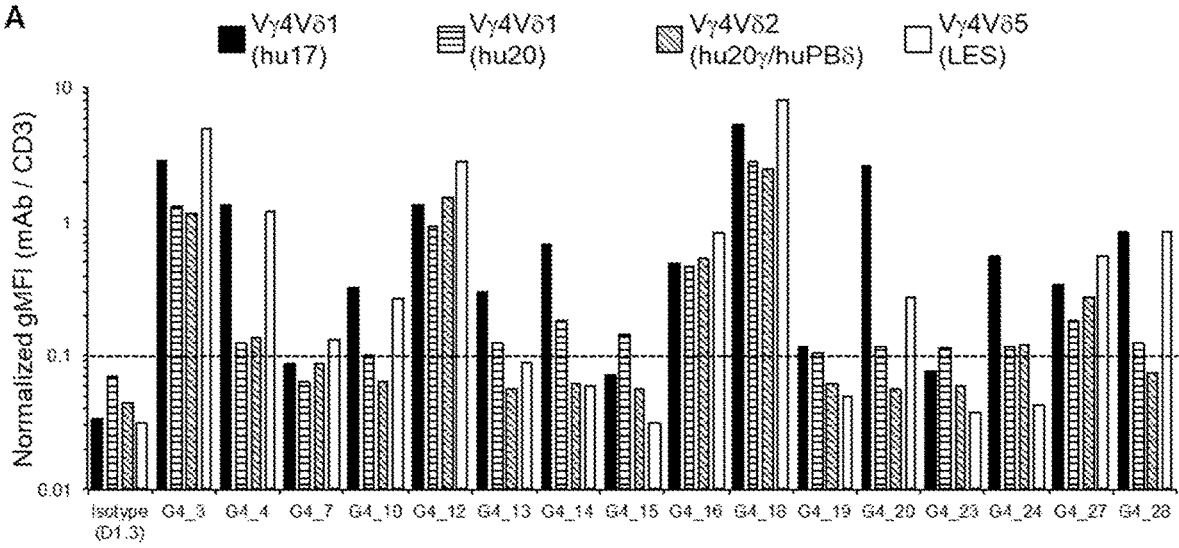
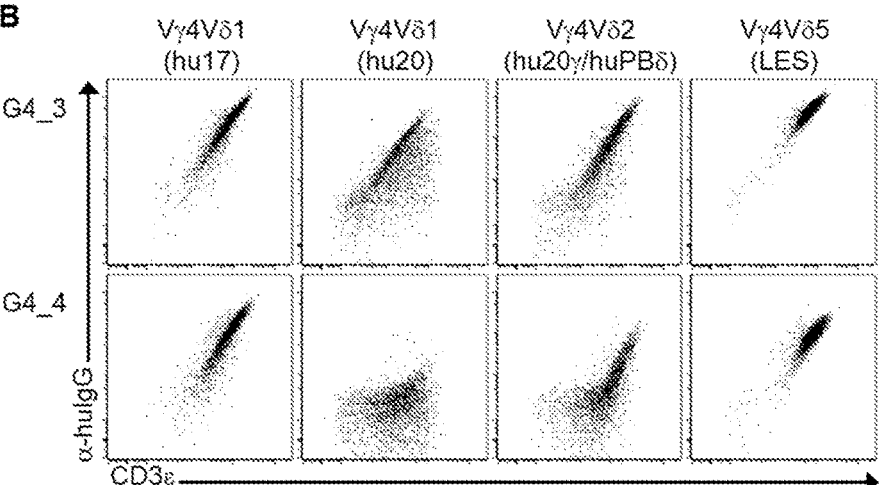
FIGURE 4

Legend:
- ☐ Staining equivalent to hu17
- ▨ Weaker staining compared to hu17 (gMFI reduced by <50%)
- ▩ No staining

| | G4_3 | G4_12 | G4_16 | G4_18 | G4_27 |
|---|---|---|---|---|---|
| hu17 | | | | | |
| hu17.Vγ2$^{CDR1}$ | weaker | | | | |
| hu17.Vγ2$^{CDR2}$ | | | | | |
| hu17.Vγ2$^{CDR1-2}$ | weaker | | | | |
| hu17$^{DG\ KM>YANL}$ | none | none | none | none | none |
| hu17$^{DG>YA}$ | none | weaker | none | none | none |
| hu17$^{KM>NL}$ | none | weaker | | none | none |
| hu17.Vγ2 | none | none | none | none | none |
| hu17.Vγ2$^{YA>DG}$ | none | none | none | none | none |
| hu17.Vγ3 | none | none | none | none | none |
| hu17.Vγ3-Vγ4$^{HV4}$ | none | weaker | none | none | |
| hu17.Vγ3-Vγ4$^{CDR2-HV4}$ | none | weaker | | weaker | |

FIGURE 5B

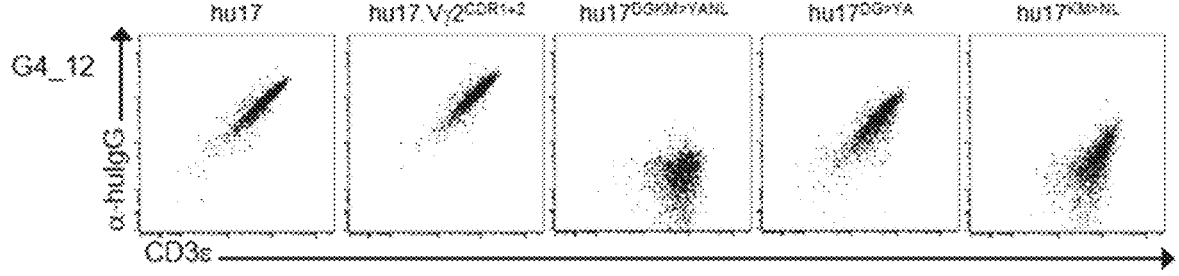

G4_12 — α-huIgG / CD3ε hu17    hu17.Vγ2$^{CDR1-2}$    hu17$^{DGKM>YANL}$    hu17$^{DG>YA}$    hu17$^{KM>NL}$

FIGURE 5C

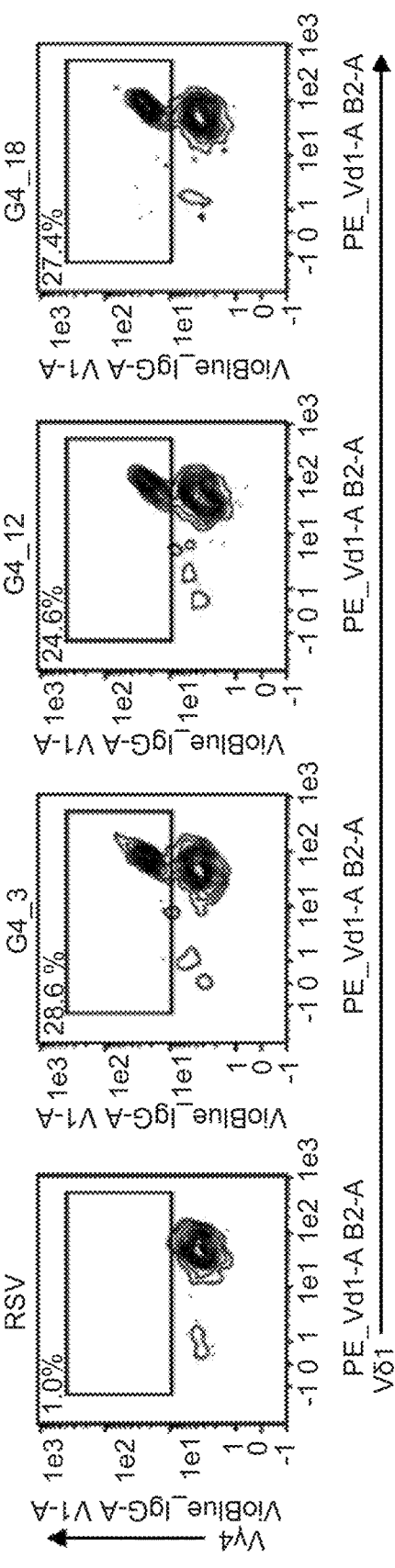
FIGURE 7 (contd)

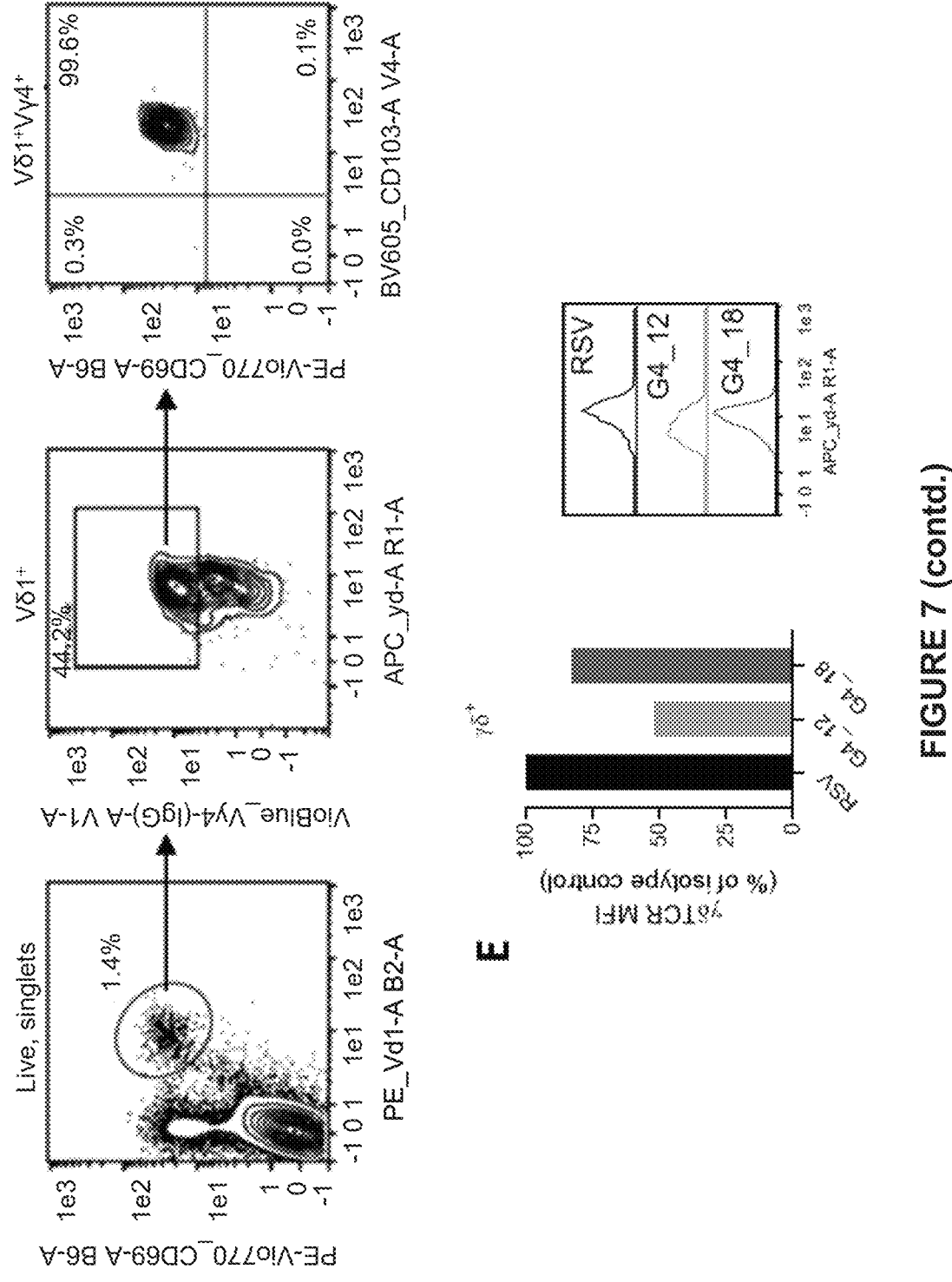
FIGURE 7 (contd.)

SEQUENCE LISTING

<160> NUMBER OF SEQ ID NOS: 350

<210> SEQ ID NO 1
<211> LENGTH: 256
<212> TYPE: PRT
<213> ORGANISM: Homo sapiens
<220> FEATURE:
<221> NAME/KEY: MISC_FEATURE
<222> LOCATION: (1)..(256)
<223> OTHER INFORMATION: V gamma 4 chain of RSCB Protein Data Bank
     entry: 4MNH <400> SEQUENCE: 1

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45
```

```
Tyr Tyr Asp Ser Tyr Thr Ser Ser Val Val Leu Glu Ser Gly Ile Ser
    50              55              60

Pro Gly Lys Tyr Asp Thr Tyr Gly Ser Thr Arg Lys Asn Leu Arg Met
65              70              75              80

Ile Leu Arg Asn Leu Ile Glu Asn Asp Ser Gly Val Tyr Tyr Cys Ala
            85              90              95

Thr Trp Asp Glu Lys Tyr Tyr Lys Lys Leu Phe Gly Ser Gly Thr Thr
            100             105             110

Leu Val Val Thr Glu Asp Leu Lys Asn Val Phe Pro Pro Glu Val Ala
        115             120             125

Val Phe Glu Pro Ser Glu Ala Glu Ile Ser His Thr Gln Lys Ala Thr
    130             135             140

Leu Val Cys Leu Ala Thr Gly Phe Tyr Pro Asp His Val Glu Leu Ser
145             150             155             160

Trp Trp Val Asn Gly Lys Glu Val His Ser Gly Val Cys Thr Asp Pro
            165             170             175

Gln Pro Leu Lys Glu Gln Pro Ala Leu Asn Asp Ser Arg Tyr Ala Leu
            180             185             190

Ser Ser Arg Leu Arg Val Ser Ala Thr Phe Trp Gln Asn Pro Arg Asn
            195             200             205

His Phe Arg Cys Gln Val Gln Phe Tyr Gly Leu Ser Glu Asn Asp Glu
    210             215             220

Trp Thr Gln Asp Arg Ala Lys Pro Val Thr Gln Ile Val Ser Ala Glu
225             230             235             240

Ala Trp Gly Arg Ala Asp Ser Arg Gly Gly Leu Glu Val Leu Phe Gln
            245             250             255
```

<210> SEQ ID NO 2
<211> LENGTH: 7
<212> TYPE: PRT
<213> ORGANISM: artificial sequence
<220> FEATURE:
<223> OTHER INFORMATION: G4_1 Heavy CDR3

<400> SEQUENCE: 2

```
Gly His Trp Tyr Phe Asp Leu
1               5
```

<210> SEQ ID NO 3
<211> LENGTH: 11
<212> TYPE: PRT
<213> ORGANISM: artificial sequence
<220> FEATURE:
<223> OTHER INFORMATION: G4_2 Heavy CDR3

<400> SEQUENCE: 3

```
Phe Pro Val Ala Gly Phe Tyr Gly Met Asp Val
1               5               10
```

<210> SEQ ID NO 4
<211> LENGTH: 7
<212> TYPE: PRT
<213> ORGANISM: artificial sequence
<220> FEATURE:
<223> OTHER INFORMATION: G4_3 Heavy CDR3

<400> SEQUENCE: 4

```
Gly Gly Trp Leu Tyr Asp Tyr
1               5
```

-continued

<210> SEQ ID NO 5
<211> LENGTH: 10
<212> TYPE: PRT
<213> ORGANISM: artificial sequence
<220> FEATURE:
<223> OTHER INFORMATION: G4_4 Heavy CDR3

<400> SEQUENCE: 5

Ser Ser Val Gly Trp Trp Ser Phe Asp Tyr
1               5                   10

<210> SEQ ID NO 6
<211> LENGTH: 11
<212> TYPE: PRT
<213> ORGANISM: artificial sequence
<220> FEATURE:
<223> OTHER INFORMATION: G4_5 Heavy CDR3

<400> SEQUENCE: 6

Gly Gly Thr Gly Gly Asp His Val Phe Ala Tyr
1               5                   10

<210> SEQ ID NO 7
<211> LENGTH: 11
<212> TYPE: PRT
<213> ORGANISM: artificial sequence
<220> FEATURE:
<223> OTHER INFORMATION: G4_6 Heavy CDR3

<400> SEQUENCE: 7

Ala Asp Tyr Gly Val Val Tyr Tyr Phe Asp Tyr
1               5                   10

<210> SEQ ID NO 8
<211> LENGTH: 10
<212> TYPE: PRT
<213> ORGANISM: artificial sequence
<220> FEATURE:
<223> OTHER INFORMATION: G4_7 Heavy CDR3

<400> SEQUENCE: 8

Ile Gly Tyr Ser Ser Ser Ser Phe Asp Tyr
1               5                   10

<210> SEQ ID NO 9
<211> LENGTH: 13
<212> TYPE: PRT
<213> ORGANISM: artificial sequence
<220> FEATURE:
<223> OTHER INFORMATION: G4_10 Heavy CDR3

<400> SEQUENCE: 9

Asp Gly Ala Val Asp Phe Trp Arg Asn Gly Met Asp Val
1               5                   10

<210> SEQ ID NO 10
<211> LENGTH: 9
<212> TYPE: PRT
<213> ORGANISM: artificial sequence
<220> FEATURE:
<223> OTHER INFORMATION: G4_12 Heavy CDR3

<400> SEQUENCE: 10

Val Ala Asn Gly Asp Phe Leu Asp Tyr
1               5

```
<210> SEQ ID NO 11
<211> LENGTH: 8
<212> TYPE: PRT
<213> ORGANISM: artificial sequence
<220> FEATURE:
<223> OTHER INFORMATION: G4_13 Heavy CDR3

<400> SEQUENCE: 11

Gly Gly Leu Gly Met Val Asp Pro
1               5

<210> SEQ ID NO 12
<211> LENGTH: 8
<212> TYPE: PRT
<213> ORGANISM: artificial sequence
<220> FEATURE:
<223> OTHER INFORMATION: G4_14 Heavy CDR3

<400> SEQUENCE: 12

Asp Thr Ala His Gly Met Asp Val
1               5

<210> SEQ ID NO 13
<211> LENGTH: 13
<212> TYPE: PRT
<213> ORGANISM: artificial sequence
<220> FEATURE:
<223> OTHER INFORMATION: G4_15 Heavy CDR3

<400> SEQUENCE: 13

Asp Asn Ser His Leu Asp Gln Val Trp Trp Phe Asp Pro
1               5                   10

<210> SEQ ID NO 14
<211> LENGTH: 10
<212> TYPE: PRT
<213> ORGANISM: artificial sequence
<220> FEATURE:
<223> OTHER INFORMATION: G4_16 Heavy CDR3

<400> SEQUENCE: 14

Asp Tyr Gly Asp Phe Tyr Gly Met Asp Val
1               5                   10

<210> SEQ ID NO 15
<211> LENGTH: 9
<212> TYPE: PRT
<213> ORGANISM: artificial sequence
<220> FEATURE:
<223> OTHER INFORMATION: G4_18 Heavy CDR3

<400> SEQUENCE: 15

Asp Leu Asp Leu Ser Ser Leu Asp Tyr
1               5

<210> SEQ ID NO 16
<211> LENGTH: 12
<212> TYPE: PRT
<213> ORGANISM: artificial sequence
<220> FEATURE:
<223> OTHER INFORMATION: G4_19 Heavy CDR3

<400> SEQUENCE: 16

Glu Arg Gly Tyr Ser Tyr Gly Asp Gly Met Asp Val
1               5                   10

<210> SEQ ID NO 17
```

```
<211> LENGTH: 10
<212> TYPE: PRT
<213> ORGANISM: artificial sequence
<220> FEATURE:
<223> OTHER INFORMATION: G4_20 Heavy CDR3

<400> SEQUENCE: 17

Gly Asn Ser Arg Ser Asp Ala Phe Asp Ile
1               5                   10

<210> SEQ ID NO 18
<211> LENGTH: 11
<212> TYPE: PRT
<213> ORGANISM: artificial sequence
<220> FEATURE:
<223> OTHER INFORMATION: G4_22 Heavy CDR3

<400> SEQUENCE: 18

Asp Ser Thr Ala Val Thr Asp Trp Phe Asp Pro
1               5                   10

<210> SEQ ID NO 19
<211> LENGTH: 11
<212> TYPE: PRT
<213> ORGANISM: artificial sequence
<220> FEATURE:
<223> OTHER INFORMATION: G4_23 Heavy CDR3

<400> SEQUENCE: 19

Gly Glu Val Ala Ala Leu Tyr Tyr Phe Asp Tyr
1               5                   10

<210> SEQ ID NO 20
<211> LENGTH: 10
<212> TYPE: PRT
<213> ORGANISM: artificial sequence
<220> FEATURE:
<223> OTHER INFORMATION: G4_24 Heavy CDR3

<400> SEQUENCE: 20

Asp Trp Ser Ser Thr Arg Ser Phe Asp Tyr
1               5                   10

<210> SEQ ID NO 21
<211> LENGTH: 14
<212> TYPE: PRT
<213> ORGANISM: artificial sequence
<220> FEATURE:
<223> OTHER INFORMATION: G4_25 Heavy CDR3

<400> SEQUENCE: 21

Ser Leu Arg Asp Gly Tyr Asn Tyr Ile Gly Ser Leu Gly Tyr
1               5                   10

<210> SEQ ID NO 22
<211> LENGTH: 11
<212> TYPE: PRT
<213> ORGANISM: artificial sequence
<220> FEATURE:
<223> OTHER INFORMATION: G4_26 Heavy CDR3

<400> SEQUENCE: 22

Ser Arg Gly Ser Gly Trp Phe Pro Leu Gly Tyr
1               5                   10

<210> SEQ ID NO 23
<211> LENGTH: 13
```

```
<212> TYPE: PRT
<213> ORGANISM: artificial sequence
<220> FEATURE:
<223> OTHER INFORMATION: G4_27 Heavy CDR3

<400> SEQUENCE: 23

His Gly Ala Tyr Gly Asp Tyr Pro Asp Thr Phe Asp Ile
1               5                   10

<210> SEQ ID NO 24
<211> LENGTH: 16
<212> TYPE: PRT
<213> ORGANISM: artificial sequence
<220> FEATURE:
<223> OTHER INFORMATION: G4_28 Heavy CDR3

<400> SEQUENCE: 24

Ser Tyr Val Asp Thr Ala Met Arg Tyr Tyr Tyr Tyr Met Asp Val
1               5                   10                  15

<210> SEQ ID NO 25
<211> LENGTH: 9
<212> TYPE: PRT
<213> ORGANISM: artificial sequence
<220> FEATURE:
<223> OTHER INFORMATION: G4_1 Light CDR3

<400> SEQUENCE: 25

Gln Gln Ser Tyr Ser Thr Pro Val Thr
1               5

<210> SEQ ID NO 26
<211> LENGTH: 9
<212> TYPE: PRT
<213> ORGANISM: artificial sequence
<220> FEATURE:
<223> OTHER INFORMATION: G4_2 Light CDR3

<400> SEQUENCE: 26

Leu Glu Asp Tyr Asn Tyr Leu Trp Thr
1               5

<210> SEQ ID NO 27
<211> LENGTH: 9
<212> TYPE: PRT
<213> ORGANISM: artificial sequence
<220> FEATURE:
<223> OTHER INFORMATION: G4_3 Light CDR3

<400> SEQUENCE: 27

Gln Gln Ser Tyr Ser Thr Pro Gln Thr
1               5

<210> SEQ ID NO 28
<211> LENGTH: 9
<212> TYPE: PRT
<213> ORGANISM: artificial sequence
<220> FEATURE:
<223> OTHER INFORMATION: G4_4 Light CDR3

<400> SEQUENCE: 28

Gln Gln Tyr Tyr Ser Thr Pro Leu Thr
1               5

<210> SEQ ID NO 29
<211> LENGTH: 9
<212> TYPE: PRT
```

-continued

```
<213> ORGANISM: artificial sequence
<220> FEATURE:
<223> OTHER INFORMATION: G4_5 Light CDR3

<400> SEQUENCE: 29

Gln Gln Ser Tyr Ser Thr Pro Tyr Thr
1               5

<210> SEQ ID NO 30
<211> LENGTH: 9
<212> TYPE: PRT
<213> ORGANISM: artificial sequence
<220> FEATURE:
<223> OTHER INFORMATION: G4_6 Light CDR3

<400> SEQUENCE: 30

Gln Gln Ser Tyr Ser Thr Pro Tyr Thr
1               5

<210> SEQ ID NO 31
<211> LENGTH: 9
<212> TYPE: PRT
<213> ORGANISM: artificial sequence
<220> FEATURE:
<223> OTHER INFORMATION: G4_7 Light CDR3

<400> SEQUENCE: 31

Met Gln Gly Leu Gln Thr Pro Tyr Thr
1               5

<210> SEQ ID NO 32
<211> LENGTH: 9
<212> TYPE: PRT
<213> ORGANISM: artificial sequence
<220> FEATURE:
<223> OTHER INFORMATION: G4_10 Light CDR3

<400> SEQUENCE: 32

Met Gln Gly Thr Leu Trp Pro Pro Thr
1               5

<210> SEQ ID NO 33
<211> LENGTH: 8
<212> TYPE: PRT
<213> ORGANISM: artificial sequence
<220> FEATURE:
<223> OTHER INFORMATION: G4_12 Light CDR3

<400> SEQUENCE: 33

Ser Ser His Ala Ser Pro Arg Val
1               5

<210> SEQ ID NO 34
<211> LENGTH: 10
<212> TYPE: PRT
<213> ORGANISM: artificial sequence
<220> FEATURE:
<223> OTHER INFORMATION: G4_13 Light CDR3

<400> SEQUENCE: 34

Gln Ser Tyr Asp Ser Ser Ile Tyr Val Val
1               5                   10

<210> SEQ ID NO 35
<211> LENGTH: 10
<212> TYPE: PRT
<213> ORGANISM: artificial sequence
```

-continued

```
<220> FEATURE:
<223> OTHER INFORMATION: G4_14 Light CDR3

<400> SEQUENCE: 35

Gln Ser Tyr Asp Ser Ser Thr His Val Val
1               5                   10

<210> SEQ ID NO 36
<211> LENGTH: 8
<212> TYPE: PRT
<213> ORGANISM: artificial sequence
<220> FEATURE:
<223> OTHER INFORMATION: G4_15 Light CDR3

<400> SEQUENCE: 36

Ser Ser Tyr Gly Ser Gly Ser Val
1               5

<210> SEQ ID NO 37
<211> LENGTH: 10
<212> TYPE: PRT
<213> ORGANISM: artificial sequence
<220> FEATURE:
<223> OTHER INFORMATION: G4_16 Light CDR3

<400> SEQUENCE: 37

Thr Ser Tyr Ala Gly Ser Asn Thr Leu Ile
1               5                   10

<210> SEQ ID NO 38
<211> LENGTH: 11
<212> TYPE: PRT
<213> ORGANISM: artificial sequence
<220> FEATURE:
<223> OTHER INFORMATION: G4_18 Light CDR3

<400> SEQUENCE: 38

Gln Ser Ala Asp Ser Ser Gly Thr Tyr Thr Val
1               5                   10

<210> SEQ ID NO 39
<211> LENGTH: 10
<212> TYPE: PRT
<213> ORGANISM: artificial sequence
<220> FEATURE:
<223> OTHER INFORMATION: G4_19 Light CDR3

<400> SEQUENCE: 39

Gln Ser Tyr Asp Ser Ser Asn His Val Val
1               5                   10

<210> SEQ ID NO 40
<211> LENGTH: 9
<212> TYPE: PRT
<213> ORGANISM: artificial sequence
<220> FEATURE:
<223> OTHER INFORMATION: G4_20 Light CDR3

<400> SEQUENCE: 40

Gln Ala Trp Asp Ser Ser Thr Val Val
1               5

<210> SEQ ID NO 41
<211> LENGTH: 9
<212> TYPE: PRT
<213> ORGANISM: artificial sequence
<220> FEATURE:
```

<223> OTHER INFORMATION: G4_22 Light CDR3

<400> SEQUENCE: 41

Gln Gln Ser Tyr Ser Ile Pro Trp Thr
1               5

<210> SEQ ID NO 42
<211> LENGTH: 9
<212> TYPE: PRT
<213> ORGANISM: artificial sequence
<220> FEATURE:
<223> OTHER INFORMATION: G4_23 Light CDR3

<400> SEQUENCE: 42

Gln Gln Tyr Tyr Ser Thr Pro Arg Thr
1               5

<210> SEQ ID NO 43
<211> LENGTH: 9
<212> TYPE: PRT
<213> ORGANISM: artificial sequence
<220> FEATURE:
<223> OTHER INFORMATION: G4_24 Light CDR3

<400> SEQUENCE: 43

Gln Gln Tyr Tyr Ser Thr Pro Pro Thr
1               5

<210> SEQ ID NO 44
<211> LENGTH: 8
<212> TYPE: PRT
<213> ORGANISM: artificial sequence
<220> FEATURE:
<223> OTHER INFORMATION: G4_25 Light CDR3

<400> SEQUENCE: 44

Ser Ser Tyr Gly Ser Gly Ser Val
1               5

<210> SEQ ID NO 45
<211> LENGTH: 8
<212> TYPE: PRT
<213> ORGANISM: artificial sequence
<220> FEATURE:
<223> OTHER INFORMATION: G4_26 Light CDR3

<400> SEQUENCE: 45

Ser Ser Phe Gly Ser Gly Ser Ile
1               5

<210> SEQ ID NO 46
<211> LENGTH: 11
<212> TYPE: PRT
<213> ORGANISM: artificial sequence
<220> FEATURE:
<223> OTHER INFORMATION: G4_27 Light CDR3

<400> SEQUENCE: 46

Asn Ser Arg Asp Ser Ser Gly Asn His Leu Val
1               5                   10

<210> SEQ ID NO 47
<211> LENGTH: 9
<212> TYPE: PRT
<213> ORGANISM: artificial sequence
<220> FEATURE:
<223> OTHER INFORMATION: G4_28 Light CDR3

```
<400> SEQUENCE: 47

Asn Ser Arg Asp Ser Ser Gly Val Val
1               5

<210> SEQ ID NO 48
<211> LENGTH: 8
<212> TYPE: PRT
<213> ORGANISM: artificial sequence
<220> FEATURE:
<223> OTHER INFORMATION: G4_1 Heavy CDR2

<400> SEQUENCE: 48

Ile Ser Ser Ser Ser Ser Tyr Ile
1               5

<210> SEQ ID NO 49
<211> LENGTH: 8
<212> TYPE: PRT
<213> ORGANISM: artificial sequence
<220> FEATURE:
<223> OTHER INFORMATION: G4_2 Heavy CDR2

<400> SEQUENCE: 49

Val Asp Pro Glu Asp Gly Gln Ser
1               5

<210> SEQ ID NO 50
<211> LENGTH: 8
<212> TYPE: PRT
<213> ORGANISM: artificial sequence
<220> FEATURE:
<223> OTHER INFORMATION: G4_3 Heavy CDR2

<400> SEQUENCE: 50

Ile Ser Ser Ser Ser Ser Tyr Ile
1               5

<210> SEQ ID NO 51
<211> LENGTH: 8
<212> TYPE: PRT
<213> ORGANISM: artificial sequence
<220> FEATURE:
<223> OTHER INFORMATION: G4_4 Heavy CDR2

<400> SEQUENCE: 51

Ile Ser Gly Ser Gly Gly Ser Thr
1               5

<210> SEQ ID NO 52
<211> LENGTH: 8
<212> TYPE: PRT
<213> ORGANISM: artificial sequence
<220> FEATURE:
<223> OTHER INFORMATION: G4_5 Heavy CDR2

<400> SEQUENCE: 52

Ile Gly Ala Tyr Asn Gly Asn Thr
1               5

<210> SEQ ID NO 53
<211> LENGTH: 8
<212> TYPE: PRT
<213> ORGANISM: artificial sequence
<220> FEATURE:
<223> OTHER INFORMATION: G4_6 Heavy CDR2
```

-continued

```
<400> SEQUENCE: 53

Ile Ser Gly Ser Gly Gly Ser Thr
1               5

<210> SEQ ID NO 54
<211> LENGTH: 8
<212> TYPE: PRT
<213> ORGANISM: artificial sequence
<220> FEATURE:
<223> OTHER INFORMATION: G4_7 Heavy CDR2

<400> SEQUENCE: 54

Ile Lys Gln Asp Gly Ser Ile Ile
1               5

<210> SEQ ID NO 55
<211> LENGTH: 8
<212> TYPE: PRT
<213> ORGANISM: artificial sequence
<220> FEATURE:
<223> OTHER INFORMATION: G4_10 Heavy CDR2

<400> SEQUENCE: 55

Ile Ser Gly Ser Gly Gly Ser Thr
1               5

<210> SEQ ID NO 56
<211> LENGTH: 7
<212> TYPE: PRT
<213> ORGANISM: artificial sequence
<220> FEATURE:
<223> OTHER INFORMATION: G4_12 Heavy CDR2

<400> SEQUENCE: 56

Ile Tyr Ser Gly Gly Ser Thr
1               5

<210> SEQ ID NO 57
<211> LENGTH: 8
<212> TYPE: PRT
<213> ORGANISM: artificial sequence
<220> FEATURE:
<223> OTHER INFORMATION: G4_13 Heavy CDR2

<400> SEQUENCE: 57

Ile Ser Gly Thr Ser Ser Tyr Ile
1               5

<210> SEQ ID NO 58
<211> LENGTH: 8
<212> TYPE: PRT
<213> ORGANISM: artificial sequence
<220> FEATURE:
<223> OTHER INFORMATION: G4_14 Heavy CDR2

<400> SEQUENCE: 58

Ile Asp Pro Ser Asp Ser Tyr Thr
1               5

<210> SEQ ID NO 59
<211> LENGTH: 8
<212> TYPE: PRT
<213> ORGANISM: artificial sequence
<220> FEATURE:
<223> OTHER INFORMATION: G4_15 Heavy CDR2

<400> SEQUENCE: 59
```

```
Ile Asn Pro Ser Gly Ser Ser Thr
1               5

<210> SEQ ID NO 60
<211> LENGTH: 8
<212> TYPE: PRT
<213> ORGANISM: artificial sequence
<220> FEATURE:
<223> OTHER INFORMATION: G4_16 Heavy CDR2

<400> SEQUENCE: 60

Ile Ser Ala Tyr Asn Gly Asn Thr
1               5

<210> SEQ ID NO 61
<211> LENGTH: 8
<212> TYPE: PRT
<213> ORGANISM: artificial sequence
<220> FEATURE:
<223> OTHER INFORMATION: G4_18 Heavy CDR2

<400> SEQUENCE: 61

Ile Asn Pro Asn Ser Gly Gly Thr
1               5

<210> SEQ ID NO 62
<211> LENGTH: 8
<212> TYPE: PRT
<213> ORGANISM: artificial sequence
<220> FEATURE:
<223> OTHER INFORMATION: G4_19 Heavy CDR2

<400> SEQUENCE: 62

Ile Asn Pro Ser Gly Gly Ser Thr
1               5

<210> SEQ ID NO 63
<211> LENGTH: 8
<212> TYPE: PRT
<213> ORGANISM: artificial sequence
<220> FEATURE:
<223> OTHER INFORMATION: G4_20 Heavy CDR2

<400> SEQUENCE: 63

Ile Ile Pro Ile Phe Gly Thr Ala
1               5

<210> SEQ ID NO 64
<211> LENGTH: 8
<212> TYPE: PRT
<213> ORGANISM: artificial sequence
<220> FEATURE:
<223> OTHER INFORMATION: G4_22 Heavy CDR2

<400> SEQUENCE: 64

Val Ser Gly Ser Gly Gly Thr Thr
1               5

<210> SEQ ID NO 65
<211> LENGTH: 8
<212> TYPE: PRT
<213> ORGANISM: artificial sequence
<220> FEATURE:
<223> OTHER INFORMATION: G4_23 Heavy CDR2

<400> SEQUENCE: 65
```

```
Ile Trp Tyr Asp Gly Ser Asn Lys
1               5

<210> SEQ ID NO 66
<211> LENGTH: 9
<212> TYPE: PRT
<213> ORGANISM: artificial sequence
<220> FEATURE:
<223> OTHER INFORMATION: G4_24 Heavy CDR2

<400> SEQUENCE: 66

Thr Tyr Tyr Arg Ser Arg Trp Tyr Asn
1               5

<210> SEQ ID NO 67
<211> LENGTH: 8
<212> TYPE: PRT
<213> ORGANISM: artificial sequence
<220> FEATURE:
<223> OTHER INFORMATION: G4_25 Heavy CDR2

<400> SEQUENCE: 67

Ile Ile Pro Ile Phe Gly Thr Ala
1               5

<210> SEQ ID NO 68
<211> LENGTH: 8
<212> TYPE: PRT
<213> ORGANISM: artificial sequence
<220> FEATURE:
<223> OTHER INFORMATION: G4_26 Heavy CDR2

<400> SEQUENCE: 68

Ile Ile Pro Ile Phe Gly Thr Ala
1               5

<210> SEQ ID NO 69
<211> LENGTH: 8
<212> TYPE: PRT
<213> ORGANISM: artificial sequence
<220> FEATURE:
<223> OTHER INFORMATION: G4_27 Heavy CDR2

<400> SEQUENCE: 69

Ile Tyr Pro Gly Asp Ser Asp Thr
1               5

<210> SEQ ID NO 70
<211> LENGTH: 8
<212> TYPE: PRT
<213> ORGANISM: artificial sequence
<220> FEATURE:
<223> OTHER INFORMATION: G4_28 Heavy CDR2

<400> SEQUENCE: 70

Ile Ser Ala Gly Gly Gly Ser Thr
1               5

<210> SEQ ID NO 71
<211> LENGTH: 8
<212> TYPE: PRT
<213> ORGANISM: artificial sequence
<220> FEATURE:
<223> OTHER INFORMATION: G4_1 Heavy CDR1

<400> SEQUENCE: 71

Gly Phe Thr Phe Ser Ser Tyr Ser
```

```
1               5
```

```
<210> SEQ ID NO 72
<211> LENGTH: 8
<212> TYPE: PRT
<213> ORGANISM: artificial sequence
<220> FEATURE:
<223> OTHER INFORMATION: G4_2 Heavy CDR1

<400> SEQUENCE: 72

Gly Tyr Pro Phe Thr Asp Tyr Tyr
1               5
```

```
<210> SEQ ID NO 73
<211> LENGTH: 8
<212> TYPE: PRT
<213> ORGANISM: artificial sequence
<220> FEATURE:
<223> OTHER INFORMATION: G4_3 Heavy CDR1

<400> SEQUENCE: 73

Gly Phe Thr Phe Ser Ser Tyr Ser
1               5
```

```
<210> SEQ ID NO 74
<211> LENGTH: 8
<212> TYPE: PRT
<213> ORGANISM: artificial sequence
<220> FEATURE:
<223> OTHER INFORMATION: G4_4 Heavy CDR1

<400> SEQUENCE: 74

Gly Phe Thr Phe Ser Ser Tyr Ala
1               5
```

```
<210> SEQ ID NO 75
<211> LENGTH: 8
<212> TYPE: PRT
<213> ORGANISM: artificial sequence
<220> FEATURE:
<223> OTHER INFORMATION: G4_5 Heavy CDR1

<400> SEQUENCE: 75

Gly Tyr Thr Phe Thr Ser Tyr Gly
1               5
```

```
<210> SEQ ID NO 76
<211> LENGTH: 8
<212> TYPE: PRT
<213> ORGANISM: artificial sequence
<220> FEATURE:
<223> OTHER INFORMATION: G4_6 Heavy CDR1

<400> SEQUENCE: 76

Gly Phe Thr Phe Ser Ser Tyr Ala
1               5
```

```
<210> SEQ ID NO 77
<211> LENGTH: 8
<212> TYPE: PRT
<213> ORGANISM: artificial sequence
<220> FEATURE:
<223> OTHER INFORMATION: G4_7 Heavy CDR1

<400> SEQUENCE: 77

Gly Phe Thr Phe Ser His Tyr Trp
1               5
```

-continued

```
<210> SEQ ID NO 78
<211> LENGTH: 8
<212> TYPE: PRT
<213> ORGANISM: artificial sequence
<220> FEATURE:
<223> OTHER INFORMATION: G4_10 Heavy CDR1

<400> SEQUENCE: 78

Gly Phe Thr Phe Ser Ser Tyr Ala
1               5

<210> SEQ ID NO 79
<211> LENGTH: 8
<212> TYPE: PRT
<213> ORGANISM: artificial sequence
<220> FEATURE:
<223> OTHER INFORMATION: G4_12 Heavy CDR1

<400> SEQUENCE: 79

Gly Phe Thr Val Ser Ser Asn Tyr
1               5

<210> SEQ ID NO 80
<211> LENGTH: 8
<212> TYPE: PRT
<213> ORGANISM: artificial sequence
<220> FEATURE:
<223> OTHER INFORMATION: G4_13 Heavy CDR1

<400> SEQUENCE: 80

Gly Phe Thr Phe Ser Ser Tyr Ser
1               5

<210> SEQ ID NO 81
<211> LENGTH: 8
<212> TYPE: PRT
<213> ORGANISM: artificial sequence
<220> FEATURE:
<223> OTHER INFORMATION: G4_14 Heavy CDR1

<400> SEQUENCE: 81

Gly Tyr Ser Phe Thr Ser Tyr Trp
1               5

<210> SEQ ID NO 82
<211> LENGTH: 8
<212> TYPE: PRT
<213> ORGANISM: artificial sequence
<220> FEATURE:
<223> OTHER INFORMATION: G4_15 Heavy CDR1

<400> SEQUENCE: 82

Gly Tyr Thr Phe Thr Arg His Tyr
1               5

<210> SEQ ID NO 83
<211> LENGTH: 8
<212> TYPE: PRT
<213> ORGANISM: artificial sequence
<220> FEATURE:
<223> OTHER INFORMATION: G4_16 Heavy CDR1

<400> SEQUENCE: 83

Gly Tyr Thr Phe Thr Ser Tyr Gly
1               5
```

<210> SEQ ID NO 84
<211> LENGTH: 8
<212> TYPE: PRT
<213> ORGANISM: artificial sequence
<220> FEATURE:
<223> OTHER INFORMATION: G4_18 Heavy CDR1

<400> SEQUENCE: 84

Gly Tyr Thr Phe Thr Gly Tyr Tyr
1               5

<210> SEQ ID NO 85
<211> LENGTH: 8
<212> TYPE: PRT
<213> ORGANISM: artificial sequence
<220> FEATURE:
<223> OTHER INFORMATION: G4_19 Heavy CDR1

<400> SEQUENCE: 85

Gly Tyr Thr Leu Thr Ser Tyr Tyr
1               5

<210> SEQ ID NO 86
<211> LENGTH: 8
<212> TYPE: PRT
<213> ORGANISM: artificial sequence
<220> FEATURE:
<223> OTHER INFORMATION: G4_20 Heavy CDR1

<400> SEQUENCE: 86

Gly Gly Thr Phe Ser Ser Tyr Ala
1               5

<210> SEQ ID NO 87
<211> LENGTH: 8
<212> TYPE: PRT
<213> ORGANISM: artificial sequence
<220> FEATURE:
<223> OTHER INFORMATION: G4_22 Heavy CDR1

<400> SEQUENCE: 87

Gly Phe Thr Phe Ser Thr Tyr Ala
1               5

<210> SEQ ID NO 88
<211> LENGTH: 8
<212> TYPE: PRT
<213> ORGANISM: artificial sequence
<220> FEATURE:
<223> OTHER INFORMATION: G4_23 Heavy CDR1

<400> SEQUENCE: 88

Gly Phe Thr Phe Ser Ser Tyr Gly
1               5

<210> SEQ ID NO 89
<211> LENGTH: 10
<212> TYPE: PRT
<213> ORGANISM: artificial sequence
<220> FEATURE:
<223> OTHER INFORMATION: G4_24 Heavy CDR1

<400> SEQUENCE: 89

Gly Ala Ser Val Ser Ser Asn Ser Val Ala
1               5                   10

```
<210> SEQ ID NO 90
<211> LENGTH: 8
<212> TYPE: PRT
<213> ORGANISM: artificial sequence
<220> FEATURE:
<223> OTHER INFORMATION: G4_25 Heavy CDR1

<400> SEQUENCE: 90

Gly Gly Thr Phe Ser Ser Tyr Ala
1               5

<210> SEQ ID NO 91
<211> LENGTH: 8
<212> TYPE: PRT
<213> ORGANISM: artificial sequence
<220> FEATURE:
<223> OTHER INFORMATION: G4_26 Heavy CDR1

<400> SEQUENCE: 91

Gly Gly Thr Phe Ser Ser Tyr Ala
1               5

<210> SEQ ID NO 92
<211> LENGTH: 8
<212> TYPE: PRT
<213> ORGANISM: artificial sequence
<220> FEATURE:
<223> OTHER INFORMATION: G4_27 Heavy CDR1

<400> SEQUENCE: 92

Gly Tyr Ser Phe Thr Ser Tyr Trp
1               5

<210> SEQ ID NO 93
<211> LENGTH: 8
<212> TYPE: PRT
<213> ORGANISM: artificial sequence
<220> FEATURE:
<223> OTHER INFORMATION: G4_28 Heavy CDR1

<400> SEQUENCE: 93

Gly Phe Thr Phe Asp Asp Tyr Ala
1               5

<210> SEQ ID NO 94
<211> LENGTH: 6
<212> TYPE: PRT
<213> ORGANISM: artificial sequence
<220> FEATURE:
<223> OTHER INFORMATION: G4_1 Light CDR1

<400> SEQUENCE: 94

Gln Asp Ile Ser Asn Tyr
1               5

<210> SEQ ID NO 95
<211> LENGTH: 6
<212> TYPE: PRT
<213> ORGANISM: artificial sequence
<220> FEATURE:
<223> OTHER INFORMATION: G4_2 Light CDR1

<400> SEQUENCE: 95

Gln Asp Ile Ser Asn Tyr
1               5

<210> SEQ ID NO 96
```

-continued

```
<211> LENGTH: 6
<212> TYPE: PRT
<213> ORGANISM: artificial sequence
<220> FEATURE:
<223> OTHER INFORMATION: G4_3 Light CDR1

<400> SEQUENCE: 96

Gln Asp Ile Ser Asn Tyr
1               5

<210> SEQ ID NO 97
<211> LENGTH: 12
<212> TYPE: PRT
<213> ORGANISM: artificial sequence
<220> FEATURE:
<223> OTHER INFORMATION: G4_4 Light CDR1

<400> SEQUENCE: 97

Gln Ser Val Leu Ser Ser Ser Asn Asn Asn Asn Tyr
1               5                   10

<210> SEQ ID NO 98
<211> LENGTH: 6
<212> TYPE: PRT
<213> ORGANISM: artificial sequence
<220> FEATURE:
<223> OTHER INFORMATION: G4_5 Light CDR1

<400> SEQUENCE: 98

Gln Ser Ile Ser Ser Tyr
1               5

<210> SEQ ID NO 99
<211> LENGTH: 6
<212> TYPE: PRT
<213> ORGANISM: artificial sequence
<220> FEATURE:
<223> OTHER INFORMATION: G4_6 Light CDR1

<400> SEQUENCE: 99

Gln Ser Ile Ser Thr Tyr
1               5

<210> SEQ ID NO 100
<211> LENGTH: 11
<212> TYPE: PRT
<213> ORGANISM: artificial sequence
<220> FEATURE:
<223> OTHER INFORMATION: G4_7 Light CDR1

<400> SEQUENCE: 100

Gln Ser Leu Leu His Ser Asn Arg Phe Asn Tyr
1               5                   10

<210> SEQ ID NO 101
<211> LENGTH: 11
<212> TYPE: PRT
<213> ORGANISM: artificial sequence
<220> FEATURE:
<223> OTHER INFORMATION: G4_10 Light CDR1

<400> SEQUENCE: 101

Gln Ser Leu Glu Tyr Ser Asp Gly Asn Thr Tyr
1               5                   10

<210> SEQ ID NO 102
<211> LENGTH: 9
```

```
<212> TYPE: PRT
<213> ORGANISM: artificial sequence
<220> FEATURE:
<223> OTHER INFORMATION: G4_12 Light CDR1

<400> SEQUENCE: 102

Ser Ser Asp Val Gly Gly Tyr Asn Phe
1               5

<210> SEQ ID NO 103
<211> LENGTH: 8
<212> TYPE: PRT
<213> ORGANISM: artificial sequence
<220> FEATURE:
<223> OTHER INFORMATION: G4_13 Light CDR1

<400> SEQUENCE: 103

Ser Gly Ser Ile Ala Ser Asn Tyr
1               5

<210> SEQ ID NO 104
<211> LENGTH: 8
<212> TYPE: PRT
<213> ORGANISM: artificial sequence
<220> FEATURE:
<223> OTHER INFORMATION: G4_14 Light CDR1

<400> SEQUENCE: 104

Arg Gly Ser Ile Ala Gly Asn Tyr
1               5

<210> SEQ ID NO 105
<211> LENGTH: 9
<212> TYPE: PRT
<213> ORGANISM: artificial sequence
<220> FEATURE:
<223> OTHER INFORMATION: G4_15 Light CDR1

<400> SEQUENCE: 105

Ser Ser Asp Val Gly Gly Tyr Asn Tyr
1               5

<210> SEQ ID NO 106
<211> LENGTH: 9
<212> TYPE: PRT
<213> ORGANISM: artificial sequence
<220> FEATURE:
<223> OTHER INFORMATION: G4_16 Light CDR1

<400> SEQUENCE: 106

Ser Ser Asp Ile Gly Ala Phe Asn Ser
1               5

<210> SEQ ID NO 107
<211> LENGTH: 6
<212> TYPE: PRT
<213> ORGANISM: artificial sequence
<220> FEATURE:
<223> OTHER INFORMATION: G4_18 Light CDR1

<400> SEQUENCE: 107

Ala Leu Ala Lys Gln Tyr
1               5

<210> SEQ ID NO 108
<211> LENGTH: 8
<212> TYPE: PRT
```

```
<213> ORGANISM: artificial sequence
<220> FEATURE:
<223> OTHER INFORMATION: G4_19 Light CDR1

<400> SEQUENCE: 108

Ser Gly Ser Ile Ala Ser Asn Tyr
1               5

<210> SEQ ID NO 109
<211> LENGTH: 6
<212> TYPE: PRT
<213> ORGANISM: artificial sequence
<220> FEATURE:
<223> OTHER INFORMATION: G4_20 Light CDR1

<400> SEQUENCE: 109

Lys Leu Gly Asp Lys Phe
1               5

<210> SEQ ID NO 110
<211> LENGTH: 6
<212> TYPE: PRT
<213> ORGANISM: artificial sequence
<220> FEATURE:
<223> OTHER INFORMATION: G4_22 Light CDR1

<400> SEQUENCE: 110

Gln Asp Ile Ser Asn Tyr
1               5

<210> SEQ ID NO 111
<211> LENGTH: 6
<212> TYPE: PRT
<213> ORGANISM: artificial sequence
<220> FEATURE:
<223> OTHER INFORMATION: G4_23 Light CDR1

<400> SEQUENCE: 111

Gln Gly Ile Ser Asn Ser
1               5

<210> SEQ ID NO 112
<211> LENGTH: 12
<212> TYPE: PRT
<213> ORGANISM: artificial sequence
<220> FEATURE:
<223> OTHER INFORMATION: G4_24 Light CDR1

<400> SEQUENCE: 112

Gln Ser Val Leu Tyr Ser Ser Asn Asn Lys Asn Tyr
1               5                   10

<210> SEQ ID NO 113
<211> LENGTH: 9
<212> TYPE: PRT
<213> ORGANISM: artificial sequence
<220> FEATURE:
<223> OTHER INFORMATION: G4_25 Light CDR1

<400> SEQUENCE: 113

Ser Ser Asp Val Gly Gly Tyr Asn Tyr
1               5

<210> SEQ ID NO 114
<211> LENGTH: 9
<212> TYPE: PRT
<213> ORGANISM: artificial sequence
```

<220> FEATURE:
<223> OTHER INFORMATION: G4_26 Light CDR1

<400> SEQUENCE: 114

Ser Ser Asp Val Gly Ser Tyr Asn Leu
1               5

<210> SEQ ID NO 115
<211> LENGTH: 6
<212> TYPE: PRT
<213> ORGANISM: artificial sequence
<220> FEATURE:
<223> OTHER INFORMATION: G4_27 Light CDR1

<400> SEQUENCE: 115

Ser Leu Arg Asn Phe Tyr
1               5

<210> SEQ ID NO 116
<211> LENGTH: 6
<212> TYPE: PRT
<213> ORGANISM: artificial sequence
<220> FEATURE:
<223> OTHER INFORMATION: G4_28 Light CDR1

<400> SEQUENCE: 116

Ser Leu Arg Asn Tyr Tyr
1               5

<210> SEQ ID NO 117
<211> LENGTH: 116
<212> TYPE: PRT
<213> ORGANISM: artificial sequence
<220> FEATURE:
<223> OTHER INFORMATION: TRGV4 full heavy variable sequence G4_1

<400> SEQUENCE: 117

Glu Val Gln Leu Leu Glu Ser Gly Gly Gly Val Val Gln Pro Gly Arg
1               5                   10                  15

Pro Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Trp Tyr Phe Asp Leu Trp Gly Arg Gly Thr Leu Val
            100                 105                 110

Thr Val Ser Ser
        115

<210> SEQ ID NO 118
<211> LENGTH: 120
<212> TYPE: PRT
<213> ORGANISM: artificial sequence
<220> FEATURE:
<223> OTHER INFORMATION: TRGV4 full heavy variable sequence G4_2

<400> SEQUENCE: 118

Gln Met Gln Leu Val Gln Ser Gly Ala Glu Val Lys Lys Pro Gly Ala

-continued

```
1               5               10              15

Thr Val Lys Ile Ser Cys Lys Val Ser Gly Tyr Pro Phe Thr Asp Tyr
            20              25              30

Tyr Ile His Trp Val Gln Gln Ala Pro Gly Lys Gly Leu Glu Trp Met
        35              40              45

Gly Leu Val Asp Pro Glu Asp Gly Gln Ser Arg Ser Ala Glu Arg Phe
    50              55              60

Gln Gly Arg Val Thr Ile Thr Ala Asp Thr Ser Thr Asp Thr Ala Tyr
65              70              75              80

Met Glu Leu Ser Ser Leu Arg Ser Glu Asp Thr Ala Val Tyr Tyr Cys
            85              90              95

Ala Thr Phe Pro Val Ala Gly Phe Tyr Gly Met Asp Val Trp Gly Gln
            100             105             110

Gly Thr Leu Val Thr Val Ser Ser
        115             120
```

<210> SEQ ID NO 119
<211> LENGTH: 116
<212> TYPE: PRT
<213> ORGANISM: artificial sequence
<220> FEATURE:
<223> OTHER INFORMATION: TRGV4 full heavy variable sequence G4_3

<400> SEQUENCE: 119

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ser Met Asn Trp Val Arg Gln Ala Pro Gly Lys Gly Leu Glu Trp Val
        35              40              45

Ser Ser Ile Ser Ser Ser Ser Ser Tyr Ile Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Gly Gly Trp Leu Tyr Asp Tyr Trp Gly Gln Gly Thr Leu Val
            100             105             110

Thr Val Ser Ser
        115
```

<210> SEQ ID NO 120
<211> LENGTH: 119
<212> TYPE: PRT
<213> ORGANISM: artificial sequence
<220> FEATURE:
<223> OTHER INFORMATION: TRGV4 full heavy variable sequence G4_4

<400> SEQUENCE: 120

```
Gln Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Ser Tyr
            20              25              30

Ala Met Ser Trp Val Arg Gln Ala Pro Gly Lys Gly Leu Glu Trp Val
        35              40              45

Ser Ala Ile Ser Gly Ser Gly Gly Ser Thr Tyr Tyr Ala Asp Ser Val
    50              55              60
```

```
Lys Gly Arg Phe Thr Ile Ser Arg Asp Asn Ser Lys Asn Thr Leu Tyr
65                  70                  75                  80

Leu Gln Met Ser Ser Leu Arg Val Glu Asp Thr Ala Val Tyr Tyr Cys
                85                  90                  95

Ala Lys Ser Ser Val Gly Trp Trp Ser Phe Asp Tyr Trp Gly Gln Gly
            100                 105                 110

Thr Met Val Thr Val Ser Ser
        115
```

<210> SEQ ID NO 121
<211> LENGTH: 120
<212> TYPE: PRT
<213> ORGANISM: artificial sequence
<220> FEATURE:
<223> OTHER INFORMATION: TRGV4 full heavy variable sequence G4_5

<400> SEQUENCE: 121

```
Glu Val Gln Leu Val Gln Ser Gly Ala Glu Val Lys Lys Pro Gly Ser
1                5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Gly Ala Tyr Asn Gly Asn Thr Asn Tyr Ala Gln Lys Leu
        50                  55                  60

Gln Gly Arg Val Thr Met Ser Thr Asp Thr Ser Thr Ser Thr Ala Tyr
65                  70                  75                  80

Met Glu Leu Arg Ser Pro Arg Ser Asp Asp Thr Ala Val Tyr Tyr Cys
                85                  90                  95

Ala Arg Gly Gly Thr Gly Gly Asp His Val Phe Ala Tyr Trp Gly Gln
            100                 105                 110

Gly Thr Thr Val Thr Val Ser Ser
        115                 120
```

<210> SEQ ID NO 122
<211> LENGTH: 120
<212> TYPE: PRT
<213> ORGANISM: artificial sequence
<220> FEATURE:
<223> OTHER INFORMATION: TRGV4 full heavy variable sequence G4_6

<400> SEQUENCE: 122

```
Glu Val Gln Leu Val Glu Ser Gly Gly Gly Leu Val Gln Pro Gly Gly
1                5                  10                  15

Pro Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Asp Tyr Gly Val Val Tyr Tyr Phe Asp Tyr Trp Gly Gln
            100                 105                 110

Gly Thr Met Val Thr Val Ser Ser
        115                 120
```

<210> SEQ ID NO 123
<211> LENGTH: 119
<212> TYPE: PRT
<213> ORGANISM: artificial sequence
<220> FEATURE:
<223> OTHER INFORMATION: TRGV4 full heavy variable sequence G4_7

<400> SEQUENCE: 123

Glu Val Gln Leu Val Glu Ser Gly Gly Gly Trp Val Gln Ser Gly Gly
1               5                   10                  15

Ser Leu Arg Pro Ser Cys Ala Ala Ser Gly Phe Thr Phe Ser His Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Ile Ile Tyr Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Ile Gly Tyr Ser Ser Ser Ser Phe Asp Tyr Trp Gly Arg Gly
            100                 105                 110

Thr Leu Val Thr Val Ser Ser
        115

<210> SEQ ID NO 124
<211> LENGTH: 122
<212> TYPE: PRT
<213> ORGANISM: artificial sequence
<220> FEATURE:
<223> OTHER INFORMATION: TRGV4 full heavy variable sequence G4_10

<400> SEQUENCE: 124

Gln Val Gln Leu Val Glu Ser Gly Gly Gly Val Val Gln Pro Gly Arg
1               5                   10                  15

Pro Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Val Asp Phe Trp Arg Asn Gly Met Asp Val Trp
            100                 105                 110

Gly Arg Gly Thr Leu Val Thr Val Ser Ser
        115                 120

<210> SEQ ID NO 125
<211> LENGTH: 117
<212> TYPE: PRT
<213> ORGANISM: artificial sequence
<220> FEATURE:
<223> OTHER INFORMATION: TRGV4 full heavy variable sequence G4_12

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Val Ala Asn Gly Asp Phe Leu Asp Tyr Trp Gly Arg Gly Thr Leu
            100                 105                 110

Val Thr Val Ser Ser
        115
```

<210> SEQ ID NO 126
<211> LENGTH: 117
<212> TYPE: PRT
<213> ORGANISM: artificial sequence
<220> FEATURE:
<223> OTHER INFORMATION: TRGV4 full heavy variable sequence G4_13

<400> SEQUENCE: 126

```
Gln Val Gln Leu Val Glu Ser Gly Ala Glu Val Lys Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Gly Thr Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
            85                  90                  95

Ala Arg Gly Gly Leu Gly Met Val Asp Pro Trp Gly Gln Gly Thr Leu
            100                 105                 110

Val Thr Val Ser Ser
        115
```

<210> SEQ ID NO 127
<211> LENGTH: 117
<212> TYPE: PRT
<213> ORGANISM: artificial sequence
<220> FEATURE:
<223> OTHER INFORMATION: TRGV4 full heavy variable sequence G4_14

<400> SEQUENCE: 127

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60
```

```
Pro Gly His Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Ala Asp Thr Ala His Gly Met Asp Val Trp Gly Arg Gly Thr Leu
            100             105             110

Val Thr Val Ser Ser
        115
```

<210> SEQ ID NO 128
<211> LENGTH: 122
<212> TYPE: PRT
<213> ORGANISM: artificial sequence
<220> FEATURE:
<223> OTHER INFORMATION: TRGV4 full heavy variable sequence G4_15

<400> SEQUENCE: 128

```
Glu Val Gln Leu Val Gln Ser Glu Ala Glu Val Lys Lys Pro Gly Ala
1               5               10              15

Ser Val Lys Val Ser Cys Lys Ala Ser Gly Tyr Thr Phe Thr Arg His
            20              25              30

Tyr Met His Trp Val Arg Gln Ala Pro Gly Gln Gly Leu Glu Trp Met
        35              40              45

Gly Leu Ile Asn Pro Ser Gly Ser Ser Thr Val Tyr Ala Gln Lys Phe
    50              55              60

Gln Gly Arg Val Thr Leu Thr Arg Asp Thr Ser Thr Ser Thr Asp Tyr
65              70              75              80

Met Glu Leu Ser Ser Leu Arg Ser Glu Asp Thr Ala Val Tyr Tyr Cys
            85              90              95

Ala Arg Asp Asn Ser His Leu Asp Gln Val Trp Trp Phe Asp Pro Trp
            100             105             110

Gly Gln Gly Thr Leu Val Thr Val Ser Ser
        115             120
```

<210> SEQ ID NO 129
<211> LENGTH: 119
<212> TYPE: PRT
<213> ORGANISM: artificial sequence
<220> FEATURE:
<223> OTHER INFORMATION: TRGV4 full heavy variable sequence G4_16

<400> SEQUENCE: 129

```
Glu Val Gln Leu Leu Glu Ser Gly Ala Glu Val Lys Lys Pro Gly Ala
1               5               10              15

Ser Val Lys Val Ser Cys Lys Ala Ser Gly Tyr Thr Phe Thr Ser Tyr
            20              25              30

Gly Ile Ser Trp Val Arg Gln Ala Pro Gly Gln Gly Leu Glu Trp Met
        35              40              45

Gly Trp Ile Ser Ala Tyr Asn Gly Asn Thr Asn Tyr Ala Gln Lys Leu
    50              55              60

Gln Gly Arg Val Thr Met Thr Thr Asp Thr Ser Thr Ser Thr Ala Tyr
65              70              75              80

Met Glu Leu Arg Ser Leu Arg Ser Asp Asp Thr Ala Val Tyr Tyr Cys
            85              90              95

Ala Arg Asp Tyr Gly Asp Phe Tyr Gly Met Asp Val Trp Gly Gln Gly
            100             105             110

Thr Leu Val Thr Val Ser Ser
```

115

<210> SEQ ID NO 130
<211> LENGTH: 118
<212> TYPE: PRT
<213> ORGANISM: artificial sequence
<220> FEATURE:
<223> OTHER INFORMATION: TRGV4 full heavy variable sequence G4_18

<400> SEQUENCE: 130

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Ala Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Asp Leu Ser Ser Leu Asp Tyr Trp Gly Arg Gly Thr
            100                 105                 110

Leu Val Thr Val Ser Ser
        115

<210> SEQ ID NO 131
<211> LENGTH: 121
<212> TYPE: PRT
<213> ORGANISM: artificial sequence
<220> FEATURE:
<223> OTHER INFORMATION: TRGV4 full heavy variable sequence G4_19

<400> SEQUENCE: 131

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Ser Tyr Gly Asp Gly Met Asp Val Trp Gly
            100                 105                 110

Gln Gly Thr Thr Val Thr Val Ser Ser
        115                 120

<210> SEQ ID NO 132
<211> LENGTH: 119
<212> TYPE: PRT
<213> ORGANISM: artificial sequence
<220> FEATURE:
<223> OTHER INFORMATION: TRGV4 full heavy variable sequence G4_20

<400> SEQUENCE: 132

-continued

```
Gln Val Gln Leu Val Glu Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Val Asp Lys Ser Thr Arg Thr Ala Tyr
65              70                  75                  80

Met Glu Leu Ser Ser Leu Arg Ser Lys Asp Thr Ala Val Tyr Tyr Cys
            85                  90                  95

Ala Arg Gly Asn Ser Arg Ser Asp Ala Phe Asp Ile Trp Gly Gln Gly
            100                 105                 110

Thr Met Val Thr Val Ser Ser
        115
```

<210> SEQ ID NO 133
<211> LENGTH: 120
<212> TYPE: PRT
<213> ORGANISM: artificial sequence
<220> FEATURE:
<223> OTHER INFORMATION: TRGV4 full heavy variable sequence G4_22

<400> SEQUENCE: 133

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Val Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Lys Asp Ser Thr Ala Val Thr Asp Trp Phe Asp Pro Trp Gly Arg
            100                 105                 110

Gly Thr Leu Val Thr Val Ser Ser
        115                 120
```

<210> SEQ ID NO 134
<211> LENGTH: 120
<212> TYPE: PRT
<213> ORGANISM: artificial sequence
<220> FEATURE:
<223> OTHER INFORMATION: TRGV4 full heavy variable sequence G4_23

<400> SEQUENCE: 134

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
        50               55                60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Val Ala Ala Leu Tyr Tyr Phe Asp Tyr Trp Gly Gln
            100                 105                 110

Gly Thr Leu Val Thr Val Ser Ser
        115                 120

<210> SEQ ID NO 135
<211> LENGTH: 122
<212> TYPE: PRT
<213> ORGANISM: artificial sequence
<220> FEATURE:
<223> OTHER INFORMATION: TRGV4 full heavy variable sequence G4_24

<400> SEQUENCE: 135

Gln Val Gln Leu Gln Gln Ser Gly Pro Gly Leu Val Lys Pro Ser Gln
1               5                   10                  15

Thr Leu Ser Leu Thr Cys Ala Ile Ser Gly Ala Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Arg Trp Tyr Asn Asp Tyr Ala
        50                  55                  60

Leu Ser Val Lys Ser Arg Ile Ile Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Trp Ser Ser Thr Arg Ser Phe Asp Tyr Trp
            100                 105                 110

Gly Arg Gly Thr Leu Val Thr Val Ser Ser
        115                 120

<210> SEQ ID NO 136
<211> LENGTH: 123
<212> TYPE: PRT
<213> ORGANISM: artificial sequence
<220> FEATURE:
<223> OTHER INFORMATION: TRGV4 full heavy variable sequence G4_25

<400> SEQUENCE: 136

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Arg Asp Gly Tyr Asn Tyr Ile Gly Ser Leu Gly Tyr
            100                 105                 110
```

-continued

Trp Gly Gln Gly Thr Leu Val Thr Val Ser Ser
        115                     120

<210> SEQ ID NO 137
<211> LENGTH: 120
<212> TYPE: PRT
<213> ORGANISM: artificial sequence
<220> FEATURE:
<223> OTHER INFORMATION: TRGV4 full heavy variable sequence G4_26

<400> SEQUENCE: 137

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Arg Gly Ser Gly Trp Phe Pro Leu Gly Tyr Trp Gly Gln
            100                 105                 110

Gly Thr Leu Val Thr Val Ser Ser
        115                 120

<210> SEQ ID NO 138
<211> LENGTH: 122
<212> TYPE: PRT
<213> ORGANISM: artificial sequence
<220> FEATURE:
<223> OTHER INFORMATION: TRGV4 full heavy variable sequence G4_27

<400> SEQUENCE: 138

Gln Val Gln Leu Val Gln Ser Gly Ala Glu Val Lys Lys Pro Gly Glu
1               5                   10                  15

Ser Leu Lys Ile Ser Cys Lys Ser Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Phe Ser Ala Asp Glu Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Ala Tyr Gly Asp Tyr Pro Asp Thr Phe Asp Ile Trp
            100                 105                 110

Gly Gln Gly Thr Leu Val Thr Val Ser Ser
        115                 120

<210> SEQ ID NO 139
<211> LENGTH: 125
<212> TYPE: PRT
<213> ORGANISM: artificial sequence
<220> FEATURE:
<223> OTHER INFORMATION: TRGV4 full heavy variable sequence G4_28

<400> SEQUENCE: 139

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Ala Gly Gly Gly Ser Thr Asn Tyr Ala Gly Ser Val
    50                  55                  60

Lys Gly Arg Phe Thr Val Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Ser Tyr Val Asp Thr Ala Met Arg Tyr Tyr Tyr Tyr Tyr Met
            100                 105                 110

Asp Val Trp Gly Gln Gly Thr Met Val Thr Val Ser Ser
        115                 120                 125

<210> SEQ ID NO 140
<211> LENGTH: 109
<212> TYPE: PRT
<213> ORGANISM: artificial sequence
<220> FEATURE:
<223> OTHER INFORMATION: TRGV4 full light variable sequence G4_1

<400> SEQUENCE: 140

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Asp Ala Ser Asn Leu Glu Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Val Thr Phe Gly Pro Gly Thr Lys Val Glu Ile Lys
            100                 105

<210> SEQ ID NO 141
<211> LENGTH: 109
<212> TYPE: PRT
<213> ORGANISM: artificial sequence
<220> FEATURE:
<223> OTHER INFORMATION: TRGV4 full light variable sequence G4_2

<400> SEQUENCE: 141

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

```
Ser Gly Ser Gly Ser Gly Thr Asp Phe Thr Leu Thr Ile Ser Gly Leu
65              70                  75                  80

Gln Pro Glu Asp Phe Ala Thr Tyr Tyr Cys Leu Glu Asp Tyr Asn Tyr
                85                  90                  95

Leu Trp Thr Phe Gly Gln Gly Thr Lys Leu Glu Ile Lys
            100                 105

<210> SEQ ID NO 142
<211> LENGTH: 109
<212> TYPE: PRT
<213> ORGANISM: artificial sequence
<220> FEATURE:
<223> OTHER INFORMATION: TRGV4 full light variable sequence G4_3

<400> SEQUENCE: 142

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
                20                  25                  30

Asn Tyr Leu Asn Trp Tyr Gln Gln Lys Pro Gly Lys Ala Pro Lys Leu
            35                  40                  45

Leu Ile Tyr Asp Ala Ser Asn Leu Glu Thr Gly Val Pro Ser Arg Phe
        50                  55                  60

Ser Gly Ser Gly Ser Gly Thr Asp Phe Thr Leu Thr Ile Ser Ser Leu
65              70                  75                  80

Gln Pro Glu Asp Phe Ala Thr Tyr Phe Cys Gln Gln Ser Tyr Ser Thr
                85                  90                  95

Pro Gln Thr Phe Gly Gln Gly Thr Lys Val Asp Ile Lys
            100                 105

<210> SEQ ID NO 143
<211> LENGTH: 115
<212> TYPE: PRT
<213> ORGANISM: artificial sequence
<220> FEATURE:
<223> OTHER INFORMATION: TRGV4 full light variable sequence G4_4

<400> SEQUENCE: 143

Ala Ser Asp Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
                20                  25                  30

Ser Ser Ser Asn Asn Asn Asn Tyr Leu Ala Trp Tyr Gln Gln Arg Pro
            35                  40                  45

Gly Gln Pro Pro Lys Leu Leu Phe Tyr Trp Ala Ser Thr Arg Glu Ser
        50                  55                  60

Gly Val Pro Asp Arg Phe Ser Gly Ser Gly Ser Gly Thr Ser Phe Thr
65              70                  75                  80

Leu Thr Ile Thr Ser Leu Gln Ala Glu Asp Val Ala Val Tyr Tyr Cys
                85                  90                  95

Gln Gln Tyr Tyr Ser Thr Pro Leu Thr Phe Gly Gly Gly Thr Lys Leu
            100                 105                 110

Glu Ile Lys
        115

<210> SEQ ID NO 144
<211> LENGTH: 109
<212> TYPE: PRT
<213> ORGANISM: artificial sequence
```

```
<220> FEATURE:
<223> OTHER INFORMATION: TRGV4 full light variable sequence G4_5

<400> SEQUENCE: 144

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Tyr Thr Phe Gly Gln Gly Thr Lys Val Glu Ile Lys
            100                 105

<210> SEQ ID NO 145
<211> LENGTH: 109
<212> TYPE: PRT
<213> ORGANISM: artificial sequence
<220> FEATURE:
<223> OTHER INFORMATION: TRGV4 full light variable sequence G4_6

<400> SEQUENCE: 145

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Thr Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Pro
65                  70                  75                  80

Gln Pro Glu Asp Phe Ala Thr Tyr Tyr Cys Gln Gln Ser Tyr Ser Thr
                85                  90                  95

Pro Tyr Thr Phe Gly Gln Gly Thr Lys Val Glu Ile Lys
            100                 105

<210> SEQ ID NO 146
<211> LENGTH: 114
<212> TYPE: PRT
<213> ORGANISM: artificial sequence
<220> FEATURE:
<223> OTHER INFORMATION: TRGV4 full light variable sequence G4_7

<400> SEQUENCE: 146

Ala Ser Asp Ile Val Met Thr Gln Ser Pro Leu Ser Leu Pro Val Thr
1               5                   10                  15

Pro Gly Glu Pro Ala Ser Ile Ser Cys Arg Ser Ser Gln Ser Leu Leu
            20                  25                  30

His Ser Asn Arg Phe Asn Tyr Leu Asp Trp Tyr Leu Gln Lys Pro Gly
        35                  40                  45

Gln Ser Pro Gln Leu Leu Ile Tyr Leu Gly Ser Asn Arg Ala Ser Gly
    50                  55                  60
```

-continued

```
Val Pro Asp Arg Phe Ser Gly Ser Gly Ser Gly Thr Asp Phe Thr Leu
65                  70                  75                  80

Lys Ile Ser Arg Val Glu Ala Glu Asp Val Gly Val Tyr Tyr Cys Met
                85                  90                  95

Gln Gly Leu Gln Thr Pro Tyr Thr Phe Gly Gln Gly Thr Lys Val Asp
                100                 105                 110

Ile Lys

<210> SEQ ID NO 147
<211> LENGTH: 114
<212> TYPE: PRT
<213> ORGANISM: artificial sequence
<220> FEATURE:
<223> OTHER INFORMATION: TRGV4 full light variable sequence G4_10

<400> SEQUENCE: 147

Ala Ser Asp Ile Val Met Thr Gln Pro Pro Leu Ser Leu Pro Val Thr
1                   5                   10                  15

Leu Gly His Pro Ala Ser Ile Ser Cys Lys Ser Ser Gln Ser Leu Glu
                20                  25                  30

Tyr Ser Asp Gly Asn Thr Tyr Leu Asn Trp Phe Gln Gln Arg Pro Gly
                35                  40                  45

Gln Ser Pro Arg Arg Leu Ile Tyr Lys Val Ser Asn Arg Asp Ser Gly
                50                  55                  60

Ala Pro Asp Arg Phe Ser Gly Ser Gly Ser Gly Thr Asp Phe Thr Leu
65                  70                  75                  80

Glu Ile Ser Arg Val Glu Ala Glu Asp Val Gly Val Tyr Tyr Cys Met
                85                  90                  95

Gln Gly Thr Leu Trp Pro Pro Thr Phe Gly Gln Gly Thr Lys Val Asp
                100                 105                 110

Ile Lys

<210> SEQ ID NO 148
<211> LENGTH: 110
<212> TYPE: PRT
<213> ORGANISM: artificial sequence
<220> FEATURE:
<223> OTHER INFORMATION: TRGV4 full light variable sequence G4_12

<400> SEQUENCE: 148

Ala Ser Gln Ser Val Leu Thr Gln Pro Ala Ser Val Ser Gly Ser Pro
1                   5                   10                  15

Gly Gln Ser Ile Thr Ile Ser Cys Thr Gly Thr Ser Ser Asp Val Gly
                20                  25                  30

Gly Tyr Asn Phe Val Ser Trp Tyr Gln Gln His Pro Gly Lys Ala Pro
                35                  40                  45

Lys Leu Met Ile Tyr Glu Val Thr Asn Arg Pro Ser Gly Val Pro Asp
                50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser His Ala
                85                  90                  95

Ser Pro Arg Val Phe Gly Thr Gly Thr Lys Val Thr Val Leu
                100                 105                 110

<210> SEQ ID NO 149
<211> LENGTH: 113
<212> TYPE: PRT
```

-continued

```
<213> ORGANISM: artificial sequence
<220> FEATURE:
<223> OTHER INFORMATION: TRGV4 full light variable sequence G4_13

<400> SEQUENCE: 149

Ala Ser Asn Phe Met Leu Thr Gln Pro His Ser Val Ser Glu Ser Pro
1               5                   10                  15

Gly Lys Thr Val Thr Ile Ser Cys Thr Arg Ser Ser Gly Ser Ile Ala
            20                  25                  30

Ser Asn Tyr Val Gln Trp Tyr Gln Gln Arg Pro Gly Ser Ser Pro Ser
        35                  40                  45

Thr Val Ile Tyr Glu Asp Asn Gln Arg Pro Ser Gly Val Pro Asp Arg
    50                  55                  60

Phe Ser Gly Ser Ile Asp Ser Ser Asn Ser Ala Ser Leu Thr Ile
65                  70                  75                  80

Ser Gly Leu Arg Thr Glu Asp Glu Ala Asp Tyr Tyr Cys Gln Ser Tyr
                85                  90                  95

Asp Ser Ser Ile Tyr Val Val Phe Gly Gly Gly Thr Lys Leu Thr Val
            100                 105                 110

Leu

<210> SEQ ID NO 150
<211> LENGTH: 113
<212> TYPE: PRT
<213> ORGANISM: artificial sequence
<220> FEATURE:
<223> OTHER INFORMATION: TRGV4 full light variable sequence G4_14

<400> SEQUENCE: 150

Ala Ser Asn Phe Met Leu Thr Gln Pro His Ser Val Ser Glu Ser Pro
1               5                   10                  15

Gly Lys Thr Val Thr Ile Ser Cys Thr Arg Ser Arg Gly Ser Ile Ala
            20                  25                  30

Gly Asn Tyr Val His Trp Tyr Gln Gln Arg Pro Gly Arg Ala Pro Thr
        35                  40                  45

Thr Val Ile Tyr Arg Asp Lys Glu Arg Pro Ser Gly Val Pro Asp Arg
    50                  55                  60

Ile Ser Gly Ser Ile Asp Ser Ser Ser Asn Ser Ala Ser Leu Thr Ile
65                  70                  75                  80

Ser Gly Leu Lys Thr Glu Asp Glu Ala Asp Tyr Tyr Cys Gln Ser Tyr
                85                  90                  95

Asp Ser Ser Thr His Val Val Phe Gly Gly Gly Thr Lys Leu Thr Val
            100                 105                 110

Leu

<210> SEQ ID NO 151
<211> LENGTH: 110
<212> TYPE: PRT
<213> ORGANISM: artificial sequence
<220> FEATURE:
<223> OTHER INFORMATION: TRGV4 full light variable sequence G4_15

<400> SEQUENCE: 151

Ala Ser Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
```

-continued

```
            35                      40                      45
Lys Leu Met Ile Tyr Asp Val Ser Asn Arg Pro Ser Gly Val Ser Asn
    50                      55                      60

Arg Phe Ser Gly Ser Lys Ser Gly Asn Thr Ala Ser Leu Thr Ile Ser
65                      70                      75                      80

Gly Leu Gln Ala Glu Asp Glu Ala Asp Tyr Tyr Cys Ser Ser Tyr Gly
                85                      90                      95

Ser Gly Ser Val Phe Gly Thr Gly Thr Lys Leu Thr Val Leu
            100                     105                     110

<210> SEQ ID NO 152
<211> LENGTH: 112
<212> TYPE: PRT
<213> ORGANISM: artificial sequence
<220> FEATURE:
<223> OTHER INFORMATION: TRGV4 full light variable sequence G4_16

<400> SEQUENCE: 152

Ala Ser Gln Ser Val Leu Thr Gln Pro Pro Ser Ala Ser Gly Ser Pro
1                   5                       10                      15

Gly Gln Ser Val Thr Phe Ser Cys Thr Gly Thr Ser Ser Asp Ile Gly
                20                      25                      30

Ala Phe Asn Ser Val Ser Trp Tyr Gln Gln His Pro Gly Lys Ala Pro
            35                      40                      45

Lys Leu Leu Ile Tyr Glu Ile Thr Lys Arg Pro Ser Gly Val Pro Asp
    50                      55                      60

Arg Phe Ser Gly Ser Lys Ser Gly Asn Thr Ala Ser Leu Thr Ile Ser
65                      70                      75                      80

Val Leu Gln Ala Glu Asp Glu Ala Asp Tyr Tyr Cys Thr Ser Tyr Ala
                85                      90                      95

Gly Ser Asn Thr Leu Ile Phe Gly Gly Gly Thr Lys Val Thr Val Leu
                100                     105                     110

<210> SEQ ID NO 153
<211> LENGTH: 110
<212> TYPE: PRT
<213> ORGANISM: artificial sequence
<220> FEATURE:
<223> OTHER INFORMATION: TRGV4 full light variable sequence G4_18

<400> SEQUENCE: 153

Ala Ser Ser Tyr Glu Leu Thr Gln Pro Pro Ser Val Thr Glu Ser Pro
1                   5                       10                      15

Gly Gln Thr Ala Arg Ile Thr Cys Ser Gly Asp Ala Leu Ala Lys Gln
                20                      25                      30

Tyr Ala Tyr Trp Tyr Gln Gln Lys Pro Gly Gln Ala Pro Val Leu Val
            35                      40                      45

Ile Tyr Arg Asp Ser Glu Arg Pro Ser Glu Ile Pro Glu Arg Phe Ser
    50                      55                      60

Gly Ser Ser Ser Gly Thr Thr Val Thr Leu Thr Ile Ser Gly Val Gln
65                      70                      75                      80

Ala Glu Asp Glu Ala Asp Tyr Tyr Cys Gln Ser Ala Asp Ser Ser Gly
                85                      90                      95

Thr Tyr Thr Val Phe Gly Gly Gly Thr Lys Leu Thr Val Leu
                100                     105                     110

<210> SEQ ID NO 154
<211> LENGTH: 113
```

<212> TYPE: PRT
<213> ORGANISM: artificial sequence
<220> FEATURE:
<223> OTHER INFORMATION: TRGV4 full light variable sequence G4_19

<400> SEQUENCE: 154

Ala Ser Asn Phe Met Leu Thr Gln Pro His Ser Val Ser Glu Ser Pro
1               5                   10                  15

Gly Lys Thr Val Thr Ile Ser Cys Thr Arg Ser Ser Gly Ser Ile Ala
            20                  25                  30

Ser Asn Tyr Val Gln Trp Tyr Gln Gln Arg Pro Gly Ser Pro Pro Ile
        35                  40                  45

Thr Leu Ile Tyr Asp Asp Asp Gln Arg Pro Ser Gly Val Pro His Arg
    50                  55                  60

Phe Ser Gly Ser Ile Asp Thr Ser Ser Asn Pro Ala Ser Leu Thr Ile
65                  70                  75                  80

Ser Gly Leu Lys Thr Glu Asp Glu Ala Asp Tyr Tyr Cys Gln Ser Tyr
                85                  90                  95

Asp Ser Ser Asn His Val Val Phe Gly Gly Gly Thr Lys Leu Thr Val
            100                 105                 110

Leu

<210> SEQ ID NO 155
<211> LENGTH: 108
<212> TYPE: PRT
<213> ORGANISM: artificial sequence
<220> FEATURE:
<223> OTHER INFORMATION: TRGV4 full light variable sequence G4_20

<400> SEQUENCE: 155

Ala Ser Ser Tyr Glu Leu Thr His Pro Pro Ser Val Ser Val Ser Pro
1               5                   10                  15

Gly Gln Thr Ala Ser Ile Thr Cys Ser Gly Asp Lys Leu Gly Asp Lys
            20                  25                  30

Phe Val Ser Trp Tyr His Gln Lys Pro Gly Gln Ser Pro Val Leu Val
        35                  40                  45

Ile Tyr Gln Asp Ser Lys Arg Pro Ser Gly Ile Pro Glu Arg Phe Ser
    50                  55                  60

Gly Ser Asn Ser Gly Asn Thr Ala Thr Leu Thr Ile Ser Gly Thr Arg
65                  70                  75                  80

Ala Met Asp Glu Ala Asp Tyr Tyr Cys Gln Ala Trp Asp Ser Ser Thr
                85                  90                  95

Val Val Phe Gly Gly Gly Thr Lys Leu Thr Val Leu
            100                 105

<210> SEQ ID NO 156
<211> LENGTH: 109
<212> TYPE: PRT
<213> ORGANISM: artificial sequence
<220> FEATURE:
<223> OTHER INFORMATION: TRGV4 full light variable sequence G4_22

<400> SEQUENCE: 156

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

-continued

Leu Ile Tyr Ala Ala Ser Ser Leu Gln Ser Gly Val Pro Ser Arg Phe
    50                  55                  60

Ser Val Ser Gly Ser Gly Thr Asp Phe Thr Leu Thr Ile Ser Asn Leu
65                  70                  75                  80

Gln Pro Glu Asp Phe Ala Thr Tyr Tyr Cys Gln Gln Ser Tyr Ser Ile
                85                  90                  95

Pro Trp Thr Phe Gly Gln Gly Thr Lys Val Glu Ile Lys
                100                 105

<210> SEQ ID NO 157
<211> LENGTH: 109
<212> TYPE: PRT
<213> ORGANISM: artificial sequence
<220> FEATURE:
<223> OTHER INFORMATION: TRGV4 full light variable sequence G4_23

<400> SEQUENCE: 157

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
                20                  25                  30

Asn Ser Leu Ala Trp Tyr Gln Gln Lys Pro Gly Lys Ala Pro Lys Leu
            35                  40                  45

Leu Leu Tyr Ala Ala Ser Arg Leu Glu Ser Gly Val Pro Ser Arg Phe
    50                  55                  60

Ser Gly Ser Gly Ser Gly Thr Asp Tyr Thr Leu Thr Ile Ser Ser Leu
65                  70                  75                  80

Gln Pro Glu Asp Phe Ala Thr Tyr Tyr Cys Gln Gln Tyr Tyr Ser Thr
                85                  90                  95

Pro Arg Thr Phe Gly Gly Gly Thr Lys Leu Glu Ile Lys
                100                 105

<210> SEQ ID NO 158
<211> LENGTH: 115
<212> TYPE: PRT
<213> ORGANISM: artificial sequence
<220> FEATURE:
<223> OTHER INFORMATION: TRGV4 full light variable sequence G4_24

<400> SEQUENCE: 158

Ala Ser Asp Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
                20                  25                  30

Tyr Ser Ser Asn Asn Lys Asn Tyr Leu Ala Trp Tyr Gln Gln Lys Pro
            35                  40                  45

Gly Gln Pro Pro Lys Leu Leu Ile Ser Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Asn Ser Leu Gln Ser Glu Asp Val Ala Ile Tyr Tyr Cys
                85                  90                  95

Gln Gln Tyr Tyr Ser Thr Pro Pro Thr Phe Gly Gln Gly Thr Lys Leu
                100                 105                 110

Glu Ile Lys
        115

<210> SEQ ID NO 159
<211> LENGTH: 110
<212> TYPE: PRT
<213> ORGANISM: artificial sequence
<220> FEATURE:
<223> OTHER INFORMATION: TRGV4 full light variable sequence G4_25

<400> SEQUENCE: 159

Ala Ser Gln Ser Ala Leu Thr Gln Pro Arg Ser Val Ser Gly Ser Pro
1               5                   10                  15

Gly Gln Ser Val Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Met Ile Tyr Glu Val Ser Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Gly
                85                  90                  95

Ser Gly Ser Val Phe Gly Thr Gly Thr Lys Leu Thr Val Leu
            100                 105                 110

<210> SEQ ID NO 160
<211> LENGTH: 110
<212> TYPE: PRT
<213> ORGANISM: artificial sequence
<220> FEATURE:
<223> OTHER INFORMATION: TRGV4 full light variable sequence G4_26

<400> SEQUENCE: 160

Ala Ser Gln Ser Gly Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Ser Tyr Asn Leu Val Ser Trp Tyr Gln Gln His Pro Gly Lys Ala Pro
        35                  40                  45

Lys Leu Met Ile Tyr Glu Val Ser Lys Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Phe Gly
                85                  90                  95

Ser Gly Ser Ile Phe Gly Thr Gly Thr Lys Leu Thr Val Leu
            100                 105                 110

<210> SEQ ID NO 161
<211> LENGTH: 110
<212> TYPE: PRT
<213> ORGANISM: artificial sequence
<220> FEATURE:
<223> OTHER INFORMATION: TRGV4 full light variable sequence G4_27

<400> SEQUENCE: 161

Ala Ser Ser Tyr Glu Leu Thr Gln Asp Pro Ala Val Ser Val Ala Leu
1               5                   10                  15

Gly Gln Thr Val Ser Ile Thr Cys Gln Gly Asp Ser Leu Arg Asn Phe
            20                  25                  30

Tyr Ala Asn Trp Tyr Gln Gln Lys Pro Gly Gln Ala Pro Val Leu Val
        35                  40                  45

Ile Tyr Gly Lys Asn Asn Arg Pro Ser Gly Ile Pro Asp Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Asn Ser Arg Asp Ser Ser Gly
                85                  90                  95

Asn His Leu Val Phe Gly Gly Gly Thr Gln Leu Thr Val Leu
            100                 105                 110

<210> SEQ ID NO 162
<211> LENGTH: 108
<212> TYPE: PRT
<213> ORGANISM: artificial sequence
<220> FEATURE:
<223> OTHER INFORMATION: TRGV4 full light variable sequence G4_28

<400> SEQUENCE: 162

Ala Ser Ser Tyr Glu Leu Thr Gln Asp Pro Ala Val Ser Val Ala Leu
1               5                   10                  15

Gly Gln Thr Val Thr Ile Thr Cys Gln Gly Asp Ser Leu Arg Asn Tyr
            20                  25                  30

Tyr Ala Ser Trp Tyr Arg Gln Lys Pro Gly Gln Thr Pro Val Leu Val
        35                  40                  45

Val Tyr Gly Lys Asn Asn Arg Pro Ser Gly Ile Pro Asp Arg Phe Ser
    50                  55                  60

Val Ser Ala Ser Gly Asn Thr Ala Ser Leu Thr Ile Thr Gly Ala Gln
65                  70                  75                  80

Ala Glu Asp Glu Gly Asp Tyr Tyr Cys Asn Ser Arg Asp Ser Ser Gly
                85                  90                  95

Val Val Phe Gly Gly Gly Thr Lys Val Thr Val Leu
            100                 105

<210> SEQ ID NO 163
<211> LENGTH: 275
<212> TYPE: PRT
<213> ORGANISM: artificial sequence
<220> FEATURE:
<223> OTHER INFORMATION: scFv sequence G4_1

<400> SEQUENCE: 163

Glu Val Gln Leu Leu Glu Ser Gly Gly Gly Val Val Gln Pro Gly Arg
1               5                   10                  15

Pro Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Trp Tyr Phe Asp Leu Trp Gly Arg Gly Thr Leu Val
            100                 105                 110

Thr Val Ser Ser Gly Gly Gly Gly Ser Gly Gly Gly Gly Ser Gly Gly
            115                 120                 125

Gly Ala Ser Asp Ile Gln Met Thr Gln Ser Pro Ser Ser Leu Ser Ala

-continued

```
              130                 135                 140

Ser Val Gly Asp Arg Val Thr Ile Thr Cys Gln Ala Ser Gln Asp Ile
145                 150                 155                 160

Ser Asn Tyr Leu Asn Trp Tyr Gln Gln Lys Pro Gly Lys Ala Pro Lys
                    165                 170                 175

Leu Leu Ile Tyr Asp Ala Ser Asn Leu Glu Thr Gly Val Pro Ser Arg
                    180                 185                 190

Phe Ser Gly Ser Gly Ser Gly Thr Asp Phe Thr Leu Thr Ile Ser Ser
                    195                 200                 205

Leu Gln Pro Glu Asp Phe Ala Thr Tyr Tyr Cys Gln Gln Ser Tyr Ser
                    210                 215                 220

Thr Pro Val Thr Phe Gly Pro Gly Thr Lys Val Glu Ile Lys Arg Thr
225                 230                 235                 240

Ala Ala Ala Ser Ala His His His His His His Lys Leu Asp Tyr Lys
                    245                 250                 255

Asp His Asp Gly Asp Tyr Lys Asp His Asp Ile Asp Tyr Lys Asp Asp
                    260                 265                 270

Asp Asp Lys
            275

<210> SEQ ID NO 164
<211> LENGTH: 279
<212> TYPE: PRT
<213> ORGANISM: artificial sequence
<220> FEATURE:
<223> OTHER INFORMATION: scFv sequence G4_2

<400> SEQUENCE: 164

Gln Met Gln Leu Val Gln Ser Gly Ala Glu Val Lys Lys Pro Gly Ala
1               5                   10                  15

Thr Val Lys Ile Ser Cys Lys Val Ser Gly Tyr Pro Phe Thr Asp Tyr
                20                  25                  30

Tyr Ile His Trp Val Gln Gln Ala Pro Gly Lys Gly Leu Glu Trp Met
        35                  40                  45

Gly Leu Val Asp Pro Glu Asp Gly Gln Ser Arg Ser Ala Glu Arg Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Pro Val Ala Gly Phe Tyr Gly Met Asp Val Trp Gly Gln
                100                 105                 110

Gly Thr Leu Val Thr Val Ser Ser Gly Gly Gly Gly Ser Gly Gly Gly
        115                 120                 125

Gly Ser Gly Gly Gly Ala Ser Asp Ile Gln Met Thr Gln Ser Pro Ser
    130                 135                 140

Ser Leu Ser Ala Ser Val Gly Asp Arg Val Thr Ile Thr Cys Gln Ala
145                 150                 155                 160

Ser Gln Asp Ile Ser Asn Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
                180                 185                 190

Val Pro Ser Arg Phe Ser Gly Ser Gly Ser Gly Thr Asp Phe Thr Leu
        195                 200                 205

Thr Ile Ser Gly Leu Gln Pro Glu Asp Phe Ala Thr Tyr Tyr Cys Leu
```

```
            210                 215                 220

Glu Asp Tyr Asn Tyr Leu Trp Thr Phe Gly Gln Gly Thr Lys Leu Glu
225                 230                 235                 240

Ile Lys Arg Thr Ala Ala Ala Ser Ala His His His His His Lys
                245                 250                 255

Leu Asp Tyr Lys Asp His Asp Gly Asp Tyr Lys Asp His Asp Ile Asp
                260                 265                 270

Tyr Lys Asp Asp Asp Asp Lys
        275
```

```
<210> SEQ ID NO 165
<211> LENGTH: 275
<212> TYPE: PRT
<213> ORGANISM: artificial sequence
<220> FEATURE:
<223> OTHER INFORMATION: scFv sequence G4_3

<400> SEQUENCE: 165
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Trp Leu Tyr Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Ala Ser Asp Ile Gln Met Thr Gln Ser Pro Ser Ser Leu Ser Ala
        130                 135                 140

Ser Val Gly Asp Arg Val Thr Ile Thr Cys Gln Ala Ser Gln Asp Ile
145                 150                 155                 160

Ser Asn Tyr Leu Asn Trp Tyr Gln Gln Lys Pro Gly Lys Ala Pro Lys
                165                 170                 175

Leu Leu Ile Tyr Asp Ala Ser Asn Leu Glu Thr Gly Val Pro Ser Arg
            180                 185                 190

Phe Ser Gly Ser Gly Ser Gly Thr Asp Phe Thr Leu Thr Ile Ser Ser
            195                 200                 205

Leu Gln Pro Glu Asp Phe Ala Thr Tyr Phe Cys Gln Gln Ser Tyr Ser
        210                 215                 220

Thr Pro Gln Thr Phe Gly Gln Gly Thr Lys Val Asp Ile Lys Arg Thr
225                 230                 235                 240

Ala Ala Ala Ser Ala His His His His His His Lys Leu Asp Tyr Lys
                245                 250                 255

Asp His Asp Gly Asp Tyr Lys Asp His Asp Ile Asp Tyr Lys Asp Asp
            260                 265                 270

Asp Asp Lys
        275
```

<210> SEQ ID NO 166
<211> LENGTH: 284
<212> TYPE: PRT
<213> ORGANISM: artificial sequence
<220> FEATURE:
<223> OTHER INFORMATION: scFv sequence G4_4

<400> SEQUENCE: 166

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Val Glu Asp Thr Ala Val Tyr Tyr Cys
                85                  90                  95

Ala Lys Ser Ser Val Gly Trp Trp Ser Phe Asp Tyr Trp Gly Gln Gly
            100                 105                 110

Thr Met Val Thr Val Ser Ser Gly Gly Gly Gly Ser Gly Gly Gly Gly
            115                 120                 125

Ser Gly Gly Gly Ala Ser Asp Ile Val Met Thr Gln Ser Pro Asp Ser
        130                 135                 140

Leu Ala Val Ser Leu Gly Glu Arg Ala Thr Ile Asn Cys Lys Ser Ser
145                 150                 155                 160

Gln Ser Val Leu Ser Ser Ser Asn Asn Asn Asn Tyr Leu Ala Trp Tyr
                165                 170                 175

Gln Gln Arg Pro Gly Gln Pro Pro Lys Leu Leu Phe Tyr Trp Ala Ser
            180                 185                 190

Thr Arg Glu Ser Gly Val Pro Asp Arg Phe Ser Gly Ser Gly Ser Gly
            195                 200                 205

Thr Ser Phe Thr Leu Thr Ile Thr Ser Leu Gln Ala Glu Asp Val Ala
        210                 215                 220

Val Tyr Tyr Cys Gln Gln Tyr Tyr Ser Thr Pro Leu Thr Phe Gly Gly
225                 230                 235                 240

Gly Thr Lys Leu Glu Ile Lys Arg Thr Ala Ala Ala Ser Ala His His
                245                 250                 255

His His His His Lys Leu Asp Tyr Lys Asp His Asp Gly Asp Tyr Lys
            260                 265                 270

Asp His Asp Ile Asp Tyr Lys Asp Asp Asp Asp Lys
        275                 280

<210> SEQ ID NO 167
<211> LENGTH: 279
<212> TYPE: PRT
<213> ORGANISM: artificial sequence
<220> FEATURE:
<223> OTHER INFORMATION: scFv sequence G4_5

<400> SEQUENCE: 167

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

```
Gly Ile Ser Trp Val Arg Gln Ala Pro Gly Gln Gly Leu Glu Trp Met
    35                  40                  45

Gly Trp Ile Gly Ala Tyr Asn Gly Asn Thr Asn Tyr Ala Gln Lys Leu
    50                  55                  60

Gln Gly Arg Val Thr Met Ser Thr Asp Thr Ser Thr Ser Thr Ala Tyr
65                  70                  75                  80

Met Glu Leu Arg Ser Pro Arg Ser Asp Asp Thr Ala Val Tyr Tyr Cys
                85                  90                  95

Ala Arg Gly Gly Thr Gly Gly Asp His Val Phe Ala Tyr Trp Gly Gln
            100                 105                 110

Gly Thr Thr Val Thr Val Ser Ser Gly Gly Gly Gly Ser Gly Gly Gly
            115                 120                 125

Gly Ser Gly Gly Gly Ala Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
    210                 215                 220

Gln Ser Tyr Ser Thr Pro Tyr Thr Phe Gly Gln Gly Thr Lys Val Glu
225                 230                 235                 240

Ile Lys Arg Thr Ala Ala Ala Ser Ala His His His His His His Lys
            245                 250                 255

Leu Asp Tyr Lys Asp His Asp Gly Asp Tyr Lys Asp His Asp Ile Asp
            260                 265                 270

Tyr Lys Asp Asp Asp Asp Lys
            275

<210> SEQ ID NO 168
<211> LENGTH: 279
<212> TYPE: PRT
<213> ORGANISM: artificial sequence
<220> FEATURE:
<223> OTHER INFORMATION: scFv sequence G4_6

<400> SEQUENCE: 168

Glu Val Gln Leu Val Glu Ser Gly Gly Gly Leu Val Gln Pro Gly Gly
1               5                   10                  15

Pro Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Asp Tyr Gly Val Val Tyr Tyr Phe Asp Tyr Trp Gly Gln
            100                 105                 110
```

```
Gly Thr Met Val Thr Val Ser Ser Gly Gly Gly Ser Gly Gly Gly
        115                 120                 125

Gly Ser Gly Gly Gly Ala Ser Asp Ile Gln Met Thr Gln Ser Pro Ser
        130                 135                 140

Ser Leu Ser Ala Ser Val Gly Asp Arg Val Thr Ile Thr Cys Arg Ala
145                 150                 155                 160

Ser Gln Ser Ile Ser Thr Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
        180                 185                 190

Val Pro Ser Arg Phe Ser Gly Ser Gly Ser Gly Thr Asp Phe Thr Leu
        195                 200                 205

Thr Ile Ser Ser Pro Gln Pro Glu Asp Phe Ala Thr Tyr Tyr Cys Gln
        210                 215                 220

Gln Ser Tyr Ser Thr Pro Tyr Thr Phe Gly Gln Gly Thr Lys Val Glu
225                 230                 235                 240

Ile Lys Arg Thr Ala Ala Ala Ser Ala His His His His His His Lys
                245                 250                 255

Leu Asp Tyr Lys Asp His Asp Gly Asp Tyr Lys Asp His Asp Ile Asp
        260                 265                 270

Tyr Lys Asp Asp Asp Asp Lys
        275
```

```
<210> SEQ ID NO 169
<211> LENGTH: 283
<212> TYPE: PRT
<213> ORGANISM: artificial sequence
<220> FEATURE:
<223> OTHER INFORMATION: scFv sequence G4_7

<400> SEQUENCE: 169
```

```
Glu Val Gln Leu Val Glu Ser Gly Gly Gly Trp Val Gln Ser Gly Gly
1               5                   10                  15

Ser Leu Arg Pro Ser Cys Ala Ala Ser Gly Phe Thr Phe Ser His Tyr
        20                  25                  30

Trp Met Ser Trp Val Arg Gln Ala Pro Gly Lys Gly Leu Glu Trp Val
        35                  40                  45

Ala Asn Ile Lys Gln Asp Gly Ser Ile Ile Tyr Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Ile Gly Tyr Ser Ser Ser Ser Phe Asp Tyr Trp Gly Arg Gly
        100                 105                 110

Thr Leu Val Thr Val Ser Ser Gly Gly Gly Gly Ser Gly Gly Gly Gly
        115                 120                 125

Ser Gly Gly Gly Ala Ser Asp Ile Val Met Thr Gln Ser Pro Leu Ser
        130                 135                 140

Leu Pro Val Thr Pro Gly Glu Pro Ala Ser Ile Ser Cys Arg Ser Ser
145                 150                 155                 160

Gln Ser Leu Leu His Ser Asn Arg Phe Asn Tyr Leu Asp Trp Tyr Leu
                165                 170                 175

Gln Lys Pro Gly Gln Ser Pro Gln Leu Leu Ile Tyr Leu Gly Ser Asn
        180                 185                 190
```

-continued

```
Arg Ala Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
        210                 215                 220

Tyr Tyr Cys Met Gln Gly Leu Gln Thr Pro Tyr Thr Phe Gly Gln Gly
225                 230                 235                 240

Thr Lys Val Asp Ile Lys Arg Thr Ala Ala Ala Ser Ala His His His
        245                 250                 255

His His His Lys Leu Asp Tyr Lys Asp His Asp Gly Asp Tyr Lys Asp
        260                 265                 270

His Asp Ile Asp Tyr Lys Asp Asp Asp Lys
        275                 280
```

```
<210> SEQ ID NO 170
<211> LENGTH: 286
<212> TYPE: PRT
<213> ORGANISM: artificial sequence
<220> FEATURE:
<223> OTHER INFORMATION: scFv sequence G4_10

<400> SEQUENCE: 170
```

```
Gln Val Gln Leu Val Glu Ser Gly Gly Gly Val Val Gln Pro Gly Arg
1               5                   10                  15

Pro Leu Arg Leu Ser Cys Ala Ala Ser Gly Phe Thr Phe Ser Ser Tyr
        20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Val Asp Phe Trp Arg Asn Gly Met Asp Val Trp
        100                 105                 110

Gly Arg Gly Thr Leu Val Thr Val Ser Ser Gly Gly Gly Gly Ser Gly
        115                 120                 125

Gly Gly Gly Ser Gly Gly Gly Ala Ser Asp Ile Val Met Thr Gln Pro
        130                 135                 140

Pro Leu Ser Leu Pro Val Thr Leu Gly His Pro Ala Ser Ile Ser Cys
145                 150                 155                 160

Lys Ser Ser Gln Ser Leu Glu Tyr Ser Asp Gly Asn Thr Tyr Leu Asn
                165                 170                 175

Trp Phe Gln Gln Arg Pro Gly Gln Ser Pro Arg Arg Leu Ile Tyr Lys
                180                 185                 190

Val Ser Asn Arg Asp Ser Gly Ala Pro Asp Arg Phe Ser Gly Ser Gly
        195                 200                 205

Ser Gly Thr Asp Phe Thr Leu Glu Ile Ser Arg Val Glu Ala Glu Asp
        210                 215                 220

Val Gly Val Tyr Tyr Cys Met Gln Gly Thr Leu Trp Pro Pro Thr Phe
225                 230                 235                 240

Gly Gln Gly Thr Lys Val Asp Ile Lys Arg Thr Ala Ala Ala Ser Ala
        245                 250                 255

His His His His His His Lys Leu Asp Tyr Lys Asp His Asp Gly Asp
        260                 265                 270
```

```
Tyr Lys Asp His Asp Ile Asp Tyr Lys Asp Asp Asp Lys
    275             280             285

<210> SEQ ID NO 171
<211> LENGTH: 277
<212> TYPE: PRT
<213> ORGANISM: artificial sequence
<220> FEATURE:
<223> OTHER INFORMATION: scFv sequence G4_12

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Ala Asn Gly Asp Phe Leu Asp Tyr Trp Gly Arg Gly Thr Leu
            100                 105                 110

Val Thr Val Ser Ser Gly Gly Gly Gly Ser Gly Gly Gly Gly Ser Gly
            115                 120                 125

Gly Gly Ala Ser Gln Ser Val Leu Thr Gln Pro Ala Ser Val Ser Gly
        130                 135                 140

Ser Pro Gly Gln Ser Ile Thr Ile Ser Cys Thr Gly Thr Ser Ser Asp
145                 150                 155                 160

Val Gly Gly Tyr Asn Phe Val Ser Trp Tyr Gln Gln His Pro Gly Lys
                165                 170                 175

Ala Pro Lys Leu Met Ile Tyr Glu Val Thr Asn Arg Pro Ser Gly Val
            180                 185                 190

Pro Asp Arg Phe Ser Gly Ser Lys Ser Gly Asn Thr Ala Ser Leu Thr
            195                 200                 205

Ile Ser Gly Leu Gln Ala Glu Asp Glu Ala Asp Tyr Tyr Cys Ser Ser
        210                 215                 220

His Ala Ser Pro Arg Val Phe Gly Thr Gly Thr Lys Val Thr Val Leu
225                 230                 235                 240

Arg Thr Ala Ala Ala Ser Ala His His His His His Lys Leu Asp
                245                 250                 255

Tyr Lys Asp His Asp Gly Asp Tyr Lys Asp His Asp Ile Asp Tyr Lys
            260                 265                 270

Asp Asp Asp Asp Lys
        275

<210> SEQ ID NO 172
<211> LENGTH: 280
<212> TYPE: PRT
<213> ORGANISM: artificial sequence
<220> FEATURE:
<223> OTHER INFORMATION: scFv sequence G4_13

<400> SEQUENCE: 172

Gln Val Gln Leu Val Glu Ser Gly Ala Glu Val Lys Lys Pro Gly Gly
1               5                   10                  15
```

```
Ser Leu Arg Leu Ser Cys Ala Ala Ser Gly Phe Thr Phe Ser Ser Tyr
        20              25              30

Ser Met Asn Trp Val Arg Gln Ala Pro Gly Lys Gly Leu Glu Trp Val
        35              40              45

Ser Ser Ile Ser Gly Thr Ser Ser Tyr Ile Tyr Tyr Ala Asp Ser Val
    50              55              60

Lys Gly Arg Phe Thr Ile Ser Arg Asp Asn Ala Lys Asn Ser Leu Tyr
65              70              75              80

Leu Gln Met Ser Ser Leu Arg Ala Glu Asp Thr Ala Val Tyr Tyr Cys
                85              90              95

Ala Arg Gly Gly Leu Gly Met Val Asp Pro Trp Gly Gln Gly Thr Leu
            100             105             110

Val Thr Val Ser Ser Gly Gly Gly Gly Ser Gly Gly Gly Gly Ser Gly
            115             120             125

Gly Gly Ala Ser Asn Phe Met Leu Thr Gln Pro His Ser Val Ser Glu
        130             135             140

Ser Pro Gly Lys Thr Val Thr Ile Ser Cys Thr Arg Ser Ser Gly Ser
145             150             155             160

Ile Ala Ser Asn Tyr Val Gln Trp Tyr Gln Gln Arg Pro Gly Ser Ser
                165             170             175

Pro Ser Thr Val Ile Tyr Glu Asp Asn Gln Arg Pro Ser Gly Val Pro
            180             185             190

Asp Arg Phe Ser Gly Ser Ile Asp Ser Ser Ser Asn Ser Ala Ser Leu
            195             200             205

Thr Ile Ser Gly Leu Arg Thr Glu Asp Glu Ala Asp Tyr Tyr Cys Gln
        210             215             220

Ser Tyr Asp Ser Ser Ile Tyr Val Val Phe Gly Gly Gly Thr Lys Leu
225             230             235             240

Thr Val Leu Arg Thr Ala Ala Ala Ser Ala His His His His His His
            245             250             255

Lys Leu Asp Tyr Lys Asp His Asp Gly Asp Tyr Lys Asp His Asp Ile
            260             265             270

Asp Tyr Lys Asp Asp Asp Asp Lys
        275             280
```

<210> SEQ ID NO 173
<211> LENGTH: 280
<212> TYPE: PRT
<213> ORGANISM: artificial sequence
<220> FEATURE:
<223> OTHER INFORMATION: scFv sequence G4_14

<400> SEQUENCE: 173

```
Glu Val Gln Leu Val Gln Ser Gly Ala Glu Val Lys Lys Pro Gly Glu
1               5               10              15

Ser Leu Arg Ile Ser Cys Lys Gly Ser Gly Tyr Ser Phe Thr Ser Tyr
        20              25              30

Trp Ile Ser Trp Val Arg Gln Met Pro Gly Lys Gly Leu Glu Trp Met
        35              40              45

Gly Arg Ile Asp Pro Ser Asp Ser Tyr Thr Asn Tyr Ser Pro Ser Phe
    50              55              60

Pro Gly His Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
                85              90              95
```

```
Ala Ala Asp Thr Ala His Gly Met Asp Val Trp Gly Arg Gly Thr Leu
            100                 105                 110

Val Thr Val Ser Ser Gly Gly Gly Ser Gly Gly Gly Gly Ser Gly
            115                 120                 125

Gly Gly Ala Ser Asn Phe Met Leu Thr Gln Pro His Ser Val Ser Glu
            130                 135                 140

Ser Pro Gly Lys Thr Val Thr Ile Ser Cys Thr Arg Ser Arg Gly Ser
145                 150                 155                 160

Ile Ala Gly Asn Tyr Val His Trp Tyr Gln Gln Arg Pro Gly Arg Ala
                165                 170                 175

Pro Thr Thr Val Ile Tyr Arg Asp Lys Glu Arg Pro Ser Gly Val Pro
                180                 185                 190

Asp Arg Ile Ser Gly Ser Ile Asp Ser Ser Ser Asn Ser Ala Ser Leu
            195                 200                 205

Thr Ile Ser Gly Leu Lys Thr Glu Asp Glu Ala Asp Tyr Tyr Cys Gln
    210                 215                 220

Ser Tyr Asp Ser Ser Thr His Val Val Phe Gly Gly Gly Thr Lys Leu
225                 230                 235                 240

Thr Val Leu Arg Thr Ala Ala Ala Ser Ala His His His His His His
                245                 250                 255

Lys Leu Asp Tyr Lys Asp His Asp Gly Asp Tyr Lys Asp His Asp Ile
                260                 265                 270

Asp Tyr Lys Asp Asp Asp Asp Lys
                275                 280
```

<210> SEQ ID NO 174
<211> LENGTH: 282
<212> TYPE: PRT
<213> ORGANISM: artificial sequence
<220> FEATURE:
<223> OTHER INFORMATION: scFv sequence G4_15

<400> SEQUENCE: 174

```
Glu Val Gln Leu Val Gln Ser Glu Ala Glu Val Lys Lys Pro Gly Ala
1               5                   10                  15

Ser Val Lys Val Ser Cys Lys Ala Ser Gly Tyr Thr Phe Thr Arg His
                20                  25                  30

Tyr Met His Trp Val Arg Gln Ala Pro Gly Gln Gly Leu Glu Trp Met
            35                  40                  45

Gly Leu Ile Asn Pro Ser Gly Ser Ser Thr Val Tyr Ala Gln Lys Phe
    50                  55                  60

Gln Gly Arg Val Thr Leu Thr Arg Asp Thr Ser Thr Ser Thr Asp Tyr
65                  70                  75                  80

Met Glu Leu Ser Ser Leu Arg Ser Glu Asp Thr Ala Val Tyr Tyr Cys
                85                  90                  95

Ala Arg Asp Asn Ser His Leu Asp Gln Val Trp Trp Phe Asp Pro Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ala Ser Gln Ser Ala Leu Thr Gln Pro
            130                 135                 140

Ala Ser Val Ser Gly Ser Pro Gly Gln Ser Ile Thr Ile Ser Cys Thr
145                 150                 155                 160

Gly Thr Ser Ser Asp Val Gly Gly Tyr Asn Tyr Val Ser Trp Tyr Gln
                165                 170                 175
```

```
Gln His Pro Gly Lys Ala Pro Lys Leu Met Ile Tyr Asp Val Ser Asn
            180                 185                 190

Arg Pro Ser Gly Val Ser Asn Arg Phe Ser Gly Ser Lys Ser Gly Asn
            195                 200                 205

Thr Ala Ser Leu Thr Ile Ser Gly Leu Gln Ala Glu Asp Glu Ala Asp
            210                 215                 220

Tyr Tyr Cys Ser Ser Tyr Gly Ser Gly Ser Val Phe Gly Thr Gly Thr
225                 230                 235                 240

Lys Leu Thr Val Leu Arg Thr Ala Ala Ala Ser Ala His His His His
            245                 250                 255

His His Lys Leu Asp Tyr Lys Asp His Asp Gly Asp Tyr Lys Asp His
            260                 265                 270

Asp Ile Asp Tyr Lys Asp Asp Asp Asp Lys
            275                 280
```

```
<210> SEQ ID NO 175
<211> LENGTH: 281
<212> TYPE: PRT
<213> ORGANISM: artificial sequence
<220> FEATURE:
<223> OTHER INFORMATION: scFv sequence G4_16

<400> SEQUENCE: 175
```

```
Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
            50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Gly Asp Phe Tyr Gly Met Asp Val Trp Gly Gln Gly
            100                 105                 110

Thr Leu Val Thr Val Ser Ser Gly Gly Gly Gly Ser Gly Gly Gly Gly
            115                 120                 125

Ser Gly Gly Gly Ala Ser Gln Ser Val Leu Thr Gln Pro Pro Ser Ala
            130                 135                 140

Ser Gly Ser Pro Gly Gln Ser Val Thr Phe Ser Cys Thr Gly Thr Ser
145                 150                 155                 160

Ser Asp Ile Gly Ala Phe Asn Ser Val Ser Trp Tyr Gln Gln His Pro
                165                 170                 175

Gly Lys Ala Pro Lys Leu Leu Ile Tyr Glu Ile Thr Lys Arg Pro Ser
            180                 185                 190

Gly Val Pro Asp Arg Phe Ser Gly Ser Lys Ser Gly Asn Thr Ala Ser
            195                 200                 205

Leu Thr Ile Ser Val Leu Gln Ala Glu Asp Glu Ala Asp Tyr Tyr Cys
            210                 215                 220

Thr Ser Tyr Ala Gly Ser Asn Thr Leu Ile Phe Gly Gly Gly Thr Lys
225                 230                 235                 240

Val Thr Val Leu Arg Thr Ala Ala Ala Ser Ala His His His His His
            245                 250                 255
```

His Lys Leu Asp Tyr Lys Asp His Asp Gly Asp Tyr Lys Asp His Asp
            260                 265                 270

Ile Asp Tyr Lys Asp Asp Asp Lys
        275                 280

<210> SEQ ID NO 176
<211> LENGTH: 278
<212> TYPE: PRT
<213> ORGANISM: artificial sequence
<220> FEATURE:
<223> OTHER INFORMATION: scFv sequence G4_18

<400> SEQUENCE: 176

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Ala Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Asp Leu Ser Ser Leu Asp Tyr Trp Gly Arg Gly Thr
            100                 105                 110

Leu Val Thr Val Ser Ser Gly Gly Gly Gly Ser Gly Gly Gly Gly Ser
            115                 120                 125

Gly Gly Gly Ala Ser Ser Tyr Glu Leu Thr Gln Pro Pro Ser Val Thr
        130                 135                 140

Glu Ser Pro Gly Gln Thr Ala Arg Ile Thr Cys Ser Gly Asp Ala Leu
145                 150                 155                 160

Ala Lys Gln Tyr Ala Tyr Trp Tyr Gln Gln Lys Pro Gly Gln Ala Pro
                165                 170                 175

Val Leu Val Ile Tyr Arg Asp Ser Glu Arg Pro Ser Glu Ile Pro Glu
            180                 185                 190

Arg Phe Ser Gly Ser Ser Ser Gly Thr Thr Val Thr Leu Thr Ile Ser
        195                 200                 205

Gly Val Gln Ala Glu Asp Glu Ala Asp Tyr Tyr Cys Gln Ser Ala Asp
    210                 215                 220

Ser Ser Gly Thr Tyr Thr Val Phe Gly Gly Gly Thr Lys Leu Thr Val
225                 230                 235                 240

Leu Arg Thr Ala Ala Ala Ser Ala His His His His His His Lys Leu
                245                 250                 255

Asp Tyr Lys Asp His Asp Gly Asp Tyr Lys Asp His Asp Ile Asp Tyr
            260                 265                 270

Lys Asp Asp Asp Asp Lys
        275

<210> SEQ ID NO 177
<211> LENGTH: 284
<212> TYPE: PRT
<213> ORGANISM: artificial sequence
<220> FEATURE:
<223> OTHER INFORMATION: scFv sequence G4_19

-continued

<400> SEQUENCE: 177

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Ser Tyr Gly Asp Gly Met Asp Val Trp Gly
            100                 105                 110

Gln Gly Thr Thr Val Thr Val Ser Ser Gly Gly Gly Ser Gly Gly
            115                 120                 125

Gly Gly Ser Gly Gly Gly Ala Ser Asn Phe Met Leu Thr Gln Pro His
        130                 135                 140

Ser Val Ser Glu Ser Pro Gly Lys Thr Val Thr Ile Ser Cys Thr Arg
145                 150                 155                 160

Ser Ser Gly Ser Ile Ala Ser Asn Tyr Val Gln Trp Tyr Gln Gln Arg
                165                 170                 175

Pro Gly Ser Pro Pro Ile Thr Leu Ile Tyr Asp Asp Asp Gln Arg Pro
            180                 185                 190

Ser Gly Val Pro His Arg Phe Ser Gly Ser Ile Asp Thr Ser Ser Asn
            195                 200                 205

Pro Ala Ser Leu Thr Ile Ser Gly Leu Lys Thr Glu Asp Glu Ala Asp
        210                 215                 220

Tyr Tyr Cys Gln Ser Tyr Asp Ser Ser Asn His Val Val Phe Gly Gly
225                 230                 235                 240

Gly Thr Lys Leu Thr Val Leu Arg Thr Ala Ala Ala Ser Ala His His
            245                 250                 255

His His His His Lys Leu Asp Tyr Lys Asp His Asp Gly Asp Tyr Lys
            260                 265                 270

Asp His Asp Ile Asp Tyr Lys Asp Asp Asp Asp Lys
            275                 280
```

<210> SEQ ID NO 178
<211> LENGTH: 277
<212> TYPE: PRT
<213> ORGANISM: artificial sequence
<220> FEATURE:
<223> OTHER INFORMATION: scFv sequence G4_20

<400> SEQUENCE: 178

```
Gln Val Gln Leu Val Glu Ser Gly Ala Glu Val Lys Lys Pro Gly Ala
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Val Asp Lys Ser Thr Arg Thr Ala Tyr
```

225                                        226
-continued

```
65              70              75              80

Met Glu Leu Ser Ser Leu Arg Ser Lys Asp Thr Ala Val Tyr Tyr Cys
                85              90              95

Ala Arg Gly Asn Ser Arg Ser Asp Ala Phe Asp Ile Trp Gly Gln Gly
            100             105             110

Thr Met Val Thr Val Ser Ser Gly Gly Gly Ser Gly Gly Gly
            115             120             125

Ser Gly Gly Gly Ala Ser Ser Tyr Glu Leu Thr His Pro Pro Ser Val
        130             135             140

Ser Val Ser Pro Gly Gln Thr Ala Ser Ile Thr Cys Ser Gly Asp Lys
145             150             155             160

Leu Gly Asp Lys Phe Val Ser Trp Tyr His Gln Lys Pro Gly Gln Ser
            165             170             175

Pro Val Leu Val Ile Tyr Gln Asp Ser Lys Arg Pro Ser Gly Ile Pro
            180             185             190

Glu Arg Phe Ser Gly Ser Asn Ser Gly Asn Thr Ala Thr Leu Thr Ile
            195             200             205

Ser Gly Thr Arg Ala Met Asp Glu Ala Asp Tyr Tyr Cys Gln Ala Trp
        210             215             220

Asp Ser Ser Thr Val Val Phe Gly Gly Gly Thr Lys Leu Thr Val Leu
225             230             235             240

Arg Thr Ala Ala Ala Ser Ala His His His His His His Lys Leu Asp
            245             250             255

Tyr Lys Asp His Asp Gly Asp Tyr Lys Asp His Asp Ile Asp Tyr Lys
            260             265             270

Asp Asp Asp Asp Lys
        275
```

<210> SEQ ID NO 179
<211> LENGTH: 279
<212> TYPE: PRT
<213> ORGANISM: artificial sequence
<220> FEATURE:
<223> OTHER INFORMATION: scFv sequence G4_22

<400> SEQUENCE: 179

```
Gln Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Thr Tyr
                20              25              30

Ala Met Ser Trp Val Arg Gln Ala Pro Gly Lys Gly Leu Glu Trp Val
            35              40              45

Ser Thr Val Ser Gly Ser Gly Gly Thr Thr Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Asp Ser Thr Ala Val Thr Asp Trp Phe Asp Pro Trp Gly Arg
            100             105             110

Gly Thr Leu Val Thr Val Ser Ser Gly Gly Gly Gly Ser Gly Gly Gly
            115             120             125

Gly Ser Gly Gly Gly Ala Ser Asp Ile Gln Met Thr Gln Ser Pro Ser
        130             135             140

Ser Leu Ser Ala Ser Val Gly Asp Arg Val Thr Ile Thr Cys Gln Ala
```

-continued

```
145                150                155                160

Ser Gln Asp Ile Ser Asn Tyr Leu Asn Trp Tyr Gln Gln Lys Pro Gly
                 165                170                175

Lys Ala Pro Lys Leu Leu Ile Tyr Ala Ala Ser Ser Leu Gln Ser Gly
             180                185                190

Val Pro Ser Arg Phe Ser Val Ser Gly Ser Gly Thr Asp Phe Thr Leu
             195                200                205

Thr Ile Ser Asn Leu Gln Pro Glu Asp Phe Ala Thr Tyr Tyr Cys Gln
         210                215                220

Gln Ser Tyr Ser Ile Pro Trp Thr Phe Gly Gln Gly Thr Lys Val Glu
225                230                235                240

Ile Lys Arg Thr Ala Ala Ala Ser Ala His His His His His Lys
                 245                250                255

Leu Asp Tyr Lys Asp His Asp Gly Asp Tyr Lys Asp His Asp Ile Asp
                 260                265                270

Tyr Lys Asp Asp Asp Asp Lys
             275

<210> SEQ ID NO 180
<211> LENGTH: 279
<212> TYPE: PRT
<213> ORGANISM: artificial sequence
<220> FEATURE:
<223> OTHER INFORMATION: scFv sequence G4_23

<400> SEQUENCE: 180

Glu Val Gln Leu Val Glu Ser Gly Gly Gly Val Val Gln Pro Gly Arg
1                5                  10                 15

Ser Leu Arg Leu Ser Cys Ala Ala Ser Gly Phe Thr Phe Ser Ser Tyr
             20                 25                 30

Gly Met His Trp Val Arg Gln Ala Pro Gly Lys Gly Leu Glu Trp Val
         35                 40                 45

Ala Val Ile Trp Tyr Asp Gly Ser Asn Lys Tyr Tyr Ala Asp Ser Val
     50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
                 85                 90                 95

Ala Arg Gly Glu Val Ala Ala Leu Tyr Tyr Phe Asp Tyr Trp Gly Gln
             100                105                110

Gly Thr Leu Val Thr Val Ser Ser Gly Gly Gly Gly Ser Gly Gly Gly
         115                120                125

Gly Ser Gly Gly Gly Ala Ser Asp Ile Gln Met Thr Gln Ser Pro Ser
     130                135                140

Ser Leu Ser Ala Ser Val Gly Asp Arg Val Thr Ile Thr Cys Arg Ala
145                150                155                160

Ser Gln Gly Ile Ser Asn Ser Leu Ala Trp Tyr Gln Gln Lys Pro Gly
                 165                170                175

Lys Ala Pro Lys Leu Leu Leu Tyr Ala Ala Ser Arg Leu Glu Ser Gly
             180                185                190

Val Pro Ser Arg Phe Ser Gly Ser Gly Ser Gly Thr Asp Tyr Thr Leu
             195                200                205

Thr Ile Ser Ser Leu Gln Pro Glu Asp Phe Ala Thr Tyr Tyr Cys Gln
         210                215                220

Gln Tyr Tyr Ser Thr Pro Arg Thr Phe Gly Gly Gly Thr Lys Leu Glu
```

-continued

```
225            230            235            240

Ile Lys Arg Thr Ala Ala Ala Ser Ala His His His His His Lys
            245            250            255

Leu Asp Tyr Lys Asp His Asp Gly Asp Tyr Lys Asp His Asp Ile Asp
        260            265            270

Tyr Lys Asp Asp Asp Asp Lys
        275

<210> SEQ ID NO 181
<211> LENGTH: 287
<212> TYPE: PRT
<213> ORGANISM: artificial sequence
<220> FEATURE:
<223> OTHER INFORMATION: scFv sequence G4_24

<400> SEQUENCE: 181

Gln Val Gln Leu Gln Gln Ser Gly Pro Gly Leu Val Lys Pro Ser Gln
1               5               10              15

Thr Leu Ser Leu Thr Cys Ala Ile Ser Gly Ala Ser Val Ser Ser Asn
            20              25              30

Ser Val Ala Trp Asn Trp Ile Arg Gln Ser Pro Ser Arg Gly Leu Glu
        35              40              45

Trp Leu Gly Arg Thr Tyr Tyr Arg Ser Arg Trp Tyr Asn Asp Tyr Ala
    50              55              60

Leu Ser Val Lys Ser Arg Ile Ile Ile Asn Pro Asp Thr Ser Lys Asn
65              70              75              80

Gln Phe Ser Leu Gln Leu Asn Ser Val Thr Pro Glu Asp Thr Ala Val
            85              90              95

Tyr Tyr Cys Ala Arg Asp Trp Ser Ser Thr Arg Ser Phe Asp Tyr Trp
            100             105             110

Gly Arg Gly Thr Leu Val Thr Val Ser Ser Gly Gly Gly Gly Ser Gly
        115             120             125

Gly Gly Gly Ser Gly Gly Gly Ala Ser Asp Ile Val Met Thr Gln Ser
        130             135             140

Pro Asp Ser Leu Ala Val Ser Leu Gly Glu Arg Ala Thr Ile Asn Cys
145             150             155             160

Lys Ser Ser Gln Ser Val Leu Tyr Ser Ser Asn Asn Lys Asn Tyr Leu
            165             170             175

Ala Trp Tyr Gln Gln Lys Pro Gly Gln Pro Pro Lys Leu Leu Ile Ser
            180             185             190

Trp Ala Ser Thr Arg Glu Ser Gly Val Pro Asp Arg Phe Ser Gly Ser
            195             200             205

Gly Ser Gly Thr Asp Phe Thr Leu Thr Ile Asn Ser Leu Gln Ser Glu
        210             215             220

Asp Val Ala Ile Tyr Tyr Cys Gln Gln Tyr Tyr Ser Thr Pro Pro Thr
225             230             235             240

Phe Gly Gln Gly Thr Lys Leu Glu Ile Lys Arg Thr Ala Ala Ala Ser
            245             250             255

Ala His His His His His His Lys Leu Asp Tyr Lys Asp His Asp Gly
            260             265             270

Asp Tyr Lys Asp His Asp Ile Asp Tyr Lys Asp Asp Asp Asp Lys
        275             280             285

<210> SEQ ID NO 182
<211> LENGTH: 283
<212> TYPE: PRT
```

```
<213> ORGANISM: artificial sequence
<220> FEATURE:
<223> OTHER INFORMATION: scFv sequence G4_25

<400> SEQUENCE: 182

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Arg Asp Gly Tyr Asn Tyr Ile Gly Ser Leu Gly Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ala Ser Gln Ser Ala Leu Thr Gln
    130                 135                 140

Pro Arg Ser Val Ser Gly Ser Pro Gly Gln Ser Val Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Val Ser
            180                 185                 190

Asn Arg Pro Ser Gly Val Ser Asn Arg Phe Ser Gly Ser Lys Ser Gly
            195                 200                 205

Asn Thr Ala Ser Leu Thr Ile Ser Gly Leu Gln Ala Glu Asp Glu Ala
        210                 215                 220

Asp Tyr Tyr Cys Ser Ser Tyr Gly Ser Gly Ser Val Phe Gly Thr Gly
225                 230                 235                 240

Thr Lys Leu Thr Val Leu Arg Thr Ala Ala Ala Ser Ala His His His
            245                 250                 255

His His His Lys Leu Asp Tyr Lys Asp His Asp Gly Asp Tyr Lys Asp
            260                 265                 270

His Asp Ile Asp Tyr Lys Asp Asp Asp Lys
        275                 280

<210> SEQ ID NO 183
<211> LENGTH: 280
<212> TYPE: PRT
<213> ORGANISM: artificial sequence
<220> FEATURE:
<223> OTHER INFORMATION: scFv sequence G4_26

<400> SEQUENCE: 183

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45
```

```
Gly Gly Ile Ile Pro Ile Phe Gly Thr Ala Asn Tyr Ala Gln Lys Phe
    50              55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Ser Ser Arg Gly Ser Gly Trp Phe Pro Leu Gly Tyr Trp Gly Gln
            100             105             110

Gly Thr Leu Val Thr Val Ser Ser Gly Gly Gly Gly Ser Gly Gly Gly
        115             120             125

Gly Ser Gly Gly Gly Ala Ser Gln Ser Gly Leu Thr Gln Pro Ala Ser
    130             135             140

Val Ser Gly Ser Pro Gly Gln Ser Ile Thr Ile Ser Cys Thr Gly Thr
145             150             155             160

Ser Ser Asp Val Gly Ser Tyr Asn Leu Val Ser Trp Tyr Gln Gln His
            165             170             175

Pro Gly Lys Ala Pro Lys Leu Met Ile Tyr Glu Val Ser Lys Arg Pro
            180             185             190

Ser Gly Val Ser Asn Arg Phe Ser Gly Ser Lys Ser Gly Asn Thr Ala
            195             200             205

Ser Leu Thr Ile Ser Gly Leu Gln Ala Glu Asp Glu Ala Asp Tyr Tyr
    210             215             220

Cys Ser Ser Phe Gly Ser Gly Ser Ile Phe Gly Thr Gly Thr Lys Leu
225             230             235             240

Thr Val Leu Arg Thr Ala Ala Ala Ser Ala His His His His His His
            245             250             255

Lys Leu Asp Tyr Lys Asp His Asp Gly Asp Tyr Lys Asp His Asp Ile
            260             265             270

Asp Tyr Lys Asp Asp Asp Asp Lys
    275             280
```

```
<210> SEQ ID NO 184
<211> LENGTH: 282
<212> TYPE: PRT
<213> ORGANISM: artificial sequence
<220> FEATURE:
<223> OTHER INFORMATION: scFv sequence G4_27

<400> SEQUENCE: 184
```

```
Gln Val Gln Leu Val Gln Ser Gly Ala Glu Val Lys Lys Pro Gly Glu
1               5                   10                  15

Ser Leu Lys Ile Ser Cys Lys Ser Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50              55                  60

Gln Gly Gln Val Thr Phe Ser Ala Asp Glu Ser Ile Ser Thr Ala Tyr
65              70                  75                  80

Leu Gln Trp Ser Ser Leu Lys Ala Ser Asp Thr Ala Met Tyr Tyr Cys
                85                  90                  95

Ala Arg His Gly Ala Tyr Gly Asp Tyr Pro Asp Thr Phe Asp Ile Trp
            100             105             110

Gly Gln Gly Thr Leu Val Thr Val Ser Ser Gly Gly Gly Gly Ser Gly
        115             120             125
```

-continued

```
Gly Gly Gly Ser Gly Gly Gly Ala Ser Ser Tyr Glu Leu Thr Gln Asp
    130             135             140

Pro Ala Val Ser Val Ala Leu Gly Gln Thr Val Ser Ile Thr Cys Gln
145             150             155             160

Gly Asp Ser Leu Arg Asn Phe Tyr Ala Asn Trp Tyr Gln Gln Lys Pro
                165             170             175

Gly Gln Ala Pro Val Leu Val Ile Tyr Gly Lys Asn Asn Arg Pro Ser
                180             185             190

Gly Ile Pro Asp Arg Phe Ser Gly Ser Ser Ser Gly Asn Thr Ala Ser
                195             200             205

Leu Thr Ile Thr Gly Ala Gln Ala Glu Asp Glu Ala Asp Tyr Tyr Cys
    210             215             220

Asn Ser Arg Asp Ser Ser Gly Asn His Leu Val Phe Gly Gly Gly Thr
225             230             235             240

Gln Leu Thr Val Leu Arg Thr Ala Ala Ala Ser Ala His His His His
                245             250             255

His His Lys Leu Asp Tyr Lys Asp His Asp Gly Asp Tyr Lys Asp His
                260             265             270

Asp Ile Asp Tyr Lys Asp Asp Asp Asp Lys
                275             280
```

```
<210> SEQ ID NO 185
<211> LENGTH: 283
<212> TYPE: PRT
<213> ORGANISM: artificial sequence
<220> FEATURE:
<223> OTHER INFORMATION: scFv sequence G4_28

<400> SEQUENCE: 185
```

```
Gln Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Asp Asp Tyr
                20              25              30

Ala Met His Trp Val Arg Gln Ala Pro Gly Lys Gly Leu Glu Trp Val
                35              40              45

Ser Gly Ile Ser Ala Gly Gly Gly Ser Thr Asn Tyr Ala Gly Ser Val
    50              55              60

Lys Gly Arg Phe Thr Val Ser Arg Asp Thr Ser Lys Asn Thr Leu Tyr
65              70              75              80

Leu Gln Met Asn Ser Leu Arg Ala Glu Asp Thr Ala Val Tyr Tyr Cys
                85              90              95

Val Lys Ser Tyr Val Asp Thr Ala Met Arg Tyr Tyr Tyr Tyr Tyr Met
                100             105             110

Asp Val Trp Gly Gln Gly Thr Met Val Thr Val Ser Ser Gly Gly Gly
            115             120             125

Gly Ser Gly Gly Gly Gly Ser Gly Gly Gly Ala Ser Ser Tyr Glu Leu
    130             135             140

Thr Gln Asp Pro Ala Val Ser Val Ala Leu Gly Gln Thr Val Thr Ile
145             150             155             160

Thr Cys Gln Gly Asp Ser Leu Arg Asn Tyr Tyr Ala Ser Trp Tyr Arg
                165             170             175

Gln Lys Pro Gly Gln Thr Pro Val Leu Val Val Tyr Gly Lys Asn Asn
                180             185             190

Arg Pro Ser Gly Ile Pro Asp Arg Phe Ser Val Ser Ala Ser Gly Asn
                195             200             205
```

```
Thr Ala Ser Leu Thr Ile Thr Gly Ala Gln Ala Glu Asp Glu Gly Asp
    210                 215                 220

Tyr Tyr Cys Asn Ser Arg Asp Ser Ser Gly Val Val Phe Gly Gly Gly
225                 230                 235                 240

Thr Lys Val Thr Val Leu Arg Thr Ala Ala Ala Ser Ala His His His
                245                 250                 255

His His His Lys Leu Asp Tyr Lys Asp His Asp Gly Asp Tyr Lys Asp
                260                 265                 270

His Asp Ile Asp Tyr Lys Asp Asp Asp Lys
        275                 280
```

```
<210> SEQ ID NO 186
<211> LENGTH: 13
<212> TYPE: PRT
<213> ORGANISM: artificial sequence
<220> FEATURE:
<223> OTHER INFORMATION: Linker

<400> SEQUENCE: 186

Gly Gly Gly Gly Ser Gly Gly Gly Gly Ser Gly Gly Gly
1               5                   10
```

```
<210> SEQ ID NO 187
<211> LENGTH: 348
<212> TYPE: DNA
<213> ORGANISM: artificial sequence
<220> FEATURE:
<223> OTHER INFORMATION: Nucleotide VH sequence G4_1

<400> SEQUENCE: 187
gaggtgcagc tgttggagtc tggggggggc gtggtccagc ctgggaggc cctgagactc      60 tcctgtgcag cgtctggatt caccttcagt agctatagca tgaactgggt ccgccaggct     120
ccagggaagg ggctggagtg ggtctcatcc attagtagta gtagtagtta catatactac     180
gcagactcag tgaagggccg attcaccatc tccagagaca attccaagaa cacgctgtat     240
ctgcaaatga acagcctgag agccgaggac acggccgtat attactgtgc gaaaggacac     300
tggtacttcg atctctgggg ccgtggcacc ctggtcaccg tctcgagt               348
```

```
<210> SEQ ID NO 188
<211> LENGTH: 360
<212> TYPE: DNA
<213> ORGANISM: artificial sequence
<220> FEATURE:
<223> OTHER INFORMATION: Nucleotide VH sequence G4_2

<400> SEQUENCE: 188
cagatgcagc tggtgcagtc tggggctgag gtgaagaagc ctggggctac agtgaaaatc      60
tcctgcaagg tttctggata cccttttcacc gactactata tccactgggt gcaacaggcc    120
cctggaaaag ggcttgagtg gatggggactt gttgatcctg aggatgggca aagtagatcc    180
gcggagaggt tccagggcag agtcaccata accgcggaca cgtctacaga cacagcctac     240
atggagctga gcagcctgag atctgaggac acggccgtgt attactgtgc aacattccca     300
gtggctggat tctacggtat ggacgtctgg ggccagggaa ccctggtcac cgtctcgagt     360
```

```
<210> SEQ ID NO 189
<211> LENGTH: 348
<212> TYPE: DNA
<213> ORGANISM: artificial sequence
<220> FEATURE:
<223> OTHER INFORMATION: Nucleotide VH sequence G4_3
```

<400> SEQUENCE: 189
gaggtgcagc tggtggagtc cggggggaggc ttggtccagc cggggggggtc cctgagactc        60 tcctgtgcag cctctggatt caccttcagt agctatagca tgaactgggt ccgccaggct        120
ccagggaagg ggctggagtg ggtctcatcc attagtagta gtagtagtta catatactac        180
gcagactccg tgaagggccg gttcaccatc tccagagaca attccaagaa cacgctgtat        240
ctgcaaatga acagcctgag agccgaggac acggccgtgt attactgtgc gagaggaggg        300
tggctatatg actactgggg ccaaggaacc ctggtcaccg tctcgagt               348

<210> SEQ ID NO 190
<211> LENGTH: 357
<212> TYPE: DNA
<213> ORGANISM: artificial sequence
<220> FEATURE:
<223> OTHER INFORMATION: Nucleotide VH sequence G4_4

<400> SEQUENCE: 190
caggtgcagc tggtggagtc tggggggaggc ttggtacagc ctggggggtc cctgagactc        60
tcctgtgcag cctctggatt caccttagc agctatgcca tgagctgggt ccgccaggct        120
ccagggaagg ggctggagtg ggtctcagct attagtggta gtggtggtag cacatactac        180
gcagactccg tgaagggccg gttcaccatc tccagagaca attccaaaaa caccctgtat        240
ctgcaaatga gcagcctgag agtcgaagac acggccgtat attattgtgc gaaatcgtcg        300
gtgggctggt ggtcttttga ctactgggggc caagggacaa tggtcaccgt ctcgagt         357

<210> SEQ ID NO 191
<211> LENGTH: 360
<212> TYPE: DNA
<213> ORGANISM: artificial sequence
<220> FEATURE:
<223> OTHER INFORMATION: Nucleotide VH sequence G4_5

<400> SEQUENCE: 191
gaagtgcagc tggtgcagtc tggggggctgag gtgaagaagc ctgggtcctc ggtgaaggtc        60
tcctgcaagg cttctggtta caccttttacc agctacggta tcagctgggt gcgacaggcc        120
cctggacaag ggcttgagtg gatgggatgg atcggcgctt acaatggtaa cacaaactat        180
gcacagaagc tccagggcag agtcaccatg agcacagaca catccacgag cacagcctac        240
atggagctga ggagcccgag atctgacgac acggccgtgt attactgtgc gagaggcggg        300
acggggggtg accacgtctt tgcctactgg gggcaaggga ccacggtcac cgtctcgagt        360

<210> SEQ ID NO 192
<211> LENGTH: 360
<212> TYPE: DNA
<213> ORGANISM: artificial sequence
<220> FEATURE:
<223> OTHER INFORMATION: Nucleotide VH sequence G4_6

<400> SEQUENCE: 192
gaggtgcagc tggtggagtc tggggggaggc ttggtacagc ctgggggggcc cctgagactc        60 tcctgtgcag cctctggatt caccttttagc agctatgcca tgaactgggt ccgccaggct        120
ccagggaagg ggctggagtg ggtctcagct attagtggta gtggtggtag cacatactac        180
gcagactccg tgaagggccg gttcaccatc tccagagaca attccaagaa cacgctgtat        240
ctgcaaatga acagcctgag agccgaggac acggccgtat attactgtgc gaaagccgac        300

```
tacggggtgg tctactactt tgactactgg ggccaaggga caatggtcac cgtctcgagt      360
```

```
<210> SEQ ID NO 193
<211> LENGTH: 357
<212> TYPE: DNA
<213> ORGANISM: artificial sequence
<220> FEATURE:
<223> OTHER INFORMATION: Nucleotide VH sequence G4_7

<400> SEQUENCE: 193
gaggtgcagc tggtggagtc tggggggaggc tgggtccagt ctggggggtc cctgagaccc      60
tcctgtgcag cctctggatt caccttagt cactattgga tgagttgggt ccgccaggct      120
ccagggaagg ggctggagtg ggtggccaac ataaagcaag atggaagtat catatactat      180
gcagactctg tgaagggccg attcaccatc tccaggaca acgccaagaa ctcagtgtat      240
ctgcaaatga acagcctgag agccgaggac acggctgtgt attactgtgc gagaattggg      300
tatagcagct cgtctttga ctactggggc cgtggcaccc tggtcaccgt ctcgagt      357
```

```
<210> SEQ ID NO 194
<211> LENGTH: 366
<212> TYPE: DNA
<213> ORGANISM: artificial sequence
<220> FEATURE:
<223> OTHER INFORMATION: Nucleotide VH sequence G4_10

<400> SEQUENCE: 194
caggtgcagc tggtggagtc tggggggaggc gtggtccagc ctgggaggcc cctgagactc      60
tcctgtgcag cctctggatt caccttcagt agctatgcta tgcactgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaagatggg      300
gccgtggatt tttggcgaaa cggtatggac gtctggggcc gtggcaccct ggtcaccgtc      360
tcgagt                                                                  366
```

```
<210> SEQ ID NO 195
<211> LENGTH: 351
<212> TYPE: DNA
<213> ORGANISM: artificial sequence
<220> FEATURE:
<223> OTHER INFORMATION: Nucleotide VH sequence G4_12

<400> SEQUENCE: 195
gaggtgcagc tgttggagtc tggaggaggc ttggtccagc ctggggggtc cctgagactc      60
tcctgtgcag cctctgggtt caccgtcagt agcaactaca tgagctgggt ccgccaggct      120
ccagggaagg ggctggagtg ggtctcagtt atttatagcg gtggtagcac atactacgca      180
gactccgtga agggccgatt caccatctcc cgacacaatt ccaagaacac gctgtatctt      240
caaatgaaca gcctgagagc tgaggacacg gccgtgtatt actgtgcgag agtagcgaac      300
ggtgactttc ttgactactg gggccgtggc accctggtca ccgtctcgag t              351
```

```
<210> SEQ ID NO 196
<211> LENGTH: 351
<212> TYPE: DNA
<213> ORGANISM: artificial sequence
<220> FEATURE:
<223> OTHER INFORMATION: Nucleotide VH sequence G4_13

<400> SEQUENCE: 196
```

```
caggtgcagc tggtggagtc tgggggctgag gtgaagaagc ctggggggtc cctgagactc      60
tcctgtgcag cctctggatt caccttcagt agctatagca tgaactgggt ccgccaggct     120
ccagggaagg ggctggagtg ggtctcatcc attagtggta ctagtagtta catatactac     180
gcagactctg tgaagggccg attcaccatc tccagagaca acgccaagaa ctcactgtat     240
ctgcaaatga gcagcctgag agccgaggac acggctgttt attactgtgc gagaggaggg     300
ctcgggatgg tcgacccctg gggccaggga accctggtca ccgtctcgag t             351
```

```
<210> SEQ ID NO 197
<211> LENGTH: 351
<212> TYPE: DNA
<213> ORGANISM: artificial sequence
<220> FEATURE:
<223> OTHER INFORMATION: Nucleotide VH sequence G4_14

<400> SEQUENCE: 197
gaagtgcagc tggtgcagtc cggagcagag gtgaaaaagc ccgggggagtc tctgaggatc      60 tcctgtaagg gttctggata cagctttacc agctactgga tcagctgggt gcgccagatg     120
cccgggaaag gcctggagtg gatggggagg attgatccta gtgactctta taccaactac     180
agcccgtcct tcccaggcca cgtcaccatc tcagctgaca agtccatcag cactgcctac     240
ctgcagtgga gcagcctgaa ggcctcggac accgccatgt attactgtgc ggcggataca     300
gctcacggta tggacgtctg gggccgtggc accctggtca ccgtctcgag t             351
```

```
<210> SEQ ID NO 198
<211> LENGTH: 366
<212> TYPE: DNA
<213> ORGANISM: artificial sequence
<220> FEATURE:
<223> OTHER INFORMATION: Nucleotide VH sequence G4_15

<400> SEQUENCE: 198
gaagtgcagc tggtgcagtc tgaggctgag gtgaagaagc ctggggcctc agtgaaggtt      60
tcctgcaagg cctctggata caccttcacc aggcattata tgcactgggt gcgacaggcc     120
cccggacaag ggcttgagtg gatgggacta atcaaccota gtggtagtag cacagtctac     180
gcacagaagt tccagggcag agtcaccttg accaggggaca cgtccacgag cacagactac     240
atggagctga gcagcctgag atctgaggac acggccgtct attattgtgc gagagataat     300
agtcacctcg accaggtttg gtggttcgac ccctggggcc agggcaccct ggtcaccgtc     360
tcgagt                                                                 366
```

```
<210> SEQ ID NO 199
<211> LENGTH: 357
<212> TYPE: DNA
<213> ORGANISM: artificial sequence
<220> FEATURE:
<223> OTHER INFORMATION: Nucleotide VH sequence G4_16

<400> SEQUENCE: 199
gaggtgcagc tgttggagtc tggagctgag gtgaagaagc ctggggcctc agtgaaggtc      60
tcctgcaagg cttctggtta caccttttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagactac     300
```

-continued

```
ggtgacttct acggtatgga cgtctggggc caaggaaccc tggtcaccgt ctcgagt          357
```

<210> SEQ ID NO 200
<211> LENGTH: 354
<212> TYPE: DNA
<213> ORGANISM: artificial sequence
<220> FEATURE:
<223> OTHER INFORMATION: Nucleotide VH sequence G4_18

<400> SEQUENCE: 200

```
gaggtgcagc tggtggagtc tggggctgag gtgaagaagc ctggggcctc agtgaaggtc          60
tcctgcaagg cttctggata caccttcacc ggctactata tgcactgggt gcgacaggcc         120
cctggacaag ggcttgagtg gatgggacgg atcaaccota acagtggtgg cacaaactat         180
gcacagaagt ttcagggcag ggtcaccatg accagggacg cgtccatcag cacagcctac         240
atggagctga gcaggctgag atctgacgac acggccgtgt attactgtgc gagagatctt          300
gatctatcct cccttgacta ctggggccgt ggcaccctgg tcaccgtctc gagt             354
```

<210> SEQ ID NO 201
<211> LENGTH: 363
<212> TYPE: DNA
<213> ORGANISM: artificial sequence
<220> FEATURE:
<223> OTHER INFORMATION: Nucleotide VH sequence G4_19

<400> SEQUENCE: 201

```
gaagtgcagc tggtgcagtc tggggctgag gtgaagaagc ctggggcctc agtgaaggtt          60
tcctgcaagg catctggata caccctcacc agctactata tgcactgggt gcgacaggcc         120
cctggacaag ggcttgagtg gatgggaata atcaaccota gtggtggtag cacaagctac         180
gcacagaagt tccagggcag agtcaccatg accagggaca cgtccacgag cacagtctac          240
atggagctga gcagcctgag atctgaggac acggccgtgt attactgtgc gagagagcgt          300
ggatacagct atggtgacgg tatggacgtc tggggggcaag ggaccacggt caccgtctcg         360
agt                                                                       363
```

<210> SEQ ID NO 202
<211> LENGTH: 357
<212> TYPE: DNA
<213> ORGANISM: artificial sequence
<220> FEATURE:
<223> OTHER INFORMATION: Nucleotide VH sequence G4_20

<400> SEQUENCE: 202

```
caggtgcagc tggtggagtc tggagctgag gtgaagaagc ctggggcctc ggtgaaggtc          60
tcctgcaagg cttctggagg caccttcagc agctatgcta tcagctgggt gcgacaggcc         120
cctggacaag ggcttgagtg gatgggaggg atcatcccta tctttggtac agcaaactac         180
gcacagaagt tccagggcag agtcacgatt accgtggaca aatccacgcg cacagcctac          240
atggagctga gcagcctgag atctaaggac acggccgtgt attactgtgc gaggggggaat        300 agcagaagtg atgcttttga tatctggggc caaggggacaa tggtcaccgt ctcgagt          357
```

<210> SEQ ID NO 203
<211> LENGTH: 360
<212> TYPE: DNA
<213> ORGANISM: artificial sequence
<220> FEATURE:
<223> OTHER INFORMATION: Nucleotide VH sequence G4_22

<400> SEQUENCE: 203

-continued

```
caggtgcagt tggtggagtc tggggggaggc ttggtacagc ctggggggtc cctgagactc     60
tcctgtgcag cctctggatt cacctttagc acctatgcca tgagctgggt ccgccaggct    120
ccagggaagg ggctggagtg ggtctcaact gttagtggta gtggtggtac cacatactac    180
gcagactccg tgaagggccg gttcaccatc tccagagaca attccaagaa cacgctgtat    240
ctgcaaatga acagcctgag agccgaagac acggccgtat attactgtgc gaaagattca    300
acggcggtga ctgactggtt cgaccctgg ggccgtggca ccctggtcac cgtctcgagt    360
```

<210> SEQ ID NO 204
<211> LENGTH: 360
<212> TYPE: DNA
<213> ORGANISM: artificial sequence
<220> FEATURE:
<223> OTHER INFORMATION: Nucleotide VH sequence G4_23

<400> SEQUENCE: 204

```
gaggtgcagc tggtggagtc tggggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagggggaa    300 gtggctgcct tgtactactt tgactactgg ggccagggaa ccctggtcac cgtctcgagt    360
```

<210> SEQ ID NO 205
<211> LENGTH: 366
<212> TYPE: DNA
<213> ORGANISM: artificial sequence
<220> FEATURE:
<223> OTHER INFORMATION: Nucleotide VH sequence G4_24

<400> SEQUENCE: 205

```
caggtacagc tgcagcagtc aggtccagga ctggtgaagc cctcgcagac cctctcactc     60
acctgtgcca tctccggggc cagtgtctct agcaacagtg ttgcttggaa ctggatcagg    120
cagtccccat cgagaggcct tgagtggctg gggaggacac tacaggtc caggtggtat    180 aatgattatg cattatctgt gaaaagtcga ataatcatca acccagacac atccaagaac    240
cagttctccc tgcagctgaa ctctgtgacc cccgaggaca cggctgtgta ttactgtgca    300
agagattgga gcagcacccg atcctttgac tactgggggcc gtggcaccct ggtcaccgtc    360
tcgagt                                                             366
```

<210> SEQ ID NO 206
<211> LENGTH: 369
<212> TYPE: DNA
<213> ORGANISM: artificial sequence
<220> FEATURE:
<223> OTHER INFORMATION: Nucleotide VH sequence G4_25

<400> SEQUENCE: 206

```
gaggtgcagc tggtggagtc tggggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca atccacgag cacagcctac    240 atggagctga gcagcctgag atctgaggac acggccgtgt attactgtgc gagatctctt    300
```

-continued

```
agagatggct acaattacat cggaagttta ggctactggg gccagggcac cctggtcacc    360
gtctcgagt                                                            369
```

```
<210> SEQ ID NO 207
<211> LENGTH: 360
<212> TYPE: DNA
<213> ORGANISM: artificial sequence
<220> FEATURE:
<223> OTHER INFORMATION: Nucleotide VH sequence G4_26

<400> SEQUENCE: 207
caggtccagc ttgtgcagtc tgggggctgag gtgaagaagc ctggatcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcttac    240
atggagctga gcagcctgag atctgaagac acggctgtgt attactgtgc gagctcccgg    300
ggcagtggct ggtttccttt gggttactgg ggccaaggaa ccctggtcac cgtctcgagt    360
```

```
<210> SEQ ID NO 208
<211> LENGTH: 366
<212> TYPE: DNA
<213> ORGANISM: artificial sequence
<220> FEATURE:
<223> OTHER INFORMATION: Nucleotide VH sequence G4_27

<400> SEQUENCE: 208
caggtccagc tggtacagtc tggagcagag gtgaaaaagc ccgggggagtc tctgaagatc     60 tcctgtaaga gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccttc tcagccgacg agtccatcag taccgcctac    240
ctgcagtgga gcagcctgaa ggcctcggac accgccatgt attactgtgc gagacatggc    300
gcctacggtg actacccgga tacttttgat atctggggcc agggcaccct ggtcaccgtc    360
tcgagt                                                               366
```

```
<210> SEQ ID NO 209
<211> LENGTH: 375
<212> TYPE: DNA
<213> ORGANISM: artificial sequence
<220> FEATURE:
<223> OTHER INFORMATION: Nucleotide VH sequence G4_28

<400> SEQUENCE: 209
caggtgcagc tggtggagtc tggggggaggc ttggtacagc ctggggggtc cctgagactc     60
tcctgtgcag cctctggatt cacctttgat gattatgcca tgcactgggt ccggcaagct    120
ccagggaagg ggctggagtg ggtctcaggt attagtgctg gtggtggtag cacaaactac    180
gcaggctccg tgaagggccg gttcaccgtc tccagggaca cgtccaagaa cacactttat    240
ctgcaaatga acagcctgag agccgaggac acggccgtgt attactgtgt gaagtcctac    300
gtggatacag ctatgcgcta ctactactac tacatggacg tctggggcca agggacaatg    360
gtcaccgtct cgagt                                                     375
```

```
<210> SEQ ID NO 210
<211> LENGTH: 321
<212> TYPE: DNA
<213> ORGANISM: artificial sequence
```

-continued

```
<220> FEATURE:
<223> OTHER INFORMATION: Nucleotide VL sequence G4_1

<400> SEQUENCE: 210
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat ttcactctca ccatcagcag tctgcaacct     240
gaagattttg caacttacta ctgtcaacag agttacagta cccccgtcac tttcggccct     300
gggaccaagg tggaaatcaa a                                                321

<210> SEQ ID NO 211
<211> LENGTH: 321
<212> TYPE: DNA
<213> ORGANISM: artificial sequence
<220> FEATURE:
<223> OTHER INFORMATION: Nucleotide VL sequence G4_2

<400> SEQUENCE: 211
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcgg cctgcagcct     240
gaagattttg caacttacta ctgtctagaa gattacaact acctgtggac gttcggccaa     300
gggaccaagc tggagatcaa a                                                321

<210> SEQ ID NO 212
<211> LENGTH: 321
<212> TYPE: DNA
<213> ORGANISM: artificial sequence
<220> FEATURE:
<223> OTHER INFORMATION: Nucleotide VL sequence G4_3

<400> SEQUENCE: 212
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtgggtc tgggacagat ttcactctca ccatcagcag tctgcaacct     240
gaagattttg caacttactt ctgtcaacag agttacagta cccccccagac gttcggccaa     300 gggaccaaag tggatatcaa a                                                321

<210> SEQ ID NO 213
<211> LENGTH: 339
<212> TYPE: DNA
<213> ORGANISM: artificial sequence
<220> FEATURE:
<223> OTHER INFORMATION: Nucleotide VL sequence G4_4

<400> SEQUENCE: 213
gatattgtga tgacccagtc tccagactcc ctggctgtgt ctctgggcga gagggccacc      60
atcaactgca agtccagcca gagtgttttg tccagctcca acaataacaa ctacttagct     120
tggtaccaac agagaccagg acagcctcct aagctgctct tttactgggc atctacccgg     180
gaatcggggg tccctgaccg attcagtggc agcgggtctg gaacatcttt cactctcacc     240
```

-continued

```
atcaccagcc tgcaggctga agatgtggcg gtttattact gtcagcaata ttattccact    300
cctctcactt tcggcggagg gaccaagctg gagatcaaa                          339

<210> SEQ ID NO 214
<211> LENGTH: 321
<212> TYPE: DNA
<213> ORGANISM: artificial sequence
<220> FEATURE:
<223> OTHER INFORMATION: Nucleotide VL sequence G4_5

<400> SEQUENCE: 214
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagcg gcagtggatc tgggacagat ttcactctca ctatcagcag cctgcagcct    240
gaagattttg caacttacta ctgtcaacag agttacagta ccccctacac ttttggccag    300
gggaccaagg tggaaatcaa a                                             321

<210> SEQ ID NO 215
<211> LENGTH: 321
<212> TYPE: DNA
<213> ORGANISM: artificial sequence
<220> FEATURE:
<223> OTHER INFORMATION: Nucleotide VL sequence G4_6

<400> SEQUENCE: 215
gacatccaga tgacccagtc tccatcctcc ctgtctgcat ctgtaggaga cagagtcacc     60
atcacttgcc gggcaagtca gagcattagc acctatttaa attggtatca gcagaaacca    120
gggaaagccc ctaagctcct gatctatgct gcatccagtt tgcagagtgg ggtcccatca    180
aggttcagtg gcagtggatc tgggacagat ttcactctca ccatcagcag tccgcaacct    240
gaagattttg caacttacta ctgtcaacag agttacagta ccccgtacac ttttggccag    300
gggaccaagg tggaaatcaa a                                             321

<210> SEQ ID NO 216
<211> LENGTH: 336
<212> TYPE: DNA
<213> ORGANISM: artificial sequence
<220> FEATURE:
<223> OTHER INFORMATION: Nucleotide VL sequence G4_7

<400> SEQUENCE: 216
gatattgtga tgacgcagtc tccactctcc ctgcccgtca cccctggaga gccggcctcc     60
atctcctgca ggtccagtca gagcctcctg catagtaata gattcaacta tttggattgg    120
tacctgcaga agccagggca gtctccacag ctcctgatct atttgggttc taatcgggcc    180
tccggggtcc ctgacaggtt cagtggcagt ggatctggca cagattttac actgaaaatc    240
agcagagtgg aggctgagga tgttgggggtt tattactgca tgcaaggtct acaaactccg    300
tacacttttg gccaggggac caaagtggat atcaaa                             336

<210> SEQ ID NO 217
<211> LENGTH: 336
<212> TYPE: DNA
<213> ORGANISM: artificial sequence
<220> FEATURE:
<223> OTHER INFORMATION: Nucleotide VL sequence G4_10

<400> SEQUENCE: 217
```

```
gatattgtga tgacgcagcc tccactctcc ctgcccgtca cccttggaca tccggcctcc     60
atctcctgca agtctagtca aagcctcgaa tatagtgatg gaaacaccta cttgaattgg    120
tttcagcaga ggccaggcca atctccaagg cgcctcattt ataaggtttc taaccgggac    180 tctgggccc  ccgacagatt cagcgggagt gggtcaggca ctgatttcac actggaaatc    240
agcagggtgg aggctgagga tgttggagtt tattactgta tgcaaggtac actctggcct    300
cccacgttcg gccaagggac caaagtggat atcaaa                             336

<210> SEQ ID NO 218
<211> LENGTH: 324
<212> TYPE: DNA
<213> ORGANISM: artificial sequence
<220> FEATURE:
<223> OTHER INFORMATION: Nucleotide VL sequence G4_12

<400> SEQUENCE: 218
cagtctgtgc tgactcagcc tgcctccgtg tctgggtctc ctggacagtc gatcaccatc     60
tcctgcactg gaaccagcag tgacgttggt ggttataact ttgtctcctg gtaccaacaa    120
cacccaggca aagcccccaa actcatgatt tatgaggtca ctaatcggcc ctcaggggtc    180
cctgatcggt tctctggctc caagtctggc aacacggcct ccctgaccat ctctgggctc    240
caggctgagg acgaggctga ttattactgc agctcacatg caagccccag ggtcttcgga    300
actgggacca aggtcaccgt ccta                                         324

<210> SEQ ID NO 219
<211> LENGTH: 333
<212> TYPE: DNA
<213> ORGANISM: artificial sequence
<220> FEATURE:
<223> OTHER INFORMATION: Nucleotide VL sequence G4_13

<400> SEQUENCE: 219
aattttatgc tgactcagcc ccactctgtg tcggagtctc cggggaagac ggtaaccatc     60
tcctgcaccc gcagcagtgg cagcattgcc agcaactatg tgcagtggta ccagcagcgc    120
ccgggcagtt cccccagcac tgtgatctat gaggataacc aaagaccctc aggggtccct    180
gatcggttct ctggctccat cgacagctcc tccaactctg cctccctcac catctctgga    240
ctgaggactg aggacgaggc tgactactac tgtcagtctt atgatagcag catttatgtg    300
gtattcggcg gagggaccaa gctgaccgtc cta                                333

<210> SEQ ID NO 220
<211> LENGTH: 333
<212> TYPE: DNA
<213> ORGANISM: artificial sequence
<220> FEATURE:
<223> OTHER INFORMATION: Nucleotide VL sequence G4_14

<400> SEQUENCE: 220
aattttatgc tgactcagcc ccactctgtg tcggagtctc cggggaagac ggtaaccata     60
tcctgcaccc gcagccgtgg cagcattgcc ggcaactatg tgcactggta ccagcagcgc    120
ccagggcgtg cccccaccac tgtgatctat cgggataagg aaagaccctc tggggtccct    180
gatcgaatct ctggctccat cgacagctcc tccaactctg cctccctcac catctctgga    240
ctgaagactg aggacgaggc tgattactat tgtcagtctt atgatagcag cacccatgtg    300
gtattcggcg gagggaccaa gctgaccgtc cta                                333
```

-continued

```
<210> SEQ ID NO 221
<211> LENGTH: 324
<212> TYPE: DNA
<213> ORGANISM: artificial sequence
<220> FEATURE:
<223> OTHER INFORMATION: Nucleotide VL sequence G4_15

<400> SEQUENCE: 221
cagtctgcgc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgacgtca gtaatcggcc ctcaggggtt     180
tctaatcgct tctctggctc caagtctggc aacacggcct ccctgaccat ctctgggctc     240
caggctgagg acgaggctga ttattactgc agctcgtatg gaagcggcag cgtcttcgga     300
actgggacca agctgaccgt ccta                                            324

<210> SEQ ID NO 222
<211> LENGTH: 330
<212> TYPE: DNA
<213> ORGANISM: artificial sequence
<220> FEATURE:
<223> OTHER INFORMATION: Nucleotide VL sequence G4_16

<400> SEQUENCE: 222
cagtctgtgc tgactcagcc tccctccgcg tccgggtctc ctggacagtc agtcaccttc      60
tcctgcactg gaaccagcag tgacattggt gcttttaact ctgtctcttg gtaccaacag     120
cacccaggca aagcccccaa actcctaatt tatgagatca ctaagcggcc ctcaggggtc     180
cctgatcgct tctctggctc caagtctggc aacacggcct ccctgaccat ctctgtgctc     240
caggctgaag atgaggctga ttattactgc acctcatatg caggcagcaa cactttgatc     300
ttcggcggag ggaccaaggt caccgtccta                                      330

<210> SEQ ID NO 223
<211> LENGTH: 324
<212> TYPE: DNA
<213> ORGANISM: artificial sequence
<220> FEATURE:
<223> OTHER INFORMATION: Nucleotide VL sequence G4_18

<400> SEQUENCE: 223
tcctatgagc tgacacagcc accctcggtg acagagtccc caggacagac ggccaggatc      60
acctgctctg gagatgcatt ggcaaagcaa tatgcttatt ggtaccagca gaagccaggc     120
caggcccctg tgttggtgat atatagagac agtgagaggc cttcagagat ccctgagcga     180
ttctctggct ccagctcagg gacaacagtc acgttgacca tcagtggagt ccaggcagaa     240
gacgaggctg actattactg tcaatcagca gacagcagtg gtacttatac agtatttggc     300
ggagggacca agctgaccgt ccta                                            324

<210> SEQ ID NO 224
<211> LENGTH: 333
<212> TYPE: DNA
<213> ORGANISM: artificial sequence
<220> FEATURE:
<223> OTHER INFORMATION: Nucleotide VL sequence G4_19

<400> SEQUENCE: 224
aattttatgc tgactcagcc ccactctgtg tcggagtctc cggggaagac ggtcaccatc      60
tcctgcaccc gcagcagtgg cagcattgcc agcaactatg tacagtggta ccagcagcgc     120
```

-continued

```
ccgggcagtc cccccatcac tttgatatat gatgatgacc aaagaccctc tggggtccct        180
catcggttct ctggctccat cgacacctca tccaaccctg cctccctcac catctctgga        240
ctgaagactg aggacgaggc tgactactac tgtcagtctt atgatagcag caatcatgtg        300
gtattcggcg gagggaccaa gctgaccgtc cta                                      333

<210> SEQ ID NO 225
<211> LENGTH: 318
<212> TYPE: DNA
<213> ORGANISM: artificial sequence
<220> FEATURE:
<223> OTHER INFORMATION: Nucleotide VL sequence G4_20

<400> SEQUENCE: 225
tcctatgagc tgactcatcc accctcagtg tccgtgtccc caggacagac agccagcatc         60
acctgctctg gagataaatt gggggataag tttgtttcct ggtatcacca aaagccaggc        120
cagtcccctg tgctggtcat ctatcaagat agcaagcggc cctcaggat ccctgagcgc         180 ttctcaggct ccaattctgg gaacacagcc actctgacca tcagcgggac ccgggctatg        240
gatgaggctg actattactg tcaggcgtgg gacagcagca ctgtggtatt cggcggaggg        300
accaagctga ccgtccta                                                      318

<210> SEQ ID NO 226
<211> LENGTH: 321
<212> TYPE: DNA
<213> ORGANISM: artificial sequence
<220> FEATURE:
<223> OTHER INFORMATION: Nucleotide VL sequence G4_22

<400> SEQUENCE: 226
gacatccaga tgacccagtc tccatcctcc ctgtctgcat ctgtaggaga cagagtcacc         60
atcacttgcc aggcgagtca ggacattagc aactatttaa attggtatca gcagaaacca        120
gggaaagccc ctaagctcct gatctatgct gcatccagtc tgcaaagtgg ggtcccatca        180
aggttcagcg tcagtggatc tgggacagat ttcactctca ccatcagcaa cctgcagcct        240
gaagattttg caacttatta ctgtcaacag agttacagta tcccgtggac gttcggccaa        300
gggaccaagg tggagatcaa a                                                  321

<210> SEQ ID NO 227
<211> LENGTH: 321
<212> TYPE: DNA
<213> ORGANISM: artificial sequence
<220> FEATURE:
<223> OTHER INFORMATION: Nucleotide VL sequence G4_23

<400> SEQUENCE: 227
gacatccaga tgacccagtc tccatcctcc ctgtctgcat ctgtaggaga cagagtcacc         60
atcacttgcc gggcgagtca gggcattagc aattctttag cctggtatca gcagaaacca        120
gggaaagccc ctaagctcct gctctatgct gcgtccagat tggaaagtgg ggtcccatcc        180
aggtttagtg gcagtggatc tgggacggat tacaccctca ccatcagcag cctgcagcct        240
gaagattttg caacttatta ctgtcaacag tattatagta cccctcgcac tttcggcgga        300
gggaccaagc tggagatcaa a                                                  321

<210> SEQ ID NO 228
<211> LENGTH: 339
<212> TYPE: DNA
```

```
<213> ORGANISM: artificial sequence
<220> FEATURE:
<223> OTHER INFORMATION: Nucleotide VL sequence G4_24

<400> SEQUENCE: 228
gatattgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagttgttga tttcctgggc ttctacccgg     180
gaatctgggg tccctgaccg attcagtggc agcgggtctg ggacagattt cactctcacc     240
atcaacagcc tacagtctga agatgtggca atttattact gtcagcaata ttattctacc     300
cctccgacgt tcggccaggg gaccaagctg gagatcaaa                            339

<210> SEQ ID NO 229
<211> LENGTH: 324
<212> TYPE: DNA
<213> ORGANISM: artificial sequence
<220> FEATURE:
<223> OTHER INFORMATION: Nucleotide VL sequence G4_25

<400> SEQUENCE: 229
cagtctgcgc tgactcagcc tcgctcagtg tccgggtctc ctggacagtc agtcaccatc      60
tcctgcactg gaaccagcag tgatgttggt ggttataact atgtctcctg gtaccaacag     120
cacccaggca aagcccccaa actcatgatt tatgaggtca gtaatcggcc ctcagggggtt     180 tctaatcgct tctctggctc caagtctggc aacacggcct ccctgaccat ctctgggctc     240
caggctgagg acgaggctga ttattactgc agctcgtatg gaagcggcag cgtcttcgga     300
actgggacca agctgaccgt ccta                                            324

<210> SEQ ID NO 230
<211> LENGTH: 324
<212> TYPE: DNA
<213> ORGANISM: artificial sequence
<220> FEATURE:
<223> OTHER INFORMATION: Nucleotide VL sequence G4_26

<400> SEQUENCE: 230
cagtctgggc tgactcagcc tgcctccgtg tctgggtctc ctggacagtc gatcaccatc      60
tcctgcactg gaaccagcag tgatgttggg agttataacc ttgtctcctg gtaccaacag     120
cacccaggca aagcccccaa actcatgatt tatgaggtca gtaagcggcc ctcagggggtt     180 tctaatcgct tctctggctc caagtctggc aacacggcct ccctgaccat ctctgggctc     240
caggctgagg acgaggctga ttattactgc agctcgtttg gaagcggcag catcttcgga     300
actgggacca agctgaccgt ccta                                            324

<210> SEQ ID NO 231
<211> LENGTH: 324
<212> TYPE: DNA
<213> ORGANISM: artificial sequence
<220> FEATURE:
<223> OTHER INFORMATION: Nucleotide VL sequence G4_27

<400> SEQUENCE: 231
tcctatgagc tgactcagga cccagctgtg tctgtggccc tgggacagac agtcagtatc      60
acatgccaag agacagcct cagaaacttt tatgcaaact ggtaccagca aaagccagga      120
caggcccctg tacttgtcat ctatggtaaa aacaaccggc cctcagggat cccagaccga     180
ttctctggct ccagctcagg aaacacagct tccttgacca tcactggggc tcaggcggaa     240
```

-continued

```
gatgaggctg actattactg taactcccgg gacagcagtg gtaaccatct ggtattcggc        300
ggagggaccc agctcaccgt ccta                                              324
```

```
<210> SEQ ID NO 232
<211> LENGTH: 318
<212> TYPE: DNA
<213> ORGANISM: artificial sequence
<220> FEATURE:
<223> OTHER INFORMATION: Nucleotide VL sequence G4_28
```

```
<400> SEQUENCE: 232
```

```
tcctatgagc tgactcagga ccctgctgtg tctgtggcct tgggacagac agtcacgatc         60
acatgccaag gagacagcct cagaaactat tatgcaagct ggtaccggca gaagccagga        120
cagacccctg tacttgtcgt ctatggtaaa aacaaccggc cctcaggat cccagaccga        180 ttctctgtct ccgcctcagg taacacagct tccttgacca tcactgggc tcaggcggaa        240 gatgagggtg actattactg taactcccgg gacagcagtg gtgtggtttt cggcggaggg        300
accaaggtca ccgtcccta                                                    318
```

```
<210> SEQ ID NO 233
<211> LENGTH: 662
<212> TYPE: PRT
<213> ORGANISM: artificial sequence
<220> FEATURE:
<223> OTHER INFORMATION: G4_1 IgG1 antibody sequence?
```

```
<400> SEQUENCE: 233
```

```
Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Asp Ala Ser Asn Leu Glu Thr Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Val Thr Phe Gly Pro Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Glu Val Gln Leu Leu Glu Ser Gly
    210                 215                 220
```

-continued

```
Gly Gly Val Val Gln Pro Gly Arg Pro Leu Arg Leu Ser Cys Ala Ala
225             230             235             240

Ser Gly Phe Thr Phe Ser Ser Tyr Ser Met Asn Trp Val Arg Gln Ala
            245             250             255

Pro Gly Lys Gly Leu Glu Trp Val Ser Ser Ile Ser Ser Ser Ser Ser
            260             265             270

Tyr Ile Tyr Tyr Ala Asp Ser Val Lys Gly Arg Phe Thr Ile Ser Arg
        275             280             285

Asp Asn Ser Lys Asn Thr Leu Tyr Leu Gln Met Asn Ser Leu Arg Ala
    290             295             300

Glu Asp Thr Ala Val Tyr Tyr Cys Ala Lys Gly His Trp Tyr Phe Asp
305             310             315             320

Leu Trp Gly Arg Gly Thr Leu Val Thr Val Ser Ser Ala Ser Thr Lys
            325             330             335

Gly Pro Ser Val Phe Pro Leu Ala Pro Ser Ser Lys Ser Thr Ser Gly
            340             345             350

Gly Thr Ala Ala Leu Gly Cys Leu Val Lys Asp Tyr Phe Pro Glu Pro
        355             360             365

Val Thr Val Ser Trp Asn Ser Gly Ala Leu Thr Ser Gly Val His Thr
    370             375             380

Phe Pro Ala Val Leu Gln Ser Ser Gly Leu Tyr Ser Leu Ser Ser Val
385             390             395             400

Val Thr Val Pro Ser Ser Ser Leu Gly Thr Gln Thr Tyr Ile Cys Asn
            405             410             415

Val Asn His Lys Pro Ser Asn Thr Lys Val Asp Lys Lys Val Glu Pro
            420             425             430

Lys Ser Cys Asp Lys Thr His Thr Cys Pro Pro Cys Pro Ala Pro Glu
            435             440             445

Leu Leu Gly Gly Pro Ser Val Phe Leu Phe Pro Pro Lys Pro Lys Asp
    450             455             460

Thr Leu Met Ile Ser Arg Thr Pro Glu Val Thr Cys Val Val Val Asp
465             470             475             480

Val Ser His Glu Asp Pro Glu Val Lys Phe Asn Trp Tyr Val Asp Gly
            485             490             495

Val Glu Val His Asn Ala Lys Thr Lys Pro Arg Glu Glu Gln Tyr Asn
            500             505             510

Ser Thr Tyr Arg Val Val Ser Val Leu Thr Val Leu His Gln Asp Trp
        515             520             525

Leu Asn Gly Lys Glu Tyr Lys Cys Lys Val Ser Asn Lys Ala Leu Pro
    530             535             540

Ala Pro Ile Glu Lys Thr Ile Ser Lys Ala Lys Gly Gln Pro Arg Glu
545             550             555             560

Pro Gln Val Tyr Thr Leu Pro Pro Ser Arg Asp Glu Leu Thr Lys Asn
            565             570             575

Gln Val Ser Leu Thr Cys Leu Val Lys Gly Phe Tyr Pro Ser Asp Ile
            580             585             590

Ala Val Glu Trp Glu Ser Asn Gly Gln Pro Glu Asn Asn Tyr Lys Thr
        595             600             605

Thr Pro Pro Val Leu Asp Ser Asp Gly Ser Phe Phe Leu Tyr Ser Lys
    610             615             620

Leu Thr Val Asp Lys Ser Arg Trp Gln Gln Gly Asn Val Phe Ser Cys
625             630             635             640

Ser Val Met His Glu Ala Leu His Asn His Tyr Thr Gln Lys Ser Leu
```

```
                     645                 650                 655

Ser Leu Ser Pro Gly Lys
                     660
```

<210> SEQ ID NO 234
<211> LENGTH: 666
<212> TYPE: PRT
<213> ORGANISM: artificial sequence
<220> FEATURE:
<223> OTHER INFORMATION: G4_2 IgG1 antibody sequence

<400> SEQUENCE: 234

```
Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Gly Leu
65                  70                  75                  80

Gln Pro Glu Asp Phe Ala Thr Tyr Tyr Cys Leu Glu Asp Tyr Asn Tyr
                85                  90                  95

Leu Trp Thr Phe Gly Gln Gly Thr Lys Leu Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
            195                 200                 205

Lys Ser Phe Asn Arg Gly Glu Cys Gln Met Gln Leu Val Gln Ser Gly
        210                 215                 220

Ala Glu Val Lys Lys Pro Gly Ala Thr Val Lys Ile Ser Cys Lys Val
225                 230                 235                 240

Ser Gly Tyr Pro Phe Thr Asp Tyr Tyr Ile His Trp Val Gln Gln Ala
                245                 250                 255

Pro Gly Lys Gly Leu Glu Trp Met Gly Leu Val Asp Pro Glu Asp Gly
            260                 265                 270

Gln Ser Arg Ser Ala Glu Arg Phe Gln Gly Arg Val Thr Ile Thr Ala
        275                 280                 285

Asp Thr Ser Thr Asp Thr Ala Tyr Met Glu Leu Ser Ser Leu Arg Ser
    290                 295                 300

Glu Asp Thr Ala Val Tyr Tyr Cys Ala Thr Phe Pro Val Ala Gly Phe
305                 310                 315                 320

Tyr Gly Met Asp Val Trp Gly Gln Gly Thr Leu Val Thr Val Ser Ser
                325                 330                 335

Ala Ser Thr Lys Gly Pro Ser Val Phe Pro Leu Ala Pro Ser Ser Lys
```

-continued

```
                340             345             350
Ser Thr Ser Gly Gly Thr Ala Ala Leu Gly Cys Leu Val Lys Asp Tyr
        355             360             365

Phe Pro Glu Pro Val Thr Val Ser Trp Asn Ser Gly Ala Leu Thr Ser
        370             375             380

Gly Val His Thr Phe Pro Ala Val Leu Gln Ser Ser Gly Leu Tyr Ser
385             390             395             400

Leu Ser Ser Val Val Thr Val Pro Ser Ser Ser Leu Gly Thr Gln Thr
                405             410             415

Tyr Ile Cys Asn Val Asn His Lys Pro Ser Asn Thr Lys Val Asp Lys
                420             425             430

Lys Val Glu Pro Lys Ser Cys Asp Lys Thr His Thr Cys Pro Pro Cys
                435             440             445

Pro Ala Pro Glu Leu Leu Gly Gly Pro Ser Val Phe Leu Phe Pro Pro
                450             455             460

Lys Pro Lys Asp Thr Leu Met Ile Ser Arg Thr Pro Glu Val Thr Cys
465             470             475             480

Val Val Val Asp Val Ser His Glu Asp Pro Glu Val Lys Phe Asn Trp
                485             490             495

Tyr Val Asp Gly Val Glu Val His Asn Ala Lys Thr Lys Pro Arg Glu
                500             505             510

Glu Gln Tyr Asn Ser Thr Tyr Arg Val Val Ser Val Leu Thr Val Leu
                515             520             525

His Gln Asp Trp Leu Asn Gly Lys Glu Tyr Lys Cys Lys Val Ser Asn
        530             535             540

Lys Ala Leu Pro Ala Pro Ile Glu Lys Thr Ile Ser Lys Ala Lys Gly
545             550             555             560

Gln Pro Arg Glu Pro Gln Val Tyr Thr Leu Pro Pro Ser Arg Asp Glu
                565             570             575

Leu Thr Lys Asn Gln Val Ser Leu Thr Cys Leu Val Lys Gly Phe Tyr
                580             585             590

Pro Ser Asp Ile Ala Val Glu Trp Glu Ser Asn Gly Gln Pro Glu Asn
        595             600             605

Asn Tyr Lys Thr Thr Pro Pro Val Leu Asp Ser Asp Gly Ser Phe Phe
        610             615             620

Leu Tyr Ser Lys Leu Thr Val Asp Lys Ser Arg Trp Gln Gln Gly Asn
625             630             635             640

Val Phe Ser Cys Ser Val Met His Glu Ala Leu His Asn His Tyr Thr
                645             650             655

Gln Lys Ser Leu Ser Leu Ser Pro Gly Lys
        660             665
```

```
<210> SEQ ID NO 235
<211> LENGTH: 662
<212> TYPE: PRT
<213> ORGANISM: artificial sequence
<220> FEATURE:
<223> OTHER INFORMATION: G4_3 IgG1 antibody sequence

<400> SEQUENCE: 235

Ala Ser Asp Ile Gln Met Thr Gln Ser Pro Ser Ser Leu Ser Ala Ser
1               5               10              15

Val Gly Asp Arg Val Thr Ile Thr Cys Gln Ala Ser Gln Asp Ile Ser
                20              25              30

Asn Tyr Leu Asn Trp Tyr Gln Gln Lys Pro Gly Lys Ala Pro Lys Leu
```

```
               35                    40                    45
Leu Ile Tyr Asp Ala Ser Asn Leu Glu Thr Gly Val Pro Ser Arg Phe
    50                    55                    60
Ser Gly Ser Gly Ser Gly Thr Asp Phe Thr Leu Thr Ile Ser Ser Leu
65                    70                    75                    80
Gln Pro Glu Asp Phe Ala Thr Tyr Phe Cys Gln Gln Ser Tyr Ser Thr
                  85                    90                    95
Pro Gln Thr Phe Gly Gln Gly Thr Lys Val Asp Ile Lys Arg Thr Ala
                  100                   105                   110
Ala Ala Pro Ser Val Phe Ile Phe Pro Pro Ser Asp Glu Gln Leu Lys
                  115                   120                   125
Ser Gly Thr Ala Ser Val Val Cys Leu Leu Asn Asn Phe Tyr Pro Arg
    130                   135                   140
Glu Ala Lys Val Gln Trp Lys Val Asp Asn Ala Leu Gln Ser Gly Asn
145                   150                   155                   160
Ser Gln Glu Ser Val Thr Glu Gln Asp Ser Lys Asp Ser Thr Tyr Ser
                  165                   170                   175
Leu Ser Ser Thr Leu Thr Leu Ser Lys Ala Asp Tyr Glu Lys His Lys
                  180                   185                   190
Leu Tyr Ala Cys Glu Val Thr His Gln Gly Leu Ser Ser Pro Val Thr
              195                   200                   205
Lys Ser Phe Asn Arg Gly Glu Cys Glu Val Gln Leu Val Glu Ser Gly
    210                   215                   220
Gly Gly Leu Val Gln Pro Gly Gly Ser Leu Arg Leu Ser Cys Ala Ala
225                   230                   235                   240
Ser Gly Phe Thr Phe Ser Ser Tyr Ser Met Asn Trp Val Arg Gln Ala
                  245                   250                   255
Pro Gly Lys Gly Leu Glu Trp Val Ser Ser Ile Ser Ser Ser Ser Ser
                  260                   265                   270
Tyr Ile Tyr Tyr Ala Asp Ser Val Lys Gly Arg Phe Thr Ile Ser Arg
              275                   280                   285
Asp Asn Ser Lys Asn Thr Leu Tyr Leu Gln Met Asn Ser Leu Arg Ala
    290                   295                   300
Glu Asp Thr Ala Val Tyr Tyr Cys Ala Arg Gly Gly Trp Leu Tyr Asp
305                   310                   315                   320
Tyr Trp Gly Gln Gly Thr Leu Val Thr Val Ser Ser Ala Ser Thr Lys
                  325                   330                   335
Gly Pro Ser Val Phe Pro Leu Ala Pro Ser Ser Lys Ser Thr Ser Gly
                  340                   345                   350
Gly Thr Ala Ala Leu Gly Cys Leu Val Lys Asp Tyr Phe Pro Glu Pro
              355                   360                   365
Val Thr Val Ser Trp Asn Ser Gly Ala Leu Thr Ser Gly Val His Thr
    370                   375                   380
Phe Pro Ala Val Leu Gln Ser Ser Gly Leu Tyr Ser Leu Ser Ser Val
385                   390                   395                   400
Val Thr Val Pro Ser Ser Ser Leu Gly Thr Gln Thr Tyr Ile Cys Asn
                  405                   410                   415
Val Asn His Lys Pro Ser Asn Thr Lys Val Asp Lys Lys Val Glu Pro
                  420                   425                   430
Lys Ser Cys Asp Lys Thr His Thr Cys Pro Pro Cys Pro Ala Pro Glu
              435                   440                   445
Leu Leu Gly Gly Pro Ser Val Phe Leu Phe Pro Pro Lys Pro Lys Asp
    450                   455                   460
```

```
Thr Leu Met Ile Ser Arg Thr Pro Glu Val Thr Cys Val Val Val Asp
465             470             475             480

Val Ser His Glu Asp Pro Glu Val Lys Phe Asn Trp Tyr Val Asp Gly
            485             490             495

Val Glu Val His Asn Ala Lys Thr Lys Pro Arg Glu Glu Gln Tyr Asn
            500             505             510

Ser Thr Tyr Arg Val Val Ser Val Leu Thr Val Leu His Gln Asp Trp
            515             520             525

Leu Asn Gly Lys Glu Tyr Lys Cys Lys Val Ser Asn Lys Ala Leu Pro
        530             535             540

Ala Pro Ile Glu Lys Thr Ile Ser Lys Ala Lys Gly Gln Pro Arg Glu
545             550             555             560

Pro Gln Val Tyr Thr Leu Pro Pro Ser Arg Asp Glu Leu Thr Lys Asn
            565             570             575

Gln Val Ser Leu Thr Cys Leu Val Lys Gly Phe Tyr Pro Ser Asp Ile
            580             585             590

Ala Val Glu Trp Glu Ser Asn Gly Gln Pro Glu Asn Asn Tyr Lys Thr
            595             600             605

Thr Pro Pro Val Leu Asp Ser Asp Gly Ser Phe Phe Leu Tyr Ser Lys
        610             615             620

Leu Thr Val Asp Lys Ser Arg Trp Gln Gln Gly Asn Val Phe Ser Cys
625             630             635             640

Ser Val Met His Glu Ala Leu His Asn His Tyr Thr Gln Lys Ser Leu
            645             650             655

Ser Leu Ser Pro Gly Lys
            660
```

```
<210> SEQ ID NO 236
<211> LENGTH: 671
<212> TYPE: PRT
<213> ORGANISM: artificial sequence
<220> FEATURE:
<223> OTHER INFORMATION: G4_4 IgG1 antibody sequence

<400> SEQUENCE: 236
```

```
Ala Ser Asp Ile Val Met Thr Gln Ser Pro Asp Ser Leu Ala Val Ser
1               5               10              15

Leu Gly Glu Arg Ala Thr Ile Asn Cys Lys Ser Ser Gln Ser Val Leu
            20              25              30

Ser Ser Ser Asn Asn Asn Asn Tyr Leu Ala Trp Tyr Gln Gln Arg Pro
        35              40              45

Gly Gln Pro Pro Lys Leu Leu Phe Tyr Trp Ala Ser Thr Arg Glu Ser
    50              55              60

Gly Val Pro Asp Arg Phe Ser Gly Ser Gly Ser Gly Thr Ser Phe Thr
65              70              75              80

Leu Thr Ile Thr Ser Leu Gln Ala Glu Asp Val Ala Val Tyr Tyr Cys
            85              90              95

Gln Gln Tyr Tyr Ser Thr Pro Leu Thr Phe Gly Gly Gly Thr Lys Leu
            100             105             110

Glu Ile Lys Arg Thr Ala Ala Ala Pro Ser Val Phe Ile Phe Pro Pro
        115             120             125

Ser Asp Glu Gln Leu Lys Ser Gly Thr Ala Ser Val Val Cys Leu Leu
        130             135             140

Asn Asn Phe Tyr Pro Arg Glu Ala Lys Val Gln Trp Lys Val Asp Asn
145             150             155             160
```

```
Ala Leu Gln Ser Gly Asn Ser Gln Glu Ser Val Thr Glu Gln Asp Ser
              165                 170                 175

Lys Asp Ser Thr Tyr Ser Leu Ser Ser Thr Leu Thr Leu Ser Lys Ala
              180                 185                 190

Asp Tyr Glu Lys His Lys Leu Tyr Ala Cys Glu Val Thr His Gln Gly
              195                 200                 205

Leu Ser Ser Pro Val Thr Lys Ser Phe Asn Arg Gly Glu Cys Gln Val
              210                 215                 220

Gln Leu Val Glu Ser Gly Gly Gly Leu Val Gln Pro Gly Gly Ser Leu
225                 230                 235                 240

Arg Leu Ser Cys Ala Ala Ser Gly Phe Thr Phe Ser Ser Tyr Ala Met
              245                 250                 255

Ser Trp Val Arg Gln Ala Pro Gly Lys Gly Leu Glu Trp Val Ser Ala
              260                 265                 270

Ile Ser Gly Ser Gly Gly Ser Thr Tyr Tyr Ala Asp Ser Val Lys Gly
              275                 280                 285

Arg Phe Thr Ile Ser Arg Asp Asn Ser Lys Asn Thr Leu Tyr Leu Gln
              290                 295                 300

Met Ser Ser Leu Arg Val Glu Asp Thr Ala Val Tyr Tyr Cys Ala Lys
305                 310                 315                 320

Ser Ser Val Gly Trp Trp Ser Phe Asp Tyr Trp Gly Gln Gly Thr Met
              325                 330                 335

Val Thr Val Ser Ser Ala Ser Thr Lys Gly Pro Ser Val Phe Pro Leu
              340                 345                 350

Ala Pro Ser Ser Lys Ser Thr Ser Gly Gly Thr Ala Ala Leu Gly Cys
              355                 360                 365

Leu Val Lys Asp Tyr Phe Pro Glu Pro Val Thr Val Ser Trp Asn Ser
              370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
              405                 410                 415

Leu Gly Thr Gln Thr Tyr Ile Cys Asn Val Asn His Lys Pro Ser Asn
              420                 425                 430

Thr Lys Val Asp Lys Lys Val Glu Pro Lys Ser Cys Asp Lys Thr His
              435                 440                 445

Thr Cys Pro Pro Cys Pro Ala Pro Glu Leu Leu Gly Gly Pro Ser Val
              450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
              485                 490                 495

Val Lys Phe Asn Trp Tyr Val Asp Gly Val Glu Val His Asn Ala Lys
              500                 505                 510

Thr Lys Pro Arg Glu Glu Gln Tyr Asn Ser Thr Tyr Arg Val Val Ser
              515                 520                 525

Val Leu Thr Val Leu His Gln Asp Trp Leu Asn Gly Lys Glu Tyr Lys
              530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
              565                 570                 575
```

-continued

```
Pro Ser Arg Asp Glu Leu Thr Lys Asn Gln Val Ser Leu Thr Cys Leu
            580                 585                 590

Val Lys Gly Phe Tyr Pro Ser Asp Ile Ala Val Glu Trp Glu Ser Asn
            595                 600                 605

Gly Gln Pro Glu Asn Asn Tyr Lys Thr Thr Pro Pro Val Leu Asp Ser
            610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 237
<211> LENGTH: 666
<212> TYPE: PRT
<213> ORGANISM: artificial sequence
<220> FEATURE:
<223> OTHER INFORMATION: G4_5 IgG1 antibody sequence

<400> SEQUENCE: 237

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
            35                  40                  45

Leu Ile Tyr Ala Ala Ser Ser Leu Gln Ser Gly Val Pro Ser Arg Phe
            50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Tyr Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
            195                 200                 205

Lys Ser Phe Asn Arg Gly Glu Cys Glu Val Gln Leu Val Gln Ser Gly
            210                 215                 220

Ala Glu Val Lys Lys Pro Gly Ser Ser Val Lys Val Ser Cys Lys Ala
225                 230                 235                 240

Ser Gly Tyr Thr Phe Thr Ser Tyr Gly Ile Ser Trp Val Arg Gln Ala
                245                 250                 255

Pro Gly Gln Gly Leu Glu Trp Met Gly Trp Ile Gly Ala Tyr Asn Gly
            260                 265                 270
```

-continued

```
Asn Thr Asn Tyr Ala Gln Lys Leu Gln Gly Arg Val Thr Met Ser Thr
        275                 280                 285

Asp Thr Ser Thr Ser Thr Ala Tyr Met Glu Leu Arg Ser Pro Arg Ser
    290                 295                 300

Asp Asp Thr Ala Val Tyr Tyr Cys Ala Arg Gly Gly Thr Gly Gly Asp
305                 310                 315                 320

His Val Phe Ala Tyr Trp Gly Gln Gly Thr Thr Val Thr Val Ser Ser
                325                 330                 335

Ala Ser Thr Lys Gly Pro Ser Val Phe Pro Leu Ala Pro Ser Ser Lys
            340                 345                 350

Ser Thr Ser Gly Gly Thr Ala Ala Leu Gly Cys Leu Val Lys Asp Tyr
        355                 360                 365

Phe Pro Glu Pro Val Thr Val Ser Trp Asn Ser Gly Ala Leu Thr Ser
    370                 375                 380

Gly Val His Thr Phe Pro Ala Val Leu Gln Ser Ser Gly Leu Tyr Ser
385                 390                 395                 400

Leu Ser Ser Val Val Thr Val Pro Ser Ser Ser Leu Gly Thr Gln Thr
                405                 410                 415

Tyr Ile Cys Asn Val Asn His Lys Pro Ser Asn Thr Lys Val Asp Lys
            420                 425                 430

Lys Val Glu Pro Lys Ser Cys Asp Lys Thr His Thr Cys Pro Pro Cys
        435                 440                 445

Pro Ala Pro Glu Leu Leu Gly Gly Pro Ser Val Phe Leu Phe Pro Pro
    450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val Leu
            515                 520                 525

His Gln Asp Trp Leu Asn Gly Lys Glu Tyr Lys Cys Lys Val Ser Asn
        530                 535                 540

Lys Ala Leu Pro Ala Pro Ile Glu Lys Thr Ile Ser Lys Ala Lys Gly
545                 550                 555                 560

Gln Pro Arg Glu Pro Gln Val Tyr Thr Leu Pro Pro Ser Arg Asp Glu
                565                 570                 575

Leu Thr Lys Asn Gln Val Ser Leu Thr Cys Leu Val Lys Gly Phe Tyr
            580                 585                 590

Pro Ser Asp Ile Ala Val Glu Trp Glu Ser Asn Gly Gln Pro Glu Asn
        595                 600                 605

Asn Tyr Lys Thr Thr Pro Pro Val Leu Asp Ser Asp Gly Ser Phe Phe
    610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
                645                 650                 655

Gln Lys Ser Leu Ser Leu Ser Pro Gly Lys
            660                 665
```

<210> SEQ ID NO 238
<211> LENGTH: 666
<212> TYPE: PRT

<213> ORGANISM: artificial sequence
<220> FEATURE:
<223> OTHER INFORMATION: G4_6 IgG1 antibody sequence

<400> SEQUENCE: 238

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Thr Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Pro
65                  70                  75                  80

Gln Pro Glu Asp Phe Ala Thr Tyr Tyr Cys Gln Gln Ser Tyr Ser Thr
                85                  90                  95

Pro Tyr Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys Glu Val Gln Leu Val Glu Ser Gly
    210                 215                 220

Gly Gly Leu Val Gln Pro Gly Gly Pro Leu Arg Leu Ser Cys Ala Ala
225                 230                 235                 240

Ser Gly Phe Thr Phe Ser Ser Tyr Ala Met Asn Trp Val Arg Gln Ala
                245                 250                 255

Pro Gly Lys Gly Leu Glu Trp Val Ser Ala Ile Ser Gly Ser Gly Gly
            260                 265                 270

Ser Thr Tyr Tyr Ala Asp Ser Val Lys Gly Arg Phe Thr Ile Ser Arg
        275                 280                 285

Asp Asn Ser Lys Asn Thr Leu Tyr Leu Gln Met Asn Ser Leu Arg Ala
    290                 295                 300

Glu Asp Thr Ala Val Tyr Tyr Cys Ala Lys Ala Asp Tyr Gly Val Val
305                 310                 315                 320

Tyr Tyr Phe Asp Tyr Trp Gly Gln Gly Thr Met Val Thr Val Ser Ser
                325                 330                 335

Ala Ser Thr Lys Gly Pro Ser Val Phe Pro Leu Ala Pro Ser Ser Lys
            340                 345                 350

Ser Thr Ser Gly Gly Thr Ala Ala Leu Gly Cys Leu Val Lys Asp Tyr
        355                 360                 365

Phe Pro Glu Pro Val Thr Val Ser Trp Asn Ser Gly Ala Leu Thr Ser
    370                 375                 380

Gly Val His Thr Phe Pro Ala Val Leu Gln Ser Ser Gly Leu Tyr Ser

-continued

```
385             390             395             400

Leu Ser Ser Val Val Thr Val Pro Ser Ser Ser Leu Gly Thr Gln Thr
                405             410             415

Tyr Ile Cys Asn Val Asn His Lys Pro Ser Asn Thr Lys Val Asp Lys
            420             425             430

Lys Val Glu Pro Lys Ser Cys Asp Lys Thr His Thr Cys Pro Pro Cys
            435             440             445

Pro Ala Pro Glu Leu Leu Gly Gly Pro Ser Val Phe Leu Phe Pro Pro
            450             455             460

Lys Pro Lys Asp Thr Leu Met Ile Ser Arg Thr Pro Glu Val Thr Cys
465             470             475             480

Val Val Val Asp Val Ser His Glu Asp Pro Glu Val Lys Phe Asn Trp
                485             490             495

Tyr Val Asp Gly Val Glu Val His Asn Ala Lys Thr Lys Pro Arg Glu
            500             505             510

Glu Gln Tyr Asn Ser Thr Tyr Arg Val Val Ser Val Leu Thr Val Leu
            515             520             525

His Gln Asp Trp Leu Asn Gly Lys Glu Tyr Lys Cys Lys Val Ser Asn
            530             535             540

Lys Ala Leu Pro Ala Pro Ile Glu Lys Thr Ile Ser Lys Ala Lys Gly
545             550             555             560

Gln Pro Arg Glu Pro Gln Val Tyr Thr Leu Pro Pro Ser Arg Asp Glu
                565             570             575

Leu Thr Lys Asn Gln Val Ser Leu Thr Cys Leu Val Lys Gly Phe Tyr
            580             585             590

Pro Ser Asp Ile Ala Val Glu Trp Glu Ser Asn Gly Gln Pro Glu Asn
            595             600             605

Asn Tyr Lys Thr Thr Pro Pro Val Leu Asp Ser Asp Gly Ser Phe Phe
            610             615             620

Leu Tyr Ser Lys Leu Thr Val Asp Lys Ser Arg Trp Gln Gln Gly Asn
625             630             635             640

Val Phe Ser Cys Ser Val Met His Glu Ala Leu His Asn His Tyr Thr
                645             650             655

Gln Lys Ser Leu Ser Leu Ser Pro Gly Lys
            660             665
```

```
<210> SEQ ID NO 239
<211> LENGTH: 670
<212> TYPE: PRT
<213> ORGANISM: artificial sequence
<220> FEATURE:
<223> OTHER INFORMATION: G4_7 IgG1 antibody sequence

<400> SEQUENCE: 239

Ala Ser Asp Ile Val Met Thr Gln Ser Pro Leu Ser Leu Pro Val Thr
1               5               10              15

Pro Gly Glu Pro Ala Ser Ile Ser Cys Arg Ser Ser Gln Ser Leu Leu
            20              25              30

His Ser Asn Arg Phe Asn Tyr Leu Asp Trp Tyr Leu Gln Lys Pro Gly
            35              40              45

Gln Ser Pro Gln Leu Leu Ile Tyr Leu Gly Ser Asn Arg Ala Ser Gly
            50              55              60

Val Pro Asp Arg Phe Ser Gly Ser Gly Ser Gly Thr Asp Phe Thr Leu
65              70              75              80

Lys Ile Ser Arg Val Glu Ala Glu Asp Val Gly Val Tyr Tyr Cys Met
```

```
                85                    90                    95

Gln Gly Leu Gln Thr Pro Tyr Thr Phe Gly Gln Gly Thr Lys Val Asp
            100                   105                   110

Ile Lys Arg Thr Ala Ala Ala Pro Ser Val Phe Ile Phe Pro Pro Ser
            115                   120                   125

Asp Glu Gln Leu Lys Ser Gly Thr Ala Ser Val Val Cys Leu Leu Asn
        130                   135                   140

Asn Phe Tyr Pro Arg Glu Ala Lys Val Gln Trp Lys Val Asp Asn Ala
145                   150                   155                   160

Leu Gln Ser Gly Asn Ser Gln Glu Ser Val Thr Glu Gln Asp Ser Lys
                165                   170                   175

Asp Ser Thr Tyr Ser Leu Ser Ser Thr Leu Thr Leu Ser Lys Ala Asp
            180                   185                   190

Tyr Glu Lys His Lys Leu Tyr Ala Cys Glu Val Thr His Gln Gly Leu
            195                   200                   205

Ser Ser Pro Val Thr Lys Ser Phe Asn Arg Gly Glu Cys Glu Val Gln
        210                   215                   220

Leu Val Glu Ser Gly Gly Gly Trp Val Gln Ser Gly Gly Ser Leu Arg
225                   230                   235                   240

Pro Ser Cys Ala Ala Ser Gly Phe Thr Phe Ser His Tyr Trp Met Ser
                245                   250                   255

Trp Val Arg Gln Ala Pro Gly Lys Gly Leu Glu Trp Val Ala Asn Ile
            260                   265                   270

Lys Gln Asp Gly Ser Ile Ile Tyr Tyr Ala Asp Ser Val Lys Gly Arg
            275                   280                   285

Phe Thr Ile Ser Arg Asp Asn Ala Lys Asn Ser Val Tyr Leu Gln Met
        290                   295                   300

Asn Ser Leu Arg Ala Glu Asp Thr Ala Val Tyr Tyr Cys Ala Arg Ile
305                   310                   315                   320

Gly Tyr Ser Ser Ser Ser Phe Asp Tyr Trp Gly Arg Gly Thr Leu Val
                325                   330                   335

Thr Val Ser Ser Ala Ser Thr Lys Gly Pro Ser Val Phe Pro Leu Ala
            340                   345                   350

Pro Ser Ser Lys Ser Thr Ser Gly Gly Thr Ala Ala Leu Gly Cys Leu
        355                   360                   365

Val Lys Asp Tyr Phe Pro Glu Pro Val Thr Val Ser Trp Asn Ser Gly
        370                   375                   380

Ala Leu Thr Ser Gly Val His Thr Phe Pro Ala Val Leu Gln Ser Ser
385                   390                   395                   400

Gly Leu Tyr Ser Leu Ser Ser Val Val Thr Val Pro Ser Ser Ser Leu
                405                   410                   415

Gly Thr Gln Thr Tyr Ile Cys Asn Val Asn His Lys Pro Ser Asn Thr
            420                   425                   430

Lys Val Asp Lys Lys Val Glu Pro Lys Ser Cys Asp Lys Thr His Thr
            435                   440                   445

Cys Pro Pro Cys Pro Ala Pro Glu Leu Leu Gly Gly Pro Ser Val Phe
        450                   455                   460

Leu Phe Pro Pro Lys Pro Lys Asp Thr Leu Met Ile Ser Arg Thr Pro
465                   470                   475                   480

Glu Val Thr Cys Val Val Val Asp Val Ser His Glu Asp Pro Glu Val
                485                   490                   495

Lys Phe Asn Trp Tyr Val Asp Gly Val Glu Val His Asn Ala Lys Thr
            500                   505                   510
```

```
Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
        530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Asp Glu Leu Thr Lys Asn Gln Val Ser Leu Thr Cys Leu Val
        580                 585                 590

Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
        610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
        660                 665                 670

<210> SEQ ID NO 240
<211> LENGTH: 673
<212> TYPE: PRT
<213> ORGANISM: artificial sequence
<220> FEATURE:
<223> OTHER INFORMATION: G4_10 IgG1 antibody sequence

<400> SEQUENCE: 240

Ala Ser Asp Ile Val Met Thr Gln Pro Pro Leu Ser Leu Pro Val Thr
1                   5                   10                  15

Leu Gly His Pro Ala Ser Ile Ser Cys Lys Ser Ser Gln Ser Leu Glu
                20                  25                  30

Tyr Ser Asp Gly Asn Thr Tyr Leu Asn Trp Phe Gln Gln Arg Pro Gly
        35                  40                  45

Gln Ser Pro Arg Arg Leu Ile Tyr Lys Val Ser Asn Arg Asp Ser Gly
        50                  55                  60

Ala Pro Asp Arg Phe Ser Gly Ser Gly Ser Gly Thr Asp Phe Thr Leu
65                  70                  75                  80

Glu Ile Ser Arg Val Glu Ala Glu Asp Val Gly Val Tyr Tyr Cys Met
                85                  90                  95

Gln Gly Thr Leu Trp Pro Pro Thr Phe Gly Gln Gly Thr Lys Val Asp
                100                 105                 110

Ile Lys Arg Thr Ala Ala Ala Pro Ser Val Phe Ile Phe Pro Pro Ser
        115                 120                 125

Asp Glu Gln Leu Lys Ser Gly Thr Ala Ser Val Val Cys Leu Leu Asn
        130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
                180                 185                 190

Tyr Glu Lys His Lys Leu Tyr Ala Cys Glu Val Thr His Gln Gly Leu
        195                 200                 205
```

```
Ser Ser Pro Val Thr Lys Ser Phe Asn Arg Gly Glu Cys Gln Val Gln
    210                 215                 220

Leu Val Glu Ser Gly Gly Gly Val Val Gln Pro Gly Arg Pro Leu Arg
225                 230                 235                 240

Leu Ser Cys Ala Ala Ser Gly Phe Thr Phe Ser Ser Tyr Ala Met His
                245                 250                 255

Trp Val Arg Gln Ala Pro Gly Lys Gly Leu Glu Trp Val Ser Ala Ile
                260                 265                 270

Ser Gly Ser Gly Gly Ser Thr Tyr Tyr Ala Asp Ser Val Lys Gly Arg
                275                 280                 285

Phe Thr Ile Ser Arg Asp Asn Ser Lys Asn Thr Leu Tyr Leu Gln Met
    290                 295                 300

Asn Ser Leu Arg Ala Glu Asp Thr Ala Val Tyr Tyr Cys Ala Lys Asp
305                 310                 315                 320

Gly Ala Val Asp Phe Trp Arg Asn Gly Met Asp Val Trp Gly Arg Gly
                325                 330                 335

Thr Leu Val Thr Val Ser Ser Ala Ser Thr Lys Gly Pro Ser Val Phe
                340                 345                 350

Pro Leu Ala Pro Ser Ser Lys Ser Thr Ser Gly Gly Thr Ala Ala Leu
                355                 360                 365

Gly Cys Leu Val Lys Asp Tyr Phe Pro Glu Pro Val Thr Val Ser Trp
    370                 375                 380

Asn Ser Gly Ala Leu Thr Ser Gly Val His Thr Phe Pro Ala Val Leu
385                 390                 395                 400

Gln Ser Ser Gly Leu Tyr Ser Leu Ser Ser Val Val Thr Val Pro Ser
                405                 410                 415

Ser Ser Leu Gly Thr Gln Thr Tyr Ile Cys Asn Val Asn His Lys Pro
                420                 425                 430

Ser Asn Thr Lys Val Asp Lys Lys Val Glu Pro Lys Ser Cys Asp Lys
                435                 440                 445

Thr His Thr Cys Pro Pro Cys Pro Ala Pro Glu Leu Leu Gly Gly Pro
    450                 455                 460

Ser Val Phe Leu Phe Pro Pro Lys Pro Lys Asp Thr Leu Met Ile Ser
465                 470                 475                 480

Arg Thr Pro Glu Val Thr Cys Val Val Val Asp Val Ser His Glu Asp
                485                 490                 495

Pro Glu Val Lys Phe Asn Trp Tyr Val Asp Gly Val Glu Val His Asn
                500                 505                 510

Ala Lys Thr Lys Pro Arg Glu Glu Gln Tyr Asn Ser Thr Tyr Arg Val
                515                 520                 525

Val Ser Val Leu Thr Val Leu His Gln Asp Trp Leu Asn Gly Lys Glu
    530                 535                 540

Tyr Lys Cys Lys Val Ser Asn Lys Ala Leu Pro Ala Pro Ile Glu Lys
545                 550                 555                 560

Thr Ile Ser Lys Ala Lys Gly Gln Pro Arg Glu Pro Gln Val Tyr Thr
                565                 570                 575

Leu Pro Pro Ser Arg Asp Glu Leu Thr Lys Asn Gln Val Ser Leu Thr
                580                 585                 590

Cys Leu Val Lys Gly Phe Tyr Pro Ser Asp Ile Ala Val Glu Trp Glu
                595                 600                 605

Ser Asn Gly Gln Pro Glu Asn Asn Tyr Lys Thr Thr Pro Pro Val Leu
    610                 615                 620
```

```
Asp Ser Asp Gly Ser Phe Phe Leu Tyr Ser Lys Leu Thr Val Asp Lys
625             630                 635                 640

Ser Arg Trp Gln Gln Gly Asn Val Phe Ser Cys Ser Val Met His Glu
            645                 650                 655

Ala Leu His Asn His Tyr Thr Gln Lys Ser Leu Ser Leu Ser Pro Gly
            660                 665                 670

Lys

<210> SEQ ID NO 241
<211> LENGTH: 663
<212> TYPE: PRT
<213> ORGANISM: artificial sequence
<220> FEATURE:
<223> OTHER INFORMATION: G4_12 IgG1 antibody sequence

<400> SEQUENCE: 241

Ala Ser Gln Ser Val Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Phe Val Ser Trp Tyr Gln Gln His Pro Gly Lys Ala Pro
        35                  40                  45

Lys Leu Met Ile Tyr Glu Val Thr Asn Arg Pro Ser Gly Val Pro Asp
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser His Ala
                85                  90                  95

Ser Pro Arg Val Phe Gly Thr Gly Thr Lys Val Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Glu Val Gln Leu Leu Glu Ser Gly
    210                 215                 220

Gly Gly Leu Val Gln Pro Gly Gly Ser Leu Arg Leu Ser Cys Ala Ala
225                 230                 235                 240

Ser Gly Phe Thr Val Ser Ser Asn Tyr Met Ser Trp Val Arg Gln Ala
            245                 250                 255

Pro Gly Lys Gly Leu Glu Trp Val Ser Val Ile Tyr Ser Gly Gly Ser
            260                 265                 270

Thr Tyr Tyr Ala Asp Ser Val Lys Gly Arg Phe Thr Ile Ser Arg His
        275                 280                 285

Asn Ser Lys Asn Thr Leu Tyr Leu Gln Met Asn Ser Leu Arg Ala Glu
    290                 295                 300

Asp Thr Ala Val Tyr Tyr Cys Ala Arg Val Ala Asn Gly Asp Phe Leu
```

-continued

```
305              310             315             320

Asp Tyr Trp Gly Arg Gly Thr Leu Val Thr Val Ser Ser Ala Ser Thr
                325             330             335

Lys Gly Pro Ser Val Phe Pro Leu Ala Pro Ser Ser Lys Ser Thr Ser
                340             345             350

Gly Gly Thr Ala Ala Leu Gly Cys Leu Val Lys Asp Tyr Phe Pro Glu
                355             360             365

Pro Val Thr Val Ser Trp Asn Ser Gly Ala Leu Thr Ser Gly Val His
                370             375             380

Thr Phe Pro Ala Val Leu Gln Ser Ser Gly Leu Tyr Ser Leu Ser Ser
385             390             395             400

Val Val Thr Val Pro Ser Ser Ser Leu Gly Thr Gln Thr Tyr Ile Cys
                405             410             415

Asn Val Asn His Lys Pro Ser Asn Thr Lys Val Asp Lys Lys Val Glu
                420             425             430

Pro Lys Ser Cys Asp Lys Thr His Thr Cys Pro Pro Cys Pro Ala Pro
                435             440             445

Glu Leu Leu Gly Gly Pro Ser Val Phe Leu Phe Pro Pro Lys Pro Lys
                450             455             460

Asp Thr Leu Met Ile Ser Arg Thr Pro Glu Val Thr Cys Val Val Val
465             470             475             480

Asp Val Ser His Glu Asp Pro Glu Val Lys Phe Asn Trp Tyr Val Asp
                485             490             495

Gly Val Glu Val His Asn Ala Lys Thr Lys Pro Arg Glu Glu Gln Tyr
                500             505             510

Asn Ser Thr Tyr Arg Val Val Ser Val Leu Thr Val Leu His Gln Asp
                515             520             525

Trp Leu Asn Gly Lys Glu Tyr Lys Cys Lys Val Ser Asn Lys Ala Leu
                530             535             540

Pro Ala Pro Ile Glu Lys Thr Ile Ser Lys Ala Lys Gly Gln Pro Arg
545             550             555             560

Glu Pro Gln Val Tyr Thr Leu Pro Pro Ser Arg Asp Glu Leu Thr Lys
                565             570             575

Asn Gln Val Ser Leu Thr Cys Leu Val Lys Gly Phe Tyr Pro Ser Asp
                580             585             590

Ile Ala Val Glu Trp Glu Ser Asn Gly Gln Pro Glu Asn Asn Tyr Lys
                595             600             605

Thr Thr Pro Pro Val Leu Asp Ser Asp Gly Ser Phe Phe Leu Tyr Ser
                610             615             620

Lys Leu Thr Val Asp Lys Ser Arg Trp Gln Gln Gly Asn Val Phe Ser
625             630             635             640

Cys Ser Val Met His Glu Ala Leu His Asn His Tyr Thr Gln Lys Ser
                645             650             655

Leu Ser Leu Ser Pro Gly Lys
                660
```

```
<210> SEQ ID NO 242
<211> LENGTH: 666
<212> TYPE: PRT
<213> ORGANISM: artificial sequence
<220> FEATURE:
<223> OTHER INFORMATION: G4_13 IgG1 antibody sequence

<400> SEQUENCE: 242

Ala Ser Asn Phe Met Leu Thr Gln Pro His Ser Val Ser Glu Ser Pro
```

```
1                   5                   10                  15
Gly Lys Thr Val Thr Ile Ser Cys Thr Arg Ser Ser Gly Ser Ile Ala
                20                  25                  30

Ser Asn Tyr Val Gln Trp Tyr Gln Gln Arg Pro Gly Ser Ser Pro Ser
                35                  40                  45

Thr Val Ile Tyr Glu Asp Asn Gln Arg Pro Ser Gly Val Pro Asp Arg
        50                  55                  60

Phe Ser Gly Ser Ile Asp Ser Ser Ser Asn Ser Ala Ser Leu Thr Ile
65                  70                  75                  80

Ser Gly Leu Arg Thr Glu Asp Glu Ala Asp Tyr Tyr Cys Gln Ser Tyr
                85                  90                  95

Asp Ser Ser Ile Tyr Val Val Phe Gly Gly Gly Thr Lys Leu Thr Val
                100                 105                 110

Leu Gly Gln Pro Ala Ala Ala Pro Ser Val Thr Leu Phe Pro Pro Ser
                115                 120                 125

Ser Glu Glu Leu Gln Ala Asn Lys Ala Thr Leu Val Cys Leu Ile Ser
        130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
                180                 185                 190

Lys Ser His Arg Ser Tyr Ser Cys Gln Val Thr His Glu Gly Ser Thr
                195                 200                 205

Val Glu Lys Thr Val Ala Pro Thr Glu Cys Ser Gln Val Gln Leu Val
        210                 215                 220

Glu Ser Gly Ala Glu Val Lys Lys Pro Gly Gly Ser Leu Arg Leu Ser
225                 230                 235                 240

Cys Ala Ala Ser Gly Phe Thr Phe Ser Ser Tyr Ser Met Asn Trp Val
                245                 250                 255

Arg Gln Ala Pro Gly Lys Gly Leu Glu Trp Val Ser Ser Ile Ser Gly
                260                 265                 270

Thr Ser Ser Tyr Ile Tyr Tyr Ala Asp Ser Val Lys Gly Arg Phe Thr
                275                 280                 285

Ile Ser Arg Asp Asn Ala Lys Asn Ser Leu Tyr Leu Gln Met Ser Ser
        290                 295                 300

Leu Arg Ala Glu Asp Thr Ala Val Tyr Tyr Cys Ala Arg Gly Gly Leu
305                 310                 315                 320

Gly Met Val Asp Pro Trp Gly Gln Gly Thr Leu Val Thr Val Ser Ser
                325                 330                 335

Ala Ser Thr Lys Gly Pro Ser Val Phe Pro Leu Ala Pro Ser Ser Lys
                340                 345                 350

Ser Thr Ser Gly Gly Thr Ala Ala Leu Gly Cys Leu Val Lys Asp Tyr
                355                 360                 365

Phe Pro Glu Pro Val Thr Val Ser Trp Asn Ser Gly Ala Leu Thr Ser
        370                 375                 380

Gly Val His Thr Phe Pro Ala Val Leu Gln Ser Ser Gly Leu Tyr Ser
385                 390                 395                 400

Leu Ser Ser Val Val Thr Val Pro Ser Ser Ser Leu Gly Thr Gln Thr
                405                 410                 415

Tyr Ile Cys Asn Val Asn His Lys Pro Ser Asn Thr Lys Val Asp Lys
                420                 425                 430
```

```
Lys Val Glu Pro Lys Ser Cys Asp Lys Thr His Thr Cys Pro Pro Cys
        435             440             445

Pro Ala Pro Glu Leu Leu Gly Gly Pro Ser Val Phe Leu Phe Pro Pro
    450             455             460

Lys Pro Lys Asp Thr Leu Met Ile Ser Arg Thr Pro Glu Val Thr Cys
465             470             475             480

Val Val Val Asp Val Ser His Glu Asp Pro Glu Val Lys Phe Asn Trp
            485             490             495

Tyr Val Asp Gly Val Glu Val His Asn Ala Lys Thr Lys Pro Arg Glu
            500             505             510

Glu Gln Tyr Asn Ser Thr Tyr Arg Val Val Ser Val Leu Thr Val Leu
        515             520             525

His Gln Asp Trp Leu Asn Gly Lys Glu Tyr Lys Cys Lys Val Ser Asn
    530             535             540

Lys Ala Leu Pro Ala Pro Ile Glu Lys Thr Ile Ser Lys Ala Lys Gly
545             550             555             560

Gln Pro Arg Glu Pro Gln Val Tyr Thr Leu Pro Pro Ser Arg Asp Glu
            565             570             575

Leu Thr Lys Asn Gln Val Ser Leu Thr Cys Leu Val Lys Gly Phe Tyr
            580             585             590

Pro Ser Asp Ile Ala Val Glu Trp Glu Ser Asn Gly Gln Pro Glu Asn
        595             600             605

Asn Tyr Lys Thr Thr Pro Pro Val Leu Asp Ser Asp Gly Ser Phe Phe
    610             615             620

Leu Tyr Ser Lys Leu Thr Val Asp Lys Ser Arg Trp Gln Gln Gly Asn
625             630             635             640

Val Phe Ser Cys Ser Val Met His Glu Ala Leu His Asn His Tyr Thr
            645             650             655

Gln Lys Ser Leu Ser Leu Ser Pro Gly Lys
        660             665
```

```
<210> SEQ ID NO 243
<211> LENGTH: 666
<212> TYPE: PRT
<213> ORGANISM: artificial sequence
<220> FEATURE:
<223> OTHER INFORMATION: G4_14 IgG1 antibody sequence

<400> SEQUENCE: 243
```

```
Ala Ser Asn Phe Met Leu Thr Gln Pro His Ser Val Ser Glu Ser Pro
1               5               10              15

Gly Lys Thr Val Thr Ile Ser Cys Thr Arg Ser Arg Gly Ser Ile Ala
            20              25              30

Gly Asn Tyr Val His Trp Tyr Gln Gln Arg Pro Gly Arg Ala Pro Thr
        35              40              45

Thr Val Ile Tyr Arg Asp Lys Glu Arg Pro Ser Gly Val Pro Asp Arg
    50              55              60

Ile Ser Gly Ser Ile Asp Ser Ser Ser Asn Ser Ala Ser Leu Thr Ile
65              70              75              80

Ser Gly Leu Lys Thr Glu Asp Glu Ala Asp Tyr Tyr Cys Gln Ser Tyr
            85              90              95

Asp Ser Ser Thr His Val Val Phe Gly Gly Gly Thr Lys Leu Thr Val
            100             105             110

Leu Gly Gln Pro Ala Ala Ala Pro Ser Val Thr Leu Phe Pro Pro Ser
        115             120             125
```

```
Ser Glu Glu Leu Gln Ala Asn Lys Ala Thr Leu Val Cys Leu Ile Ser
    130             135             140
Asp Phe Tyr Pro Gly Ala Val Thr Val Ala Trp Lys Ala Asp Ser Ser
145             150             155             160
Pro Val Lys Ala Gly Val Glu Thr Thr Thr Pro Ser Lys Gln Ser Asn
                165             170             175
Asn Lys Tyr Ala Ala Ser Ser Tyr Leu Ser Leu Thr Pro Glu Gln Trp
            180             185             190
Lys Ser His Arg Ser Tyr Ser Cys Gln Val Thr His Glu Gly Ser Thr
            195             200             205
Val Glu Lys Thr Val Ala Pro Thr Glu Cys Ser Glu Val Gln Leu Val
    210             215             220
Gln Ser Gly Ala Glu Val Lys Lys Pro Gly Glu Ser Leu Arg Ile Ser
225             230             235             240
Cys Lys Gly Ser Gly Tyr Ser Phe Thr Ser Tyr Trp Ile Ser Trp Val
            245             250             255
Arg Gln Met Pro Gly Lys Gly Leu Glu Trp Met Gly Arg Ile Asp Pro
            260             265             270
Ser Asp Ser Tyr Thr Asn Tyr Ser Pro Ser Phe Pro Gly His Val Thr
    275             280             285
Ile Ser Ala Asp Lys Ser Ile Ser Thr Ala Tyr Leu Gln Trp Ser Ser
    290             295             300
Leu Lys Ala Ser Asp Thr Ala Met Tyr Tyr Cys Ala Ala Asp Thr Ala
305             310             315             320
His Gly Met Asp Val Trp Gly Arg Gly Thr Leu Val Thr Val Ser Ser
            325             330             335
Ala Ser Thr Lys Gly Pro Ser Val Phe Pro Leu Ala Pro Ser Ser Lys
            340             345             350
Ser Thr Ser Gly Gly Thr Ala Ala Leu Gly Cys Leu Val Lys Asp Tyr
            355             360             365
Phe Pro Glu Pro Val Thr Val Ser Trp Asn Ser Gly Ala Leu Thr Ser
    370             375             380
Gly Val His Thr Phe Pro Ala Val Leu Gln Ser Ser Gly Leu Tyr Ser
385             390             395             400
Leu Ser Ser Val Val Thr Val Pro Ser Ser Ser Leu Gly Thr Gln Thr
            405             410             415
Tyr Ile Cys Asn Val Asn His Lys Pro Ser Asn Thr Lys Val Asp Lys
            420             425             430
Lys Val Glu Pro Lys Ser Cys Asp Lys Thr His Thr Cys Pro Pro Cys
            435             440             445
Pro Ala Pro Glu Leu Leu Gly Gly Pro Ser Val Phe Leu Phe Pro Pro
    450             455             460
Lys Pro Lys Asp Thr Leu Met Ile Ser Arg Thr Pro Glu Val Thr Cys
465             470             475             480
Val Val Val Asp Val Ser His Glu Asp Pro Glu Val Lys Phe Asn Trp
            485             490             495
Tyr Val Asp Gly Val Glu Val His Asn Ala Lys Thr Lys Pro Arg Glu
            500             505             510
Glu Gln Tyr Asn Ser Thr Tyr Arg Val Val Ser Val Leu Thr Val Leu
            515             520             525
His Gln Asp Trp Leu Asn Gly Lys Glu Tyr Lys Cys Lys Val Ser Asn
    530             535             540
```

-continued

```
Lys Ala Leu Pro Ala Pro Ile Glu Lys Thr Ile Ser Lys Ala Lys Gly
545                 550                 555                 560

Gln Pro Arg Glu Pro Gln Val Tyr Thr Leu Pro Pro Ser Arg Asp Glu
                565                 570                 575

Leu Thr Lys Asn Gln Val Ser Leu Thr Cys Leu Val Lys Gly Phe Tyr
            580                 585                 590

Pro Ser Asp Ile Ala Val Glu Trp Glu Ser Asn Gly Gln Pro Glu Asn
            595                 600                 605

Asn Tyr Lys Thr Thr Pro Pro Val Leu Asp Ser Asp Gly Ser Phe Phe
        610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
                645                 650                 655

Gln Lys Ser Leu Ser Leu Ser Pro Gly Lys
            660                 665
```

```
<210> SEQ ID NO 244
<211> LENGTH: 668
<212> TYPE: PRT
<213> ORGANISM: artificial sequence
<220> FEATURE:
<223> OTHER INFORMATION: G4_15 IgG1 antibody sequence

<400> SEQUENCE: 244
```

```
Ala Ser Gln Ser Ala Leu Thr Gln Pro Ala Ser Val Ser Gly Ser Pro
1                   5                   10                  15

Gly Gln Ser Ile Thr Ile Ser Cys Thr Gly Thr Ser Ser Asp Val Gly
                20                  25                  30

Gly Tyr Asn Tyr Val Ser Trp Tyr Gln Gln His Pro Gly Lys Ala Pro
            35                  40                  45

Lys Leu Met Ile Tyr Asp Val Ser Asn Arg Pro Ser Gly Val Ser Asn
        50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Gly
                85                  90                  95

Ser Gly Ser Val Phe Gly Thr Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser Glu Val Gln Leu Val Gln Ser Glu
        210                 215                 220

Ala Glu Val Lys Lys Pro Gly Ala Ser Val Lys Val Ser Cys Lys Ala
225                 230                 235                 240
```

-continued

```
Ser Gly Tyr Thr Phe Thr Arg His Tyr Met His Trp Val Arg Gln Ala
            245                 250                 255

Pro Gly Gln Gly Leu Glu Trp Met Gly Leu Ile Asn Pro Ser Gly Ser
            260                 265                 270

Ser Thr Val Tyr Ala Gln Lys Phe Gln Gly Arg Val Thr Leu Thr Arg
            275                 280                 285

Asp Thr Ser Thr Ser Thr Asp Tyr Met Glu Leu Ser Ser Leu Arg Ser
    290                 295                 300

Glu Asp Thr Ala Val Tyr Tyr Cys Ala Arg Asp Asn Ser His Leu Asp
305                 310                 315                 320

Gln Val Trp Trp Phe Asp Pro Trp Gly Gln Gly Thr Leu Val Thr Val
                325                 330                 335

Ser Ser Ala Ser Thr Lys Gly Pro Ser Val Phe Pro Leu Ala Pro Ser
            340                 345                 350

Ser Lys Ser Thr Ser Gly Gly Thr Ala Ala Leu Gly Cys Leu Val Lys
            355                 360                 365

Asp Tyr Phe Pro Glu Pro Val Thr Val Ser Trp Asn Ser Gly Ala Leu
    370                 375                 380

Thr Ser Gly Val His Thr Phe Pro Ala Val Leu Gln Ser Ser Gly Leu
385                 390                 395                 400

Tyr Ser Leu Ser Ser Val Val Thr Val Pro Ser Ser Ser Leu Gly Thr
                405                 410                 415

Gln Thr Tyr Ile Cys Asn Val Asn His Lys Pro Ser Asn Thr Lys Val
            420                 425                 430

Asp Lys Lys Val Glu Pro Lys Ser Cys Asp Lys Thr His Thr Cys Pro
            435                 440                 445

Pro Cys Pro Ala Pro Glu Leu Leu Gly Gly Pro Ser Val Phe Leu Phe
    450                 455                 460

Pro Pro Lys Pro Lys Asp Thr Leu Met Ile Ser Arg Thr Pro Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
            515                 520                 525

Val Leu His Gln Asp Trp Leu Asn Gly Lys Glu Tyr Lys Cys Lys Val
    530                 535                 540

Ser Asn Lys Ala Leu Pro Ala Pro Ile Glu Lys Thr Ile Ser Lys Ala
545                 550                 555                 560

Lys Gly Gln Pro Arg Glu Pro Gln Val Tyr Thr Leu Pro Pro Ser Arg
                565                 570                 575

Asp Glu Leu Thr Lys Asn Gln Val Ser Leu Thr Cys Leu Val Lys Gly
            580                 585                 590

Phe Tyr Pro Ser Asp Ile Ala Val Glu Trp Glu Ser Asn Gly Gln Pro
            595                 600                 605

Glu Asn Asn Tyr Lys Thr Thr Pro Pro Val Leu Asp Ser Asp Gly Ser
    610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
```

-continued

```
                660                 665

<210> SEQ ID NO 245
<211> LENGTH: 667
<212> TYPE: PRT
<213> ORGANISM: artificial sequence
<220> FEATURE:
<223> OTHER INFORMATION: G4_16 IgG1 antibody sequence

<400> SEQUENCE: 245

Ala Ser Gln Ser Val Leu Thr Gln Pro Pro Ser Ala Ser Gly Ser Pro
1               5                   10                  15

Gly Gln Ser Val Thr Phe Ser Cys Thr Gly Thr Ser Ser Asp Ile Gly
            20                  25                  30

Ala Phe Asn Ser Val Ser Trp Tyr Gln Gln His Pro Gly Lys Ala Pro
        35                  40                  45

Lys Leu Leu Ile Tyr Glu Ile Thr Lys Arg Pro Ser Gly Val Pro Asp
    50                  55                  60

Arg Phe Ser Gly Ser Lys Ser Gly Asn Thr Ala Ser Leu Thr Ile Ser
65                  70                  75                  80

Val Leu Gln Ala Glu Asp Glu Ala Asp Tyr Tyr Cys Thr Ser Tyr Ala
                85                  90                  95

Gly Ser Asn Thr Leu Ile Phe Gly Gly Gly Thr Lys Val Thr Val Leu
            100                 105                 110

Gly Gln Pro Ala Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
            195                 200                 205

Glu Lys Thr Val Ala Pro Thr Glu Cys Ser Glu Val Gln Leu Leu Glu
    210                 215                 220

Ser Gly Ala Glu Val Lys Lys Pro Gly Ala Ser Val Lys Val Ser Cys
225                 230                 235                 240

Lys Ala Ser Gly Tyr Thr Phe Thr Ser Tyr Gly Ile Ser Trp Val Arg
            245                 250                 255

Gln Ala Pro Gly Gln Gly Leu Glu Trp Met Gly Trp Ile Ser Ala Tyr
            260                 265                 270

Asn Gly Asn Thr Asn Tyr Ala Gln Lys Leu Gln Gly Arg Val Thr Met
        275                 280                 285

Thr Thr Asp Thr Ser Thr Ser Thr Ala Tyr Met Glu Leu Arg Ser Leu
    290                 295                 300

Arg Ser Asp Asp Thr Ala Val Tyr Tyr Cys Ala Arg Asp Tyr Gly Asp
305                 310                 315                 320

Phe Tyr Gly Met Asp Val Trp Gly Gln Gly Thr Leu Val Thr Val Ser
                325                 330                 335

Ser Ala Ser Thr Lys Gly Pro Ser Val Phe Pro Leu Ala Pro Ser Ser
            340                 345                 350

Lys Ser Thr Ser Gly Gly Thr Ala Ala Leu Gly Cys Leu Val Lys Asp
```

-continued

```
            355                 360                 365

Tyr Phe Pro Glu Pro Val Thr Val Ser Trp Asn Ser Gly Ala Leu Thr
    370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Leu Gly Thr Gln
                405                 410                 415

Thr Tyr Ile Cys Asn Val Asn His Lys Pro Ser Asn Thr Lys Val Asp
                420                 425                 430

Lys Lys Val Glu Pro Lys Ser Cys Asp Lys Thr His Thr Cys Pro Pro
                435                 440                 445

Cys Pro Ala Pro Glu Leu Leu Gly Gly Pro Ser Val Phe Leu Phe Pro
        450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
                500                 505                 510

Glu Glu Gln Tyr Asn Ser Thr Tyr Arg Val Val Ser Val Leu Thr Val
            515                 520                 525

Leu His Gln Asp Trp Leu Asn Gly Lys Glu Tyr Lys Cys Lys Val Ser
    530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Asp
                565                 570                 575

Glu Leu Thr Lys Asn Gln Val Ser Leu Thr Cys Leu Val Lys Gly Phe
                580                 585                 590

Tyr Pro Ser Asp Ile Ala Val Glu Trp Glu Ser Asn Gly Gln Pro Glu
            595                 600                 605

Asn Asn Tyr Lys Thr Thr Pro Pro Val Leu Asp Ser Asp Gly Ser Phe
    610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly Lys
            660                 665
```

```
<210> SEQ ID NO 246
<211> LENGTH: 664
<212> TYPE: PRT
<213> ORGANISM: artificial sequence
<220> FEATURE:
<223> OTHER INFORMATION: G4_18 IgG1 antibody sequence

<400> SEQUENCE: 246

Ala Ser Ser Tyr Glu Leu Thr Gln Pro Pro Ser Val Thr Glu Ser Pro
1               5                   10                  15

Gly Gln Thr Ala Arg Ile Thr Cys Ser Gly Asp Ala Leu Ala Lys Gln
                20                  25                  30

Tyr Ala Tyr Trp Tyr Gln Gln Lys Pro Gly Gln Ala Pro Val Leu Val
        35                  40                  45

Ile Tyr Arg Asp Ser Glu Arg Pro Ser Glu Ile Pro Glu Arg Phe Ser
```

-continued

```
        50              55              60

Gly Ser Ser Ser Gly Thr Thr Val Thr Leu Thr Ile Ser Gly Val Gln
65              70              75              80

Ala Glu Asp Glu Ala Asp Tyr Tyr Cys Gln Ser Ala Asp Ser Ser Gly
                85              90              95

Thr Tyr Thr Val Phe Gly Gly Gly Thr Lys Leu Thr Val Leu Gly Gln
                100             105             110

Pro Ala Ala Ala Pro Ser Val Thr Leu Phe Pro Pro Ser Ser Glu Glu
        115             120             125

Leu Gln Ala Asn Lys Ala Thr Leu Val Cys Leu Ile Ser Asp Phe Tyr
        130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
                180             185             190

Arg Ser Tyr Ser Cys Gln Val Thr His Glu Gly Ser Thr Val Glu Lys
        195             200             205

Thr Val Ala Pro Thr Glu Cys Ser Glu Val Gln Leu Val Glu Ser Gly
        210             215             220

Ala Glu Val Lys Lys Pro Gly Ala Ser Val Lys Val Ser Cys Lys Ala
225             230             235             240

Ser Gly Tyr Thr Phe Thr Gly Tyr Tyr Met His Trp Val Arg Gln Ala
                245             250             255

Pro Gly Gln Gly Leu Glu Trp Met Gly Arg Ile Asn Pro Asn Ser Gly
                260             265             270

Gly Thr Asn Tyr Ala Gln Lys Phe Gln Gly Arg Val Thr Met Thr Arg
                275             280             285

Asp Ala Ser Ile Ser Thr Ala Tyr Met Glu Leu Ser Arg Leu Arg Ser
        290             295             300

Asp Asp Thr Ala Val Tyr Tyr Cys Ala Arg Asp Leu Asp Leu Ser Ser
305             310             315             320

Leu Asp Tyr Trp Gly Arg Gly Thr Leu Val Thr Val Ser Ser Ala Ser
                325             330             335

Thr Lys Gly Pro Ser Val Phe Pro Leu Ala Pro Ser Ser Lys Ser Thr
                340             345             350

Ser Gly Gly Thr Ala Ala Leu Gly Cys Leu Val Lys Asp Tyr Phe Pro
                355             360             365

Glu Pro Val Thr Val Ser Trp Asn Ser Gly Ala Leu Thr Ser Gly Val
        370             375             380

His Thr Phe Pro Ala Val Leu Gln Ser Ser Gly Leu Tyr Ser Leu Ser
385             390             395             400

Ser Val Val Thr Val Pro Ser Ser Ser Leu Gly Thr Gln Thr Tyr Ile
                405             410             415

Cys Asn Val Asn His Lys Pro Ser Asn Thr Lys Val Asp Lys Lys Val
                420             425             430

Glu Pro Lys Ser Cys Asp Lys Thr His Thr Cys Pro Pro Cys Pro Ala
        435             440             445

Pro Glu Leu Leu Gly Gly Pro Ser Val Phe Leu Phe Pro Pro Lys Pro
        450             455             460

Lys Asp Thr Leu Met Ile Ser Arg Thr Pro Glu Val Thr Cys Val Val
465             470             475             480
```

-continued

```
Val Asp Val Ser His Glu Asp Pro Glu Val Lys Phe Asn Trp Tyr Val
                485             490             495

Asp Gly Val Glu Val His Asn Ala Lys Thr Lys Pro Arg Glu Glu Gln
            500             505             510

Tyr Asn Ser Thr Tyr Arg Val Val Ser Val Leu Thr Val Leu His Gln
        515             520             525

Asp Trp Leu Asn Gly Lys Glu Tyr Lys Cys Lys Val Ser Asn Lys Ala
    530             535             540

Leu Pro Ala Pro Ile Glu Lys Thr Ile Ser Lys Ala Lys Gly Gln Pro
545             550             555             560

Arg Glu Pro Gln Val Tyr Thr Leu Pro Pro Ser Arg Asp Glu Leu Thr
                565             570             575

Lys Asn Gln Val Ser Leu Thr Cys Leu Val Lys Gly Phe Tyr Pro Ser
            580             585             590

Asp Ile Ala Val Glu Trp Glu Ser Asn Gly Gln Pro Glu Asn Asn Tyr
        595             600             605

Lys Thr Thr Pro Pro Val Leu Asp Ser Asp Gly Ser Phe Phe Leu Tyr
        610             615             620

Ser Lys Leu Thr Val Asp Lys Ser Arg Trp Gln Gln Gly Asn Val Phe
625             630             635             640

Ser Cys Ser Val Met His Glu Ala Leu His Asn His Tyr Thr Gln Lys
                645             650             655

Ser Leu Ser Leu Ser Pro Gly Lys
                660

<210> SEQ ID NO 247
<211> LENGTH: 670
<212> TYPE: PRT
<213> ORGANISM: artificial sequence
<220> FEATURE:
<223> OTHER INFORMATION: G4_19 IgG1 antibody sequence

<400> SEQUENCE: 247

Ala Ser Asn Phe Met Leu Thr Gln Pro His Ser Val Ser Glu Ser Pro
1               5               10              15

Gly Lys Thr Val Thr Ile Ser Cys Thr Arg Ser Ser Gly Ser Ile Ala
            20              25              30

Ser Asn Tyr Val Gln Trp Tyr Gln Gln Arg Pro Gly Ser Pro Pro Ile
        35              40              45

Thr Leu Ile Tyr Asp Asp Asp Gln Arg Pro Ser Gly Val Pro His Arg
    50              55              60

Phe Ser Gly Ser Ile Asp Thr Ser Ser Asn Pro Ala Ser Leu Thr Ile
65              70              75              80

Ser Gly Leu Lys Thr Glu Asp Glu Ala Asp Tyr Tyr Cys Gln Ser Tyr
                85              90              95

Asp Ser Ser Asn His Val Val Phe Gly Gly Gly Thr Lys Leu Thr Val
            100             105             110

Leu Gly Gln Pro Ala Ala Ala Pro Ser Val Thr Leu Phe Pro Pro Ser
            115             120             125

Ser Glu Glu Leu Gln Ala Asn Lys Ala Thr Leu Val Cys Leu Ile Ser
        130             135             140

Asp Phe Tyr Pro Gly Ala Val Thr Val Ala Trp Lys Ala Asp Ser Ser
145             150             155             160

Pro Val Lys Ala Gly Val Glu Thr Thr Thr Pro Ser Lys Gln Ser Asn
                165             170             175
```

Asn Lys Tyr Ala Ala Ser Ser Tyr Leu Ser Leu Thr Pro Glu Gln Trp
                180                 185                 190

Lys Ser His Arg Ser Tyr Ser Cys Gln Val Thr His Glu Gly Ser Thr
                195                 200                 205

Val Glu Lys Thr Val Ala Pro Thr Glu Cys Ser Glu Val Gln Leu Val
                210                 215                 220

Gln Ser Gly Ala Glu Val Lys Lys Pro Gly Ala Ser Val Lys Val Ser
225                 230                 235                 240

Cys Lys Ala Ser Gly Tyr Thr Leu Thr Ser Tyr Tyr Met His Trp Val
                245                 250                 255

Arg Gln Ala Pro Gly Gln Gly Leu Glu Trp Met Gly Ile Ile Asn Pro
                260                 265                 270

Ser Gly Gly Ser Thr Ser Tyr Ala Gln Lys Phe Gln Gly Arg Val Thr
                275                 280                 285

Met Thr Arg Asp Thr Ser Thr Ser Thr Val Tyr Met Glu Leu Ser Ser
                290                 295                 300

Leu Arg Ser Glu Asp Thr Ala Val Tyr Tyr Cys Ala Arg Glu Arg Gly
305                 310                 315                 320

Tyr Ser Tyr Gly Asp Gly Met Asp Val Trp Gly Gln Gly Thr Thr Val
                325                 330                 335

Thr Val Ser Ser Ala Ser Thr Lys Gly Pro Ser Val Phe Pro Leu Ala
                340                 345                 350

Pro Ser Ser Lys Ser Thr Ser Gly Gly Thr Ala Ala Leu Gly Cys Leu
                355                 360                 365

Val Lys Asp Tyr Phe Pro Glu Pro Val Thr Val Ser Trp Asn Ser Gly
                370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
                405                 410                 415

Gly Thr Gln Thr Tyr Ile Cys Asn Val Asn His Lys Pro Ser Asn Thr
                420                 425                 430

Lys Val Asp Lys Lys Val Glu Pro Lys Ser Cys Asp Lys Thr His Thr
                435                 440                 445

Cys Pro Pro Cys Pro Ala Pro Glu Leu Leu Gly Gly Pro Ser Val Phe
                450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
                500                 505                 510

Lys Pro Arg Glu Glu Gln Tyr Asn Ser Thr Tyr Arg Val Val Ser Val
                515                 520                 525

Leu Thr Val Leu His Gln Asp Trp Leu Asn Gly Lys Glu Tyr Lys Cys
                530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Asp Glu Leu Thr Lys Asn Gln Val Ser Leu Thr Cys Leu Val
                580                 585                 590

```
Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
        610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
                660                 665                 670

<210> SEQ ID NO 248
<211> LENGTH: 663
<212> TYPE: PRT
<213> ORGANISM: artificial sequence
<220> FEATURE:
<223> OTHER INFORMATION: G4_20 IgG1 antibody sequence

<400> SEQUENCE: 248

Ala Ser Ser Tyr Glu Leu Thr His Pro Pro Ser Val Ser Val Ser Pro
1                 5                 10                 15

Gly Gln Thr Ala Ser Ile Thr Cys Ser Gly Asp Lys Leu Gly Asp Lys
                20                 25                 30

Phe Val Ser Trp Tyr His Gln Lys Pro Gly Gln Ser Pro Val Leu Val
            35                 40                 45

Ile Tyr Gln Asp Ser Lys Arg Pro Ser Gly Ile Pro Glu Arg Phe Ser
        50                 55                 60

Gly Ser Asn Ser Gly Asn Thr Ala Thr Leu Thr Ile Ser Gly Thr Arg
65                 70                 75                 80

Ala Met Asp Glu Ala Asp Tyr Tyr Cys Gln Ala Trp Asp Ser Ser Thr
                85                 90                 95

Val Val Phe Gly Gly Gly Thr Lys Leu Thr Val Leu Gly Gln Pro Ala
                100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
        195                 200                 205

Ala Pro Thr Glu Cys Ser Gln Val Gln Leu Val Glu Ser Gly Ala Glu
        210                 215                 220

Val Lys Lys Pro Gly Ala Ser Val Lys Val Ser Cys Lys Ala Ser Gly
225                 230                 235                 240

Gly Thr Phe Ser Ser Tyr Ala Ile Ser Trp Val Arg Gln Ala Pro Gly
                245                 250                 255

Gln Gly Leu Glu Trp Met Gly Gly Ile Ile Pro Ile Phe Gly Thr Ala
                260                 265                 270

Asn Tyr Ala Gln Lys Phe Gln Gly Arg Val Thr Ile Thr Val Asp Lys
        275                 280                 285
```

-continued

```
Ser Thr Arg Thr Ala Tyr Met Glu Leu Ser Ser Leu Arg Ser Lys Asp
    290             295             300
Thr Ala Val Tyr Tyr Cys Ala Arg Gly Asn Ser Arg Ser Asp Ala Phe
305             310             315             320
Asp Ile Trp Gly Gln Gly Thr Met Val Thr Val Ser Ser Ala Ser Thr
            325             330             335
Lys Gly Pro Ser Val Phe Pro Leu Ala Pro Ser Ser Lys Ser Thr Ser
            340             345             350
Gly Gly Thr Ala Ala Leu Gly Cys Leu Val Lys Asp Tyr Phe Pro Glu
        355             360             365
Pro Val Thr Val Ser Trp Asn Ser Gly Ala Leu Thr Ser Gly Val His
    370             375             380
Thr Phe Pro Ala Val Leu Gln Ser Ser Gly Leu Tyr Ser Leu Ser Ser
385             390             395             400
Val Val Thr Val Pro Ser Ser Ser Leu Gly Thr Gln Thr Tyr Ile Cys
            405             410             415
Asn Val Asn His Lys Pro Ser Asn Thr Lys Val Asp Lys Lys Val Glu
            420             425             430
Pro Lys Ser Cys Asp Lys Thr His Thr Cys Pro Pro Cys Pro Ala Pro
            435             440             445
Glu Leu Leu Gly Gly Pro Ser Val Phe Leu Phe Pro Pro Lys Pro Lys
    450             455             460
Asp Thr Leu Met Ile Ser Arg Thr Pro Glu Val Thr Cys Val Val Val
465             470             475             480
Asp Val Ser His Glu Asp Pro Glu Val Lys Phe Asn Trp Tyr Val Asp
            485             490             495
Gly Val Glu Val His Asn Ala Lys Thr Lys Pro Arg Glu Glu Gln Tyr
            500             505             510
Asn Ser Thr Tyr Arg Val Val Ser Val Leu Thr Val Leu His Gln Asp
            515             520             525
Trp Leu Asn Gly Lys Glu Tyr Lys Cys Lys Val Ser Asn Lys Ala Leu
    530             535             540
Pro Ala Pro Ile Glu Lys Thr Ile Ser Lys Ala Lys Gly Gln Pro Arg
545             550             555             560
Glu Pro Gln Val Tyr Thr Leu Pro Pro Ser Arg Asp Glu Leu Thr Lys
            565             570             575
Asn Gln Val Ser Leu Thr Cys Leu Val Lys Gly Phe Tyr Pro Ser Asp
            580             585             590
Ile Ala Val Glu Trp Glu Ser Asn Gly Gln Pro Glu Asn Asn Tyr Lys
            595             600             605
Thr Thr Pro Pro Val Leu Asp Ser Asp Gly Ser Phe Phe Leu Tyr Ser
    610             615             620
Lys Leu Thr Val Asp Lys Ser Arg Trp Gln Gln Gly Asn Val Phe Ser
625             630             635             640
Cys Ser Val Met His Glu Ala Leu His Asn His Tyr Thr Gln Lys Ser
            645             650             655
Leu Ser Leu Ser Pro Gly Lys
            660
```

<210> SEQ ID NO 249
<211> LENGTH: 666
<212> TYPE: PRT
<213> ORGANISM: artificial sequence
<220> FEATURE:
<223> OTHER INFORMATION: G4_22 IgG1 antibody sequence

<400> SEQUENCE: 249

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Val Ser Gly Ser Gly Thr Asp Phe Thr Leu Thr Ile Ser Asn Leu
65                  70                  75                  80

Gln Pro Glu Asp Phe Ala Thr Tyr Tyr Cys Gln Gln Ser Tyr Ser Ile
                85                  90                  95

Pro Trp Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
            195                 200                 205

Lys Ser Phe Asn Arg Gly Glu Cys Gln Val Gln Leu Val Glu Ser Gly
    210                 215                 220

Gly Gly Leu Val Gln Pro Gly Gly Ser Leu Arg Leu Ser Cys Ala Ala
225                 230                 235                 240

Ser Gly Phe Thr Phe Ser Thr Tyr Ala Met Ser Trp Val Arg Gln Ala
                245                 250                 255

Pro Gly Lys Gly Leu Glu Trp Val Ser Thr Val Ser Gly Ser Gly Gly
            260                 265                 270

Thr Thr Tyr Tyr Ala Asp Ser Val Lys Gly Arg Phe Thr Ile Ser Arg
            275                 280                 285

Asp Asn Ser Lys Asn Thr Leu Tyr Leu Gln Met Asn Ser Leu Arg Ala
    290                 295                 300

Glu Asp Thr Ala Val Tyr Tyr Cys Ala Lys Asp Ser Thr Ala Val Thr
305                 310                 315                 320

Asp Trp Phe Asp Pro Trp Gly Arg Gly Thr Leu Val Thr Val Ser Ser
            325                 330                 335

Ala Ser Thr Lys Gly Pro Ser Val Phe Pro Leu Ala Pro Ser Ser Lys
            340                 345                 350

Ser Thr Ser Gly Gly Thr Ala Ala Leu Gly Cys Leu Val Lys Asp Tyr
            355                 360                 365

Phe Pro Glu Pro Val Thr Val Ser Trp Asn Ser Gly Ala Leu Thr Ser
    370                 375                 380

Gly Val His Thr Phe Pro Ala Val Leu Gln Ser Ser Gly Leu Tyr Ser
385                 390                 395                 400

Leu Ser Ser Val Val Thr Val Pro Ser Ser Ser Leu Gly Thr Gln Thr

```
                  405              410              415
Tyr Ile Cys Asn Val Asn His Lys Pro Ser Asn Thr Lys Val Asp Lys
            420              425              430

Lys Val Glu Pro Lys Ser Cys Asp Lys Thr His Thr Cys Pro Pro Cys
            435              440              445

Pro Ala Pro Glu Leu Leu Gly Gly Pro Ser Val Phe Leu Phe Pro Pro
        450              455              460

Lys Pro Lys Asp Thr Leu Met Ile Ser Arg Thr Pro Glu Val Thr Cys
465              470              475              480

Val Val Val Asp Val Ser His Glu Asp Pro Glu Val Lys Phe Asn Trp
                485              490              495

Tyr Val Asp Gly Val Glu Val His Asn Ala Lys Thr Lys Pro Arg Glu
            500              505              510

Glu Gln Tyr Asn Ser Thr Tyr Arg Val Val Ser Val Leu Thr Val Leu
            515              520              525

His Gln Asp Trp Leu Asn Gly Lys Glu Tyr Lys Cys Lys Val Ser Asn
        530              535              540

Lys Ala Leu Pro Ala Pro Ile Glu Lys Thr Ile Ser Lys Ala Lys Gly
545              550              555              560

Gln Pro Arg Glu Pro Gln Val Tyr Thr Leu Pro Pro Ser Arg Asp Glu
                565              570              575

Leu Thr Lys Asn Gln Val Ser Leu Thr Cys Leu Val Lys Gly Phe Tyr
            580              585              590

Pro Ser Asp Ile Ala Val Glu Trp Glu Ser Asn Gly Gln Pro Glu Asn
            595              600              605

Asn Tyr Lys Thr Thr Pro Pro Val Leu Asp Ser Asp Gly Ser Phe Phe
        610              615              620

Leu Tyr Ser Lys Leu Thr Val Asp Lys Ser Arg Trp Gln Gln Gly Asn
625              630              635              640

Val Phe Ser Cys Ser Val Met His Glu Ala Leu His Asn His Tyr Thr
                645              650              655

Gln Lys Ser Leu Ser Leu Ser Pro Gly Lys
            660              665
```

```
<210> SEQ ID NO 250
<211> LENGTH: 666
<212> TYPE: PRT
<213> ORGANISM: artificial sequence
<220> FEATURE:
<223> OTHER INFORMATION: G4_23 IgG1 antibody sequence

<400> SEQUENCE: 250

Ala Ser Asp Ile Gln Met Thr Gln Ser Pro Ser Ser Leu Ser Ala Ser
1               5              10              15

Val Gly Asp Arg Val Thr Ile Thr Cys Arg Ala Ser Gln Gly Ile Ser
            20              25              30

Asn Ser Leu Ala Trp Tyr Gln Gln Lys Pro Gly Lys Ala Pro Lys Leu
        35              40              45

Leu Leu Tyr Ala Ala Ser Arg Leu Glu Ser Gly Val Pro Ser Arg Phe
        50              55              60

Ser Gly Ser Gly Ser Gly Thr Asp Tyr Thr Leu Thr Ile Ser Ser Leu
65              70              75              80

Gln Pro Glu Asp Phe Ala Thr Tyr Tyr Cys Gln Gln Tyr Tyr Ser Thr
                85              90              95

Pro Arg Thr Phe Gly Gly Gly Thr Lys Leu Glu Ile Lys Arg Thr Ala
```

-continued

```
                100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Leu Tyr Ala Cys Glu Val Thr His Gln Gly Leu Ser Ser Pro Val Thr
                195                 200                 205

Lys Ser Phe Asn Arg Gly Glu Cys Glu Val Gln Leu Val Glu Ser Gly
        210                 215                 220

Gly Gly Val Val Gln Pro Gly Arg Ser Leu Arg Leu Ser Cys Ala Ala
225                 230                 235                 240

Ser Gly Phe Thr Phe Ser Ser Tyr Gly Met His Trp Val Arg Gln Ala
                245                 250                 255

Pro Gly Lys Gly Leu Glu Trp Val Ala Val Ile Trp Tyr Asp Gly Ser
                260                 265                 270

Asn Lys Tyr Tyr Ala Asp Ser Val Lys Gly Arg Phe Thr Ile Ser Arg
        275                 280                 285

Asp Asn Ser Lys Asn Thr Leu Tyr Leu Gln Met Asn Ser Leu Arg Ala
        290                 295                 300

Glu Asp Thr Ala Val Tyr Tyr Cys Ala Arg Gly Glu Val Ala Ala Leu
305                 310                 315                 320

Tyr Tyr Phe Asp Tyr Trp Gly Gln Gly Thr Leu Val Thr Val Ser Ser
                325                 330                 335

Ala Ser Thr Lys Gly Pro Ser Val Phe Pro Leu Ala Pro Ser Ser Lys
                340                 345                 350

Ser Thr Ser Gly Gly Thr Ala Ala Leu Gly Cys Leu Val Lys Asp Tyr
                355                 360                 365

Phe Pro Glu Pro Val Thr Val Ser Trp Asn Ser Gly Ala Leu Thr Ser
        370                 375                 380

Gly Val His Thr Phe Pro Ala Val Leu Gln Ser Ser Gly Leu Tyr Ser
385                 390                 395                 400

Leu Ser Ser Val Val Thr Val Pro Ser Ser Ser Leu Gly Thr Gln Thr
                405                 410                 415

Tyr Ile Cys Asn Val Asn His Lys Pro Ser Asn Thr Lys Val Asp Lys
                420                 425                 430

Lys Val Glu Pro Lys Ser Cys Asp Lys Thr His Thr Cys Pro Pro Cys
        435                 440                 445

Pro Ala Pro Glu Leu Leu Gly Gly Pro Ser Val Phe Leu Phe Pro Pro
        450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
                500                 505                 510

Glu Gln Tyr Asn Ser Thr Tyr Arg Val Val Ser Val Leu Thr Val Leu
                515                 520                 525
```

```
His Gln Asp Trp Leu Asn Gly Lys Glu Tyr Lys Cys Lys Val Ser Asn
    530                 535                 540
```

```
Lys Ala Leu Pro Ala Pro Ile Glu Lys Thr Ile Ser Lys Ala Lys Gly
545                 550                 555                 560
```

```
Gln Pro Arg Glu Pro Gln Val Tyr Thr Leu Pro Pro Ser Arg Asp Glu
                565                 570                 575
```

```
Leu Thr Lys Asn Gln Val Ser Leu Thr Cys Leu Val Lys Gly Phe Tyr
                580                 585                 590
```

```
Pro Ser Asp Ile Ala Val Glu Trp Glu Ser Asn Gly Gln Pro Glu Asn
                595                 600                 605
```

```
Asn Tyr Lys Thr Thr Pro Pro Val Leu Asp Ser Asp Gly Ser Phe Phe
    610                 615                 620
```

```
Leu Tyr Ser Lys Leu Thr Val Asp Lys Ser Arg Trp Gln Gln Gly Asn
625                 630                 635                 640
```

```
Val Phe Ser Cys Ser Val Met His Glu Ala Leu His Asn His Tyr Thr
                645                 650                 655
```

```
Gln Lys Ser Leu Ser Leu Ser Pro Gly Lys
                660                 665
```

```
<210> SEQ ID NO 251
<211> LENGTH: 674
<212> TYPE: PRT
<213> ORGANISM: artificial sequence
<220> FEATURE:
<223> OTHER INFORMATION: G4_24 IgG1 antibody sequence
```

```
<400> SEQUENCE: 251
```

```
Ala Ser Asp Ile Val Met Thr Gln Ser Pro Asp Ser Leu Ala Val Ser
1               5                   10                  15
```

```
Leu Gly Glu Arg Ala Thr Ile Asn Cys Lys Ser Ser Gln Ser Val Leu
                20                  25                  30
```

```
Tyr Ser Ser Asn Asn Lys Asn Tyr Leu Ala Trp Tyr Gln Gln Lys Pro
            35                  40                  45
```

```
Gly Gln Pro Pro Lys Leu Leu Ile Ser Trp Ala Ser Thr Arg Glu Ser
    50                  55                  60
```

```
Gly Val Pro Asp Arg Phe Ser Gly Ser Gly Ser Gly Thr Asp Phe Thr
65                  70                  75                  80
```

```
Leu Thr Ile Asn Ser Leu Gln Ser Glu Asp Val Ala Ile Tyr Tyr Cys
                85                  90                  95
```

```
Gln Gln Tyr Tyr Ser Thr Pro Pro Thr Phe Gly Gln Gly Thr Lys Leu
            100                 105                 110
```

```
Glu Ile Lys Arg Thr Ala Ala Ala Pro Ser Val Phe Ile Phe Pro Pro
    115                 120                 125
```

```
Ser Asp Glu Gln Leu Lys Ser Gly Thr Ala Ser Val Val Cys Leu Leu
    130                 135                 140
```

```
Asn Asn Phe Tyr Pro Arg Glu Ala Lys Val Gln Trp Lys Val Asp Asn
145                 150                 155                 160
```

```
Ala Leu Gln Ser Gly Asn Ser Gln Glu Ser Val Thr Glu Gln Asp Ser
                165                 170                 175
```

```
Lys Asp Ser Thr Tyr Ser Leu Ser Ser Thr Leu Thr Leu Ser Lys Ala
            180                 185                 190
```

```
Asp Tyr Glu Lys His Lys Leu Tyr Ala Cys Glu Val Thr His Gln Gly
            195                 200                 205
```

```
Leu Ser Ser Pro Val Thr Lys Ser Phe Asn Arg Gly Glu Cys Gln Val
    210                 215                 220
```

```
Gln Leu Gln Gln Ser Gly Pro Gly Leu Val Lys Pro Ser Gln Thr Leu
225             230             235             240

Ser Leu Thr Cys Ala Ile Ser Gly Ala Ser Val Ser Ser Asn Ser Val
            245             250             255

Ala Trp Asn Trp Ile Arg Gln Ser Pro Ser Arg Gly Leu Glu Trp Leu
            260             265             270

Gly Arg Thr Tyr Tyr Arg Ser Arg Trp Tyr Asn Asp Tyr Ala Leu Ser
            275             280             285

Val Lys Ser Arg Ile Ile Ile Asn Pro Asp Thr Ser Lys Asn Gln Phe
            290             295             300

Ser Leu Gln Leu Asn Ser Val Thr Pro Glu Asp Thr Ala Val Tyr Tyr
305             310             315             320

Cys Ala Arg Asp Trp Ser Ser Thr Arg Ser Phe Asp Tyr Trp Gly Arg
            325             330             335

Gly Thr Leu Val Thr Val Ser Ser Ala Ser Thr Lys Gly Pro Ser Val
            340             345             350

Phe Pro Leu Ala Pro Ser Ser Lys Ser Thr Ser Gly Gly Thr Ala Ala
            355             360             365

Leu Gly Cys Leu Val Lys Asp Tyr Phe Pro Glu Pro Val Thr Val Ser
            370             375             380

Trp Asn Ser Gly Ala Leu Thr Ser Gly Val His Thr Phe Pro Ala Val
385             390             395             400

Leu Gln Ser Ser Gly Leu Tyr Ser Leu Ser Ser Val Val Thr Val Pro
            405             410             415

Ser Ser Ser Leu Gly Thr Gln Thr Tyr Ile Cys Asn Val Asn His Lys
            420             425             430

Pro Ser Asn Thr Lys Val Asp Lys Lys Val Glu Pro Lys Ser Cys Asp
            435             440             445

Lys Thr His Thr Cys Pro Pro Cys Pro Ala Pro Glu Leu Leu Gly Gly
            450             455             460

Pro Ser Val Phe Leu Phe Pro Pro Lys Pro Lys Asp Thr Leu Met Ile
465             470             475             480

Ser Arg Thr Pro Glu Val Thr Cys Val Val Val Asp Val Ser His Glu
            485             490             495

Asp Pro Glu Val Lys Phe Asn Trp Tyr Val Asp Gly Val Glu Val His
            500             505             510

Asn Ala Lys Thr Lys Pro Arg Glu Glu Gln Tyr Asn Ser Thr Tyr Arg
            515             520             525

Val Val Ser Val Leu Thr Val Leu His Gln Asp Trp Leu Asn Gly Lys
            530             535             540

Glu Tyr Lys Cys Lys Val Ser Asn Lys Ala Leu Pro Ala Pro Ile Glu
545             550             555             560

Lys Thr Ile Ser Lys Ala Lys Gly Gln Pro Arg Glu Pro Gln Val Tyr
            565             570             575

Thr Leu Pro Pro Ser Arg Asp Glu Leu Thr Lys Asn Gln Val Ser Leu
            580             585             590

Thr Cys Leu Val Lys Gly Phe Tyr Pro Ser Asp Ile Ala Val Glu Trp
            595             600             605

Glu Ser Asn Gly Gln Pro Glu Asn Asn Tyr Lys Thr Thr Pro Pro Val
            610             615             620

Leu Asp Ser Asp Gly Ser Phe Phe Leu Tyr Ser Lys Leu Thr Val Asp
625             630             635             640
```

```
Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 252
<211> LENGTH: 669
<212> TYPE: PRT
<213> ORGANISM: artificial sequence
<220> FEATURE:
<223> OTHER INFORMATION: G4_25 IgG1 antibody sequence

<400> SEQUENCE: 252

Ala Ser Gln Ser Ala Leu Thr Gln Pro Arg Ser Val Ser Gly Ser Pro
1               5                   10                  15

Gly Gln Ser Val Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Met Ile Tyr Glu Val Ser Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Gly
                85                  90                  95

Ser Gly Ser Val Phe Gly Thr Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Glu Val Gln Leu Val Glu Ser Gly
    210                 215                 220

Ala Glu Val Lys Lys Pro Gly Ser Ser Val Lys Val Ser Cys Lys Ala
225                 230                 235                 240

Ser Gly Gly Thr Phe Ser Ser Tyr Ala Ile Ser Trp Val Arg Gln Ala
                245                 250                 255

Pro Gly Gln Gly Leu Glu Trp Met Gly Gly Ile Ile Pro Ile Phe Gly
            260                 265                 270

Thr Ala Asn Tyr Ala Gln Lys Phe Gln Gly Arg Val Thr Ile Thr Ala
        275                 280                 285

Asp Lys Ser Thr Ser Thr Ala Tyr Met Glu Leu Ser Ser Leu Arg Ser
    290                 295                 300

Glu Asp Thr Ala Val Tyr Tyr Cys Ala Arg Ser Leu Arg Asp Gly Tyr
305                 310                 315                 320

Asn Tyr Ile Gly Ser Leu Gly Tyr Trp Gly Gln Gly Thr Leu Val Thr
```

-continued

```
                    325              330              335
Val Ser Ser Ala Ser Thr Lys Gly Pro Ser Val Phe Pro Leu Ala Pro
            340              345              350

Ser Ser Lys Ser Thr Ser Gly Gly Thr Ala Ala Leu Gly Cys Leu Val
            355              360              365

Lys Asp Tyr Phe Pro Glu Pro Val Thr Val Ser Trp Asn Ser Gly Ala
            370              375              380

Leu Thr Ser Gly Val His Thr Phe Pro Ala Val Leu Gln Ser Ser Gly
385              390              395              400

Leu Tyr Ser Leu Ser Ser Val Val Thr Val Pro Ser Ser Ser Leu Gly
            405              410              415

Thr Gln Thr Tyr Ile Cys Asn Val Asn His Lys Pro Ser Asn Thr Lys
            420              425              430

Val Asp Lys Lys Val Glu Pro Lys Ser Cys Asp Lys Thr His Thr Cys
            435              440              445

Pro Pro Cys Pro Ala Pro Glu Leu Leu Gly Gly Pro Ser Val Phe Leu
            450              455              460

Phe Pro Pro Lys Pro Lys Asp Thr Leu Met Ile Ser Arg Thr Pro Glu
465              470              475              480

Val Thr Cys Val Val Val Asp Val Ser His Glu Asp Pro Glu Val Lys
            485              490              495

Phe Asn Trp Tyr Val Asp Gly Val Glu Val His Asn Ala Lys Thr Lys
            500              505              510

Pro Arg Glu Glu Gln Tyr Asn Ser Thr Tyr Arg Val Val Ser Val Leu
            515              520              525

Thr Val Leu His Gln Asp Trp Leu Asn Gly Lys Glu Tyr Lys Cys Lys
            530              535              540

Val Ser Asn Lys Ala Leu Pro Ala Pro Ile Glu Lys Thr Ile Ser Lys
545              550              555              560

Ala Lys Gly Gln Pro Arg Glu Pro Gln Val Tyr Thr Leu Pro Pro Ser
            565              570              575

Arg Asp Glu Leu Thr Lys Asn Gln Val Ser Leu Thr Cys Leu Val Lys
            580              585              590

Gly Phe Tyr Pro Ser Asp Ile Ala Val Glu Trp Glu Ser Asn Gly Gln
            595              600              605

Pro Glu Asn Asn Tyr Lys Thr Thr Pro Pro Val Leu Asp Ser Asp Gly
            610              615              620

Ser Phe Phe Leu Tyr Ser Lys Leu Thr Val Asp Lys Ser Arg Trp Gln
625              630              635              640

Gln Gly Asn Val Phe Ser Cys Ser Val Met His Glu Ala Leu His Asn
            645              650              655

His Tyr Thr Gln Lys Ser Leu Ser Leu Ser Pro Gly Lys
            660              665
```

<210> SEQ ID NO 253
<211> LENGTH: 666
<212> TYPE: PRT
<213> ORGANISM: artificial sequence
<220> FEATURE:
<223> OTHER INFORMATION: G4_26 IgG1 antibody sequence

<400> SEQUENCE: 253

```
Ala Ser Gln Ser Gly Leu Thr Gln Pro Ala Ser Val Ser Gly Ser Pro
1               5               10              15

Gly Gln Ser Ile Thr Ile Ser Cys Thr Gly Thr Ser Ser Asp Val Gly
```

-continued

```
                  20                  25                  30
Ser Tyr Asn Leu Val Ser Trp Tyr Gln Gln His Pro Gly Lys Ala Pro
        35                  40                  45
Lys Leu Met Ile Tyr Glu Val Ser Lys Arg Pro Ser Gly Val Ser Asn
    50                  55                  60
Arg Phe Ser Gly Ser Lys Ser Gly Asn Thr Ala Ser Leu Thr Ile Ser
65                  70                  75                  80
Gly Leu Gln Ala Glu Asp Glu Ala Asp Tyr Tyr Cys Ser Ser Phe Gly
                85                  90                  95
Ser Gly Ser Ile Phe Gly Thr Gly Thr Lys Leu Thr Val Leu Gly Gln
                100                 105                 110
Pro Ala Ala Ala Pro Ser Val Thr Leu Phe Pro Pro Ser Ser Glu Glu
        115                 120                 125
Leu Gln Ala Asn Lys Ala Thr Leu Val Cys Leu Ile Ser Asp Phe Tyr
        130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
                195                 200                 205
Thr Val Ala Pro Thr Glu Cys Ser Gln Val Gln Leu Val Gln Ser Gly
        210                 215                 220
Ala Glu Val Lys Lys Pro Gly Ser Ser Val Lys Val Ser Cys Lys Ala
225                 230                 235                 240
Ser Gly Gly Thr Phe Ser Ser Tyr Ala Ile Ser Trp Val Arg Gln Ala
                245                 250                 255
Pro Gly Gln Gly Leu Glu Trp Met Gly Gly Ile Ile Pro Ile Phe Gly
                260                 265                 270
Thr Ala Asn Tyr Ala Gln Lys Phe Gln Gly Arg Val Thr Ile Thr Ala
                275                 280                 285
Asp Glu Ser Thr Ser Thr Ala Tyr Met Glu Leu Ser Ser Leu Arg Ser
        290                 295                 300
Glu Asp Thr Ala Val Tyr Tyr Cys Ala Ser Ser Arg Gly Ser Gly Trp
305                 310                 315                 320
Phe Pro Leu Gly Tyr Trp Gly Gln Gly Thr Leu Val Thr Val Ser Ser
                325                 330                 335
Ala Ser Thr Lys Gly Pro Ser Val Phe Pro Leu Ala Pro Ser Ser Lys
                340                 345                 350
Ser Thr Ser Gly Gly Thr Ala Ala Leu Gly Cys Leu Val Lys Asp Tyr
                355                 360                 365
Phe Pro Glu Pro Val Thr Val Ser Trp Asn Ser Gly Ala Leu Thr Ser
        370                 375                 380
Gly Val His Thr Phe Pro Ala Val Leu Gln Ser Ser Gly Leu Tyr Ser
385                 390                 395                 400
Leu Ser Ser Val Val Thr Val Pro Ser Ser Ser Leu Gly Thr Gln Thr
                405                 410                 415
Tyr Ile Cys Asn Val Asn His Lys Pro Ser Asn Thr Lys Val Asp Lys
                420                 425                 430
Lys Val Glu Pro Lys Ser Cys Asp Lys Thr His Thr Cys Pro Pro Cys
        435                 440                 445
```

-continued

```
Pro Ala Pro Glu Leu Leu Gly Gly Pro Ser Val Phe Leu Phe Pro Pro
    450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val Leu
        515                 520                 525

His Gln Asp Trp Leu Asn Gly Lys Glu Tyr Lys Cys Lys Val Ser Asn
    530                 535                 540

Lys Ala Leu Pro Ala Pro Ile Glu Lys Thr Ile Ser Lys Ala Lys Gly
545                 550                 555                 560

Gln Pro Arg Glu Pro Gln Val Tyr Thr Leu Pro Pro Ser Arg Asp Glu
                565                 570                 575

Leu Thr Lys Asn Gln Val Ser Leu Thr Cys Leu Val Lys Gly Phe Tyr
            580                 585                 590

Pro Ser Asp Ile Ala Val Glu Trp Glu Ser Asn Gly Gln Pro Glu Asn
        595                 600                 605

Asn Tyr Lys Thr Thr Pro Pro Val Leu Asp Ser Asp Gly Ser Phe Phe
    610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
                645                 650                 655

Gln Lys Ser Leu Ser Leu Ser Pro Gly Lys
            660                 665

<210> SEQ ID NO 254
<211> LENGTH: 668
<212> TYPE: PRT
<213> ORGANISM: artificial sequence
<220> FEATURE:
<223> OTHER INFORMATION: G4_27 IgG1 antibody sequence

<400> SEQUENCE: 254

Ala Ser Ser Tyr Glu Leu Thr Gln Asp Pro Ala Val Ser Val Ala Leu
1               5                   10                  15

Gly Gln Thr Val Ser Ile Thr Cys Gln Gly Asp Ser Leu Arg Asn Phe
            20                  25                  30

Tyr Ala Asn Trp Tyr Gln Gln Lys Pro Gly Gln Ala Pro Val Leu Val
        35                  40                  45

Ile Tyr Gly Lys Asn Asn Arg Pro Ser Gly Ile Pro Asp Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Asn Ser Arg Asp Ser Ser Gly
                85                  90                  95

Asn His Leu Val Phe Gly Gly Gly Thr Gln Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

-continued

```
Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
                180             185             190

Arg Ser Tyr Ser Cys Gln Val Thr His Glu Gly Ser Thr Val Glu Lys
            195             200             205

Thr Val Ala Pro Thr Glu Cys Ser Gln Val Gln Leu Val Gln Ser Gly
    210             215             220

Ala Glu Val Lys Lys Pro Gly Glu Ser Leu Lys Ile Ser Cys Lys Ser
225             230             235             240

Ser Gly Tyr Ser Phe Thr Ser Tyr Trp Ile Gly Trp Val Arg Gln Met
                245             250             255

Pro Gly Lys Gly Leu Glu Trp Met Gly Ile Ile Tyr Pro Gly Asp Ser
            260             265             270

Asp Thr Arg Tyr Ser Pro Ser Phe Gln Gly Gln Val Thr Phe Ser Ala
            275             280             285

Asp Glu Ser Ile Ser Thr Ala Tyr Leu Gln Trp Ser Ser Leu Lys Ala
    290             295             300

Ser Asp Thr Ala Met Tyr Tyr Cys Ala Arg His Gly Ala Tyr Gly Asp
305             310             315             320

Tyr Pro Asp Thr Phe Asp Ile Trp Gly Gln Gly Thr Leu Val Thr Val
                325             330             335

Ser Ser Ala Ser Thr Lys Gly Pro Ser Val Phe Pro Leu Ala Pro Ser
            340             345             350

Ser Lys Ser Thr Ser Gly Gly Thr Ala Ala Leu Gly Cys Leu Val Lys
            355             360             365

Asp Tyr Phe Pro Glu Pro Val Thr Val Ser Trp Asn Ser Gly Ala Leu
    370             375             380

Thr Ser Gly Val His Thr Phe Pro Ala Val Leu Gln Ser Ser Gly Leu
385             390             395             400

Tyr Ser Leu Ser Ser Val Val Thr Val Pro Ser Ser Ser Leu Gly Thr
                405             410             415

Gln Thr Tyr Ile Cys Asn Val Asn His Lys Pro Ser Asn Thr Lys Val
            420             425             430

Asp Lys Lys Val Glu Pro Lys Ser Cys Asp Lys Thr His Thr Cys Pro
            435             440             445

Pro Cys Pro Ala Pro Glu Leu Leu Gly Gly Pro Ser Val Phe Leu Phe
    450             455             460

Pro Pro Lys Pro Lys Asp Thr Leu Met Ile Ser Arg Thr Pro Glu Val
465             470             475             480

Thr Cys Val Val Val Asp Val Ser His Glu Asp Pro Glu Val Lys Phe
            485             490             495

Asn Trp Tyr Val Asp Gly Val Glu Val His Asn Ala Lys Thr Lys Pro
            500             505             510

Arg Glu Glu Gln Tyr Asn Ser Thr Tyr Arg Val Val Ser Val Leu Thr
            515             520             525

Val Leu His Gln Asp Trp Leu Asn Gly Lys Glu Tyr Lys Cys Lys Val
    530             535             540

Ser Asn Lys Ala Leu Pro Ala Pro Ile Glu Lys Thr Ile Ser Lys Ala
545             550             555             560
```

-continued

```
Lys Gly Gln Pro Arg Glu Pro Gln Val Tyr Thr Leu Pro Pro Ser Arg
            565             570             575

Asp Glu Leu Thr Lys Asn Gln Val Ser Leu Thr Cys Leu Val Lys Gly
            580             585             590

Phe Tyr Pro Ser Asp Ile Ala Val Glu Trp Glu Ser Asn Gly Gln Pro
            595             600             605

Glu Asn Asn Tyr Lys Thr Thr Pro Pro Val Leu Asp Ser Asp Gly Ser
        610             615             620

Phe Phe Leu Tyr Ser Lys Leu Thr Val Asp Lys Ser Arg Trp Gln Gln
625             630             635             640

Gly Asn Val Phe Ser Cys Ser Val Met His Glu Ala Leu His Asn His
                645             650             655

Tyr Thr Gln Lys Ser Leu Ser Leu Ser Pro Gly Lys
            660             665

<210> SEQ ID NO 255
<211> LENGTH: 669
<212> TYPE: PRT
<213> ORGANISM: artificial sequence
<220> FEATURE:
<223> OTHER INFORMATION: G4_28 IgG1 antibody sequence

<400> SEQUENCE: 255

Ala Ser Ser Tyr Glu Leu Thr Gln Asp Pro Ala Val Ser Val Ala Leu
1               5               10              15

Gly Gln Thr Val Thr Ile Thr Cys Gln Gly Asp Ser Leu Arg Asn Tyr
            20              25              30

Tyr Ala Ser Trp Tyr Arg Gln Lys Pro Gly Gln Thr Pro Val Leu Val
            35              40              45

Val Tyr Gly Lys Asn Asn Arg Pro Ser Gly Ile Pro Asp Arg Phe Ser
        50              55              60

Val Ser Ala Ser Gly Asn Thr Ala Ser Leu Thr Ile Thr Gly Ala Gln
65              70              75              80

Ala Glu Asp Glu Gly Asp Tyr Tyr Cys Asn Ser Arg Asp Ser Ser Gly
                85              90              95

Val Val Phe Gly Gly Gly Thr Lys Val Thr Val Leu Gly Gln Pro Ala
            100             105             110

Ala Ala Pro Ser Val Thr Leu Phe Pro Pro Ser Ser Glu Glu Leu Gln
            115             120             125

Ala Asn Lys Ala Thr Leu Val Cys Leu Ile Ser Asp Phe Tyr Pro Gly
        130             135             140

Ala Val Thr Val Ala Trp Lys Ala Asp Ser Ser Pro Val Lys Ala Gly
145             150             155             160

Val Glu Thr Thr Thr Pro Ser Lys Gln Ser Asn Asn Lys Tyr Ala Ala
                165             170             175

Ser Ser Tyr Leu Ser Leu Thr Pro Glu Gln Trp Lys Ser His Arg Ser
            180             185             190

Tyr Ser Cys Gln Val Thr His Glu Gly Ser Thr Val Glu Lys Thr Val
            195             200             205

Ala Pro Thr Glu Cys Ser Gln Val Gln Leu Val Glu Ser Gly Gly Gly
        210             215             220

Leu Val Gln Pro Gly Gly Ser Leu Arg Leu Ser Cys Ala Ala Ser Gly
225             230             235             240

Phe Thr Phe Asp Asp Tyr Ala Met His Trp Val Arg Gln Ala Pro Gly
            245             250             255
```

```
Lys Gly Leu Glu Trp Val Ser Gly Ile Ser Ala Gly Gly Gly Ser Thr
            260                 265                 270

Asn Tyr Ala Gly Ser Val Lys Gly Arg Phe Thr Val Ser Arg Asp Thr
            275                 280                 285

Ser Lys Asn Thr Leu Tyr Leu Gln Met Asn Ser Leu Arg Ala Glu Asp
        290                 295                 300

Thr Ala Val Tyr Tyr Cys Val Lys Ser Tyr Val Asp Thr Ala Met Arg
305                 310                 315                 320

Tyr Tyr Tyr Tyr Tyr Met Asp Val Trp Gly Gln Gly Thr Met Val Thr
                325                 330                 335

Val Ser Ser Ala Ser Thr Lys Gly Pro Ser Val Phe Pro Leu Ala Pro
            340                 345                 350

Ser Ser Lys Ser Thr Ser Gly Gly Thr Ala Ala Leu Gly Cys Leu Val
            355                 360                 365

Lys Asp Tyr Phe Pro Glu Pro Val Thr Val Ser Trp Asn Ser Gly Ala
        370                 375                 380

Leu Thr Ser Gly Val His Thr Phe Pro Ala Val Leu Gln Ser Ser Gly
385                 390                 395                 400

Leu Tyr Ser Leu Ser Ser Val Val Thr Val Pro Ser Ser Ser Leu Gly
            405                 410                 415

Thr Gln Thr Tyr Ile Cys Asn Val Asn His Lys Pro Ser Asn Thr Lys
            420                 425                 430

Val Asp Lys Lys Val Glu Pro Lys Ser Cys Asp Lys Thr His Thr Cys
            435                 440                 445

Pro Pro Cys Pro Ala Pro Glu Leu Leu Gly Gly Pro Ser Val Phe Leu
        450                 455                 460

Phe Pro Pro Lys Pro Lys Asp Thr Leu Met Ile Ser Arg Thr Pro Glu
465                 470                 475                 480

Val Thr Cys Val Val Val Asp Val Ser His Glu Asp Pro Glu Val Lys
                485                 490                 495

Phe Asn Trp Tyr Val Asp Gly Val Glu Val His Asn Ala Lys Thr Lys
            500                 505                 510

Pro Arg Glu Glu Gln Tyr Asn Ser Thr Tyr Arg Val Val Ser Val Leu
            515                 520                 525

Thr Val Leu His Gln Asp Trp Leu Asn Gly Lys Glu Tyr Lys Cys Lys
        530                 535                 540

Val Ser Asn Lys Ala Leu Pro Ala Pro Ile Glu Lys Thr Ile Ser Lys
545                 550                 555                 560

Ala Lys Gly Gln Pro Arg Glu Pro Gln Val Tyr Thr Leu Pro Pro Ser
            565                 570                 575

Arg Asp Glu Leu Thr Lys Asn Gln Val Ser Leu Thr Cys Leu Val Lys
            580                 585                 590

Gly Phe Tyr Pro Ser Asp Ile Ala Val Glu Trp Glu Ser Asn Gly Gln
            595                 600                 605

Pro Glu Asn Asn Tyr Lys Thr Thr Pro Pro Val Leu Asp Ser Asp Gly
        610                 615                 620

Ser Phe Phe Leu Tyr Ser Lys Leu Thr Val Asp Lys Ser Arg Trp Gln
625                 630                 635                 640

Gln Gly Asn Val Phe Ser Cys Ser Val Met His Glu Ala Leu His Asn
                645                 650                 655

His Tyr Thr Gln Lys Ser Leu Ser Leu Ser Pro Gly Lys
            660                 665
```

-continued

```
<210> SEQ ID NO 256
<211> LENGTH: 270
<212> TYPE: PRT
<213> ORGANISM: artificial sequence
<220> FEATURE:
<223> OTHER INFORMATION: TRGV4(4MNH) TRAC antigen sequence

<400> SEQUENCE: 256

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
            100                 105                 110

Leu Val Val Thr Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Thr Thr Ala Pro Ser Ala Gln Leu Glu
                245                 250                 255

Lys Glu Leu Gln Ala Leu Glu Lys Glu Asn Ala Gln Leu Glu
            260                 265                 270

<210> SEQ ID NO 257
<211> LENGTH: 282
<212> TYPE: PRT
<213> ORGANISM: artificial sequence
<220> FEATURE:
<223> OTHER INFORMATION: V gamma 4 (4MNH) GV4TRBC leucine zipper
      heterodimer antigen sequence

<400> SEQUENCE: 257

Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
            20                  25                  30

Ile His Trp Tyr Leu His Gln Glu Gly Lys Ala Pro Gln Arg Leu Leu
        35                  40                  45
```

-continued

```
Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
                100                 105                 110

Leu Val Val Thr Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Ala Leu
                180                 185                 190

Ser Ser Arg Leu Arg Val Ser Ala Thr Phe Trp Gln Asn Pro Arg Asn
                195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Thr Thr Ala Pro Ser Ala Gln Leu Glu
                245                 250                 255

Lys Glu Leu Gln Ala Leu Glu Lys Glu Asn Ala Gln Leu Glu Trp Glu
                260                 265                 270

Leu Gln Ala Leu Glu Lys Glu Leu Ala Gln
        275                 280
```

```
<210> SEQ ID NO 258
<211> LENGTH: 348
<212> TYPE: PRT
<213> ORGANISM: artificial sequence
<220> FEATURE:
<223> OTHER INFORMATION: V gamma 4 TRGV4(4MNH) Fc heterodimer antigen
      sequence

<400> SEQUENCE: 258
```

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Thr Gly Tyr
                20                  25                  30

Ile His Trp Tyr Leu His Gln Glu Gly Lys Ala Pro Gln Arg Leu Leu
            35                  40                  45

Tyr Tyr Asp Ser Tyr Thr Ser Ser Val Val Leu Glu Ser Gly Ile Ser
    50                  55                  60

Pro Gly Lys Tyr Asp Thr Tyr Gly Ser Thr Arg Lys Asn Leu Arg Met
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
                100                 105                 110

Leu Val Val Thr Glu Asp Ala Ala Ala Asp Lys Thr His Thr Cys Pro
```

-continued

```
              115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Ser His Glu Ala Leu His Ser His
                325                 330                 335

His Thr Gln Lys Ser Leu Ser Leu Ser Pro Gly Lys
            340                 345
```

```
<210> SEQ ID NO 259
<211> LENGTH: 282
<212> TYPE: PRT
<213> ORGANISM: artificial sequence
<220> FEATURE:
<223> OTHER INFORMATION: V gamma 2 (4MNH) GV2TRBC leucine zipper
      heterodimer antigen sequence

<400> SEQUENCE: 259
```

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
            20                  25                  30

Ile His Trp Tyr Leu His Gln Glu Gly Lys Ala Pro Gln Arg Leu Gln
        35                  40                  45

Tyr Tyr Asp Ser Tyr Asn Ser Lys Val Val Leu Glu Ser Gly Val Ser
    50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp Glu Lys Tyr Tyr Lys Lys Leu Phe Gly Ser Gly Thr Thr
            100                 105                 110

Leu Val Val Thr Glu Asp Leu Lys Asn Val Phe Pro Pro Glu Val Ala
        115                 120                 125
```

```
Val Phe Glu Pro Ser Glu Ala Glu Ile Ser His Thr Gln Lys Ala Thr
    130             135             140

Leu Val Cys Leu Ala Thr Gly Phe Tyr Pro Asp His Val Glu Leu Ser
145             150             155             160

Trp Trp Val Asn Gly Lys Glu Val His Ser Gly Val Ser Thr Asp Pro
                165             170             175

Gln Pro Leu Lys Glu Gln Pro Ala Leu Asn Asp Ser Arg Tyr Ala Leu
            180             185             190

Ser Ser Arg Leu Arg Val Ser Ala Thr Phe Trp Gln Asn Pro Arg Asn
            195             200             205

His Phe Arg Cys Gln Val Gln Phe Tyr Gly Leu Ser Glu Asn Asp Glu
    210             215             220

Trp Thr Gln Asp Arg Ala Lys Pro Val Thr Gln Ile Val Ser Ala Glu
225             230             235             240

Ala Trp Gly Arg Ala Asp Cys Thr Thr Ala Pro Ser Ala Gln Leu Glu
                245             250             255

Lys Glu Leu Gln Ala Leu Glu Lys Glu Asn Ala Gln Leu Glu Trp Glu
            260             265             270

Leu Gln Ala Leu Glu Lys Glu Leu Ala Gln
            275             280
```

```
<210> SEQ ID NO 260
<211> LENGTH: 348
<212> TYPE: PRT
<213> ORGANISM: artificial sequence
<220> FEATURE:
<223> OTHER INFORMATION: V gamma 2 TRGV2(4MNH) Fc heterodimer antigen
      sequence

<400> SEQUENCE: 260
```

```
Ser Ser Asn Leu Glu Gly Arg Thr Lys Ser Val Ile Arg Gln Thr Gly
1               5               10              15

Ser Ser Ala Glu Ile Thr Cys Asp Leu Ala Glu Gly Ser Asn Gly Tyr
            20              25              30

Ile His Trp Tyr Leu His Gln Glu Gly Lys Ala Pro Gln Arg Leu Gln
        35              40              45

Tyr Tyr Asp Ser Tyr Asn Ser Lys Val Val Leu Glu Ser Gly Val Ser
    50              55              60

Pro Gly Lys Tyr Tyr Thr Tyr Ala Ser Thr Arg Asn Asn Leu Arg Leu
65              70              75              80

Ile Leu Arg Asn Leu Ile Glu Asn Asp Ser Gly Val Tyr Tyr Cys Ala
            85              90              95

Thr Trp Asp Glu Lys Tyr Tyr Lys Lys Leu Phe Gly Ser Gly Thr Thr
            100             105             110

Leu Val Val Thr Glu Asp Ala Ala Ala Asp Lys Thr His Thr Cys Pro
            115             120             125

Pro Cys Pro Ala Pro Glu Leu Leu Gly Gly Pro Ser Val Phe Leu Phe
    130             135             140

Pro Pro Lys Pro Lys Asp Thr Leu Met Ile Ser Arg Thr Pro Glu Val
145             150             155             160

Thr Cys Val Val Val Asp Val Ser His Glu Asp Pro Glu Val Lys Phe
                165             170             175

Asn Trp Tyr Val Asp Gly Val Glu Val His Asn Ala Lys Thr Lys Pro
            180             185             190

Arg Glu Glu Gln Tyr Asn Ser Thr Tyr Arg Val Val Ser Val Leu Thr
            195             200             205
```

-continued

```
Val Leu His Gln Asp Trp Leu Asn Gly Lys Glu Tyr Lys Cys Lys Val
    210             215             220
```

```
Ser Asn Lys Ala Leu Pro Ala Pro Ile Glu Lys Thr Ile Ser Lys Ala
225             230             235             240
```

```
Lys Gly Gln Pro Arg Glu Pro Gln Val Tyr Thr Leu Pro Pro Ser Arg
                245             250             255
```

```
Asp Glu Leu Thr Lys Asn Gln Val Ser Leu Thr Cys Leu Val Lys Gly
            260             265             270
```

```
Phe Tyr Pro Ser Asp Ile Ala Val Glu Trp Glu Ser Asn Gly Gln Pro
        275             280             285
```

```
Glu Asn Asn Tyr Lys Thr Thr Pro Pro Val Leu Asp Ser Asp Gly Ser
    290             295             300
```

```
Phe Phe Leu Tyr Ser Lys Leu Thr Val Asp Lys Ser Arg Trp Gln Gln
305             310             315             320
```

```
Gly Asn Val Phe Ser Cys Ser Val Ser His Glu Ala Leu His Ser His
                325             330             335
```

```
His Thr Gln Lys Ser Leu Ser Leu Ser Pro Gly Lys
            340             345
```

```
<210> SEQ ID NO 261
<211> LENGTH: 107
<212> TYPE: PRT
<213> ORGANISM: artificial sequence
<220> FEATURE:
<223> OTHER INFORMATION: TRGV4 full light variable sequence G4_1 no
      N-terminal AS

<400> SEQUENCE: 261
```

```
Asp Ile Gln Met Thr Gln Ser Pro Ser Ser Leu Ser Ala Ser Val Gly
1               5               10              15
```

```
Asp Arg Val Thr Ile Thr Cys Gln Ala Ser Gln Asp Ile Ser Asn Tyr
            20              25              30
```

```
Leu Asn Trp Tyr Gln Gln Lys Pro Gly Lys Ala Pro Lys Leu Leu Ile
        35              40              45
```

```
Tyr Asp Ala Ser Asn Leu Glu Thr Gly Val Pro Ser Arg Phe Ser Gly
    50              55              60
```

```
Ser Gly Ser Gly Thr Asp Phe Thr Leu Thr Ile Ser Ser Leu Gln Pro
65              70              75              80
```

```
Glu Asp Phe Ala Thr Tyr Tyr Cys Gln Gln Ser Tyr Ser Thr Pro Val
                85              90              95
```

```
Thr Phe Gly Pro Gly Thr Lys Val Glu Ile Lys
            100             105
```

```
<210> SEQ ID NO 262
<211> LENGTH: 107
<212> TYPE: PRT
<213> ORGANISM: artificial sequence
<220> FEATURE:
<223> OTHER INFORMATION: TRGV4 full light variable sequence G4_2 no
      N-terminal AS

<400> SEQUENCE: 262
```

```
Asp Ile Gln Met Thr Gln Ser Pro Ser Ser Leu Ser Ala Ser Val Gly
1               5               10              15
```

```
Asp Arg Val Thr Ile Thr Cys Gln Ala Ser Gln Asp Ile Ser Asn Tyr
            20              25              30
```

```
Leu Asn Trp Tyr Gln Gln Lys Pro Gly Lys Ala Pro Lys Leu Leu Ile
        35              40              45
```

-continued

```
Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Gly Leu Gln Pro
65              70              75              80

Glu Asp Phe Ala Thr Tyr Tyr Cys Leu Glu Asp Tyr Asn Tyr Leu Trp
            85              90              95

Thr Phe Gly Gln Gly Thr Lys Leu Glu Ile Lys
            100             105

<210> SEQ ID NO 263
<211> LENGTH: 107
<212> TYPE: PRT
<213> ORGANISM: artificial sequence
<220> FEATURE:
<223> OTHER INFORMATION: TRGV4 full light variable sequence G4_3 no
      N-terminal AS

<400> SEQUENCE: 263

Asp Ile Gln Met Thr Gln Ser Pro Ser Ser Leu Ser Ala Ser Val Gly
1               5               10              15

Asp Arg Val Thr Ile Thr Cys Gln Ala Ser Gln Asp Ile Ser Asn Tyr
            20              25              30

Leu Asn Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Phe Cys Gln Gln Ser Tyr Ser Thr Pro Gln
            85              90              95

Thr Phe Gly Gln Gly Thr Lys Val Asp Ile Lys
            100             105

<210> SEQ ID NO 264
<211> LENGTH: 113
<212> TYPE: PRT
<213> ORGANISM: artificial sequence
<220> FEATURE:
<223> OTHER INFORMATION: TRGV4 full light variable sequence G4_4 no
      N-terminal AS

<400> SEQUENCE: 264

Asp Ile Val Met Thr Gln Ser Pro Asp Ser Leu Ala Val Ser Leu Gly
1               5               10              15

Glu Arg Ala Thr Ile Asn Cys Lys Ser Ser Gln Ser Val Leu Ser Ser
            20              25              30

Ser Asn Asn Asn Asn Tyr Leu Ala Trp Tyr Gln Gln Arg Pro Gly Gln
        35              40              45

Pro Pro Lys Leu Leu Phe Tyr Trp Ala Ser Thr Arg Glu Ser Gly Val
    50              55              60

Pro Asp Arg Phe Ser Gly Ser Gly Ser Gly Thr Ser Phe Thr Leu Thr
65              70              75              80

Ile Thr Ser Leu Gln Ala Glu Asp Val Ala Val Tyr Tyr Cys Gln Gln
            85              90              95

Tyr Tyr Ser Thr Pro Leu Thr Phe Gly Gly Gly Thr Lys Leu Glu Ile
            100             105             110

Lys
```

```
<210> SEQ ID NO 265
<211> LENGTH: 107
<212> TYPE: PRT
<213> ORGANISM: artificial sequence
<220> FEATURE:
<223> OTHER INFORMATION: TRGV4 full light variable sequence G4_5 no
      N-terminal AS

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 266
<211> LENGTH: 107
<212> TYPE: PRT
<213> ORGANISM: artificial sequence
<220> FEATURE:
<223> OTHER INFORMATION: TRGV4 full light variable sequence G4_6 no
      N-terminal AS

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Pro Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 267
<211> LENGTH: 112
<212> TYPE: PRT
<213> ORGANISM: artificial sequence
<220> FEATURE:
<223> OTHER INFORMATION: TRGV4 full light variable sequence G4_7 no
      N-terminal AS

<400> SEQUENCE: 267

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
                20                    25                    30

Asn Arg Phe Asn Tyr Leu Asp Trp Tyr Leu Gln Lys Pro Gly Gln Ser
            35                    40                    45

Pro Gln Leu Leu Ile Tyr Leu Gly Ser Asn Arg Ala Ser Gly Val Pro
        50                    55                    60

Asp Arg Phe Ser Gly Ser Gly Ser Gly Thr Asp Phe Thr Leu Lys Ile
65                    70                    75                    80

Ser Arg Val Glu Ala Glu Asp Val Gly Val Tyr Tyr Cys Met Gln Gly
                85                    90                    95

Leu Gln Thr Pro Tyr Thr Phe Gly Gln Gly Thr Lys Val Asp Ile Lys
            100                   105                   110

<210> SEQ ID NO 268
<211> LENGTH: 112
<212> TYPE: PRT
<213> ORGANISM: artificial sequence
<220> FEATURE:
<223> OTHER INFORMATION: TRGV4 full light variable sequence G4_10 no
      N-terminal AS

<400> SEQUENCE: 268

Asp Ile Val Met Thr Gln Pro Pro Leu Ser Leu Pro Val Thr Leu Gly
1                   5                    10                    15

His Pro Ala Ser Ile Ser Cys Lys Ser Ser Gln Ser Leu Glu Tyr Ser
                20                    25                    30

Asp Gly Asn Thr Tyr Leu Asn Trp Phe Gln Gln Arg Pro Gly Gln Ser
            35                    40                    45

Pro Arg Arg Leu Ile Tyr Lys Val Ser Asn Arg Asp Ser Gly Ala Pro
        50                    55                    60

Asp Arg Phe Ser Gly Ser Gly Ser Gly Thr Asp Phe Thr Leu Glu Ile
65                    70                    75                    80

Ser Arg Val Glu Ala Glu Asp Val Gly Val Tyr Tyr Cys Met Gln Gly
                85                    90                    95

Thr Leu Trp Pro Pro Thr Phe Gly Gln Gly Thr Lys Val Asp Ile Lys
            100                   105                   110

<210> SEQ ID NO 269
<211> LENGTH: 108
<212> TYPE: PRT
<213> ORGANISM: artificial sequence
<220> FEATURE:
<223> OTHER INFORMATION: TRGV4 full light variable sequence G4_12 no
      N-terminal AS

<400> SEQUENCE: 269

Gln Ser Val Leu Thr Gln Pro Ala Ser Val Ser Gly Ser Pro Gly Gln
1                   5                    10                    15

Ser Ile Thr Ile Ser Cys Thr Gly Thr Ser Ser Asp Val Gly Gly Tyr
                20                    25                    30

Asn Phe Val Ser Trp Tyr Gln Gln His Pro Gly Lys Ala Pro Lys Leu
            35                    40                    45

Met Ile Tyr Glu Val Thr Asn Arg Pro Ser Gly Val Pro Asp Arg Phe
        50                    55                    60

Ser Gly Ser Lys Ser Gly Asn Thr Ala Ser Leu Thr Ile Ser Gly Leu
65                    70                    75                    80

Gln Ala Glu Asp Glu Ala Asp Tyr Tyr Cys Ser Ser His Ala Ser Pro
                85                    90                    95

Arg Val Phe Gly Thr Gly Thr Lys Val Thr Val Leu
```

```
                    100                 105

<210> SEQ ID NO 270
<211> LENGTH: 111
<212> TYPE: PRT
<213> ORGANISM: artificial sequence
<220> FEATURE:
<223> OTHER INFORMATION: TRGV4 full light variable sequence G4_13 no
      N-terminal AS

<400> SEQUENCE: 270

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Ser Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Ser
                85                  90                  95

Ser Ile Tyr Val Val Phe Gly Gly Gly Thr Lys Leu Thr Val Leu
            100                 105                 110

<210> SEQ ID NO 271
<211> LENGTH: 111
<212> TYPE: PRT
<213> ORGANISM: artificial sequence
<220> FEATURE:
<223> OTHER INFORMATION: TRGV4 full light variable sequence G4_14 no
      N-terminal AS

<400> SEQUENCE: 271

Asn Phe Met Leu Thr Gln Pro His Ser Val Ser Glu Ser Pro Gly Lys
1               5                   10                  15

Thr Val Thr Ile Ser Cys Thr Arg Ser Arg Gly Ser Ile Ala Gly Asn
            20                  25                  30

Tyr Val His Trp Tyr Gln Gln Arg Pro Gly Arg Ala Pro Thr Thr Val
        35                  40                  45

Ile Tyr Arg Asp Lys Glu Arg Pro Ser Gly Val Pro Asp Arg Ile Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Thr His Val Val Phe Gly Gly Gly Thr Lys Leu Thr Val Leu
            100                 105                 110

<210> SEQ ID NO 272
<211> LENGTH: 108
<212> TYPE: PRT
<213> ORGANISM: artificial sequence
<220> FEATURE:
<223> OTHER INFORMATION: TRGV4 full light variable sequence G4_15 no
      N-terminal AS

<400> SEQUENCE: 272

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Ser Gly
                85                  90                  95

Ser Val Phe Gly Thr Gly Thr Lys Leu Thr Val Leu
            100                 105
```

<210> SEQ ID NO 273
<211> LENGTH: 110
<212> TYPE: PRT
<213> ORGANISM: artificial sequence
<220> FEATURE:
<223> OTHER INFORMATION: TRGV4 full light variable sequence G4_16 no
      N-terminal AS

<400> SEQUENCE: 273

```
Gln Ser Val Leu Thr Gln Pro Pro Ser Ala Ser Gly Ser Pro Gly Gln
1               5                   10                  15

Ser Val Thr Phe Ser Cys Thr Gly Thr Ser Ser Asp Ile Gly Ala Phe
            20                  25                  30

Asn Ser Val Ser Trp Tyr Gln Gln His Pro Gly Lys Ala Pro Lys Leu
        35                  40                  45

Leu Ile Tyr Glu Ile Thr Lys Arg Pro Ser Gly Val Pro Asp Arg Phe
    50                  55                  60

Ser Gly Ser Lys Ser Gly Asn Thr Ala Ser Leu Thr Ile Ser Val Leu
65                  70                  75                  80

Gln Ala Glu Asp Glu Ala Asp Tyr Tyr Cys Thr Ser Tyr Ala Gly Ser
                85                  90                  95

Asn Thr Leu Ile Phe Gly Gly Gly Thr Lys Val Thr Val Leu
            100                 105                 110
```

<210> SEQ ID NO 274
<211> LENGTH: 108
<212> TYPE: PRT
<213> ORGANISM: artificial sequence
<220> FEATURE:
<223> OTHER INFORMATION: TRGV4 full light variable sequence G4_18 no
      N-terminal AS

<400> SEQUENCE: 274

```
Ser Tyr Glu Leu Thr Gln Pro Pro Ser Val Thr Glu Ser Pro Gly Gln
1               5                   10                  15

Thr Ala Arg Ile Thr Cys Ser Gly Asp Ala Leu Ala Lys Gln Tyr Ala
            20                  25                  30

Tyr Trp Tyr Gln Gln Lys Pro Gly Gln Ala Pro Val Leu Val Ile Tyr
        35                  40                  45

Arg Asp Ser Glu Arg Pro Ser Glu Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95
```

```
Thr Val Phe Gly Gly Gly Thr Lys Leu Thr Val Leu
        100                 105

<210> SEQ ID NO 275
<211> LENGTH: 111
<212> TYPE: PRT
<213> ORGANISM: artificial sequence
<220> FEATURE:
<223> OTHER INFORMATION: TRGV4 full light variable sequence G4_19 no
    N-terminal AS

<400> SEQUENCE: 275

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Pro Pro Ile Thr Leu
        35                  40                  45

Ile Tyr Asp Asp Asp Gln Arg Pro Ser Gly Val Pro His Arg Phe Ser
    50                  55                  60

Gly Ser Ile Asp Thr Ser Ser Asn Pro Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Val Val Phe Gly Gly Gly Thr Lys Leu Thr Val Leu
            100                 105                 110

<210> SEQ ID NO 276
<211> LENGTH: 106
<212> TYPE: PRT
<213> ORGANISM: artificial sequence
<220> FEATURE:
<223> OTHER INFORMATION: TRGV4 full light variable sequence G4_20 no
    N-terminal AS

<400> SEQUENCE: 276

Ser Tyr Glu Leu Thr His Pro Pro Ser Val Ser Val Ser Pro Gly Gln
1               5                   10                  15

Thr Ala Ser Ile Thr Cys Ser Gly Asp Lys Leu Gly Asp Lys Phe Val
            20                  25                  30

Ser Trp Tyr His Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Arg Ala Met
65                  70                  75                  80

Asp Glu Ala Asp Tyr Tyr Cys Gln Ala Trp Asp Ser Ser Thr Val Val
                85                  90                  95

Phe Gly Gly Gly Thr Lys Leu Thr Val Leu
            100                 105

<210> SEQ ID NO 277
<211> LENGTH: 107
<212> TYPE: PRT
<213> ORGANISM: artificial sequence
<220> FEATURE:
<223> OTHER INFORMATION: TRGV4 full light variable sequence G4_22 no
    N-terminal AS

<400> SEQUENCE: 277
```

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Val
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Ser Tyr Ser Ile Pro Trp
                85                  90                  95

Thr Phe Gly Gln Gly Thr Lys Val Glu Ile Lys
            100                 105
```

```
<210> SEQ ID NO 278
<211> LENGTH: 107
<212> TYPE: PRT
<213> ORGANISM: artificial sequence
<220> FEATURE:
<223> OTHER INFORMATION: TRGV4 full light variable sequence G4_23 no
      N-terminal AS

<400> SEQUENCE: 278
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro Arg
                85                  90                  95

Thr Phe Gly Gly Gly Thr Lys Leu Glu Ile Lys
            100                 105
```

```
<210> SEQ ID NO 279
<211> LENGTH: 113
<212> TYPE: PRT
<213> ORGANISM: artificial sequence
<220> FEATURE:
<223> OTHER INFORMATION: TRGV4 full light variable sequence G4_24 no
      N-terminal AS

<400> SEQUENCE: 279
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

-continued

```
Ile Asn Ser Leu Gln Ser Glu Asp Val Ala Ile Tyr Tyr Cys Gln Gln
            85                  90                  95

Tyr Tyr Ser Thr Pro Pro Thr Phe Gly Gln Gly Thr Lys Leu Glu Ile
            100                 105                 110

Lys

<210> SEQ ID NO 280
<211> LENGTH: 108
<212> TYPE: PRT
<213> ORGANISM: artificial sequence
<220> FEATURE:
<223> OTHER INFORMATION: TRGV4 full light variable sequence G4_25 no
      N-terminal AS

<400> SEQUENCE: 280

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Ser Gly
                85                  90                  95

Ser Val Phe Gly Thr Gly Thr Lys Leu Thr Val Leu
            100                 105

<210> SEQ ID NO 281
<211> LENGTH: 108
<212> TYPE: PRT
<213> ORGANISM: artificial sequence
<220> FEATURE:
<223> OTHER INFORMATION: TRGV4 full light variable sequence G4_26 no
      N-terminal AS

<400> SEQUENCE: 281

Gln Ser Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Phe Gly Ser Gly
                85                  90                  95

Ser Ile Phe Gly Thr Gly Thr Lys Leu Thr Val Leu
            100                 105

<210> SEQ ID NO 282
<211> LENGTH: 108
<212> TYPE: PRT
<213> ORGANISM: artificial sequence
<220> FEATURE:
<223> OTHER INFORMATION: TRGV4 full light variable sequence G4_27 no
```

```
          N-terminal AS

<400> SEQUENCE: 282

Ser Tyr Glu Leu Thr Gln Asp Pro Ala Val Ser Val Ala Leu Gly Gln
1                5                  10                  15

Thr Val Ser Ile Thr Cys Gln Gly Asp Ser Leu Arg Asn Phe Tyr Ala
            20                  25                  30

Asn Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Gln Leu Thr Val Leu
            100                 105

<210> SEQ ID NO 283
<211> LENGTH: 106
<212> TYPE: PRT
<213> ORGANISM: artificial sequence
<220> FEATURE:
<223> OTHER INFORMATION: TRGV4 full light variable sequence G4_28 no
      N-terminal AS

<400> SEQUENCE: 283

Ser Tyr Glu Leu Thr Gln Asp Pro Ala Val Ser Val Ala Leu Gly Gln
1                5                  10                  15

Thr Val Thr Ile Thr Cys Gln Gly Asp Ser Leu Arg Asn Tyr Tyr Ala
            20                  25                  30

Ser Trp Tyr Arg Gln Lys Pro Gly Gln Thr Pro Val Leu Val Val Tyr
        35                  40                  45

Gly Lys Asn Asn Arg Pro Ser Gly Ile Pro Asp Arg Phe Ser Val Ser
    50                  55                  60

Ala Ser Gly Asn Thr Ala Ser Leu Thr Ile Thr Gly Ala Gln Ala Glu
65                  70                  75                  80

Asp Glu Gly Asp Tyr Tyr Cys Asn Ser Arg Asp Ser Ser Gly Val Val
                85                  90                  95

Phe Gly Gly Gly Thr Lys Val Thr Val Leu
            100                 105

<210> SEQ ID NO 284
<211> LENGTH: 446
<212> TYPE: PRT
<213> ORGANISM: artificial sequence
<220> FEATURE:
<223> OTHER INFORMATION: G4_1 IgG1 antibody heavy chain sequence

<400> SEQUENCE: 284

Glu Val Gln Leu Leu Glu Ser Gly Gly Gly Val Val Gln Pro Gly Arg
1                5                  10                  15

Pro Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Trp Tyr Phe Asp Leu Trp Gly Arg Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 285
<211> LENGTH: 450
<212> TYPE: PRT
<213> ORGANISM: artificial sequence
<220> FEATURE:
<223> OTHER INFORMATION: G4_2 IgG1 antibody heavy chain sequence -continued

```
<400> SEQUENCE: 285

Gln Met Gln Leu Val Gln Ser Gly Ala Glu Val Lys Lys Pro Gly Ala
1               5                   10                  15

Thr Val Lys Ile Ser Cys Lys Val Ser Gly Tyr Pro Phe Thr Asp Tyr
            20                  25                  30

Tyr Ile His Trp Val Gln Gln Ala Pro Gly Lys Gly Leu Glu Trp Met
        35                  40                  45

Gly Leu Val Asp Pro Glu Asp Gly Gln Ser Arg Ser Ala Glu Arg Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Pro Val Ala Gly Phe Tyr Gly Met Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

-continued

```
                        405               410               415

Lys Ser Arg Trp Gln Gln Gly Asn Val Phe Ser Cys Ser Val Met His
            420               425               430

Glu Ala Leu His Asn His Tyr Thr Gln Lys Ser Leu Ser Leu Ser Pro
        435               440               445

Gly Lys
    450

<210> SEQ ID NO 286
<211> LENGTH: 446
<212> TYPE: PRT
<213> ORGANISM: artificial sequence
<220> FEATURE:
<223> OTHER INFORMATION: G4_3 IgG1 antibody heavy chain sequence

<400> SEQUENCE: 286

Glu Val Gln Leu Val Glu Ser Gly Gly Gly Leu Val Gln Pro Gly Gly
1               5               10               15

Ser Leu Arg Leu Ser Cys Ala Ala Ser Gly Phe Thr Phe Ser Ser Tyr
            20              25              30

Ser Met Asn Trp Val Arg Gln Ala Pro Gly Lys Gly Leu Glu Trp Val
            35              40              45

Ser Ser Ile Ser Ser Ser Ser Ser Tyr Ile Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Gly Gly Trp Leu Tyr Asp Tyr Trp Gly Gln Gly Thr Leu Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
        130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Asp Lys Thr His Thr
        210             215             220

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
                245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
            275             280             285

Lys Pro Arg Glu Glu Gln Tyr Asn Ser Thr Tyr Arg Val Val Ser Val
        290             295             300

Leu Thr Val Leu His Gln Asp Trp Leu Asn Gly Lys Glu Tyr Lys Cys
```

```
305                310                315                320
Lys Val Ser Asn Lys Ala Leu Pro Ala Pro Ile Glu Lys Thr Ile Ser
                325                330                335

Lys Ala Lys Gly Gln Pro Arg Glu Pro Gln Val Tyr Thr Leu Pro Pro
                340                345                350

Ser Arg Asp Glu Leu Thr Lys Asn Gln Val Ser Leu Thr Cys Leu Val
                355                360                365

Lys Gly Phe Tyr Pro Ser Asp Ile Ala Val Glu Trp Glu Ser Asn Gly
                370                375                380

Gln Pro Glu Asn Asn Tyr Lys Thr Thr Pro Pro Val Leu Asp Ser Asp
385                390                395                400

Gly Ser Phe Phe Leu Tyr Ser Lys Leu Thr Val Asp Lys Ser Arg Trp
                405                410                415

Gln Gln Gly Asn Val Phe Ser Cys Ser Val Met His Glu Ala Leu His
                420                425                430

Asn His Tyr Thr Gln Lys Ser Leu Ser Leu Ser Pro Gly Lys
                435                440                445

<210> SEQ ID NO 287
<211> LENGTH: 449
<212> TYPE: PRT
<213> ORGANISM: artificial sequence
<220> FEATURE:
<223> OTHER INFORMATION: G4_4 IgG1 antibody heavy chain sequence

<400> SEQUENCE: 287

Gln Val Gln Leu Val Glu Ser Gly Gly Gly Leu Val Gln Pro Gly Gly
1                5                10                15

Ser Leu Arg Leu Ser Cys Ala Ala Ser Gly Phe Thr Phe Ser Ser Tyr
                20                25                30

Ala Met Ser Trp Val Arg Gln Ala Pro Gly Lys Gly Leu Glu Trp Val
                35                40                45

Ser Ala Ile Ser Gly Ser Gly Gly Ser Thr Tyr Tyr Ala Asp Ser Val
                50                55                60

Lys Gly Arg Phe Thr Ile Ser Arg Asp Asn Ser Lys Asn Thr Leu Tyr
65                70                75                80

Leu Gln Met Ser Ser Leu Arg Val Glu Asp Thr Ala Val Tyr Tyr Cys
                85                90                95

Ala Lys Ser Ser Val Gly Trp Trp Ser Phe Asp Tyr Trp Gly Gln Gly
                100                105                110

Thr Met Val Thr Val Ser Ser Ala Ser Thr Lys Gly Pro Ser Val Phe
                115                120                125

Pro Leu Ala Pro Ser Ser Lys Ser Thr Ser Gly Gly Thr Ala Ala Leu
                130                135                140

Gly Cys Leu Val Lys Asp Tyr Phe Pro Glu Pro Val Thr Val Ser Trp
145                150                155                160

Asn Ser Gly Ala Leu Thr Ser Gly Val His Thr Phe Pro Ala Val Leu
                165                170                175

Gln Ser Ser Gly Leu Tyr Ser Leu Ser Ser Val Val Thr Val Pro Ser
                180                185                190

Ser Ser Leu Gly Thr Gln Thr Tyr Ile Cys Asn Val Asn His Lys Pro
                195                200                205

Ser Asn Thr Lys Val Asp Lys Lys Val Glu Pro Lys Ser Cys Asp Lys
                210                215                220

Thr His Thr Cys Pro Pro Cys Pro Ala Pro Glu Leu Leu Gly Gly Pro
```

```
             225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
                 260                 265                 270

Pro Glu Val Lys Phe Asn Trp Tyr Val Asp Gly Val Glu Val His Asn
                 275                 280                 285

Ala Lys Thr Lys Pro Arg Glu Glu Gln Tyr Asn Ser Thr Tyr Arg Val
         290                 295                 300

Val Ser Val Leu Thr Val Leu His Gln Asp Trp Leu Asn Gly Lys Glu
     305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
                 340                 345                 350

Leu Pro Pro Ser Arg Asp Glu Leu Thr Lys Asn Gln Val Ser Leu Thr
                 355                 360                 365

Cys Leu Val Lys Gly Phe Tyr Pro Ser Asp Ile Ala Val Glu Trp Glu
         370                 375                 380

Ser Asn Gly Gln Pro Glu Asn Asn Tyr Lys Thr Thr Pro Pro Val Leu
     385                 390                 395                 400

Asp Ser Asp Gly Ser Phe Phe Leu Tyr Ser Lys Leu Thr Val Asp Lys
                 405                 410                 415

Ser Arg Trp Gln Gln Gly Asn Val Phe Ser Cys Ser Val Met His Glu
                 420                 425                 430

Ala Leu His Asn His Tyr Thr Gln Lys Ser Leu Ser Leu Ser Pro Gly
         435                 440                 445

Lys
```

```
<210> SEQ ID NO 288
<211> LENGTH: 450
<212> TYPE: PRT
<213> ORGANISM: artificial sequence
<220> FEATURE:
<223> OTHER INFORMATION: G4_5 IgG1 antibody heavy chain sequence

<400> SEQUENCE: 288

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Gly Ala Tyr Asn Gly Asn Thr Asn Tyr Ala Gln Lys Leu
        50                  55                  60

Gln Gly Arg Val Thr Met Ser Thr Asp Thr Ser Thr Ser Thr Ala Tyr
65                  70                  75                  80

Met Glu Leu Arg Ser Pro Arg Ser Asp Asp Thr Ala Val Tyr Tyr Cys
                85                  90                  95

Ala Arg Gly Gly Thr Gly Gly Asp His Val Phe Ala Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450
```

```
<210> SEQ ID NO 289
<211> LENGTH: 450
<212> TYPE: PRT
<213> ORGANISM: artificial sequence
<220> FEATURE:
<223> OTHER INFORMATION: G4_6 IgG1 antibody heavy chain sequence

<400> SEQUENCE: 289
```

```
Glu Val Gln Leu Val Glu Ser Gly Gly Gly Leu Val Gln Pro Gly Gly
1                   5                   10                  15

Pro Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50              55              60
```

```
Lys Gly Arg Phe Thr Ile Ser Arg Asp Asn Ser Lys Asn Thr Leu Tyr
65              70              75              80
```

```
Leu Gln Met Asn Ser Leu Arg Ala Glu Asp Thr Ala Val Tyr Tyr Cys
                85              90              95
```

```
Ala Lys Ala Asp Tyr Gly Val Val Tyr Tyr Phe Asp Tyr Trp Gly Gln
            100             105             110
```

```
Gly Thr Met Val Thr Val Ser Ser Ala Ser Thr Lys Gly Pro Ser Val
        115             120             125
```

```
Phe Pro Leu Ala Pro Ser Ser Lys Ser Thr Ser Gly Gly Thr Ala Ala
    130             135             140
```

```
Leu Gly Cys Leu Val Lys Asp Tyr Phe Pro Glu Pro Val Thr Val Ser
145             150             155             160
```

```
Trp Asn Ser Gly Ala Leu Thr Ser Gly Val His Thr Phe Pro Ala Val
            165             170             175
```

```
Leu Gln Ser Ser Gly Leu Tyr Ser Leu Ser Ser Val Val Thr Val Pro
        180             185             190
```

```
Ser Ser Ser Leu Gly Thr Gln Thr Tyr Ile Cys Asn Val Asn His Lys
        195             200             205
```

```
Pro Ser Asn Thr Lys Val Asp Lys Lys Val Glu Pro Lys Ser Cys Asp
    210             215             220
```

```
Lys Thr His Thr Cys Pro Pro Cys Pro Ala Pro Glu Leu Leu Gly Gly
225             230             235             240
```

```
Pro Ser Val Phe Leu Phe Pro Pro Lys Pro Lys Asp Thr Leu Met Ile
            245             250             255
```

```
Ser Arg Thr Pro Glu Val Thr Cys Val Val Val Asp Val Ser His Glu
            260             265             270
```

```
Asp Pro Glu Val Lys Phe Asn Trp Tyr Val Asp Gly Val Glu Val His
        275             280             285
```

```
Asn Ala Lys Thr Lys Pro Arg Glu Glu Gln Tyr Asn Ser Thr Tyr Arg
    290             295             300
```

```
Val Val Ser Val Leu Thr Val Leu His Gln Asp Trp Leu Asn Gly Lys
305             310             315             320
```

```
Glu Tyr Lys Cys Lys Val Ser Asn Lys Ala Leu Pro Ala Pro Ile Glu
            325             330             335
```

```
Lys Thr Ile Ser Lys Ala Lys Gly Gln Pro Arg Glu Pro Gln Val Tyr
            340             345             350
```

```
Thr Leu Pro Pro Ser Arg Asp Glu Leu Thr Lys Asn Gln Val Ser Leu
        355             360             365
```

```
Thr Cys Leu Val Lys Gly Phe Tyr Pro Ser Asp Ile Ala Val Glu Trp
    370             375             380
```

```
Glu Ser Asn Gly Gln Pro Glu Asn Asn Tyr Lys Thr Thr Pro Pro Val
385             390             395             400
```

```
Leu Asp Ser Asp Gly Ser Phe Phe Leu Tyr Ser Lys Leu Thr Val Asp
            405             410             415
```

```
Lys Ser Arg Trp Gln Gln Gly Asn Val Phe Ser Cys Ser Val Met His
            420             425             430
```

```
Glu Ala Leu His Asn His Tyr Thr Gln Lys Ser Leu Ser Leu Ser Pro
        435             440             445
```

```
Gly Lys
    450
```

```
<210> SEQ ID NO 290
<211> LENGTH: 449
<212> TYPE: PRT
<213> ORGANISM: artificial sequence
<220> FEATURE:
<223> OTHER INFORMATION: G4_7 IgG1 antibody heavy chain sequence

<400> SEQUENCE: 290

Glu Val Gln Leu Val Glu Ser Gly Gly Gly Trp Val Gln Ser Gly Gly
1               5                   10                  15

Ser Leu Arg Pro Ser Cys Ala Ala Ser Gly Phe Thr Phe Ser His Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Ile Ile Tyr Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Ile Gly Tyr Ser Ser Ser Phe Asp Tyr Trp Gly Arg Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
    355                 360                 365
```

-continued

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 291
<211> LENGTH: 452
<212> TYPE: PRT
<213> ORGANISM: artificial sequence
<220> FEATURE:
<223> OTHER INFORMATION: G4_10 IgG1 antibody heavy chain sequence

<400> SEQUENCE: 291
```

```
Gln Val Gln Leu Val Glu Ser Gly Gly Gly Val Val Gln Pro Gly Arg
1               5                   10                  15

Pro Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Val Asp Phe Trp Arg Asn Gly Met Asp Val Trp
                100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
```

-continued

```
            275                 280                 285
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 292
<211> LENGTH: 447
<212> TYPE: PRT
<213> ORGANISM: artificial sequence
<220> FEATURE:
<223> OTHER INFORMATION: G4_12 IgG1 antibody heavy chain sequence

<400> SEQUENCE: 292

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Val Ala Asn Gly Asp Phe Leu Asp Tyr Trp Gly Arg Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
```

-continued

```
                  180              185              190

Leu Gly Thr Gln Thr Tyr Ile Cys Asn Val Asn His Lys Pro Ser Asn
        195              200              205

Thr Lys Val Asp Lys Lys Val Glu Pro Lys Ser Cys Asp Lys Thr His
        210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
                245              250              255

Pro Glu Val Thr Cys Val Val Val Asp Val Ser His Glu Asp Pro Glu
                260              265              270

Val Lys Phe Asn Trp Tyr Val Asp Gly Val Glu Val His Asn Ala Lys
        275              280              285

Thr Lys Pro Arg Glu Glu Gln Tyr Asn Ser Thr Tyr Arg Val Val Ser
        290              295              300

Val Leu Thr Val Leu His Gln Asp Trp Leu Asn Gly Lys Glu Tyr Lys
305              310              315              320

Cys Lys Val Ser Asn Lys Ala Leu Pro Ala Pro Ile Glu Lys Thr Ile
                325              330              335

Ser Lys Ala Lys Gly Gln Pro Arg Glu Pro Gln Val Tyr Thr Leu Pro
                340              345              350

Pro Ser Arg Asp Glu Leu Thr Lys Asn Gln Val Ser Leu Thr Cys Leu
                355              360              365

Val Lys Gly Phe Tyr Pro Ser Asp Ile Ala Val Glu Trp Glu Ser Asn
        370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
                405              410              415

Trp Gln Gln Gly Asn Val Phe Ser Cys Ser Val Met His Glu Ala Leu
                420              425              430

His Asn His Tyr Thr Gln Lys Ser Leu Ser Leu Ser Pro Gly Lys
        435              440              445
```

```
<210> SEQ ID NO 293
<211> LENGTH: 447
<212> TYPE: PRT
<213> ORGANISM: artificial sequence
<220> FEATURE:
<223> OTHER INFORMATION: G4_13 IgG1 antibody heavy chain sequence

<400> SEQUENCE: 293

Gln Val Gln Leu Val Glu Ser Gly Ala Glu Val Lys Lys Pro Gly Gly
1               5               10               15

Ser Leu Arg Leu Ser Cys Ala Ala Ser Gly Phe Thr Phe Ser Ser Tyr
                20              25              30

Ser Met Asn Trp Val Arg Gln Ala Pro Gly Lys Gly Leu Glu Trp Val
        35              40              45

Ser Ser Ile Ser Gly Thr Ser Ser Tyr Ile Tyr Tyr Ala Asp Ser Val
        50              55              60

Lys Gly Arg Phe Thr Ile Ser Arg Asp Asn Ala Lys Asn Ser Leu Tyr
65              70              75              80

Leu Gln Met Ser Ser Leu Arg Ala Glu Asp Thr Ala Val Tyr Tyr Cys
                85              90              95

Ala Arg Gly Gly Leu Gly Met Val Asp Pro Trp Gly Gln Gly Thr Leu
```

-continued

```
                100               105               110
Val Thr Val Ser Ser Ala Ser Thr Lys Gly Pro Ser Val Phe Pro Leu
            115               120               125

Ala Pro Ser Ser Lys Ser Thr Ser Gly Gly Thr Ala Ala Leu Gly Cys
    130               135               140

Leu Val Lys Asp Tyr Phe Pro Glu Pro Val Thr Val Ser Trp Asn Ser
145               150               155               160

Gly Ala Leu Thr Ser Gly Val His Thr Phe Pro Ala Val Leu Gln Ser
            165               170               175

Ser Gly Leu Tyr Ser Leu Ser Ser Val Val Thr Val Pro Ser Ser Ser
            180               185               190

Leu Gly Thr Gln Thr Tyr Ile Cys Asn Val Asn His Lys Pro Ser Asn
            195               200               205

Thr Lys Val Asp Lys Lys Val Glu Pro Lys Ser Cys Asp Lys Thr His
    210               215               220

Thr Cys Pro Pro Cys Pro Ala Pro Glu Leu Leu Gly Gly Pro Ser Val
225               230               235               240

Phe Leu Phe Pro Pro Lys Pro Lys Asp Thr Leu Met Ile Ser Arg Thr
            245               250               255

Pro Glu Val Thr Cys Val Val Val Asp Val Ser His Glu Asp Pro Glu
            260               265               270

Val Lys Phe Asn Trp Tyr Val Asp Gly Val Glu Val His Asn Ala Lys
            275               280               285

Thr Lys Pro Arg Glu Glu Gln Tyr Asn Ser Thr Tyr Arg Val Val Ser
    290               295               300

Val Leu Thr Val Leu His Gln Asp Trp Leu Asn Gly Lys Glu Tyr Lys
305               310               315               320

Cys Lys Val Ser Asn Lys Ala Leu Pro Ala Pro Ile Glu Lys Thr Ile
            325               330               335

Ser Lys Ala Lys Gly Gln Pro Arg Glu Pro Gln Val Tyr Thr Leu Pro
            340               345               350

Pro Ser Arg Asp Glu Leu Thr Lys Asn Gln Val Ser Leu Thr Cys Leu
            355               360               365

Val Lys Gly Phe Tyr Pro Ser Asp Ile Ala Val Glu Trp Glu Ser Asn
    370               375               380

Gly Gln Pro Glu Asn Asn Tyr Lys Thr Thr Pro Pro Val Leu Asp Ser
385               390               395               400

Asp Gly Ser Phe Phe Leu Tyr Ser Lys Leu Thr Val Asp Lys Ser Arg
            405               410               415

Trp Gln Gln Gly Asn Val Phe Ser Cys Ser Val Met His Glu Ala Leu
            420               425               430

His Asn His Tyr Thr Gln Lys Ser Leu Ser Leu Ser Pro Gly Lys
            435               440               445
```

```
<210> SEQ ID NO 294
<211> LENGTH: 447
<212> TYPE: PRT
<213> ORGANISM: artificial sequence
<220> FEATURE:
<223> OTHER INFORMATION: G4_14 IgG1 antibody heavy chain sequence

<400> SEQUENCE: 294

Glu Val Gln Leu Val Gln Ser Gly Ala Glu Val Lys Lys Pro Gly Glu
1               5               10               15

Ser Leu Arg Ile Ser Cys Lys Gly Ser Gly Tyr Ser Phe Thr Ser Tyr
```

```
               20              25              30

Trp Ile Ser Trp Val Arg Gln Met Pro Gly Lys Gly Leu Glu Trp Met
           35              40              45

Gly Arg Ile Asp Pro Ser Asp Ser Tyr Thr Asn Tyr Ser Pro Ser Phe
       50              55              60

Pro Gly His Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
               85              90              95

Ala Ala Asp Thr Ala His Gly Met Asp Val Trp Gly Arg Gly Thr Leu
           100             105             110

Val Thr Val Ser Ser Ala Ser Thr Lys Gly Pro Ser Val Phe Pro Leu
           115             120             125

Ala Pro Ser Ser Lys Ser Thr Ser Gly Gly Thr Ala Ala Leu Gly Cys
       130             135             140

Leu Val Lys Asp Tyr Phe Pro Glu Pro Val Thr Val Ser Trp Asn Ser
145             150             155             160

Gly Ala Leu Thr Ser Gly Val His Thr Phe Pro Ala Val Leu Gln Ser
           165             170             175

Ser Gly Leu Tyr Ser Leu Ser Ser Val Val Thr Val Pro Ser Ser Ser
           180             185             190

Leu Gly Thr Gln Thr Tyr Ile Cys Asn Val Asn His Lys Pro Ser Asn
           195             200             205

Thr Lys Val Asp Lys Lys Val Glu Pro Lys Ser Cys Asp Lys Thr His
       210             215             220

Thr Cys Pro Pro Cys Pro Ala Pro Glu Leu Leu Gly Gly Pro Ser Val
225             230             235             240

Phe Leu Phe Pro Pro Lys Pro Lys Asp Thr Leu Met Ile Ser Arg Thr
           245             250             255

Pro Glu Val Thr Cys Val Val Val Asp Val Ser His Glu Asp Pro Glu
           260             265             270

Val Lys Phe Asn Trp Tyr Val Asp Gly Val Glu Val His Asn Ala Lys
           275             280             285

Thr Lys Pro Arg Glu Glu Gln Tyr Asn Ser Thr Tyr Arg Val Val Ser
       290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
           325             330             335

Ser Lys Ala Lys Gly Gln Pro Arg Glu Pro Gln Val Tyr Thr Leu Pro
           340             345             350

Pro Ser Arg Asp Glu Leu Thr Lys Asn Gln Val Ser Leu Thr Cys Leu
           355             360             365

Val Lys Gly Phe Tyr Pro Ser Asp Ile Ala Val Glu Trp Glu Ser Asn
           370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
           405             410             415

Trp Gln Gln Gly Asn Val Phe Ser Cys Ser Val Met His Glu Ala Leu
           420             425             430

His Asn His Tyr Thr Gln Lys Ser Leu Ser Leu Ser Pro Gly Lys
           435             440             445
```

-continued

```
<210> SEQ ID NO 295
<211> LENGTH: 452
<212> TYPE: PRT
<213> ORGANISM: artificial sequence
<220> FEATURE:
<223> OTHER INFORMATION: G4_15 IgG1 antibody heavy chain sequence

<400> SEQUENCE: 295

Glu Val Gln Leu Val Gln Ser Glu Ala Glu Val Lys Lys Pro Gly Ala
1               5                   10                  15

Ser Val Lys Val Ser Cys Lys Ala Ser Gly Tyr Thr Phe Thr Arg His
            20                  25                  30

Tyr Met His Trp Val Arg Gln Ala Pro Gly Gln Gly Leu Glu Trp Met
        35                  40                  45

Gly Leu Ile Asn Pro Ser Gly Ser Ser Thr Val Tyr Ala Gln Lys Phe
    50                  55                  60

Gln Gly Arg Val Thr Leu Thr Arg Asp Thr Ser Thr Ser Thr Asp Tyr
65                  70                  75                  80

Met Glu Leu Ser Ser Leu Arg Ser Glu Asp Thr Ala Val Tyr Tyr Cys
                85                  90                  95

Ala Arg Asp Asn Ser His Leu Asp Gln Val Trp Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
    355                 360                 365
```

```
Ser Leu Thr Cys Leu Val Lys Gly Phe Tyr Pro Ser Asp Ile Ala Val
    370             375             380

Glu Trp Glu Ser Asn Gly Gln Pro Glu Asn Asn Tyr Lys Thr Thr Pro
385             390             395             400

Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly Lys
    450

<210> SEQ ID NO 296
<211> LENGTH: 449
<212> TYPE: PRT
<213> ORGANISM: artificial sequence
<220> FEATURE:
<223> OTHER INFORMATION: G4_16 IgG1 antibody heavy chain sequence

<400> SEQUENCE: 296

Glu Val Gln Leu Leu Glu Ser Gly Ala Glu Val Lys Lys Pro Gly Ala
1               5               10              15

Ser Val Lys Val Ser Cys Lys Ala Ser Gly Tyr Thr Phe Thr Ser Tyr
            20              25              30

Gly Ile Ser Trp Val Arg Gln Ala Pro Gly Gln Gly Leu Glu Trp Met
        35              40              45

Gly Trp Ile Ser Ala Tyr Asn Gly Asn Thr Asn Tyr Ala Gln Lys Leu
    50              55              60

Gln Gly Arg Val Thr Met Thr Thr Asp Thr Ser Thr Ser Thr Ala Tyr
65              70              75              80

Met Glu Leu Arg Ser Leu Arg Ser Asp Asp Thr Ala Val Tyr Tyr Cys
            85              90              95

Ala Arg Asp Tyr Gly Asp Phe Tyr Gly Met Asp Val Trp Gly Gln Gly
            100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Cys Pro Pro Cys Pro Ala Pro Glu Leu Leu Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270
```

```
Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 297
<211> LENGTH: 448
<212> TYPE: PRT
<213> ORGANISM: artificial sequence
<220> FEATURE:
<223> OTHER INFORMATION: G4_18 IgG1 antibody heavy chain sequence

<400> SEQUENCE: 297
```

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Ala Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Asp Leu Asp Leu Ser Ser Leu Asp Tyr Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
        195             200             205

Asn Thr Lys Val Asp Lys Lys Val Glu Pro Lys Ser Cys Asp Lys Thr
    210             215             220

His Thr Cys Pro Pro Cys Pro Ala Pro Glu Leu Leu Gly Gly Pro Ser
225             230             235             240

Val Phe Leu Phe Pro Pro Lys Pro Lys Asp Thr Leu Met Ile Ser Arg
                245             250             255

Thr Pro Glu Val Thr Cys Val Val Val Asp Val Ser His Glu Asp Pro
            260             265             270

Glu Val Lys Phe Asn Trp Tyr Val Asp Gly Val Glu Val His Asn Ala
        275             280             285

Lys Thr Lys Pro Arg Glu Glu Gln Tyr Asn Ser Thr Tyr Arg Val Val
    290             295             300

Ser Val Leu Thr Val Leu His Gln Asp Trp Leu Asn Gly Lys Glu Tyr
305             310             315             320

Lys Cys Lys Val Ser Asn Lys Ala Leu Pro Ala Pro Ile Glu Lys Thr
                325             330             335

Ile Ser Lys Ala Lys Gly Gln Pro Arg Glu Pro Gln Val Tyr Thr Leu
            340             345             350

Pro Pro Ser Arg Asp Glu Leu Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Lys Leu Thr Val Asp Lys Ser
                405             410             415

Arg Trp Gln Gln Gly Asn Val Phe Ser Cys Ser Val Met His Glu Ala
            420             425             430

Leu His Asn His Tyr Thr Gln Lys Ser Leu Ser Leu Ser Pro Gly Lys
            435             440             445

<210> SEQ ID NO 298
<211> LENGTH: 451
<212> TYPE: PRT
<213> ORGANISM: artificial sequence
<220> FEATURE:
<223> OTHER INFORMATION: G4_19 IgG1 antibody heavy chain sequence

<400> SEQUENCE: 298

Glu Val Gln Leu Val Gln Ser Gly Ala Glu Val Lys Lys Pro Gly Ala
1               5               10              15

Ser Val Lys Val Ser Cys Lys Ala Ser Gly Tyr Thr Leu Thr Ser Tyr
            20              25              30

Tyr Met His Trp Val Arg Gln Ala Pro Gly Gln Gly Leu Glu Trp Met
        35              40              45

Gly Ile Ile Asn Pro Ser Gly Gly Ser Thr Ser Tyr Ala Gln Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95
```

-continued

```
Ala Arg Glu Arg Gly Tyr Ser Tyr Gly Asp Gly Met Asp Val Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450
```

<210> SEQ ID NO 299
<211> LENGTH: 449
<212> TYPE: PRT
<213> ORGANISM: artificial sequence
<220> FEATURE:
<223> OTHER INFORMATION: G4_20 IgG1 antibody heavy chain sequence

<400> SEQUENCE: 299

-continued

```
Gln Val Gln Leu Val Glu Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Val Asp Lys Ser Thr Arg Thr Ala Tyr
65                  70                  75                  80

Met Glu Leu Ser Ser Leu Arg Ser Lys Asp Thr Ala Val Tyr Tyr Cys
                85                  90                  95

Ala Arg Gly Asn Ser Arg Ser Asp Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

-continued

```
                      420                 425                 430
Ala Leu His Asn His Tyr Thr Gln Lys Ser Leu Ser Leu Ser Pro Gly
        435                 440                 445

Lys

<210> SEQ ID NO 300
<211> LENGTH: 450
<212> TYPE: PRT
<213> ORGANISM: artificial sequence
<220> FEATURE:
<223> OTHER INFORMATION: G4_22 IgG1 antibody heavy chain sequence

<400> SEQUENCE: 300

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
        20                  25                  30

Ala Met Ser Trp Val Arg Gln Ala Pro Gly Lys Gly Leu Glu Trp Val
        35                  40                  45

Ser Thr Val Ser Gly Ser Gly Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Thr Ala Val Thr Asp Trp Phe Asp Pro Trp Gly Arg
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335
```

-continued

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 301
<211> LENGTH: 450
<212> TYPE: PRT
<213> ORGANISM: artificial sequence
<220> FEATURE:
<223> OTHER INFORMATION: G4_23 IgG1 antibody heavy chain sequence

<400> SEQUENCE: 301

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Glu Val Ala Ala Leu Tyr Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                    165                 170                 175

Leu Gln Ser Ser Gly Leu Tyr Ser Leu Ser Ser Val Val Thr Val Pro
                    180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240
```

-continued

```
Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
        290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
                325             330             335

Lys Thr Ile Ser Lys Ala Lys Gly Gln Pro Arg Glu Pro Gln Val Tyr
            340             345             350

Thr Leu Pro Pro Ser Arg Asp Glu Leu Thr Lys Asn Gln Val Ser Leu
            355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450

<210> SEQ ID NO 302
<211> LENGTH: 452
<212> TYPE: PRT
<213> ORGANISM: artificial sequence
<220> FEATURE:
<223> OTHER INFORMATION: G4_24 IgG1 antibody heavy chain sequence

<400> SEQUENCE: 302

Gln Val Gln Leu Gln Gln Ser Gly Pro Gly Leu Val Lys Pro Ser Gln
1               5               10              15

Thr Leu Ser Leu Thr Cys Ala Ile Ser Gly Ala Ser Val Ser Ser Asn
            20              25              30

Ser Val Ala Trp Asn Trp Ile Arg Gln Ser Pro Ser Arg Gly Leu Glu
        35              40              45

Trp Leu Gly Arg Thr Tyr Tyr Arg Ser Arg Trp Tyr Asn Asp Tyr Ala
    50              55              60

Leu Ser Val Lys Ser Arg Ile Ile Ile Asn Pro Asp Thr Ser Lys Asn
65              70              75              80

Gln Phe Ser Leu Gln Leu Asn Ser Val Thr Pro Glu Asp Thr Ala Val
            85              90              95

Tyr Tyr Cys Ala Arg Asp Trp Ser Ser Thr Arg Ser Phe Asp Tyr Trp
            100             105             110

Gly Arg Gly Thr Leu Val Thr Val Ser Ser Ala Ser Thr Lys Gly Pro
        115             120             125

Ser Val Phe Pro Leu Ala Pro Ser Ser Lys Ser Thr Ser Gly Gly Thr
    130             135             140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 303
<211> LENGTH: 453
<212> TYPE: PRT
<213> ORGANISM: artificial sequence
<220> FEATURE:
<223> OTHER INFORMATION: G4_25 IgG1 antibody heavy chain sequence

<400> SEQUENCE: 303

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

-continued

```
Gly Gly Ile Ile Pro Ile Phe Gly Thr Ala Asn Tyr Ala Gln Lys Phe
    50              55              60

Gln Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Ser Leu Arg Asp Gly Tyr Asn Tyr Ile Gly Ser Leu Gly Tyr
            100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450
```

-continued

```
<210> SEQ ID NO 304
<211> LENGTH: 450
<212> TYPE: PRT
<213> ORGANISM: artificial sequence
<220> FEATURE:
<223> OTHER INFORMATION: G4_26 IgG1 antibody heavy chain sequence

<400> SEQUENCE: 304

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Arg Gly Ser Gly Trp Phe Pro Leu Gly Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

-continued

```
Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

```
<210> SEQ ID NO 305
<211> LENGTH: 452
<212> TYPE: PRT
<213> ORGANISM: artificial sequence
<220> FEATURE:
<223> OTHER INFORMATION: G4_27 IgG1 antibody heavy chain sequence

<400> SEQUENCE: 305
```

```
Gln Val Gln Leu Val Gln Ser Gly Ala Glu Val Lys Lys Pro Gly Glu
1               5               10              15

Ser Leu Lys Ile Ser Cys Lys Ser Ser Gly Tyr Ser Phe Thr Ser Tyr
            20              25              30

Trp Ile Gly Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Phe Ser Ala Asp Glu Ser Ile Ser Thr Ala Tyr
65              70              75              80

Leu Gln Trp Ser Ser Leu Lys Ala Ser Asp Thr Ala Met Tyr Tyr Cys
            85              90              95

Ala Arg His Gly Ala Tyr Gly Asp Tyr Pro Asp Thr Phe Asp Ile Trp
            100             105             110

Gly Gln Gly Thr Leu Val Thr Val Ser Ser Ala Ser Thr Lys Gly Pro
        115             120             125

Ser Val Phe Pro Leu Ala Pro Ser Ser Lys Ser Thr Ser Gly Gly Thr
    130             135             140

Ala Ala Leu Gly Cys Leu Val Lys Asp Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ser Ser Gly Leu Tyr Ser Leu Ser Ser Val Val Thr
            180             185             190

Val Pro Ser Ser Ser Leu Gly Thr Gln Thr Tyr Ile Cys Asn Val Asn
            195             200             205

His Lys Pro Ser Asn Thr Lys Val Asp Lys Lys Val Glu Pro Lys Ser
        210             215             220

Cys Asp Lys Thr His Thr Cys Pro Pro Cys Pro Ala Pro Glu Leu Leu
225             230             235             240

Gly Gly Pro Ser Val Phe Leu Phe Pro Pro Lys Pro Lys Asp Thr Leu
            245             250             255

Met Ile Ser Arg Thr Pro Glu Val Thr Cys Val Val Val Asp Val Ser
            260             265             270
```

-continued

```
His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 306
<211> LENGTH: 455
<212> TYPE: PRT
<213> ORGANISM: artificial sequence
<220> FEATURE:
<223> OTHER INFORMATION: G4_28 IgG1 antibody heavy chain sequence

<400> SEQUENCE: 306

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Ala Gly Gly Gly Ser Thr Asn Tyr Ala Gly Ser Val
    50                  55                  60

Lys Gly Arg Phe Thr Val Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Ser Tyr Val Asp Thr Ala Met Arg Tyr Tyr Tyr Tyr Tyr Met
            100                 105                 110

Asp Val Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                    340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455
```

```
<210> SEQ ID NO 307
<211> LENGTH: 216
<212> TYPE: PRT
<213> ORGANISM: artificial sequence
<220> FEATURE:
<223> OTHER INFORMATION: G4_1 IgG1 antibody light chain sequence

<400> SEQUENCE: 307

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
            20                  25                  30

Asn Tyr Leu Asn Trp Tyr Gln Gln Lys Pro Gly Lys Ala Pro Lys Leu
        35                  40                  45

Leu Ile Tyr Asp Ala Ser Asn Leu Glu Thr Gly Val Pro Ser Arg Phe
    50                  55                  60

Ser Gly Ser Gly Ser Gly Thr Asp Phe Thr Leu Thr Ile Ser Ser Leu
65                  70                  75                  80
```

```
Gln Pro Glu Asp Phe Ala Thr Tyr Tyr Cys Gln Gln Ser Tyr Ser Thr
                    85                  90                  95

Pro Val Thr Phe Gly Pro Gly Thr Lys Val Glu Ile Lys Arg Thr Ala
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Leu Tyr Ala Cys Glu Val Thr His Gln Gly Leu Ser Ser Pro Val Thr
                195                 200                 205

Lys Ser Phe Asn Arg Gly Glu Cys
        210                 215

<210> SEQ ID NO 308
<211> LENGTH: 216
<212> TYPE: PRT
<213> ORGANISM: artificial sequence
<220> FEATURE:
<223> OTHER INFORMATION: G4_2 IgG1 antibody light chain sequence

<400> SEQUENCE: 308

Ala Ser Asp Ile Gln Met Thr Gln Ser Pro Ser Ser Leu Ser Ala Ser
1                   5                   10                  15

Val Gly Asp Arg Val Thr Ile Thr Cys Gln Ala Ser Gln Asp Ile Ser
                20                  25                  30

Asn Tyr Leu Asn Trp Tyr Gln Gln Lys Pro Gly Lys Ala Pro Lys Leu
                35                  40                  45

Leu Ile Tyr Ala Ala Ser Ser Leu Gln Ser Gly Val Pro Ser Arg Phe
        50                  55                  60

Ser Gly Ser Gly Ser Gly Thr Asp Phe Thr Leu Thr Ile Ser Gly Leu
65                  70                  75                  80

Gln Pro Glu Asp Phe Ala Thr Tyr Tyr Cys Leu Glu Asp Tyr Asn Tyr
                    85                  90                  95

Leu Trp Thr Phe Gly Gln Gly Thr Lys Leu Glu Ile Lys Arg Thr Ala
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Leu Tyr Ala Cys Glu Val Thr His Gln Gly Leu Ser Ser Pro Val Thr
                195                 200                 205

Lys Ser Phe Asn Arg Gly Glu Cys
        210                 215
```

<210> SEQ ID NO 309
<211> LENGTH: 216
<212> TYPE: PRT
<213> ORGANISM: artificial sequence
<220> FEATURE:
<223> OTHER INFORMATION: G4_3 IgG1 antibody light chain sequence

<400> SEQUENCE: 309

Ala Ser Asp Ile Gln Met Thr Gln Ser Pro Ser Ser Leu Ser Ala Ser
1               5                   10                  15

Val Gly Asp Arg Val Thr Ile Thr Cys Gln Ala Ser Gln Asp Ile Ser
                20                  25                  30

Asn Tyr Leu Asn Trp Tyr Gln Gln Lys Pro Gly Lys Ala Pro Lys Leu
            35                  40                  45

Leu Ile Tyr Asp Ala Ser Asn Leu Glu Thr Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Phe Cys Gln Gln Ser Tyr Ser Thr
                85                  90                  95

Pro Gln Thr Phe Gly Gln Gly Thr Lys Val Asp Ile Lys Arg Thr Ala
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 310
<211> LENGTH: 222
<212> TYPE: PRT
<213> ORGANISM: artificial sequence
<220> FEATURE:
<223> OTHER INFORMATION: G4_4 IgG1 antibody light chain sequence

<400> SEQUENCE: 310

Ala Ser Asp Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
                20                  25                  30

Ser Ser Ser Asn Asn Asn Asn Tyr Leu Ala Trp Tyr Gln Gln Arg Pro
        35                  40                  45

Gly Gln Pro Pro Lys Leu Leu Phe Tyr Trp Ala Ser Thr Arg Glu Ser
        50                  55                  60

Gly Val Pro Asp Arg Phe Ser Gly Ser Gly Ser Gly Thr Ser Phe Thr
65                  70                  75                  80

Leu Thr Ile Thr Ser Leu Gln Ala Glu Asp Val Ala Val Tyr Tyr Cys
                85                  90                  95

```
Gln Gln Tyr Tyr Ser Thr Pro Leu Thr Phe Gly Gly Gly Thr Lys Leu
            100             105                 110

Glu Ile Lys Arg Thr Ala Ala Ala Pro Ser Val Phe Ile Phe Pro Pro
            115             120             125

Ser Asp Glu Gln Leu Lys Ser Gly Thr Ala Ser Val Val Cys Leu Leu
            130             135             140

Asn Asn Phe Tyr Pro Arg Glu Ala Lys Val Gln Trp Lys Val Asp Asn
145             150             155             160

Ala Leu Gln Ser Gly Asn Ser Gln Glu Ser Val Thr Glu Gln Asp Ser
            165             170             175

Lys Asp Ser Thr Tyr Ser Leu Ser Ser Thr Leu Thr Leu Ser Lys Ala
            180             185             190

Asp Tyr Glu Lys His Lys Leu Tyr Ala Cys Glu Val Thr His Gln Gly
            195             200             205

Leu Ser Ser Pro Val Thr Lys Ser Phe Asn Arg Gly Glu Cys
            210             215             220
```

```
<210> SEQ ID NO 311
<211> LENGTH: 216
<212> TYPE: PRT
<213> ORGANISM: artificial sequence
<220> FEATURE:
<223> OTHER INFORMATION: G4_5 IgG1 antibody light chain sequence

<400> SEQUENCE: 311
```

```
Ala Ser Asp Ile Gln Met Thr Gln Ser Pro Ser Ser Leu Ser Ala Ser
1               5               10              15

Val Gly Asp Arg Val Thr Ile Thr Cys Arg Ala Ser Gln Ser Ile Ser
            20              25              30

Ser Tyr Leu Asn Trp Tyr Gln Gln Lys Pro Gly Lys Ala Pro Lys Leu
            35              40              45

Leu Ile Tyr Ala Ala Ser Ser Leu Gln Ser Gly Val Pro Ser Arg Phe
            50              55              60

Ser Gly Ser Gly Ser Gly Thr Asp Phe Thr Leu Thr Ile Ser Ser Leu
65              70              75              80

Gln Pro Glu Asp Phe Ala Thr Tyr Tyr Cys Gln Gln Ser Tyr Ser Thr
            85              90              95

Pro Tyr Thr Phe Gly Gln Gly Thr Lys Val Glu Ile Lys Arg Thr Ala
            100             105             110

Ala Ala Pro Ser Val Phe Ile Phe Pro Pro Ser Asp Glu Gln Leu Lys
            115             120             125

Ser Gly Thr Ala Ser Val Val Cys Leu Leu Asn Asn Phe Tyr Pro Arg
            130             135             140

Glu Ala Lys Val Gln Trp Lys Val Asp Asn Ala Leu Gln Ser Gly Asn
145             150             155             160

Ser Gln Glu Ser Val Thr Glu Gln Asp Ser Lys Asp Ser Thr Tyr Ser
            165             170             175

Leu Ser Ser Thr Leu Thr Leu Ser Lys Ala Asp Tyr Glu Lys His Lys
            180             185             190

Leu Tyr Ala Cys Glu Val Thr His Gln Gly Leu Ser Ser Pro Val Thr
            195             200             205

Lys Ser Phe Asn Arg Gly Glu Cys
            210             215
```

```
<210> SEQ ID NO 312
```

```
<211> LENGTH: 216
<212> TYPE: PRT
<213> ORGANISM: artificial sequence
<220> FEATURE:
<223> OTHER INFORMATION: G4_6 IgG1 antibody light chain sequence

<400> SEQUENCE: 312

Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Thr Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Pro
65                  70                  75                  80

Gln Pro Glu Asp Phe Ala Thr Tyr Tyr Cys Gln Gln Ser Tyr Ser Thr
                85                  90                  95

Pro Tyr Thr Phe Gly Gln Gly Thr Lys Val Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 313
<211> LENGTH: 221
<212> TYPE: PRT
<213> ORGANISM: artificial sequence
<220> FEATURE:
<223> OTHER INFORMATION: G4_7 IgG1 antibody light chain sequence

<400> SEQUENCE: 313

Ala Ser Asp Ile Val Met Thr Gln Ser Pro Leu Ser Leu Pro Val Thr
1               5                   10                  15

Pro Gly Glu Pro Ala Ser Ile Ser Cys Arg Ser Ser Gln Ser Leu Leu
            20                  25                  30

His Ser Asn Arg Phe Asn Tyr Leu Asp Trp Tyr Leu Gln Lys Pro Gly
        35                  40                  45

Gln Ser Pro Gln Leu Leu Ile Tyr Leu Gly Ser Asn Arg Ala Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Val Gly Val Tyr Tyr Cys Met
                85                  90                  95

Gln Gly Leu Gln Thr Pro Tyr Thr Phe Gly Gln Gly Thr Lys Val Asp
```

-continued

```
                100                  105                  110
Ile Lys Arg Thr Ala Ala Ala Pro Ser Val Phe Ile Phe Pro Pro Ser
        115                  120                  125

Asp Glu Gln Leu Lys Ser Gly Thr Ala Ser Val Val Cys Leu Leu Asn
    130                  135                  140

Asn Phe Tyr Pro Arg Glu Ala Lys Val Gln Trp Lys Val Asp Asn Ala
145                  150                  155                  160

Leu Gln Ser Gly Asn Ser Gln Glu Ser Val Thr Glu Gln Asp Ser Lys
                165                  170                  175

Asp Ser Thr Tyr Ser Leu Ser Ser Thr Leu Thr Leu Ser Lys Ala Asp
                180                  185                  190

Tyr Glu Lys His Lys Leu Tyr Ala Cys Glu Val Thr His Gln Gly Leu
            195                  200                  205

Ser Ser Pro Val Thr Lys Ser Phe Asn Arg Gly Glu Cys
    210                  215                  220

<210> SEQ ID NO 314
<211> LENGTH: 221
<212> TYPE: PRT
<213> ORGANISM: artificial sequence
<220> FEATURE:
<223> OTHER INFORMATION: G4_10 IgG1 antibody light chain sequence

<400> SEQUENCE: 314

Ala Ser Asp Ile Val Met Thr Gln Pro Pro Leu Ser Leu Pro Val Thr
1                   5                   10                  15

Leu Gly His Pro Ala Ser Ile Ser Cys Lys Ser Ser Gln Ser Leu Glu
                20                  25                  30

Tyr Ser Asp Gly Asn Thr Tyr Leu Asn Trp Phe Gln Gln Arg Pro Gly
            35                  40                  45

Gln Ser Pro Arg Arg Leu Ile Tyr Lys Val Ser Asn Arg Asp Ser Gly
    50                  55                  60

Ala Pro Asp Arg Phe Ser Gly Ser Gly Ser Gly Thr Asp Phe Thr Leu
65                  70                  75                  80

Glu Ile Ser Arg Val Glu Ala Glu Asp Val Gly Val Tyr Tyr Cys Met
                85                  90                  95

Gln Gly Thr Leu Trp Pro Pro Thr Phe Gly Gln Gly Thr Lys Val Asp
            100                  105                  110

Ile Lys Arg Thr Ala Ala Ala Pro Ser Val Phe Ile Phe Pro Pro Ser
        115                  120                  125

Asp Glu Gln Leu Lys Ser Gly Thr Ala Ser Val Val Cys Leu Leu Asn
    130                  135                  140

Asn Phe Tyr Pro Arg Glu Ala Lys Val Gln Trp Lys Val Asp Asn Ala
145                  150                  155                  160

Leu Gln Ser Gly Asn Ser Gln Glu Ser Val Thr Glu Gln Asp Ser Lys
                165                  170                  175

Asp Ser Thr Tyr Ser Leu Ser Ser Thr Leu Thr Leu Ser Lys Ala Asp
                180                  185                  190

Tyr Glu Lys His Lys Leu Tyr Ala Cys Glu Val Thr His Gln Gly Leu
            195                  200                  205

Ser Ser Pro Val Thr Lys Ser Phe Asn Arg Gly Glu Cys
    210                  215                  220

<210> SEQ ID NO 315
<211> LENGTH: 216
<212> TYPE: PRT
```

<213> ORGANISM: artificial sequence
<220> FEATURE:
<223> OTHER INFORMATION: G4_12 IgG1 antibody light chain sequence

<400> SEQUENCE: 315

```
Ala Ser Gln Ser Val Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Phe Val Ser Trp Tyr Gln Gln His Pro Gly Lys Ala Pro
        35                  40                  45

Lys Leu Met Ile Tyr Glu Val Thr Asn Arg Pro Ser Gly Val Pro Asp
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser His Ala
                85                  90                  95

Ser Pro Arg Val Phe Gly Thr Gly Thr Lys Val Thr Val Leu Gly Gln
            100                 105                 110

Pro Ala Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 316
<211> LENGTH: 219
<212> TYPE: PRT
<213> ORGANISM: artificial sequence
<220> FEATURE:
<223> OTHER INFORMATION: G4_13 IgG1 antibody light chain sequence

<400> SEQUENCE: 316

```
Ala Ser Asn Phe Met Leu Thr Gln Pro His Ser Val Ser Glu Ser Pro
1               5                   10                  15

Gly Lys Thr Val Thr Ile Ser Cys Thr Arg Ser Ser Gly Ser Ile Ala
            20                  25                  30

Ser Asn Tyr Val Gln Trp Tyr Gln Gln Arg Pro Gly Ser Ser Pro Ser
        35                  40                  45

Thr Val Ile Tyr Glu Asp Asn Gln Arg Pro Ser Gly Val Pro Asp Arg
    50                  55                  60

Phe Ser Gly Ser Ile Asp Ser Ser Ser Asn Ser Ala Ser Leu Thr Ile
65                  70                  75                  80

Ser Gly Leu Arg Thr Glu Asp Glu Ala Asp Tyr Tyr Cys Gln Ser Tyr
                85                  90                  95

Asp Ser Ser Ile Tyr Val Val Phe Gly Gly Gly Thr Lys Leu Thr Val
            100                 105                 110
```

```
Leu Gly Gln Pro Ala Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser
    210                 215
```

```
<210> SEQ ID NO 317
<211> LENGTH: 219
<212> TYPE: PRT
<213> ORGANISM: artificial sequence
<220> FEATURE:
<223> OTHER INFORMATION: G4_14 IgG1 antibody light chain sequence

<400> SEQUENCE: 317
```

```
Ala Ser Asn Phe Met Leu Thr Gln Pro His Ser Val Ser Glu Ser Pro
1               5                   10                  15

Gly Lys Thr Val Thr Ile Ser Cys Thr Arg Ser Arg Gly Ser Ile Ala
                20                  25                  30

Gly Asn Tyr Val His Trp Tyr Gln Gln Arg Pro Gly Arg Ala Pro Thr
            35                  40                  45

Thr Val Ile Tyr Arg Asp Lys Glu Arg Pro Ser Gly Val Pro Asp Arg
        50                  55                  60

Ile Ser Gly Ser Ile Asp Ser Ser Ser Asn Ser Ala Ser Leu Thr Ile
65                  70                  75                  80

Ser Gly Leu Lys Thr Glu Asp Glu Ala Asp Tyr Tyr Cys Gln Ser Tyr
                85                  90                  95

Asp Ser Ser Thr His Val Val Phe Gly Gly Gly Thr Lys Leu Thr Val
            100                 105                 110

Leu Gly Gln Pro Ala Ala Ala Pro Ser Val Thr Leu Phe Pro Pro Ser
        115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser
    210                 215
```

```
<210> SEQ ID NO 318
<211> LENGTH: 216
<212> TYPE: PRT
<213> ORGANISM: artificial sequence
<220> FEATURE:
```

<223> OTHER INFORMATION: G4_15 IgG1 antibody light chain sequence

<400> SEQUENCE: 318

```
Ala Ser Gln Ser Ala Leu Thr Gln Pro Ala Ser Val Ser Gly Ser Pro
1               5                   10                  15

Gly Gln Ser Ile Thr Ile Ser Cys Thr Gly Thr Ser Ser Asp Val Gly
            20                  25                  30

Gly Tyr Asn Tyr Val Ser Trp Tyr Gln Gln His Pro Gly Lys Ala Pro
        35                  40                  45

Lys Leu Met Ile Tyr Asp Val Ser Asn Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Gly
            85                  90                  95

Ser Gly Ser Val Phe Gly Thr Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

<210> SEQ ID NO 319
<211> LENGTH: 218
<212> TYPE: PRT
<213> ORGANISM: artificial sequence
<220> FEATURE:
<223> OTHER INFORMATION: G4_16 IgG1 antibody light chain sequence

<400> SEQUENCE: 319

```
Ala Ser Gln Ser Val Leu Thr Gln Pro Pro Ser Ala Ser Gly Ser Pro
1               5                   10                  15

Gly Gln Ser Val Thr Phe Ser Cys Thr Gly Thr Ser Ser Asp Ile Gly
            20                  25                  30

Ala Phe Asn Ser Val Ser Trp Tyr Gln Gln His Pro Gly Lys Ala Pro
        35                  40                  45

Lys Leu Leu Ile Tyr Glu Ile Thr Lys Arg Pro Ser Gly Val Pro Asp
    50                  55                  60

Arg Phe Ser Gly Ser Lys Ser Gly Asn Thr Ala Ser Leu Thr Ile Ser
65                  70                  75                  80

Val Leu Gln Ala Glu Asp Glu Ala Asp Tyr Tyr Cys Thr Ser Tyr Ala
            85                  90                  95

Gly Ser Asn Thr Leu Ile Phe Gly Gly Gly Thr Lys Val Thr Val Leu
            100                 105                 110

Gly Gln Pro Ala Ala Ala Pro Ser Val Thr Leu Phe Pro Pro Ser Ser
        115                 120                 125
```

```
Glu Glu Leu Gln Ala Asn Lys Ala Thr Leu Val Cys Leu Ile Ser Asp
    130             135             140

Phe Tyr Pro Gly Ala Val Thr Val Ala Trp Lys Ala Asp Ser Ser Pro
145             150             155             160

Val Lys Ala Gly Val Glu Thr Thr Thr Pro Ser Lys Gln Ser Asn Asn
            165             170             175

Lys Tyr Ala Ala Ser Ser Tyr Leu Ser Leu Thr Pro Glu Gln Trp Lys
            180             185             190

Ser His Arg Ser Tyr Ser Cys Gln Val Thr His Glu Gly Ser Thr Val
            195             200             205

Glu Lys Thr Val Ala Pro Thr Glu Cys Ser
    210             215
```

<210> SEQ ID NO 320
<211> LENGTH: 216
<212> TYPE: PRT
<213> ORGANISM: artificial sequence
<220> FEATURE:
<223> OTHER INFORMATION: G4_18 IgG1 antibody light chain sequence

<400> SEQUENCE: 320

```
Ala Ser Ser Tyr Glu Leu Thr Gln Pro Pro Ser Val Thr Glu Ser Pro
1               5               10              15

Gly Gln Thr Ala Arg Ile Thr Cys Ser Gly Asp Ala Leu Ala Lys Gln
            20              25              30

Tyr Ala Tyr Trp Tyr Gln Gln Lys Pro Gly Gln Ala Pro Val Leu Val
            35              40              45

Ile Tyr Arg Asp Ser Glu Arg Pro Ser Glu Ile Pro Glu Arg Phe Ser
    50              55              60

Gly Ser Ser Ser Gly Thr Thr Val Thr Leu Thr Ile Ser Gly Val Gln
65              70              75              80

Ala Glu Asp Glu Ala Asp Tyr Tyr Cys Gln Ser Ala Asp Ser Ser Gly
            85              90              95

Thr Tyr Thr Val Phe Gly Gly Gly Thr Lys Leu Thr Val Leu Gly Gln
            100             105             110

Pro Ala Ala Ala Pro Ser Val Thr Leu Phe Pro Pro Ser Ser Glu Glu
            115             120             125

Leu Gln Ala Asn Lys Ala Thr Leu Val Cys Leu Ile Ser Asp Phe Tyr
    130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
            165             170             175

Ala Ala Ser Ser Tyr Leu Ser Leu Thr Pro Glu Gln Trp Lys Ser His
            180             185             190

Arg Ser Tyr Ser Cys Gln Val Thr His Glu Gly Ser Thr Val Glu Lys
            195             200             205

Thr Val Ala Pro Thr Glu Cys Ser
    210             215
```

<210> SEQ ID NO 321
<211> LENGTH: 219
<212> TYPE: PRT
<213> ORGANISM: artificial sequence
<220> FEATURE:
<223> OTHER INFORMATION: G4_19 IgG1 antibody light chain sequence -continued

<400> SEQUENCE: 321

```
Ala Ser Asn Phe Met Leu Thr Gln Pro His Ser Val Ser Glu Ser Pro
1               5                   10                  15

Gly Lys Thr Val Thr Ile Ser Cys Thr Arg Ser Ser Gly Ser Ile Ala
            20                  25                  30

Ser Asn Tyr Val Gln Trp Tyr Gln Gln Arg Pro Gly Ser Pro Pro Ile
        35                  40                  45

Thr Leu Ile Tyr Asp Asp Asp Gln Arg Pro Ser Gly Val Pro His Arg
    50                  55                  60

Phe Ser Gly Ser Ile Asp Thr Ser Ser Asn Pro Ala Ser Leu Thr Ile
65                  70                  75                  80

Ser Gly Leu Lys Thr Glu Asp Glu Ala Asp Tyr Tyr Cys Gln Ser Tyr
                85                  90                  95

Asp Ser Ser Asn His Val Val Phe Gly Gly Gly Thr Lys Leu Thr Val
                100                 105                 110

Leu Gly Gln Pro Ala Ala Ala Pro Ser Val Thr Leu Phe Pro Pro Ser
            115                 120                 125

Ser Glu Glu Leu Gln Ala Asn Lys Ala Thr Leu Val Cys Leu Ile Ser
    130                 135                 140

Asp Phe Tyr Pro Gly Ala Val Thr Val Ala Trp Lys Ala Asp Ser Ser
145                 150                 155                 160

Pro Val Lys Ala Gly Val Glu Thr Thr Thr Pro Ser Lys Gln Ser Asn
                165                 170                 175

Asn Lys Tyr Ala Ala Ser Ser Tyr Leu Ser Leu Thr Pro Glu Gln Trp
            180                 185                 190

Lys Ser His Arg Ser Tyr Ser Cys Gln Val Thr His Glu Gly Ser Thr
        195                 200                 205

Val Glu Lys Thr Val Ala Pro Thr Glu Cys Ser
    210                 215
```

<210> SEQ ID NO 322
<211> LENGTH: 214
<212> TYPE: PRT
<213> ORGANISM: artificial sequence
<220> FEATURE:
<223> OTHER INFORMATION: G4_20 IgG1 antibody light chain sequence

<400> SEQUENCE: 322

```
Ala Ser Ser Tyr Glu Leu Thr His Pro Pro Ser Val Ser Val Ser Pro
1               5                   10                  15

Gly Gln Thr Ala Ser Ile Thr Cys Ser Gly Asp Lys Leu Gly Asp Lys
            20                  25                  30

Phe Val Ser Trp Tyr His Gln Lys Pro Gly Gln Ser Pro Val Leu Val
        35                  40                  45

Ile Tyr Gln Asp Ser Lys Arg Pro Ser Gly Ile Pro Glu Arg Phe Ser
    50                  55                  60

Gly Ser Asn Ser Gly Asn Thr Ala Thr Leu Thr Ile Ser Gly Thr Arg
65                  70                  75                  80

Ala Met Asp Glu Ala Asp Tyr Tyr Cys Gln Ala Trp Asp Ser Ser Thr
                85                  90                  95

Val Val Phe Gly Gly Gly Thr Lys Leu Thr Val Leu Gly Gln Pro Ala
                100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
```

```
      130                135                140

Ala Val Thr Val Ala Trp Lys Ala Asp Ser Ser Pro Val Lys Ala Gly
145                150                155                160

Val Glu Thr Thr Thr Pro Ser Lys Gln Ser Asn Asn Lys Tyr Ala Ala
               165                170                175

Ser Ser Tyr Leu Ser Leu Thr Pro Glu Gln Trp Lys Ser His Arg Ser
               180                185                190

Tyr Ser Cys Gln Val Thr His Glu Gly Ser Thr Val Glu Lys Thr Val
           195                200                205

Ala Pro Thr Glu Cys Ser
       210

<210> SEQ ID NO 323
<211> LENGTH: 216
<212> TYPE: PRT
<213> ORGANISM: artificial sequence
<220> FEATURE:
<223> OTHER INFORMATION: G4_22 IgG1 antibody light chain sequence

<400> SEQUENCE: 323

Ala Ser Asp Ile Gln Met Thr Gln Ser Pro Ser Ser Leu Ser Ala Ser
1                5                10                15

Val Gly Asp Arg Val Thr Ile Thr Cys Gln Ala Ser Gln Asp Ile Ser
               20                25                30

Asn Tyr Leu Asn Trp Tyr Gln Gln Lys Pro Gly Lys Ala Pro Lys Leu
           35                40                45

Leu Ile Tyr Ala Ala Ser Ser Leu Gln Ser Gly Val Pro Ser Arg Phe
       50                55                60

Ser Val Ser Gly Ser Gly Thr Asp Phe Thr Leu Thr Ile Ser Asn Leu
65                70                75                80

Gln Pro Glu Asp Phe Ala Thr Tyr Tyr Cys Gln Gln Ser Tyr Ser Ile
               85                90                95

Pro Trp Thr Phe Gly Gln Gly Thr Lys Val Glu Ile Lys Arg Thr Ala
           100                105                110

Ala Ala Pro Ser Val Phe Ile Phe Pro Pro Ser Asp Glu Gln Leu Lys
           115                120                125

Ser Gly Thr Ala Ser Val Val Cys Leu Leu Asn Asn Phe Tyr Pro Arg
       130                135                140

Glu Ala Lys Val Gln Trp Lys Val Asp Asn Ala Leu Gln Ser Gly Asn
145                150                155                160

Ser Gln Glu Ser Val Thr Glu Gln Asp Ser Lys Asp Ser Thr Tyr Ser
               165                170                175

Leu Ser Ser Thr Leu Thr Leu Ser Lys Ala Asp Tyr Glu Lys His Lys
           180                185                190

Leu Tyr Ala Cys Glu Val Thr His Gln Gly Leu Ser Ser Pro Val Thr
       195                200                205

Lys Ser Phe Asn Arg Gly Glu Cys
       210                215

<210> SEQ ID NO 324
<211> LENGTH: 216
<212> TYPE: PRT
<213> ORGANISM: artificial sequence
<220> FEATURE:
<223> OTHER INFORMATION: G4_23 IgG1 antibody light chain sequence

<400> SEQUENCE: 324
```

-continued

```
Ala Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Gly Ile Ser
            20                  25                  30

Asn Ser Leu Ala Trp Tyr Gln Gln Lys Pro Gly Lys Ala Pro Lys Leu
        35                  40                  45

Leu Leu Tyr Ala Ala Ser Arg Leu Glu Ser Gly Val Pro Ser Arg Phe
    50                  55                  60

Ser Gly Ser Gly Ser Gly Thr Asp Tyr Thr Leu Thr Ile Ser Ser Leu
65                  70                  75                  80

Gln Pro Glu Asp Phe Ala Thr Tyr Tyr Cys Gln Gln Tyr Tyr Ser Thr
                85                  90                  95

Pro Arg Thr Phe Gly Gly Gly Thr Lys Leu Glu Ile Lys Arg Thr Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 325
<211> LENGTH: 222
<212> TYPE: PRT
<213> ORGANISM: artificial sequence
<220> FEATURE:
<223> OTHER INFORMATION: G4_24 IgG1 antibody light chain sequence

<400> SEQUENCE: 325

Ala Ser Asp Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Ser Trp Ala Ser Thr Arg Glu Ser
    50                  55                  60

Gly Val Pro Asp Arg Phe Ser Gly Ser Gly Ser Gly Thr Asp Phe Thr
65                  70                  75                  80

Leu Thr Ile Asn Ser Leu Gln Ser Glu Asp Val Ala Ile Tyr Tyr Cys
                85                  90                  95

Gln Gln Tyr Tyr Ser Thr Pro Pro Thr Phe Gly Gln Gly Thr Lys Leu
            100                 105                 110

Glu Ile Lys Arg Thr Ala Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140
```

```
Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
                180                 185                 190

Asp Tyr Glu Lys His Lys Leu Tyr Ala Cys Glu Val Thr His Gln Gly
            195                 200                 205

Leu Ser Ser Pro Val Thr Lys Ser Phe Asn Arg Gly Glu Cys
        210                 215                 220

<210> SEQ ID NO 326
<211> LENGTH: 216
<212> TYPE: PRT
<213> ORGANISM: artificial sequence
<220> FEATURE:
<223> OTHER INFORMATION: G4_25 IgG1 antibody light chain sequence

<400> SEQUENCE: 326

Ala Ser Gln Ser Ala Leu Thr Gln Pro Arg Ser Val Ser Gly Ser Pro
1                   5                   10                  15

Gly Gln Ser Val Thr Ile Ser Cys Thr Gly Thr Ser Ser Asp Val Gly
                20                  25                  30

Gly Tyr Asn Tyr Val Ser Trp Tyr Gln Gln His Pro Gly Lys Ala Pro
            35                  40                  45

Lys Leu Met Ile Tyr Glu Val Ser Asn Arg Pro Ser Gly Val Ser Asn
        50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Gly
                85                  90                  95

Ser Gly Ser Val Phe Gly Thr Gly Thr Lys Leu Thr Val Leu Gly Gln
                100                 105                 110

Pro Ala Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 327
<211> LENGTH: 216
<212> TYPE: PRT
<213> ORGANISM: artificial sequence
<220> FEATURE:
<223> OTHER INFORMATION: G4_26 IgG1 antibody light chain sequence

<400> SEQUENCE: 327

Ala Ser Gln Ser Gly Leu Thr Gln Pro Ala Ser Val Ser Gly Ser Pro
1                   5                   10                  15
```

```
Gly Gln Ser Ile Thr Ile Ser Cys Thr Gly Thr Ser Ser Asp Val Gly
        20                  25                  30

Ser Tyr Asn Leu Val Ser Trp Tyr Gln Gln His Pro Gly Lys Ala Pro
        35                  40                  45

Lys Leu Met Ile Tyr Glu Val Ser Lys Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Ser Ser Phe Gly
                85                  90                  95

Ser Gly Ser Ile Phe Gly Thr Gly Thr Lys Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 328
<211> LENGTH: 216
<212> TYPE: PRT
<213> ORGANISM: artificial sequence
<220> FEATURE:
<223> OTHER INFORMATION: G4_27 IgG1 antibody light chain sequence

<400> SEQUENCE: 328

Ala Ser Ser Tyr Glu Leu Thr Gln Asp Pro Ala Val Ser Val Ala Leu
1               5                   10                  15

Gly Gln Thr Val Ser Ile Thr Cys Gln Gly Asp Ser Leu Arg Asn Phe
        20                  25                  30

Tyr Ala Asn Trp Tyr Gln Gln Lys Pro Gly Gln Ala Pro Val Leu Val
        35                  40                  45

Ile Tyr Gly Lys Asn Asn Arg Pro Ser Gly Ile Pro Asp Arg Phe Ser
    50                  55                  60

Gly Ser Ser Ser Gly Asn Thr Ala Ser Leu Thr Ile Thr Gly Ala Gln
65                  70                  75                  80

Ala Glu Asp Glu Ala Asp Tyr Tyr Cys Asn Ser Arg Asp Ser Ser Gly
                85                  90                  95

Asn His Leu Val Phe Gly Gly Gly Thr Gln Leu Thr Val Leu Gly Gln
            100                 105                 110

Pro Ala Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 329
<211> LENGTH: 214
<212> TYPE: PRT
<213> ORGANISM: artificial sequence
<220> FEATURE:
<223> OTHER INFORMATION: G4_28 IgG1 antibody light chain sequence

<400> SEQUENCE: 329

Ala Ser Ser Tyr Glu Leu Thr Gln Asp Pro Ala Val Ser Val Ala Leu
1               5                   10                  15

Gly Gln Thr Val Thr Ile Thr Cys Gln Gly Asp Ser Leu Arg Asn Tyr
            20                  25                  30

Tyr Ala Ser Trp Tyr Arg Gln Lys Pro Gly Gln Thr Pro Val Leu Val
        35                  40                  45

Val Tyr Gly Lys Asn Asn Arg Pro Ser Gly Ile Pro Asp Arg Phe Ser
    50                  55                  60

Val Ser Ala Ser Gly Asn Thr Ala Ser Leu Thr Ile Thr Gly Ala Gln
65                  70                  75                  80

Ala Glu Asp Glu Gly Asp Tyr Tyr Cys Asn Ser Arg Asp Ser Ser Gly
                85                  90                  95

Val Val Phe Gly Gly Gly Thr Lys Val Thr Val Leu Gly Gln Pro Ala
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 330
<211> LENGTH: 107
<212> TYPE: PRT
<213> ORGANISM: artificial sequence
<220> FEATURE:
<223> OTHER INFORMATION: Human Kappa light constant sequence (preferred
      allotype and without cloning artefacts)

<400> SEQUENCE: 330

Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
        20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
        100                 105

<210> SEQ ID NO 331
<211> LENGTH: 106
<212> TYPE: PRT
<213> ORGANISM: artificial sequence
<220> FEATURE:
<223> OTHER INFORMATION: Human Lambda light constant sequence (IGLC2
      without cloning artefacts)

<400> SEQUENCE: 331

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
        20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
        100                 105

<210> SEQ ID NO 332
<211> LENGTH: 330
<212> TYPE: PRT
<213> ORGANISM: artificial sequence
<220> FEATURE:
<223> OTHER INFORMATION: Human IgG1 constant domain

<400> SEQUENCE: 332

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys

-continued

```
             100                 105                 110
Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                 165                 170                 175

Glu Gln Tyr Asn Ser Thr Tyr Arg Val Val Ser Val Leu Thr Val Leu
             180                 185                 190

His Gln Asp Trp Leu Asn Gly Lys Glu Tyr Lys Cys Lys Val Ser Asn
         195                 200                 205

Lys Ala Leu Pro Ala Pro Ile Glu Lys Thr Ile Ser Lys Ala Lys Gly
     210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                 245                 250                 255

Pro Ser Asp Ile Ala Val Glu Trp Glu Ser Asn Gly Gln Pro Glu Asn
                 260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
         290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                 325                 330
```

```
<210> SEQ ID NO 333
<211> LENGTH: 330
<212> TYPE: PRT
<213> ORGANISM: artificial sequence
<220> FEATURE:
<223> OTHER INFORMATION: Human IgG1 constant domain with LAGA
      substitution

<400> SEQUENCE: 333
```

```
Ala Ser Thr Lys Gly Pro Ser Val Phe Pro Leu Ala Pro Ser Ser Lys
1                 5                  10                 15

Ser Thr Ser Gly Gly Thr Ala Ala Leu Gly Cys Leu Val Lys Asp Tyr
             20                  25                 30

Phe Pro Glu Pro Val Thr Val Ser Trp Asn Ser Gly Ala Leu Thr Ser
         35                  40                 45

Gly Val His Thr Phe Pro Ala Val Leu Gln Ser Ser Gly Leu Tyr Ser
     50                  55                 60

Leu Ser Ser Val Val Thr Val Pro Ser Ser Ser Leu Gly Thr Gln Thr
65                  70                 75                 80

Tyr Ile Cys Asn Val Asn His Lys Pro Ser Asn Thr Lys Val Asp Lys
                 85                  90                 95

Lys Val Glu Pro Lys Ser Cys Asp Lys Thr His Thr Cys Pro Pro Cys
             100                 105                 110

Pro Ala Pro Glu Leu Ala Gly Ala Pro Ser Val Phe Leu Phe Pro Pro
         115                 120                 125
```

```
Lys Pro Lys Asp Thr Leu Met Ile Ser Arg Thr Pro Glu Val Thr Cys
    130             135             140
```

```
Val Val Val Asp Val Ser His Glu Asp Pro Glu Val Lys Phe Asn Trp
145             150             155             160
```

```
Tyr Val Asp Gly Val Glu Val His Asn Ala Lys Thr Lys Pro Arg Glu
                165             170             175
```

```
Glu Gln Tyr Asn Ser Thr Tyr Arg Val Val Ser Val Leu Thr Val Leu
            180             185             190
```

```
His Gln Asp Trp Leu Asn Gly Lys Glu Tyr Lys Cys Lys Val Ser Asn
            195             200             205
```

```
Lys Ala Leu Pro Ala Pro Ile Glu Lys Thr Ile Ser Lys Ala Lys Gly
    210             215             220
```

```
Gln Pro Arg Glu Pro Gln Val Tyr Thr Leu Pro Pro Ser Arg Asp Glu
225             230             235             240
```

```
Leu Thr Lys Asn Gln Val Ser Leu Thr Cys Leu Val Lys Gly Phe Tyr
            245             250             255
```

```
Pro Ser Asp Ile Ala Val Glu Trp Glu Ser Asn Gly Gln Pro Glu Asn
            260             265             270
```

```
Asn Tyr Lys Thr Thr Pro Pro Val Leu Asp Ser Asp Gly Ser Phe Phe
            275             280             285
```

```
Leu Tyr Ser Lys Leu Thr Val Asp Lys Ser Arg Trp Gln Gln Gly Asn
    290             295             300
```

```
Val Phe Ser Cys Ser Val Met His Glu Ala Leu His Asn His Tyr Thr
305             310             315             320
```

```
Gln Lys Ser Leu Ser Leu Ser Pro Gly Lys
            325             330
```

```
<210> SEQ ID NO 334
<211> LENGTH: 99
<212> TYPE: PRT
<213> ORGANISM: Homo sapiens
<220> FEATURE:
<221> NAME/KEY: MISC_FEATURE
<222> LOCATION: (1)..(99)
<223> OTHER INFORMATION: Human TRGV4

<400> SEQUENCE: 334
```

```
Ser Ser Asn Leu Glu Gly Arg Thr Lys Ser Val Ile Arg Gln Thr Gly
1               5               10              15
```

```
Ser Ser Ala Glu Ile Thr Cys Asp Leu Ala Glu Gly Ser Thr Gly Tyr
            20              25              30
```

```
Ile His Trp Tyr Leu His Gln Glu Gly Lys Ala Pro Gln Arg Leu Leu
            35              40              45
```

```
Tyr Tyr Asp Ser Tyr Thr Ser Ser Val Val Leu Glu Ser Gly Ile Ser
    50              55              60
```

```
Pro Gly Lys Tyr Asp Thr Tyr Gly Ser Thr Arg Lys Asn Leu Arg Met
65              70              75              80
```

```
Ile Leu Arg Asn Leu Ile Glu Asn Asp Ser Gly Val Tyr Tyr Cys Ala
            85              90              95
```

```
Thr Trp Asp
```

```
<210> SEQ ID NO 335
<211> LENGTH: 99
<212> TYPE: PRT
<213> ORGANISM: Homo sapiens
<220> FEATURE:
<221> NAME/KEY: MISC_FEATURE
<222> LOCATION: (1)..(99)
```

<223> OTHER INFORMATION: Human TRGV2

<400> SEQUENCE: 335

```
Ser Ser Asn Leu Glu Gly Arg Thr Lys Ser Val Ile Arg Gln Thr Gly
1               5                   10                  15

Ser Ser Ala Glu Ile Thr Cys Asp Leu Ala Glu Gly Ser Asn Gly Tyr
            20                  25                  30

Ile His Trp Tyr Leu His Gln Glu Gly Lys Ala Pro Gln Arg Leu Gln
        35                  40                  45

Tyr Tyr Asp Ser Tyr Asn Ser Lys Val Val Leu Glu Ser Gly Val Ser
    50                  55                  60

Pro Gly Lys Tyr Tyr Thr Tyr Ala Ser Thr Arg Asn Asn Leu Arg Leu
65                  70                  75                  80

Ile Leu Arg Asn Leu Ile Glu Asn Asp Ser Gly Val Tyr Tyr Cys Ala
                85                  90                  95

Thr Trp Asp
```

<210> SEQ ID NO 336
<211> LENGTH: 99
<212> TYPE: PRT
<213> ORGANISM: Homo sapiens
<220> FEATURE:
<221> NAME/KEY: MISC_FEATURE
<222> LOCATION: (1)..(99)
<223> OTHER INFORMATION: Human TRGV8

<400> SEQUENCE: 336

```
Ser Ser Asn Leu Glu Gly Arg Thr Lys Ser Val Thr Arg Pro Thr Gly
1               5                   10                  15

Ser Ser Ala Val Ile Thr Cys Asp Leu Pro Val Glu Asn Ala Val Tyr
            20                  25                  30

Thr His Trp Tyr Leu His Gln Glu Gly Lys Ala Pro Gln Arg Leu Leu
        35                  40                  45

Tyr Tyr Asp Ser Tyr Asn Ser Arg Val Val Leu Glu Ser Gly Ile Ser
    50                  55                  60

Arg Glu Lys Tyr His Thr Tyr Ala Ser Thr Gly Lys Ser Leu Lys Phe
65                  70                  75                  80

Ile Leu Glu Asn Leu Ile Glu Arg Asp Ser Gly Val Tyr Tyr Cys Ala
                85                  90                  95

Thr Trp Asp
```

<210> SEQ ID NO 337
<211> LENGTH: 95
<212> TYPE: PRT
<213> ORGANISM: Homo sapiens
<220> FEATURE:
<221> NAME/KEY: MISC_FEATURE
<222> LOCATION: (1)..(95)
<223> OTHER INFORMATION: Human TRDV1

<400> SEQUENCE: 337

```
Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
        35                  40                  45

Ile Arg Gln Gly Ser Asp Glu Gln Asn Ala Lys Ser Gly Arg Tyr Ser
    50                  55                  60
```

-continued

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Glu
                85                  90                  95

<210> SEQ ID NO 338
<211> LENGTH: 96
<212> TYPE: PRT
<213> ORGANISM: Homo sapiens
<220> FEATURE:
<221> NAME/KEY: MISC_FEATURE
<222> LOCATION: (1)..(96)
<223> OTHER INFORMATION: Human TRDV2

<400> SEQUENCE: 338

Ala Ile Glu Leu Val Pro Glu His Gln Thr Val Pro Val Ser Ile Gly
1               5                   10                  15

Val Pro Ala Thr Leu Arg Cys Ser Met Lys Gly Glu Ala Ile Gly Asn
                20                  25                  30

Tyr Tyr Ile Asn Trp Tyr Arg Lys Thr Gln Gly Asn Thr Ile Thr Phe
            35                  40                  45

Ile Tyr Arg Glu Lys Asp Ile Tyr Gly Pro Gly Phe Lys Asp Asn Phe
        50                  55                  60

Gln Gly Asp Ile Asp Ile Ala Lys Asn Leu Ala Val Leu Lys Ile Leu
65                  70                  75                  80

Ala Pro Ser Glu Arg Asp Glu Gly Ser Tyr Tyr Cys Ala Cys Asp Thr
                85                  90                  95

<210> SEQ ID NO 339
<211> LENGTH: 90
<212> TYPE: PRT
<213> ORGANISM: Artificial Sequence
<220> FEATURE:
<223> OTHER INFORMATION: synthetic

<400> SEQUENCE: 339

Val Ile Arg Gln Thr Gly Ser Ser Ala Glu Ile Thr Cys Asp Leu Ala
1               5                   10                  15

Glu Gly Ser Thr Gly Tyr Ile His Trp Tyr Leu His Gln Glu Gly Lys
                20                  25                  30

Ala Pro Gln Arg Leu Leu Tyr Tyr Asp Ser Tyr Thr Ser Ser Val Val
            35                  40                  45

Leu Glu Ser Gly Ile Ser Pro Gly Lys Tyr Asp Thr Tyr Gly Ser Thr
        50                  55                  60

Arg Lys Asn Leu Arg Met Ile Leu Arg Asn Leu Ile Glu Asn Asp Ser
65                  70                  75                  80

Gly Val Tyr Tyr Cys Ala Thr Trp Asp Gly
                85                  90

<210> SEQ ID NO 340
<211> LENGTH: 90
<212> TYPE: PRT
<213> ORGANISM: Artificial Sequence
<220> FEATURE:
<223> OTHER INFORMATION: synthetic

<400> SEQUENCE: 340

Val Ile Arg Gln Thr Gly Ser Ser Ala Glu Ile Thr Cys Asp Leu Ala
1               5                   10                  15

Glu Gly Ser Asn Gly Tyr Ile His Trp Tyr Leu His Gln Glu Gly Lys

-continued

```
              20              25              30

Ala Pro Gln Arg Leu Leu Tyr Tyr Asp Ser Tyr Thr Ser Ser Val Val
       35              40              45

Leu Glu Ser Gly Ile Ser Pro Gly Lys Tyr Asp Thr Tyr Gly Ser Thr
   50              55              60

Arg Lys Asn Leu Arg Met Ile Leu Arg Asn Leu Ile Glu Asn Asp Ser
65              70              75              80

Gly Val Tyr Tyr Cys Ala Thr Trp Asp Gly
              85              90

<210> SEQ ID NO 341
<211> LENGTH: 90
<212> TYPE: PRT
<213> ORGANISM: Artificial Sequence
<220> FEATURE:
<223> OTHER INFORMATION: synthetic

<400> SEQUENCE: 341

Val Ile Arg Gln Thr Gly Ser Ser Ala Glu Ile Thr Cys Asp Leu Ala
1               5              10              15

Glu Gly Ser Thr Gly Tyr Ile His Trp Tyr Leu His Gln Glu Gly Lys
              20              25              30

Ala Pro Gln Arg Leu Leu Tyr Tyr Asp Ser Tyr Asn Ser Lys Val Val
       35              40              45

Leu Glu Ser Gly Ile Ser Pro Gly Lys Tyr Asp Thr Tyr Gly Ser Thr
   50              55              60

Arg Lys Asn Leu Arg Met Ile Leu Arg Asn Leu Ile Glu Asn Asp Ser
65              70              75              80

Gly Val Tyr Tyr Cys Ala Thr Trp Asp Gly
              85              90

<210> SEQ ID NO 342
<211> LENGTH: 90
<212> TYPE: PRT
<213> ORGANISM: Artificial Sequence
<220> FEATURE:
<223> OTHER INFORMATION: artificial

<400> SEQUENCE: 342

Val Ile Arg Gln Thr Gly Ser Ser Ala Glu Ile Thr Cys Asp Leu Ala
1               5              10              15

Glu Gly Ser Asn Gly Tyr Ile His Trp Tyr Leu His Gln Glu Gly Lys
              20              25              30

Ala Pro Gln Arg Leu Leu Tyr Tyr Asp Ser Tyr Asn Ser Lys Val Val
       35              40              45

Leu Glu Ser Gly Ile Ser Pro Gly Lys Tyr Asp Thr Tyr Gly Ser Thr
   50              55              60

Arg Lys Asn Leu Arg Met Ile Leu Arg Asn Leu Ile Glu Asn Asp Ser
65              70              75              80

Gly Val Tyr Tyr Cys Ala Thr Trp Asp Gly
              85              90

<210> SEQ ID NO 343
<211> LENGTH: 90
<212> TYPE: PRT
<213> ORGANISM: Artificial Sequence
<220> FEATURE:
<223> OTHER INFORMATION: synthetic

<400> SEQUENCE: 343
```

-continued

```
Val Ile Arg Gln Thr Gly Ser Ser Ala Glu Ile Thr Cys Asp Leu Ala
1               5                   10                  15

Glu Gly Ser Thr Gly Tyr Ile His Trp Tyr Leu His Gln Glu Gly Lys
                20                  25                  30

Ala Pro Gln Arg Leu Leu Tyr Tyr Asp Ser Tyr Thr Ser Ser Val Val
            35                  40                  45

Leu Glu Ser Gly Ile Ser Pro Gly Lys Tyr Tyr Thr Tyr Ala Ser Thr
        50                  55                  60

Arg Asn Asn Leu Arg Leu Ile Leu Arg Asn Leu Ile Glu Asn Asp Ser
65                  70                  75                  80

Gly Val Tyr Tyr Cys Ala Thr Trp Asp Gly
                85                  90
```

<210> SEQ ID NO 344
<211> LENGTH: 90
<212> TYPE: PRT
<213> ORGANISM: Artificial Sequence
<220> FEATURE:
<223> OTHER INFORMATION: synthetic

<400> SEQUENCE: 344

```
Val Ile Arg Gln Thr Gly Ser Ser Ala Glu Ile Thr Cys Asp Leu Ala
1               5                   10                  15

Glu Gly Ser Thr Gly Tyr Ile His Trp Tyr Leu His Gln Glu Gly Lys
                20                  25                  30

Ala Pro Gln Arg Leu Leu Tyr Tyr Asp Ser Tyr Thr Ser Ser Val Val
            35                  40                  45

Leu Glu Ser Gly Ile Ser Pro Gly Lys Tyr Tyr Thr Tyr Ala Ser Thr
        50                  55                  60

Arg Lys Asn Leu Arg Met Ile Leu Arg Asn Leu Ile Glu Asn Asp Ser
65                  70                  75                  80

Gly Val Tyr Tyr Cys Ala Thr Trp Asp Gly
                85                  90
```

<210> SEQ ID NO 345
<211> LENGTH: 90
<212> TYPE: PRT
<213> ORGANISM: Artificial Sequence
<220> FEATURE:
<223> OTHER INFORMATION: synthetic

<400> SEQUENCE: 345

```
Val Ile Arg Gln Thr Gly Ser Ser Ala Glu Ile Thr Cys Asp Leu Ala
1               5                   10                  15

Glu Gly Ser Thr Gly Tyr Ile His Trp Tyr Leu His Gln Glu Gly Lys
                20                  25                  30

Ala Pro Gln Arg Leu Leu Tyr Tyr Asp Ser Tyr Thr Ser Ser Val Val
            35                  40                  45

Leu Glu Ser Gly Ile Ser Pro Gly Lys Tyr Asp Thr Tyr Gly Ser Thr
        50                  55                  60

Arg Asn Asn Leu Arg Leu Ile Leu Arg Asn Leu Ile Glu Asn Asp Ser
65                  70                  75                  80

Gly Val Tyr Tyr Cys Ala Thr Trp Asp Gly
                85                  90
```

<210> SEQ ID NO 346
<211> LENGTH: 90
<212> TYPE: PRT

<213> ORGANISM: Artificial Sequence
<220> FEATURE:
<223> OTHER INFORMATION: synthetic

<400> SEQUENCE: 346

Val Ile Arg Gln Thr Gly Ser Ser Ala Glu Ile Thr Cys Asp Leu Ala
1               5                   10                  15

Glu Gly Ser Asn Gly Tyr Ile His Trp Tyr Leu His Gln Glu Gly Lys
                20                  25                  30

Ala Pro Gln Arg Leu Gln Tyr Tyr Asp Ser Tyr Asn Ser Lys Val Val
            35                  40                  45

Leu Glu Ser Gly Val Ser Pro Gly Lys Tyr Tyr Thr Tyr Ala Ser Thr
        50                  55                  60

Arg Asn Asn Leu Arg Leu Ile Leu Arg Asn Leu Ile Glu Asn Asp Ser
65                  70                  75                  80

Gly Val Tyr Tyr Cys Ala Thr Trp Asp Gly
                85                  90

<210> SEQ ID NO 347
<211> LENGTH: 90
<212> TYPE: PRT
<213> ORGANISM: Artificial Sequence
<220> FEATURE:
<223> OTHER INFORMATION: synthetic

<400> SEQUENCE: 347

Val Ile Arg Gln Thr Gly Ser Ser Ala Glu Ile Thr Cys Asp Leu Ala
1               5                   10                  15

Glu Gly Ser Asn Gly Tyr Ile His Trp Tyr Leu His Gln Glu Gly Lys
                20                  25                  30

Ala Pro Gln Arg Leu Gln Tyr Tyr Asp Ser Tyr Asn Ser Lys Val Val
            35                  40                  45

Leu Glu Ser Gly Val Ser Pro Gly Lys Tyr Asp Thr Tyr Gly Ser Thr
        50                  55                  60

Arg Asn Asn Leu Arg Leu Ile Leu Arg Asn Leu Ile Glu Asn Asp Ser
65                  70                  75                  80

Gly Val Tyr Tyr Cys Ala Thr Trp Asp Gly
                85                  90

<210> SEQ ID NO 348
<211> LENGTH: 90
<212> TYPE: PRT
<213> ORGANISM: Artificial Sequence
<220> FEATURE:
<223> OTHER INFORMATION: synthetic

<400> SEQUENCE: 348

Val Thr Arg Gln Thr Gly Ser Ser Ala Glu Ile Thr Cys Asp Leu Thr
1               5                   10                  15

Val Thr Asn Thr Phe Tyr Ile His Trp Tyr Leu His Gln Glu Gly Lys
                20                  25                  30

Ala Pro Gln Arg Leu Leu Tyr Tyr Asp Val Ser Thr Ala Arg Asp Val
            35                  40                  45

Leu Glu Ser Gly Leu Ser Pro Gly Lys Tyr Tyr Thr His Thr Pro Arg
        50                  55                  60

Arg Trp Ser Trp Ile Leu Arg Leu Gln Asn Leu Ile Glu Asn Asp Ser
65                  70                  75                  80

Gly Val Tyr Tyr Cys Ala Thr Trp Asp Gly
                85                  90

-continued

```
<210> SEQ ID NO 349
<211> LENGTH: 90
<212> TYPE: PRT
<213> ORGANISM: Artificial Sequence
<220> FEATURE:
<223> OTHER INFORMATION: synthetic

<400> SEQUENCE: 349

Val Thr Arg Gln Thr Gly Ser Ser Ala Glu Ile Thr Cys Asp Leu Thr
1               5                   10                  15

Val Thr Asn Thr Phe Tyr Ile His Trp Tyr Leu His Gln Glu Gly Lys
            20                  25                  30

Ala Pro Gln Arg Leu Leu Tyr Tyr Asp Val Ser Thr Ala Arg Asp Val
        35                  40                  45

Leu Glu Ser Gly Leu Ser Pro Gly Lys Tyr Asp Thr Tyr Gly Ser Thr
    50                  55                  60

Arg Lys Asn Leu Arg Met Ile Leu Arg Asn Leu Ile Glu Asn Asp Ser
65                  70                  75                  80

Gly Val Tyr Tyr Cys Ala Thr Trp Asp Gly
            85                  90

<210> SEQ ID NO 350
<211> LENGTH: 90
<212> TYPE: PRT
<213> ORGANISM: Artificial Sequence
<220> FEATURE:
<223> OTHER INFORMATION: synthetic

<400> SEQUENCE: 350

Val Thr Arg Gln Thr Gly Ser Ser Ala Glu Ile Thr Cys Asp Leu Thr
1               5                   10                  15

Val Thr Asn Thr Phe Tyr Ile His Trp Tyr Leu His Gln Glu Gly Lys
            20                  25                  30

Ala Pro Gln Arg Leu Leu Tyr Tyr Asp Ser Tyr Thr Ser Ser Val Val
        35                  40                  45

Leu Glu Ser Gly Ile Ser Pro Gly Lys Tyr Asp Thr Tyr Gly Ser Thr
    50                  55                  60

Arg Lys Asn Leu Arg Met Ile Leu Arg Asn Leu Ile Glu Asn Asp Ser
65                  70                  75                  80

Gly Val Tyr Tyr Cys Ala Thr Trp Asp Gly
            85                  90
```

ANTIBODIES

RELATED APPLICATIONS

This application is a U.S. National Phase filing under 35 U.S.C. § 371 of International Patent Application No. PCT/GB2021/050459, filed Feb. 24, 2021, which claims priority from GB Application No. 2002581.3, filed Feb. 24, 2020, the entire contents of which are incorporated herein by reference.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 15, 2025, is named T083370026US00-SUBEQ-ARM and is 493,972 bytes in size.

FIELD OF THE INVENTION

The invention relates to antibodies and fragments thereof directed to the T cell receptor of gamma delta T cells.

BACKGROUND OF THE INVENTION

The growing interest in T cell immunotherapy for cancer has focused on the evident capacity of subsets of CD8+ and CD4+ alpha beta (αβ) T cells to recognize cancer cells and to mediate host-protective functional potentials, particularly when de-repressed by clinically mediated antagonism of inhibitory pathways exerted by PD-1, CTLA-4, and other receptors. However, αβ T cells are MHC-restricted which can lead to graft versus host disease.

Gamma delta T cells (γδ T cells) represent a subset of T cells that express on their surface a distinct, defining γδ T-cell receptor (TCR). This TCR is made up of one gamma (γ) and one delta (δ) chain, each of which undergoes chain rearrangement but have a limited number of V genes as compared to αβ T cells. The main TRVG gene segments encoding Vγ are TRGV2, TRGV3, TRGV4, TRGV5, TRGV8, TRGV9 and non-functional genes TRGV10, TRGV11, TRGVA and TRGVB. The most frequent TRDV gene segments encode Vδ1, Vδ2, and Vδ3, plus several V segments that have both Vδ and Vα designation (Adams et al., 296:30-40 (2015) *Cell Immunol.*). Human γδ T cells can be broadly classified based on their TCR chains, as certain γ and δ types are found on cells more prevalently, though not exclusively, in one or more tissue types. For example, most blood-resident γδ T cells express a Vδ2 TCR, commonly Vγ9Vδ2, whereas this is less common among tissue-resident γδ T cells such as those in the skin, which more frequently use the Vδ1 TCR paired with gamma chains, for example often paired with Vγ4 in the gut.

However to date, due to high homology between Vγ4 TCR and other TRGV family members such as the Vγ2 TCR, modalities capable of targeting only the Vγ4 TCR have not been possible. Therefore there is an unmet need for antibodies specific for Vγ4, including such specific antibodies that specifically bind or modulate the Vγ4 TCR.

SUMMARY OF THE INVENTION

According to a first aspect of the invention, there is provided an isolated antibody or fragment thereof, which specifically binds to a gamma variable 4 (Vγ4) chain of a γδ

T cell receptor (TCR) and not to a gamma variable 2 (Vγ2) chain of a γδ TCR. It should be understood that this is with reference to a Vγ4 chain and a Vγ2 from the same species. Preferably, according to all aspects and embodiments described herein, the species is *Homo sapiens* (human) and therefore the invention provides an isolated antibody or fragment thereof, which specifically binds to a human gamma variable 4 (Vγ4) chain of a γδ T cell receptor (TCR) and not to a human gamma variable 2 (Vγ2) chain of a γδ TCR. For instance, the human Vγ4 chain may have a sequence according to amino acids 1-99 of SEQ ID NO. 1 and/or the human Vγ2 chain may have a sequence according to SEQ ID NO. 335. In other species, the isolated antibody or fragment thereof, specifically binds to the species-specific ortholog of the human gamma variable 4 (Vγ4) chain of a γδ T cell receptor (TCR) and not to the species-specific ortholog of the human gamma variable 2 (Vγ2) chain of a γδ TCR. Thus, the invention provides an isolated antibody or fragment thereof, which specifically binds to a human gamma variable 4 (Vγ4) chain of a γδ T cell receptor (TCR) having a sequence corresponding to amino acids 1-99 of SEQ ID NO. 1 or non-human ortholog thereof and not to a human gamma variable 2 (Vγ2) chain of a γδ TCR having a sequence corresponding to SEQ ID NO. 335 or non-human ortholog thereof. Ortholog in this context may mean a gamma chain sequence with the highest sequence similarity to the reference sequence, or preferably one which possesses the same function (e.g. interaction with orthologous cognate ligands in vivo). For instance, in mouse, the protein designated under the Heilig & Tonegave nomenclature as Vγ7 is functionally most closely related to human Vγ4 (Barros et al. (2016) Cell, 167:203-218.e17).

This is a significant advancement to the field. For instance, in humans, the Vγ4 chain and Vγ2 chain are highly homologous (sequence identity of 91%), differing in respect of only 9 amino acids. Three of these nine changes map across CDR1 and CDR2, whilst four of these nine changes map to a sub-region of framework region 3 (FR3)—amino acids 67-82 of SEQ ID NO: 1. Due to the very high sequence similarity between the Vγ4 chain and Vγ2 chain, it was previously thought that it would not be possible to develop an antibody or fragment thereof able to specifically distinguish between the human Vγ4 chain and Vγ2 chain of a γδ TCR. Surprisingly and contrary to the prevailing view in the art, the present inventors have been able to develop such antibodies using the methods described in more detail herein. Thus, the invention provides antibodies and fragments thereof which are able to specifically modulate Vγ4-containing γδ TCRs.

The antibody or fragment thereof of the invention may bind to an epitope of the human Vγ4 chain of the γδ TCR comprising one or more amino acid residues within amino acid region 67-82 of SEQ ID NO: 1.

According to a further aspect of the invention, there is provided an isolated anti-Vγ4 antibody or fragment thereof, which comprises one or more of:

- a CDR3 comprising a sequence having at least 80% sequence identity with any one of SEQ ID NOs: 2-47, preferably with SEQ ID NO: 10 and/or 33;
- a CDR2 comprising a sequence having at least 80% sequence identity with any one of SEQ ID NOs: 48-70 and SEQUENCES: A1-A23 (of FIG. 1), preferably with SEQ ID NO: 56 and/or A9; and/or
- a CDR1 comprising a sequence having at least 80% sequence identity with any one of SEQ ID NOs: 71-116, preferably with SEQ ID NO: 79 and/or 102.

In some aspects, the isolated anti-Vγ4 antibody or fragment thereof may comprise one or more of:

a heavy chain CDR3 (HCDR3) comprising a sequence having at least 80% sequence identity with any one of SEQ ID NOs: 2-24, preferably with SEQ ID NO: 10;

a heavy chain CDR2 (HCDR2) comprising a sequence having at least 80% sequence identity with any one of SEQ ID NOs: 48-70, preferably with SEQ ID NO: 56; and/or a heavy chain CDR1 (HCDR1) comprising a sequence having at least 80% sequence identity with any one of SEQ ID NOs: 71-93, preferably with SEQ ID NO: 79.

Alternatively, or in addition to, the isolated anti-Vγ4 antibody or fragment thereof may comprise one or more of:

a light chain CDR3 (LCDR3) comprising a sequence having at least 80% sequence identity with any one of SEQ ID NOs: 25-47, preferably with SEQ ID NO: 33;

a light chain CDR2 (LCDR2) comprising a sequence having at least 80% sequence identity with any one of SEQUENCES: A1-A23 (of FIG. 1), preferably with SEQ ID NO: A9; and/or a light chain CDR1 (LCDR1) comprising a sequence having at least 80% sequence identity with any one of SEQ ID NOs: 94-116, preferably with SEQ ID NO: 102.

According to a further aspect of the invention, there is provided an isolated anti-Vγ4 antibody or fragment thereof, which comprises an amino acid sequence having at least 80% sequence identity with any one of SEQ ID NOs: 117-162. In some aspects, the isolated anti-Vγ4 antibody or fragment thereof may comprise a heavy chain variable (VH) amino acid sequence having at least 80% sequence identity with any one of SEQ ID NOs: 117-139, preferably with SEQ ID NO: 125. Alternatively, or in addition to, the isolated anti-Vγ4 antibody or fragment thereof may comprise a light chain variable (VL) amino acid sequence having at least 80% sequence identity with any one of SEQ ID NOs: 140-162, preferably with SEQ ID NO: 148.

The invention further provides an isolated anti-Vγ4 antibody or fragment thereof comprising one or more of:

(a) a VH comprising a HCDR1 having SEQ ID NO: 79, a HCDR2 having SEQ ID NO: 56 and a HCDR3 having SEQ ID NO: 10, optionally wherein the VH comprises SEQ ID NO: 125; and a VL comprising a LCDR1 having SEQ ID NO: 102, a LCDR2 having SEQUENCE A9 (of FIG. 1) and a LCDR3 having SEQ ID NO: 33, optionally wherein the VL comprises SEQ ID NO: 148;

(b) a VH comprising a HCDR1 having SEQ ID NO: 86, a HCDR2 having SEQ ID NO: 63 and a HCDR3 having SEQ ID NO: 17, optionally wherein the VH comprises SEQ ID NO: 132; and a VL comprising a LCDR1 having SEQ ID NO: 109, a LCDR2 having SEQUENCE A16 (of FIG. 1) and a LCDR3 having SEQ ID NO: 40, optionally wherein the VL comprises SEQ ID NO: 155;

(c) a VH comprising a HCDR1 having SEQ ID NO: 73, a HCDR2 having SEQ ID NO: 50 and a HCDR3 having SEQ ID NO: 4, optionally wherein the VH comprises SEQ ID NO: 119; and a VL comprising a LCDR1 having SEQ ID NO: 96, a LCDR2 having SEQUENCE A3 (of FIG. 1) and a LCDR3 having SEQ ID NO: 27, optionally wherein the VL comprises SEQ ID NO: 142;

(d) a VH comprising a HCDR1 having SEQ ID NO: 83, a HCDR2 having SEQ ID NO: 60 and a HCDR3 having SEQ ID NO: 14, optionally wherein the VH comprises SEQ ID NO: 129; and a VL comprising a LCDR1 having SEQ ID NO: 106, a LCDR2 having SEQUENCE A13 (of FIG. 1) and a LCDR3 having SEQ ID NO: 37, optionally wherein the VL comprises SEQ ID NO: 152;

(e) a VH comprising a HCDR1 having SEQ ID NO: 84, a HCDR2 having SEQ ID NO: 61 and a HCDR3 having SEQ ID NO: 15, optionally wherein the VH comprises SEQ ID NO: 130; and a VL comprising a LCDR1 having SEQ ID NO: 107, a LCDR2 having SEQUENCE A14 (of FIG. 1) and a LCDR3 having SEQ ID NO: 38, optionally wherein the VL comprises SEQ ID NO: 153;

(f) a VH comprising a HCDR1 having SEQ ID NO: 88, a HCDR2 having SEQ ID NO: 65 and a HCDR3 having SEQ ID NO: 19, optionally wherein the VH comprises SEQ ID NO: 134; and a VL comprising a LCDR1 having SEQ ID NO: 111, a LCDR2 having SEQUENCE A18 (of FIG. 1) and a LCDR3 having SEQ ID NO: 42, optionally wherein the VL comprises SEQ ID NO: 157;

(g) a VH comprising a HCDR1 having SEQ ID NO: 92, a HCDR2 having SEQ ID NO: 69 and a HCDR3 having SEQ ID NO: 23, optionally wherein the VH comprises SEQ ID NO: 138; and a VL comprising a LCDR1 having SEQ ID NO: 115, a LCDR2 having SEQUENCE A22 (of FIG. 1) and a LCDR3 having SEQ ID NO: 46, optionally wherein the VL comprises SEQ ID NO: 161;

(h) a VH comprising a HCDR1 having SEQ ID NO: 71, a HCDR2 having SEQ ID NO: 48 and a HCDR3 having SEQ ID NO: 2, optionally wherein the VH comprises SEQ ID NO: 117; and a VL comprising a LCDR1 having SEQ ID NO: 94, a LCDR2 having SEQUENCE A1 (of FIG. 1) and a LCDR3 having SEQ ID NO: 25, optionally wherein the VL comprises SEQ ID NO: 140;

(i) a VH comprising a HCDR1 having SEQ ID NO: 72, a HCDR2 having SEQ ID NO: 49 and a HCDR3 having SEQ ID NO: 3, optionally wherein the VH comprises SEQ ID NO: 118; and a VL comprising a LCDR1 having SEQ ID NO: 95, a LCDR2 having SEQUENCE A2 (of FIG. 1) and a LCDR3 having SEQ ID NO: 26, optionally wherein the VL comprises SEQ ID NO: 141;

(j) a VH comprising a HCDR1 having SEQ ID NO: 74, a HCDR2 having SEQ ID NO: 51 and a HCDR3 having SEQ ID NO: 5, optionally wherein the VH comprises SEQ ID NO: 120; and a VL comprising a LCDR1 having SEQ ID NO: 97, a LCDR2 having SEQUENCE A4 (of FIG. 1) and a LCDR3 having SEQ ID NO: 28, optionally wherein the VL comprises SEQ ID NO: 143;

(k) a VH comprising a HCDR1 having SEQ ID NO: 75, a HCDR2 having SEQ ID NO: 52 and a HCDR3 having SEQ ID NO: 6, optionally wherein the VH comprises SEQ ID NO: 121; and a VL comprising a LCDR1 having SEQ ID NO: 98, a LCDR2 having SEQUENCE A5 (of FIG. 1) and a LCDR3 having SEQ ID NO: 29, optionally wherein the VL comprises SEQ ID NO: 144;

(l) a VH comprising a HCDR1 having SEQ ID NO: 76, a HCDR2 having SEQ ID NO: 53 and a HCDR3 having SEQ ID NO: 7, optionally wherein the VH comprises SEQ ID NO: 122; and a VL comprising a LCDR1 having SEQ ID NO: 99, a LCDR2 having SEQUENCE A6 (of FIG. 1) and a LCDR3 having SEQ ID NO: 30, optionally wherein the VL comprises SEQ ID NO: 145;

(m) a VH comprising a HCDR1 having SEQ ID NO: 77, a HCDR2 having SEQ ID NO: 54 and a HCDR3 having SEQ ID NO: 8, optionally wherein the VH comprises SEQ ID NO: 123; and a VL comprising a LCDR1 having SEQ ID NO: 100, a LCDR2 having SEQUENCE A7 (of FIG. 1) and a LCDR3 having SEQ ID NO: 31, optionally wherein the VL comprises SEQ ID NO: 146;

(n) a VH comprising a HCDR1 having SEQ ID NO: 78, a HCDR2 having SEQ ID NO: 55 and a HCDR3 having SEQ ID NO: 9, optionally wherein the VH comprises SEQ ID NO: 124; and a VL comprising a LCDR1 having SEQ ID NO: 101, a LCDR2 having SEQUENCE A8 (of FIG. 1) and a LCDR3 having SEQ ID NO: 32, optionally wherein the VL comprises SEQ ID NO: 147;

(o) a VH comprising a HCDR1 having SEQ ID NO: 80, a HCDR2 having SEQ ID NO: 57 and a HCDR3 having SEQ ID NO: 11, optionally wherein the VH comprises SEQ ID NO: 126; and a VL comprising a LCDR1 having SEQ ID NO: 103, a LCDR2 having SEQUENCE A10 (of FIG. 1) and a LCDR3 having SEQ ID NO: 34, optionally wherein the VL comprises SEQ ID NO: 149;

(p) a VH comprising a HCDR1 having SEQ ID NO: 81, a HCDR2 having SEQ ID NO: 58 and a HCDR3 having SEQ ID NO: 12, optionally wherein the VH comprises SEQ ID NO: 127; and a VL comprising a LCDR1 having SEQ ID NO: 104, a LCDR2 having SEQUENCE A11 (of FIG. 1) and a LCDR3 having SEQ ID NO: 35, optionally wherein the VL comprises SEQ ID NO: 150;

(q) a VH comprising a HCDR1 having SEQ ID NO: 82, a HCDR2 having SEQ ID NO: 59 and a HCDR3 having SEQ ID NO: 13, optionally wherein the VH comprises SEQ ID NO: 128; and a VL comprising a LCDR1 having SEQ ID NO: 105, a LCDR2 having SEQUENCE A12 (of FIG. 1) and a LCDR3 having SEQ ID NO: 36, optionally wherein the VL comprises SEQ ID NO: 151;

(r) a VH comprising a HCDR1 having SEQ ID NO: 85, a HCDR2 having SEQ ID NO: 62 and a HCDR3 having SEQ ID NO: 16, optionally wherein the VH comprises SEQ ID NO: 131; and a VL comprising a LCDR1 having SEQ ID NO: 108, a LCDR2 having SEQUENCE A15 (of FIG. 1) and a LCDR3 having SEQ ID NO: 39, optionally wherein the VL comprises SEQ ID NO: 154;

(s) a VH comprising a HCDR1 having SEQ ID NO: 87, a HCDR2 having SEQ ID NO: 64 and a HCDR3 having SEQ ID NO: 18, optionally wherein the VH comprises SEQ ID NO: 133; and a VL comprising a LCDR1 having SEQ ID NO: 110, a LCDR2 having SEQUENCE A17 (of FIG. 1) and a LCDR3 having SEQ ID NO: 41, optionally wherein the VL comprises SEQ ID NO: 156;

(t) a VH comprising a HCDR1 having SEQ ID NO: 89, a HCDR2 having SEQ ID NO: 66 and a HCDR3 having SEQ ID NO: 20, optionally wherein the VH comprises SEQ ID NO: 135; and a VL comprising a LCDR1 having SEQ ID NO: 112, a LCDR2 having SEQUENCE A19 (of FIG. 1) and a LCDR3 having SEQ ID NO: 43, optionally wherein the VL comprises SEQ ID NO: 158;

(u) a VH comprising a HCDR1 having SEQ ID NO: 90, a HCDR2 having SEQ ID NO: 67 and a HCDR3 having SEQ ID NO: 21, optionally wherein the VH comprises SEQ ID NO: 136; and a VL comprising a LCDR1 having SEQ ID NO: 113, a LCDR2 having SEQUENCE A20 (of FIG. 1) and a LCDR3 having SEQ ID NO: 44, optionally wherein the VL comprises SEQ ID NO: 159;

(v) a VH comprising a HCDR1 having SEQ ID NO: 91, a HCDR2 having SEQ ID NO: 68 and a HCDR3 having SEQ ID NO: 22, optionally wherein the VH comprises SEQ ID NO: 137; and a VL comprising a LCDR1 having SEQ ID NO: 114, a LCDR2 having SEQUENCE A21 (of FIG. 1) and a LCDR3 having SEQ ID NO: 45, optionally wherein the VL comprises SEQ ID NO: 160;

and/or (w) a VH comprising a HCDR1 having SEQ ID NO: 93, a HCDR2 having SEQ ID NO: 70 and a HCDR3 having SEQ ID NO: 24, optionally wherein the VH comprises SEQ ID NO: 139; and a VL comprising a LCDR1 having SEQ ID NO: 116, a LCDR2 having SEQUENCE A23 (of FIG. 1) and a LCDR3 having SEQ ID NO: 47, optionally wherein the VL comprises SEQ ID NO: 162.

According to a further aspect of the invention, there is provided an isolated anti-Vγ4 antibody or fragment thereof which comprises an amino acid sequence having at least 80% sequence identity with any one of SEQ ID NOs: 163-185.

According to a further aspect of the invention, there is provided an isolated anti-Vγ4 antibody which comprises an amino acid sequence having at least 80% sequence identity with any one of SEQ ID NOs: 233-255. In a related aspect of the invention, there is provided an isolated anti-Vγ4 antibody which comprises or consists of a heavy chain amino acid sequence having at least 80% sequence identity with any one of SEQ ID NOs: 284-306 and/or a light chain amino acid sequence having at least 80% sequence identity with any one of SEQ ID NOs: 307-329.

The invention further provides an anti-Vγ4 antibody or fragment thereof that specifically binds to a Vγ4 chain of a γδ T cell receptor (TCR) and competes with binding to the Vγ4 chain of a γδ T cell receptor (TCR) with an antibody or fragment thereof of the invention as defined herein.

According to a further aspect of the invention, there is provided a polynucleotide sequence encoding the anti-Vγ4 antibody or fragment thereof as defined herein. For example, there is provided a polynucleotide sequence encoding an anti-Vγ4 antibody or fragment thereof comprising a sequence having at least 70% sequence identity with any of SEQ ID NOs: 187-232. Preferably, the polynucleotide sequence encoding the anti-Vγ4 antibody or fragment thereof comprises a sequence of any of SEQ ID NOs: 187-232.

According to a further aspect of the invention, there is provided an expression vector comprising a polynucleotide sequence of the invention as defined herein. For example, there is provided an expression vector comprising a VH-encoding polynucleotide sequence of any of SEQ ID NOs: 187-209 and/or a VL-encoding polynucleotide sequence of any of SEQ ID NOs: 210-232.

According to a further aspect of the invention, there is provided a cell comprising the polynucleotide sequence or the expression vector of the invention as defined herein. There is also provided a method for producing any antibody or fragment thereof of the invention, comprising culturing a cell of the invention in a cell culture medium. It will be understood in this context that said cell may be referred to as a "host cell", as further defined herein.

According to a further aspect of the invention, there is provided a composition comprising the antibody or fragment thereof of the invention as defined herein. There is also provided a pharmaceutical composition comprising the antibody or fragment thereof of the invention as defined herein, together with a pharmaceutically acceptable diluent or carrier.

In a further aspect of the invention, there is provided a kit comprising an anti-Vγ4 antibody or fragment thereof of the invention or a pharmaceutical composition of the invention, optionally comprising instructions for use and/or an additional therapeutically active agent.

According to a further aspect of the invention, there is provided an isolated anti-Vγ4 antibody or fragment thereof of the invention or the pharmaceutical composition of the invention as defined herein, for use as a medicament. Similarly, there is provided a method of treating a disease or disorder (e.g. cancer, an infectious disease or an inflammatory disease) in a subject in need thereof, comprising administering to the subject a therapeutically effective amount of an isolated anti-Vγ4 antibody or fragment thereof of the invention or the pharmaceutical composition of the invention as defined herein.

As described above, prior to the development of the present invention it was conventionally held that it would not be possible to develop an antibody or fragment thereof able to specifically bind the Vγ4 chain, particularly human Vγ4. This was due to the high degree of sequence similarity (91%) between the human Vγ4 chain and Vγ2 chain of a γδ TCR. To overcome this significant challenge, the inventors developed specific antigens and methodologies. Thus, according to a further aspect of the invention, there is provided an isolated antigen comprising an amino acid sequence having at least 80% sequence identity with SEQ ID NO: 256 for use in generating an anti-Vγ4 antibody or fragment thereof. Another important aspect of the antigen preparation process was to design antigens which were suitable for expression as a protein. The γδ TCR is a complex protein involving a heterodimer with inter-chain and intra-chain disulphide bonds. A leucine zipper (LZ) format and Fc format were used to generate soluble TCR antigens to be used in the phage display selections. Thus, the invention also provides an isolated antigen comprising an amino acid sequence having at least 80% sequence identity with SEQ ID NO: 257 or 258 for use in generating an anti-Vγ4 antibody or fragment thereof.

Furthermore, gamma delta (γδ) T cells are polyclonal with CDR3 polyclonality. In order to avoid a situation where generated antibodies would be selected against the CDR3 sequence (as the CDR3 sequence will differ from TCR clone to TCR clone), the antigen design involved maintaining a consistent CDR3 in different formats. This design aimed to generate antibodies recognising a sequence within the gamma-4 variable domain, which is germline encoded and therefore the same in all clones, thus providing antibodies which recognise a wider subset of γδ T cells. Furthermore, through this iterative approach of selecting of antibodies which bind this gamma-4 specific region in multiple formats combined with deselecting binders that also bind the highly similar gamma-2 specific regions and which contained the exact same hypervariable CDR3 sequence, antibodies were identified with exquisite selectivity. Specifically, and surprisingly, in some instances as described herein, antibodies were identified which bind to the region N-terminal of CDR3 on the human gamma 4 antigen but which did not bind the equivalent region N-terminal of CDR3 of the highly related human gamma 2 antigen. This was remarkable given the high degree of homology between gamma-4 and gamma-2 in this region combined with the fact the very minor sequence differences between these two gamma chains are scattered: three of the nine changes mapping across gamma variable chain CDR1 and CDR2, whilst four of the nine changes map to a sub-region of framework region 3 (FR3) known as 'hypervariable region 4' which is N-terminal of the gamma variable chain CDR3.

Thus, according to a further aspect of the invention, there is provided a method of generating an anti-Vγ4 antibody or fragment thereof comprising:

(i) designing a series of antigens comprising a TCR gamma variable 4 (TRGV4) amino acid sequence wherein the CDR3 sequence of the TRGV4 is the same for all antigens in the series;
(ii) exposing a first antigen designed in step (i) to an antibody library;
(iii) isolating the antibodies or fragments thereof which bind to the antigen;
(iv) exposing the isolated antibodies or fragments thereof to a second antigen designed in step (i); and
(v) isolating the antibodies or fragments thereof which bind to both the first and second antigen.

The method may further include:
exposing the isolated antibodies or fragments thereof which bind to the first antigen and/or second antigen to an antigen comprising a TCR gamma variable amino acid sequence which is not TRGV4 (e.g. a TCR gamma variable 2 (TRGV2) or a TCR gamma variable 8 (TRGV8) amino acid sequence); and
isolating the antibodies or fragments thereof which bind to the first antigen and/or second antigen but which do not bind to an antigen comprising a TCR gamma variable amino acid sequence which is not TRGV4.

The TRGV4, TRGV2 and TRGV8 amino acid sequences preferably correspond to human TRGV4, TRGV2 and TRGV8 respectively. Human TRGV4 corresponds to amino acids 1-99 of SEQ ID NO: 1. Human TRGV2 and TRGV8 correspond to amino acid sequences corresponding to SEQ ID NOs: 335 and 336 respectively.

According to a further aspect of the invention, there is provided an antibody obtained by the method as defined herein.

BRIEF DESCRIPTION OF THE FIGURES

FIG. 1: Complementarity Determining Region (CDR) sequences of exemplary anti-Vγ4 antibodies of the invention. Shown are the CDR sequences for exemplary anti-Vγ4 antibodies of the invention. The corresponding SEQ ID NO. is shown to the right of each sequence.

FIG. 3: A comparison of antibody binding to Vγ4Vδ1 TCRs presented as either recombinant antigens or as recombinant cell surface receptors. (A) Normalized and log transformed X/Y plot of antibody binding to either the DV1-GV4 antigen via Delfia® ELISA (Y-axis) or to JRT3-hu17 cells (X-axis). Vertical grey dotted line indicates the cut-off for mAbs considered negative (left) and positive (right) for JRT3-hu17 binding in this study. X-axis gMFI signal was normalized to CD3 to account for the variation in TCR expression between each construct. (B) Flow data plot to further illustrate the negative/positive cut-off. Antibody G4_26 (mid-left panel) exhibits the highest normalized gMFI value among the negative group and exhibits a similar plot to the negative isotype control (D1.3; far left panel). G4_15 (middle panel) has the lowest normalized gMFI value among the positive group and exhibits a clear, albeit weak, staining enhancement when compared to the D1.3 isotype control. Examples of intermediate (G4_16; mid-right) and strong (G4_18; far right) signals are also provided for reference.

FIG. 4: Antibody binding to a panel of recombinantly expressed γ4 TCRs containing differing CDR3 sequences and/or paired with differing delta chains. (A) Histogram representation of antibody binding signals generated against recombinant TCRs expressed on Jurkat cells. Sequential analysis presented as follows: Antibody binding signal against Vγ4Vδ1-hu17 (black bars); antibody binding signal against Vγ4Vδ1-hu20 (horizontal striped bars); antibody binding signal against Vγ4Vδ2 hu20γ-PBδ (diagonal striped bars); antibody binding signal against Vγ4Vδ5-LES (white bars). All binding signals normalized to CD3 to account for the variation in TCR expression between differing TCR constructs in JRT3 cells. (B) Example flow data for two of the lead antibodies in this study to further illustrate the difference between an exemplar antibody (G4_3) shown positive for all Vγ4 TCRs versus another lead antibody (G4_4) shown positive for only some of the Vγ4 TCRs.

DETAILED DESCRIPTION OF THE INVENTION

Definitions

Figure 2A:
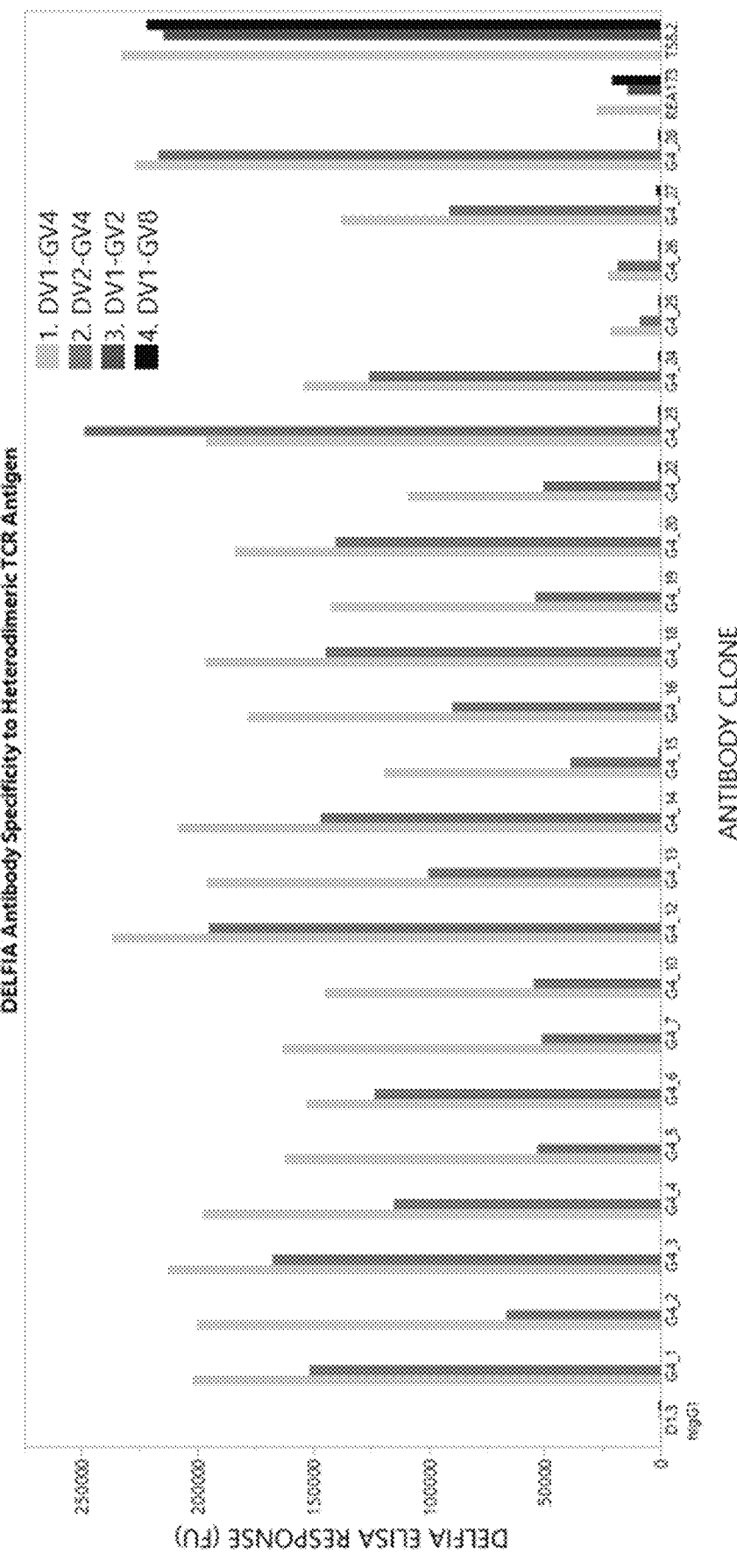
FIG. 2: Antibody specificity against heterodimeric TCR antigens via DELFIA Elisa Assay. (A) Presented are the results for all antibodies that passed QC assessment (Analytical SEC-HPLC) and which also exhibited specificity for human Vγ4 chain. These antibodies (X-axis) were tested for binding against four different recombinant heterodimeric human TCRs respectively (DV1-GV4; DV2-GV4; DV1-GV2; DV1-GV8). Controls include the isotype controlled anti-chicken lysozyme D1.3 antibody (in-house, far left) plus anti-Vδ1 antibodies REA173 (Miltenyi) and TS8.2 (Fisher)—far right. (B) Quantification of the data shown in (A) and further showing the fold-change increase in binding of each example clone to the human Vγ4 chain versus the human Vγ2 chain.

Unless defined otherwise, all technical and scientific terms used herein have the meaning commonly understood by a person skilled in the art to which this invention belongs. As used herein, the following terms have the meanings ascribed to them below.

Gamma delta (γδ) T cells represent a small subset of T cells that express on their surface a distinct, defining T Cell Receptor (TCR). This TCR is made up of one gamma (γ) and one delta (δ) chain. Each chain contains a variable (V) region, a constant (C) region, a transmembrane region and a cytoplasmic tail. The V region contains an antigen binding site. There are two major sub-types of human γδ T cells: one that is dominant in the peripheral blood and one that is dominant in non-haematopoietic tissues. The two sub-types may be defined by the type of δ and/or γ present on the cells.

For example, most blood-resident γδ T cells express a Vδ2 TCR, for example Vγ9Vδ2, whereas this is less common among tissue-resident γδ T cells, which more frequently use Vδ1 for example in skin and Vγ4 in the gut. References to "Vγ4 T cells" refer to γδ T cells with a Vγ4 chain, i.e. Vγ4+ cells.

References to "gamma variable 4" may also be referred to as Vγ4 or Vg4. A gamma variable 4 polypeptide, or a nucleotide encoding a TCR chain containing this region, or the TCR protein complex comprising this region, may be referred to as "TRGV4". Antibodies or fragments thereof which interact with the Vγ4 chain of a γδ TCR, are all effectively antibodies or fragments thereof which bind to Vγ4 and may referred to as "anti-TCR gamma variable 4 antibodies or fragments thereof" or "anti-Vγ4 antibodies or fragments thereof". Reference to a human Vγ4 polypeptide may mean a polypeptide having an amino acid sequence corresponding to amino acids 1-99 of SEQ ID NO. 1. This 99 amino-acid sequence also corresponds to SEQ ID NO: 334. Therefore, it should be understood that reference herein to amino acids 1-99 of SEQ ID NO. 1 may be used interchangeably with reference to SEQ ID NO: 334, according to all aspects and embodiments of the invention. For instance, reference herein to amino acid region 67-82 of SEQ ID NO: 1 is equivalent with amino acid region 67-82 of SEQ ID NO: 334 and may be used interchangeably herein.

References to "delta variable 1" may also be referred to as Vδ1 or Vd1. A delta variable 1 polypeptide, or a nucleotide encoding a TCR chain containing this region, or the TCR protein complex comprising this region, may be referred to as "TRDV1". Antibodies or fragments thereof which interact with the Vδ1 chain of a γδ TCR, are all effectively antibodies or fragments thereof which bind to Vδ1 and may referred to as "anti-TCR delta variable 1 antibodies or fragments thereof" or "anti-Vδ1 antibodies or fragments thereof". Reference to a human Vδ1 polypeptide may mean a polypeptide having an amino acid sequence corresponding to SEQ ID NO. 337.

References to "gamma variable 2" may also be referred to as Vγ2 or Vg2. A gamma variable 2 polypeptide, or a nucleotide encoding a TCR chain containing this region, or the TCR protein complex comprising this region, may be referred to as "TRGV2". Antibodies or fragments thereof which interact with the Vγ2 chain of a γδ TCR, are all effectively antibodies or fragments thereof which bind to Vγ2 and may referred to as "anti-TCR gamma variable 2 antibodies or fragments thereof" or "anti-Vγ2 antibodies or fragments thereof". Reference to a human Vγ2 polypeptide may mean a polypeptide having an amino acid sequence corresponding to SEQ ID NO. 335.

References to "gamma variable 8" may also be referred to as Vγ8 or Vg8. A gamma variable 8 polypeptide, or a nucleotide encoding a TCR chain containing this region, or the TCR protein complex comprising this region, may be referred to as "TRGV2". Antibodies or fragments thereof which interact with the Vγ8 chain of a γδ TCR, are all effectively antibodies or fragments thereof which bind to Vγ8 and may referred to as "anti-TCR gamma variable 8 antibodies or fragments thereof" or "anti-Vγ8 antibodies or fragments thereof". Reference to a human Vγ8 polypeptide may mean a polypeptide having an amino acid sequence corresponding to SEQ ID NO. 336.

The term "antibody" includes any antibody protein construct comprising at least one antibody variable domain comprising at least one antigen binding site (ABS). Antibodies include, but are not limited to, immunoglobulins of types IgA, IgG, IgE, IgD, IgM (as well as subtypes thereof). The overall structure of Immunoglobulin G (IgG) antibodies assembled from two identical heavy (H)-chain and two identical light (L)-chain polypeptides is well established and highly conserved in mammals (Padlan (1994) *Mol. Immunol.* 31:169-217).

A conventional antibody or immunoglobulin (Ig) is a protein comprising four polypeptide chains: two heavy (H) chains and two light (L) chains. Each chain is divided into a constant region and a variable domain. The heavy (H) chain variable domains are abbreviated herein as VH, and the light (L) chain variable domains are abbreviated herein as VL. These domains, domains related thereto and domains derived therefrom, may be referred to herein as immunoglobulin chain variable domains. The VH and VL domains (also referred to as VH and VL regions) can be further subdivided into regions, termed "complementarity determining regions" ("CDRs"), interspersed with regions that are more conserved, termed "framework regions" ("FRs"). The framework and complementarity determining regions have been precisely defined (Kabat et al. Sequences of Proteins of Immunological Interest, *Fifth Edition U.S. Department of Health and Human Services*, (1991) NIH Publication Number 91-3242). There are also alternative numbering conventions for CDR sequences, for example those set out in Chothia et al. (1989) Nature 342:877-883. In a conventional antibody, each VH and VL is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulphide bonds, and the heavy chains similarly connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system.

A fragment of the antibody (which may also be referred to as "antibody fragment", "immunoglobulin fragment", "antigen-binding fragment" or "antigen-binding polypeptide") as used herein refers to a portion of an antibody (or constructs that contain said portion) that specifically binds to the target, the gamma variable 4 (Vγ4) chain of a γδ T cell receptor (e.g. a molecule in which one or more immunoglobulin chains is not full length, but which specifically binds to the target). Examples of binding fragments encompassed within the term antibody fragment include:

(i) a Fab fragment (a monovalent fragment consisting of the VL, VH, CL and CH1 domains);

(ii) a F(ab')2 fragment (a bivalent fragment consisting of two Fab fragments linked by a disulphide bridge at the hinge region);

(iii) a Fd fragment (consisting of the VH and CH1 domains);

(iv) a Fv fragment (consisting of the VL and VH domains of a single arm of an antibody);

(v) a single chain variable fragment, scFv (consisting of VL and VH domains joined, using recombinant methods, by a synthetic linker that enables them to be made as a single protein chain in which the VL and VH regions pair to form monovalent molecules);

(vi) a VH (an immunoglobulin chain variable domain consisting of a VH domain);

(vii) a VL (an immunoglobulin chain variable domain consisting of a VL domain);

(viii) a domain antibody (dAb, consisting of either the VH or VL domain);

(ix) a minibody (consisting of a pair of scFv fragments which are linked via CH3 domains); and (x) a diabody (consisting of a noncovalent dimer of scFv fragments that consist of a VH domain from one antibody connected by a small peptide linker to a VL domain from another antibody).

"Human antibody" refers to antibodies having variable and constant regions derived from human germline immunoglobulin sequences. Human subjects administered with said human antibodies do not generate cross-species antibody responses (for example termed HAMA responses-human-anti-mouse antibody) to the primary amino acids contained within said antibodies. Said human antibodies may include amino acid residues not encoded by human germline immunoglobulin sequences (e.g. mutations introduced by random or site-specific mutagenesis or by somatic mutation), for example in the CDRs and in particular CDR3. However, the term is not intended to include antibodies in which CDR sequences derived from the germline of another mammalian species, such as a mouse, have been grafted onto human framework sequences. Human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences, may also be referred to as "recombinant human antibodies".

Substituting at least one amino acid residue in the framework region of a non-human immunoglobulin variable domain with the corresponding residue from a human variable domain is referred to as "humanisation". Humanisation of a variable domain may reduce immunogenicity in humans.

"Specificity" refers to the number of different types of antigens or antigenic determinants to which a particular antibody or fragment thereof can bind. The specificity of an antibody is the ability of the antibody to recognise a particular antigen as a unique molecular entity and distinguish it from another. An antibody that "specifically binds" to an antigen or an epitope is a term well understood in the art. A molecule is said to exhibit "specific binding" if it reacts more frequently, more rapidly, with greater duration and/or with greater affinity with a particular target antigen or epitope, than it does with alternative targets. An antibody "specifically binds" to a target antigen or epitope if it binds with greater affinity, avidity, more readily, and/or with greater duration than it binds to other substances. An antibody (or fragment thereof) may be considered to specifically bind to a target if the binding is statistically significant compared to a non-relevant binder.

"Affinity", represented by the equilibrium constant for the dissociation of an antigen with an antigen-binding polypeptide (KD), is a measure of the binding strength between an antigenic determinant and an antigen-binding site on the antibody (or fragment thereof): the lesser the value of the KD, the stronger the binding strength between an antigenic determinant and the antigen-binding polypeptide. Alternatively, the affinity can also be expressed as the affinity constant (KA), which is 1/KD. Affinity can be determined by known methods, depending on the specific antigen of interest. For example, KD may be determined by surface plasmon resonance.

Any KD value less than $10^{-6}$ is considered to indicate binding. Specific binding of an antibody, or fragment thereof, to an antigen or antigenic determinant can be determined in any suitable known manner, including, for example, Scatchard analysis and/or competitive binding assays, such as radioimmunoassays (RIA), enzyme immunoassays (EIA) and sandwich competition assays, equilibrium dialysis, equilibrium binding, gel filtration, ELISA, surface plasmon resonance, or spectroscopy (e.g. using a fluorescence assay) and the different variants thereof known in the art.

"Avidity" is the measure of the strength of binding between an antibody, or fragment thereof, and the pertinent antigen. Avidity is related to both the affinity between an antigenic determinant and its antigen binding site on the antibody and the number of pertinent binding sites present on the antibody.

"Human tissue Vγ4+ cells," and "haemopoietic and blood Vγ4+ cells" and "tumour infiltrating lymphocyte (TIL) Vγ4+ cells," are defined as Vγ4+ cells contained in or derived from either human tissue or the haemopoietic blood system or human tumours respectively. All said cell types can be identified by their (i) location or from where they are derived and (ii) their expression of the Vγ4+ TCR.

Suitably, the antibody or fragment thereof (i.e. polypeptide) of the invention is isolated. An "isolated" polypeptide is one that is removed from its original environment. The term "isolated" may be used to refer to an antibody that is substantially free of other antibodies having different antigenic specificities (e.g. an isolated antibody that specifically binds Vγ4, or a fragment thereof, is substantially free of antibodies that specifically bind antigens other than Vγ4). The term "isolated" may also be used to refer to preparations where the isolated antibody is sufficiently pure to be administered therapeutically when formulated as an active ingredient of a pharmaceutical composition, or at least 70-80% (w/w) pure, more preferably, at least 80-90% (w/w) pure, even more preferably, 90-95% pure; and, most preferably, at least 95%, 96%, 97%, 98%, 99%, or 100% (w/w) pure.

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

The antibody or fragment thereof may be a "functionally active variant" which also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that essentially does not alter the biological function of the polypeptide. By way of non-limiting example, said functionally active variants may still function when the frameworks containing the CDRs are modified, when the CDRs themselves are modified, when said CDRs are grafted to alternate frameworks, or when N- or C-terminal extensions are incorporated. Further, CDR-containing binding domains may be paired with differing partner chains such as those shared with another antibody. Upon sharing with so called 'common' light or 'common' heavy chains, said binding domains may still function. Further, said binding domains may function when multimerized. Further, 'antibodies or fragments thereof' may also comprise functional variants wherein the VH or VL or constant domains have been modified away or towards a different canonical sequence (for example as listed at IMGT.org) and which still function.

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or "identical" to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

In some embodiments, any specified % sequence identity of a sequence is calculated without the sequences of all 6 CDRs of the antibody. For example, the anti-Vγ4 antibody or antigen-binding fragment thereof may comprise a variable heavy chain region sequence having at least 70%, 75%, 80%, 85%, 90%, 91%, 92%, 93%, 94%, 95%, 96%, 97%, 98% or 99% to a specified variable heavy chain region sequence and/or a variable light chain region sequence having at least 70%, 75%, 80%, 85%, 90%, 91%, 92%, 93%, 94%, 95%, 96%, 97%, 98% or 99% identity to a specified variable light chain region sequence, wherein any amino acid variations occur only in the framework regions of the variable heavy and light chain region sequences. In such embodiments, the anti-Vγ4 antibody or fragment thereof having certain sequence identities retain the complete heavy and light chain CDR1, CDR2 and CDR3 sequences of the corresponding anti-Vγ4 antibody or fragment thereof.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If first and second polypeptide sequences are 9 amino acid residues long and share 6 identical residues, the first and second polypeptide sequences share greater than 66% identity (the first and second polypeptide sequences share 66.7% identity).

Alternatively, for the purposes of comparing a first, reference polypeptide sequence to a second, comparison polypeptide sequence, the number of additions, substitutions and/or deletions made to the first sequence to produce the second sequence may be ascertained. An "addition" is the addition of one amino acid residue into the sequence of the first polypeptide (including addition at either terminus of the first polypeptide). A "substitution" is the substitution of one amino acid residue in the sequence of the first polypeptide with one different amino acid residue. Said substitution may be conservative or non-conservative. A "deletion" is the deletion of one amino acid residue from the sequence of the first polypeptide (including deletion at either terminus of the first polypeptide).

Using the three letter and one letter codes, the naturally occurring amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
| --- | --- |
| Non-polar aliphatic | Glycine |
| | Alanine |
| | Valine |
| | Methionine |
| | Leucine |
| | Isoleucine |
| Aromatic | Phenylalanine |
| | Tyrosine |
| | Tryptophan |
| Polar uncharged | Serine |
| | Threonine |
| | Cysteine |
| | Proline |
| | Asparagine |
| | Glutamine |
| Negatively charged | Aspartate |
| | Glutamate |
| Positively charged | Lysine |
| | Arginine |
| | Histidine |

Suitably, a hydrophobic amino acid residue is a non-polar amino acid. More suitably, a hydrophobic amino acid residue is selected from V, I, L, M, F, W or C. In some embodiments, a hydrophobic amino acid residue is selected from glycine, alanine, valine, methionine, leucine, isoleucine, phenylalanine, tyrosine, or tryptophan.

As used herein, numbering of polypeptide sequences and definitions of CDRs and FRs are as defined according to the Kabat system (Kabat et al., 1991, herein incorporated by reference in its entirety). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

References herein to an "epitope" refer to the portion of the target which is specifically bound by the antibody or fragment thereof. Epitopes may also be referred to as "antigenic determinants". An antibody binds "essentially the same epitope" as another antibody when they both recognize identical or sterically overlapping epitopes. Commonly used methods to determine whether two antibodies bind to identical or overlapping epitopes are competition assays, which can be configured in a number of different formats (e.g. well plates using radioactive or enzyme labels, or flow cytometry on antigen-expressing cells) using either labelled antigen or labelled antibody. An antibody binds "the same epitope" as another antibody when they both recognize identical epitopes (i.e. all contact points between the antigen and the antibody are the same). For example, an antibody may bind the same epitope as another antibody when all contact points across a specified region of an antigen are identified as the same with the aid of a characterization method such as antibody/antigen cross-linking-coupled MS, HDX, X-ray crystallography, cryo-EM, or mutagenesis.

Further, with aid of such characterization methods, it is also possible to characterize antibodies which bind essentially the same epitope by recognizing some but not all of the identical contact points. Specifically, such antibodies may share a sufficient number of identical contact points in a specified antigenic region to deliver a broadly equivalent technical effect and/or equivalent antigen interaction selectivity. Additionally, in some instances whereby antibodies recognize essentially the same epitope and confer a broadly equivalent technical effect and/or interaction selectivity, it can also be useful to define the epitope binding footprint by the totality of antigen contacts inclusive of the most N-terminal antigen contact point through to the most C-terminal antigen contact point.

Epitopes found on protein targets may be defined as "linear epitopes" or "conformational epitopes". Linear epitopes are formed by a continuous sequence of amino acids in a protein antigen. Conformational epitopes are formed of amino acids that are discontinuous in the protein sequence, but which are brought together upon folding of the protein into its three-dimensional structure.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors, such as viral vectors (e.g. replication defective retroviruses, adenoviruses and adeno-associated viruses), which serve equivalent functions, and also bacteriophage and phagemid systems. The term "recombinant host cell" (or simply "host cell"), as used herein, is intended to refer to a cell into which a recombinant expression vector has been introduced. Such terms are intended to refer not only to the particular subject cell but to the progeny of such a cell, for example, when said progeny are employed to make a cell line or cell bank which is then optionally stored, provided, sold, transferred, or employed to manufacture an antibody or fragment thereof as described herein.

References to "subject", "patient" or "individual" refer to a subject, in particular a mammalian subject, to be treated. Mammalian subjects include humans, non-human primates, farm animals (such as cows), sports animals, or pet animals, such as dogs, cats, guinea pigs, rabbits, rats or mice. In some embodiments, the subject is a human. In alternative embodiments, the subject is a non-human mammal, such as a mouse.

The term "sufficient amount" means an amount sufficient to produce a desired effect. The term "therapeutically effective amount" is an amount that is effective to ameliorate a symptom of a disease or disorder. A therapeutically effective amount can be a "prophylactically effective amount" as prophylaxis can be considered therapy.

A disease or disorder is "ameliorated" if the severity of a sign or symptom of the disease or disorder, the frequency with which such a sign or symptom is experienced by a subject, or both, is reduced.

As used herein, "treating a disease or disorder" means reducing the frequency and/or severity of at least one sign or symptom of the disease or disorder experienced by a subject.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues.

"Inflammation" refers to a chronic or acute triggering of the immune system resulting in an inflamed cell, cell type, tissue, or organ.

As used herein, the term "about" includes up to and including 10% greater and up to and including 10% lower than the value specified, suitably up to and including 5% greater and up to and including 5% lower than the value specified, especially the value specified. The term "between", includes the values of the specified boundaries.

In Vivo Methods of Modulating γδ T Cells

According to one aspect of the invention, there is provided an in vivo method of modulating gamma variable 4 chain (Vγ4) T cells comprising administering an anti-Vγ4 antibody or fragment thereof as defined herein to a patient.

In Vivo Modulation of Vγ4 T Cells May Include:

expansion of the Vγ4 T cells, e.g. by selectively increasing the number of Vγ4 T cells or promotion of survival of Vγ4 T cells;

stimulation of the Vγ4 T cells, e.g. by increasing Vγ4 T cell potency, i.e. increasing target cell killing;

degranulation of Vγ4 T cells.

Such modulation of Vγ4 T cells may include, for example, Vγ4 T cell activation or Vγ4 T cell inhibition. In one embodiment, the Vγ4 T cells are activated by administering an anti-Vγ4 antibody or fragment thereof as defined herein. In an alternative embodiment, the Vγ4 T cells are inhibited by administering an anti-Vγ4 antibody or fragment thereof as defined herein. In an alternative embodiment, the Vγ4 T cells are not inhibited after administration of an anti-Vγ4 antibody or fragment thereof as defined herein.

In one embodiment, there is provided a method of modulating Vγ4 T cells comprising administering an anti-TCR gamma 4 variable antibody or fragment thereof to a patient. In one embodiment, there is provided an anti-TCR gamma 4 variable antibody or fragment thereof for use in an in vivo method of modulating Vγ4 T cells. In one embodiment, there is provided the use of an anti-TCR gamma 4 variable antibody or fragment thereof in the manufacture of a medicament for the in vivo modulation of Vγ4 T cells.

In one embodiment, the in vivo modulation comprises activation of the Vγ4 T cells, in particular n in vivo expansion of the Vγ4 T cells. Therefore, according to an aspect of the invention, there is provided an in vivo method of expanding Vγ4 T cells comprising administering an anti-Vγ4 antibody or fragment thereof as defined herein to a patient. Such expansion of Vγ4 T cells may be achieved through the selective increase in number of Vγ4 T cells and/or through the promotion of survival of Vγ4 T cells.

As used herein, references to "expanded" refers to patients having a larger number of cells than before administration of the antibody or fragment thereof.

Antibodies or Fragments Thereof

According to a first aspect of the invention, there is provided an isolated antibody or fragment thereof, which specifically binds to a variable gamma 4 (Vγ4) chain of a γδ T cell receptor (TCR). In particular, the antibody or fragment thereof does not bind to (or cross react with) a variable gamma 2 (Vγ2) chain of a γδ TCR. It should be understood that this is with reference to a Vγ4 chain and a Vγ2 from the same species. Preferably, the species is *Homo sapiens* (human) and therefore the invention provides an isolated antibody or fragment thereof, which specifically binds to a human gamma variable 4 (Vγ4) chain of a γδ T cell receptor (TCR) and not to a human gamma variable 2 (Vγ2) chain of a γδ TCR. For instance, the human Vγ4 chain may have a sequence according to amino acids 1-99 of SEQ ID NO. 1 and/or the human Vγ2 chain may have a sequence according to SEQ ID NO. 335. In other species, the isolated antibody or fragment thereof, specifically binds to the species-specific ortholog of the human gamma variable 4 (Vγ4) chain of a γδ T cell receptor (TCR) and not to the species-specific ortholog of the human gamma variable 2 (Vγ2) chain of a γδ TCR. Thus, the invention provides an isolated antibody or fragment thereof, which specifically binds to a human gamma variable 4 (Vγ4) chain of a γδ T cell receptor (TCR) having a sequence corresponding to amino acids 1-99 of SEQ ID NO. 1 or non-human ortholog thereof and not to a human gamma variable 2 (Vγ2) chain of a γδ TCR having a sequence corresponding to SEQ ID NO. 335 or non-human ortholog thereof. Ortholog in this context may mean a gamma chain sequence with the highest sequence similarity to the reference sequence, or preferably one which possesses the same function (e.g. interaction with orthologous cognate ligands in vivo). For instance, in mouse, the protein designated under the Heilig & Tonegave nomenclature as Vγ7 is functionally most closely related to human Vγ4 (Barros et al. (2016) Cell, 167:203-218.e17).

This development is profound. In humans, for example, the Vγ4 and Vγ2 chains share 91% sequence identity (they only differ by nine amino acids). Therefore this has made it difficult to obtain antibodies which bind to (human) Vγ4 and not to (human) Vγ2 and, prior to the invention, it was not expected in the art to be possible to produce such antibodies.

When referring to an antibody or fragment thereof of the invention which specifically binds to a Vγ4 chain of a γδ

TCR, this generally means that binding of the antibody or fragment thereof to the Vγ4 chain is statistically significantly increased relative to a negative control antibody and/or a negative control antigen (e.g. as measured via binding in an ELISA assay, optionally a DELFIA ELISA assay, or SPR). The level detected in respect of the negative control antibody and/or negative control antigen may be considered the background level for the assay used, representing "noise" in the assay system as would be well-understood by the skilled person. In particular embodiments, signal levels above a pre-determined threshold relative to the background level may be considered to represent detection of binding (e.g. about 1-fold, 2-fold, 3-fold, 4-fold, 5-fold or more above the background level). For instance, in a DELFIA® ELISA assay a signal level 5-fold or more above the background level may be considered to indicate binding of the antibody to the antigen. The skilled person is well able to determine a suitable threshold based on the assay system being used. Conversely, when referring to an antibody or fragment thereof of the invention which does not bind to (or cross react with) a Vγ2 chain of a γδ TCR, this generally means that binding of the antibody or fragment thereof to the Vγ2 chain is not statistically significantly increased relative to a negative control antibody and/or a negative control antigen (e.g. as measured via binding in an ELISA assay, optionally a DELFIA® ELISA assay, or SPR). This is demonstrated, for example, in FIG. 2A and discussed in Example 4. According to all aspects and embodiments of the invention disclosed herein, this property may also be expressed as the fold-change difference in detected binding levels (e.g. as measured via binding in an ELISA assay, optionally a DELFIA® ELISA assay, or SPR) between the antibody or fragment thereof and the Vγ4 chain versus the antibody or fragment thereof and the Vγ2 chain. For instance, the antibody or fragment thereof may show an at least about 50-fold, 60-fold, 70-fold, 80-fold, 90-fold, 100-fold, 150-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, 10000-fold, 15000-fold, 25000-fold, 50000-fold, 75000-fold, 95000-fold or more increase in binding to the Vγ4 chain as compared against binding to the Vγ2 chain. This is demonstrated, for example, in FIG. 2B and discussed in Example 4. However these fold increases are deemed conservative inasmuch to calculate them it has been assumed all Vγ2 signal above controls is not background noise. However, and as discussed previously, a skilled person may instead exclude low signal above background in such DELFIA® ELISA assays as assay noise (e.g. about 1-fold, 2-fold, 3-fold, 4-fold, 5-fold or more above the background level) and so consider signal below these thresholds as non-specific background binding.

In one embodiment, the antibody or fragment thereof is an scFv, Fab, Fab', F(ab')2, Fv, variable domain (e.g. VH or VL), diabody, minibody or monoclonal antibody. In a particular embodiment, the antibody or fragment thereof is an scFv. In another particular embodiment, the antibody is a monoclonal antibody.

Antibodies of the invention can be of any class, e.g. IgG, IgA, IgM, IgE, IgD, or isotypes thereof, and can comprise a kappa or lambda light chain. In one embodiment, the antibody is an IgG antibody, for example, at least one of isotypes, IgG1, IgG2, IgG3 or IgG4. In on embodiment, the antibody is an IgG1. In a further embodiment, the antibody may be in a format, such as an IgG format, that has been modified to confer desired properties, such as having the Fc mutated to reduce effector function, extend half life, alter ADCC, or improve hinge stability. Such modifications are well known in the art and exemplary embodiments are described herein. For instance, an antibody or fragment thereof of the invention may comprise an IgG1 constant domain comprising an amino acid sequence according to SEQ ID NO: 332 or 333.

In one embodiment, the antibody or fragment thereof is human. Thus, the antibody or fragment thereof may be derived from a human immunoglobulin (Ig) sequence. The CDR, framework and/or constant region of the antibody (or fragment thereof) may be derived from a human Ig sequence, in particular a human IgG sequence. The CDR, framework and/or constant region may be substantially identical for a human Ig sequence, in particular a human IgG sequence. An advantage of using human antibodies is that they have low or no immunogenicity in humans.

An antibody or fragment thereof can also be chimeric, for example a mouse-human antibody chimera.

Alternatively, the antibody or fragment thereof is derived from a non-human species, such as a mouse. Such non-human antibodies can be modified to increase their similarity to antibody variants produced naturally in humans, thus the antibody or fragment thereof can be partially or fully humanised. Therefore, in one embodiment, the antibody or fragment thereof is humanised.

Antibodies Targeted to Epitopes

Provided herein are antibodies (or fragments thereof) which bind to an epitope of the Vγ4 chain of a γδ TCR. Binding of the epitope on the Vγ4 chain may optionally have an effect on γδ TCR activity, such as activation or inhibition. The antibodies (or fragments thereof) may have a blocking effect by prevention of the binding or interaction of another antibody or molecule. The antibodies of the invention are specific for the Vγ4 chain of a γδ TCR, and do not bind epitopes of other antigens, such as the Vγ2 chain of a γδ TCR or the Vγ8 chain of a γδ TCR, as defined herein.

In one embodiment, the epitope may be an activating epitope of a γδ T cell. An "activating" epitope can include, for example, modulation of a TCR-associated function, such as TCR downregulation, degranulation of the cell, cytoxicity, proliferation, mobilisation, increased survival or resistance to exhaustion, intracellular signaling, cytokine or growth factor secretion, phenotypic change, or a change in gene expression. For example, the binding of the activating epitope may stimulate expansion (i.e. proliferation) of the γδ T cell population, preferably the Vγ4+ T cell population. Accordingly, these antibodies can be used to modulate γδ T cell activation, and, thereby, to modulate the immune response. Therefore, in one embodiment, binding of the activating epitope downregulates the γδ TCR. In an additional or alternative embodiment, binding of the activating epitope activates degranulation of the γδ T cell. In a further additional or alternative embodiment, binding of the activating epitope activates the γδ T cell to kill target cells (e.g. cancer cells).

In one embodiment, the present invention provides isolated antibodies or fragments thereof that block Vγ4 and prevent TCR binding (e.g. through steric hinderance). By blocking Vγ4, the antibody may prevent TCR activation and/or signalling. The epitope may therefore be an inhibitory epitope of a γδ T cell. An "inhibitory" epitope can include, for example, blocking TCR function, thereby inhibiting TCR activation.

The epitope is preferably comprised of at least one extracellular, soluble, hydrophilic, external or cytoplasmic portion of the Vγ4 chain of a γδ TCR.

In particular embodiments, the epitope does not comprise an epitope found in a non-germline encoded region of the Vγ4 chain of the γδ TCR, in particular CDR3 of the Vγ4 chain. In a preferred embodiment, the epitope is within a framework region of the Vγ4 chain of the γδ TCR, which may be the hypervariable 4 region of framework region 3. It will be appreciated that such binding allows for the unique recognition of the Vγ4 chain in general without the restriction to the sequences of the TCR which are highly variable between Vγ4 chains (in particular CDR3). As such, it will be appreciated that any Vγ4 chain-comprising γδ TCR may be recognised using the antibodies or fragments thereof as defined herein, irrespective of the specificity of the γδ TCR.

It is possible that the γδ receptor can bind a variety of modulating ligands independently and via spatially distinct domains. Consistent with such multi-modal ligand binding, recent studies by Melandri et al. (2018) Nat. Immunol. 19:1352-1365 have shown that human TCR binding to the endogenous BTNL3 ligand is via a discrete domain located N-terminal of CDR3 on the γ4 chain. The authors highlight that because BTNL3 binding is mediated via this specific germline region of the TCR, the more C-terminal, somatically recombined CDR3 loop remains free to bind other ligands independently. Furthermore, this sub-region of framework region 3 (FR3) (which may also be referred to as 'hypervariable region 4' (HV4)) differs from the human γ2 chain by four amino acids. However, no specific anti-Vγ4 antibodies were disclosed in Melandri et al. nor was it suggested how such antibodies could be derived. Indeed, the prevailing view was that this would not be possible due to the significant sequence homology shared between the human Vγ4 and Vγ2 chains (91% sequence identity).

An antibody which binds within the HV4 region may allow the CDR3 region of the γ4 chain to still bind, with the added advantage of providing a binder which is specific to γ4 over γ2. Furthermore, as the HV4 is germline-encoded, some antibodies targeting this region may recognise all Vγ4 chains, while other antibodies that recognise Vγ4 may be specific for certain Vγ4 chains.

The present invention now provides antibodies and fragments thereof which may specifically bind to the HV4 region of the Vγ4 chain. Therefore, in one embodiment, the antibody or fragment thereof binds to an epitope of the HV4 region of the Vγ4 chain. The HV4 region comprises amino acids 67 to 82 of SEQ ID NO: 1. Therefore, in one embodiment, the epitope comprises one or more amino acid residues within amino acid region 67-82 of SEQ ID NO: 1, e.g. the portion of the Vγ4 chain which is not part of the CDR1, CDR2 and/or CDR3 sequences. In so doing, the antibody or fragment thereof may modulate the interaction between the Vγ4+ TCR and BTNL3/8. In one embodiment, the epitope does not comprise amino acid residues within amino acid region 96-106 (CDR3) of SEQ ID NO: 1. In one embodiment, the epitope does not comprise amino acid residues within amino acid region 50-57 (CDR2) of SEQ ID NO: 1. In one embodiment, the epitope does not comprise amino acid residues within amino acid region 27-32 (CDR1) of SEQ ID NO: 1.

In particular embodiments, the antibody or fragment thereof may, upon binding to one or more of amino acids 67 to 82 of SEQ ID NO: 1, activate the Vγ4+ TCR In a similar manner to the well characterised αβ T cells, γδ T cells utilize a distinct set of somatically rearranged variable (V), diversity (D) (for β and δ only), joining (J), and constant (C) genes, although γδ T cells contain fewer V, D, and J segments than αβ T cells. In one embodiment, the epitope bound by the antibodies (or fragments thereof) does not comprise an epitope found in the J region of the Vγ4 chain. The antibody or fragment may therefore only bind in the V region of the Vγ4 chain. Thus, in one embodiment, the epitope consists of an epitope in the V region of the γδ TCR (e.g. amino acid residues 1-99 of SEQ ID NO: 1).

Reference to the epitope are made in relation to the Vγ4 sequence described in Luoma et al. (2013) *Immunity* 39:1032-1042, and RCSB Protein Data Bank entry: 4MNH, shown as SEQ ID NO: 1:

(SEQ ID NO: 1)
SSNLEGRTKSVIRQTGSSAEITCDLAEGSTGYIHWYLHQEGKAPQRLLYY

DSYTSSVVLESGISPGKYDTYGSTRKNLRMILRNLIENDSGVYYCATWDE

KYYKKLFGSGTTLVVTEDLKNVFPPEVAVFEPSEAEISHTQKATLVCLAT

GFYPDHVELSWWWNGKEVHSGVCTDPQPLKEQPALNDSRYALSSRLRVSA

TFWQNPRNHFRCQVQFYGLSENDEWTQDRAKPVTQ1VSAEAWGRADSRGG

LEVLFQ

SEQ ID NO: 1 represents a soluble TCR comprising a V region (also referred to as the variable domain) and a J region. The V region comprises amino acid residues 1-99, the J region comprises amino acid residues 102-116 and the constant region from TCRβ comprises amino acid residues 117-256. Within the V region, CDR1 is defined as amino acid residues 27 to 32 of SEQ ID NO: 1, CDR2 is defined as amino acid residues 50 to 57 of SEQ ID NO: 1, and CDR3 is defined as amino acid residues 96 to 106 of SEQ ID NO: 1.

The inventors have identified that amino acids K76 (i.e. lysine at position 76) and M80 (i.e. methionine at position 80) of SEQ ID NO: 1 may be particularly important for binding to the HV4 region of the (human) Vγ4 chain (Example 6). Thus, the epitope may comprise, or consist of, K76 and/or M80 of SEQ ID NO: 1.

The inventors have further identified that amino acids within the amino acid region 71-79 of SEQ ID NO: 1 may be particularly important for binding to the HV4 region of the (human) Vγ4 chain. Thus, in a further embodiment, the epitope comprises one or more amino acid residues within amino acid region 71-79 of SEQ ID NO: 1.

In one embodiment, the epitope comprises one or more, such as two, three, four, five, six, seven, eight, nine, ten or more amino acid residues within the described region.

In one embodiment, the epitope comprises one or more (such as 5 or more, such as 10 or more) amino acid residues within amino acid region 67-82 of SEQ ID NO: 1. In a further embodiment the epitope comprises one or more (such as 3 or more, such as 5 or more) amino acid residues within amino acid region 71-79 of SEQ ID NO: 1.

It will be further understood that said antibody (or fragment thereof) does not need to bind to all amino acids within the defined range. Such epitopes may be referred to as linear epitopes. For example, an antibody which binds to an epitope comprising amino acid residues within amino acid region 67-82 of SEQ ID NO: 1, may only bind with one or more of the amino acid residues in said range, e.g. the amino acid residues at each end of the range (i.e. amino acids 67 and 82), optionally including amino acids within the range (i.e. amino acids 71, 73, 75, 76 and 79).

For instance, the inventors have found that amino acid residues 71, 73, 75, 76 and 79 of SEQ ID NO: 1 may form the epitope to which the anti-Vγ4 antibody or fragment thereof binds (Example 8). Thus, in one embodiment, the epitope comprises at least one of amino acid residues 71, 73, 75, 76 and 79 of SEQ ID NO: 1. In further embodiments, the epitope comprises one, two, three, four or five (in particular four or five) amino acids selected from amino acid residues 71, 73, 75, 76 and 79 of SEQ ID NO: 1.

In a further embodiment, the epitope consists of one or more amino acid residues within amino acid regions: 67-82 of SEQ ID NO: 1. In a further embodiment, the epitope consists of one or more amino acid residues within amino acid regions: 71-79 of SEQ ID NO: 1.

In a further embodiment, the epitope comprises amino acid residues: 71-79 of SEQ ID NO: 1, or suitably consists of amino acid residues: 71-79 of SEQ ID NO: 1. In a yet further embodiment, the epitope comprises amino acid residues: 71, 73, 75, 76 and 79 of SEQ ID NO: 1, or suitably consists of amino acid residues: 71, 73, 75, 76 and 79 of SEQ ID NO: 1.

Various techniques are known in the art to establish which epitope is bound by an antibody. Exemplary techniques include, for example, routine cross-blocking assays, alanine scanning mutational analysis, peptide blot analysis, peptide cleavage analysis crystallographic studies and NMR analysis. In addition, methods such as epitope excision, epitope extraction and chemical modification of antigens can be employed. Another method that can be used to identify the amino acids within a polypeptide with which an antibody interacts is hydrogen/deuterium exchange detected by mass spectrometry (as described in Example 8). In general terms, the hydrogen/deuterium exchange method involves deuterium-labelling the protein of interest, followed by binding the antibody to the deuterium-labelled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labelled residues which correspond to the specific amino acids with which the antibody interacts.

In addition, or as an alternative, antigen chimerization & mutagenesis studies can be used to identify the amino acids within a polypeptide with which an antibody interacts (as described in Example 6). In general terms, this method involves creating a series of one or more chimeric antigens wherein the amino acid sequence of a first reference antigen may be systematically altered based on the amino acid sequence of a second reference antigen in order to substitute one or more of the amino acids in the first reference antigen with respective amino acids from the second reference antigen. "Respective amino acids" in this context means amino acids in equivalent positions within the sequence of the first reference antigen and second reference antigen upon sequence alignment thereof. Binding of the test antibody to each of the first reference antigen, second reference antigen and/or series of one or more chimeric antigens is then measured. Loss/gain of binding to each antigen can then be attributed to specific amino acid changes made relative to the first reference sequence and/or second reference sequence. It may be already known whether or not the antibody is capable of binding or not to the first reference antigen and/or the second reference antigen. For instance, as described in Example 6, the first reference antigen may be a human Vγ4 chain and the second reference antigen may be a human Vγ2 chain, with the series of chimeric antigens made by replacing one or more of the amino acids in the Vγ4 chain sequence with the respective one or more amino acids in the Vγ2 chain sequence.

Antibody Sequences

The isolated anti-Vγ4 antibodies, or fragments thereof, of the invention may be described with reference to their CDR sequences.

According to a further aspect of the invention, there is provided an isolated anti-Vγ4 antibody or fragment thereof, which comprises one or more of:

a CDR3 comprising a sequence having at least 80% sequence identity with any one of SEQ ID NOs: 2-47, preferably with SEQ ID NO: 10 and/or 33;

a CDR2 comprising a sequence having at least 80% sequence identity with any one of SEQ ID NOs: 48-70 and SEQUENCES: A1-A23 (of FIG. 1), preferably with SEQ ID NO: 56 and/or A9; and/or a CDR1 comprising a sequence having at least 80% sequence identity with any one of SEQ ID NOs: 71-116, preferably with SEQ ID NO: 79 and/or 102.

According to one aspect of the invention, there is provided an isolated anti-Vγ4 antibody or fragment thereof, which comprises a CDR3 comprising a sequence having at least 80% sequence identity with any one of SEQ ID NOs: 2-47. In one embodiment, the antibody or fragment thereof comprises a CDR2 comprising a sequence having at least 80% sequence identity with any one of SEQ ID NOs: 48-70 and SEQUENCES: A1-A23 (of FIG. 1). In one embodiment, the antibody or fragment thereof comprises a CDR1 comprising a sequence having at least 80% sequence identity with any one of SEQ ID NOs: 71-116.

In some aspects, the isolated anti-Vγ4 antibody or fragment thereof may comprise one or more of:

a heavy chain CDR3 (HCDR3) comprising a sequence having at least 80% sequence identity with any one of SEQ ID NOs: 2-24, preferably with SEQ ID NO: 10;

a heavy chain CDR2 (HCDR2) comprising a sequence having at least 80% sequence identity with any one of SEQ ID NOs: 48-70, preferably with SEQ ID NO: 56; and/or a heavy chain CDR1 (HCDR1) comprising a sequence having at least 80% sequence identity with any one of SEQ ID NOs: 71-93, preferably with SEQ ID NO: 79.

Alternatively, or in addition to, the isolated anti-Vγ4 antibody or fragment thereof may comprise one or more of:

a light chain CDR3 (LCDR3) comprising a sequence having at least 80% sequence identity with any one of SEQ ID NOs: 25-47, preferably with SEQ ID NO: 33;

a light chain CDR2 (LCDR2) comprising a sequence having at least 80% sequence identity with any one of SEQUENCES: A1-A23 (of FIG. 1), preferably with SEQ ID NO: A9; and/or a light chain CDR1 (LCDR1) comprising a sequence having at least 80% sequence identity with any one of SEQ ID NOs: 94-116, preferably with SEQ ID NO: 102.

In one embodiment, the antibody or fragment thereof comprises a CDR3 comprising a sequence having at least 85%, 90%, 95%, 97%, 98% or 99% sequence identity with any one of SEQ ID NOS: 2-47. In one embodiment, the antibody or fragment thereof comprises a CDR2 comprising a sequence having at least 85%, 90%, 95%, 97%, 98% or 99% sequence identity with any one of SEQ ID NOs: 48-70 and SEQUENCES: A1-A23 (of FIG. 1). In one embodiment, the antibody or fragment thereof comprises a CDR1 comprising a sequence having at least 85%, 90%, 95%, 97%, 98% or 99% sequence identity with any one of SEQ ID NOs: 71-116.

In one embodiment, the antibody or fragment thereof comprises a CDR3 consisting of a sequence having at least 85%, 90%, 95%, 97%, 98% or 99% sequence identity with any one of SEQ ID NOs: 2-47. In one embodiment, the antibody or fragment thereof comprises a CDR2 consisting of a sequence having at least 85%, 90%, 95%, 97%, 98% or 99% sequence identity with any one of SEQ ID NOs: 48-70 and SEQUENCES: A1-A23 (of FIG. 1). In one embodiment, the antibody or fragment thereof comprises a CDR1 consisting of a sequence having at least 85%, 90%, 95%, 97%, 98% or 99% sequence identity with any one of SEQ ID NOs: 71-116.

According to a further aspect of the invention, there is provided an antibody or fragment thereof, which comprises a VH region comprising a CDR3 comprising a sequence having at least 80% sequence identity with any one of SEQ ID NOs: 2-24 and/or a VL region comprising a CDR3 comprising a sequence having at least 80% sequence identity with any one of SEQ ID NOs: 25-47. According to a further aspect of the invention, there is provided an antibody or fragment thereof, which comprises a VH region comprising a CDR3 consisting of a sequence having at least 80% sequence identity with any one of SEQ ID NOs: 2-24 and/or a VL region comprising a CDR3 consisting of a sequence having at least 80% sequence identity with any one of SEQ ID NOs: 25-47.

According to a further aspect of the invention, there is provided an antibody or fragment thereof, which comprises a VH region comprising a CDR3 comprising a sequence having at least 90% sequence identity with any one of SEQ ID NOs: 2-24 and/or a VL region comprising a CDR3 comprising a sequence having at least 90% sequence identity with any one of SEQ ID NOs: 25-47. According to a further aspect of the invention, there is provided an antibody or fragment thereof, which comprises a VH region comprising a CDR3 consisting of a sequence having at least 90% sequence identity with any one of SEQ ID NOs: 2-24 and/or a VL region comprising a CDR3 consisting of a sequence having at least 90% sequence identity with any one of SEQ ID NOs: 25-47.

According to a further aspect of the invention, there is provided an antibody or fragment thereof, which comprises a VH region comprising a CDR3 comprising a sequence having at least 95% sequence identity with any one of SEQ ID NOs: 2-24 and/or a VL region comprising a CDR3 comprising a sequence having at least 95% sequence identity with any one of SEQ ID NOs: 25-47. According to a further aspect of the invention, there is provided an antibody or fragment thereof, which comprises a VH region comprising a CDR3 consisting of a sequence having at least 95% sequence identity with any one of SEQ ID NOs: 2-24 and/or a VL region comprising a CDR3 consisting of a sequence having at least 95% sequence identity with any one of SEQ ID NOs: 25-47.

According to a further aspect of the invention, there is provided an antibody or fragment thereof, which comprises a VH region comprising a CDR3 comprising a sequence having at least 80% sequence identity with any one of SEQ ID NOs: 2-24 and a VL region comprising a CDR3 comprising a sequence having at least 80% sequence identity with any one of SEQ ID NOs: 25-47. According to a further aspect of the invention, there is provided an antibody or fragment thereof, which comprises a VH region comprising a CDR3 consisting of a sequence having at least 80% sequence identity with any one of SEQ ID NOs: 2-24 and a VL region comprising a CDR3 consisting of a sequence having at least 80% sequence identity with any one of SEQ ID NOs: 25-47.

Embodiments which refer herein to "at least 80%" or "80% or greater", will be understood to include all values equal to or greater than 80%, such as 85%, 90%, 95%, 97%, 98%, 99% or 100% sequence identity. In one embodiment, the antibody or fragment of the invention comprises at least 85%, such as at least 90%, at least 95%, at least 97%, at least 98% or at least 99% sequence identity to the specified sequence.

Instead of percentage sequence identity, the embodiments may also be defined with one or more amino acid changes, for examples one or more additions, substitutions and/or deletions. In one embodiment, the sequence may comprise up to five amino acid changes, such as up to three amino acid changes, in particular up to two amino acid changes. For example, the sequence may comprise up to five amino acid substitutions, such as up to three amino acid substitutions, in particular up to one or two amino acid substitutions. For example, CDR3 of the antibody or fragment thereof of the present invention may comprise or more suitably consist of a sequence having no more than 2, more suitably no more than 1 substitution(s) compared to any one of SEQ ID NOs: 2-47.

Suitably any residues of CDR1, CDR2 or CDR3 differing from their corresponding residues in SEQ ID NO: 2-116 and SEQUENCES: A1-A23 are conservative substitutions with respect to their corresponding residues. For example, any residues of CDR3 differing from their corresponding residues in SEQ ID NOs: 2-47 are conservative substitutions with respect to their corresponding residues.

In one embodiment, the antibody or fragment thereof comprises:
- (i) a VH region comprising a CDR3 comprising a sequence having at least 80% sequence identity with any one of SEQ ID NOs: 2-24;
- (ii) a VH region comprising a CDR2 comprising a sequence having at least 80% sequence identity with any one of SEQ ID NOs: 48-70;
- (iii) a VH region comprising a CDR1 comprising a sequence having at least 80% sequence identity with any one of SEQ ID NOs: 71-93;
- (iv) a VL region comprising a CDR3 comprising a sequence having at least 80% sequence identity with any one of SEQ ID NOs: 25-47;
- (v) a VL region comprising a CDR2 comprising a sequence having at least 80% sequence identity with any one of SEQUENCES: A1-A23 (of FIG. 1); and/or
- (vi) a VL region comprising a CDR1 comprising a sequence having at least 80% sequence identity with any one of SEQ ID NOs: 94-116.

In one embodiment, the antibody or fragment thereof comprises a heavy chain with:
- (i) a VH region comprising a CDR3 comprising a sequence having at least 80% sequence identity with any one of SEQ ID NOs: 2-24;
- (ii) a VH region comprising a CDR2 comprising a sequence having at least 80% sequence identity with any one of SEQ ID NOs: 48-70; and
- (iii) a VH region comprising a CDR1 comprising a sequence having at least 80% sequence identity with any one of SEQ ID NOs: 71-93.

In one embodiment, the antibody or fragment thereof comprises a light chain with:

- (i) a VL region comprising a CDR3 comprising a sequence having at least 80% sequence identity with any one of SEQ ID NOs: 25-47;
- (ii) a VL region comprising a CDR2 comprising a sequence having at least 80% sequence identity with any one of SEQUENCES: A1-A23 (of FIG. 1); and
- (iii) a VL region comprising a CDR1 comprising a sequence having at least 80% sequence identity with any one of SEQ ID NOs: 94-116.

In one embodiment, the antibody or fragment thereof comprises (or consists of) a VH region comprising a CDR3 comprising a sequence having at least 80% sequence identity with any one of SEQ ID NOs: 2-24, such as SEQ ID NOs: 10, 4, 14, 15, 17, 19 or 23. In one embodiment, the antibody or fragment thereof comprises (or consists of) a VH region comprising a CDR2 comprising a sequence having at least 80% sequence identity with any one of SEQ ID NOs: 48-70, such as SEQ ID NOs: 56, 50, 60, 61, 63, 65 or 69. In one embodiment, the antibody or fragment thereof comprises (or consists of) a VH region comprising a CDR1 comprising a sequence having at least 80% sequence identity with any one of SEQ ID NOs: 71-93, such as SEQ ID NOs: 79, 73, 83, 84, 86, 88 or 92.

In one embodiment, the VH region comprises a CDR3 comprising a sequence of SEQ ID NO: 10, a CDR2 comprising a sequence of SEQ ID NO: 56, and a CDR1 comprising a sequence of SEQ ID NO: 79. In one embodiment, the CDR3 consists of a sequence of SEQ ID NO: 10, the CDR2 consists of a sequence of SEQ ID NO: 56, and the CDR1 consists of a sequence of SEQ ID NO: 79.

In one embodiment, the VH region comprises a CDR3 comprising a sequence of SEQ ID NO: 4, a CDR2 comprising a sequence of SEQ ID NO: 50, and a CDR1 comprising a sequence of SEQ ID NO: 73. In one embodiment, the CDR3 consists of a sequence of SEQ ID NO: 4, the CDR2 consists of a sequence of SEQ ID NO: 50, and the CDR1 consists of a sequence of SEQ ID NO: 73.

In one embodiment, the VH region comprises a CDR3 comprising a sequence of SEQ ID NO: 14, a CDR2 comprising a sequence of SEQ ID NO: 60, and a CDR1 comprising a sequence of SEQ ID NO: 83. In one embodiment, the CDR3 consists of a sequence of SEQ ID NO: 14, the CDR2 consists of a sequence of SEQ ID NO: 60, and the CDR1 consists of a sequence of SEQ ID NO: 83.

In one embodiment, the VH region comprises a CDR3 comprising a sequence of SEQ ID NO: 15, a CDR2 comprising a sequence of SEQ ID NO: 61, and a CDR1 comprising a sequence of SEQ ID NO: 84. In one embodiment, the CDR3 consists of a sequence of SEQ ID NO: 15, the CDR2 consists of a sequence of SEQ ID NO: 61, and the CDR1 consists of a sequence of SEQ ID NO: 84.

In one embodiment, the VH region comprises a CDR3 comprising a sequence of SEQ ID NO: 17, a CDR2 comprising a sequence of SEQ ID NO: 63, and a CDR1 comprising a sequence of SEQ ID NO: 86. In one embodiment, the CDR3 consists of a sequence of SEQ ID NO: 17, the CDR2 consists of a sequence of SEQ ID NO: 63, and the CDR1 consists of a sequence of SEQ ID NO: 86.

In one embodiment, the VH region comprises a CDR3 comprising a sequence of SEQ ID NO: 19, a CDR2 comprising a sequence of SEQ ID NO: 65, and a CDR1 comprising a sequence of SEQ ID NO: 88. In one embodiment, the CDR3 consists of a sequence of SEQ ID NO: 19, the CDR2 consists of a sequence of SEQ ID NO: 65, and the CDR1 consists of a sequence of SEQ ID NO: 88.

In one embodiment, the VH region comprises a CDR3 comprising a sequence of SEQ ID NO: 23, a CDR2 comprising a sequence of SEQ ID NO: 69, and a CDR1 comprising a sequence of SEQ ID NO: 92. In one embodiment, the CDR3 consists of a sequence of SEQ ID NO: 23, the CDR2 consists of a sequence of SEQ ID NO: 69, and the CDR1 consists of a sequence of SEQ ID NO: 92.

In one embodiment, the antibody or fragment thereof comprises (or consists of) a VL region comprising a CDR3 comprising a sequence having at least 80% sequence identity with any one of SEQ ID NOs: 25-47, such as SEQ ID NOs: 33, 27, 37, 38, 40, 42 or 46. In one embodiment, the antibody or fragment thereof comprises (or consists of) a VL region comprising a CDR2 comprising a sequence having at least 80% sequence identity with any one of SEQUENCES: A1-A23 (of FIG. 1), such as SEQUENCES: A9, A3, A13, A14, A16, A18 or A22. In one embodiment, the antibody or fragment thereof comprises (or consists of) a VL region comprising a CDR1 comprising a sequence having at least 80% sequence identity with any one of SEQ ID NOs: 94-116, such as SEQ ID NOs: 102, 96, 106, 107, 109, 111 or 115.

In one embodiment, the VL region comprises a CDR3 comprising a sequence of SEQ ID NO: 33, a CDR2 comprising a sequence of SEQUENCE: A9, and a CDR1 comprising a sequence of SEQ ID NO: 102. In one embodiment, the CDR3 consists of a sequence of SEQ ID NO: 33, the CDR2 consists of a sequence of SEQUENCE: A9, and the CDR1 consists of a sequence of SEQ ID NO: 102.

In one embodiment, the VL region comprises a CDR3 comprising a sequence of SEQ ID NO: 27, a CDR2 comprising a sequence of SEQUENCE: A3, and a CDR1 comprising a sequence of SEQ ID NO: 96. In one embodiment, the CDR3 consists of a sequence of SEQ ID NO: 27, the CDR2 consists of a sequence of SEQUENCE: A3, and the CDR1 consists of a sequence of SEQ ID NO: 96.

In one embodiment, the VL region comprises a CDR3 comprising a sequence of SEQ ID NO: 37, a CDR2 comprising a sequence of SEQUENCE: A13, and a CDR1 comprising a sequence of SEQ ID NO: 106. In one embodiment, the CDR3 consists of a sequence of SEQ ID NO: 37, the CDR2 consists of a sequence of SEQUENCE: A13, and the CDR1 consists of a sequence of SEQ ID NO: 106.

In one embodiment, the VL region comprises a CDR3 comprising a sequence of SEQ ID NO: 38, a CDR2 comprising a sequence of SEQUENCE: A14, and a CDR1 comprising a sequence of SEQ ID NO: 107. In one embodiment, the CDR3 consists of a sequence of SEQ ID NO: 38, the CDR2 consists of a sequence of SEQUENCE: A14, and the CDR1 consists of a sequence of SEQ ID NO: 107.

In one embodiment, the VL region comprises a CDR3 comprising a sequence of SEQ ID NO: 40, a CDR2 comprising a sequence of SEQUENCE: A16, and a CDR1 comprising a sequence of SEQ ID NO: 109. In one embodiment, the CDR3 consists of a sequence of SEQ ID NO: 40, the CDR2 consists of a sequence of SEQUENCE: A16, and the CDR1 consists of a sequence of SEQ ID NO: 109.

In one embodiment, the VL region comprises a CDR3 comprising a sequence of SEQ ID NO: 42, a CDR2 comprising a sequence of SEQUENCE: A18, and a CDR1 comprising a sequence of SEQ ID NO: 111. In one embodiment, the CDR3 consists of a sequence of SEQ ID NO: 42, the CDR2 consists of a sequence of SEQUENCE: A18, and the CDR1 consists of a sequence of SEQ ID NO: 111.

In one embodiment, the VL region comprises a CDR3 comprising a sequence of SEQ ID NO: 46, a CDR2 comprising a sequence of SEQUENCE: A22, and a CDR1 comprising a sequence of SEQ ID NO: 115. In one embodiment, the CDR3 consists of a sequence of SEQ ID NO: 46, the CDR2 consists of a sequence of SEQUENCE: A22, and the CDR1 consists of a sequence of SEQ ID NO: 115.

In one embodiment, the antibody or fragment thereof comprises one or more CDR sequences as described in FIG. 1. In a further embodiment, the antibody or fragment thereof comprises one or more (such as all) CDR sequences of clone 1140_P01_G08 [G4_12] or clone 1139_P01_A04 [G4_03] as described in FIG. 1.

Thus, the invention provides an isolated anti-Vγ4 antibody or fragment thereof comprising one or more of:

(a) a VH comprising a HCDR1 having SEQ ID NO: 79, a HCDR2 having SEQ ID NO: 56 and a HCDR3 having SEQ ID NO: 10, optionally wherein the VH comprises or consists of SEQ ID NO: 125; and
  a VL comprising a LCDR1 having SEQ ID NO: 102, a LCDR2 having SEQUENCE A9 (of FIG. 1) and a LCDR3 having SEQ ID NO: 33, optionally wherein the VL comprises or consists of SEQ ID NO: 148;

(b) a VH comprising a HCDR1 having SEQ ID NO: 86, a HCDR2 having SEQ ID NO: 63 and a HCDR3 having SEQ ID NO: 17, optionally wherein the VH comprises or consists of SEQ ID NO: 132; and
  a VL comprising a LCDR1 having SEQ ID NO: 109, a LCDR2 having SEQUENCE A16 (of FIG. 1) and a LCDR3 having SEQ ID NO: 40, optionally wherein the VL comprises or consists of SEQ ID NO: 155;

(c) a VH comprising a HCDR1 having SEQ ID NO: 73, a HCDR2 having SEQ ID NO: 50 and a HCDR3 having SEQ ID NO: 4, optionally wherein the VH comprises or consists of SEQ ID NO: 119; and
  a VL comprising a LCDR1 having SEQ ID NO: 96, a LCDR2 having SEQUENCE A3 (of FIG. 1) and a LCDR3 having SEQ ID NO: 27, optionally wherein the VL comprises or consists of SEQ ID NO: 142;

(d) a VH comprising a HCDR1 having SEQ ID NO: 83, a HCDR2 having SEQ ID NO: 60 and a HCDR3 having SEQ ID NO: 14, optionally wherein the VH comprises or consists of SEQ ID NO: 129; and
  a VL comprising a LCDR1 having SEQ ID NO: 106, a LCDR2 having SEQUENCE A13 (of FIG. 1) and a LCDR3 having SEQ ID NO: 37, optionally wherein the VL comprises or consists of SEQ ID NO: 152;

(e) a VH comprising a HCDR1 having SEQ ID NO: 84, a HCDR2 having SEQ ID NO: 61 and a HCDR3 having SEQ ID NO: 15, optionally wherein the VH comprises or consists of SEQ ID NO: 130; and
  a VL comprising a LCDR1 having SEQ ID NO: 107, a LCDR2 having SEQUENCE A14 (of FIG. 1) and a LCDR3 having SEQ ID NO: 38, optionally wherein the VL comprises or consists of SEQ ID NO: 153;

(f) a VH comprising a HCDR1 having SEQ ID NO: 88, a HCDR2 having SEQ ID NO: 65 and a HCDR3 having SEQ ID NO: 19, optionally wherein the VH comprises or consists of SEQ ID NO: 134; and
  a VL comprising a LCDR1 having SEQ ID NO: 111, a LCDR2 having SEQUENCE A18 (of FIG. 1) and a LCDR3 having SEQ ID NO: 42, optionally wherein the VL comprises or consists of SEQ ID NO: 157;

(g) a VH comprising a HCDR1 having SEQ ID NO: 92, a HCDR2 having SEQ ID NO: 69 and a HCDR3 having SEQ ID NO: 23, optionally wherein the VH comprises or consists of SEQ ID NO: 138; and
  a VL comprising a LCDR1 having SEQ ID NO: 115, a LCDR2 having SEQUENCE A22 (of FIG. 1) and a LCDR3 having SEQ ID NO: 46, optionally wherein the VL comprises or consists of SEQ ID NO: 161;

(h) a VH comprising a HCDR1 having SEQ ID NO: 71, a HCDR2 having SEQ ID NO: 48 and a HCDR3 having SEQ ID NO: 2, optionally wherein the VH comprises or consists of SEQ ID NO: 117; and a VL comprising a LCDR1 having SEQ ID NO: 94, a LCDR2 having SEQUENCE A1 (of FIG. 1) and a LCDR3 having SEQ ID NO: 25, optionally wherein the VL comprises or consists of SEQ ID NO: 140;

(i) a VH comprising a HCDR1 having SEQ ID NO: 72, a HCDR2 having SEQ ID NO: 49 and a HCDR3 having SEQ ID NO: 3, optionally wherein the VH comprises or consists of SEQ ID NO: 118; and a VL comprising a LCDR1 having SEQ ID NO: 95, a LCDR2 having SEQUENCE A2 (of FIG. 1) and a LCDR3 having SEQ ID NO: 26, optionally wherein the VL comprises or consists of SEQ ID NO: 141;

(j) a VH comprising a HCDR1 having SEQ ID NO: 74, a HCDR2 having SEQ ID NO: 51 and a HCDR3 having SEQ ID NO: 5, optionally wherein the VH comprises or consists of SEQ ID NO: 120; and a VL comprising a LCDR1 having SEQ ID NO: 97, a LCDR2 having SEQUENCE A4 (of FIG. 1) and a LCDR3 having SEQ ID NO: 28, optionally wherein the VL comprises or consists of SEQ ID NO: 143;

(k) a VH comprising a HCDR1 having SEQ ID NO: 75, a HCDR2 having SEQ ID NO: 52 and a HCDR3 having SEQ ID NO: 6, optionally wherein the VH comprises or consists of SEQ ID NO: 121; and a VL comprising a LCDR1 having SEQ ID NO: 98, a LCDR2 having SEQUENCE A5 (of FIG. 1) and a LCDR3 having SEQ ID NO: 29, optionally wherein the VL comprises or consists of SEQ ID NO: 144;

(l) a VH comprising a HCDR1 having SEQ ID NO: 76, a HCDR2 having SEQ ID NO: 53 and a HCDR3 having SEQ ID NO: 7, optionally wherein the VH comprises or consists of SEQ ID NO: 122; and a VL comprising a LCDR1 having SEQ ID NO: 99, a LCDR2 having SEQUENCE A6 (of FIG. 1) and a LCDR3 having SEQ ID NO: 30, optionally wherein the VL comprises or consists of SEQ ID NO: 145;

(m) a VH comprising a HCDR1 having SEQ ID NO: 77, a HCDR2 having SEQ ID NO: 54 and a HCDR3 having SEQ ID NO: 8, optionally wherein the VH comprises or consists of SEQ ID NO: 123; and a VL comprising a LCDR1 having SEQ ID NO: 100, a LCDR2 having SEQUENCE A7 (of FIG. 1) and a LCDR3 having SEQ ID NO: 31, optionally wherein the VL comprises or consists of SEQ ID NO: 146;

(n) a VH comprising a HCDR1 having SEQ ID NO: 78, a HCDR2 having SEQ ID NO: 55 and a HCDR3 having SEQ ID NO: 9, optionally wherein the VH comprises or consists of SEQ ID NO: 124; and a VL comprising a LCDR1 having SEQ ID NO: 101, a LCDR2 having SEQUENCE A8 (of FIG. 1) and a LCDR3 having SEQ ID NO: 32, optionally wherein the VL comprises or consists of SEQ ID NO: 147;

(o) a VH comprising a HCDR1 having SEQ ID NO: 80, a HCDR2 having SEQ ID NO: 57 and a HCDR3 having SEQ ID NO: 11, optionally wherein the VH comprises or consists of SEQ ID NO: 126; and a VL comprising a LCDR1 having SEQ ID NO: 103, a LCDR2 having SEQUENCE A10 (of FIG. 1) and a LCDR3 having SEQ ID NO: 34, optionally wherein the VL comprises or consists of SEQ ID NO: 149;

(p) a VH comprising a HCDR1 having SEQ ID NO: 81, a HCDR2 having SEQ ID NO: 58 and a HCDR3 having SEQ ID NO: 12, optionally wherein the VH comprises or consists of SEQ ID NO: 127; and a VL comprising a LCDR1 having SEQ ID NO: 104, a LCDR2 having SEQUENCE A11 (of FIG. 1) and a LCDR3 having SEQ ID NO: 35, optionally wherein the VL comprises or consists of SEQ ID NO: 150;

(q) a VH comprising a HCDR1 having SEQ ID NO: 82, a HCDR2 having SEQ ID NO: 59 and a HCDR3 having SEQ ID NO: 13, optionally wherein the VH comprises or consists of SEQ ID NO: 128; and a VL comprising a LCDR1 having SEQ ID NO: 105, a LCDR2 having SEQUENCE A12 (of FIG. 1) and a LCDR3 having SEQ ID NO: 36, optionally wherein the VL comprises or consists of SEQ ID NO: 151;

(r) a VH comprising a HCDR1 having SEQ ID NO: 85, a HCDR2 having SEQ ID NO: 62 and a HCDR3 having SEQ ID NO: 16, optionally wherein the VH comprises or consists of SEQ ID NO: 131; and a VL comprising a LCDR1 having SEQ ID NO: 108, a LCDR2 having SEQUENCE A15 (of FIG. 1) and a LCDR3 having SEQ ID NO: 39, optionally wherein the VL comprises or consists of SEQ ID NO: 154;

(s) a VH comprising a HCDR1 having SEQ ID NO: 87, a HCDR2 having SEQ ID NO: 64 and a HCDR3 having SEQ ID NO: 18, optionally wherein the VH comprises or consists of SEQ ID NO: 133; and a VL comprising a LCDR1 having SEQ ID NO: 110, a LCDR2 having SEQUENCE A17 (of FIG. 1) and a LCDR3 having SEQ ID NO: 41, optionally wherein the VL comprises or consists of SEQ ID NO: 156;

(t) a VH comprising a HCDR1 having SEQ ID NO: 89, a HCDR2 having SEQ ID NO: 66 and a HCDR3 having SEQ ID NO: 20, optionally wherein the VH comprises or consists of SEQ ID NO: 135; and a VL comprising a LCDR1 having SEQ ID NO: 112, a LCDR2 having SEQUENCE A19 (of FIG. 1) and a LCDR3 having SEQ ID NO: 43, optionally wherein the VL comprises or consists of SEQ ID NO: 158;

(u) a VH comprising a HCDR1 having SEQ ID NO: 90, a HCDR2 having SEQ ID NO: 67 and a HCDR3 having SEQ ID NO: 21, optionally wherein the VH comprises or consists of SEQ ID NO: 136; and a VL comprising a LCDR1 having SEQ ID NO: 113, a LCDR2 having SEQUENCE A20 (of FIG. 1) and a LCDR3 having SEQ ID NO: 44, optionally wherein the VL comprises or consists of SEQ ID NO: 159;

(v) a VH comprising a HCDR1 having SEQ ID NO: 91, a HCDR2 having SEQ ID NO: 68 and a HCDR3 having SEQ ID NO: 22, optionally wherein the VH comprises or consists of SEQ ID NO: 137; and a VL comprising a LCDR1 having SEQ ID NO: 114, a LCDR2 having SEQUENCE A21 (of FIG. 1) and a LCDR3 having SEQ ID NO: 45, optionally wherein the VL comprises or consists of SEQ ID NO: 160;

and/or (w) a VH comprising a HCDR1 having SEQ ID NO: 93, a HCDR2 having SEQ ID NO: 70 and a HCDR3 having SEQ ID NO: 24, optionally wherein the VH comprises or consists of SEQ ID NO: 139; and a VL comprising a LCDR1 having SEQ ID NO: 116, a LCDR2 having SEQUENCE A23 (of FIG. 1) and a LCDR3 having SEQ ID NO: 47, optionally wherein the VL comprises or consists of SEQ ID NO: 162.

Suitably the VH and VL regions recited above each comprise four framework regions (FR1-FR4). In one embodiment, the antibody or fragment thereof comprises a framework region (e.g. FR1, FR2, FR3 and/or FR4) comprising a sequence having at least 80% sequence identity with the framework region in any one of SEQ ID NOs: 117-162. In one embodiment, the antibody or fragment thereof comprises a framework region (e.g. FR1, FR2, FR3 and/or FR4) comprising a sequence having at least 90%, such as at least 95%, 97% or 99% sequence identity with the framework region in any one of SEQ ID NOs: 117-162. In one embodiment, the antibody or fragment thereof comprises a framework region (e.g. FR1, FR2, FR3 and/or FR4) comprising a sequence in any one of SEQ ID NOs: 117-162. In one embodiment, the antibody or fragment thereof comprises a framework region (e.g. FR1, FR2, FR3 and/or FR4) consisting of a sequence in any one of SEQ ID NOs: 117-162.

The antibodies described herein may be defined by their full light chain and/or heavy chain variable sequences. Therefore, according to a further aspect of the invention, there is provided an isolated anti-Vγ4 antibody or fragment thereof, which comprises an amino acid sequence having at least 80% sequence identity with any one of SEQ ID NOs: 117-162. According to a further aspect of the invention, there is provided an isolated anti-Vγ4 antibody or fragment thereof, which consists of an amino acid sequence having at least 80% sequence identity with any one of SEQ ID NOs: 117-162.

In one embodiment, the antibody or fragment thereof comprises a VH region comprising an amino acid sequence having at least 80% sequence identity with any one of SEQ ID NOs: 117-139. In one embodiment, the antibody or fragment thereof comprises a VH region consisting of an amino acid sequence having at least 80% sequence identity with any one of SEQ ID NOs: 117-139. In a further embodiment, the VH region comprises an amino acid sequence having at least 80% sequence identity with any one of SEQ ID NOs: 125, 119, 129, 130, 132, 134 or 138. In a further embodiment, the VH region consists of an amino acid sequence having at least 80% sequence identity with any one of SEQ ID NOs: 125, 119, 129, 130, 132, 134 or 138.

In one embodiment, the antibody or fragment thereof comprises a VL region comprising an amino acid sequence having at least 80% sequence identity with any one of SEQ ID NOs: 140-162. In one embodiment, the antibody or fragment thereof comprises a VL region consisting of an amino acid sequence having at least 80% sequence identity with any one of SEQ ID NOs: 140-162. In a further embodiment, the VL region comprises an amino acid sequence having at least 80% sequence identity with any one of SEQ ID NOs: 148, 142, 152, 153, 155, 157 or 161. In a further embodiment, the VL region consists of an amino acid sequence having at least 80% sequence identity with any one of SEQ ID NOs: 148, 142, 152, 153, 155, 157 or 161.

In a further embodiment, the antibody or fragment thereof comprises a VH region comprising an amino acid sequence having at least 80% sequence identity with any one of SEQ ID NOs: 117-139 and a VL region comprising an amino acid sequence having at least 80% sequence identity with any one of SEQ ID NOs: 140-162. In a further embodiment, the antibody or fragment thereof comprises a VH region consisting of an amino acid sequence having at least 80% sequence identity with any one of SEQ ID NOs: 117-139 and a VL region consisting of an amino acid sequence having at least 80% sequence identity with any one of SEQ ID NOs: 140-162.

In one embodiment, the antibody or fragment thereof comprises a VH region comprising an amino acid sequence of SEQ ID NO: 125 (1140_P01_G08) [G4_12]. In one embodiment, the antibody or fragment thereof comprises a VH region consisting of an amino acid sequence of SEQ ID NO: 125. In one embodiment, the antibody or fragment thereof comprises a VL region comprising an amino acid sequence of SEQ ID NO: 148 (1140_P01_G08) [G4_12]. In one embodiment, the antibody or fragment thereof comprises a VL region consisting of an amino acid sequence of SEQ ID NO: 148.

In one embodiment, the antibody or fragment thereof comprises a VH region comprising an amino acid sequence of SEQ ID NO: 125 and a VL region comprising an amino acid sequence of SEQ ID NO: 148. In one embodiment, the antibody or fragment thereof comprises a VH region consisting of an amino acid sequence of SEQ ID NO: 125 and a VL region consisting of an amino acid sequence of SEQ ID NO: 148.

In one embodiment, the antibody or fragment thereof comprises a VH region comprising an amino acid sequence of SEQ ID NO: 119 (1139_P01_A04) [G4_3]. In one embodiment, the antibody or fragment thereof comprises a VH region consisting of an amino acid sequence of SEQ ID NO: 119. In one embodiment, the antibody or fragment thereof comprises a VL region comprising an amino acid sequence of SEQ ID NO: 142 (1139_P01_A04) [G4_3]. In one embodiment, the antibody or fragment thereof comprises a VL region consisting of an amino acid sequence of SEQ ID NO: 142.

In one embodiment, the antibody or fragment thereof comprises a VH region comprising an amino acid sequence of SEQ ID NO: 119 and a VL region comprising an amino acid sequence of SEQ ID NO: 142. In one embodiment, the antibody or fragment thereof comprises a VH region consisting of an amino acid sequence of SEQ ID NO: 119 and a VL region consisting of an amino acid sequence of SEQ ID NO: 142.

In one embodiment, the antibody or fragment thereof comprises a VH region comprising an amino acid sequence of SEQ ID NO: 129 (1248_P02_D10) [G4_16]. In one embodiment, the antibody or fragment thereof comprises a VH region consisting of an amino acid sequence of SEQ ID NO: 129. In one embodiment, the antibody or fragment thereof comprises a VL region comprising an amino acid sequence of SEQ ID NO: 152 (1248_P02_D10) [G4_16]. In one embodiment, the antibody or fragment thereof comprises a VL region consisting of an amino acid sequence of SEQ ID NO: 152.

In one embodiment, the antibody or fragment thereof comprises a VH region comprising an amino acid sequence of SEQ ID NO: 129 and a VL region comprising an amino acid sequence of SEQ ID NO: 152. In one embodiment, the antibody or fragment thereof comprises a VH region consisting of an amino acid sequence of SEQ ID NO: 129 and a VL region consisting of an amino acid sequence of SEQ ID NO: 152.

In one embodiment, the antibody or fragment thereof comprises a VH region comprising an amino acid sequence of SEQ ID NO: 130 (1254_P01_H04) [G4_18]. In one embodiment, the antibody or fragment thereof comprises a VH region consisting of an amino acid sequence of SEQ ID NO: 130. In one embodiment, the antibody or fragment thereof comprises a VL region comprising an amino acid sequence of SEQ ID NO: 153 (1254_P01_H04) [G4_18]. In one embodiment, the antibody or fragment thereof comprises a VL region consisting of an amino acid sequence of SEQ ID NO: 153.

In one embodiment, the antibody or fragment thereof comprises a VH region comprising an amino acid sequence of SEQ ID NO: 130 and a VL region comprising an amino acid sequence of SEQ ID NO: 153. In one embodiment, the antibody or fragment thereof comprises a VH region consisting of an amino acid sequence of SEQ ID NO: 130 and a VL region consisting of an amino acid sequence of SEQ ID NO: 153.

In one embodiment, the antibody or fragment thereof comprises a VH region comprising an amino acid sequence of SEQ ID NO: 132 (1254_P02_G02) [G4_20]. In one embodiment, the antibody or fragment thereof comprises a VH region consisting of an amino acid sequence of SEQ ID NO: 132. In one embodiment, the antibody or fragment thereof comprises a VL region comprising an amino acid sequence of SEQ ID NO: 155 (1254_P02_G02) [G4_20]. In one embodiment, the antibody or fragment thereof comprises a VL region consisting of an amino acid sequence of SEQ ID NO: 155.

In one embodiment, the antibody or fragment thereof comprises a VH region comprising an amino acid sequence of SEQ ID NO: 132 and a VL region comprising an amino acid sequence of SEQ ID NO: 155. In one embodiment, the antibody or fragment thereof comprises a VH region consisting of an amino acid sequence of SEQ ID NO: 132 and a VL region consisting of an amino acid sequence of SEQ ID NO: 155.

In one embodiment, the antibody or fragment thereof comprises a VH region comprising an amino acid sequence of SEQ ID NO: 134 (1253_P03_H05) [G4_23]. In one embodiment, the antibody or fragment thereof comprises a VH region consisting of an amino acid sequence of SEQ ID NO: 134. In one embodiment, the antibody or fragment thereof comprises a VL region comprising an amino acid sequence of SEQ ID NO: 157 (1253_P03_H05) [G4_23]. In one embodiment, the antibody or fragment thereof comprises a VL region consisting of an amino acid sequence of SEQ ID NO: 157.

In one embodiment, the antibody or fragment thereof comprises a VH region comprising an amino acid sequence of SEQ ID NO: 134 and a VL region comprising an amino acid sequence of SEQ ID NO: 157. In one embodiment, the antibody or fragment thereof comprises a VH region consisting of an amino acid sequence of SEQ ID NO: 134 and a VL region consisting of an amino acid sequence of SEQ ID NO: 157.

In one embodiment, the antibody or fragment thereof comprises a VH region comprising an amino acid sequence of SEQ ID NO: 138 (1248_P02_C10) [G4_27]. In one embodiment, the antibody or fragment thereof comprises a VH region consisting of an amino acid sequence of SEQ ID NO: 138. In one embodiment, the antibody or fragment thereof comprises a VL region comprising an amino acid sequence of SEQ ID NO: 161 (1248_P02_C10) [G4_27]. In one embodiment, the antibody or fragment thereof comprises a VL region consisting of an amino acid sequence of SEQ ID NO: 161.

In one embodiment, the antibody or fragment thereof comprises a VH region comprising an amino acid sequence of SEQ ID NO: 138 and a VL region comprising an amino acid sequence of SEQ ID NO: 161. In one embodiment, the antibody or fragment thereof comprises a VH region consisting of an amino acid sequence of SEQ ID NO: 138 and a VL region consisting of an amino acid sequence of SEQ ID NO: 161.

For fragments comprising both the VH and VL regions, these may be associated either covalently (e.g. via disulphide bonds or a linker) or non-covalently. The antibody fragment described herein may comprise an scFv, i.e. a fragment comprising a VH region and a VL region joined by a linker. In one embodiment, the VH and VL region are joined by a (e.g. synthetic) polypeptide linker. The polypeptide linker may comprise a $(Gly_4Ser)_n$ linker, where n=from 1 to 8, e.g. 2, 3, 4, 5 or 7. The polypeptide linker may comprise a $[(Gly_4Ser)_n(Gly_3AlaSer)_m]_p$ linker, where n=from 1 to 8, e.g. 2, 3, 4, 5 or 7, m=from 0 to 8, e.g. 0, 1, 2 or 3, and p=from 1 to 8, e.g. 1, 2 or 3. In a further embodiment, the linker comprises SEQ ID NO: 186. In a further embodiment, the linker consists of SEQ ID NO: 186.

In one embodiment, the antibody or fragment thereof comprises an amino acid sequence having at least 80% sequence identity with any one of SEQ ID NOs: 163-185. In a further embodiment, the antibody or fragment thereof comprises an amino acid sequence of any one of SEQ ID NOs: 163-185. In a yet further embodiment, the antibody or fragment thereof comprises an amino acid sequence of SEQ ID NOs: 171, 165, 175, 176, 178, 180 or 184.

In one embodiment, the antibody or fragment thereof consists of an amino acid sequence having at least 80% sequence identity with any one of SEQ ID NOs: 163-185. In a further embodiment, the antibody or fragment thereof consists of an amino acid sequence of any one of SEQ ID NOs: 163-185. In a yet further embodiment, the antibody or fragment thereof consists of an amino acid sequence of SEQ ID NOs: 171, 165, 175, 176, 178, 180 or 184.

As described herein, the antibodies may be in any format. In a preferred embodiment, the antibody is in an IgG1 format. Therefore, in one embodiment, the antibody or fragment thereof comprises an amino acid sequence having at least 80% sequence identity with any one of SEQ ID NOs: 233-255. In a further embodiment, the antibody or fragment thereof comprises an amino acid sequence of any one of SEQ ID NOs: 233-255. In a yet further embodiment, the antibody or fragment thereof comprises an amino acid sequence of SEQ ID NOs: 235, 241, 245, 246 or 254.

In one embodiment, the antibody or fragment thereof consists of an amino acid sequence having at least 80% sequence identity with any one of SEQ ID NOs: 233-255. In a further embodiment, the antibody or fragment thereof consists of an amino acid sequence of any one of SEQ ID NOS: 233-255. In a yet further embodiment, the antibody or fragment thereof consists of an amino acid sequence of SEQ ID NOs: 235, 241, 245, 246 or 254.

Alternatively, there is provided an antibody or fragment thereof which comprises or consists of a heavy chain amino acid sequence having at least 80% sequence identity with any one of SEQ ID NOs: 284-306 and/or a light chain amino acid sequence having at least 80% sequence identity with any one of SEQ ID NOs: 307-329. Thus, there is provided an antibody or fragment thereof which comprises or consists of a heavy chain amino acid sequence according to any one of SEQ ID NOs: 284-306 and/or a light chain amino acid sequence according to any one of SEQ ID NOS: 307-329. In a particular embodiment, the antibody or fragment thereof comprises or consists of a heavy chain amino acid sequence according to SEQ ID NO: 292 and a light chain amino acid sequence according to SEQ ID NO: 315 (clone G4_12). In a further embodiment, the antibody or fragment thereof comprises or consists of a heavy chain amino acid sequence according to SEQ ID NO: 286 and a light chain amino acid sequence according to SEQ ID NO: 309 (clone G4_3). In a further embodiment, the antibody or fragment thereof comprises or consists of a heavy chain amino acid sequence according to SEQ ID NO: 296 and a light chain amino acid sequence according to SEQ ID NO: 319 (clone G4_16). In a further embodiment, the antibody or fragment thereof comprises or consists of a heavy chain amino acid sequence according to SEQ ID NO: 297 and a light chain amino acid sequence according to SEQ ID NO: 320 (clone G4_18). In a further embodiment, the antibody or fragment thereof comprises or consists of a heavy chain amino acid sequence according to SEQ ID NO: 299 and a light chain amino acid sequence according to SEQ ID NO: 322 (clone G4_20). In a further embodiment, the antibody or fragment thereof comprises or consists of a heavy chain amino acid sequence according to SEQ ID NO: 301 and a light chain amino acid sequence according to SEQ ID NO: 324 (clone G4_23). In a further embodiment, the antibody or fragment thereof comprises or consists of a heavy chain amino acid sequence according to SEQ ID NO: 305 and a light chain amino acid sequence according to SEQ ID NO: 328 (clone G4_27). In other embodiments, the antibody or fragment thereof comprises or consists of:

(a) a heavy chain amino acid sequence according to SEQ ID NO: 284 and a light chain amino acid sequence according to SEQ ID NO: 307 (clone G4_1);

(b) a heavy chain amino acid sequence according to SEQ ID NO: 285 and a light chain amino acid sequence according to SEQ ID NO: 308 (clone G4_2);

(c) a heavy chain amino acid sequence according to SEQ ID NO: 287 and a light chain amino acid sequence according to SEQ ID NO: 310 (clone G4_4);

(d) a heavy chain amino acid sequence according to SEQ ID NO: 288 and a light chain amino acid sequence according to SEQ ID NO: 311 (clone G4_5);

(e) a heavy chain amino acid sequence according to SEQ ID NO: 289 and a light chain amino acid sequence according to SEQ ID NO: 312 (clone G4_6);

(f) a heavy chain amino acid sequence according to SEQ ID NO: 290 and a light chain amino acid sequence according to SEQ ID NO: 313 (clone G4_7);

(g) a heavy chain amino acid sequence according to SEQ ID NO: 291 and a light chain amino acid sequence according to SEQ ID NO: 314 (clone G4_10);

(h) a heavy chain amino acid sequence according to SEQ ID NO: 293 and a light chain amino acid sequence according to SEQ ID NO: 316 (clone G4_13);

(i) a heavy chain amino acid sequence according to SEQ ID NO: 294 and a light chain amino acid sequence according to SEQ ID NO: 317 (clone G4_14);

(j) a heavy chain amino acid sequence according to SEQ ID NO: 295 and a light chain amino acid sequence according to SEQ ID NO: 318 (clone G4_15);

(k) a heavy chain amino acid sequence according to SEQ ID NO: 298 and a light chain amino acid sequence according to SEQ ID NO: 321 (clone G4_19);

(l) a heavy chain amino acid sequence according to SEQ ID NO: 300 and a light chain amino acid sequence according to SEQ ID NO: 323 (clone G4_22);

(m) a heavy chain amino acid sequence according to SEQ ID NO: 302 and a light chain amino acid sequence according to SEQ ID NO: 325 (clone G4_24);

(n) a heavy chain amino acid sequence according to SEQ ID NO: 303 and a light chain amino acid sequence according to SEQ ID NO: 326 (clone G4_25);

(o) a heavy chain amino acid sequence according to SEQ ID NO: 304 and a light chain amino acid sequence according to SEQ ID NO: 327 (clone G4_26); or (p) a heavy chain amino acid sequence according to SEQ ID NO: 306 and a light chain amino acid sequence according to SEQ ID NO: 329 (clone G4_28).

Competing Antibodies

In one embodiment, the antibody or fragment thereof which specifically binds to a Vγ4 chain of a γδ TCR and not to a Vγ2 chain of a γδ TCR binds to the same, or essentially the same, epitope as, or competes with, an antibody or fragment thereof as defined or exemplified herein. One can easily determine whether an antibody binds to the same epitope as, or competes for binding with, a reference anti-Vγ4 antibody by using routine methods known in the art. For example, to determine if a test antibody binds to the same epitope as a reference anti-Vγ4 antibody of the invention, the reference antibody is allowed to bind to a Vγ4 protein or peptide under saturating conditions. Next, the ability of a test antibody to bind to the Vγ4 chain is assessed. If the test antibody is able to bind to Vγ4 following saturation binding with the reference anti-Vγ4 antibody, it can be concluded that the test antibody binds to a different epitope than the reference anti-Vγ4 antibody. On the other hand, if the test antibody is not able to bind to the Vγ4 chain following saturation binding with the reference anti-Vγ4 antibody, then the test antibody may bind to the same epitope as the epitope bound by the reference anti-Vγ4 antibody of the invention.

The present invention also includes anti-Vγ4 antibodies or fragments thereof that compete for binding to Vγ4 with an antibody or fragment thereof as defined herein, or an antibody having the CDR sequences of any of the exemplary antibodies described herein. For example, competitive assays can be performed with the antibody of the present invention in order to determine what proteins, antibodies, and other antagonists compete for binding to the Vγ4 chain with the antibody of the present invention and/or share the epitope. These assays are readily known to those of skill in the art; they evaluate competition between antagonists or ligands for a limited number of binding sites on a protein, e.g., Vγ4. The antibody (or fragment thereof) is immobilized or insolubilized before or after the competition and the sample bound to the Vγ4 chain is separated from the unbound sample, for example, by decanting (where the antibody was pre-insolubilized) or by centrifuging (where the antibody was precipitated after the competitive reaction). Also, the competitive binding may be determined by whether the function is altered by the binding or lack of binding of the antibody to the protein, e.g., whether antibody molecule inhibits or potentiates the enzymatic activity of, for example, a label. ELISA and other functional assays may be used, as known in the art and described herein.

Two antibodies bind to the same or overlapping epitope if each competitively inhibits (blocks) binding of the other to the target antigen. That is, a 1-, 5-, 10-, 20- or 100-fold or more excess of one antibody inhibits binding of the other by at least 50% but preferably 75%, 90% or even 99% as measured in a competitive binding assay. Alternatively, two antibodies have the same epitope if essentially all amino acid mutations in the target antigen that reduce or eliminate binding of one antibody also reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Antibody Sequence Modifications

The antibodies and fragments thereof may be modified using known methods. Sequence modifications to antibody molecules described herein can be readily incorporate by those skilled in the art. The following examples are non-limiting.

During antibody discovery and sequence recovery from phage libraries, desired antibody variable domains may be re-formatted into full length IgG by sub-cloning. To accelerate the process, variable domains are often transferred using restriction enzymes. These restriction sites may introduce additional/alternate amino acids and away from the canonical sequence (such canonical sequences may be found, for example, in the international ImMunoGeneTics [IMGT] information system, see http://www.imgt.org). These may be introduced as kappa or lambda light chain sequence modifications.

Kappa Light Chain Modifications

The kappa light chain variable sequences may be cloned using restriction sites (e.g. Nhe1-Not1) during re-formatting into full length IgG. More specifically, at the kappa light chain N-terminus, an additional Ala-Ser sequence was introduced to support cloning. Preferably, this additional AS sequence is then removed during further development such to generate the canonical N-terminal sequence. Hence, in one embodiment, kappa light chain containing antibodies described herein do not contain an AS sequence at their N-termini, i.e. SEQ ID NOs: 140-147 and 156-158 do not comprise the initial AS sequence. It will be understood that this embodiment also applies to other sequences included herein which contain this sequence.

Additional amino acid changes may be made to support cloning. For example, for the antibodies described herein, at the kappa light-chain variable-domain/constant domain border a valine-to-alanine change was introduced to support cloning when preparing full-length sequences. This resulted in a kappa constant domain modification. Specifically this results in the constant domain beginning RTAAAPS (from a NotI restriction site). Preferably, this sequence can be modified during further development to generate the canonical kappa light-chain constant regions which start with RTVAAPS. Such modifications do not change the functional properties of the antibodies. Hence, in one embodiment kappa light chain containing antibodies described herein contain a constant domain starting with the sequence RTV. Therefore, in one embodiment, sequence RTAAAPS of SEQ ID NOs: 233-240, 249-251, 307-314 and 323-325 is replaced with sequence RTVAAPS. In a preferred embodiment comprising a preferred kappa light chain constant domain allotype, the kappa light chain constant domain has an amino acid sequence according to SEQ ID NO: 330 and may be combined with any light chain variable domain disclosed herein.

Lambda Light Chain Modifications

Similar to the kappa example above, the lambda light chain variable domains may also be cloned by introducing restriction sites (e.g. Nhe1-Not1) during re-formatting into full length IgG. More specifically, at the lambda light chain N-terminus, an additional Ala-Ser sequence may be introduced to support cloning. Preferably, this additional AS sequence is then removed during further development such to generate the canonical N-terminal sequence. Hence, in one embodiment, lambda light chain containing antibodies described herein do not contain an AS sequence at their N-termini i.e. SEQ ID NOs: 148-155 and 159-162 do not comprise the initial AS sequence. It will be understood that this embodiment also applies to other sequences included herein which contain this sequence.

As another example, for the antibodies described herein at the lambda light-chain variable-domain/constant domain border a lysine-to-alanine sequence change was introduced to support cloning when preparing full-length sequences. This resulted in a lambda constant domain modification. Specifically this results in the constant domain beginning with GQPAAAPS (from a NotI restriction site). Preferably, this sequence can be modified during further development such to generate the canonical lambda light constant region which starts GQPKAAPS. Such modifications do not change the functional properties of the antibodies. Hence, in one embodiment, lambda light chain containing antibodies described herein contain a constant domain starting with the sequence GQPK. Therefore, in one embodiment, sequence GQPAAAPS of SEQ ID NOs: 241-248, 252-255, 315-322 and 326-329 is replaced with sequence GQPKAAPS. In a preferred embodiment comprising a preferred lambda light chain constant domain allotype, the lambda light chain constant domain has an amino acid sequence according to SEQ ID NO: 331 and may be combined with any light chain variable domain disclosed herein.

Lambda and Kappa Light Chain Modifications

In view of the above disclosure regarding removal of the N-terminal AS residues from the lambda and/or kappa light chain variable domains disclosed herein as SEQ ID Nos: 140-162, the isolated anti-Vγ4 antibody or fragment thereof of the invention may comprise a light chain variable (VL) amino acid sequence according to any one of SEQ ID NOs: 261-283, which correspond to SEQ ID NOs: 140-162 lacking the N-terminal AS residues. Therefore, any reference in this specification to a VL amino acid sequence according to one or more of SEQ ID NOs: 140-162 may be substituted with a VL amino acid sequence according to SEQ ID NOs: 261-283 respectively, and all such embodiments are hereby disclosed. By way of illustration, reference herein to a light chain variable domain according to SEQ ID NO: 148 (derived from clone G4_12) may be substituted with reference to SEQ ID NO: 269.

Heavy Chain Modifications

Typically, human variable heavy chain sequences start with either the basic glutamine (Q) or acidic glutamate (E). However both such sequences are then known to convert to the acidic amino acid residue, pyro-glutamate (pE). The Q to pE conversion results in a charge change to the antibody, whilst a E to pE conversion does not change the charge of the antibody. Hence, to avoid a variable charge-change over time, one option is to modify a starting heavy chain sequence from Q to E in the first instance. Hence, in one embodiment, the heavy chain of antibody described herein having a Q residue at the N-terminus of the heavy chain may contain a Q to E modification at the N-terminus. In particular, the initial residue of any of SEQ ID NOs: 118, 120, 124, 126, 132, 133, 135, 137, 138 and/or 139 may be modified from Q to E. It will be understood that this embodiment also applies to other sequences included herein which contain this sequence (i.e. any embodiment incorporating these sequences, for example into full-length antibodies or fragments thereof). In some embodiments, it may be advantageous to substitute an E residue at the N-terminus of the heavy chain to a Q residue. Accordingly, in some embodiments, the E residue at the N-terminus of any one SEQ ID NOs: 117, 119, 121-123, 125, 127-131, 134 and/or 136 may be substituted with a Q residue.

Furthermore, the C-terminus of the IgG1 constant domain ends with PGK. However the terminal basic lysine (K) is then often cleaved during expression (e.g. in CHO cells). This in turn results in a charge change to the antibody through varied loss of the C-terminal lysine residue. Therefore, one option is to remove the lysine in the first instance resulting in a uniform and consistent heavy chain C-terminus sequence ending in PG. Hence, in one embodiment, the heavy chain of an antibody described herein has the terminal K removed from its C-terminus. In particular, the antibody of the invention may comprise any one of SEQ ID NOs: 233-255 or 284-306 where the terminal lysine residue has been removed.

Optional Allotype Modifications

During antibody discovery, specific human allotypes may be employed. Optionally, the antibodies can be switched to differing human allotypes during development. By way of non-limiting example, for the kappa chain there are three human allotypes designated Km1, Km1,2 and Km3 which define three Km alleles (using allotype numbering): Km1 correlates with valine153 (IMGT V45.1) and leucine 191 (IMGT L101); Km1,2 correlates with alanine 153 (IMGT A45.1) and leucine 191 (IMGT L101); and Km3 correlates with alanine 153 (IMGT A45.1) and valine 191 (IMGT V101). Optionally, one can therefore modify a sequence from one allotype to another by standard cloning approaches. For example a L191V (IMGT L101V) change will convert a Km1,2 allotype to a Km3 allotype. For further reference on such allotypes see Jefferis and Lefranc (2009) *MAbs* 1 (4): 332-8, which is herein incorporated by reference.

Hence in one embodiment an antibody described herein contains amino acid substitutions derived from another human allotype of the same gene. In a further embodiment, the antibody contains a L191V (IMGT L101V) substitution to the kappa chain to convert the c-domain from a km1,2 to a km3 allotype.

In a preferred embodiment comprising a preferred kappa light chain constant domain allotype, the kappa light chain constant domain has an amino acid sequence according to SEQ ID NO: 330 and may be combined with any light chain variable domain disclosed herein. In an alternative preferred embodiment comprising a preferred lambda light chain constant domain allotype, the lambda light chain constant domain has an amino acid sequence according to SEQ ID NO: 331 and may be combined with any light chain variable domain disclosed herein.

Antibody Binding

The antibody or fragment thereof of the invention may bind to the Vγ4 chain of a γδ TCR with a binding affinity (KD) as measured by surface plasmon resonance of less than $3.0 \times 10^{-7}$ M (i.e. 300 nM) or less than $1.5 \times 10^{-7}$ M (i.e. 150 nM). In a further embodiment, the KD is $1.3 \times 10^{-7}$ M (i.e. 130 nM) or less, such as $1.0 \times 10^{-7}$ M (i.e. 100 nM) or less. In a yet further embodiment, the KD is less than $6.0 \times 10^{-8}$ M (i.e. 60 nM), such as less than $5.0 \times 10^{-8}$ M (i.e. 50 nM), less than $4.0 \times 10^{-8}$ M (i.e. 40 nM), less than $3.0 \times 10^{-8}$ M (i.e. 30 nM) or less than $2.0 \times 10^{-8}$ M (i.e. 20 nM). In further embodiments, the KD may be $1.0 \times 10^{-8}$ M (i.e. 10 nM) or less, such as $5.0 \times 10^{-9}$ M (i.e. 5 nM) or less, $4.0 \times 10^{-9}$ M (i.e. 4 nM) or less, $3.0 \times 10^{-9}$ M (i.e. 3 nM) or less, $2.0 \times 10^{-9}$ M (i.e. 2 nM) or less, or $1.0 \times 10^{-9}$ M (i.e. 1 nM) or less. For example, according to one aspect, there is provided a (e.g. human) anti-Vγ4 antibody which binds to the Vγ4 chain of a γδ TCR with a binding affinity (KD) as measured by surface plasmon resonance of less than $1.5 \times 10^{-7}$ M (i.e. 150 nM).

In one aspect of the invention, there is provided an antibody or fragment thereof which binds to the Vγ4 chain of a γδ TCR with a binding affinity (KD) as measured by surface plasmon resonance of less than $4.0 \times 10^{-8}$ M (i.e. 40 nM), less than $3.0 \times 10^{-8}$ M (i.e. 30 nM) or less than $2.0 \times 10^{-8}$ M (i.e. 20 nM).

In one embodiment, the binding affinity of the antibody or fragment thereof is established by coating the antibody or fragment thereof directly or indirectly (e.g. by capture with an anti-human IgG Fc) onto the surface of a sensor (e.g. an amine high capacity chip or equivalent), wherein the target bound by the antibody or fragment thereof (i.e. the Vγ4 chain of a γδ TCR) is flowed over the chip to detect binding. In alternative embodiments, the antigen may be directly or indirectly coated onto the surface of the sensor, over which test antibody or a fragment thereof is then flowed. The skilled person is well able to determine suitable test conditions. For example, suitably, a MASS-2 instrument (which may also be referred to as Sierra SPR-32) may be used at 25° C. in PBS+0.02% TWEEN (polysorbate) 20 running buffer at 30 μl/min. In other suitable embodiments, a Reichert 4SPR instrument may be used at room temperature (e.g. 25° C.) in PBS+0.05% TWEEN (polysorbate) 20 with a flowrate of 25 μl/min.

Antibody Functional Characterisation

Described herein are assays which may be used to define antibody function. For example, the antibody or fragment thereof described herein may be assessed by γδ TCR engagement, e.g. measuring downregulation of the γδ TCR upon antibody binding and/or upregulation of CD69 surface expression upon antibody binding. Surface expression of the γδ TCR or CD69 following application of the antibody or fragment thereof (optionally presented on the surface of a cell) can be measured, e.g. by flow cytometry.

The antibody or fragment thereof described herein may also be assessed by measuring γδ T cell degranulation. For example, expression of CD107a, a marker for cell degranulation, can be measured following application of the antibody or fragment thereof (optionally presented on the surface of a cell) to γδ T cells, e.g. by flow cytometry. The antibody or fragment thereof described herein may also be assessed by measuring γδ T cell-mediated killing activity (to test if the antibody has an effect on the killing activity of the γδ T cell i.e. the ability of the antibody to induce the γδ T cell to directly or indirectly kill target cells). For example, target cells may be incubated with γδ T cells in the presence of the antibody or fragment thereof (optionally presented on the surface of a cell). Following incubation, the culture may be stained with a cell viability dye to distinguish between live and dead target cells. The proportion of dead cells can then be measured, e.g. by flow cytometry.

As described herein, the antibodies or fragments thereof used in the assays may be presented on a surface, for example the surface of a cell, such as a cell comprising an Fc receptor. For example, the antibodies or fragments thereof may be presented on the surface of THP-1 cells, such as TIB-202™ cells (available from American Type Culture Collection (ATCC)). Alternatively, the antibodies or fragments thereof may be used directly in the assays.

In such functional assays, output may be measured by calculating the half maximal concentration, also referred to as "EC50" or "effective concentration at 50 percent". The term "IC50" refers to the inhibitory concentration. Both EC50 and IC50 may be measured using methods known in the art, such as flow cytometry methods. For the avoidance of doubt, the values of EC50 in the present application are provided using IgG1 formatted antibody. Such values can be easily converted based on the molecular weight of the antibody format for equivalent values as follows:

(µg/ml)/(MW in kDa)=µM

Millilitres may be denoted as "ml" or "mL" herein and used interchangeably.

The EC50 for downregulation of the γδ TCR upon antibody (or fragment) binding may be less than 0.5 g/ml, such as less than 0.4 µg/ml, 0.3 µg/ml, 0.2 µg/ml, 0.15 µg/ml, 0.1 µg/ml or 0.05 µg/ml. In particular, said EC50 values are when the antibody is measured in an IgG1 format. For example, the EC50 γδ TCR downregulation value can be measured using flow cytometry.

The EC50 for γδ T cell degranulation upon antibody (or fragment) binding may be less than 0.05 µg/ml, such as less than 0.04 µg/ml, 0.03 µg/ml, 0.02 µg/ml, 0.015 µg/ml, 0.01 µg/ml or 0.008 µg/ml. In particular, said EC50 values are when the antibody is measured in an IgG1 format. For example, the γδ T cell degranulation EC50 value can be measured by detecting CD107a expression (i.e. a marker of cell degranulation) using flow cytometry. In one embodiment, CD107a expression is measured using an anti-CD107a antibody, such as anti-human CD107a BV421 (clone H4A3) (BD Biosciences).

The EC50 for γδ T cell-mediated killing upon the antibody (or fragment) binding may be less than 0.5 µg/ml, such as less than 0.4 µg/ml, 0.3 µg/ml, 0.2 µg/ml, 0.15 µg/ml, 0.1 µg/ml or 0.07 µg/ml. In particular, said EC50 values are when the antibody is measured in an IgG1 format. For example, the EC50 γδ T cell-mediated killing value can be measured by detecting proportion of dead cells (i.e. using a cell viability dye) using flow cytometry following incubation of the antibody, γδ T cell and target cells. In one embodiment, death of the target cell is measured using a cell viability dye is Viability Dye eFluor™ 520 (ThermoFisher).

In the assays described in these aspects, the antibody or fragment thereof may be presented on the surface of a cell, such as a THP-1 cell, for example TIB-202™ (ATCC). The THP-1 cells are optionally labelled with a dye, such as CellTracker™ Orange CMTMR (ThermoFisher).

Immunoconjugates

The antibodies or fragments thereof of the present invention, may be conjugated to a therapeutic moiety, such as a cytotoxin or a chemotherapeutic agent. Such conjugates may be referred to as immunoconjugates. As used herein, the term "immunoconjugate" refers to an antibody or fragment thereof which is chemically or biologically linked to another moiety, such as a cytotoxin, a radioactive agent, a cytokine, an interferon, a target or reporter moiety, an enzyme, a toxin, a peptide or protein or a therapeutic agent. The antibody or fragment thereof may be linked to the cytotoxin, radioactive agent, cytokine, interferon, target or reporter moiety, enzyme, toxin, peptide or therapeutic agent at any location along the molecule so long as it is able to bind its target. Examples of immunoconjugates include antibody-drug conjugates and antibody-toxin fusion proteins. In one embodiment, the agent may be a second different antibody to Vγ4. In certain embodiments, the antibody may be conjugated to an agent specific for a tumor cell or a virally infected cell. The type of therapeutic moiety that may be conjugated to the anti-Vγ4 antibody will take into account the condition to be treated and the desired therapeutic effect to be achieved.

Multi-Specific Antibodies

The antibodies of the present invention may be mono-specific or they may bind additional targets and are therefore bi-specific or multi-specific. Multi-specific antibodies may be specific for different epitopes of one target polypeptide or may be specific for more than one target polypeptide. Therefore, in one embodiment, the antibody or fragment thereof comprises a first binding specificity to Vγ4 and a second binding specificity for a second target epitope.

The second binding specificity may target an antigen on the same cell as Vγ4 or on a different cell of the same tissue type or of a different tissue type. In certain embodiments, the target epitope may be on a different cell including a different T-cell, a B-cell, a tumour cell, an autoimmune tissue cell or a virally infected cell. Alternatively, the target epitope may be on the same cell.

Polynucleotides and Expression Vectors

In one aspect of the invention there is provided a polynucleotide encoding the anti-Vγ4 antibody or fragment of the invention. In one embodiment, the polynucleotide comprises or consists of a sequence having at least 70%, such as at least 80%, such as at least 90%, such as at least 95%, such as at least 99% sequence identity with SEQ ID NOs: 187-232. In one embodiment, the expression vector comprises the VH region of SEQ ID NOs: 187-209. In another embodiment, the expression vector comprises the VL region of SEQ ID NOs: 210-232. In a further embodiment the polynucleotide comprises or consists of SEQ ID NOs: 187-232. In a further aspect there is provided a cDNA comprising said polynucleotide.

In one embodiment, the polynucleotide comprises or consists of a sequence having at least 70%, such as at least 80%, such as at least 90%, such as at least 95%, such as at least 99% sequence identity with SEQ ID NOs: 195, 189, 199, 200, 202, 204, 208, 218, 212, 222, 223, 225, 227 or 231. In one embodiment, the expression vector comprises the VH region of SEQ ID NOs: 195, 189, 199, 200, 202, 204, or 208. In another embodiment, the expression vector comprises the VL region of SEQ ID NOs: 218, 212, 222, 223, 225, 227 or 231. In a further embodiment the polynucleotide comprises or consists of SEQ ID NOs: 195, 189, 199, 200, 202, 204, 208, 218, 212, 222, 223, 225, 227 or 231, in particular SEQ ID NO: 195 and/or 218; or SEQ ID NO: 189 and/or 212. In a further aspect there is provided a cDNA comprising said polynucleotide.

In one aspect of the invention there is provided a polynucleotide comprising or consisting of a sequence having at least 70%, such as at least 80%, such as at least 90%, such as at least 95%, such as at least 99% sequence identity with any one of the portions of SEQ ID NOs: 187-232 which encodes CDR1, CDR2 and/or CDR3 of the encoded immunoglobulin chain variable domain. In one embodiment, the polynucleotide comprises or consists of a sequence having at least 70%, such as at least 80%, such as at least 90%, such as at least 95%, such as at least 99% sequence identity with any one of the portions of SEQ ID NOs: 195, 189, 199, 200, 202, 204, 208, 218, 212, 222, 223, 225, 227 or 231 which encodes CDR1, CDR2 and/or CDR3 of the encoded immunoglobulin chain variable domain.

In one aspect of the invention there is provided a polynucleotide comprising or consisting of a sequence having at least 70%, such as at least 80%, such as at least 90%, such as at least 95%, such as at least 99% sequence identity with any one of the portions of SEQ ID NOs: 187-232 which encodes FR1, FR2, FR3 and/or FR4 of the encoded immunoglobulin chain variable domain. In one embodiment, the polynucleotide comprises or consists of a sequence having at least 70%, such as at least 80%, such as at least 90%, such as at least 95%, such as at least 99% sequence identity with any one of the portions of SEQ ID NOs: 195, 189, 199, 200, 202, 204, 208, 218, 212, 222, 223, 225, 227 or 231 which encodes FR1, FR2, FR3 and/or FR4 of the encoded immunoglobulin chain variable domain.

To express the antibodies, or fragments thereof, polynucleotides encoding partial or full-length light and heavy chains, as described herein, are inserted into expression vectors such that the genes are operatively linked to transcriptional and translational control sequences (which may be termed an 'expression cassette' as well understood in the art). Therefore, in one aspect of the invention there is provided an expression vector comprising a polynucleotide sequence of the invention as defined herein. In one embodiment, the expression vector comprises the VH sequence of any one of SEQ ID NOs: 187-209, such as any one of SEQ ID NOs: 195, 189, 199, 200, 202, 204 or 208. In another embodiment, the expression vector comprises the VL region of any one of SEQ ID NOS: 210-232, such as any one of SEQ ID NOs: 218, 212, 222, 223, 225, 227 or 231. Such expression vectors or cassettes may be used in pairs, suitably pairing the heavy and light chain variable sequences according to the pairing of various amino acid sequences providing the antibodies of the invention disclosed herein. In some embodiments, the expression vectors comprise a sequence having at least 70%, such as at least 80%, such as at least 90%, such as at least 95%, such as at least 99% sequence identity or 100% identity with any one of SEQ ID NOs: 187-209 (encoding a variable heavy region) and further comprises a sequence having at least 70%, such as at least 80%, such as at least 90%, such as at least 95%, such as at least 99% sequence identity or 100% identity with any one of SEQ ID NOs: 210-232 (encoding a variable light region). Again, the sequences may be provided in specific pairs as described herein to encode the antibodies of the invention.

The present invention also provides polynucleotide sequences and expression vectors and plasmids encoding all of the antibody sequences disclosed herein, including any variant antibody sequences disclosed herein optionally comprising one or more amino acid substitutions.

The polynucleotides and expression vectors of the invention may also be described in reference to the amino acid sequence encoded. Therefore, in one embodiment, the polynucleotide comprises or consists of a sequence encoding the amino acid sequence of any one of SEQ ID NOs: 1 to 186, 233-260.

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, as well as mammalian, specifically human, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis, gene reassembly, artificial gene synthesis, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used. A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity.

Expression vectors include, for example, plasmids, retroviruses, cosmids, yeast artificial chromosomes (YACs) and Epstein-Barr virus (EBV) derived episomes. The polynucleotide is ligated into a vector such that transcriptional and translational control sequences within the vector serve their intended function of regulating the transcription and translation of the polynucleotide. Expression and/or control sequences can include promoters, enhancers, transcription terminators, a start codon (i.e. ATG) 5' to the coding sequence, splicing signals for introns and stop codons. The expression vector and expression control sequences are chosen to be compatible with the expression host cell used. Thus, the invention further provides a nucleotide sequence encoding single chain variable fragments of the invention according to any one of SEQ ID NOs: 163-185, comprising a VH region and a VL region joined by a synthetic linker (encoding SEQ ID NO: 186). It will be understood that polynucleotides or expression vectors of the invention may comprise the VH region, the VL region or both (optionally including the linker). Therefore, polynucleotides encoding the VH and VL regions can be inserted into separate vectors, alternatively sequences encoding both regions are inserted into the same expression vector. The polynucleotide(s) are inserted into the expression vector by standard methods (e.g., ligation of complementary restriction sites on the polynucleotide and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described herein. The expression vector can also encode a signal peptide that facilitates secretion of the antibody (or fragment thereof) from a host cell. The polynucleotide may be cloned into the vector such that the signal peptide is linked in-frame to the amino terminus of the antibody. The signal peptide can be an immunoglobulin signal peptide or a heterologous signal peptide (i.e., a signal peptide from a non-immunoglobulin protein).

In one aspect of the invention there is provided a cell (e.g. a host cell) comprising the polynucleotide or expression vector as defined herein. It will be understood that the cell may comprise a first vector encoding the light chain of the antibody or fragment thereof, and a second vector encoding the heavy chain of the antibody or fragment thereof. Alternatively, the heavy and light chains may both be encoded on the same expression vector introduced into the cell.

In one embodiment, the polynucleotide or expression vector encodes a membrane anchor or transmembrane domain fused to the antibody or fragment thereof, wherein the antibody or fragment thereof is presented on an extracellular surface of the cell.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, transduction, encapsulation of the polynucleotide(s) in liposomes, biolistic injection and direct microinjection of the DNA into nuclei. In addition, nucleic acid molecules may be introduced into mammalian cells by viral vectors.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, Hela cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Antigen-binding fragments of antibodies such as the scFv and Fv fragments can be isolated and expressed in *E. coli* using methods known in the art.

The antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Antibodies (or fragments) of the invention can be obtained and manipulated using the techniques disclosed for example in Green and Sambrook, *Molecular Cloning: A Laboratory Manual* (2012) 4th Edition Cold Spring Harbour Laboratory Press.

Monoclonal antibodies can be produced using hybridoma technology, by fusing a specific antibody-producing B cell with a myeloma (B cell cancer) cell that is selected for its ability to grow in tissue culture and for an absence of antibody chain synthesis.

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma, b) culturing the immortalized cells (hybridoma) formed and recovering the cells producing the antibodies having the desired specificity.

Alternatively, the use of a hybridoma cell is not required. Antibodies capable of binding to the target antigens as described herein may be isolated from a suitable antibody library via routine practice, for example, using the phage display, yeast display, ribosomal display, or mammalian display technology known in the art. Accordingly, monoclonal antibodies can be obtained, for example, by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity.

Optionally, an isolated polynucleotide encoding an antibody or fragment thereof as described herein and which binds to the Vγ4 chain of a γδ T cell can also be readily manufactured to make sufficient quantities to be employed as a medicament to ameliorate the signs or symptoms of disease. When employed as a medicament in this manner, typically the polynucleotide of interest is first operatively linked to an expression vector or expression cassette designed to express said antibody or fragment thereof in a subject or patient. Such expression cassettes and methods of delivery of polynucleotides or what are sometime termed 'nucleic-based' medicaments and are well known in the art. For a recent review see Hollevoet and Declerck (2017) J. Transl. Med. 15 (1): 131.

Also provided is a method for the production of an anti-Vγ4 antibody or fragment or variant thereof, comprising culturing a host cell of the invention in a cell culture medium under conditions to express the encoding nucleic acid sequence of the plasmid or vector inside the cell. The method may further comprise obtaining the anti-Vγ4 antibody or fragment or variant thereof from the cell culture supernatant. The obtained antigen-binding molecule may then be formulated into a pharmaceutical composition. Further, there is provided a method of producing a cell that expresses an anti-Vγ4 antibody or fragment or variant thereof, comprising transfecting said cell with a plasmid or vector of the invention. Said cells can then be cultured for the production of the anti-Vγ4 antibody or fragment or variant thereof.

Pharmaceutical Compositions

According to a further aspect of the invention, there is provided a composition comprising the antibody or fragment thereof as defined herein. In such embodiments, the composition may comprise the antibody, optionally in combination with other excipients. Also included are compositions comprising one or more additional active agents (e.g. active agents suitable for treating the diseases mentioned herein).

According to a further aspect of the invention, there is provided a pharmaceutical composition comprising the antibody or fragment thereof as defined herein, together with a pharmaceutically acceptable diluent or carrier. The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, salts, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or fragment thereof may be included.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions.

The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration.

It is within the scope of the invention to use the pharmaceutical composition of the invention in therapeutic methods for the treatment of diseases as described herein as an adjunct to, or in conjunction with, other established therapies normally used in the treatment of such diseases.

In a further aspect of the invention, the antibody, composition or pharmaceutical composition is administered sequentially, simultaneously or separately with at least one active agent.

Treatment Methods

According to a further aspect of the invention, there is provided an isolated anti-Vγ4 antibody or fragment thereof as defined herein for use as a medicament.

In one embodiment, the antibody or fragment thereof is for use in therapy. In particular, the antibody or fragment thereof may be for use in the treatment of cancer, an infectious disease or an inflammatory disease. In a further embodiment, the antibody or fragment thereof is for use in the treatment of cancer.

According to a further aspect of the invention, there is provided the pharmaceutical composition as defined herein for use as a medicament. In one embodiment, the pharmaceutical composition is for use in therapy, particularly for use in the treatment of cancer, an infectious disease or an inflammatory disease. In a further embodiment, the pharmaceutical composition is for use in the treatment of cancer.

According to a further aspect of the invention, there is provided a method of modulating an immune response in a subject in need thereof comprising administering a therapeutically effective amount of the isolated anti-Vγ4 antibody or fragment thereof as defined herein. In various embodiments, modulating an immune response in a subject comprises binding or targeting γδ T cells, activating γδ T cells, causing or increasing proliferation of γδ T cells, causing or increasing expansion of γδ T cells, causing or increasing γδ T cell degranulation, causing or increasing γδ T cell-mediated killing activity.

According to a further aspect of the invention, there is provided method of treating a cancer, an infectious disease or an inflammatory disease in a subject in need thereof, comprising administering a therapeutically effective amount of the isolated anti-Vγ4 antibody or fragment thereof as defined herein. Alternatively, a therapeutically effective amount of the pharmaceutical composition is administered.

According to further aspects of the invention, there is provided the use of an antibody or fragment thereof as defined herein for the manufacture of a medicament, for example in the treatment of cancer, an infectious disease or an inflammatory disease.

Uses of Antibodies or Fragments Thereof

According to a further aspect of the invention, there is provided the use of an anti-Vγ4 antibody or fragment thereof as described herein to study antigen recognition, activation, signal transduction or function of γδ T cells (in particular Vγ4 T cells). As described herein, the antibodies have been shown to be active in assays which can be used to investigate γδ T cell function. Such antibodies may also be useful for inducing the proliferation of γδ T cells, therefore may be used in methods of expanding γδ T cells (such as Vγ4 T cells).

Antibodies which bind to the Vγ4 chain can be used to detect γδ T cells. For example, the antibody may be labelled with a detectable label or reporter molecule or used as a capture ligand to selectively detect and/or isolate Vγ4 T cells in a sample. Labelled antibodies find use in many methods known in the art, for example immunohistochemistry and ELISA.

The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Fluorescent labels applied to antibodies of the invention may then be used in fluorescence-activated cell sorting (FACS) methods.

Methods of Generating Antibodies or Fragments Thereof

Described herein are soluble TCRs for use in generating antibodies. As described herein, prior to the development of the present invention it was conventionally held that it would not be possible to develop an antibody or fragment thereof able to specifically bind the Vγ4 chain, particularly the human Vγ4 chain. This was due to the high degree of sequence similarity (91%) between the human Vγ4 chain and human Vγ2 chain of a γδ TCR. To overcome this significant challenge, the inventors developed specific antigens and methodologies. Therefore, according to an aspect of the invention, there is provided an isolated antigen comprising an amino acid sequence having at least 80% sequence identity with SEQ ID NO: 256 for use in generating an anti-Vγ4 antibody or fragment thereof.

Another important aspect of the antigen preparation process was to design antigens which were suitable for expression as a protein. The γδ TCR is a complex protein involving a heterodimer with inter-chain and intra-chain disulphide bonds. A leucine zipper (LZ) format and Fc format were used to generate soluble TCR antigens to be used in the phage display selections. Thus, the invention also provides an isolated antigen comprising an amino acid sequence having at least 80% sequence identity with SEQ ID NO: 257 or 258 for use in generating an anti-Vγ4 antibody or fragment thereof.

Furthermore, gamma delta (γδ) T cells are polyclonal with CDR3 polyclonality. In order to avoid a situation where generated antibodies would be selected against the CDR3 sequence (as the CDR3 sequence will differ from TCR clone to TCR clone), the antigen design involved maintaining a consistent CDR3 in different formats. This design aimed to generate antibodies recognising a sequence within the gamma-4 variable domain, which is germline encoded and therefore the same in all clones, thus providing antibodies which recognise a wider subset of γδ T cells. Thus, according to an aspect of the invention, there is provided a method of generating an anti-Vγ4 antibody or fragment thereof comprising:

(i) designing a series of antigens comprising a TCR gamma variable 4 (Vγ4) amino acid sequence wherein the CDR3 sequence of the Vγ4 is the same for all antigens in the series;

(ii) exposing a first antigen designed in step (i) to an antibody library (e.g. by phage display);

(iii) isolating the antibodies or fragments thereof which bind to the antigen;

(iv) exposing the isolated antibodies or fragments thereof to a second antigen designed in step (i); and (v) isolating the antibodies or fragments thereof which bind to both the first and second antigen.

The TRGV4 amino acid sequence preferably corresponds to human TRGV4 with amino acid sequence corresponding to amino acids 1-99 of SEQ ID NO: 1. The series of antigens described herein may also comprise antigens (i.e. TCR gamma variable 4 chain) in different formats. Therefore, said antigens may be synthetic/recombinant antigens. For example, the antigens may be presented as a leucine zipper or Fc fusion. In one embodiment, the TCR gamma variable 4 (Vγ4) amino acid sequence comprises SEQ ID NO: 256. In one embodiment, the TCR Vγ4 amino acid sequence comprises SEQ ID NO: 257. In one embodiment, the TCR Vγ4 amino acid sequence comprises SEQ ID NO: 258.

The antigens may also comprise additional features to aid in protein expression. For example, the recombinant TCR antigens described herein may be fused to a TCRα or TCRβ constant region (see Xu et al. (2011) *PNAS* 108:2414-2419).

In one embodiment, the method further comprises exposing the isolated antibodies or fragments thereof to a second series of antigens comprising a γδ TCR with a different gamma variable chain, such as gamma variable 2 (Vγ2) or gamma variable 8 (Vγ8), and then deselecting the antibodies or fragments thereof which also bind to the second series of antigens. In particular, the method comprises exposing the isolated antibodies or fragments thereof to a second series of antigens comprising a γδ TCR with a gamma variable 2 (Vγ2) chain and deselecting the antibodies or fragments thereof which also bind to the second series of antigens. As already noted, there is a high percentage identity (about 91%) between the sequences of Vγ4 and Vγ2, therefore this ensures that antibodies which are specific for Vγ4 are selected. In one embodiment, the second series of antigens comprise a γδ TCR with a Vγ2 chain. The TRGV2 and TRGV8 amino acid sequences preferably correspond to human TRGV2 and TRGV8 with amino acid sequences corresponding to SEQ ID NOs: 335 and 336 respectively. As described above in respect of a TCR gamma variable 4 chain, the series of TRGV2 and TRGV8 antigens described herein may also comprise antigens in different formats. Therefore, said antigens may be synthetic/recombinant antigens. For example, the antigens may be presented as a leucine zipper or Fc fusion or as fusions to alpha/beta TCR constant domains (e.g. TRAC and TRBC domains). Therefore, in a further embodiment, the second series of antigens comprise SEQ ID NO: 259 and/or SEQ ID NO: 260 (antigens comprising Vγ2 variable domains).

In a further embodiment, the second series of antigens comprising a γδ TCR with a different gamma variable chain comprises the same CDR3 sequence as the first series of antigens. Thus, all antigens comprise the same CDR3 sequence (from Vγ4).

In one embodiment, the first and/or second series of antigens are presented as a leucine zipper and/or Fc fusion.

In one embodiment, the series of antigens are in a heterodimeric and/or homodimeric format.

In a further embodiment, the series of antigens comprise, together with the target (i.e. TCR gamma variable 4 chain), a paired TCR variable chain. In certain embodiments, the paired TCR variable chain is a variable δ (Vδ) chain (i.e. the antigen is in a heterodimeric format). In one embodiment, the Vγ4 chain and the Vδ chain are covalently linked by at least one disulphide bond. In further embodiments, the Vγ4 chain and the Vδ chain are paired by specific heterodimerisation interaction (e.g. leucine zipper). In an alternative embodiment, the Vγ4 chain and the Vδ chain comprise a single chain in-frame fusion. In a certain embodiment, the Vγ4 chain is N-terminal to the Vδ chain. In an alternative embodiment, the Vγ4 chain is C-terminal to the Vδ chain. In a further embodiment, the single chain in-frame fusion comprises an internal linker sequence. In an alternative embodiment, the paired TCR variable chain is another Vγ chain. In a further embodiment, the Vγ chain is the same as the target (i.e. the antigen is in a homodimeric format).

Example 2 provided herein describes an example of a series of antigens that may be used. It will be understood that the (first) series of antigens comprises antigens where a Vγ4 is present (e.g. L1, L4 and Fc4/4) and the second series of antigens comprises antigens where a Vγ4 is not present (e.g. L2, L3).

In further embodiments, the series of antigens comprises the target (i.e. TCR gamma variable 4 chain) fused in-frame to a TCR constant region. For example, said TCR constant region may be fused in-frame to the C-terminus of the Vγ4 chain. In one embodiment, the TCR constant region may be a human TCR constant region. In one embodiment, the TCR constant region is selected from the TCRα or TCRβ constant region. In another embodiment, the constant region is the TCRγ constant region. In yet further embodiments, the series of antigens may comprise a further, second TCR constant region, wherein the second TCR constant region is fused in-frame to the paired TCR variable chain. In further embodiments, the second TCR constant region is selected from the TCRα or TCRβ constant region. In a further embodiment, the constant region is TCRγ constant region.

Methods of this aspect of the invention aim to isolate antibodies (or fragments thereof) which recognise a sequence within the variable domain, which is germline encoded and therefore the same in all clones, thus providing antibodies which recognise a wider subset of Vγ4+γδ T cells.

It will be appreciated that the series of antigens as described herein may be presented in either soluble or linked/fused form or associated with cell membrane. For example, for display purposes the series of antigens may be fused or tethered to inorganic or organic materials (e.g. beads, plates, columns or phages) or expressed on a cell surface.

According to various embodiments of the present invention, the series of antigens comprising a TCR gamma variable 4 (Vγ4) amino acid sequence comprise a CDR3 sequence of the Vγ4 which is the same for all antigens. In one embodiment, the CDR3 sequence is derived from the CDR3 sequence of RSCB Protein Data Bank entries: 4MNH.

According to another aspect of the invention, there is provided a method which comprises:

(i) designing at least one first protein comprising a Vγ4 variable domain sequence;

(ii) designing at least one second protein comprising a Vγ1, Vγ2, Vγ3, Vγ5, Vγ8, Vγ9, Vγ10 or Vγ11 variable domain sequence; and (iii) selecting or isolating or identifying an antibody that exhibits a stronger binding signal or strength or characteristic to the first protein compared to the second protein.

In one embodiment, the second protein comprises a Vγ2 variable domain sequence. In a further embodiment, the method comprises at least two second proteins, such as a protein comprising a Vγ2 variable domain sequence and a protein comprising a Vγ8 variable domain sequence.

According to another aspect of the invention, there is provided a method which comprises:

(i) designing at least one first protein comprising a Vγ4 variable domain sequence;

(ii) designing at least one second protein comprising a Vγ2 variable domain sequence;

(iii) exposing an antibody library to the first protein to select for antibodies that bind the first sequence;

(iv) comparing the binding strength or signal or characteristic of the selected antibodies to the second protein; and (v) selecting, isolating or identifying antibodies that exhibit a stronger binding strength or signal or characteristic to the first protein over the binding signal or strength or characteristic to the second protein.

In one embodiment, the first protein and/or the second protein comprise multimeric proteins. In a further embodiment, the multimeric proteins comprise a paired TCR variable chain, such as a TCR variable chain derived from a delta variable chain.

In one embodiment, the first protein and/or second protein is a soluble protein. In another embodiment, the first protein and/or second protein is cell bound. In an alternative embodiment, the first protein and/or second protein is plate bound.

In one embodiment, the characteristic is the ability of the antibody to induce more TCR receptor turnover. In another embodiment, the characteristic is the ability of the antibody to upregulate CD69 on a Vγ4+ cell (e.g. compared to a Vγ2+ cell).

According to a further aspect of the invention, there is provided an antibody obtained by the method as defined herein.

CLAUSES

A set of clauses defining the invention and its preferred aspects is as follows:

1. An isolated antibody or fragment thereof, which specifically binds to a gamma variable 4 (Vγ4) chain of a γδ T cell receptor (TCR) and not to a gamma variable 2 (Vγ2) chain of a γδ TCR.

2. The isolated anti-Vγ4 antibody or fragment thereof as defined in clause 1, wherein the Vγ4 chain of the γδ TCR is human Vγ4 and the Vγ2 chain of the γδ TCR is human Vγ2.

3. The isolated anti-Vγ4 antibody or fragment thereof as defined in clause 1 or 2, which binds to an epitope of the Vγ4 chain of the γδ TCR comprising one or more amino acid residues within amino acid region 67-82 of SEQ ID NO: 1.

4. The isolated anti-Vγ4 antibody or fragment thereof as defined in any one of clauses 1 to 3, which binds to an epitope of the Vγ4 chain of the γδ TCR comprising one or more amino acid residues within amino acid region 71-79 of SEQ ID NO: 1.

5. The isolated anti-Vγ4 antibody or fragment thereof as defined in clause 4, wherein the epitope comprises at least one of amino acid residues 71, 73, 75, 76, 79 of SEQ ID NO: 1.

6. The isolated anti-Vγ4 antibody or fragment thereof as defined in any one of clauses 1 to 5, wherein the epitope consists of one or more amino acid residues within amino acid region 67-82 of SEQ ID NO: 1.

7. The isolated anti-Vγ4 antibody or fragment thereof as defined in any one of clauses 1 to 6, wherein the epitope comprises or consists of K76 and/or M80 of SEQ ID NO: 1.

8. The isolated anti-Vγ4 antibody or fragment thereof as defined in any one of clauses 1 to 7, wherein the epitope is an activating epitope of a γδ T cell.

9. The isolated anti-Vγ4 antibody or fragment thereof as defined in clause 8, wherein binding of the activating epitope: (i) downregulates the γδ TCR; (ii) activates degranulation of the γδ T cell; (iii) activates γδ T cell-mediated killing; and/or (iv) activates or increases Vγ4 chain-mediated cell signalling.

10. The isolated anti-Vγ4 antibody or fragment thereof as defined in any one of clauses 1 to 9, which only binds to an epitope in the V region of a Vγ4 chain of a γδ TCR.

11. The isolated anti-Vγ4 antibody or fragment thereof as defined in any one of clauses 1 to 10, which does not bind to an epitope found in CDR3 of a Vγ4 chain of a γδ TCR.

12. An isolated anti-Vγ4 antibody or fragment thereof, which comprises one or more of:

a CDR3 comprising a sequence having at least 80% sequence identity with any one of SEQ ID NOs: 2-47, preferably with SEQ ID NO: 10 and/or 33;

a CDR2 comprising a sequence having at least 80% sequence identity with any one of SEQ ID NOs: 48-70 and SEQUENCES: A1-A23 (of FIG. 1), preferably with SEQ ID NO: 56 and/or SEQUENCE A9; and/or a CDR1 comprising a sequence having at least 80% sequence identity with any one of SEQ ID NOs: 71-116, preferably with SEQ ID NO: 79 and/or 102.

13. The isolated anti-Vγ4 antibody or fragment thereof as defined in clause 12, which comprises a VH region comprising a CDR3 comprising a sequence having at least 80% sequence identity with any one of SEQ ID NOs: 2-24, such as SEQ ID NOs: 10, 4, 14, 15, 17, 19 or 23.

14. The isolated anti-Vγ4 antibody or fragment thereof as defined in clause 12 or clause 13, which comprises a VH region comprising a CDR2 comprising a sequence having at least 80% sequence identity with any one of SEQ ID NOs: 48-70, such as SEQ ID NOs: 56, 50, 60, 61, 63, 65 or 69.

15. The isolated anti-Vγ4 antibody or fragment thereof as defined in any one of clauses 12 to 14, which comprises a VH region comprising a CDR1 comprising a sequence having at least 80% sequence identity with any one of SEQ ID NOs: 71-93, such as SEQ ID NOs: 79, 73, 83, 84, 86, 88 or 92.

16. The isolated anti-Vγ4 antibody or fragment thereof as defined in any one of clauses 12 to 15, which comprises a VH region comprising a CDR3 comprising a sequence of SEQ ID NO: 10, a CDR2 comprising a sequence of SEQ ID NO: 56, and a CDR1 comprising a sequence of SEQ ID NO: 79.

17. The isolated anti-Vγ4 antibody or fragment thereof as defined in any one of clauses 12 to 15, which comprises a VH region comprising a CDR3 comprising a sequence of SEQ ID NO: 4, a CDR2 comprising a sequence of SEQ ID NO: 50, and a CDR1 comprising a sequence of SEQ ID NO: 73.

18. The isolated anti-Vγ4 antibody or fragment thereof as defined in any one of clauses 12 to 15, which comprises a VH region comprising a CDR3 comprising a sequence of SEQ ID NO: 14, a CDR2 comprising a sequence of SEQ ID NO: 60, and a CDR1 comprising a sequence of SEQ ID NO: 83.

19. The isolated anti-Vγ4 antibody or fragment thereof as defined in any one of clauses 12 to 15, which comprises a VH region comprising a CDR3 comprising a sequence of SEQ ID NO: 15, a CDR2 comprising a sequence of SEQ ID NO: 61, and a CDR1 comprising a sequence of SEQ ID NO: 84.

20. The isolated anti-Vγ4 antibody or fragment thereof as defined in any one of clauses 12 to 15, which comprises a VH region comprising a CDR3 comprising a sequence of SEQ ID NO: 17, a CDR2 comprising a sequence of SEQ ID NO: 63, and a CDR1 comprising a sequence of SEQ ID NO: 86.

21. The isolated anti-Vγ4 antibody or fragment thereof as defined in any one of clauses 12 to 15, which comprises a VH region comprising a CDR3 comprising a sequence of SEQ ID NO: 19, a CDR2 comprising a sequence of SEQ ID NO: 65, and a CDR1 comprising a sequence of SEQ ID NO: 88.

22. The isolated anti-Vγ4 antibody or fragment thereof as defined in any one of clauses 12 to 15, which comprises a VH region comprising a CDR3 comprising a sequence of SEQ ID NO: 23, a CDR2 comprising a sequence of SEQ ID NO: 69, and a CDR1 comprising a sequence of SEQ ID NO: 92.

23. The isolated anti-Vγ4 antibody or fragment thereof as defined in any one of clauses 12 to 22, which comprises a VL region comprising a CDR3 comprising a sequence having at least 80% sequence identity with any one of SEQ ID NOs: 25-47, such as SEQ ID NOs: 33, 27, 37, 38, 40, 42 or 46.

24. The isolated anti-Vγ4 antibody or fragment thereof as defined in any one of clauses 12 to 23, which comprises a VL region comprising a CDR2 comprising a sequence having at least 80% sequence identity with any one of SEQUENCES: A1-A23 (of FIG. 1), such as SEQUENCES: A9, A3, A13, A14, A16, A18 or A22.

25. The isolated anti-Vγ4 antibody or fragment thereof as defined in any one of clauses 12 to 26, which comprises a VL region comprising a CDR1 comprising a sequence having at least 80% sequence identity with any one of SEQ ID NOs: 94-116, such as SEQ ID NOs: 102, 96, 106, 107, 109, 111 or 115.

26. The isolated anti-Vγ4 antibody or fragment thereof as defined in any one of clauses 12 to 25, which comprises a VL region comprising a CDR3 comprising a sequence of SEQ ID NO: 33, a CDR2 comprising a sequence of SEQUENCE: A9, and a CDR1 comprising a sequence of SEQ ID NO: 102.

27. The isolated anti-Vγ4 antibody or fragment thereof as defined in any one of clauses 12 to 25, which comprises a VL region comprising a CDR3 comprising a sequence of SEQ ID NO: 27, a CDR2 comprising a sequence of SEQUENCE: A3, and a CDR1 comprising a sequence of SEQ ID NO: 96.

28. The isolated anti-Vγ4 antibody or fragment thereof as defined in any one of clauses 12 to 25, which comprises a VL region comprising a CDR3 comprising a sequence of SEQ ID NO: 37, a CDR2 comprising a sequence of SEQUENCE: A13, and a CDR1 comprising a sequence of SEQ ID NO: 106.

29. The isolated anti-Vγ4 antibody or fragment thereof as defined in any one of clauses 12 to 25, which comprises a VL region comprising a CDR3 comprising a sequence of SEQ ID NO: 38, a CDR2 comprising a sequence of SEQUENCE: A14, and a CDR1 comprising a sequence of SEQ ID NO: 107.

30. The isolated anti-Vγ4 antibody or fragment thereof as defined in any one of clauses 12 to 25, which comprises a VL region comprising a CDR3 comprising a sequence of SEQ ID NO: 40, a CDR2 comprising a sequence of SEQUENCE: A16, and a CDR1 comprising a sequence of SEQ ID NO: 109.

31. The isolated anti-Vγ4 antibody or fragment thereof as defined in any one of clauses 12 to 25, which comprises a VL region comprising a CDR3 comprising a sequence of SEQ ID NO: 42, a CDR2 comprising a sequence of SEQUENCE: A18, and a CDR1 comprising a sequence of SEQ ID NO: 111.

32. The isolated anti-Vγ4 antibody or fragment thereof as defined in any one of clauses 12 to 25, which comprises a VL region comprising a CDR3 comprising a sequence of SEQ ID NO: 46, a CDR2 comprising a sequence of SEQUENCE: A23, and a CDR1 comprising a sequence of SEQ ID NO: 115.

33. An isolated anti-Vγ4 antibody or fragment thereof which comprises a VH region comprising CDR1, CDR2 and CDR3 sequences as defined in clause 16 and a VL region comprising CDR1, CDR2 and CDR3 sequences as defined in clause 26.

34. An isolated anti-Vγ4 antibody or fragment thereof which comprises a VH region comprising CDR1, CDR2 and CDR3 sequences as defined in clause 17 and a VL region comprising CDR1, CDR2 and CDR3 sequences as defined in clause 27.

35. An isolated anti-Vγ4 antibody or fragment thereof which comprises a VH region comprising CDR1, CDR2 and CDR3 sequences as defined in clause 18 and a VL region comprising CDR1, CDR2 and CDR3 sequences as defined in clause 28.

36. An isolated anti-Vγ4 antibody or fragment thereof which comprises a VH region comprising CDR1, CDR2 and CDR3 sequences as defined in clause 19 and a VL region comprising CDR1, CDR2 and CDR3 sequences as defined in clause 29.

37. An isolated anti-Vγ4 antibody or fragment thereof which comprises a VH region comprising CDR1, CDR2 and CDR3 sequences as defined in clause 20 and a VL region comprising CDR1, CDR2 and CDR3 sequences as defined in clause 30.

38. An isolated anti-Vγ4 antibody or fragment thereof which comprises a VH region comprising CDR1, CDR2 and CDR3 sequences as defined in clause 21 and a VL region comprising CDR1, CDR2 and CDR3 sequences as defined in clause 31.

39. An isolated anti-Vγ4 antibody or fragment thereof which comprises a VH region comprising CDR1, CDR2 and CDR3 sequences as defined in clause 22 and a VL region comprising CDR1, CDR2 and CDR3 sequences as defined in clause 32.

40. An isolated anti-Vγ4 antibody or fragment thereof, which comprises an amino acid sequence having at least 80% sequence identity with any one of SEQ ID NOs: 117-162 or 261-283.

41. The isolated anti-Vγ4 antibody or fragment thereof as defined in clause 40, which comprises a VH region comprising an amino acid sequence having at least 80% sequence identity with any one of SEQ ID NOs: 117-139.

42. The isolated anti-Vγ4 antibody or fragment thereof as defined in clause 41, wherein the VH region comprises an amino acid sequence having at least 80% sequence identity with any one of SEQ ID NOs: 125, 119, 129, 130, 132, 134, or 138.

43. The isolated anti-Vγ4 antibody or fragment thereof as defined in any one of clauses 40 to 42, which comprises a VL region comprising an amino acid sequence having at least 80% sequence identity with any one of SEQ ID NOs: 140-162 or 261-283.

44. The isolated anti-Vγ4 antibody or fragment thereof as defined in clause 43, wherein the VL region comprises an amino acid sequence having at least 80% sequence identity with any one of:
   (a) SEQ ID NOs: 148, 142, 152, 153, 155, 157 or 161; or
   (b) SEQ ID NOs: 269, 263, 273, 274, 276, 278 or 282.

45. The isolated anti-Vγ4 antibody or fragment thereof as defined in any one of clauses 40 to 44, which comprises a VH region comprising an amino acid sequence of SEQ ID NO: 125 and a VL region comprising an amino acid sequence of SEQ ID NO: 148 or 269.

46. The isolated anti-Vγ4 antibody or fragment thereof as defined in any one of clauses 40 to 44, which comprises a VH region comprising an amino acid sequence of SEQ ID NO: 119 and a VL region comprising an amino acid sequence of SEQ ID NO: 142 or 263.

47. The isolated anti-Vγ4 antibody or fragment thereof as defined in any one of clauses 40 to 44, which comprises a VH region comprising an amino acid sequence of SEQ ID NO: 129 and a VL region comprising an amino acid sequence of SEQ ID NO: 152 or 273.

48. The isolated anti-Vγ4 antibody or fragment thereof as defined in any one of clauses 40 to 44, which comprises a VH region comprising an amino acid sequence of SEQ ID NO: 130 and a VL region comprising an amino acid sequence of SEQ ID NO: 153 or 274.

49. The isolated anti-Vγ4 antibody or fragment thereof as defined in any one of clauses 40 to 44, which comprises a VH region comprising an amino acid sequence of SEQ ID NO: 132 and a VL region comprising an amino acid sequence of SEQ ID NO: 155 or 276.

50. The isolated anti-Vγ4 antibody or fragment thereof as defined in any one of clauses 40 to 44, which comprises a VH region comprising an amino acid sequence of SEQ ID NO: 134 and a VL region comprising an amino acid sequence of SEQ ID NO: 157 or 278.

51. The isolated anti-Vγ4 antibody or fragment thereof as defined in any one of clauses 40 to 44, which comprises a VH region comprising an amino acid sequence of SEQ ID NO: 138 and a VL region comprising an amino acid sequence of SEQ ID NO: 161 or 282.

52. An isolated anti-Vγ4 antibody or fragment thereof comprising one or more of:
   (a) a VH comprising a HCDR1 having SEQ ID NO: 79, a HCDR2 having SEQ ID NO: 56 and a HCDR3 having SEQ ID NO: 10, optionally wherein the VH comprises SEQ ID NO: 125; and
      a VL comprising a LCDR1 having SEQ ID NO: 102, a LCDR2 having SEQUENCE A9 (of FIG. 1) and a LCDR3 having SEQ ID NO: 33, optionally wherein the VL comprises SEQ ID NO: 148 or 269;
   (b) a VH comprising a HCDR1 having SEQ ID NO: 86, a HCDR2 having SEQ ID NO: 63 and a HCDR3 having SEQ ID NO: 17, optionally wherein the VH comprises SEQ ID NO: 132; and
      a VL comprising a LCDR1 having SEQ ID NO: 109, a LCDR2 having SEQUENCE A16 (of FIG. 1) and a LCDR3 having SEQ ID NO: 40, optionally wherein the VL comprises SEQ ID NO: 155 or 276;
   (c) a VH comprising a HCDR1 having SEQ ID NO: 73, a HCDR2 having SEQ ID NO: 50 and a HCDR3 having SEQ ID NO: 4, optionally wherein the VH comprises SEQ ID NO: 119; and
      a VL comprising a LCDR1 having SEQ ID NO: 96, a LCDR2 having SEQUENCE A3 (of FIG. 1) and a LCDR3 having SEQ ID NO: 27, optionally wherein the VL comprises SEQ ID NO: 142 or 263;
   (d) a VH comprising a HCDR1 having SEQ ID NO: 83, a HCDR2 having SEQ ID NO: 60 and a HCDR3 having SEQ ID NO: 14, optionally wherein the VH comprises SEQ ID NO: 129; and
      a VL comprising a LCDR1 having SEQ ID NO: 106, a LCDR2 having SEQUENCE A13 (of FIG. 1) and a LCDR3 having SEQ ID NO: 37, optionally wherein the VL comprises SEQ ID NO: 152 or 273;
   (e) a VH comprising a HCDR1 having SEQ ID NO: 84, a HCDR2 having SEQ ID NO: 61 and a HCDR3 having SEQ ID NO: 15, optionally wherein the VH comprises SEQ ID NO: 130; and
      a VL comprising a LCDR1 having SEQ ID NO: 107, a LCDR2 having SEQUENCE A14 (of FIG. 1) and a LCDR3 having SEQ ID NO: 38, optionally wherein the VL comprises SEQ ID NO: 153 or 274;
   (f) a VH comprising a HCDR1 having SEQ ID NO: 88, a HCDR2 having SEQ ID NO: 65 and a HCDR3 having SEQ ID NO: 19, optionally wherein the VH comprises SEQ ID NO: 134; and
      a VL comprising a LCDR1 having SEQ ID NO: 111, a LCDR2 having SEQUENCE A18 (of FIG. 1) and a LCDR3 having SEQ ID NO: 42, optionally wherein the VL comprises SEQ ID NO: 157 or 278;
   (g) a VH comprising a HCDR1 having SEQ ID NO: 92, a HCDR2 having SEQ ID NO: 69 and a HCDR3 having SEQ ID NO: 23, optionally wherein the VH comprises SEQ ID NO: 138; and
      a VL comprising a LCDR1 having SEQ ID NO: 115, a LCDR2 having SEQUENCE A22 (of FIG. 1) and a LCDR3 having SEQ ID NO: 46, optionally wherein the VL comprises SEQ ID NO: 161 or 282;
   (h) a VH comprising a HCDR1 having SEQ ID NO: 71, a HCDR2 having SEQ ID NO: 48 and a HCDR3 having SEQ ID NO: 2, optionally wherein the VH comprises SEQ ID NO: 117; and
      a VL comprising a LCDR1 having SEQ ID NO: 94, a LCDR2 having SEQUENCE A1 (of FIG. 1) and a LCDR3 having SEQ ID NO: 25, optionally wherein the VL comprises SEQ ID NO: 140 or 261;

(i) a VH comprising a HCDR1 having SEQ ID NO: 72, a HCDR2 having SEQ ID NO: 49 and a HCDR3 having SEQ ID NO: 3, optionally wherein the VH comprises SEQ ID NO: 118; and
a VL comprising a LCDR1 having SEQ ID NO: 95, a LCDR2 having SEQUENCE A2 (of FIG. 1) and a LCDR3 having SEQ ID NO: 26, optionally wherein the VL comprises SEQ ID NO: 141 or 262;

(j) a VH comprising a HCDR1 having SEQ ID NO: 74, a HCDR2 having SEQ ID NO: 51 and a HCDR3 having SEQ ID NO: 5, optionally wherein the VH comprises SEQ ID NO: 120; and
a VL comprising a LCDR1 having SEQ ID NO: 97, a LCDR2 having SEQUENCE A4 (of FIG. 1) and a LCDR3 having SEQ ID NO: 28, optionally wherein the VL comprises SEQ ID NO: 143 or 264;

(k) a VH comprising a HCDR1 having SEQ ID NO: 75, a HCDR2 having SEQ ID NO: 52 and a HCDR3 having SEQ ID NO: 6, optionally wherein the VH comprises SEQ ID NO: 121; and
a VL comprising a LCDR1 having SEQ ID NO: 98, a LCDR2 having SEQUENCE A5 (of FIG. 1) and a LCDR3 having SEQ ID NO: 29, optionally wherein the VL comprises SEQ ID NO: 144 or 265;

(l) a VH comprising a HCDR1 having SEQ ID NO: 76, a HCDR2 having SEQ ID NO: 53 and a HCDR3 having SEQ ID NO: 7, optionally wherein the VH comprises SEQ ID NO: 122; and
a VL comprising a LCDR1 having SEQ ID NO: 99, a LCDR2 having SEQUENCE A6 (of FIG. 1) and a LCDR3 having SEQ ID NO: 30, optionally wherein the VL comprises SEQ ID NO: 145 or 266;

(m) a VH comprising a HCDR1 having SEQ ID NO: 77, a HCDR2 having SEQ ID NO: 54 and a HCDR3 having SEQ ID NO: 8, optionally wherein the VH comprises SEQ ID NO: 123; and
a VL comprising a LCDR1 having SEQ ID NO: 100, a LCDR2 having SEQUENCE A7 (of FIG. 1) and a LCDR3 having SEQ ID NO: 31, optionally wherein the VL comprises SEQ ID NO: 146 or 267;

(n) a VH comprising a HCDR1 having SEQ ID NO: 78, a HCDR2 having SEQ ID NO: 55 and a HCDR3 having SEQ ID NO: 9, optionally wherein the VH comprises SEQ ID NO: 124; and
a VL comprising a LCDR1 having SEQ ID NO: 101, a LCDR2 having SEQUENCE A8 (of FIG. 1) and a LCDR3 having SEQ ID NO: 32, optionally wherein the VL comprises SEQ ID NO: 147 or 268;

(o) a VH comprising a HCDR1 having SEQ ID NO: 80, a HCDR2 having SEQ ID NO: 57 and a HCDR3 having SEQ ID NO: 11, optionally wherein the VH comprises SEQ ID NO: 126; and
a VL comprising a LCDR1 having SEQ ID NO: 103, a LCDR2 having SEQUENCE A10 (of FIG. 1) and a LCDR3 having SEQ ID NO: 34, optionally wherein the VL comprises SEQ ID NO: 149 or 270;

(p) a VH comprising a HCDR1 having SEQ ID NO: 81, a HCDR2 having SEQ ID NO: 58 and a HCDR3 having SEQ ID NO: 12, optionally wherein the VH comprises SEQ ID NO: 127; and a VL comprising a LCDR1 having SEQ ID NO: 104, a LCDR2 having SEQUENCE A11 (of FIG. 1) and a LCDR3 having SEQ ID NO: 35, optionally wherein the VL comprises SEQ ID NO: 150 or 271;

(q) a VH comprising a HCDR1 having SEQ ID NO: 82, a HCDR2 having SEQ ID NO: 59 and a HCDR3 having SEQ ID NO: 13, optionally wherein the VH comprises SEQ ID NO: 128; and
a VL comprising a LCDR1 having SEQ ID NO: 105, a LCDR2 having SEQUENCE A12 (of FIG. 1) and a LCDR3 having SEQ ID NO: 36, optionally wherein the VL comprises SEQ ID NO: 151 or 272;

(r) a VH comprising a HCDR1 having SEQ ID NO: 85, a HCDR2 having SEQ ID NO: 62 and a HCDR3 having SEQ ID NO: 16, optionally wherein the VH comprises SEQ ID NO: 131; and
a VL comprising a LCDR1 having SEQ ID NO: 108, a LCDR2 having SEQUENCE A15 (of FIG. 1) and a LCDR3 having SEQ ID NO: 39, optionally wherein the VL comprises SEQ ID NO: 154 or 275;

(s) a VH comprising a HCDR1 having SEQ ID NO: 87, a HCDR2 having SEQ ID NO: 64 and a HCDR3 having SEQ ID NO: 18, optionally wherein the VH comprises SEQ ID NO: 133; and
a VL comprising a LCDR1 having SEQ ID NO: 110, a LCDR2 having SEQUENCE A17 (of FIG. 1) and a LCDR3 having SEQ ID NO: 41, optionally wherein the VL comprises SEQ ID NO: 156 or 277;

(t) a VH comprising a HCDR1 having SEQ ID NO: 89, a HCDR2 having SEQ ID NO: 66 and a HCDR3 having SEQ ID NO: 20, optionally wherein the VH comprises SEQ ID NO: 135; and
a VL comprising a LCDR1 having SEQ ID NO: 112, a LCDR2 having SEQUENCE A19 (of FIG. 1) and a LCDR3 having SEQ ID NO: 43, optionally wherein the VL comprises SEQ ID NO: 158 or 279;

(u) a VH comprising a HCDR1 having SEQ ID NO: 90, a HCDR2 having SEQ ID NO: 67 and a HCDR3 having SEQ ID NO: 21, optionally wherein the VH comprises SEQ ID NO: 136; and
a VL comprising a LCDR1 having SEQ ID NO: 113, a LCDR2 having SEQUENCE A20 (of FIG. 1) and a LCDR3 having SEQ ID NO: 44, optionally wherein the VL comprises SEQ ID NO: 159 or 280;

(v) a VH comprising a HCDR1 having SEQ ID NO: 91, a HCDR2 having SEQ ID NO: 68 and a HCDR3 having SEQ ID NO: 22, optionally wherein the VH comprises SEQ ID NO: 137; and
a VL comprising a LCDR1 having SEQ ID NO: 114, a LCDR2 having SEQUENCE A21 (of FIG. 1) and a LCDR3 having SEQ ID NO: 45, optionally wherein the VL comprises SEQ ID NO: 160 or 281;
and/or (w) a VH comprising a HCDR1 having SEQ ID NO: 93, a HCDR2 having SEQ ID NO: 70 and a HCDR3 having SEQ ID NO: 24, optionally wherein the VH comprises SEQ ID NO: 139; and
a VL comprising a LCDR1 having SEQ ID NO: 116, a LCDR2 having SEQUENCE A23 (of FIG. 1)

and a LCDR3 having SEQ ID NO: 47, optionally wherein the VL comprises SEQ ID NO: 162 or 283.

53. The isolated anti-Vγ4 antibody or fragment thereof as defined in any one of clauses 40 to 52, wherein the VH and VL region are joined by a linker, such as a polypeptide linker.

54. The isolated anti-Vγ4 antibody or fragment thereof as defined in clause 53, wherein the linker comprises a (Gly4Ser)n format, where n=1 to 8.

55. The isolated anti-Vγ4 antibody or fragment thereof as defined in clause 53 or 54, wherein the linker comprises SEQ ID NO: 186.

56. The isolated anti-Vγ4 antibody or fragment thereof as defined in clause 55, wherein the linker consists of SEQ ID NO: 186.

57. An isolated anti-Vγ4 antibody or fragment thereof which comprises an amino acid sequence having at least 80% sequence identity with any one of SEQ ID NOs: 163-185.

58. The isolated anti-Vγ4 antibody or fragment thereof as defined in clause 57, which comprises an amino acid sequence of any one of SEQ ID NOs: 163-185.

59. The isolated anti-Vγ4 antibody or fragment thereof as defined in clause 57 or clause 58, which comprises SEQ ID NO: 171, 165, 175, 176, 178, 180 or 184.

60. An isolated anti-Vγ4 antibody which comprises an amino acid sequence having at least 80% sequence identity with any one of SEQ ID NOs: 233-255.

61. The isolated anti-Vγ4 antibody as defined in clause 60, which comprises an amino acid sequence of any one of SEQ ID NOs: 233-255.

62. The isolated anti-Vγ4 antibody as defined in clause 60 or clause 61, which comprises SEQ ID NO: 235, 241, 245, 246 or 254.

63. An isolated anti-Vγ4 antibody or fragment thereof comprising a heavy chain amino acid sequence having at least 80% sequence identity with any one of SEQ ID NOs: 284-306 and/or a light chain amino acid sequence having at least 80% sequence identity with any one of SEQ ID NOs: 307-329.

64. The isolated anti-Vγ4 antibody or fragment thereof as defined in clause 63, comprising a heavy chain amino acid sequence comprising any one of SEQ ID NOs: 284-306 and/or a light chain amino acid sequence comprising any one of SEQ ID NOs: 307-329.

65. An isolated anti-Vγ4 antibody or fragment thereof, preferably as defined according to any one of clauses 1-11, which binds to the same, or essentially the same, epitope as, or competes with, an antibody or fragment thereof as defined in any one of clauses 12-64.

66. The isolated anti-Vγ4 antibody or fragment thereof as defined in any one of clauses 1-65, which is an scFv, Fab', Fab', F(ab')2, Fv, variable domain (e.g. VH or VL), diabody, minibody or full length antibody.

67. The isolated anti-Vγ4 antibody or fragment thereof as defined in clause 66, which is an scFv or a full length antibody.

68. The isolated anti-Vγ4 antibody or fragment thereof as defined in clause 67, which is a full length antibody, such as an IgG1 antibody.

69. The isolated anti-Vγ4 antibody or fragment thereof as defined in any one of clauses 1-68, which is human.

70. The isolated anti-Vγ4 antibody or fragment thereof as defined in any preceding clause, wherein the antibody modulates Vγ4 T cells.

71. The isolated anti-Vγ4 antibody or fragment thereof as defined in clause 70, wherein modulation comprises activation of Vγ4 T cells.

72. The isolated anti-Vγ4 antibody or fragment thereof as defined in clause 70, wherein modulation comprises inhibition of Vγ4 T cells.

73. The isolated anti-Vγ4 antibody or fragment thereof as defined in clause 70, wherein in modulation of Vγ4 T cells comprises:
expansion of the Vγ4 T cells, e.g. by selectively increasing the number of Vγ4 T cells or promotion of survival of Vγ4 T cells;
stimulation of the Vγ4 T cells, e.g. by increasing Vγ4 T cell potency, i.e. increasing target cell killing; and/or degranulation of Vγ4 T cells.

74. A polynucleotide sequence encoding the anti-Vγ4 antibody or fragment thereof as defined in any one of clauses 1-73.

75. A polynucleotide sequence encoding the anti-Vγ4 antibody or fragment thereof comprising a sequence having at least 70% sequence identity with any of SEQ ID NOs: 187-232.

76. A polynucleotide sequence encoding the anti-Vγ4 antibody or fragment thereof comprising a sequence of any of SEQ ID NOs: 187-232.

77. An expression vector comprising the polynucleotide sequence as defined in any one of clauses 74 to 76.

78. An expression vector comprising a VH sequence of any of SEQ ID NOs: 187-209.

79. The expression vector as defined in clause 78, wherein the VH sequence comprises SEQ ID NO: 195, 189, 199, 200, 202, 204 or 208.

80. An expression vector comprising a VL sequence of any of SEQ ID NOs: 210-232.

81. The expression vector as defined in clause 80, wherein the VL sequence comprises SEQ ID NO: 218, 212, 222, 223, 225, 227 or 231.

82. An expression vector comprising the VH sequence of clause 78 or clause 79 and the VL sequence of clause 80 or clause 81.

83. A cell comprising the polynucleotide sequence as defined in any one of clauses 74 to 76 or the expression vector as defined in any one of clauses 77 to 82.

84. A cell comprising a first expression vector as defined in clause 78 or clause 79 and a second expression vector as defined in clause 80 or clause 81.

85. A cell comprising the expression vector as defined in clause 82.

86. The cell as defined in any one of clauses 83-85, wherein the polynucleotide or expression vector encodes a membrane anchor or transmembrane domain fused to the antibody or fragment thereof, wherein the antibody or fragment thereof is presented on an extra-cellular surface of the cell.

87. A composition comprising the antibody or fragment thereof as defined in any one of clauses 1 to 73.

88. A pharmaceutical composition comprising the antibody or fragment thereof as defined in any one of clauses 1 to 73, together with a pharmaceutically acceptable diluent or carrier.

89. The isolated anti-Vγ4 antibody or fragment thereof as defined in any one of clauses 1 to 73 or the pharmaceutical composition as defined in clause 84, for use as a medicament.

90. The isolated anti-Vγ4 antibody or fragment thereof or the pharmaceutical composition as defined in clause 89 for use in the treatment of cancer, an infectious disease or an inflammatory disease.

91. A method of treating a cancer, an infectious disease or an inflammatory disease in a subject in need thereof, comprising administering a therapeutically effective amount of the isolated anti-Vγ4 antibody or fragment thereof as defined in any one of clauses 1 to 73 or the pharmaceutical composition as defined in clause 88.

92. An isolated antigen comprising an amino acid sequence having at least 80% sequence identity with any one of SEQ ID NOs: 256-258 for use in generating an anti-Vγ4 antibody or fragment thereof.

93. A method of generating an anti-Vγ4 antibody or fragment thereof comprising:

(i) designing a series of antigens comprising a TCR gamma variable 4 (Vγ4) amino acid sequence wherein the CDR3 sequence of the Vγ4 is the same for all antigens in the series;

(ii) exposing a first antigen designed in step (i) to an antibody library;

(iii) isolating the antibodies or fragments thereof which bind to the antigen;

(iv) exposing the isolated antibodies or fragments thereof to a second antigen designed in step (i); and (v) isolating the antibodies or fragments thereof which bind to both the first and second antigen.

94. The method as defined in clause 93, which further comprises exposing the isolated antibodies or fragments thereof to a second series of antigens comprising a γδ TCR with a different gamma variable chain, such as TCR gamma variable 2 (Vγ2) or TCR gamma variable 8 (Vγ8), and then deselecting the antibodies or fragments thereof which also bind to the second series of antigens.

95. The method as defined in clause 93 or clause 94, wherein the first and/or second series of antigens are presented as a leucine zipper and/or Fc fusion.

96. The method as defined in any one of clauses 93-95, wherein the series of antigens are in a heterodimeric and/or homodimeric format.

97. An antibody obtained by the method as defined in any one of clauses 93-96.

98. A kit comprising an anti-Vγ4 antibody or fragment thereof according to any one of clauses 1 to 73 or a pharmaceutical composition according to clause 88, optionally comprising instructions for use and/or an additional therapeutically active agent.

Other features and advantages of the present invention will be apparent from the description provided herein. It should be understood, however, that the description and the specific examples while indicating preferred embodiments of the invention are given by way of illustration only, since various changes and modifications will become apparent to those skilled in the art. The invention will now be described using the following, non-limiting examples:

EXAMPLES

Example 1. Materials and Methods

Antigen Preparation

The design of the soluble γδ TCR heterodimers comprising the TCRα and TCRβ constant regions used in the below Examples were generated according to Xu etal. (2011) PNAS 108: 2414-2419. Vγ or Vδ domains were fused in-frame to a TCRα or TCRβ constant region lacking the transmembrane domain, followed by a leucine zipper sequence or an Fc sequence, and a histidine tag/linker.

The expression construct was transiently transfected in mammalian EXPI HEK293 suspension cells (either as single or co-transfections for heterodimer). Secreted recombinant proteins were recovered and purified from culture supernatant by affinity chromatography. To ensure good recovery of monomer antigen, samples were further purified using preparative size exclusion chromatography (SEC). Purified antigens were analysed for purity by SDS-PAGE and aggregation state by analytical SEC.

Selected scFvs were subcloned into IgG1 frameworks using commercially available plasmids. expi293F suspension cells were transfected with said plasmids for antibody expression. For convenience, unless othenNise noted, the antibodies characterised in these Examples refer to IgG1 formatted antibodies selected from phage display as scFv. However, the antibodies of the invention may be in any antibody format as previously discussed.

Antibody Purification

IgG antibodies were batch purified from supernatants using protein A chromatography. Quality of purified IgG was analysed using ELISA, SDS-PAGE and SEC-HPLC.

Antigen Binding

Phage display selection outputs were subcloned into the scFv expression vector pSANG10 (Martin et al. (2006) BMC Biotechnol. 6: 46). Soluble scFv were expressed and screened for binding in dissociation-enhanced lanthanide fluorescence immunoassay (DELFIA) on directly immobilised targets. Hits were defined as a DELFIA signal above 3000 fluorescence units.

A DELFIA ELISA binding method was also employed to assess binding of antibody supernatants or further protein-A purified antibody. In brief, MaxiSorp plates were coated with 3 μg/ml of antigen BSA or L1 (DV1-GV4), L2 (DV1-GV2), L3 (DV1-GV8), or L4 (DV2-GV4) recombinant TCR antigen. Plates were then washed with PBS, blocked with PBS/skimmed milk and then test article added and incubated for 1 hour at room temperature. Thereafter, plates were washed with PBS–-TWEEN (polysorbate) and DELFIA Eu-N1-anti-human IgG (Perkin Elmer #1244-330) added for 1 hour at room temperature prior to further washing, addition of DELFIA enhancement solution (Perkin Elmer #4001-0010), and reading on a Pherastar microplate reader.

D1.3 hIgG1 (described in England et al. (1999) *J. Immunol.* 162:2129-2136) was used as a negative control and REA173 (Miltenyi) and TS8.2 (ThermoFisher, No. TCR1730) were used as comparator antibodies.

Antibody Studies with Recombinant JRT3-TCR Cells

The recombinant JRT3-TCR cells employed in the antibody binding, the TCR downregulation, and the CD69 upregulation studies are described previously (see Melandri et al. (2018) *Nature Immunology* 19 (12): 1352-1365, and Willcox et al. (2019) *Immunity* 51 (5): 813-825.e4).

Figure 6:
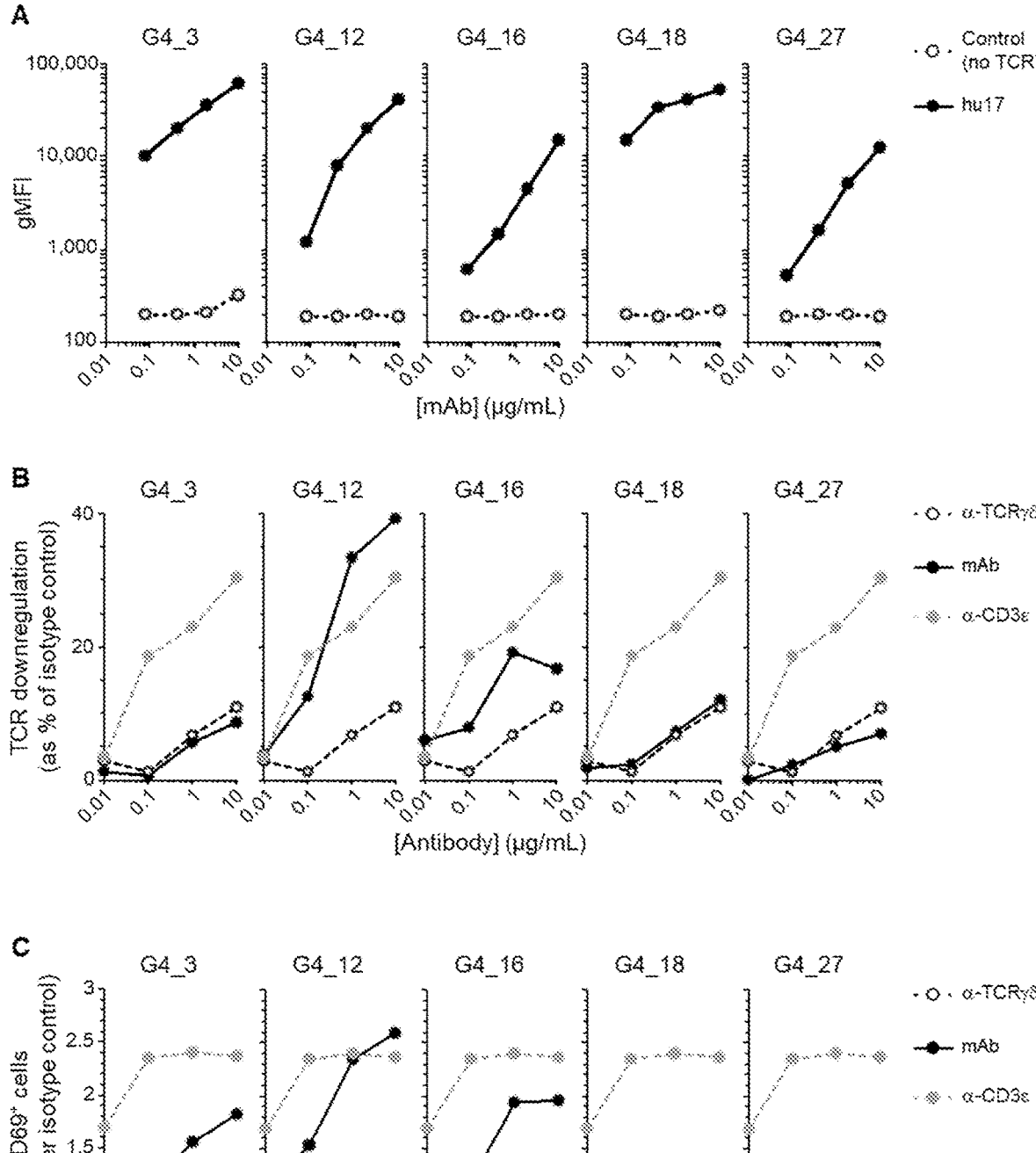
FIG. 6: Example antibody binding and conferred function on Vγ4 TCR (hu17) expressing cells. (A) Titrated binding of antibodies to JRT3-hu17 showing all example antibodies bound to JRT3-hu17 cells. Non-transduced JRT3 cells (no TCR) employed as a negative control demonstrating that expression of hu17 was essential for antibody binding. (B) Conferred TCR downregulation by titrated antibodies versus downregulation conferred by positive control antibodies: anti-CD3ε (UCHT-1, Biolegend) or anti-pan-TCRγδ (B1, Biolegend). (C) Conferred CD69 upregulation by titrated antibodies versus upregulation observed by comparator antibodies: anti-CD3ε (UCHT-1, Biolegend) or anti-pan-TCRγδ (B1, Biolegend).

For the antibody binding studies, primary staining of either 100,000 non-transduced JRT3 controls or JRT3-TCR cells were undertaken in PBS 5% FCS for 30 minutes at 4° C. with either a standard 1.0 μg/ml if the amount is not indicated or the amount indicated, such as 0.08, 0.4, 2 or 10 μg/ml in FIG. 6 of each lead antibody. Secondary staining was then carried out with A647 anti-human IgG (Biolegend). Additionally BV421 anti-CD3ε (Biolegend) or PE-Cy7 IMMU510 anti-γδTCR (Beckman Coulter) staining was undertaken as/where indicated. Cells were then washed twice in PBS 5% FCS and flow analysis undertaken on a FACS Canto II 3L.

For TCR downregulation/CD69 upregulation studies, 96 flat well plates were first pre-coated by adding to each well 20 µg/ml secondary antibodies, specifically either anti-human IgG-Fc (for the human D1.3 and Vγ4 antibodies) or anti-mouse IgG (for murine anti-CD3e or anti-Pan TCRgd) and then incubated for 2 h at 37° C. Test antibodies as indicated were first diluted to 0.01, 0.1, 1, and 10 µg/ml final concentrations. 50 µl of each concentration was then added to a well of the pre-coated plate prior to overnight incubation at 4° C. Unbound antibody was then washed twice with PBS before addition of saturating PBS 5% FCS for 1 hour at 37° C. 100,000 cells per well were then plated by 400 g spinning. Cells were then incubated for 5 hours at 37° C., 5% $CO_2$ and then transferred to a 96 well round-bottom plate for staining. Staining antibodies employed included BV421 anti-CD3& diluted 1:400 (clone OKT-3 Biolegend); PE-Cy7 anti-γδTCR diluted 1:200 (clone IMMU510 Beckman Coulter); and A647 anti-CD69 diluted 1:200 (clone FN50 Biolegend). All staining undertaken in PBS 5% FCS for 30 minutes at 4° C.

Antibody Studies with Primary Cells (PBMC)

24 well plates were first pre-coated by adding to each well 20 µg/ml (250 µl per well) anti-human IgG-Fc (Biolegend) and then incubated for 2 hours at 37° C. Unbound secondary antibody was washed twice with PBS, and isotype control (human IgG1, Biolegend) or anti-Vγ4 (clone G4_12) were first diluted to 0.1, 1, and 10 µg/ml final concentrations. 250 µl of each concentration was then added to a well of the pre-coated plate prior to overnight incubation at 4° C. Unbound antibodies were then washed twice with PBS before addition of saturating PBS 5% FCS for 1 hour at 37° C. 500,000 PBMC resuspended at $10^6$ cells per ml in complete media (RPMI supplemented with 5% heat-inactivated human AB serum [PAA laboratories], Sodium Pyruvate [1 mM] and Penicillin/Streptomycin [ThermoFisher]) were then added to each well. Cells were then incubated at 37° C., 5% $CO_2$. IL-2 or IL-2+IL-15 (100 U/ml and 10 ng/ml final concentrations, respectively) were added after 24 hours and fresh complete media supplemented with IL-2 or IL-2+ IL-15 was added every 2-3 days. On days 7 and 14 of the culture, cells were transferred to a 96 well round-bottom plate for staining. Staining antibodies employed included biotin anti-TCRVγ2/3/4 (Clone 23D12) diluted to 1 µg/ml, PE streptavidin diluted 1:100 (Biolegend); BV421 anti-CD3E diluted 1:400 (clone OKT-3 Biolegend); PE-Cy7 anti-TCRγδ diluted 1:200 (clone IMMU510 Beckman Coulter); FITC anti-Vδ2 (Clone B6 Biolegend); and A647 anti-Vγ4 (clone G4_18) diluted to 1 µg/ml. All staining undertaken in PBS 5% FCS for 30 minutes at 4° C.

MS-Based Epitope Mapping

CovalX 'Ultrafast Conformation/Linear Epitope Mapping' methodology was employed. First both protein antigen L1 (DV1-GV4) plus antibody G4_3 (1139_P01_A04) were analyzed for protein integrity and aggregation level using a high-mass MALDI. In order to determine the binding epitope of the L1 (DV1-GV4)/G4_3 complex with high resolution, the complexes were incubated with deuterated cross-linkers and subjected to multi-enzymatic proteolysis using trypsin, chymotrypsin, Asp-N, elastase and thermolysin. After enrichment of the cross-linked peptides, the samples were analyzed by high resolution mass spectrometry (nLC-LTQ-Orbitrap MS) and the data generated were analyzed using XQuest and Stavrox software.

γδ T Cell Binding Assay

The binding of antibodies to γδ T cells may be tested by incubating a fixed concentration of purified antibodies with 250000 γδ T cells. This incubation may be performed under blocking conditions, such as by the addition of huFc fragments or Ig to prevent unspecific binding of antibodies via the Fc receptor. Detection may be performed by addition of a secondary, fluorescent dye-conjugated antibody against human IgG1. For negative controls, cells may be prepared with a) an isotype antibody only (recombinant human IgG), b) the fluorescent dye-conjugated anti-human IgG antibody only and c) a combination of a) and b). A control well of completely unstained cells may be also prepared and analysed. As positive controls, a purified murine monoclonal IgG2 anti-human CD3 antibody may be used in two different concentrations and stained with a fluorescent dye-conjugated goat anti-mouse secondary antibody. The assay may be accepted if the lower concentration positive controls' mean fluorescence intensity in the FITC channel was at least tenfold as high as the highest negative control.

SPR Analysis

A MASS-2 instrument with an amine high capacity chip (both from Sierra Sensors, Germany) may be used to perform SPR analysis. 15 nM IgG may be captured via protein G to an amine high capacity chip (100 nM for TS8.2). L1 (DV1-GV4) antigen may be flown over the cell at a 1:2 dilution series from 2000 nM to 15.625 nM with the following parameters: 180 s association, 600 s dissociation, flowrate 30 µL/min, running buffer PBS+0.02% TWEEN (polysorbate) 20. All experiments were performed at room temperature on MASS-2 instrument. Steady state fitting may be determined according to Langmuir 1:1 binding using software Sierra Analyzer 3.2.

γδ TCR Downregulation and Degranulation Assay

THP-1 (TIB-202™, ATCC) target cells loaded or not with test antibodies may be labelled with CellTracker™ Orange CMTMR (ThermoFisher, C2927) and incubated with γδ T cells at 2:1 ratio in the presence of CD107a antibody (Anti-human CD107a BV421 (clone H4A3) BD Biosciences 562623). After 2 hours of incubation, the surface expression of γδ TCR (to measure TCR downregulation) and expression of CD107a (to measure degranulation) on γδ T cells may be evaluated using flow cytometry.

Killing Assay

Gamma delta T cell-mediated killing activity and effect of test antibodies on the killing activity of γδ T cells may be accessed by flow cytometry. After 4 hours of in vitro co-culture at 20:1 ratio of γδ T cells and CellTracker™ Orange CMTMR (ThermoFisher, C2927) labelled THP-1 cells (loaded or not with the antibody) may be stained with Viability Dye eFluor™ 520 (ThermoFisher, 520 65-0867-14) to distinguish between live and dead target THP-1 cells. During sample acquisition, target cells may be gated on the CellTracker™ Orange CMTMR positivity and examined for cell death based on the uptake of Viability Dye. CMTMR and eFluor™ 520 double positive cells may be recognized as the dead target cells. The killing activity of γδ T cells may be presented as a % of the dead target cells.

Example 2. Antigen Design

Gamma delta (γδ) T cells are polyclonal with CDR3 polyclonality. In order to avoid a situation where generated antibodies would be selected against the CDR3 sequence (as the CDR3 sequence will differ from TCR clone to TCR clone), the antigen design involved maintaining a consistent CDR3 in different formats. This design aimed to generate antibodies recognising a sequence within the variable domain, which is germline encoded and therefore the same in all clones, thus providing antibodies which recognise a wider subset of γδ T cells.

Another important aspect of the antigen preparation process was to design antigens which are suitable for expression as a protein. The γδ TCR is a complex protein involving a heterodimer with inter-chain and intra-chain disulphide bonds. A leucine zipper (LZ) format and Fc format were used to generate soluble TCR antigens to be used in the phage display selections. Both the LZ and Fc formats expressed well and successfully displayed the TCR (particularly heterodimeric TCRs, e.g. Vδ1Vγ4).

It was found that the CDR3 sequence from a public database entry for the γδ TCR expressed well as proteins (RSCB Protein Data Bank entry: 4MNH). This was therefore selected for antigen preparation.

Antigens containing the gamma variable 4 chain were expressed in LZ formats as a heterodimer (i.e. in combination with different delta variable chains—e.g. DV1-GV4, a heterodimer composed of a delta variable 1 chain and a gamma variable 4 chain, [termed "L1"] and DV2-GV4, a heterodimer composed of a delta variable 2 chain and a gamma variable 4 chain, [termed "L4"]) and in Fc format either as a heterodimer or as a homodimer (i.e. in combination with another gamma variable 4 chain-GV4-GV4, a homodimer composed of two gamma variable 4 chains, [termed "Fc4/4"]). All gamma variable 4 chains of the antigens contained the 4MNH CDR3. Another series of γδ TCR antigens using similar formats were designed containing different gamma variable chains (such as gamma variable 2 and gamma variable 8) and used to deselect antibodies with non-specific or off target binding (e.g. DV1-GV2, a heterodimer composed of a delta variable 1 chain and a gamma variable 2 chain, [termed "L2"] or DV1-GV8, a heterodimer composed of a delta variable 1 chain and a gamma variable 8 chain, [termed "L3"]). These antigens were also designed to include the 4MNH CDR3 to ensure that antibodies binding in the CDR3 region were also deselected.

Example 3. Phage Display

Phage display selections were performed against libraries of human scFvs using either heterodimeric LZ TCR format in round 1 and 2, with deselections on heterodimeric LZ TCR in both rounds. Or round 1 was performed using homodimeric Fc fusion TCR with deselection on human IgG1 Fc followed by round 2 on heterodimeric LZ TCR with deselection on heterodimeric LZ TCR (see Table 1).

TABLE 1

| Overview phage display selections | | | | |
|---|---|---|---|---|
| Target | Round 1 selection | Round 1 deselection | Round 2 selection | Round 2 deselection |
| GV4 | bt-L1 (DV1-GV4) | L2 (DV1-GV2) | bt-L4 (DV2-GV4) | L2 (DV1-GV2) |
| GV4 | bt-Fc4/4 (GV4-GV4) | Fc | bt-L4 (DV2-GV4) | L2 (DV1-GV2) | bt = biotin.

Selections were performed in solution phase using 100 nM biotinylated proteins. Deselections were performed using 1 μM non-biotinylated proteins.

Example 4. Antibody Selection

Hits obtained in Example 3 were sequenced (using standard methods known in the art). 130 unique clones were identified, which showed a unique combination of VH and VL CDR3. Of these 130 unique clones, 129 showed a unique VH CDR3 and 116 showed a unique VL CDR3.

Unique clones were re-arrayed and specificity was analysed by ELISA (DELFIA). A panel of 42 unique human scFv binders which bind TRGV4 but not TRGV2 or TRGV8, were identified from the selections.

Affinity ranking of the selected binders was included to aid the choice of clones going forward. A large number of binders showed affinities in the nanomolar range, reacting with 25 to 100 nM biotinylated antigen (L1). A handful of binders showed a strong reaction with 5 nM antigen, indicating possible single digit nanomolar affinities. Some binders showed no reaction with 100 nM antigen, indicating affinities in the micromolar range.

For the selection of clones to proceed with to IgG conversion, the aim was to include as many germline lineages and as many different CDR3s as possible. Further, sequence liabilities like glycosylation, integrin binding sites, CD11c/CD18 binding sites, unpaired cysteines were avoided. In addition, a variety of affinities was included. The clones chosen to be converted to IgG are shown in FIG. 1. The results from the ELISA binding (values in Fluorescence Units (FU)) are shown in FIG. 2A. Results indicate that all 23 antibodies exhibit the desired gamma 4 chain specific profile and regardless of partner delta chain. The same data is also expressed in FIG. 2B and further shows the fold-change increase in binding of each clone to the human Vγ4 chain versus the human Vγ2 chain. Fold-change increases in binding to the human Vγ4 chain versus the human Vγ2 chain ranged from an 80-fold (clone G4_26) to a 98387-fold increase (clone G4_18).

Antibody binding studies were also conducted using recombinant Jurkat (JRT3-hu17) cells. Comparison of the results from the ELISA data and flow cytometry data are shown in FIG. 3A. Antibody clones which were identified as binding to both DV1-GV4 antigen via Delfia ELISA (Y-axis) and to JRT3-hu17 cells (X-axis) were chosen for further investigation.

Example 5. Investigation of Vγ4 Antibody Binding

The capacity of the antibodies chosen in Example 4 to stain Vγ4 TCRs bearing different CDR3 sequences (hu17 vs. hu20, both Vγ4Vδ1) or delta chains (hu20γ/huPBδ, Vγ4Vδ2; LES, Vγ4Vδ5) was investigated. Results are shown in FIG. 4A and indicate that all tested antibodies show significantly increased binding to one or more of the Vγ4 TCRs used in the study relative to the D1.3 isotype control. In particular, five exemplary antibodies (G4_3, G4_12, G4_16, G4_18 and G4_27) bind all Vγ4 TCRs expressed in this study and regardless of CDR3 sequence or partner delta chain, exhibiting markedly enhanced binding signals over and above D1.3 isotype control. By way of illustration, example flow data for two of the antibodies in this study are shown in FIG. 4B and illustrate the difference between G4_3 binding (stains positive for all Vγ4 TCRs) compared to G4_4 binding (stains positively for both hu17 and LES, whereas staining against both hu20 [different CDR3 sequences compared to hu17] and hu20 g/huPBd [Vγ4Vδ2] is reduced).

Figure 5A:
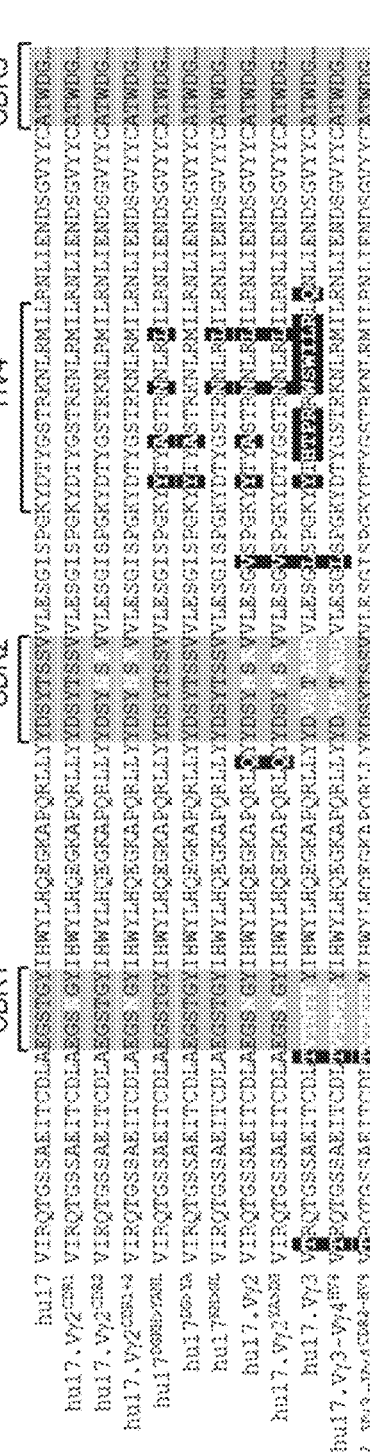
FIG. 5: Antibody binding and epitope mapping against chimeric hu17 TCRs expressed on JRT3 cells. (A) Alignment of the germline-encoded variable gamma regions of the indicated chimeric hu17 constructs is presented (from top to bottom, SEQ ID NOs: 339-350). Note that due to space limitations, the first 10 amino acids of the mature Vγ2/3/4 sequences (amino acids 1-10 of SEQ ID NO: 256 [SSNLEGRTKS]) are omitted but are identical across all constructs. Amino acids that are different from the reference hu17 sequence (wild-type Vγ4 TCR) are indicated. (B) Summary table of the reactivity of each antibody to the indicated chimeric TCR constructs. Results highlight the relative binding specificity of each indicated antibody to the individual TCRs expressed on JRT3 cells. (C) Example flow data of epitope mapping to illustrate the differential binding signals observed in this study.

Example 6. Epitope Mapping Using Chimeric Hu17 TCRs hu17 is a Vγ4/Vδ1 TCR for which the paired CDR3 sequences were cloned from a BTNL3+8-reactive human colon intraepithelial lymphocyte by single-cell PCR (as described in Melandri et al. (2018) Nat. Immunol. 19:1352-1365). Different chimeric hu17 TCR constructs were prepared as summarised in FIG. 5A. These constructs were derived from hu17 and were all described in Melandri et al. (2018) Nat. Immunol. 19:1352-1365 and Willcox et al. (2019) Immunity 51:813-825 (both of which are incorporated herein by reference).

Antibody binding was then investigated by flow cytometry against the chimeric hu17 TCRs expressed on JRT3 cells. A summary table of the reactivity of each antibody to the indicated chimeric TCR constructs is shown in FIG. 5B. The results highlight individual antibody relative binding specificity to the individual TCRs expressed on JRT3 cells. Antibodies G4_3, G4_12, G4_16, G4_18 and G4_27 were all indicated to specifically bind in or around the HV4 region because no staining or reduced staining was observed when hu17 TCR constructs containing the Vγ2 sequences in the HV4 region were used.

Example flow data of epitope mapping to illustrate the differential binding signals observed in this study is shown in FIG. 5C. In this instance, and as an example of this epitope mapping approach, G4_12 binding to the various recombinant chimeric TCRs is shown. First, G4_12 exhibits strong binding to starting hu17 TCR (far left panel). Strong binding is also observed against hu17 when the CDR1+2 sequences are exchanged in-frame for Vγ2 equivalent CDRs (centre left panel) or when the hu17 is HV4 modified to Vγ2 sequence DG>YA (centre right panel). However, a noticeable drop in binding by G4_12 is observed with alternative Vγ4 to Vγ2 amino acid substitutions (DGKM>YANL; centre panel) or KM>NL (far right panel), respectively. Hence in this instance the epitope recognized by G4_12 is located in the HV4 region (amino acids 67-82 of SEQ ID NO. 1 [KYDTYGSTRKNLRMIL]), and is heavily impacted by modifications of the underlined K and M residues to the equivalent resides found at this position in the Vγ2 HV4 region.

Example 7. Titration of Investigated Antibodies in Staining and Functional Assays Results from titration of investigated antibodies for staining and analysis by flow cytometry to JRT3-hu17 cells (concentrations ranging from 0.08 to 10 µg/mL, 5-fold dilution steps) are shown in FIG. 6A. Non-transduced JRT3 cells (no TCR) employed as a negative control. Results show all antibodies were capable of binding to JRT3 cells expressing Vγ4 TCRs.

Functional assays were then conducted by investigating TCR turnover and CD69 upregulation by titrated antibodies versus turnover conferred by anti-CD3ε binding or anti-pan-TCRγδ antibodies. The results are shown for five of the antibodies in FIGS. 6B and 6C and results for a wider selection of antibodies within the original cohort are summarised in Table 2.

TABLE 2

| TCR downregulation and activation of selected antibodies | | |
|---|---|---|
| Antibody (µg/ml) | Vγ4 TCR downregulation | Conferred Activation (CD69 fold-change increase) |
| G4_3 | + | ++ |
| G4_4 | − | − |
| G4_7 | − | − |

TABLE 2-continued

| TCR downregulation and activation of selected antibodies | | |
|---|---|---|
| Antibody (µg/ml) | Vγ4 TCR downregulation | Conferred Activation (CD69 fold-change increase) |
| G4_10 | − | − |
| G4_12 | +++ | +++ |
| G4_16 | ++ | ++ |
| G4_18 | + | + |
| G4_27 | +/− | − |

All of the listed antibodies in Table 2 have been shown to bind to the Vγ4 chain of a γδ TCR. However, as shown in the table, some of these antibodies are capable of activating the Vγ4 TCR as measured via Vγ4 TCR downregulation and/or increased CD69 expression (indicated as '+', '++' or '+++' with '+++' meaning highest relative levels of activation), whilst other antibodies show no appreciable ability to activate the Vγ4 TCR (indicated as '-').

Example 8. MS-Based Epitope Mapping

In order to determine the epitope of antigen/antibody complexes with high resolution, the protein complexes were incubated with deuterated cross-linkers and subjected to multi-enzymatic cleavage. After enrichment of the cross-linked peptides, the samples were analysed by high resolution mass spectrometry (nLC-LTQ-Orbitrap MS) and the data generated were analysed using XQuest (version 2.0) and Stavrox (version 3.6) software.

After trypsin, chymotrypsin, Asp-N, elastase and thermolysin proteolysis of the protein complex L1 (DV1-GV4)/1139_P01_A04 with deuterated d0d12, the nLC-orbitrap MS/MS analysis detected 11 cross-linked peptides between L1 (DV1-GV4) and the antibody 1139_P01_A04 (G4_3). Results of the epitope mapping results is presented in Table 3.

TABLE 3

| Results of epitope mapping for antigen/antibody complexes | |
|---|---|
| Clone ID | Epitope mapping, amino acid numbering of SEQ ID NO: 1 |
| 1139_P01_A04 (G4_3) | 71, 73, 75, 76, 79 |

This epitope mapping data correlates with the experiments above, indicating that this antibody binds within the HV4 region of the γ4 chain.

Example 9. Anti-Vγ4 Antibody Targeting and Modulation of Primary Vγ4-Positive Cells Further studies were undertaken to demonstrate anti-Vγ4 antibody targeting of primary Vγ4+ cells derived from skin, blood and gut, including cells derived from healthy and diseased patient samples.

Binding to Primary Vγ4+ Cells Derived from Skin

Firstly, anti-Vγ4 antibodies were tested for binding to primary Vγ4+ T cells expanded from the skin of two individual donors. Skin samples were prepared by removing subcutaneous fat and a 3 mm biopsy punch used to make multiple punches. Punches were placed on carbon matrix grids and placed in the well of a G-REX6 (Wilson Wolf).

Each well was filled with complete isolation medium containing AIM-V media (Gibco, Life Technologies), CTS Immune Serum Replacement (Life Technologies), IL-2 and IL-15. For the first 7 days of culture, complete isolation medium containing Amphotericin B (Life Technologies) was used ("+AMP"). Media was changed every 7 days by gently aspirating the upper media and replacing with 2× complete isolation medium (without AMP), trying not to disturb the cells at the bottom of the plate or bioreactor. Beyond three weeks in culture, the resulting egressed cells were then passaged into fresh tissue culture vessels and fresh media (e.g. AIM-V media or TexMAX media (Miltenyi)) plus recombinant IL-2, IL-4, IL-15 and IL-21 before harvest. αβ T cells also present within the culture were then removed with aid of αβ T cell depletion kits and associated protocols, such as those provided by Miltenyi. For further reference see WO2020/095059.

Following isolation, γδ T cells were first stained with viability dye in the presence of Fc block for 20 minutes at 4° C. γδ T cells were then incubated with fixed concentrations of exemplary anti-Vγ4 antibodies (0.046-100 µg/ml) or isotype control (IgG1 anti-respiratory syncytial virus (RSV) antibody) for 30 minutes at 4° C. Detection was performed by addition of a secondary, fluorescent dye-conjugated antibody against human IgG1 (IS11-12E4.23.20). Cells were then fixed and acquired on the MACSQuant16 flow cytometer. Cells were gated as single, live, IgG1 (Vγ4)$^+$. Data shown are the median fluorescent intensity (MFI) of secondary detection antibody detected bound to Vγ4$^+$ cells.

Figure 7:
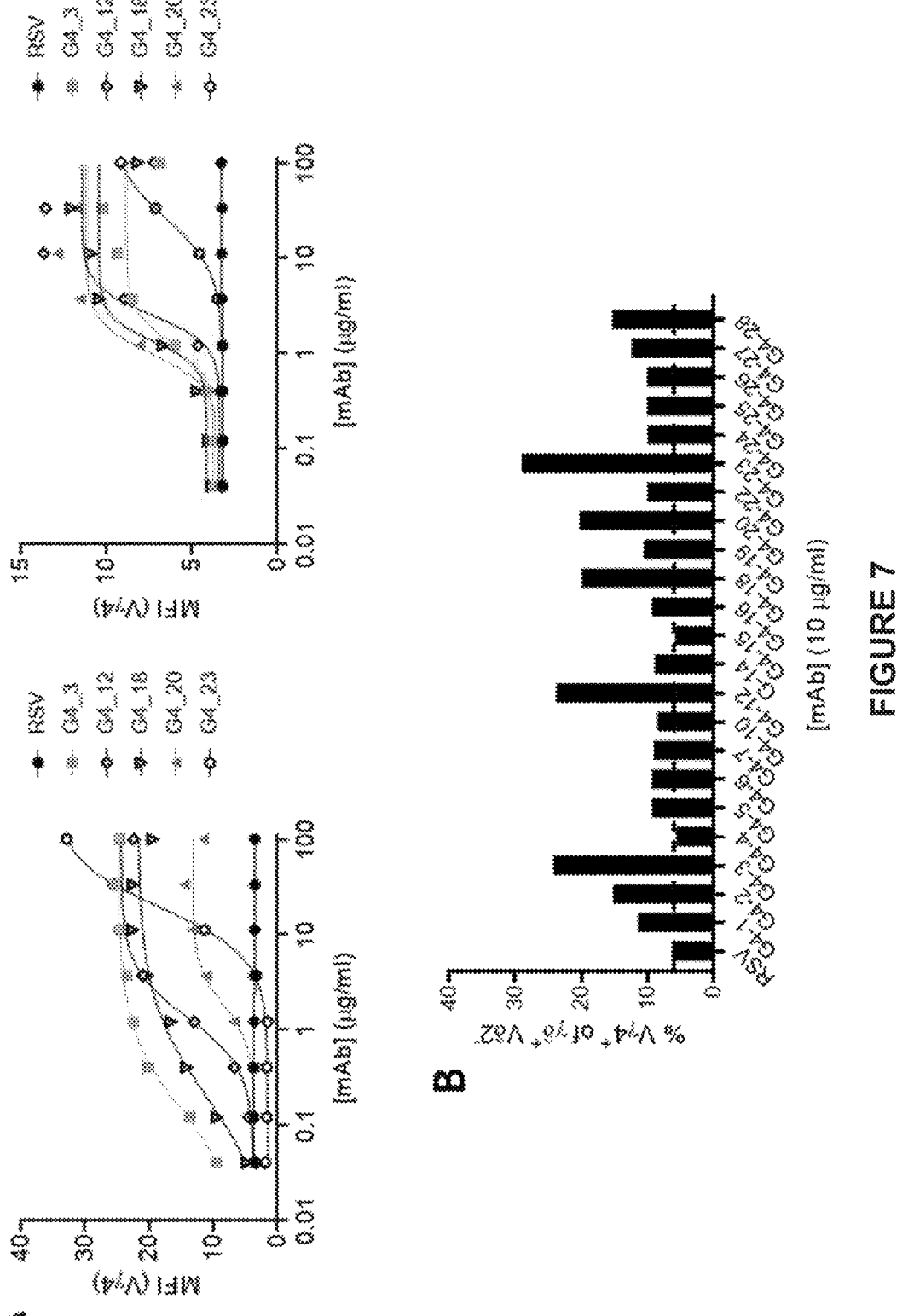
FIG. 7: Example antibody targeting and modulation of primary Vγ4-positive cells. (A) Titrated binding of anti-Vγ4 antibodies to primary Vγ4+ T cells expanded from the skin of two individual donors, showing that all example antibodies of the invention could bind to primary skin-derived Vγ4+ T cells in a dose-dependent manner. Isotype control was employed as a negative control demonstrating the specificity for Vγ4 of the example antibodies. (B) Binding of anti-Vγ4 antibodies to Vγ4+ T cells derived from peripheral blood mononuclear cells (PBMCs), showing that substantially all of the example antibodies of the invention could bind to primary blood-derived Vγ4+ T cells. RSV isotype control was employed as a negative control. (C) Binding of the anti-Vγ4 antibodies G4_3, G4_12 and G4_18 to gut-derived intraepithelial lymphocytes (IELs) from colorectal cancer (CRC) patients, showing binding of all three example antibodies to this cell population. Cells were gated as single, live, γδ+, IgG1+ (Vγ4)+. (D) Phenotyping of Vγ4+γδ T cells in the gut digest before stimulation with anti-Vγ4 antibodies, showing that example antibody, G4_18, could be used to identify Vγ4+ cells. 1.4% of live, single cells were Vδ1+. Of these, 44.2% were paired with Vγ4, and these displayed markers of tissue residency (CD69+CD103+). (E) Conferred TCR downregulation by example antibodies, G4_12 and G4_18, respectively versus downregulation conferred by isotype negative control, accompanied by representative FACS plots.

The results are shown in FIG. 7A. These data confirmed that all of the tested anti-Vγ4 antibodies were capable of binding to primary skin-derived Vγ4$^+$ T cells in a dose-dependent manner. No binding was observed with the isotype control.

Binding to Primary Vγ4$^+$ Cells Derived from Peripheral Blood Mononuclear Cells (PBMCs)

In brief, human PBMCs (Lonza, product code CC-2702) were first stained with viability dye in the presence of Fc block for 20 minutes at 4° C. Cells were then incubated with 10 µg/ml anti-Vγ4 antibodies or isotype control (RSV) for 30 minutes at 4° C., before being washed and stained extracellularly with anti-Vδ1 (REA173), anti-Vδ2 (REA771), anti-γδ (REA591) and anti-human IgG1 (IS11-12E4.23.20) for 20 minutes at 4° C. Cells were then fixed and acquired on the MACSQuant16 flow cytometer. Cells were gated as single, live, γδ$^+$ Vδ2$^-$ IgG1 (Vγ4)$^+$.

The results are shown in FIG. 7B. Data shown are % Vγ4$^+$ cells of γδ$^+$ Vδ2$^-$ cells detected using each individual antibody bound by the conjugated secondary anti-human IgG1 antibody. These data highlight the ability of substantially all of the anti-Vγ4 antibodies to bind primary blood-derived Vγ4$^+$ T cells. The strongest signals were detected using antibody G4_23, G4_3, G4_12, G4_18 or G4_20.

Binding to Primary Vγ4$^+$ Cells from Gut-Derived Intraepithelial Lymphocytes (IELs) Obtained from Colorectal Cancer (CRC) Patients For this study, human CRC tumour biopsy was shipped fresh and processed upon receipt. The biopsy was cut into pieces measuring ~2 mm$^2$ and tumour-infiltrating lymphocytes (TILs) were obtained using an adaptation of the method originally described by Kupper and Clarke (Clarke et al., 2006, *J. Invest. Dermatol.* 126, 1059-1070). Specifically, up to four 2 mm$^2$ biopsies were placed on 9 mm×9 mm×1.5 mm Cellfoam matrices, and one matrix was placed per well on a 24-well plate. Biopsies were then cultured in 2 ml Iscove's Modified Dulbecco's Medium (IMDM) supplemented with 4% human plasma, β-mercaptoethanol (50 µM), penicillin (100 U/ml), streptomycin (100 µg/ml), gentamicin (20 µg/ml), metronidazole (1 µg/ml), amphotericin B (2.5 µg/ml), HEPES (10 mM), Na Pyruvate (1 mM), MEM Non-Essential Amino Acids Solution (1×) and IL-15 (20 ng/ml, Miltenyi Biotech). 1 ml of medium was aspirated every 3 days and replaced with 1 ml complete medium containing 2× concentrated IL-15. TILs were harvested 10 days later, passed through a 70 µM nylon cell strainer, centrifuged at 300×g for 5 minutes and resuspended in complete medium for phenotyping. TILs were first stained with live/dead viability dye in the presence of Fc block for 20 minutes at 4° C. Cells were then incubated with 10 µg/ml anti-Vγ4 antibodies or isotype control (RSV) for 30 minutes at 4° C., before being washed and stained extracellularly with anti-Vδ1 (REA173), anti-γδ (REA591) and anti-human IgG1 (IS11-12E4.23.20) for 20 minutes at 4° C. Cells were then fixed and acquired on the MACSQuant16 flow cytometer. Cells were gated as single, live, γδ$^+$, IgG1$^+$ (Vγ4)$^+$.

The results are shown in FIG. 7C. Data shown are FACS plots illustrating binding of anti-Vγ4 antibodies, G4_3, G4_12 and G4_18, to primary gut-derived Vγ4$^+$ cells detected via the conjugated secondary anti-human IgG1 antibody. The data demonstrates the ability of the antibodies of the invention to bind to Vγ4$^+$ cells obtained from CRC tumour tissue.

Detection and TCR Downregulation of Human Gut-Derived γδ T Cells Conferred by Anti-Vγ4 Antibody A further study was undertaken to explore modulation of human gut-derived γδ T cells conferred by an anti-Vγ4 antibody. For these studies, normal adjacent tissue (NAT) biopsies from the colon of CRC patients were shipped fresh and processed upon receipt to obtain a single cell suspension. Specifically, the tissue was chopped in pieces measuring ~2 mm$^2$ and up to 1 g of tissue was placed into a Miltenyi C tube along with 4.7 ml RPMI with enzymes from Miltenyi's Tumour Dissociation Kit at concentrations recommended by the manufacturer aside from Enzyme R which was used at 0.2× concentration to prevent cleavage of pertinent cell surface molecules. C-Tubes were placed on the gentleMACS™ Octo Dissociator with heating blocks attached. Program 37C_h_TDK_1 for the dissociation of soft tumours was selected. After 1 hour the digest was filtered through a 70 µM filter and complete IMDM containing 4% human plasma was added to quench enzymatic activity. Cells were then washed twice and resuspended in complete IMDM for counting. At this point, cells were plated for stimulation with anti-Vγ4 antibodies, or were used for phenotyping.

In one series of experiments, the phenotype of Vγ4$^+$ γδ T cells in the gut digest before stimulation with anti-Vγ4 antibodies was determined. In brief, cells were stained with live/dead viability dye in the presence of Fc block for 20 minutes at 4° C. Cells were then incubated with 10 µg/ml G4_18 clone for 30 minutes at 4° C., before being washed and stained extracellularly with anti-Vδ1 (REA173), anti-γδ (REA591), anti-CD69 (REA824), anti-CD103 (Ber-Act8) and anti-human IgG1 (IS11-12E4.23.20) for 20 minutes at 4° C. Cells were then fixed and acquired on the MACSQuant16 flow cytometer. As shown in FIG. 7D, 1.4% of live, single cells were Vδ1$^+$. Of these, 44.2% were paired with Vγ4, and these all displayed markers of gut tissue residency (CD69$^+$ CD103$^+$) as expected for γδ T cells from the gut. These results confirm that the antibodies of the invention, in this case example antibody G4_18, can be used to specifically detect Vγ4$^+$ γδ T cells isolated from human gut tissue.

A next series of experiments measured the impact of stimulating the cells with an anti-Vγ4 antibody. 2×10⁶ cells were plated per well in a 48-well plate and were stimulated with G4_12, G4_18 or RSV IgG1 isotype control antibodies in the presence of IL-15 at a concentration of 2 ng/ml. Intraepithelial lymphocytes (IELs) isolated by enzymatic digestion were analysed by flow cytometry 24 hours post mAb stimulation. Following 24 hour stimulation, cells were stained with viability dye in the presence of Fc block for 20 minutes at 4° C. Cells were then stained extracellularly for γδTCR (REA591), fixed, and acquired on a MACSQuant16 flow cytometer. Live, single cells were gated as γδTCR⁺. FIG. 7E shows conferred γδTCR downregulation following 24 hours stimulation with G4_12 or G4_18 clones, compared with RSV isotype control, accompanied by representative FACS plots. Both anti-Vγ4 antibodies, G4_12 and G4_18, induced γδTCR downregulation relative to the RSV isotype control, with the greatest downregulation observed with G4_12.

Example 10. Further Studies Measuring the Binding Affinity (KD) to Human Vγ4 as Measured by Surface Plasmon Resonance (SPR) of Example Anti-Vγ4 Antibodies of the Invention In addition, to the SPR binding studies described in Example 4 (method described in Example 1) in respect of scFv binders, additional studies were undertaken to measure the binding affinity of select example clones to the human Vγ4 chain when clones were expressed as full IgG1 monoclonal antibodies.

In brief, the binding affinity of the antibodies to target (i.e. the human Vγ4 chain of a γδ TCR) was established by SPR analysis using a Reichert 4SPR instrument (Reichert Technologies). Antigen (L1 (DV1-GV4)) was coupled onto a Carboxymethyl Dextran Chip (Reichert Technologies) at 10 μg/ml, which resulted in an increase from baseline of approximately 750 uRIU, respectively. Antibody was flown over the cell at a 1:2 dilution series from 500 nM to 31.25 nM with the following parameters: 180 s association, 300 s dissociation, flowrate 25 L/min, running buffer PBS+0.05% TWEEN (polysorbate) 20. All experiments were performed at room temperature, with the samples kept at 4° C. before flowing over the chip. Steady state fitting was determined according to Langmuir 1:1 binding using software TraceDrawer (Reichert Technologies).

The results are shown in Table 4 and represent the average of 2 experiments per antibody (except where indicated).

TABLE 4

| Binding affinity of example antibodies of the invention for human Vγ4 | | | |
|---|---|---|---|
| Antibody clone | Experiment 1: KD (nM) | Experiment 2: KD (nM) | Average KD (nM) |
| G4_3 | 3.69 | 2.03 | 2.86 |
| G4_12 | 17.8 | 20.2 | 19 |
| G4_18 | ND | 19.9 | 19.9 |
| G4_20 | 43 | 62.1 | 52.55 |
| G4_23 | 109 | 178 | 143.5 |
| G4_27 | 261 | ND | 261 |

*ND-not determined

A range of binding affinities was determined, as expected, thus enabling a particular antibody to be selected for a particular circumstance depending on the binding affinity required. In particular, binding affinities ranged from approximately 260 nM-2.8 nM, as shown. This was consistent with the scFv studies described in Example 4.

Figure 8:
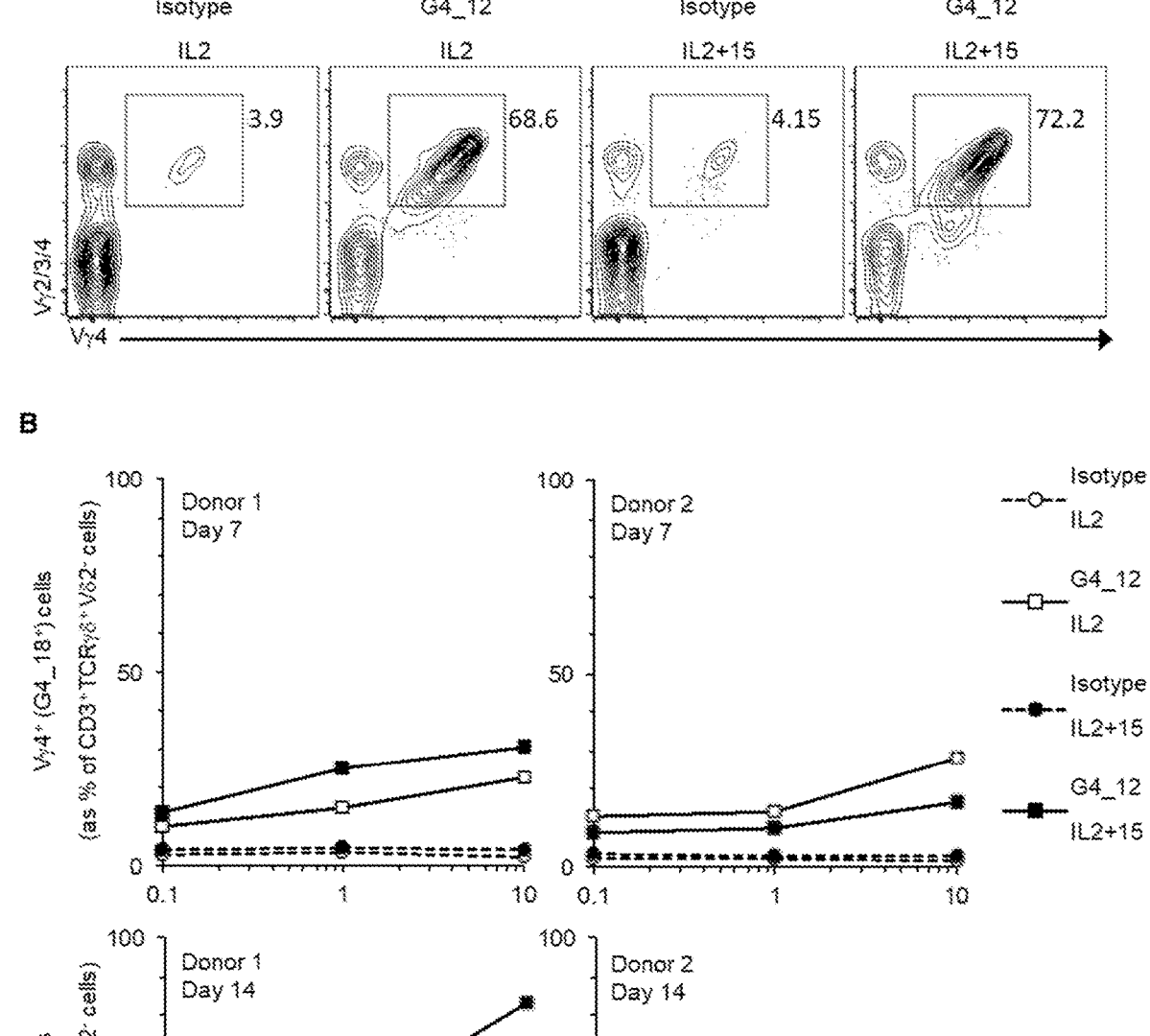
FIG. 8: Use of Vγ4-specific antibodies to increase the number of primary human Vγ4 T cells. (A) Example flow data to illustrate the increase in Vγ4 T cells (as determined by staining with clone G4_18) following a 14 day culture of PBMC with plate-bound anti-Vγ4 clone G4_12 compared to isotype control, in the presence of IL-2 or IL-2+IL-15. (B) Summary of the increase in Vγ4 T cells (as determined by staining with clone G4_18) after 7 days (top row) and 14 days (bottom row) cultures of PBMC from two donors with plate-bound anti-Vγ4 clone G4_12 compared to isotype control, in the presence of IL-2 or IL-2+IL-15.

Example 11. Use of Vγ4-Specific Antibodies to Increase the Number of Primary Human Vγ4 T Cells The antibody displaying the highest stimulatory activity on JRT3-hu17 cells (Clone G4_12, FIG. 5B,C) was further tested for its capacity to stimulate primary Vγ4+ T cells. The increase in the percentage of Vγ4 T cells in PBMC cultures following plate-bound stimulation with G4_12 compared to isotype control was analysed by flow cytometry using a panel of antibodies including A647-conjugated anti-Vγ4 clone G4_18 and is shown in FIG. 8. At days 7 and 14, the proportion of Vg4 positive cells in the presence of G4_12 antibody was greater than in cultures where the isotype control was present.

SEQUENCES

| SEQ ID NO. | Description | Sequence |
|---|---|---|
| 1 | V4 chain of RSCB Protein Data Bank entry: 4MNH | SSNLEGRTKSVIRQTGSSAEITCDLAEGSTGYIHWYLHQEGKAPQR LLYYDSYTSSVVLESGISPGKYDTYGSTRKNLRMILRNLIENDSGVY YCATWDEKYYKKLFGSGTTLVVTEDLKNVFPPEVAVFEPSEAEISH TQKATLVCLATGFYPDHVELSWWVNGKEVHSGVCTDPQPLKEQP ALNDSRYALSSRLRVSATFWQNPRNHFRCQVQFYGLSENDEWTQ DRAKPVTQIVSAEAWGRADSRGGLEVLFQ |
| 2-24 | CDR3 heavy sequences | See FIG. 1 |
| 25-47 | CDR3 light sequences | See FIG. 1 |
| 48-70 | CDR2 heavy sequences | See FIG. 1 |
| A1-A23 | CDR2 light sequences | See FIG. 1 |
| 71-93 | CDR1 heavy sequences | See FIG. 1 |

-continued

| SEQ ID NO. | Description | Sequence |
|---|---|---|
| 94-116 | CDR1 light sequences | See FIG. 1 |
| 117 | TRGV4 full heavy variable sequence G4_1 | EVQLLESGGGVVQPGRPLRLSCAASGFTFSSYSMNWVRQAPGKG LEWVSSISSSSSYIYYADSVKGRFTISRDNSKNTLYLQMNSLRAEDT AVYYCAKGHWYFDLWGRGTLVTVSS |
| 118 | TRGV4 full heavy variable sequence G4_2 | QMQLVQSGAEVKKPGATVKISCKVSGYPFTDYYIHWVQQAPGKGL EWMGLVDPEDGQSRSAERFQGRVTITADTSTDTAYMELSSLRSED TAVYYCATFPVAGFYGMDVWGQGTLVTVSS |
| 119 | TRGV4 full heavy variable sequence G4_3 | EVQLVESGGGLVQPGGSLRLSCAASGFTFSSYSMNWVRQAPGKG LEWVSSISSSSSYIYYADSVKGRFTISRDNSKNTLYLQMNSLRAEDT AVYYCARGGWLYDYWGQGTLVTVSS |
| 120 | TRGV4 full heavy variable sequence G4_4 | QVQLVESGGGLVQPGGSLRLSCAASGFTFSSYAMSWVRQAPGKG LEWVSAISGSGGSTYYADSVKGRFTISRDNSKNTLYLQMSSLRVED TAVYYCAKSSVGWWSFDYWGQGTMVTVSS |
| 121 | TRGV4 full heavy variable sequence G4_5 | EVQLVQSGAEVKKPGSSVKVSCKASGYTFTSYGISWVRQAPGQGL EWMGWIGAYNGNTNYAQKLQGRVTMSTDTSTSTAYMELRSPRSD DTAVYYCARGGTGGDHVFAYWGQGTTVTVSS |
| 122 | TRGV4 full heavy variable sequence G4_6 | EVQLVESGGGLVQPGGPLRLSCAASGFTFSSYAMNWVRQAPGKG LEWVSAISGSGGSTYYADSVKGRFTISRDNSKNTLYLQMNSLRAED TAVYYCAKADYGWYYFDYWGQGTMVTVSS |
| 123 | TRGV4 full heavy variable sequence G4_7 | EVQLVESGGGWVQSGGSLRPSCAASGFTFSHYWMSWVRQAPGK GLEWVANIKQDGSIIYYADSVKGRFTISRDNAKNSVYLQMNSLRAE DTAVYYCARIGYSSSSFDYWGRGTLVTVSS |
| 124 | TRGV4 full heavy variable sequence G4_10 | QVQLVESGGGWQPGRPLRLSCAASGFTFSSYAMHWVRQAPGKG LEWVSAISGSGGSTYYADSVKGRFTISRDNSKNTLYLQMNSLRAED TAVYYCAKDGAVDFWRNGMDVWGRGTLVTVSS |
| 125 | TRGV4 full heavy variable sequence G4_12 | EVQLLESGGGLVQPGGSLRLSCAASGFTVSSNYMSWVRQAPGKG LEWVSVIYSGGSTYYADSVKGRFTISRHNSKNTLYLQMNSLRAEDT AVYYCARVANGDFLDYWGRGTLVTVSS |
| 126 | TRGV4 full heavy variable sequence G4_13 | QVQLVESGAEVKKPGGSLRLSCAASGFTFSSYSMNWVRQAPGKG LEWVSSISGTSSYIYYADSVKGRFTISRDNAKNSLYLQMSSLRAEDT AVYYCARGGLGMVDPWGQGTLVTVSS |
| 127 | TRGV4 full heavy variable sequence G4_14 | EVQLVQSGAEVKKPGESLRISCKGSGYSFTSYWISWVRQMPGKGL EWMGRIDPSDSYTNYSPSFPGHVTISADKSISTAYLQWSSLKASDT AMYYCAADTAHGMDVWGRGTLVTVSS |
| 128 | TRGV4 full heavy variable sequence G4_15 | EVQLVQSEAEVKKPGASVKVSCKASGYTFTRHYMHWVRQAPGQG LEWMGLINPSGSSTVYAQKFQGRVTLTRDTSTSTDYMELSSLRSE DTAVYYCARDNSHLDQVWWFDPWGQGTLVTVSS |
| 129 | TRGV4 full heavy variable sequence G4_16 | EVQLLESGAEVKKPGASVKVSCKASGYTFTSYGISWRQAPGQGL EWMGWISAYNGNTNYAQKLQGRVTMTTDTSTSTAYMELRSLRSD DTAVYYCARDYGDFYGMDVWGQGTLVTVSS |
| 130 | TRGV4 full heavy variable sequence G4_18 | EVQLVESGAEVKKPGASVKVSCKASGYTFTGYYMHWVRQAPGQG LEWMGRINPNSGGTNYAQKFQGRVTMTRDASISTAYMELSRLRSD DTAVYYCARDLDLSSLDYWGRGTLVTVSS |
| 131 | TRGV4 full heavy variable sequence G4_19 | EVQLVQSGAEVKKPGASVKVSCKASGYTLTSYYMHWVRQAPGQG LEWMGIINPSGGSTSYAQKFQGRVTMTRDTSTSTVYMELSSLRSE DTAVYYCARERGYSYGDGMDVWGQGTTVTVSS |
| 132 | TRGV4 full heavy variable sequence G4_20 | QVQLVESGAEVKKPGASVKVSCKASGGTFSSYAISWVRQAPGQGL EWMGGHPIFGTANYAQKFQGRVTITVDKSTRTAYMELSSLRSKDTA VYYCARGNSRSDAFDIWGQGTMVTVSS |
| 133 | TRGV4 full heavy variable sequence G4_22 | QVQLVESGGGLVQPGGSLRLSCAASGFTFSTYAMSWVRQAPGKG LEWVSTVSGSGGTTYYADSVKGRFTISRDNSKNTLYLQMNSLRAE DTAVYYCAKDSTAVTDWFDPWGRGTLVTVSS |
| 134 | TRGV4 full heavy variable sequence G4_23 | EVQLVESGGGWQPGRSLRLSCAASGFTFSSYGMHWVRQAPGKG LEWVAVIWYDGSNKYYADSVKGRFTISRDNSKNTLYLQMNSLRAE DTAVYYCARGEVAALYYFDYWGQGTLVTVSS |

-continued

| SEQ ID NO. | Description | Sequence |
|---|---|---|
| 135 | TRGV4 full heavy variable sequence G4_24 | QVQLQQSGPGLVKPSQTLSLTCAISGASVSSNSVAWNWIRQSPSR GLEWLGRTYYRSRWYNDYALSVKSRIIINPDTSKNQFSLQLNSVTP EDTAVYYCARDWSSTRSFDYWGRGTLVTVSS |
| 136 | TRGV4 full heavy variable sequence G4_25 | EVQLVESGAEVKKPGSSVKVSCKASGGTFSSYAISWVRQAPGQGL EWMGGIIPIFGTANYAQKFQGRVTITADKSTSTAYMELSSLRSEDTA VYYCARSLRDGYNYIGSLGYWGQGTLVTVSS |
| 137 | TRGV4 full heavy variable sequence G4_26 | QVQLVQSGAEVKKPGSSVKVSCKASGGTFSSYAISWVRQAPGQG LEWMGGIIPIFGTANYAQKFQGRVTITADESTSTAYMELSSLRSEDT AVYYCASSRGSGWFPLGYWGQGTLVTVSS |
| 138 | TRGV4 full heavy variable sequence G4_27 | QVQLVQSGAEVKKPGESLKISCKSSGYSFTSYWIGWVRQMPGKGL EWMGIIYPGDSDTRYSPSFQGQVTFSADESISTAYLQWSSLKASDT AMYYCARHGAYGDYPDTFDIWGQGTLVTVSS |
| 139 | TRGV4 full heavy variable sequence G4_28 | QVQLVESGGGLVQPGGSLRLSCAASGFTFDDYAMHWVRQAPGK GLEWVSGISAGGGSTNYAGSVKGRFTVSRDTSKNTLYLQMNSLRA EDTAVYYCVKSYVDTAMRYYYYYMDVWGQGTMVTVSS |
| 140 | TRGV4 full light variable sequence G4_1 | ASDIQMTQSPSSLSASVGDRVTITCQASQDISNYLNWYQQKPGKA PKLLIYDASNLETGVPSRFSGSGSGTDFTLTISSLQPEDFATYYCQQ SYSTPVTFGPGTKVEIK |
| 141 | TRGV4 full light variable sequence G4_2 | ASDIQMTQSPSSLSASVGDRVTITCQASQDISNYLNWYQQKPGKA PKLLIYAASSLQSGVPSRFSGSGSGTDFTLTISGLQPEDFATYYCLE DYNYLWTFGQGTKLEIK |
| 142 | TRGV4 full light variable sequence G4_3 | ASDIQMTQSPSSLSASVGDRVTITCQASQDISNYLNWYQQKPGKA PKLLIYDASNLETGVPSRFSGSGSGTDFTLTISSLQPEDFATYFCQQ SYSTPQTFGQGTKVDIK |
| 143 | TRGV4 full light variable sequence G4_4 | ASDIVMTQSPDSLAVSLGERATINCKSSQSVLSSSNNNNYLAWYQ QRPGQPPKLLFYWASTRESGVPDRFSGSGSGTSFTLTITSLQAED VAVYYCQQYYSTPLTFGGGTKLEIK |
| 144 | TRGV4 full light variable sequence G4_5 | ASDIQMTQSPSSLSASVGDRVTITCRASQSISSYLNWYQQKPGKAP KLLIYAASSLQSGVPSRFSGSGSGTDFTLTISSLQPEDFATYYCQQS YSTPYTFGQGTKVEIK |
| 145 | TRGV4 full light variable sequence G4_6 | ASDIQMTQSPSSLSASVGDRVTITCRASQSISTYLNWYQQKPGKAP KLLIYAASSLQSGVPSRFSGSGSGTDFTLTISSPQPEDFATYYCQQ SYSTPYTFGQGTKVEIK |
| 146 | TRGV4 full light variable sequence G4_7 | ASDIVMTQSPLSLPVTPGEPASISCRSSQSLLHSNRFNYLDWYLQK PGQSPQLLIYLGSNRASGVPDRFSGSGSGTDFTLKISRVEAEDVGV YYCMQGLQTPYTFGQGTKVDIK |
| 147 | TRGV4 full light variable sequence G4_10 | ASDIVMTQPPLSLPVTLGHPASISCKSSQSLEYSDGNTYLNWFQQR PGQSPRRLIYKVSNRDSGAPDRFSGSGSGTDFTLEISRVEAEDVGV YYCMQGTLWPPTFGQGTKVDIK |
| 148 | TRGV4 full light variable sequence G4_12 | ASQSVLTQPASVSGSPGQSITISCTGTSSDVGGYNFVSWYQQHPG KAPKLMIYEVTNRPSGVPDRFSGSKSGNTASLTISGLQAEDEADYY CSSHASPRVFGTGTKVTVL |
| 149 | TRGV4 full light variable sequence G4_13 | ASNFMLTQPHSVSESPGKTVTISCTRSSGSIASNYVQWYQQRPGS SPSTVIYEDNQRPSGVPDRFSGSIDSSSNSASLTISGLRTEDEADYY CQSYDSSIYWFGGGTKLTVL |
| 150 | TRGV4 full light variable sequence G4_14 | ASNFMLTQPHSVSESPGKTVTISCTRSRGSIAGNYVHWYQQRPGR APTTVIYRDKERPSGVPDRISGSIDSSSNSASLTISGLKTEDEADYY CQSYDSSTHWFGGGTKLTVL |
| 151 | TRGV4 full light variable sequence G4_15 | ASQSALTQPASVSGSPGQSITISCTGTSSDVGGYNYVSWYQQHPG KAPKLMIYDVSNRPSGVSNRFSGSKSGNTASLTISGLQAEDEADYY CSSYGSGSVFGTGTKLTVL |
| 152 | TRGV4 full light variable sequence G4_16 | ASQSVLTQPPSASGSPGQSVTFSCTGTSSDIGAFNSVSWYQQHPG KAPKLLIYEITKRPSGVPDRFSGSKSGNTASLTISVLQAEDEADYYC TSYAGSNTLIFGGGTKVTVL |
| 153 | TRGV4 full light variable sequence G4_18 | ASSYELTQPPSVTESPGQTARITCSGDALAKQYAYWYQQKPGQAP VLVIYRDSERPSEIPERFSGSSSGTTVTLTISGVQAEDEADYYCQSA DSSGTYTVFGGGTKLTVL |

-continued

| SEQ ID NO. | Description | Sequence |
|---|---|---|
| 154 | TRGV4 full light variable sequence G4_19 | ASNFMLTQPHSVSESPGKTVTISCTRSSGSIASNYVQWYQQRPGS PPITLIYDDDQRPSGVPHRFSGSIDTSSNPASLTISGLKTEDEADYY CQSYDSSNHVVFGGGTKLTVL |
| 155 | TRGV4 full light variable sequence G4_20 | ASSYELTHPPSVSVSPGQTASITCSGDKLGDKFVSWYHQKPGQSP VLVIYQDSKRPSGIPERFSGSNSGNTATLTISGTRAMDEADYYCQA WDSSTVVFGGGTKLTVL |
| 156 | TRGV4 full light variable sequence G4_22 | ASDIQMTQSPSSLSASVGDRVTITCQASQDISNYLNWYQQKPGKA PKLLIYAASSLQSGVPSRFSVSGSGTDFTLTISNLQPEDFATYYCQQ SYSIPWTFGQGTKVEIK |
| 157 | TRGV4 full light variable sequence G4_23 | ASDIQMTQSPSSLSASVGDRVTITCRASQGISNSLAWYQQKPGKAP KLLLYAASRLESGVPSRFSGSGSGTDYTLTISSLQPEDFATYYCQQ YYSTPRTFGGGTKLEIK |
| 158 | TRGV4 full light variable sequence G4_24 | ASDIVMTQSPDSLAVSLGERATINCKSSQSVLYSSNNKNYLAWYQQ KPGQPPKLLISWASTRESGVPDRFSGSGSGTDFTLTINSLQSEDVAI YYCQQYYSTPPTFGQGTKLEIK |
| 159 | TRGV4 full light variable sequence G4_25 | ASQSALTQPRSVSGSPGQSVTISCTGTSSDVGGYNYVSWYQQHP GKAPKLMIYEVSNRPSGVSNRFSGSKSGNTASLTISGLQAEDEADY YCSSYGSGSVFGTGTKLTVL |
| 160 | TRGV4 full light variable sequence G4_26 | ASQSGLTQPASVSGSPGQSITISCTGTSSDVGSYNLVSWYQQHPG KAPKLMIYEVSKRPSGVSNRFSGSKSGNTASLTISGLQAEDEADYY CSSFGSGSIFGTGTKLTVL |
| 161 | TRGV4 full light variable sequence G4_27 | ASSYELTQDPAVSVALGQTVSITCQGDSLRNFYANWYQQKPGQAP VLVIYGKNNRPSGIPDRFSGSSSGNTASLTITGAQAEDEADYYCNS RDSSGNHLVFGGGTQLTVL |
| 162 | TRGV4 full light variable sequence G4_28 | ASSYELTQDPAVSVALGQTVTITCQGDSLRNYYASWYRQKPGQTP VLVVYGKNNRPSGIPDRFSVSASGNTASLTITGAQAEDEGDYYCNS RDSSGWFGGGTKVTVL |
| 163 | scFv sequence G4_1 | EVQLLESGGGVVQPGRPLRLSCAASGFTFSSYSMNWVRQAPGKG LEWVSSISSSSSYIYYADSVKGRFTISRDNSKNTLYLQMNSLRAEDT AVYYCAKGHWYFDLWGRGTLVTVSSGGGGSGGGGSGGGASDIQ MTQSPSSLSASVGDRVTITCQASQDISNYLNWYQQKPGKAPKLLIY DASNLETGVPSRFSGSGSGTDFTLTISSLQPEDFATYYCQQSYSTP VTFGPGTKVEIKRTAAASAHHHHHHKLDYKDHDGDYKDHDIDYKD DDDK |
| 164 | scFv sequence G4_2 | QMQLVQSGAEVKKPGATVKISCKVSGYPFTDYYIHWVQQAPGKGL EWMGLVDPEDGQSRSAERFQGRVTITADTSTDTAYMELSSLRSED TAVYYCATFPVAGFYGMDVWGQGTLVTVSSGGGGSGGGGSGGG ASDIQMTQSPSSLSASVGDRVTITCQASQDISNYLNWYQQKPGKA PKLLIYAASSLQSGVPSRFSGSGSGTDFTLTISGLQPEDFATYYCLE DYNYLWTFGQGTKLEIKRTAAASAHHHHHHKLDYKDHDGDYKDHD IDYKDDDDK |
| 165 | scFv sequence G4_3 | EVQLVESGGGLVQPGGSLRLSCAASGFTFSSYSMNWRQAPGKG LEWVSSISSSSSYIYYADSVKGRFTISRDNSKNTLYLQMNSLRAEDT AVYYCARGGWLYDYWGQGTLVTVSSGGGGSGGGGSGGGASDIQ MTQSPSSLSASVGDRVTITCQASQDISNYLNWYQQKPGKAPKLLIY DASNLETGVPSRFSGSGSGTDFTLTISSLQPEDFATYFCQQSYSTP QTFGQGTKVDIKRTAAASAHHHHHHKLDYKDHDGDYKDHDIDYKD DDDK |
| 166 | scFv sequence G4_4 | QVQLVESGGGLVQPGGSLRLSCAASGFTFSSYAMSWVRQAPGKG LEWVSAISGSGGSTYYADSVKGRFTISRDNSKNTLYLQMSSLRVED TAVYYCAKSSVGVWVSFDYWGQGTMVTVSSGGGGSGGGGSGGG ASDIVMTQSPDSLAVSLGERATINCKSSQSVLSSSNNNNYLAWYQ QRPGQPPKLLFYWASTRESGVPDRFSGSGSGTSFTLTITSLQAED VAVYYCQQYYSTPLTFGGGTKLEIKRTAAASAHHHHHHKLDYKDH DGDYKDHDIDYKDDDDK |
| 167 | scFv sequence G4_5 | EVQLVQSGAEVKKPGSSVKVSCKASGYTFTSYGISWVRQAPGQGL EWMGWIGAYNGNTNYAQKLQGRVTMSTDTSTSTAYMELRSPRSD DTAVYYCARGGTGGDHVFAYWGQGTTVTVSSGGGGSGGGGSGG GASDIQMTQSPSSLSASVGDRVTITCRASQSISSYLNWYQQKPGKA PKLLIYAASSLQSGVPSRFSGSGSGTDFTLTISSLQPEDFATYYCQQ SYSTPYTFGQGTKVEIKRTAAASAHHHHHHKLDYKDHDGDYKDHDI DYKDDDDK |

-continued

| SEQ ID NO. | Description | Sequence |
| --- | --- | --- |
| 168 | scFv sequence G4_6 | EVQLVESGGGLVQPGGPLRLSCAASGFTFSSYAMNWVRQAPGKG<br>LEWVSAISGSGGSTYYADSVKGRFTISRDNSKNTLYLQMNSLRAED<br>TAVYYCAKADYGVVYYFDYWGQGTMVTVSSGGGGSGGGGSGGG<br>ASDIQMTQSPSSLSASVGDRVTITCRASQSISTYLNWYQQKPGKAP<br>KLLIYAASSLQSGVPSRFSGSGSGTDFTLTISSPQPEDFATYYCQQ<br>SYSTPYTFGQGTKVEIKRTAAASAHHHHHHKLDYKDHDGDYKDHDI<br>DYKDDDDK |
| 169 | scFv sequence G4_7 | EVQLVESGGGWVQSGGSLRPSCAASGFTFSHYWMSWVRQAPGK<br>GLEWVANIKQDGSIIYYADSVKGRFTISRDNAKNSVYLQMNSLRAE<br>DTAVYYCARIGYSSSSFDYWGRGTLVTVSSGGGGSGGGGSGGGA<br>SDIVMTQSPLSLPVTPGEPASISCRSSQSLLHSNRFNYLDWYLQKP<br>GQSPQLLIYLGSNRASGVPDRFSGSGSGTDFTLKISRVEAEDVGVY<br>YCMQGLQTPYTFGQGTKVDIKRTAAASAHHHHHHKLDYKDHDGD<br>YKDHDIDYKDDDDK |
| 170 | scFv sequence G4_10 | QVQLVESGGGWQPGRPLRLSCAASGFTFSSYAMHWVRQAPGKG<br>LEWVSAISGSGGSTYYADSVKGRFTISRDNSKNTLYLQMNSLRAED<br>TAVYYCAKDGAVDFWRNGMDVWGRGTLVTVSSGGGGSGGGGS<br>GGGASDIVMTQPPLSLPVTLGHPASISCKSSQSLEYSDGNTYLNWF<br>QQRPGQSPRRLIYKVSNRDSGAPDRFSGSGSGTDFTLEISRVEAE<br>DVGVYYCMQGTLWPPTFGQGTKVDIKRTAAASAHHHHHHKLDYK<br>DHDGDYKDHDIDYKDDDDK |
| 171 | scFv sequence G4_12 | EVQLLESGGGLVQPGGSLRLSCAASGFTVSSNYMSWVRQAPGKG<br>LEWVSVIYSGGSTYYADSVKGRFTISRHNSKNTLYLQMNSLRAEDT<br>AVYYCARVANGDFLDYWGRGTLVTVSSGGGGSGGGGSGGGASQ<br>SVLTQPASVSGSPGQSITISCTGTSSDVGGYNFVSWYQQHPGKAP<br>KLMIYEVTNRPSGVPDRFSGSKSGNTASLTISGLQAEDEADYYCSS<br>HASPRVFGTGTKVTVLRTAAASAHHHHHHKLDYKDHDGDYKDHDI<br>DYKDDDDK |
| 172 | scFv sequence G4_13 | QVQLVESGAEVKKPGGSLRLSCAASGFTFSSYSMNWVRQAPGKG<br>LEWVSSISGTSSYIYYADSVKGRFTISRDNAKNSLYLQMSSLRAEDT<br>AVYYCARGGLGMVDPWGQGTLVTVSSGGGGSGGGGSGGGASN<br>FMLTQPHSVSESPGKTVTISCTRSSGSIASNYVQWYQQRPGSSPS<br>TVIYEDNQRPSGVPDRFSGSIDSSSNSASLTISGLRTEDEADYYCQ<br>SYDSSIYVVFGGGTKLTVLRTAAASAHHHHHHKLDYKDHDGDYKD<br>HDIDYKDDDDK |
| 173 | scFv sequence G4_14 | EVQLVQSGAEVKKPGESLRISCKGSGYSFTSYWISWVRQMPGKGL<br>EWMGRIDPSDSYTNYSPSFPGHVTISADKSISTAYLQWSSLKASDT<br>AMYYCAADTAHGMDVWGRGTLVTVSSGGGGSGGGGSGGGASN<br>FMLTQPHSVSESPGKTVTISCTRSRGSIAGNYVHWYQQRPGRAPT<br>TVIYRDKERPSGVPDRISGSIDSSSNSASLTISGLKTEDEADYYCQS<br>YDSSTHVVFGGGTKLTVLRTAAASAHHHHHHKLDYKDHDGDYKDH<br>DIDYKDDDDK |
| 174 | scFv sequence G4_15 | EVQLVQSEAEVKKPGASVKVSCKASGYTFTRHYMHWVRQAPGQG<br>LEWMGLINPSGSSTVYAQKFQGRVTLTRDTSTSTDYMELSSLRSE<br>DTAVYYCARDNSHLDQVWWFDPWGQGTLVTVSSGGGGSGGGG<br>SGGGASQSALTQPASVSGSPGQSITISCTGTSSDVGGYNYVSWYQ<br>QHPGKAPKLMIYDVSNRPSGVSNRFSGSKSGNTASLTISGLQAEDE<br>ADYYCSSYGSGSVFGTGTKLTVLRTAAASAHHHHHHKLDYKDHDG<br>DYKDHDIDYKDDDDK |
| 175 | scFv sequence G4_16 | EVQLLESGAEVKKPGASVKVSCKASGYTFTSYGISWVRQAPGQGL<br>EWMGWISAYNGNTNYAQKLQGRVTMTTDTSTSTAYMELRSLRSD<br>DTAVYYCARDYGDFYGMDVWGQGTLVTVSSGGGGSGGGGSGG<br>GASQSVLTQPPSASGSPGQSVTFSCTGTSSDIGAFNSVSWYQQHP<br>GKAPKLLIYEITKRPSGVPDRFSGSKSGNTASLTISVLQAEDEADYY<br>CTSYAGSNTLIFGGGTKVTVLRTAAASAHHHHHHKLDYKDHDGDY<br>KDHDIDYKDDDDK |
| 176 | scFv sequence G4_18 | EVQLVESGAEVKKPGASVKVSCKASGYTFTGYYMHWVRQAPGQG<br>LEWMGRINPNSGGTNYAQKFQGRVTMTRDASISTAYMELSRLRSD<br>DTAVYYCARDLDLSSLDYWGRGTLVTVSSGGGGSGGGGSGGGA<br>SSYELTQPPSVTESPGQTARITCSGDALAKQYAYWYQQKPGQAPV<br>LVIYRDSERPSEIPERFSGSSSGTTVTLTISGVQAEDEADYYCQSAD<br>SSGTYTVFGGGTKLTVLRTAAASAHHHHHHKLDYKDHDGDYKDHD<br>IDYKDDDDK |

-continued

| SEQ ID NO. | Description | Sequence |
| --- | --- | --- |
| 177 | scFv sequence G4_19 | EVQLVQSGAEVKKPGASVKVSCKASGYTLTSYYMHWVRQAPGQG LEWMGHNPSGGSTSYAQKFQGRVTMTRDTSTSTVYMELSSLRSE DTAVYYCARERGYSYGDGMDVWGQGTTVTVSSGGGGSGGGGS GGGASNFMLTQPHSVSESPGKTVTISCTRSSGSIASNYVQWYQQR PGSPPITLIYDDDQRPSGVPHRFSGSIDTSSNPASLTISGLKTEDEA DYYCQSYDSSNHVVFGGGTKLTVLRTAAASAHHHHHHKLDYKDHD GDYKDHDIDYKDDDDK |
| 178 | scFv sequence G4_20 | QVQLVESGAEVKKPGASVKVSCKASGGTFSSYAISWVRQAPGQGL EWMGGIIPIFGTANYAQKFQGRVTITVDKSTRTAYMELSSLRSKDTA VYYCARGNSRSDAFDIWGQGTMVTVSSGGGGSGGGGSGGGGASS YELTHPPSVSVSPGQTASITCSGDKLGDKFVSWYHQKPGQSPVLVI YQDSKRPSGIPERFSGSNSGNTATLTISGTRAMDEADYYCQAWDS STVVFGGGTKLTVLRTAAASAHHHHHHKLDYKDHDGDYKDHDIDY KDDDDK |
| 179 | scFv sequence G4_22 | QVQLVESGGGLVQPGGSLRLSCAASGFTFSTYAMSWVRQAPGKG LEWVSTVSGSGGTTYYADSVKGRFTISRDNSKNTLYLQMNSLRAE DTAVYYCAKDSTAVTDWFDPWGRGTLVTVSSGGGGSGGGGSGGG GASDIQMTQSPSSLSASVGDRVTITCQASQDISNYLNWYQQKPGK APKLLIYAASSLQSGVPSRFSGSGSGTDFTLTISNLQPEDFATYYCQ QSYSIPWTFGQGTKVEIKRTAAASAHHHHHHKLDYKDHDGDYKDH DIDYKDDDDK |
| 180 | scFv sequence G4_23 | EVQLVESGGGVVQPGRSLRLSCAASGFTFSSYGMHWVRQAPGKG LEWVAVIWYDGSNKYYADSVKGRFTISRDNSKNTLYLQMNSLRAE DTAVYYCARGEVAALYYFDYWGQGTLVTVSSGGGGSGGGGSGG GASDIQMTQSPSSLSASVGDRVTITCRASQGISNSLAWYQQKPGK APKLLLYAASRLESGVPSRFSGSGSGTDYTLTISSLQPEDFATYYC QQYYSTPRTFGGGTKLEIKRTAAASAHHHHHHKLDYKDHDGDYKD HDIDYKDDDDK |
| 181 | scFv sequence G4_24 | QVQLQQSGPGLVKPSQTLSLTCAISGASVSSNSVAWNWIRQSPSR GLEWLGRTYYRSRWYNDYALSVKSRIIINPDTSKNQFSLQLNSVTP EDTAVYYCARDWSSTRSFDYWGRGTLVTVSSGGGGSGGGGSGG GASDIVMTQSPDSLAVSLGERATINCKSSQSVLYSSNNKNYLAWYQ QKPGQPPKLLISWASTRESGVPDRFSGSGSGTDFTLTINSLQSEDV AIYYCQQYYSTPPTFGQGTKLEIKRTAAASAHHHHHHKLDYKDHDG DYKDHDIDYKDDDDK |
| 182 | scFv sequence G4_25 | EVQLVESGAEVKKPGSSVKVSCKASGGTFSSYAISWVRQAPGQGL EWMGGIIPIFGTANYAQKFQGRVTITADKSTSTAYMELSSLRSEDTA VYYCARSLRDGYNYIGSLGYWGQGTLVTVSSGGGGSGGGGSGG GASQSALTQPRSVSGSPGQSVTISCTGTSSDVGGYNYVSWYQQH PGKAPKLMIYEVSNRPSGVSNRFSGSKSGNTASLTISGLQAEDEAD YYCSSYGSGSVFGTGTKLTVLRTAAASAHHHHHHKLDYKDHDGDY KDHDIDYKDDDDK |
| 183 | scFv sequence G4_26 | QVQLVQSGAEVKKPGSSVKVSCKASGGTFSSYAISWVRQAPGQG LEWMGGIIPIFGTANYAQKFQGRVTITADESTSTAYMELSSLRSEDT AVYYCASSRGSGWFPLGYWGQGTLVTVSSGGGGSGGGGSGGG ASQSGLTQPASVSGSPGQSITISCTGTSSDVGSYNLVSWYQQHPG KAPKLMIYEVSKRPSGVSNRFSGSKSGNTASLTISGLQAEDEADYY CSSFGSGSIFGTGTKLTVLRTAAASAHHHHHHKLDYKDHDGDYKD HDIDYKDDDDK |
| 184 | scFv sequence G4_27 | QVQLVQSGAEVKKPGESLKISCKSSGYSFTSYWIGWVRQMPGKGL EWMGIIYPGDSDTRYSPSFQGQVTFSADESISTAYLQWSSLKASDT AMYYCARHGAYGDYPDTFDIWGQGTLVTVSSGGGGSGGGGSGG GASSYELTQDPAVSVALGQTVSITCQGDSLRNFYANWYQQKPGQA PVLVIYGKNNRPSGIPDRFSGSSSGNTASLTITGAQAEDEADYYCN SRDSSGNHLVFGGGTQLTVLRTAAASAHHHHHKLDYKDHDGDY KDHDIDYKDDDDK |
| 185 | scFv sequence G4_28 | QVQLVESGGGLVQPGGSLRLSCAASGFTFDDYAMHWVRQAPGK GLEWVSGISAGGGSTNYAGSVKGRFTVSRDTSKNTLYLQMNSLRA EDTAVYYCVKSYVDTAMRYYYYYMDVWGQGTMVTVSSGGGGSG GGGSGGGASSYELTQDPAVSVALGQTVTITCQGDSLRNYYASWY RQKPGQTPVLVVYGKNNRPSGIPDRFSVSASGNTASLTITGAQAED EGDYYCNSRDSSGVVFGGGTKVTVLRTAAASAHHHHHHKLDYKD HDGDYKDHDIDYKDDDDK |
| 186 | Linker | GGGGSGGGGSGGG |

-continued

| SEQ ID NO. | Description | Sequence |
|---|---|---|
| 187 | Nucleotide VH sequence G4_1 | GAGGTGCAGCTGTTGGAGTCTGGGGGAGGCGTGGTCCAGCCT GGGAGGCCCCTGAGACTCTCCTGTGCAGCGTCTGGATTCACCT TCAGTAGCTATAGCATGAACTGGGTCCGCCAGGCTCCAGGGAA GGGGCTGGAGTGGGTCTCATCCATTAGTAGTAGTAGTAGTTACA TATACTACGCAGACTCAGTGAAGGGCCGATTCACCATCTCCAGA GACAATTCCAAGAACACGCTGTATCTGCAAATGAACAGCCTGAG AGCCGAGGACACGGCCGTATATTACTGTGCGAAAGGACACTGG TACTTCGATCTCTGGGGCCGTGGCACCCTGGTCACCGTCTCGA GT |
| 188 | Nucleotide VH sequence G4_2 | CAGATGCAGCTGGTGCAGTCTGGGGCTGAGGTGAAGAAGCCTG GGGCTACAGTGAAAATCTCCTGCAAGGTTTCTGGATACCCTTTC ACCGACTACTATATCCACTGGGTGCAACAGGCCCCTGGAAAAG GGCTTGAGTGGATGGGACTTGTTGATCCTGAGGATGGGCAAAG TAGATCCGCGGAGAGGTTCCAGGGCAGAGTCACCATAACCGCG GACACGTCTACAGACACAGCCTACATGGAGCTGAGCAGCCTGA GATCTGAGGACACGGCCGTGTATTACTGTGCAACATTCCCAGTG GCTGGATTCTACGGTATGGACGTCTGGGGCCAGGGAACCCTGG TCACCGTCTCGAGT |
| 189 | Nucleotide VH sequence G4_3 | GAGGTGCAGCTGGTGGAGTCCGGGGGAGGCTTGGTCCAGCCG GGGGGGTCCCTGAGACTCTCCTGTGCAGCCTCTGGATTCACCT TCAGTAGCTATAGCATGAACTGGGTCCGCCAGGCTCCAGGGAA GGGGCTGGAGTGGGTCTCATCCATTAGTAGTAGTAGTAGTTACA TATACTACGCAGACTCCGTGAAGGGCCGGTTCACCATCTCCAGA GACAATTCCAAGAACACGCTGTATCTGCAAATGAACAGCCTGAG AGCCGAGGACACGGCCGTGTATTACTGTGCGAGAGGAGGGGTG GCTATATGACTACTGGGGCCAAGGAACCCTGGTCACCGTCTCG AGT |
| 190 | Nucleotide VH sequence G4_4 | CAGGTGCAGCTGGTGGAGTCTGGGGGAGGCTTGGTACAGCCT GGGGGGTCCCTGAGACTCTCCTGTGCAGCCTCTGGATTCACCT TTAGCAGCTATGCCATGAGCTGGGTCCGCCAGGCTCCAGGGAA GGGGCTGGAGTGGGTCTCAGCTATTAGTGGTAGTGGTGGTAGC ACATACTACGCAGACTCCGTGAAGGGCCGGTTCACCATCTCCA GAGACAATTCCAAAAACACCCTGTATCTGCAAATGAGCAGCCTG AGAGTCGAAGACACGGCCGTATATTATTGTGCGAAATCGTCGGT GGGCTGGTGGTCTTTTGACTACTGGGGCCAAGGGACAATGGTC ACCGTCTCGAGT |
| 191 | Nucleotide VH sequence G4_5 | GAAGTGCAGCTGGTGCAGTCTGGGGCTGAGGTGAAGAAGCCTG GGTCCTCGGTGAAGGTCTCCTGCAAGGCTTCTGGTTACACCTTT ACCAGCTACGGTATCAGCTGGGTGCGACAGGCCCCTGGACAAG GGCTTGAGTGGATGGGATGGATCGGCGCTTACAATGGTAACAC AAACTATGCACAGAAGCTCCAGGGCAGAGTCACCATGAGCACA GACACATCCACGAGCACAGCCTACATGGAGCTGAGGAGCCCGA GATCTGACGACACGGCCGTGTATTACTGTGCGAGAGGCGGGAC GGGGGGGTGACCACGTCTTTGCCTACTGGGGGCAAGGGACCAC GGTCACCGTCTCGAGT |
| 192 | Nucleotide VH sequence G4_6 | GAGGTGCAGCTGGTGGAGTCTGGGGGAGGCTTGGTACAGCCT GGGGGGGCCCTGAGACTCTCCTGTGCAGCCTCTGGATTCACCT TTAGCAGCTATGCCATGAACTGGGTCCGCCAGGCTCCAGGGAA GGGGCTGGAGTGGGTCTCAGCTATTAGTGGTAGTGGTGGTAGC ACATACTACGCAGACTCCGTGAAGGGCCGGTTCACCATCTCCA GAGACAATTCCAAGAACACGCTGTATCTGCAAATGAACAGCCTG AGAGCCGAGGACACGGCCGTATATTACTGTGCGAAAGCCGACT ACGGGGTGGTCTACTACTTTGACTACTGGGGCCAAGGGACAAT GGTCACCGTCTCGAGT |
| 193 | Nucleotide VH sequence G4_7 | GAGGTGCAGCTGGTGGAGTCTGGGGGAGGCTGGGTCCAGTCT GGGGGGTCCCTGAGACCCTCCTGTGCAGCCTCTGGATTCACCT TTAGTCACTATTGGATGAGTTGGGTCCGCCAGGCTCCAGGGAA GGGGCTGGAGTGGGTGGCCAACATAAAGCAAGATGGAAGTATC ATATACTATGCAGACTCTGTGAAGGGCCGATTCACCATCTCCAG GGACAACGCCAAGAACTCAGTGTATCTGCAAATGAACAGCCTGA GAGCCGAGGACACGGCCGTGTATTACTGTGCGAGAATTGGGTA TAGCAGCTCGTCTTTTGACTACTGGGGCCGTGGCACCCTGGTC ACCGTCTCGAGT |

-continued

| SEQ ID NO. | Description | Sequence |
|---|---|---|
| 194 | Nucleotide VH sequence G4_10 | CAGGTGCAGCTGGTGGAGTCTGGGGGAGGCGTGGTCCAGCCT GGGAGGCCCCTGAGACTCTCCTGTGCAGCCTCTGGATTCACCT TCAGTAGCTATGCTATGCACTGGGTCCGCCAGGCTCCAGGGAA GGGGCTGGAGTGGGTCTCAGCTATTAGTGGTAGTGGTGGTAGC ACATACTACGCAGACTCCGTGAAGGGCCGGTTCACCATCTCCA GAGACAATTCCAAGAACACGCTGTATCTGCAAATGAACAGCCTG AGAGCCGAGGACACGGCCGTATATTACTGTGCGAAAGATGGGG CCGTGGATTTTTGGCGAAACGGTATGGACGTCTGGGGCCGTGG CACCCTGGTCACCGTCTCGAGT |
| 195 | Nucleotide VH sequence G4_12 | GAGGTGCAGCTGTTGGAGTCTGGAGGAGGCTTGGTCCAGCCTG GGGGGTCCCTGAGACTCTCCTGTGCAGCCTCTGGGTTCACCGT CAGTAGCAACTACATGAGCTGGGTCCGCCAGGCTCCAGGGAAG GGGCTGGAGTGGGTCTCAGTTATTTATAGCGGTGGTAGCACATA CTACGCAGACTCCGTGAAGGGCCGATTCACCATCTCCCGACAC AATTCCAAGAACACGCTGTATCTTCAAATGAACAGCCTGAGAGC TGAGGACACGGCCGTGTATTACTGTGCGAGAGTAGCGAACGGT GACTTTCTTGACTACTGGGGCCGTGGCACCCTGGTCACCGTCT CGAGT |
| 196 | Nucleotide VH sequence G4_13 | CAGGTGCAGCTGGTGGAGTCTGGGGGCTGAGGTGAAGAAGCCT GGGGGGGTCCCTGAGACTCTCCTGTGCAGCCTCTGGATTCACCT TCAGTAGCTATAGCATGAACTGGGTCCGCCAGGCTCCAGGGAA GGGGCTGGAGTGGGTCTCATCCATTAGTGGTACTAGTAGTTACA TATACTACGCAGACTCTGTGAAGGGCCGATTCACCATCTCCAGA GACAACGCCAAGAACTCACTGTATCTGCAAATGAGCAGCCTGAG AGCCGAGGACACGGCTGTTTATTACTGTGCGAGAGGAGGGCTC GGGATGGTCGACCCCTGGGGCCAGGGAACCCTGGTCACCGTC TCGAGT |
| 197 | Nucleotide VH sequence G4_14 | GAAGTGCAGCTGGTGCAGTCCGGAGCAGAGGTGAAAAAGCCCG GGGAGTCTCTGAGGATCTCCTGTAAGGGTTCTGGATACAGCTTT ACCAGCTACTGGATCAGCTGGGTGCGCCAGATGCCCGGGAAAG GCCTGGAGTGGATGGGGAGGATTGATCCTAGTGACTCTTATACC AACTACAGCCCGTCCTTCCCAGGCCACGTCACCATCTCAGCTGA CAAGTCCATCAGCACTGCCTACCTGCAGTGGAGCAGCCTGAAG GCCTCGGACACCGCCATGTATTACTGTGCGGCGGATACAGCTC ACGGTATGGACGTCTGGGGCCGTGGCACCCTGGTCACCGTCTC GAGT |
| 198 | Nucleotide VH sequence G4_15 | GAAGTGCAGCTGGTGCAGTCTGAGGCTGAGGTGAAGAAGCCTG GGGCCTCAGTGAAGGTTTCCTGCAAGGCCTCTGGATACACCTTC ACCAGGCATTATATGCACTGGGTGCGACAGGCCCCCGGACAAG GGCTTGAGTGGATGGGACTAATCAACCCTAGTGGTAGTAGCACA GTCTACGCACAGAAGTTCCAGGGCAGAGTCACCTTGACCAGGG ACACGTCCACGAGCACAGACTACATGGAGCTGAGCAGCCTGAG ATCTGAGGACACGGCCGTCTATTATTGTGCGAGAGATAATAGTC ACCTCGACCAGGTTTGGTGGTTCGACCCCTGGGGCCAGGGCAC CCTGGTCACCGTCTCGAGT |
| 199 | Nucleotide VH sequence G4_16 | GAGGTGCAGCTGTTGGAGTCTGGAGCTGAGGTGAAGAAGCCTG GGGCCTCAGTGAAGGTCTCCTGCAAGGCTTCTGGTTACACCTTT ACCAGCTATGGTATCAGCTGGGTGCGACAGGCCCCTGGACAAG GGCTTGAGTGGATGGGATGGATCAGCGCTTACAATGGTAACAC AAACTATGCACAGAAGCTCCAGGGCAGAGTCACCATGACCACA GACACATCCACGAGCACAGCCTACATGGAGCTGAGGAGCCTGA GATCTGACGACACGGCCGTGTATTACTGTGCGAGAGACTACGG TGACTTCTACGGTATGGACGTCTGGGGCCAAGGAACCCTGGTC ACCGTCTCGAGT |
| 200 | Nucleotide VH sequence G4_18 | GAGGTGCAGCTGGTGGAGTCTGGGGCTGAGGTGAAGAAGCCT GGGGCCTCAGTGAAGGTCTCCTGCAAGGCTTCTGGATACACCT TCACCGGCTACTATATGCACTGGGTGCGACAGGCCCCTGGACA AGGGGCTTGAGTGGATGGGACGGATCAACCCTAACAGTGGTGGC ACAAACTATGCACAGAAGTTTCAGGGCAGGGTCACCATGACCAG GGACGCGTCCATCAGCACAGCCTACATGGAGCTGAGCAGGCTG AGATCTGACGACACGGCCGTGTATTACTGTGCGAGAGATCTTGA TCTATCCTCCCTTGACTACTGGGGCCGTGGCACCCTGGTCACC GTCTCGAGT |

-continued

| SEQ ID NO. | Description | Sequence |
|---|---|---|
| 201 | Nucleotide VH sequence G4_19 | GAAGTGCAGCTGGTGCAGTCTGGGGGCTGAGGTGAAGAAGCCTG GGGCCTCAGTGAAGGTTTCCTGCAAGGCATCTGGATACACCCT CACCAGCTACTATATGCACTGGGTGCGACAGGCCCCTGGACAA GGGCTTGAGTGGATGGGAATAATCAACCCTAGTGGTGGTAGCA CAAGCTACGCACAGAAGTTCCAGGGCAGAGTCACCATGACCAG GGACACGTCCACGAGCACAGTCTACATGGAGCTGAGCAGCCTG AGATCTGAGGACACGGCCGTGTATTACTGTGCGAGAGAGCGTG GATACAGCTATGGTGACGGTATGGACGTCTGGGGGCAAGGGAC CACGGTCACCGTCTCGAGT |
| 202 | Nucleotide VH sequence G4_20 | CAGGTGCAGCTGGTGGAGTCTGGAGCTGAGGTGAAGAAGCCTG GGGCCTCGGTGAAGGTCTCCTGCAAGGCTTCTGGAGGCACCTT CAGCAGCTATGCTATCAGCTGGGTGCGACAGGCCCCTGGACAA GGGCTTGAGTGGATGGGAGGGATCATCCCTATCTTTGGTACAG CAAACTACGCACAGAAGTTCCAGGGCAGAGTCACGATTACCGT GGACAAATCCACGCGCACAGCCTACATGGAGCTGAGCAGCCTG AGATCTAAGGACACGGCCGTGTATTACTGTGCGAGGGGGAATA GCAGAAGTGATGCTTTTGATATCTGGGGCCAAGGGACAATGGTC ACCGTCTCGAGT |
| 203 | Nucleotide VH sequence G4_22 | CAGGTGCAGTTGGTGGAGTCTGGGGGAGGCTTGGTACAGCCTG GGGGGTCCCTGAGACTCTCCTGTGCAGCCTCTGGATTCACCTTT AGCACCTATGCCATGAGCTGGGTCCGCCAGGCTCCAGGGAAGG GGCTGGAGTGGGTCTCAACTGTTAGTGGTAGTGGTGGTACCAC ATACTACGCAGACTCCGTGAAGGGCCGGTTCACCATCTCCAGA GACAATTCCAAGAACACGCTGTATCTGCAAATGAACAGCCTGAG AGCCGAAGCACGGCCGTATATTACTGTGCGAAAGATTCAACGG CGGTGACTGACTGGTTCGACCCCTGGGGCCGTGGCACCCTGGT CACCGTCTCGAGT |
| 204 | Nucleotide VH sequence G4_23 | GAGGTGCAGCTGGTGGAGTCTGGGGGAGGCGTGGTCCAGCCT GGGAGGTCCCTGAGACTCTCCTGTGCAGCGTCTGGATTCACCT TCAGTAGCTATGGCATGCACTGGGTCCGCCAGGCTCCAGGCAA GGGGCTGGAGTGGGTGGCAGTTATATGGTATGATGGAAGTAAT AAATACTATGCAGACTCCGTGAAGGGCCGATTCACCATCTCCAG AGACAATTCCAAGAACACGCTGTATCTGCAAATGAACAGCCTGA GAGCCGAGGACACGGCTGTGTATTACTGTGCGAGAGGGGAAGT GGCTGCCTTGTACTACTTTGACTACTGGGGCCAGGGAACCCTG GTCACCGTCTCGAGT |
| 205 | Nucleotide VH sequence G4_24 | CAGGTACAGCTGCAGCAGTCAGGTCCAGGACTGGTGAAGCCCT CGCAGACCCTCTCACTCACCTGTGCCATCTCCGGGGACAGTGT CTCTAGCAACAGTGTTGCTTGGAACTGGATCAGGCAGTCCCCAT CGAGAGGCCTTGAGTGGCTGGGGAGGACATACTACAGGTCCAG GTGGTATAATGATTATGCATTATCTGTGAAAAGTCGAATAATCAT CAACCCAGACACATCCAAGAACCAGTTCTCCCTGCAGCTGAACT CTGTGACCCCCGAGGACACGGCTGTGTATTACTGTGCAAGAGA TTGGAGCAGCACCCGATCCTTTGACTACTGGGGCCGTGGCACC CTGGTCACCGTCTCGAGT |
| 206 | Nucleotide VH sequence G4_25 | GAGGTGCAGCTGGTGGAGTCTGGGGGCTGAGGTGAAGAAGCCT GGGTCCTCGGTGAAGGTCTCCTGCAAGGCTTCTGGAGGCACCT TCAGCAGCTATGCTATCAGCTGGGTGCGACAGGCCCCTGGACA AGGGCTTGAGTGGATGGGAGGGATCATCCCTATCTTTGGTACA GCAAACTACGCACAGAAGTTCCAGGGCAGAGTCACGATTACCG CGGACAAATCCACGAGCACAGCCTACATGGAGCTGAGCAGCCT GAGATCTGAGGACACGGCCGTGTATTACTGTGCGAGATCTCTTA GAGATGGCTACAATTACATCGGAAGTTTAGGCTACTGGGGCCAG GGCACCCTGGTCACCGTCTCGAGT |
| 207 | Nucleotide VH sequence G4_26 | CAGGTCCAGCTTGTGCAGTCTGGGGCTGAGGTGAAGAAGCCTG GATCCTCGGTGAAGGTCTCCTGCAAGGCTTCTGGAGGCACCTT CAGCAGCTATGCTATCAGCTGGGTGCGACAGGCCCCTGGACAA GGGCTTGAGTGGATGGGAGGGATCATCCCTATCTTTGGTACAG CAAACTACGCACAGAAGTTCCAGGGCAGAGTCACGATTACCGC GGACGAATCCACGAGCACAGCTTACATGGAGCTGAGCAGCCTG AGATCTGAAGACACGGCTGTGTATTACTGTGCGAGCTCCCGGG GCAGTGGCTGGTTTCCTTTGGGTTACTGGGGCCAAGGAACCCT GGTCACCGTCTCGAGT |

-continued

| SEQ ID NO. | Description | Sequence |
|---|---|---|
| 208 | Nucleotide VH sequence G4_27 | CAGGTCCAGCTGGTACAGTCTGGAGCAGAGGTGAAAAAGCCCG<br>GGGAGTCTCTGAAGATCTCCTGTAAGAGTTCTGGATACAGCTTT<br>ACCAGCTACTGGATCGGCTGGGTGCGCCAGATGCCCGGGAAAG<br>GCCTGGAGTGGATGGGGATCATCTATCCTGGTGACTCTGATACC<br>AGATACAGCCCGTCCTTCCAAGGCCAGGTCACCTTCTCAGCCG<br>ACGAGTCCATCAGTACCGCCTACCTGCAGTGGAGCAGCCTGAA<br>GGCCTCGGACACCGCCATGTATTACTGTGCGAGACATGGCGCC<br>TACGGTGACTACCCGGATACTTTTGATATCTGGGGCCAGGGCAC<br>CCTGGTCACCGTCTCGAGT |
| 209 | Nucleotide VH sequence G4_28 | CAGGTGCAGCTGGTGGAGTCTGGGGGAGGCTTGGTACAGCCT<br>GGGGGGTCCCTGAGACTCTCCTGTGCAGCCTCTGGATTCACCT<br>TTGATGATTATGCCATGCACTGGGTCCGGCAAGCTCCAGGGAA<br>GGGGCTGGAGTGGGTCTCAGGTATTAGTGCTGGTGGTGGTAGC<br>ACAAACTACGCAGGCTCCGTGAAGGGCCGGTTCACCGTCTCCA<br>GGGACACGTCCAAGAACACACTTTATCTGCAAATGAACAGCCTG<br>AGAGCCGAGGACACGGCCGTGTATTACTGTGTGAAGTCCTACG<br>TGGATACAGCTATGCGCTACTACTACTACTACATGGACGTCTGG<br>GGCCAAGGGACAATGGTCACCGTCTCGAGT |
| 210 | Nucleotide VL sequence G4_1 | GACATCCAGATGACCCAGTCTCCATCCTCCCTGTCTGCATCTGT<br>AGGAGACAGAGTCACCATCACTTGCCAGGCGAGTCAGGACATT<br>AGCAACTATTTAAATTGGTATCAGCAGAAACCAGGGAAAGCCCC<br>TAAGCTCCTGATCTACGATGCATCCAATTTGGAAACAGGGGTCC<br>CATCAAGGTTCAGTGGAAGTGGATCTGGGACAGATTTCACTCTC<br>ACCATCAGCAGTCTGCAACCTGAAGATTTTGCAACTTACTACTGT<br>CAACAGAGTTACAGTACCCCCGTCACTTTCGGCCCTGGGACCAA<br>GGTGGAAATCAAA |
| 211 | Nucleotide VL sequence G4_2 | GACATCCAGATGACCCAGTCTCCATCCTCCCTGTCTGCATCTGT<br>AGGAGACAGAGTCACCATCACTTGCCAGGCGAGTCAGGACATT<br>AGCAACTATTTAAATTGGTATCAGCAGAAACCAGGGAAAGCCCC<br>TAAGCTCCTGATCTATGCTGCATCCAGTTTGCAAAGTGGGGTCC<br>CATCAAGGTTCAGTGGCAGTGGATCTGGGACAGATTTCACTCTC<br>ACCATCAGCGGCCTGCAGCCTGAAGATTTTGCAACTTACTACTG<br>TCTAGAAGATTACAACTACCTGTGGACGTTCGGCCAAGGGACCA<br>AGCTGGAGATCAAA |
| 212 | Nucleotide VL sequence G4_3 | GACATCCAGATGACCCAGTCTCCATCCTCCCTGTCTGCATCTGT<br>AGGAGACAGAGTCACCATCACTTGCCAGGCGAGTCAGGACATT<br>AGCAACTATTTAAATTGGTATCAGCAGAAACCAGGGAAAGCCCC<br>TAAGCTCCTGATCTACGATGCATCCAATTTGGAAACAGGGGTCC<br>CATCAAGGTTCAGTGGAAGTGGGTCTGGGACAGATTTCACTCTC<br>ACCATCAGCAGTCTGCAACCTGAAGATTTTGCAACTTACTTCTGT<br>CAACAGAGTTACAGTACCCCCCAGACGTTCGGCCAAGGGACCA<br>AAGTGGATATCAAA |
| 213 | Nucleotide VL sequence G4_4 | GATATTGTGATGACCCAGTCTCCAGACTCCCTGGCTGTGTCTCT<br>GGGCGAGAGGGCCACCATCAACTGCAAGTCCAGCCAGAGTGTT<br>TTGTCCAGCTCCAACAATAACAACTACTTAGCTTGGTACCAACAG<br>AGACCAGGACAGCCTCCTAAGCTGCTCTTTTACTGGGCATCTAC<br>CCGGGAATCGGGGGTCCCTGACCGATTCAGTGGCAGCGGGTCT<br>GGAACATCTTTCACTCTCACCATCACCAGCCTGCAGGCTGAAGA<br>TGTGGCGGTTTATTACTGTCAGCAATATTATTCCACTCCTCTCAC<br>TTTCGGCGGAGGGACCAAGCTGGAGATCAAA |
| 214 | Nucleotide VL sequence G4_5 | GACATCCAGATGACCCAGTCTCCATCCTCCCTGTCTGCATCTGT<br>AGGAGACAGAGTCACCATCACTTGCCGGGCAAGTCAGAGCATT<br>AGCAGCTATTTAAATTGGTATCAGCAGAAACCAGGGAAAGCCCC<br>TAAGCTCCTGATCTATGCTGCATCCAGTTTGCAAAGTGGGGTCC<br>CATCAAGGTTCAGCGGCAGTGGATCTGGGACAGATTTCACTCTC<br>ACTATCAGCAGCCTGCAGCCTGAAGATTTTGCAACTTACTACTG<br>TCAACAGAGTTACAGTACCCCCTACACTTTTGGCCAGGGGACCA<br>AGGTGGAAATCAAA |
| 215 | Nucleotide VL sequence G4_6 | GACATCCAGATGACCCAGTCTCCATCCTCCCTGTCTGCATCTGT<br>AGGAGACAGAGTCACCATCACTTGCCGGGCAAGTCAGAGCATT<br>AGCACCTATTTAAATTGGTATCAGCAGAAACCAGGGAAAGCCCC<br>TAAGCTCCTGATCTATGCTGCATCCAGTTTGCAGAGTGGGGTCC<br>CATCAAGGTTCAGTGGCAGTGGATCTGGGACAGATTTCACTCTC<br>ACCATCAGCAGTCCGCAACCTGAAGATTTTGCAACTTACTACTG<br>TCAACAGAGTTACAGTACCCCGTACACTTTTGGCCAGGGGACCA<br>AGGTGGAAATCAAA |
| 216 | Nucleotide VL sequence G4_7 | GATATTGTGATGACGCAGTCTCCACTCTCCCTGCCCGTCACCCC<br>TGGAGAGCCGGCCTCCATCTCCTGCAGGTCCAGTCAGAGCCTC<br>CTGCATAGTAATAGATTCAACTATTTGGATTGGTACCTGCAGAAG |

-continued

| SEQ ID NO. | Description | Sequence |
|---|---|---|
| | | CCAGGGCAGTCTCCACAGCTCCTGATCTATTTGGGTTCTAATCG<br>GGCCTCCGGGGTCCCTGACAGGTTCAGTGGCAGTGGATCTGGC<br>ACAGATTTTACACTGAAAATCAGCAGAGTGGAGGCTGAGGATGT<br>TGGGGTTTATTACTGCATGCAAGGTCTACAAACTCCGTACACTTT<br>TGGCCAGGGGACCAAAGTGGATATCAAA |
| 217 | Nucleotide VL<br>sequence G4_10 | GATATTGTGATGACGCAGCCTCCACTCTCCCTGCCCGTCACCCT<br>TGGACATCCGGCCTCCATCTCCTGCAAGTCTAGTCAAAGCCTCG<br>AATATAGTGATGGAAACACCTACTTGAATTGGTTTCAGCAGAGG<br>CCAGGCCAATCTCCAAGGCGCCTCATTTATAAGGTTTCTAACCG<br>GGACTCTGGGGCCCCGACAGATTCAGCGGGAGTGGGTCAGG<br>CACTGATTTCACACTGGAAATCAGCAGGGTGGAGGCTGAGGAT<br>GTTGGAGTTTATTACTGTATGCAAGGTACACTCTGGCCTCCCAC<br>GTTCGGCCAAGGGACCAAAGTGGATATCAAA |
| 218 | Nucleotide VL<br>sequence G4_12 | CAGTCTGTGCTGACTCAGCCTGCCTCCGTGTCTGGGTCTCCTG<br>GACAGTCGATCACCATCTCCTGCACTGGAACCAGCAGTGACGTT<br>GGTGGTTATAACTTTGTCTCCTGGTACCAACAACACCCAGGCAA<br>AGCCCCCAAACTCATGATTTATGAGGTCACTAATCGGCCCTCAG<br>GGGTCCCTGATCGGTTCTCTGGCTCCAAGTCTGGCAACACGGC<br>CTCCCTGACCATCTCTGGGCTCCAGGCTGAGGACGAGGCTGAT<br>TATTACTGCAGCTCACATGCAAGCCCCAGGGTCTTCGGAACTGG<br>GACCAAGGTCACCGTCCTA |
| 219 | Nucleotide VL<br>sequence G4_13 | AATTTTATGCTGACTCAGCCCCACTCTGTGTCGGAGTCTCCGGG<br>GAAGACGGTAACCATCTCCTGCACCCGCAGCAGTGGCAGCATT<br>GCCAGCAACTATGTGCAGTGGTACCAGCAGCGCCCGGGCAGTT<br>CCCCCAGCACTGTGATCTATGAGGATAACCAAAGACCCTCAGG<br>GGTCCCTGATCGGTTCTCTGGCTCCATCGACAGCTCCTCCAACT<br>CTGCCTCCCTCACCATCTCTGGACTGAGGACTGAGGACGAGGC<br>TGACTACTACTGTCAGTCTTATGATAGCAGCATTTATGTGGTATT<br>CGGCGGAGGGACCAAGCTGACCGTCCTA |
| 220 | Nucleotide VL<br>sequence G4_14 | AATTTTATGCTGACTCAGCCCCACTCTGTGTCGGAGTCTCCGGG<br>GAAGACGGTAACCATATCCTGCACCCGCAGCCGTGGCAGCATT<br>GCCGGCAACTATGTGCACTGGTACCAGCAGCGCCCAGGGCGTG<br>CCCCCACCACTGTGATCTATCGGGATAAGGAAAGACCCTCTGG<br>GGTCCCTGATCGAATCTCTGGCTCCATCGACAGCTCCTCCAACT<br>CTGCCTCCCTCACCATCTCTGGACTGAAGACTGAGGACGAGGC<br>TGATTACTATTGTCAGTCTTATGATAGCAGCACCCATGTGGTATT<br>CGGCGGAGGGACCAAGCTGACCGTCCTA |
| 221 | Nucleotide VL<br>sequence G4_15 | CAGTCTGCGCTGACTCAGCCTGCCTCCGTGTCTGGGTCTCCTG<br>GACAGTCGATCACCATCTCCTGCACTGGAACCAGCAGTGACGTT<br>GGTGGTTATAACTATGTCTCCTGGTACCAACAACACCCAGGCAA<br>AGCCCCCAAACTCATGATTTATGACGTCAGTAATCGGCCCTCAG<br>GGGTTTCTAATCGCTTCTCTGGCTCCAAGTCTGGCAACACGGCC<br>TCCCTGACCATCTCTGGGCTCCAGGCTGAGGACGAGGCTGATT<br>ATTACTGCAGCTCGTATGGAAGCGGCAGCGTCTTCGGAACTGG<br>GACCAAGCTGACCGTCCTA |
| 222 | Nucleotide VL<br>sequence G4_16 | CAGTCTGTGCTGACTCAGCCTCCCTCCGCGTCCGGGTCTCCTG<br>GACAGTCAGTCACCTTCTCCTGCACTGGAACCAGCAGTGACATT<br>GGTGCTTTTAACTCTGTCTCTTGGTACCAACAGCACCCAGGCAA<br>AGCCCCCAAACTCCTAATTTATGAGATCACTAAGCGGCCCTCAG<br>GGGTCCCTGATCGCTTCTCTGGCTCCAAGTCTGGCAACACGGC<br>CTCCCTGACCATCTCTGTGCTCCAGGCTGAAGATGAGGCTGATT<br>ATTACTGCACCTCATATGCAGGCAGCAACACTTTGATCTTCGGC<br>GGAGGGACCAAGGTCACCGTCCTA |
| 223 | Nucleotide VL<br>sequence G4_18 | TCCTATGAGCTGACACAGCCACCCTCGGTGACAGAGTCCCCAG<br>GACAGACGGCCAGGATCACCTGCTCTGGAGATGCATTGGCAAA<br>GCAATATGCTTATTGGTACCAGCAGAAGCCAGGCCAGGCCCCT<br>GTGTTGGTGATATATAGAGACAGTGAGAGGCCTTCAGAGATCCC<br>TGAGCGATTCTCTGGCTCCAGCTCAGGGACAACAGTCACGTTGA<br>CCATCAGTGGAGTCCAGGCAGAAGACGAGGCTGACTATTACTG<br>TCAATCAGCAGACAGCAGTGGTACTTATACAGTATTTGGCGGAG<br>GGACCAAGCTGACCGTCCTA |
| 224 | Nucleotide VL<br>sequence G4_19 | AATTTTATGCTGACTCAGCCCCACTCTGTGTCGGAGTCTCCGGG<br>GAAGACGGTCACCATCTCCTGCACCCGCAGCAGTGGCAGCATT<br>GCCAGCAACTATGTACAGTGGTACCAGCAGCGCCCGGGCAGTC<br>CCCCCATCACTTTGATATATGATGATGACCAAAGACCCTCTGGG<br>GTCCCTCATCGGTTCTCTGGCTCCATCGACACCTCATCCAACCC<br>TGCCTCCCTCACCATCTCTGGACTGAAGACTGAGGACGAGGCT<br>GACTACTACTGTCAGTCTTATGATAGCAGCAATCATGTGGTATTC<br>GGCGGAGGGACCAAGCTGACCGTCCTA |

-continued

| SEQ ID NO. | Description | Sequence |
|---|---|---|
| 225 | Nucleotide VL sequence G4_20 | TCCTATGAGCTGACTCATCCACCCTCAGTGTCCGTGTCCCCAGG ACAGACAGCCAGCATCACCTGCTCTGGAGATAAATTGGGGGATA AGTTTGTTTCCTGGTATCACCAAAAGCCAGGCCAGTCCCCTGTG CTGGTCATCTATAAGATAGCAAGCGGCCCTCAGGGATCCCTGA GCGCTTCTCAGGCTCCAATTCTGGGAACACAGCCACTCTGACCA TCAGCGGGACCCGGGCTATGGATGAGGCTGACTATTACTGTCA GGCGTGGGACAGCAGCACTGTGGTATTCGGCGGAGGGACCAA GCTGACCGTCCTA |
| 226 | Nucleotide VL sequence G4_22 | GACATCCAGATGACCCAGTCTCCATCCTCCCTGTCTGCATCTGT AGGAGACAGAGTCACCATCACTTGCCAGGCGAGTCAGGACATT AGCAACTATTTAAATTGGTATCAGCAGAAACCAGGGAAAGCCCC TAAGCTCCTGATCTATGCTGCATCCAGTCTGCAAAGTGGGGTCC CATCAAGGTTCAGCGTCAGTGGATCTGGGACAGATTTCACTCTC ACCATCAGCAACCTGCAGCCTGAAGATTTTGCAACTTATTACTGT CAACAGAGTTACAGTATCCCGTGGACGTTCGGCCAAGGGACCA AGGTGGAGATCAAA |
| 227 | Nucleotide VL sequence G4_23 | GACATCCAGATGACCCAGTCTCCATCCTCCCTGTCTGCATCTGT AGGAGACAGAGTCACCATCACTTGCCGGGCGAGTCAGGGCATT AGCAATTCTTTAGCCTGGTATCAGCAGAAACCAGGGAAAGCCCC TAAGCTCCTGCTCTATGCTGCGTCCAGATTGGAAAGTGGGGTCC CATCCAGGTTTAGTGGCAGTGGATCTGGGACCGGATTACACCCTC ACCATCAGCAGCCTGCAGCCTGAAGATTTTGCAACTTATTACTG TCAACAGTATTATAGTACCCCTCGCACTTTCGGCGGAGGGACCA AGGTGGAGATCAAA |
| 228 | Nucleotide VL sequence G4_24 | GATATTGTGATGACCCAGTCTCCAGACTCCCTGGCTGTGTCTCT GGGCGAGAGGGCCACCATCAACTGCAAGTCCAGCCAGAGTGTT TTATACAGCTCCAACAATAAGAACTACTTAGCTTGGTACCAGCAG AAACCAGGACAGCCTCCTAAGTTGTTGATTTCCTGGGCTTCTAC CCGGGAATCTGGGGTCCCTGACCGATTCAGTGGCAGCGGGTCT GGGACAGATTTCACTCTCACCATCAACAGCCTACAGTCTGAAGA TGTGGCAATTTATTACTGTCAGCAATATTATTCTACCCCTCCGAC GTTCGGCCAGGGGACCAAGCTGGAGATCAAA |
| 229 | Nucleotide VL sequence G4_25 | CAGTCTGCGCTGACTCAGCCTCGCTCAGTGTCCGGGTCTCCTG GACAGTCAGTCACCATCTCCTGCACTGGAACCAGCAGTGATGTT GGTGGTTATAACTATGTCTCCTGGTACCAACAGCACCCAGGCAA AGCCCCCAAACTCATGATTTATGAGGTCAGTAATCGGCCCTCAG GGGTTTCTAATCGCTTCTCTGGCTCCAAGTCTGGCAACACGGCC TCCCTGACCATCTCTGGGCTCCAGGCTGAGGACGAGGCTGATT ATTACTGCAGCTCGTATGGAAGCGGCAGCGTCTTCGGAACTGG GACCAAGCTGACCGTCCTA |
| 230 | Nucleotide VL sequence G4_26 | CAGTCTGGGCTGACTCAGCCTGCCTCCGTGTCTGGGTCTCCTG GACAGTCGATCACCATCTCCTGCACTGGAACCAGCAGTGATGTT GGGAGTTATAACCTTGTCTCCTGGTACCAACAGCACCCAGGCAA AGCCCCCAAACTCATGATTTATGAGGTCAGTAAGCGGCCCTCAG GGGTTTCTAATCGCTTCTCTGGCTCCAAGTCTGGCAACACGGCC TCCCTGACCATCTCTGGGCTCCAGGCTGAGGACGAGGCTGATT ATTACTGCAGCTCGTTTGGAAGCGGCAGCATCTTCGGAACTGG GACCAAGCTGACCGTCCTA |
| 231 | Nucleotide VL sequence G4_27 | TCCTATGAGCTGACTCAGGACCCAGCTGTGTCTGTGGCCCTGG GACAGACAGTCAGTATCACATGCCAAGGAGACAGCCTCAGAAA CTTTTATGCAAACTGGTACCAGCAAAAGCCAGGACAGGCCCCTG TACTTGTCATCTATGGTAAAAACAACCGGCCCTCAGGGATCCCA GACCGATTCTCTGGCTCCAGCTCAGGAAACACAGCTTCCTTGAC CATCACTGGGGCTCAGGCGGAAGATGAGGCTGACTATTACTGT AACTCCCGGGACAGCAGTGGTAACCATCTGGTATTCGGCGGAG GGACCCAGCTCACCGTCCTA |
| 232 | Nucleotide VL sequence G4_28 | TCCTATGAGCTGACTCAGGACCCTGCTGTGTCTGTGGCCTTGG GACAGACAGTCACGATCACATGCCAAGGAGACAGCCTCAGAAA CTATTATGCAAGCTGGTACCGGCAGAAGCCAGGACAGACCCCT GTACTTGTCGTCTATGGTAAAAACAACCGGCCCTCAGGGATCCC AGACCGATTCTCTGTCTCCGCCTCAGGTAACACAGCTTCCTTGA CCATCACTGGGGCTCAGGCGGAAGATGAGGGTGACTATTACTG TAACTCCCGGGACAGCAGTGGTGTGGTTTTCGGCGGAGGGACC AAGGTCACCGTCCTA |
| 233 | G4_1 IgG1 antibody sequence | ASDIQMTQSPSSLSASVGDRVTITCQASQDISNYLNWYQQKPGKA PKLLIYDASNLETGVPSRFSGSGSGTDFTLTISSLQPEDFATYYCQQ SYSTPVTFGPGTKVEIKRTAAAPSVFIFPPSDEQLKSGTASVVCLLN NFYPREAKVQWKVDNALQSGNSQESVTEQDSKDSTYSLSSTLTLS |

-continued

| SEQ ID NO. | Description | Sequence |
|---|---|---|
| | | KADYEKHKLYACEVTHQGLSSPVTKSFNRGECEVQLLESGGGVVQ<br>PGRPLRLSCAASGFTFSSYSMNWVRQAPGKGLEWVSSISSSSSYI<br>YYADSVKGRFTISRDNSKNTLYLQMNSLRAEDTAVYYCAKGHWYF<br>DLWGRGTLVTVSSASTKGPSVFPLAPSSKSTSGGTAALGCLVKDY<br>FPEPVTVSWNSGALTSGVHTFPAVLQSSGLYSLSSVVTVPSSSLGT<br>QTYICNVNHKPSNTKVDKKVEPKSCDKTHTCPPCPAPELLGGPSVF<br>LFPPKPKDTLMISRTPEVTCVVVDVSHEDPEVKFNWYVDGVEVHN<br>AKTKPREEQYNSTYRVVSVLTVLHQDWLNGKEYKCKVSNKALPAPI<br>EKTISKAKGQPREPQVYTLPPSRDELTKNQVSLTCLVKGFYPSDIAV<br>EWESNGQPENNYKTTPPVLDSDGSFFLYSKLTVDKSRWQQGNVF<br>SCSVMHEALHNHYTQKSLSLSPGK |
| 234 | G4_2 IgG1<br>antibody<br>sequence | ASDIQMTQSPSSLSASVGDRVTITCQASQDISNYLNWYQQKPGKA<br>PKLLIYAASSLQSGVPSRFSGSGSGTDFTLTISGLQPEDFATYYCLE<br>DYNYLWTFGQGTKLEIKRTAAAPSVFIFPPSDEQLKSGTASVVCLLN<br>NFYPREAKVQWKVDNALQSGNSQESVTEQDSKDSTYSLSSTLTLS<br>KADYEKHKLYACEVTHQGLSSPVTKSFNRGECQMQLVQSGAEVK<br>KPGATVKISCKVSGYPFTDYYIHWVQQAPGKGLEWMGLVDPEDG<br>QSRSAERFQGRVTITADTSTDTAYMELSSLRSEDTAVYYCATFPVA<br>GFYGMDVWGQGTLVTVSSASTKGPSVFPLAPSSKSTSGGTAALG<br>CLVKDYFPEPVTVSWNSGALTSGVHTFPAVLQSSGLYSLSSVVTVP<br>SSSLGTQTYICNVNHKPSNTKVDKKVEPKSCDKTHTCPPCPAPELL<br>GGPSVFLFPPKPKDTLMISRTPEVTCVWDVSHEDPEVKFNWYVD<br>GVEVHNAKTKPREEQYNSTYRVVSVLTVLHQDWLNGKEYKCKVSN<br>KALPAPIEKTISKAKGQPREPQVYTLPPSRDELTKNQVSLTCLVKGF<br>YPSDIAVEWESNGQPENNYKTTPPVLDSDGSFFLYSKLTVDKSRW<br>QQGNVFSCSVMHEALHNHYTQKSLSLSPGK |
| 235 | G4_3 IgG1<br>antibody<br>sequence | ASDIQMTQSPSSLSASVGDRVTITCQASQDISNYLNWYQQKPGKA<br>PKLLIYDASNLETGVPSRFSGSGSGTDFTLTISSLQPEDFATYFCQQ<br>SYSTPQTFGQGTKVDIKRTAAAPSVFIFPPSDEQLKSGTASVVCLLN<br>NFYPREAKVQWKVDNALQSGNSQESVTEQDSKDSTYSLSSTLTLS<br>KADYEKHKLYACEVTHQGLSSPVTKSFNRGECEVQLVESGGGLVQ<br>PGGSLRLSCAASGFTFSSYSMNWVRQAPGKGLEWVSSISSSSSYI<br>YYADSVKGRFTISRDNSKNTLYLQMNSLRAEDTAVYYCARGGWLY<br>DYWGQGTLVTVSSASTKGPSVFPLAPSSKSTSGGTAALGCLVKDY<br>FPEPVTVSWNSGALTSGVHTFPAVLQSSGLYSLSSWTVPSSSLGT<br>QTYICNVNHKPSNTKVDKKVEPKSCDKTHTCPPCPAPELLGGPSVF<br>LFPPKPKDTLMISRTPEVTCVVVDVSHEDPEVKFNWYVDGVEVHN<br>AKTKPREEQYNSTYRVVSVLTVLHQDWLNGKEYKCKVSNKALPAPI<br>EKTISKAKGQPREPQVYTLPPSRDELTKNQVSLTCLVKGFYPSDIAV<br>EWESNGQPENNYKTTPPVLDSDGSFFLYSKLTVDKSRWQQGNVF<br>SCSVMHEALHNHYTQKSLSLSPGK |
| 236 | G4_4 IgG1<br>antibody<br>sequence | ASDIVMTQSPDSLAVSLGERATINCKSSQSVLSSSNNNNYLAWYQ<br>QRPGQPPKLLFYWASTRESGVPDRFSGSGSGTSFTLTITSLQAED<br>VAVYYCQQYYSTPLTFGGGTKLEIKRTAAAPSVFIFPPSDEQLKSGT<br>ASVVCLLNNFYPREAKVQWKVDNALQSGNSQESVTEQDSKDSTY<br>SLSSTLTLSKADYEKHKLYACEVTHQGLSSPVTKSFNRGECQVQLV<br>ESGGGLVQPGGSLRLSCAASGFTFSSYAMSWVRQAPGKGLEWVS<br>AISGSGGSTYYADSVKGRFTISRDNSKNTLYLQMSSLRVEDTAVYY<br>CAKSSVGWWSFDYWGQGTMVTVSSASTKGPSVFPLAPSSKSTSG<br>GTAALGCLVKDYFPEPVTVSWNSGALTSGVHTFPAVLQSSGLYSL<br>SSWTVPSSSLGTQTYICNVNHKPSNTKVDKKVEPKSCDKTHTCPP<br>CPAPELLGGPSVFLFPPKPKDTLMISRTPEVTCVVVDVSHEDPEVK<br>FNWYVDGVEVHNAKTKPREEQYNSTYRWSVLTVLHQDWLNGKE<br>YKCKVSNKALPAPIEKTISKAKGQPREPQVYTLPPSRDELTKNQVSL<br>TCLVKGFYPSDIAVEWESNGQPENNYKTTPPVLDSDGSFFLYSKLT<br>VDKSRWQQGNVFSCSVMHEALHNHYTQKSLSLSPGK |
| 237 | G4_5 IgG1<br>antibody<br>sequence | ASDIQMTQSPSSLSASVGDRVTITCRASQSISSYLNWYQQKPGKAP<br>KLLIYAASSLQSGVPSRFSGSGSGTDFTLTISSLQPEDFATYYCQQS<br>YSTPYTFGQGTKVEIKRTAAAPSVFIFPPSDEQLKSGTASVVCLLNN<br>FYPREAKVQWKVDNALQSGNSQESVTEQDSKDSTYSLSSTLTLSK<br>ADYEKHKLYACEVTHQGLSSPVTKSFNRGECEVQLVQSGAEVKKP<br>GSSVKVSCKASGYTFTSYGISWVRQAPGQGLEWMGWIGAYNGNT<br>NYAQKLQGRVTMSTDTSTSTAYMELRSPRSDDTAVYYCARGGTG<br>GDHVFAYWGQGTTVTVSSASTKGPSVFPLAPSSKSTSGGTAALGC<br>LVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLG<br>GPSVFLFPPKPKDTLMISRTPEVTCVVVDVSHEDPEVKFNWYVDG<br>VEVHNAKTKPREEQYNSTYRVVSVLTVLHQDWLNGKEYKCKVSNK<br>ALPAPIEKTISKAKGQPREPQVYTLPPSRDELTKNQVSLTCLVKGFY<br>PSDIAVEWESNGQPENNYKTTPPVLDSDGSFFLYSKLTVDKSRWQ<br>QGNVFSCSVMHEALHNHYTQKSLSLSPGK |

-continued

| SEQ ID NO. | Description | Sequence |
|---|---|---|
| 238 | G4_6 IgG1 antibody sequence | ASDIQMTQSPSSLSASVGDRVTITCRASQSISTYLNWYQQKPGKAP<br>KLLIYAASSLQSGVPSRFSGSGSGTDFTLTISSPQPEDFATYYCQQ<br>SYSTPYTFGQGTKVEIKRTAAAPSVFIFPPSDEQLKSGTASVVCLLN<br>NFYPREAKVQWKVDNALQSGNSQESVTEQDSKDSTYSLSSTLTLS<br>KADYEKHKLYACEVTHQGLSSPVTKSFNRGECEVQLVESGGGLVQ<br>PGGPLRLSCAASGFTFSSYAMNWVRQAPGKGLEWVSAISGSGGS<br>TYYADSVKGRFTISRDNSKNTLYLQMNSLRAEDTAVYYCAKADYGV<br>VYYFDYWGQGTMVTVSSASTKGPSVFPLAPSSKSTSGGTAALGCL<br>VKDYFPEPVTVSWNSGALTSGVHTFPAVLQSSGLYSLSSWTVPSS<br>SLGTQTYICNVNHKPSNTKVDKKVEPKSCDKTHTCPPCPAPELLGG<br>PSVFLFPPKPKDTLMISRTPEVTCVWVDVSHEDPEVKFNWYVDGVE<br>VHNAKTKPREEQYNSTYRVVSVLTVLHQDWLNGKEYKCKVSNKAL<br>PAPIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGK |
| 239 | G4_7 IgG1 antibody sequence | ASDIVMTQSPLSLPVTPGEPASISCRSSQSLLHSNRFNYLDWYLQK<br>PGQSPQLLIYLGSNRASGVPDRFSGSGSGTDFTLKISRVEAEDVGV<br>YYCMQGLQTPYTFGQGTKVDIKRTAAAPSVFIFPPSDEQLKSGTAS<br>VVCLLNNFYPREAKVQWKVDNALQSGNSQESVTEQDSKDSTYSLS<br>STLTLSKADYEKHKLYACEVTHQGLSSPVTKSFNRGECEVQLVESG<br>GGWVQSGGGSLRPSCAASGFTFSHYWMSWVRQAPGKGLEWVANI<br>KQDGSIIYYADSVKGRFTISRDNAKNSVYLQMNSLRAEDTAVYYCA<br>RIGYSSSSFDYWGRGTLVTVSSASTKGPSVFPLAPSSKSTSGGTAA<br>LGCLVKDYFPEPVTVSWNSGALTSGVHTFPAVLQSSGLYSLSSWT<br>VPSSSLGTQTYICNVNHKPSNTKVDKKVEPKSCDKTHTCPPCPAPE<br>LLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVYTLPPSRDELTKNQVSLTCLVKG<br>FYPSDIAVEWESNGQPENNYKTTPPVLDSDGSFFLYSKLTVDKSR<br>WQQGNVFSCSVMHEALHNHYTQKSLSLSPGK |
| 240 | G4_10 IgG1 antibody sequence | ASDIVMTQPPLSLPVTLGHPASISCKSSQSLEYSDGNTYLNWFQQR<br>PGQSPRRLIYKVSNRDSGAPDRFSGSGSGTDFTLEISRVEAEDVGV<br>YYCMQGTLWPPTFGQGTKVDIKRTAAAPSVFIFPPSDEQLKSGTAS<br>VVCLLNNFYPREAKVQWKVDNALQSGNSQESVTEQDSKDSTYSLS<br>STLTLSKADYEKHKLYACEVTHQGLSSPVTKSFNRGECQVQLVES<br>GGGVVQPGRPLRLSCAASGFTFSSYAMHWVRQAPGKGLEWVSAI<br>SGSGGSTYYADSVKGRFTISRDNSKNTLYLQMNSLRAEDTAVYYC<br>AKDGAVDFWRNGMDVWGRGTLVTVSSASTKGPSVFPLAPSSKST<br>SGGTAALGCLVKDYFPEPVTVSWNSGALTSGVHTFPAVLQSSGLY<br>SLSSWTVPSSSLGTQTYICNVNHKPSNTKVDKKVEPKSCDKTHTC<br>PPCPAPELLGGPSVFLFPPKPKDTLMISRTPEVTCVVVDVSHEDPE<br>VKFNWYVDGVEVHNAKTKPREEQYNSTYRVVSVLTVLHQDWLNG<br>KEYKCKVSNKALPAPIEKTISKAKGQPREPQVYTLPPSRDELTKNQ<br>VSLTCLVKGFYPSDIAVEWESNGQPENNYKTTPPVLDSDGSFFLYS<br>KLTVDKSRWQQGNVFSCSVMHEALHNHYTQKSLSLSPGK |
| 241 | G4_12 IgG1 antibody sequence | ASQSVLTQPASVSGSPGQSITISCTGTSSDVGGYNFVSWYQQHPG<br>KAPKLMIYEVTNRPSGVPDRFSGSKSGNTASLTISGLQAEDEADYY<br>CSSHASPRVFGTGTKVTVLGQPAAAPSVTLFPPSSEELQANKATLV<br>CLISDFYPGAVTVAWKADSSPVKAGVETTTPSKQSNNKYAASSYLS<br>LTPEQWKSHRSYSCQVTHEGSTVEKTVAPTECSEVQLLESGGGLV<br>QPGGSLRLSCAASGFTVSSNYMSWVRQAPGKGLEWVSVIYSGGS<br>TYYADSVKGRFTISRHNSKNTLYLQMNSLRAEDTAVYYCARVANG<br>DFLDYWGRGTLVTVSSASTKGPSVFPLAPSSKSTSGGTAALGCLV<br>KDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEV<br>HNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGN<br>VFSCSVMHEALHNHYTQKSLSLSPGK |
| 242 | G4_13 IgG1 antibody sequence | ASNFMLTQPHSVSESPGKTVTISCTRSSGSIASNYVQWYQQRPGS<br>SPSTVIYEDNQRPSGVPDRFSGSIDSSSNSASLTISGLRTEDEADYY<br>CQSYDSSIYVVFGGGTKLTVLGQPAAAPSVTLFPPSSEELQANKAT<br>LVCLISDFYPGAVTVAWKADSPVKAGVETTTPSKQSNNKYAASSY<br>LSLTPEQWKSHRSYSCQVTHEGSTVEKTVAPTECSQVQLVESGAE<br>VKKPGGSLRLSCAASGFTFSSYSMNWVRQAPGKGLEWVSSISGTS<br>SYIYYADSVKGRFTISRDNAKNSLYLQMSSLRAEDTAVYYCARGGL<br>GMVDPWGQGTLVTVSSASTKGPSVFPLAPSSKSTSGGTAALGCLV<br>KDYFPEPVTVSWNSGALTSGVHTFPAVLQSSGLYSLSSVVTVPSSS |

| SEQ ID NO. | Description | Sequence |
|---|---|---|
| | | LGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEV<br>HNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGN<br>VFSCSVMHEALHNHYTQKSLSLSPGK |
| 243 | G4_14 IgG1<br>antibody<br>sequence | ASNFMLTQPHSVSESPGKTVTISCTRSRGSIAGNYVHWYQQRPGR<br>APTTVIYRDKERPSGVPDRISGSIDSSSNSASLTISGLKTEDEADYY<br>CQSYDSSTHVVFGGGTKLTVLGQPAAAPSVTLFPPSSEELQANKA<br>TLVCLISDFYPGAVTVAWKADSSPVKAGVETTTPSKQSNNKYAASS<br>YLSLTPEQWKSHRSYSCQVTHEGSTVEKTVAPTECSEVQLVQSGA<br>EVKKPGESLRISCKGSGYSFTSYWISWVRQMPGKGLEWMGRIDPS<br>DSYTNYSPSFPGHVTISADKSISTAYLQWSSLKASDTAMYYCAADT<br>AHGMDVWGRGTLVTVSSASTKGPSVFPLAPSSKSTSGGTAALGCL<br>VKDYFPEPVTVSWNSGALTSGVHTFPAVLQSSGLYSLSSWTVPSS<br>SLGTQTYICNVNHKPSNTKVDKKVEPKSCDKTHTCPPCPAPELLGG<br>PSVFLFPPKPKDTLMISRTPEVTCVWDVSHEDPEVKFNWYVDGVE<br>VHNAKTKPREEQYNSTYRVVSVLTVLHQDWLNGKEYKCKVSNKAL<br>PAPIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVMHEALHNHYTQKSLSLSPGK |
| 244 | G4_15 IgG1<br>antibody<br>sequence | ASQSALTQPASVSGSPGQSITISCTGTSSDVGGYNYVSWYQQHPG<br>KAPKLMIYDVSNRPSGVSNRFSGSKSGNTASLTISGLQAEDEADYY<br>CSSYGSGSVFGTGTKLTVLGQPAAAPSVTLFPPSSEELQANKATLV<br>CLISDFYPGAVTVAWKADSSPVKAGVETTTPSKQSNNKYAASSYLS<br>LTPEQWKSHRSYSCQVTHEGSTVEKTVAPTECSEVQLVQSEAEVK<br>KPGASVKVSCKASGYTFTRHYMHWVRQAPGQGLEWMGLINPSGS<br>STVYAQKFQGRVTLTRDTSTSTDYMELSSLRSEDTAVYYCARDNS<br>HLDQVWWFDPWGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAP<br>ELLGGPSVFLFPPKPKDTLMISRTPEVTCVWDVSHEDPEVKFNWY<br>VDGVEVHNAKTKPREEQYNSTYRWSVLTVLHQDWLNGKEYKCKV<br>SNKALPAPIEKTISKAKGQPREPQVYTLPPSRDELTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPGK |
| 245 | G4_16 IgG1<br>antibody<br>sequence | ASQSVLTQPPSASGSPGQSVTFSCTGTSSDIGAFNSVSWYQQHPG<br>KAPKLLIYEITKRPSGVPDRFSGSKSGNTASLTISVLQAEDEADYYC<br>TSYAGSNTLIFGGGTKVTVLGQPAAAPSVTLFPPSSEELQANKATL<br>VCLISDFYPGAVTVAWKADSSPVKAGVETTTPSKQSNNKYAASSYL<br>SLTPEQWKSHRSYSCQVTHEGSTVEKTVAPTECSEVQLLESGAEV<br>KKPGASVKVSCKASGYTFTSYGISWVRQAPGQGLEWMGWISAYN<br>GNTNYAQKLQGRVTMTTDTSTSTAYMELRSLRSDDTAVYYCARDY<br>GDFYGMDVWGQGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPE<br>LLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVYTLPPSRDELTKNQVSLTCLVKG<br>FYPSDIAVEWESNGQPENNYKTTPPVLDSDGSFFLYSKLTVDKSR<br>WQQGNVFSCSVMHEALHNHYTQKSLSLSPGK |
| 246 | G4_18 IgG1<br>antibody<br>sequence | ASSYELTQPPSVTESPGQTARITCSGDALAKQYAYWYQQKPGQAP<br>VLVIYRDSERPSEIPERFSGSSSGTTVTLTISGVQAEDEADYYCQSA<br>DSSGTYTVFGGGTKLTVLGQPAAAPSVTLFPPSSEELQANKATLVC<br>LISDFYPGAVTVAWKADSSPVKAGVETTTPSKQSNNKYAASSYLSL<br>TPEQWKSHRSYSCQVTHEGSTVEKTVAPTECSEVQLVESGAEVKK<br>PGASVKVSCKASGYTFTGYYMHWVRQAPGQGLEWMGRINPNSG<br>GTNYAQKFQGRVTMTRDASISTAYMELSRLRSDDTAVYYCARDLD<br>LSSSLDYWGRGTLVTVSSASTKGPSVFPLAPSSKSTSGGTAALGCLV<br>KDYFPEPVTVSWNSGALTSGVHTFPAVLQSSGLYSLSSVVTVPSSS<br>LGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEV<br>HNAKTKPREEQYNSTYRVVSVLTVLHQDWLNGKEYKCKVSNKALP<br>APIEKTISKAKGQPREPQVYTLPPSRDELTKNQVSLTCLVKGFYPSD<br>IAVEWESNGQPENNYKTTPPVLDSDGSFFLYSKLTVDKSRWQQGN<br>VFSCSVMHEALHNHYTQKSLSLSPGK |
| 247 | G4_19 IgG1<br>antibody<br>sequence | ASNFMLTQPHSVSESPGKTVTISCTRSSGSIASNYVQWYQQRPGS<br>PPITLIYDDDQRPSGVPHRFSGSIDTSSNPASLTISGLKTEDEADYY<br>CQSYDSSNHVVFGGGTKLTVLGQPAAAPSVTLFPPSSEELQANKA<br>TLVCLISDFYPGAVTVAWKADSSPVKAGVETTTPSKQSNNKYAASS<br>YLSLTPEQWKSHRSYSCQVTHEGSTVEKTVAPTECSEVQLVQSGA<br>EVKKPGASVKVSCKASGYTLTSYYMHWVRQAPGQGLEWMGIINPS |

-continued

| SEQ ID NO. | Description | Sequence |
|---|---|---|
| | | GGSTSYAQKFQGRVTMRDTSTSTVYMELSSLRSEDTAVYYCARE |
| | | RGYSYGDGMDVWGQGTTVTVSSASTKGPSVFPLAPSSKSTSGGT |
| | | AALGCLVKDYFPEPVTVSWNSGALTSGVHTFPAVLQSSGLYSLSSV |
| | | VTVPSSSLGTQTYICNVNHKPSNTKVDKKVEPKSCDKTHTCPPCPA |
| | | PELLGGPSVFLFPPKPKDTLMISRTPEVTCVVVDVSHEDPEVKFNW |
| | | YVDGVEVHNAKTKPREEQYNSTYRVVSVLTVLHQDWLNGKEYKCK |
| | | VSNKALPAPIEKTISKAKGQPREPQVYTLPPSRDELTKNQVSLTCLV |
| | | KGFYPSDIAVEWESNGQPENNYKTTPPVLDSDGSFFLYSKLTVDKS |
| | | RWQQGNVFSCSVMHEALHNHYTQKSLSLSPGK |
| 248 | G4_20 IgG1 antibody sequence | ASSYELTHPPSVSVSPGQTASITCSGDKLGDKFVSWYHQKPGQSP VLVIYQDSKRPSGIPERFSGSNSGNTATLTISGTRAMDEADYYCQA WDSSTWFGGGTKLTVLGQPAAAPSVTLFPPSSEELQANKATLVCL ISDFYPGAVTVAWKADSSPVKAGVETTTPSKQSNNKYAASSYLSLT PEQWKSHRSYSCQVTHEGSTVEKTVAPTECSQVQLVESGAEVKK PGASVKVSCKASGGTFSSYAISWVRQAPGQGLEWMGGIIPIFGTAN YAQKFQGRVTITVDKSTRTAYMELSSLRSKDTAVYYCARGNSRSD AFDIWGQGTMVTVSSASTKGPSVFPLAPSSKSTSGGTAALGCLVK DYFPEPVTVSWNSGALTSGVHTFPAVLQSSGLYSLSSVVTVPSSSL GTQTYICNVNHKPSNTKVDKKVEPKSCDKTHTCPPCPAPELLGGP SVFLFPPKPKDTLMISRTPEVTCVVVDVSHEDPEVKFNWYVDGVEV HNAKTKPREEQYNSTYRVVSVLTVLHQDWLNGKEYKCKVSNKALP APIEKTISKAKGQPREPQVYTLPPSRDELTKNQVSLTCLVKGFYPSD IAVEWESNGQPENNYKTTPPVLDSDGSFFLYSKLTVDKSRWQQGN VFSCSVMHEALHNHYTQKSLSLSPGK |
| 249 | G4_22 IgG1 antibody sequence | ASDIQMTQSPSSLSASVGDRVTITCQASQDISNYLNWYQQKPGKA PKLLIYAASSLQSGVPSRFSVSGSGTDFTLTISNLQPEDFATYYCQQ SYSIPWTFGQGTKVEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGECQVQLVESGGGLVQ PGGSLRLSCAASGFTFSTYAMSWVRQAPGKGLEWVSTVSGSGGT TYYADSVKGRFTISRDNSKNTLYLQMNSLRAEDTAVYYCAKDSTAV TDWFDPWGRGTLVTVSSASTKGPSVFPLAPSSKSTSGGTAALGCL VKDYFPEPVTVSWNSGALTSGVHTFPAVLQSSGLYSLSSWTVPSS SLGTQTYICNVNHKPSNTKVDKKVEPKSCDKTHTCPPCPAPELLGG PSVFLFPPKPKDTLMISRTPEVTCVVVDVSHEDPEVKFNWYVDGVE VHNAKTKPREEQYNSTYRVVSVLTVLHQDWLNGKEYKCKVSNKAL PAPIEKTISKAKGQPREPQVYTLPPSRDELTKNQVSLTCLVKGFYPS DIAVEWESNGQPENNYKTTPPVLDSDGSFFLYSKLTVDKSRWQQG NVFSCSVMHEALHNHYTQKSLSLSPGK |
| 250 | G4_23 IgG1 antibody sequence | ASDIQMTQSPSSLSASVGDRVTITCRASQGISNSLAWYQQKPGKAP KLLLYAASRLESGVPSRFSGSGSGTDYTLTISSLQPEDFATYYCQQ YYSTPRTFGGGTKLEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGECEVQLVESGGGVVQ PGRSLRLSCAASGFTFSSYGMHWVRQAPGKGLEWVAVIWYDGSN KYYADSVKGRFTISRDNSKNTLYLQMNSLRAEDTAVYYCARGEVA ALYYFDYWGQGTLVTVSSASTKGPSVFPLAPSSKSTSGGTAALGC LVKDYFPEPVTVSWNSGALTSGVHTFPAVLQSSGLYSLSSVVTVPS SSLGTQTYICNVNHKPSNTKVDKKVEPKSCDKTHTCPPCPAPELLG GPSVFLFPPKPKDTLMISRTPEVTCVVVDVSHEDPEVKFNWYVDG VEVHNAKTKPREEQYNSTYRVVSVLTVLHQDWLNGKEYKCKVSNK ALPAPIEKTISKAKGQPREPQVYTLPPSRDELTKNQVSLTCLVKGFY PSDIAVEWESNGQPENNYKTTPPVLDSDGSFFLYSKLTVDKSRWQ QGNVFSCSVMHEALHNHYTQKSLSLSPGK |
| 251 | G4_24 IgG1 antibody sequence | ASDIVMTQSPDSLAVSLGERATINCKSSQSVLYSSNNKNYLAWYQQ KPGQPPKLLISWASTRESGVPDRFSGSGSGTDFTLTINSLQSEDVAI YYCQQYYSTPPTFGQGTKLEIKRTAAAPSVFIFPPSDEQLKSGTAS VVCLLNNFYPREAKVQWKVDNALQSGNSQESVTEQDSKDSTYSLS STLTLSKADYEKHKLYACEVTHQGLSSPVTKSFNRGECQVQLQQS GPGLVKPSQTLSLTCAISGASVSSNSVAWNWIRQSPSRGLEWLGR TYYRSRWYNDYALSVKSRIIINPDTSKNQFSLQLNSVTPEDTAVYYC ARDWSSTRSFDYWGRGTLVTVSSASTKGPSVFPLAPSSKSTSGGT AALGCLVKDYFPEPVTVSWNSGALTSGVHTFPAVLQSSGLYSLSSV VTVPSSSLGTQTYICNVNHKPSNTKVDKKVEPKSCDKTHTCPPCPA PELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSRDELTKNQVSLTCLV KGFYPSDIAVEWESNGQPENNYKTTPPVLDSDGSFFLYSKLTVDKS RWQQGNVFSCSVMHEALHNHYTQKSLSLSPGK |
| 252 | G4_25 IgG1 antibody sequence | ASQSALTQPRSVSGSPGQSVTISCTGTSSDVGGYNYVSWYQQHP GKAPKLMIYEVSNRPSGVSNRFSGSKSGNTASLTISGLQAEDEADY YCSSYGSGSVFGTGTKLTVLGQPAAAPSVTLFPPSSEELQANKATL |

-continued

| SEQ ID NO. | Description | Sequence |
|---|---|---|
| | | VCLISDFYPGAVTVAWKADSSPVKAGVETTTPSKQSNNKYAASSYL<br>SLTPEQWKSHRSYSCQVTHEGSTVEKTVAPTECSEVQLVESGAEV<br>KKPGSSVKVSCKASGGTFSSYAISWVRQAPGQGLEWMGGIIPIFGT<br>ANYAQKFQGRVTITADKSTSTAYMELSSLRSEDTAVYYCARSLRDG<br>YNYIGSLGYWGQGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPE<br>LLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVS<br>NKALPAPIEKTISKAKGQPREPQVYTLPPSRDELTKNQVSLTCLVKG<br>FYPSDIAVEWESNGQPENNYKTTPPVLDSDGSFFLYSKLTVDKSR<br>WQQGNVFSCSVMHEALHNHYTQKSLSLSPGK |
| 253 | G4_26 IgG1<br>antibody<br>sequence | ASQSGLTQPASVSGSPGQSITISCTGTSSDVGSYNLVSWYQQHPG<br>KAPKLMIYEVSKRPSGVSNRFSGSKSGNTASLTISGLQAEDEADYY<br>CSSFGSGSIFGTGTKLTVLGQPAAAPSVTLFPPSSEELQANKATLV<br>CLISDFYPGAVTVAWKADSSPVKAGVETTTPSKQSNNKYAASSYLS<br>LTPEQWKSHRSYSCQVTHEGSTVEKTVAPTECSQVQLVQSGAEV<br>KKPGSSVKVSCKASGGTFSSYAISWVRQAPGQGLEWMGGIIPIFGT<br>ANYAQKFQGRVTITADESTSTAYMELSSLRSEDTAVYYCASSRGS<br>GWFPLGYWGQGTLVTVSSASTKGPSVFPLAPSSKSTSGGTAALGC<br>LVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLG<br>GPSVFLFPPKPKDTLMISRTPEVTCVVVDVSHEDPEVKFNWYVDG<br>VEVHNAKTKPREEQYNSTYRWSVLTVLHQDWLNGKEYKCKVSNK<br>ALPAPIEKTISKAKGQPREPQVYTLPPSRDELTKNQVSLTCLVKGFY<br>PSDIAVEWESNGQPENNYKTTPPVLDSDGSFFLYSKLTVDKSRWQ<br>QGNVFSCSVMHEALHNHYTQKSLSLSPGK |
| 254 | G4_27 IgG1<br>antibody<br>sequence | ASSYELTQDPAVSVALGQTVSITCQGDSLRNFYANWYQQKPGQAP<br>VLVIYGKNNRPSGIPDRFSGSSSGNTASLTITGAQAEDEADYYCNS<br>RDSSGNHLVFGGGTQLTVLGQPAAAPSVTLFPPSSEELQANKATL<br>VCLISDFYPGAVTVAWKADSSPVKAGVETTTPSKQSNNKYAASSYL<br>SLTPEQWKSHRSYSCQVTHEGSTVEKTVAPTECSQVQLVQSGAE<br>VKKPGESLKISCKSSGYSFTSYWIGWVRQMPGKGLEWMGIIYPGD<br>SDTRYSPSFQGQVTFSADESISTAYLQWSSLKASDTAMYYCARHG<br>AYGDYPDTFDIWGQGTLVTVSSASTKGPSVFPLAPSSKSTSGGTA<br>ALGCLVKDYFPEPVTVSWNSGALTSGVHTFPAVLQSSGLYSLSSVV<br>TVPSSSLGTQTYICNVNHKPSNTKVDKKVEPKSCDKTHTCPPCPAP<br>ELLGGPSVFLFPPKPKDTLMISRTPEVTCVWDVSHEDPEVKFNWY<br>VDGVEVHNAKTKPREEQYNSTYRWSVLTVLHQDWLNGKEYKCKV<br>SNKALPAPIEKTISKAKGQPREPQVYTLPPSRDELTKNQVSLTCLVK<br>GFYPSDIAVEWESNGQPENNYKTTPPVLDSDGSFFLYSKLTVDKSR<br>WQQGNVFSCSVMHEALHNHYTQKSLSLSPGK |
| 255 | G4_28 IgG1<br>antibody<br>sequence | ASSYELTQDPAVSVALGQTVTITCQGDSLRNYYASWYRQKPGQTP<br>VLVVYGKNNRPSGIPDRFSVSASGNTASLTITGAQAEDEGDYYCNS<br>RDSSGVVFGGGTKVTVLGQPAAAPSVTLFPPSSEELQANKATLVCL<br>ISDFYPGAVTVAWKADSSPVKAGVETTTPSKQSNNKYAASSYLSLT<br>PEQWKSHRSYSCQVTHEGSTVEKTVAPTECSQVQLVESGGGLVQ<br>PGGSLRLSCAASGFTFDDYAMHWVRQAPGKGLEWVSGISAGGGS<br>TNYAGSVKGRFTVSRDTSKNTLYLQMNSLRAEDTAVYYCVKSYVD<br>TAMRYYYYYMDVWGQGTMVTVSSASTKGPSVFPLAPSSKSTSGG<br>TAALGCLVKDYFPEPVTVSWNSGALTSGVHTFPAVLQSSGLYSLSS<br>VVTVPSSSLGTQTYICNVNHKPSNTKVDKKVEPKSCDKTHTCPPCP<br>APELLGGPSVFLFPPKPKDTLMISRTPEVTCVVVDVSHEDPEVKFN<br>WYVDGVEVHNAKTKPREEQYNSTYRWSVLTVLHQDWLNGKEYK<br>CKVSNKALPAPIEKTISKAKGQPREPQVYTLPPSRDELTKNQVSLTC<br>LVKGFYPSDIAVEWESNGQPENNYKTTPPVLDSDGSFFLYSKLTVD<br>KSRWQQGNVFSCSVMHEALHNHYTQKSLSLSPGK |
| 256 | TRGV4(4MNH)<br>TRAC antigen<br>sequence | SSNLEGRTKSVIRQTGSSAEITCDLAEGSTGYIHWYLHQEGKAPQR<br>LLYYDSYTSSVVLESGISPGKYDTYGSTRKNLRMILRNLIENDSGVY<br>YCATWDEKYYKKLFGSGTTLVVTEDLKNVFPPEVAVFEPSEAEISH<br>TQKATLVCLATGFYPDHVELSWWVNGKEVHSGVSTDPQPLKEQP<br>ALNDSRYALSSRLRVSATFWQNPRNHFRCQVQFYGLSENDEWTQ<br>DRAKPVTQIVSAEAWGRADCTTAPSAQLEKELQALEKENAQLE |
| 257 | Vγ4-<br>(4MNH)GV4TRB<br>Cleucine zipper<br>heterodimer<br>antigen sequence | SSNLEGRTKSVIRQTGSSAEITCDLAEGSTGYIHWYLHQEGKAPQR<br>LLYYDSYTSSVVLESGISPGKYDTYGSTRKNLRMILRNLIENDSGVY<br>YCATWDEKYYKKLFGSGTTLVVTEDLKNVFPPEVAVFEPSEAEISH<br>TQKATLVCLATGFYPDHVELSWWVNGKEVHSGVSTDPQPLKEQP<br>ALNDSRYALSSRLRVSATFWQNPRNHFRCQVQFYGLSENDEWTQ<br>DRAKPVTQIVSAEAWGRADCTTAPSAQLEKELQALEKENAQLEWE<br>LQALEKELAQ |

| SEQ ID NO. | Description | Sequence |
|---|---|---|
| 258 | Vγ4-<br>TRGV4(4MNH)<br>Fc heterodimer<br>antigen sequence | SSNLEGRTKSVIRQTGSSAEITCDLAEGSTGYIHWYLHQEGKAPQR<br>LLYYDSYTSSVVLESGISPGKYDTYGSTRKNLRMILRNLIENDSGVY<br>YCATWDEKYYKKLFGSGTTLVVTEDAAADKTHTCPPCPAPELLGG<br>PSVFLFPPKPKDTLMISRTPEVTCVWVDVSHEDPEVKFNWYVDGVE<br>VHNAKTKPREEQYNSTYRVVSVLTVLHQDWLNGKEYKCKVSNKAL<br>PAPIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVSHEALHSHHTQKSLSLSPGK |
| 259 | Vγ2-<br>(4MNH)GV2TRB<br>Cleucine zipper<br>heterodimer<br>antigen sequence | SSNLEGRTKSVIRQTGSSAEITCDLAEGSNGYIHWYLHQEGKAPQR<br>LQYYDSYNSKVVLESGVSPGKYYTYASTRNNLRLILRNLIENDSGVY<br>YCATWDEKYYKKLFGSGTTLVVTEDLKNVFPPEVAVFEPSEAEISH<br>TQKATLVCLATGFYPDHVELSWWVNGKEVHSGVSTDPQPLKEQP<br>ALNDSRYALSSRLRVSATFWQNPRNHFRCQVQFYGLSENDEWTQ<br>DRAKPVTQIVSAEAWGRADCTTAPSAQLEKELQALEKENAQLEWE<br>LQALEKELAQ |
| 260 | Vγ2-<br>TRGV2(4MNH)<br>Fc heterodimer<br>antigen sequence | SSNLEGRTKSVIRQTGSSAEITCDLAEGSNGYIHWYLHQEGKAPQR<br>LQYYDSYNSKVVLESGVSPGKYYTYASTRNNLRLILRNLIENDSGVY<br>YCATWDEKYYKKLFGSGTTLVVTEDAAADKTHTCPPCPAPELLGG<br>PSVFLFPPKPKDTLMISRTPEVTCVVVDVSHEDPEVKFNWYVDGVE<br>VHNAKTKPREEQYNSTYRVVSVLTVLHQDWLNGKEYKCKVSNKAL<br>PAPIEKTISKAKGQPREPQVYTLPPSRDELTKNQVSLTCLVKGFYPS<br>DIAVEWESNGQPENNYKTTPPVLDSDGSFFLYSKLTVDKSRWQQG<br>NVFSCSVSHEALHSHHTQKSLSLSPGK |
| 261 | TRGV4 full light<br>variable sequence<br>G4_1-no N-<br>terminal AS | DIQMTQSPSSLSASVGDRVTITCQASQDISNYLNWYQQKPGKAPKL<br>LIYDASNLETGVPSRFSGSGSGTDFTLTISSLQPEDFATYYCQQSYS<br>TPVTFGPGTKVEIK |
| 262 | TRGV4 full light<br>variable sequence<br>G4_2-no N-<br>terminal AS | DIQMTQSPSSLSASVGDRVTITCQASQDISNYLNWYQQKPGKAPKL<br>LIYAASSLQSGVPSRFSGSGSGTDFTLTISGLQPEDFATYYCLEDYN<br>YLWTFGQGTKLEIK |
| 263 | TRGV4 full light<br>variable sequence<br>G4_3-no N-<br>terminal AS | DIQMTQSPSSLSASVGDRVTITCQASQDISNYLNWYQQKPGKAPKL<br>LIYDASNLETGVPSRFSGSGSGTDFTLTISSLQPEDFATYFCQQSYS<br>TPQTFGQGTKVDIK |
| 264 | TRGV4 full light<br>variable sequence<br>G4_4-no N-<br>terminal AS | DIVMTQSPDSLAVSLGERATINCKSSQSVLSSSNNNNYLAWYQQR<br>PGQPPKLLFYWASTRESGVPDRFSGSGSGTSFTLTITSLQAEDVAV<br>YYCQQYYSTPLTFGGGTKLEIK |
| 265 | TRGV4 full light<br>variable sequence<br>G4_5-no N-<br>terminal AS | DIQMTQSPSSLSASVGDRVTITCRASQSISSYLNWYQQKPGKAPKL<br>LIYAASSLQSGVPSRFSGSGSGTDFTLTISSLQPEDFATYYCQQSY<br>STPYTFGQGTKVEIK |
| 266 | TRGV4 full light<br>variable sequence<br>G4_6-no N-<br>terminal AS | DIQMTQSPSSLSASVGDRVTITCRASQSISTYLNWYQQKPGKAPKL<br>LIYAASSLQSGVPSRFSGSGSGTDFTLTISSPQPEDFATYYCQQSY<br>STPYTFGQGTKVEIK |
| 267 | TRGV4 full light<br>variable sequence<br>G4_7-no N-<br>terminal AS | DIVMTQSPLSLPVTPGEPASISCRSSQSLLHSNRFNYLDWYLQKPG<br>QSPQLLIYLGSNRASGVPDRFSGSGSGTDFTLKISRVEAEDVGVYY<br>CMQGLQTPYTFGQGTKVDIK |
| 268 | TRGV4 full light<br>variable sequence<br>G4_10-no N-<br>terminal AS | DIVMTQPPLSLPVTLGHPASICKSSQSLEYSDGNTYLNWFQQRPG<br>QSPRRLIYKVSNRDSGAPDRFSGSGSGTDFTLEISRVEAEDVGVYY<br>CMQGTLWPPTFGQGTKVDIK |
| 269 | TRGV4 full light<br>variable sequence<br>G4_12-no N-<br>terminal AS | QSVLTQPASVSGSPGQSITISCTGTSSDVGGYNFVSWYQQHPGKA<br>PKLMIYEVTNRPSGVPDRFSGSKSGNTASLTISGLQAEDEADYYCS<br>SHASPRVFGTGTKVTVL |
| 270 | TRGV4 full light<br>variable sequence<br>G4_13-no N-<br>terminal AS | NFMLTQPHSVSESPGKTVTISCTRSSGSIASNYVQWYQQRPGSSP<br>STVIYEDNQRPSGVPDRFSGSIDSSSNSASLTISGLRTEDEADYYC<br>QSYDSSIYVVFGGGTKLTVL |

-continued

| SEQ ID NO. | Description | Sequence |
|---|---|---|
| 271 | TRGV4 full light variable sequence G4_14-no N-terminal AS | NFMLTQPHSVSESPGKTVTISCTRSRGSIAGNYVHWYQQRPGRAP TTVIYRDKERPSGVPDRISGSIDSSSNSASLTISGLKTEDEADYYCQ SYDSSTHVVFGGGTKLTVL |
| 272 | TRGV4 full light variable sequence G4_15-no N-terminal AS | QSALTQPASVSGSPGQSITISCTGTSSDVGGYNYVSWYQQHPGKA PKLMIYDVSNRPSGVSNRFSGSKSGNTASLTISGLQAEDEADYYCS SYGSGSVFGTGTKLTVL |
| 273 | TRGV4 full light variable sequence G4_16-no N-terminal AS | QSVLTQPPSASGSPGQSVTFSCTGTSSDIGAFNSVSWYQQHPGKA PKLLIYEITKRPSGVPDRFSGSKSGNTASLTISVLQAEDEADYYCTS YAGSNTLIFGGGTKVTVL |
| 274 | TRGV4 full light variable sequence G4_18-no N-terminal AS | SYELTQPPSVTESPGQTARITCSGDALAKQYAYWYQQKPGQAPVL VIIYRDSERPSEIPERFSGSSSGTTVTLTISGVQAEDEADYYCQSADS SGTYTVFGGGTKLTVL |
| 275 | TRGV4 full light variable sequence G4_19-no N-terminal AS | NFMLTQPHSVSESPGKTVTISCTRSSGSIASNYVQWYQQRPGSPPI TLIYDDDQRPSGVPHRFSGSIDTSSNPASLTISGLKTEDEADYYCQS YDSSNHVVFGGGTKLTVL |
| 276 | TRGV4 full light variable sequence G4_20-no N-terminal AS | SYELTHPPSVSVSPGQTASITCSGDKLGDKFVSWYHQKPGQSPVL VIYQDSKRPSGIPERFSGSNSGNTATLTISGTRAMDEADYYCQAWD SSTVVFGGGTKLTVL |
| 277 | TRGV4 full light variable sequence G4_22-no N-terminal AS | DIQMTQSPSSLSASVGDRVTITCQASQDISNYLNWYQQKPGKAPKL LIYAASSLQSGVPSRFSVSGSGTDFTLTISNLQPEDFATYYCQQSYS IPWTFGQGTKVEIK |
| 278 | TRGV4 full light variable sequence G4_23-no N-terminal AS | DIQMTQSPSSLSASVGDRVTITCRASQGISNSLAWYQQKPGKAPKL LLYAASRLESGVPSRFSGSGSGTDYTLTISSLQPEDFATYYCQQYY STPRTFGGGTKLEIK |
| 279 | TRGV4 full light variable sequence G4_24-no N-terminal AS | DIVMTQSPDSLAVSLGERATINCKSSQSVLYSSNNKNYLAWYQQKP GQPPKLLISWASTRESGVPDRFSGSGSGTDFTLTINSLQSEDVAIYY CQQYYSTPPTFGQGTKLEIK |
| 280 | TRGV4 full light variable sequence G4_25-no N-terminal AS | QSALTQPRSVSGSPGQSVTISCTGTSSDVGGYNYVSWYQQHPGK APKLMIYEVSNRPSGVSNRFSGSKSGNTASLTISGLQAEDEADYYC SSYGSGSVFGTGTKLTVL |
| 281 | TRGV4 full light variable sequence G4_26-no N-terminal AS | QSGLTQPASVSGSPGQSITISCTGTSSDVGSYNLVSWYQQHPGKA PKLMIYEVSKRPSGVSNRFSGSKSGNTASLTISGLQAEDEADYYCS SFGSGSIFGTGTKLTVL |
| 282 | TRGV4 full light variable sequence G4_27-no N-terminal AS | SYELTQDPAVSVALGQTVSITCQGDSLRNFYANWYQQKPGQAPVL VIYGKNNRPSGIPDRFSGSSSGNTASLTITGAQAEDEADYYCNSRD SSGNHLVFGGGTQLTVL |
| 283 | TRGV4 full light variable sequence G4_28-no N-terminal AS | SYELTQDPAVSVALGQTVTITCQGDSLRNYYASWYRQKPGQTPVL VVYGKNNRPSGIPDRFSVSASGNTASLTITGAQAEDEGDYYCNSR DSSGVVFGGGTKVTVL |
| 284 | G4_1 IgG1 antibody heavy chain sequence | EVQLLESGGGVVQPGRPLRLSCAASGFTFSSYSMNWVRQAPGKG LEWVSSISSSSSYIYYADSVKGRFTISRDNSKNTLYLQMNSLRAEDT AVYYCAKGHWYFDLWGRGTLVTVSSASTKGPSVFPLAPSSKSTSG GTAALGCLVKDYFPEPVTVSWNSGALTSGVHTFPAVLQSSGLYSL SSVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVSVLTVLHQDWLNGKE YKCKVSNKALPAPIEKTISKAKGQPREPQVYTLPPSRDELTKNQVSL TCLVKGFYPSDIAVEWESNGQPENNYKTTPPVLDSDGSFFLYSKLT VDKSRWQQGNVFSCSVMHEALHNHYTQKSLSLSPGK |

| SEQ ID NO. | Description | Sequence |
|---|---|---|
| 285 | G4_2 IgG1 antibody heavy chain sequence | QMQLVQSGAEVKKPGATVKISCKVSGYPFTDYYIHWVQQAPGKGL EWMGLVDPEDGQSRSAERFQGRVTITADTSTDTAYMELSSLRSED TAVYYCATFPVAGFYGMDVWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 286 | G4_3 IgG1 antibody heavy chain sequence | EVQLVESGGGLVQPGGSLRLSCAASGFTSSYSMNWVRQAPGKG LEWVSSISSSSSYIYYADSVKGRFTISRDNSKNTLYLQMNSLRAEDT AVYYCARGGWLYDYWGQGTLVTVSSASTKGPSVFPLAPSSKSTS GGTAALGCLVKDYFPEPVTVSWNSGALTSGVHTFPAVLQSSGLYS LSSVVTVPSSSLGTQTYICNVNHKPSNTKVDKKVEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK |
| 287 | G4_4 IgG1 antibody heavy chain sequence | QVQLVESGGGLVQPGGSLRLSCAASGFTFSSYAMSWVRQAPGKG LEWVSAISGSGGSTYYADSVKGRFTISRDNSKNTLYLQMNSLRVED TAVYYCAKSSVGWWSFDYWGQGTMVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 288 | G4_5 IgG1 antibody heavy chain sequence | EVQLVQSGAEVKKPGSSVKVSCKASGYTFTSYGISWVRQAPGQGL EWMGWIGAYNGNTNYAQKLQGRVTMSTDTSTSTAYMELRSPRSD DTAVYYCARGGTGGDHVFAYWGQGTTVTVSSASTKGPSVFPLAP SSKSTSGGTAALGCLVKDYFPEPVTVSWNSGALTSGVHTFPAVLQ SSGLYSLSSWTVPSSSLGTQTYICNVNHKPSNTKVDKKVEPKSCD KTHTCPPCPAPELLGGPSVFLFPPKPKDTLMISRTPEVTCVWDVS HEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 289 | G4_6 IgG1 antibody heavy chain sequence | EVQLVESGGGLVQPGGPLRLSCAASGFTFSSYAMNWVRQAPGKG LEWVSAISGSGGSTYYADSVKGRFTISRDNSKNTLYLQMNSLRAED TAVYYCAKADYGVVYYFDYWGQGTMVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCWDVSHE DPEVKFNWYVDGVEVHNAKTKPREEQYNSTYRVVSVLTVLHQDW LNGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 290 | G4_7 IgG1 antibody heavy chain sequence | EVQLVESGGGWVQSGGGSLRPSCAASGFTFSHYWMSWVRQAPGK GLEWVANIKQDGSIIYYADSVKGRFTISRDNAKNSVYLQMNSLRAE DTAVYYCARIGYSSSSFDYWGRGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKTH TCPPCPAPELLGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 291 | G4_10 IgG1 antibody heavy chain sequence | QVQLVESGGGVVQPGRPLRLSCAASGFTFSSYAMHWVRQAPGKG LEWVSAISGSGGSTYYADSVKGRFTISRDNSKNTLYLQMNSLRAED TAVYYCAKDGAVDFWRNGMDVWGRGTLVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCWDV SHEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDG SFFLYSKLTVDKSRWQQGNVFSCSVMHEALHNHYTQKSLSLSPGK |

| SEQ ID NO. | Description | Sequence |
|---|---|---|
| 292 | G4_12 IgG1 antibody heavy chain sequence | EVQLLESGGGLVQPGGSLRLSCAASGFTVSSNYMSWVRQAPGKG LEWVSVIYSGGSTYYADSVKGRFTISRHNSKNTLYLQMNSLRAEDT AVYYCARVANGDFLDYWGRGTLVTVSSASTKGPSVFPLAPSSKST SGGTAALGCLVKDYFPEPVTVSWNSGALTSGVHTFPAVLQSSGLY SLSSWTVPSSSLGTQTYICNVNHKPSNTKVDKKVEPKSCDKTHTC PPCPAPELLGGPSVFLFPPKPKDTLMISRTPEVTCVVVDVSHEDPE VKFNWYVDGVEVHNAKTKPREEQYNSTYRVVSVLTVLHQDWLNG KEYKCKVSNKALPAPIEKTISKAKGQPREPQVYTLPPSRDELTKNQ VSLTCLVKGFYPSDIAVEWESNGQPENNYKTTPPVLDSDGSFFLYS KLTVDKSRWQQGNVFSCSVMHEALHNHYTQKSLSLSPGK |
| 293 | G4_13 IgG1 antibody heavy chain sequence | QVQLVESGAEVKKPGGSLRLSCAASGFTFSSYSMNWVRQAPGKG LEWVSSISGTSSYIYYADSVKGRFTISRDNAKNSLYLQMSSLRAEDT AVYYCARGGLGMVDPWGQGTLVTVSSASTKGPSVFPLAPSSKSTS GGTAALGCLVKDYFPEPVTVSWNSGALTSGVHTFPAVLQSSGLYS LSSVVTVPSSSLGTQTYICNVNHKPSNTKVDKKVEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK |
| 294 | G4_14 IgG1 antibody heavy chain sequence | EVQLVQSGAEVKKPGESLRISCKGSGYSFTSYWISWVRQMPGKGL EWMGRIDPSDSYTNYSPSFPGHVTISADKSISTAYLQWSSLKASDT AMYYCAADTAHGMDVWGRGTLVTVSSASTKGPSVFPLAPSSKSTS GGTAALGCLVKDYFPEPVTVSWNSGALTSGVHTFPAVLQSSGLYS LSSVVTVPSSSLGTQTYICNVNHKPSNTKVDKKVEPKSCDKTHTCP PCPAPELLGGPSVFLFPPKPKDTLMISRTPEVTCWVDVSHEDPEV KFNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK |
| 295 | G4_15 IgG1 antibody heavy chain sequence | EVQLVQSEAEVKKPGASVKVSCKASGYTFTRHYMHWVRQAPGQG LEWMGLINPSGGSSTVYAQKFQGRVTLTRDTSTSTDYMELSSLRSE DTAVYYCARDNSHLDQVWWFDPWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 296 | G4_16 IgG1 antibody heavy chain sequence | EVQLLESGAEVKKPGASVKVSCKASGYTFTSYGISWVRQAPGQGL EWMGWISAYNGNTNYAQKLQGRVTMTTDTSTSTAYMELRSLRSD DTAVYYCARDYGDFYGMDVWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCWDVSH EDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 297 | G4_18 IgG1 antibody heavy chain sequence | EVQLVESGAEVKKPGASVKVSCKASGYTFTGYYMHWVRQAPGQG LEWMGRINPNSGGTNYAQKFQGRVTMTRDASISTAYMELSRLRSD DTAVYYCARDLDLSSLDYWGRGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKKVEPKSCDKTH TCPPCPAPELLGGPSVFLFPPKPKDTLMISRTPEVTCWDVSHED PEVKFNWYVDGVEVHNAKTKPREEQYNSTYRVVSVLTVLHQDWL NGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 298 | G4_19 IgG1 antibody heavy chain sequence | EVQLVQSGAEVKKPGASVKVSCKASGYTLTSYYMHWVRQAPGQG LEWMGIINPSGGSTSYAQKFQGRVTMTRDTSTSTVYMELSSLRSE DTAVYYCARERGYSYGDGMDVWGQGTTVTVSSASTKGPSVFPLA PSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLMISRTPEVTCWDV SHEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDG SFFLYSKLTVDKSRWQQGNVFSCSVMHEALHNHYTQKSLSLSPGK |

| SEQ ID NO. | Description | Sequence |
|---|---|---|
| 299 | G4_20 IgG1 antibody heavy chain sequence | QVQLVESGAEVKKPGASVKVSCKASGGTFSSYAISWVRQAPGQGL EWMGGIIPIFGTANYAQKFQGRVTITVDKSTRTAYMELSSLRSKDTA VYYCARGNSRSDAFDIWGQGTMVTVSSASTKGPSVFPLAPSSKST SGGTAALGCLVKDYFPEPVTVSWNSGALTSGVHTFPAVLQSSGLY SLSSWTVPSSSLGTQTYICNVNHKPSNTKVDKKVEPKSCDKTHTC PPCPAPELLGGPSVFLFPPKPKDTLMISRTPEVTCVVVDVSHEDPE VKFNWYVDGVEVHNAKTKPREEQYNSTYRVVSVLTVLHQDWLNG KEYKCKVSNKALPAPIEKTISKAKGQPREPQVYTLPPSRDELTKNQ VSLTCLVKGFYPSDIAVEWESNGQPENNYKTTPPVLDSDGSFFLYS KLTVDKSRWQQGNVFSCSVMHEALHNHYTQKSLSLSPGK |
| 300 | G4_22 IgG1 antibody heavy chain sequence | QVQLVESGGGLVQPGGSLRLSCAASGFTFSTYAMSWVRQAPGKG LEWVSTVSGSGGTTYYADSVKGRFTISRDNSKNTLYLQMNSLRAE DTAVYYCAKDSTAVTDWFDPWGRGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCVWDVSH EDPEVKFNWYVDGVEVHNAKTKPREEQYNSTYRWSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 301 | G4_23 IgG1 antibody heavy chain sequence | EVQLVESGGGVVQPGRSLRLSCAASGFTFSSYGMHWVRQAPGKG LEWVAVIWYDGSNKYYADSVKGRFTISRDNSKNTLYLQMNSLRAE DTAVYYCARGEVAALYYFDYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCVWDVSH EDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 302 | G4_24 IgG1 antibody heavy chain sequence | QVQLQQSGPGLVKPSQTLSLTCAISGASVSSNSVAWNWIRQSPSR GLEWLGRTYYRSRWYNDYALSVKSRIIINPDTSKNQFSLQLNSVTP EDTAVYYCARDWSSTRSFDYWGRGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCVWDVSH EDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 303 | G4_25 IgG1 antibody heavy chain sequence | EVQLVESGAEVKKPGSSVKVSCKASGGTFSSYAISWVRQAPGQGL EWMGGIIPIFGTANYAQKFQGRVTITADKSTSTAYMELSSLRSEDTA VYYCARSLRDGYNYIGSLGYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCVWDVSH EDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 304 | G4_26 IgG1 antibody heavy chain sequence | QVQLVQSGAEVKKPGSSVKVSCKASGGTFSSYAISWVRQAPGQG LEWMGGIIPIFGTANYAQKFQGRVTITADESTSTAYMELSSLRSEDT AVYYCASSRGSGWFPLGYWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKKVEPKSCDKT HTCPPCPAPELLGGPSVFLFPPKPKDTLMISRTPEVTCVWDVSHE DPEVKFNWYVDGVEVHNAKTKPREEQYNSTYRVVSVLTVLHQDW LNGKEYKCKVSNKALPAPIEKTISKAKGQPREPQVYTLPPSRDELTK NQVSLTCLVKGFYPSDIAVEWESNGQPENNYKTTPPVLDSDGSFFL YSKLTVDKSRWQQGNVFSCSVMHEALHNHYTQKSLSLSPGK |
| 305 | G4_27 IgG1 antibody heavy chain sequence | QVQLVQSGAEVKKPGESLKISCKSSGYSFTSYWIGWVRQMPGKGL EWMGIIYPGDSDTRYSPSFQGQVTFSADESISTAYLQWSSLKASDT AMYYCARHGAYGDYPDTFDIWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKKVEPKSCDK THTCPPCPAPELLGGPSVFLFPPKPKDTLMISRTPEVTCVWDVSH EDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |

-continued

| SEQ ID NO. | Description | Sequence |
|---|---|---|
| 306 | G4_28 IgG1 antibody heavy chain sequence | QVQLVESGGGLVQPGGSLRLSCAASGFTFDDYAMHWVRQAPGK GLEWVSGISAGGGSTNYAGSVKGRFTVSRDTSKNTLYLQMNSLRA EDTAVYYCVKSYVDTAMRYYYYYMDVWGQGTMVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKKV EPKSCDKTHTCPPCPAPELLGGPSVFLFPPKPKDTLMISRTPEVTC VWDVSHEDPEVKFNWYVDGVEVHNAKTKPREEQYNSTYRVVSVL TVLHQDWLNGKEYKCKVSNKALPAPIEKTISKAKGQPREPQVYTLP PSRDELTKNQVSLTCLVKGFYPSDIAVEWESNGQPENNYKTTPPVL DSDGSFFLYSKLTVDKSRWQQGNVFSCSVMHEALHNHYTQKSLSL SPGK |
| 307 | G4_1 IgG1 antibody light chain sequence | ASDIQMTQSPSSLSASVGDRVTITCQASQDISNYLNWYQQKPGKA PKLLIYDASNLETGVPSRFSGSGSGTDFTLTISSLQPEDFATYYCQQ SYSTPVTFGPGTKVEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 308 | G4_2 IgG1 antibody light chain sequence | ASDIQMTQSPSSLSASVGDRVTITCQASQDISNYLNWYQQKPGKA PKLLIYAASSLQSGVPSRFSGSGSGTDFTLTISGLQPEDFATYYCLE DYNYLWTFGQGTKLEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 309 | G4_3 IgG1 antibody light chain sequence | ASDIQMTQSPSSLSASVGDRVTITCQASQDISNYLNWYQQKPGKA PKLLIYDASNLETGVPSRFSGSGSGTDFTLTISSLQPEDFATYFCQQ SYSTPQTFGQGTKVDIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 310 | G4_4 IgG1 antibody light chain sequence | ASDIVMTQSPDSLAVSLGERATINCKSSQSVLSSSNNNNYLAWYQ QRPGQPPKLLFYWASTRESGVPDRFSGSGSGTSFTLTITSLQAED VAVYYCQQYYSTPLTFGGGTKLEIKRTAAAPSVFIFPPSDEQLKSGT ASVVCLLNNFYPREAKVQWKVDNALQSGNSQESVTEQDSKDSTY SLSSTLTLSKADYEKHKLYACEVTHQGLSSPVTKSFNRGEC |
| 311 | G4_5 IgG1 antibody light chain sequence | ASDIQMTQSPSSLSASVGDRVTITCRASQSISSYLNWYQQKPGKAP KLLIYAASSLQSGVPSRFSGSGSGTDFTLTISSLQPEDFATYYCQQS YSTPYTFGQGTKVEIKRTAAAPSVFIFPPSDEQLKSGTASVVCLLNN FYPREAKVQWKVDNALQSGNSQESVTEQDSKDSTYSLSSTLTLSK ADYEKHKLYACEVTHQGLSSPVTKSFNRGEC |
| 312 | G4_6 IgG1 antibody light chain sequence | ASDIQMTQSPSSLSASVGDRVTITCRASQSISTYLNWYQQKPGKAP KLLIYAASSLQSGVPSRFSGSGSGTDFTLTISSPQPEDFATYYCQQ SYSTPYTFGQGTKVEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 313 | G4_7 IgG1 antibody light chain sequence | ASDIVMTQSPLSLPVTPGEPASISCRSSQSLLHSNRFNYLDWYLQK PGQSPQLLIYLGSNRASGVPDRFSGSGSGTDFTLKISRVEAEDVGV YYCMQGLQTPYTFGQGTKVDIKRTAAAPSVFIFPPSDEQLKSGTAS VVCLLNNFYPREAKVQWKVDNALQSGNSQESVTEQDSKDSTYSLS STLTLSKADYEKHKLYACEVTHQGLSSPVTKSFNRGEC |
| 314 | G4_10 IgG1 antibody light chain sequence | ASDIVMTQPPLSLPVTLGHPASISCKSSQSLEYSDGNTYLNWFQQR PGQSPRRLIYKVSNRDSGAPDRFSGSGSGTDFTLEISRVEAEDVGV YYCMQGTLWPPTFGQGTKVDIKRTAAAPSVFIFPPSDEQLKSGTAS VVCLLNNFYPREAKVQWKVDNALQSGNSQESVTEQDSKDSTYSLS STLTLSKADYEKHKLYACEVTHQGLSSPVTKSFNRGEC |
| 315 | G4_12 IgG1 antibody light chain sequence | ASQSVLTQPASVSGSPGQSITISCTGTSSDVGGYNFVSWYQQHPG KAPKLMIYEVTNRPSGVPDRFSGSKSGNTASLTISGLQAEDEADYY CSSHASPRVFGTGTKVTVLGQPAAAPSVTLFPPSSEELQANKATLV CLISDFYPGAVTVAWKADSSPVKAGVETTTPSKQSNNKYAASSYLS LTPEQWKSHRSYSCQVTHEGSTVEKTVAPTECS |
| 316 | G4_13 IgG1 antibody light chain sequence | ASNFMLTQPHSVSESPGKTVTISCTRSSGSIASNYVQWYQQRPGS SPSTVIYEDNQRPSGVPDRFSGSIDSSSNSASLTISGLRTEDEADYY CQSYDSSIYVVFGGGTKLTVLGQPAAAPSVTLFPPSSEELQANKAT LVCLISDFYPGAVTVAWKADSSPVKAGVETTTPSKQSNNKYAASSY LSLTPEQWKSHRSYSCQVTHEGSTVEKTVAPTECS |
| 317 | G4_14 IgG1 antibody light chain sequence | ASNFMLTQPHSVSESPGKTVTISCTRSRGSIAGNYVHWYQQRPGR APTTVIYRDKERPSGVPDRISGSIDSSSNSASLTISGLKTEDEADYY CQSYDSSTHVVFGGGTKLTVLGQPAAAPSVTLFPPSSEELQANKA TLVCLISDFYPGAVTVAWKADSSPVKAGVETTTPSKQSNNKYAASS YLSLTPEQWKSHRSYSCQVTHEGSTVEKTVAPTECS |

| SEQ ID NO. | Description | Sequence |
|---|---|---|
| 318 | G4_15 IgG1 antibody light chain sequence | ASQSALTQPASVSGSPGQSITISCTGTSSDVGGYNYVSWYQQHPG KAPKLMIYDVSNRPSGVSNRFSGSKSGNTASLTISGLQAEDEADYY CSSYGSGSVFGTGTKLTVLGQPAAAPSVTLFPPSSEELQANKATLV CLISDFYPGAVTVAWKADSSPVKAGVETTTPSKQSNNKYAASSYLS LTPEQWKSHRSYSCQVTHEGSTVEKTVAPTECS |
| 319 | G4_16 IgG1 antibody light chain sequence | ASQSVLTQPPSASGSPGQSVTFSCTGTSSDIGAFNSVSWYQQHPG KAPKLLIYEITKRPSGVPDRFSGSKSGNTASLTISVLQAEDEADYYC TSYAGSNTLIFGGGTKVTVLGQPAAAPSVTLFPPSSEELQANKATL VCLISDFYPGAVTVAWKADSSPVKAGVETTTPSKQSNNKYAASSYL SLTPEQWKSHRSYSCQVTHEGSTVEKTVAPTECS |
| 320 | G4_18 IgG1 antibody light chain sequence | ASSYELTQPPSVTESPGQTARITCSGDALAKQYAYWYQQKPGQAP VLVIYRDSERPSEIPERFSGSSSGTTVTLTISGVQAEDEADYYCQSA DSSGTYTVFGGGTKLTVLGQPAAAPSVTLFPPSSEELQANKATLVC LISDFYPGAVTVAWKADSSPVKAGVETTTPSKQSNNKYAASSYLSL TPEQWKSHRSYSCQVTHEGSTVEKTVAPTECS |
| 321 | G4_19 IgG1 antibody light chain sequence | ASNFMLTQPHSVSESPGKTVTISCTRSSGSIASNYVQWYQQRPGS PPITLIYDDDQRPSGVPHRFSGSIDTSSNPASLTISGLKTEDEADYY CQSYDSSNHVVFGGGTKLTVLGQPAAAPSVTLFPPSSEELQANKA TLVCLISDFYPGAVTVAWKADSSPVKAGVETTTPSKQSNNKYAASS YLSLTPEQWKSHRSYSCQVTHEGSTVEKTVAPTECS |
| 322 | G4_20 IgG1 antibody light chain sequence | ASSYELTHPPSVSVSPGQTASITCSGDKLGDKFVSWYHQKPGQSP VLVIYQDSKRPSGIPERFSGSNSGNTATLTISGTRAMDEADYYCQA WDSSTWFGGGTKLTVLGQPAAAPSVTLFPPSSEELQANKATLVCL ISDFYPGAVTVAWKADSSPVKAGVETTTPSKQSNNKYAASSYLSLT PEQWKSHRSYSCQVTHEGSTVEKTVAPTECS |
| 323 | G4_22 IgG1 antibody light chain sequence | ASDIQMTQSPSSLSASVGDRVTITCQASQDISNYLNWYQQKPGKA PKLLIYAASSLQSGVPSRFSVSGSGTDFTLTISNLQPEDFATYYCQQ SYSIPWTFGQGTKVEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 324 | G4_23 IgG1 antibody light chain sequence | ASDIQMTQSPSSLSASVGDRVTITCRASQGISNSLAWYQQKPGKAP KLLLYAASRLESGVPSRFSGSGSGTDYTLTISSLQPEDFATYYCQQ YYSTPRTFGGGTKLEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| 325 | G4_24 IgG1 antibody light chain sequence | ASDIVMTQSPDSLAVSLGERATINCKSSQSVLYSSNNKNYLAWYQQ KPGQPPKLLISWASTRESGVPDRFSGSGSGTDFTLTINSLQSEDVAI YYCQQYYSTPPTFGQGTKLEIKRTAAAPSVFIFPPSDEQLKSGTAS VVCLLNNFYPREAKVQWKVDNALQSGNSQESVTEQDSKDSTYSLS STLTLSKADYEKHKLYACEVTHQGLSSPVTKSFNRGEC |
| 326 | G4_25 IgG1 antibody light chain sequence | ASQSALTQPRSVSGSPGQSVTISCTGTSSDVGGYNYVSWYQQHP GKAPKLMIYEVSNRPSGVSNRFSGSKSGNTASLTISGLQAEDEADY YCSSYGSGSVFGTGTKLTVLGQPAAAPSVTLFPPSSEELQANKATL VCLISDFYPGAVTVAWKADSSPVKAGVETTTPSKQSNNKYAASSYL SLTPEQWKSHRSYSCQVTHEGSTVEKTVAPTECS |
| 327 | G4_26 IgG1 antibody light chain sequence | ASQSGLTQPASVSGSPGQSITISCTGTSSDVGSYNLVSWYQQHPG KAPKLMIYEVSKRPSGVSNRFSGSKSGNTASLTISGLQAEDEADYY CSSFGSGSIFGTGTKLTVLGQPAAAPSVTLFPPSSEELQANKATLV CLISDFYPGAVTVAWKADSSPVKAGVETTTPSKQSNNKYAASSYLS LTPEQWKSHRSYSCQVTHEGSTVEKTVAPTECS |
| 328 | G4_27 IgG1 antibody light chain sequence | ASSYELTQDPAVSVALGQTVSITCQGDSLRNFYANWYQQKPGQAP VLVIYGKNNRPSGIPDRFSGSSSGNTASLTITGAQAEDEADYYCNS RDSSGNHLVFGGGTQLTVLGQPAAAPSVTLFPPSSEELQANKATL VCLISDFYPGAVTVAWKADSSPVKAGVETTTPSKQSNNKYAASSYL SLTPEQWKSHRSYSCQVTHEGSTVEKTVAPTECS |
| 329 | G4_28 IgG1 antibody light chain sequence | ASSYELTQDPAVSVALGQTVTITCQGDSLRNYYASWYRQKPGQTP VLVVYGKNNRPSGIPDRFSVSASGNTASLTITGAQAEDEGDYYCNS RDSSGVVFGGGTKVTVLGQPAAAPSVTLFPPSSEELQANKATLVCL ISDFYPGAVTVAWKADSSPVKAGVETTTPSKQSNNKYAASSYLSLT PEQWKSHRSYSCQVTHEGSTVEKTVAPTECS |

-continued

| SEQ ID NO. | Description | Sequence |
| --- | --- | --- |
| 330 | Human Kappa light constant sequence (preferred allotype) | RTVAAPSVFIFPPSDEQLKSGTASVVCLLNNFYPREAKVQWKVDNA LQSGNSQESVTEQDSKDSTYSLSSTLTLSKADYEKHKVYACEVTH QGLSSPVTKSFNRGEC |
| 331 | Human Lambda light constant sequence (IGLC2) | GQPKAAPSVTLFPPSSEELQANKATLVCLISDFYPGAVTVAWKADS SPVKAGVETTTPSKQSNNKYAASSYLSLTPEQWKSHRSYSCQVTH EGSTVEKTVAPTECS |
| 332 | Human IgG1 constant domain | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPAPIEKTISKAKGQPR EPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| 333 | Human IgG1 constant domain with LAGA substitution | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELAGAPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPAPIEKTISKAKGQPR EPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| 334 | human TRGV4 | SSNLEGRTKSVIRQTGSSAEITCDLAEGSTGYIHWYLHQEGKAPQR LLYYDSYTSSVVLESGISPGKYDTYGSTRKNLRMILRNLIENDSGVY YCATWD |
| 335 | human TRGV2 | SSNLEGRTKSVIRQTGSSAEITCDLAEGSNGYIHWYLHQEGKAPQR LQYYDSYNSKVVLESGVSPGKYYTYASTRNNLRLILRNLIENDSGVY YCATWD |
| 336 | human TRGV8 | SSNLEGRTKSVTRPTGSSAVITCDLPVENAVYTHWYLHQEGKAPQ RLLYYDSYNSRVVLESGISREKYHTYASTGKSLKFILENLIERDSGV YYCATWD |
| 337 | human TRDV1 | AQKVTQAQSSVSMPVRKAVTLNCLYETSWWSYYIFWYKQLPSKE MIFLIRQGSDEQNAKSGRYSVNFKKAAKSVALTISALQLEDSAKYFC ALGE |
| 338 | human TRDV2 | AIELVPEHQTVPVSIGVPATLRCSMKGEAIGNYYINWYRKTQGNTIT FIYREKDIYGPGFKDNFQGDIDIAKNLAVLKILAPSERDEGSYYCACD T |

The invention claimed is:

1. An isolated anti-gamma variable 4 (anti-Vγ4) antibody or fragment thereof comprising:

(a) a heavy chain variable (VH) amino acid sequence comprising a heavy chain complementarity determining region 1 (HCDR1) of SEQ ID NO: 79, a heavy chain complementarity determining region 2 (HCDR2) of SEQ ID NO: 56 and a heavy chain complementarity determining region 3 (HCDR3) of SEQ ID NO: 10; and
a light chain variable (VL) amino acid sequence comprising a light chain complementarity determining region 1 (LCDR1) of SEQ ID NO: 102, a light chain complementarity determining region 2 (LCDR2) of EVT and a light chain complementarity determining region 3 (LCDR3) of SEQ ID NO: 33;

(b) a VH amino acid sequence comprising a HCDR1 of SEQ ID NO: 86, a HCDR2 of SEQ ID NO: 63 and a HCDR3 of SEQ ID NO: 17; and a VL amino acid sequence comprising a LCDR1 of SEQ ID NO: 109, a LCDR2 of QDS and a LCDR3 of SEQ ID NO: 40;

(c) a VH amino acid sequence comprising a HCDR1 of SEQ ID NO: 73, a HCDR2 of SEQ ID NO: 50 and a HCDR3 of SEQ ID NO: 4; and a VL comprising a LCDR1 of SEQ ID NO: 96, a LCDR2 of DAS and a LCDR3 of SEQ ID NO: 27;

(d) a VH amino acid sequence comprising a HCDR1 of SEQ ID NO: 83, a HCDR2 of SEQ ID NO: 60 and a HCDR3 of SEQ ID NO: 14; and a VL amino acid sequence comprising a LCDR1 of SEQ ID NO: 106, a LCDR2 of EIT and a LCDR3 of SEQ ID NO: 37;

(e) a VH amino acid sequence comprising a HCDR1 of SEQ ID NO: 84, a HCDR2 of SEQ ID NO: 61 and a HCDR3 of SEQ ID NO: 15; and a VL amino acid sequence comprising a LCDR1 of SEQ ID NO: 107, a LCDR2 of RDS and a LCDR3 of SEQ ID NO: 38;

(f) a VH amino acid sequence comprising a HCDR1 of SEQ ID NO: 88, a HCDR2 of SEQ ID NO: 65 and a HCDR3 of SEQ ID NO: 19; and a VL amino acid sequence comprising a LCDR1 of SEQ ID NO: 111, a LCDR2 of AAS and a LCDR3 of SEQ ID NO: 42;

(g) a VH amino acid sequence comprising a HCDR1 of SEQ ID NO: 92, a HCDR2 of SEQ ID NO: 69 and a HCDR3 of SEQ ID NO: 23; and a VL amino acid sequence comprising a LCDR1 of SEQ ID NO: 115, a LCDR2 of GKN and a LCDR3 of SEQ ID NO: 46;

(h) a VH amino acid sequence comprising a HCDR1 of SEQ ID NO: 71, a HCDR2 of SEQ ID NO: 48 and a HCDR3 of SEQ ID NO: 2; and a VL amino acid sequence comprising a LCDR1 of SEQ ID NO: 94, a LCDR2 of DAS and a LCDR3 of SEQ ID NO: 25;

(i) a VH amino acid sequence comprising a HCDR1 of SEQ ID NO: 72, a HCDR2 of SEQ ID NO: 49 and a HCDR3 of SEQ ID NO: 3; and a VL amino acid sequence comprising a LCDR1 of SEQ ID NO: 95, a LCDR2 of AAS and a LCDR3 of SEQ ID NO: 26;

(j) a VH amino acid sequence comprising a HCDR1 of SEQ ID NO: 74, a HCDR2 of SEQ ID NO: 51 and a HCDR3 of SEQ ID NO: 5; and a VL amino acid sequence comprising a LCDR1 of SEQ ID NO: 97, a LCDR2 of WAS and a LCDR3 of SEQ ID NO: 28;

(k) a VH amino acid sequence comprising a HCDR1 of SEQ ID NO: 75, a HCDR2 of SEQ ID NO: 52 and a HCDR3 of SEQ ID NO: 6; and a VL amino acid sequence comprising a LCDR1 of SEQ ID NO: 98, a LCDR2 of AAS and a LCDR3 of SEQ ID NO: 29;

(l) a VH amino acid sequence comprising a HCDR1 of SEQ ID NO: 76, a HCDR2 of SEQ ID NO: 53 and a HCDR3 of SEQ ID NO: 7; and a VL amino acid sequence comprising a LCDR1 of SEQ ID NO: 99, a LCDR2 of AAS and a LCDR3 of SEQ ID NO: 30;

(m) a VH amino acid sequence comprising a HCDR1 of SEQ ID NO: 77, a HCDR2 of SEQ ID NO: 54 and a HCDR3 of SEQ ID NO: 8; and a VL amino acid sequence comprising a LCDR1 of SEQ ID NO: 100, a LCDR2 of LGS and a LCDR3 of SEQ ID NO: 31;

(n) a VH amino acid sequence comprising a HCDR1 of SEQ ID NO: 78, a HCDR2 of SEQ ID NO: 55 and a HCDR3 of SEQ ID NO: 9; and a VL amino acid sequence comprising a LCDR1 of SEQ ID NO: 101, a LCDR2 of KVS and a LCDR3 of SEQ ID NO: 32;

(o) a VH amino acid sequence comprising a HCDR1 of SEQ ID NO: 80, a HCDR2 of SEQ ID NO: 57 and a HCDR3 of SEQ ID NO: 11; and a VL amino acid sequence comprising a LCDR1 of SEQ ID NO: 103, a LCDR2 of EDN and a LCDR3 of SEQ ID NO: 34;

(p) a VH amino acid sequence comprising a HCDR1 of SEQ ID NO: 81, a HCDR2 of SEQ ID NO: 58 and a HCDR3 of SEQ ID NO: 12; and a VL amino acid sequence comprising a LCDR1 of SEQ ID NO: 104, a LCDR2 of RDK and a LCDR3 of SEQ ID NO: 35;

(q) a VH amino acid sequence comprising a HCDR1 of SEQ ID NO: 82, a HCDR2 of SEQ ID NO: 59 and a HCDR3 of SEQ ID NO: 13; and a VL amino acid sequence comprising a LCDR1 of SEQ ID NO: 105, a LCDR2 of DVS and a LCDR3 of SEQ ID NO: 36;

(r) a VH amino acid sequence comprising a HCDR1 of SEQ ID NO: 85, a HCDR2 of SEQ ID NO: 62 and a HCDR3 of SEQ ID NO: 16; and a VL amino acid sequence comprising a LCDR1 of SEQ ID NO: 108, a LCDR2 of DDD and a LCDR3 of SEQ ID NO: 39;

(s) a VH amino acid sequence comprising a HCDR1 of SEQ ID NO: 87, a HCDR2 of SEQ ID NO: 64 and a HCDR3 of SEQ ID NO: 18; and a VL amino acid sequence comprising a LCDR1 of SEQ ID NO: 110, a LCDR2 of AAS and a LCDR3 of SEQ ID NO: 41;

(t) a VH amino acid sequence comprising a HCDR1 of SEQ ID NO: 89, a HCDR2 of SEQ ID NO: 66 and a HCDR3 of SEQ ID NO: 20; and a VL amino acid sequence comprising a LCDR1 of SEQ ID NO: 112, a LCDR2 of WAS and a LCDR3 of SEQ ID NO: 43;

(u) a VH amino acid sequence comprising a HCDR1 of SEQ ID NO: 90, a HCDR2 of SEQ ID NO: 67 and a HCDR3 of SEQ ID NO: 21; and a VL amino acid sequence comprising a LCDR1 of SEQ ID NO: 113, a LCDR2 of EVS and a LCDR3 of SEQ ID NO: 44;

(v) a VH amino acid sequence comprising a HCDR1 of SEQ ID NO: 91, a HCDR2 of SEQ ID NO: 68 and a HCDR3 of SEQ ID NO: 22; and a VL amino acid sequence comprising a LCDR1 of SEQ ID NO: 114, a LCDR2 of EVS and a LCDR3 of SEQ ID NO: 45;

or (w) a VH amino acid sequence comprising a HCDR1 of SEQ ID NO: 93, a HCDR2 of SEQ ID NO: 70 and a HCDR3 of SEQ ID NO: 24; and a VL amino acid sequence comprising a LCDR1 of SEQ ID NO: 116, a LCDR2 of GKN and a LCDR3 of SEQ ID NO: 47.

2. The isolated anti-Vγ4 antibody or fragment thereof of claim 1 comprising an amino acid sequence of any one of SEQ ID NOs: 163-185.

3. The isolated anti-Vγ4 antibody or fragment thereof of claim 1 comprising an amino acid sequence of any one of SEQ ID NOs: 233-255.

4. The isolated anti-Vγ4 antibody or fragment thereof of claim 1 comprising a heavy chain amino acid sequence of any one of SEQ ID NOs: 284-306 and a light chain amino acid sequence of any one of SEQ ID NOs: 307-329.

5. The isolated anti-Vγ4 antibody or fragment thereof of claim 1, wherein the isolated anti-Vγ4 antibody or fragment thereof is:

(i) an scFv or a full length antibody; and/or (ii) a human antibody or fragment thereof.

6. A polynucleotide sequence encoding the anti-Vγ4 antibody or fragment thereof of claim 1.

7. An expression vector comprising the polynucleotide sequence of claim 6.

8. A cell comprising the polynucleotide sequence of claim 6.

9. A composition comprising the antibody or fragment thereof of claim 1.

10. A pharmaceutical composition comprising the antibody or fragment thereof of claim 1 and a pharmaceutically acceptable diluent or carrier.

11. A kit comprising an anti-Vγ4 antibody or fragment thereof of claim 1.

12. The isolated anti-Vγ4 antibody or fragment thereof of claim 1 comprising:

(a) a VH comprising an amino acid sequence of SEQ ID NO: 125; and
  a VL comprising an amino acid sequence of SEQ ID NO: 148 or 269;

(b) a VH comprising an amino acid sequence of SEQ ID NO: 132; and
  a VL comprising an amino acid sequence of SEQ ID NO: 155 or 276;

(c) a VH comprising an amino acid sequence of SEQ ID NO: 119; and
  a VL comprising an amino acid sequence of SEQ ID NO: 142 or 263;

(d) a VH comprising an amino acid sequence of SEQ ID NO: 129; and
  a VL comprising an amino acid sequence of SEQ ID NO: 152 or 273;

(e) a VH comprising an amino acid sequence of SEQ ID NO: 130; and
  a VL comprising an amino acid sequence of SEQ ID NO: 153 or 274;

(f) a VH comprising an amino acid sequence of SEQ ID NO: 134; and
  a VL comprising an amino acid sequence of SEQ ID NO: 157 or 278;

(g) a VH comprising an amino acid sequence of SEQ ID NO: 138; and
  a VL comprising an amino acid sequence of SEQ ID NO: 161 or 282;

(h) a VH comprising an amino acid sequence of SEQ ID NO: 117; and
  a VL comprising an amino acid sequence of SEQ ID NO: 140 or 261;

(i) a VH comprising an amino acid sequence of SEQ ID NO: 118; and
  a VL comprising an amino acid sequence of SEQ ID NO: 141 or 262;

(j) a VH comprising an amino acid sequence of SEQ ID NO: 120; and
  a VL comprising an amino acid sequence of SEQ ID NO: 143 or 264;

(k) a VH comprising an amino acid sequence of SEQ ID NO: 121; and
  a VL comprising an amino acid sequence of SEQ ID NO: 144 or 265;

(l) a VH comprising an amino acid sequence of SEQ ID NO: 122; and
  a VL comprising an amino acid sequence of SEQ ID NO: 145 or 266;

(m) a VH comprising an amino acid sequence of SEQ ID NO: 123; and
  a VL comprising an amino acid sequence of SEQ ID NO: 146 or 267;

(n) a VH comprising an amino acid sequence of SEQ ID NO: 124; and
  a VL comprising an amino acid sequence of SEQ ID NO: 147 or 268;

(o) a VH comprising an amino acid sequence of SEQ ID NO: 126; and
  a VL comprising an amino acid sequence of SEQ ID NO: 149 or 270;

(p) a VH comprising an amino acid sequence of SEQ ID NO: 127; and
  a VL comprising an amino acid sequence of SEQ ID NO: 150 or 271;

(q) a VH comprising an amino acid sequence of SEQ ID NO: 128; and
  a VL comprising an amino acid sequence of SEQ ID NO: 151 or 272;

(r) a VH comprising an amino acid sequence of SEQ ID NO: 131; and
  a VL comprising an amino acid sequence of SEQ ID NO: 154 or 275;

(s) a VH comprising an amino acid sequence of SEQ ID NO: 133; and
  a VL comprising an amino acid sequence of SEQ ID NO: 156 or 277;

(t) a VH comprising an amino acid sequence of SEQ ID NO: 135; and
  a VL comprising an amino acid sequence of SEQ ID NO: 158 or 279;

(u) a VH comprising an amino acid sequence of SEQ ID NO: 136; and
  a VL comprising an amino acid sequence of SEQ ID NO: 159 or 280;

(v) a VH comprising an amino acid sequence of SEQ ID NO: 137; and
  a VL comprising an amino acid sequence of SEQ ID NO: 160 or 281; or (w) a VH comprising an amino acid sequence of SEQ ID NO: 139; and
  a VL comprising an amino acid sequence of SEQ ID NO: 162 or 283.

13. A method of expanding a Vγ4+ T cell, the method comprising contacting the Vγ4+ T cell with the isolated anti-Vγ4 antibody or fragment thereof of claim 1.

14. A method of detecting a Vγ4+ T cell, the method comprising contacting a sample comprising the Vγ4+ T cell with the isolated anti-Vγ4 antibody or fragment thereof of claim 1.

15. A method of treating a cancer, an infectious disease or an inflammatory disease in a subject in need thereof, the method comprising administering a therapeutically effective amount of the isolated anti-Vγ4 antibody or fragment thereof of claim 1 to the subject.

* * * * *